United States Patent
Kauppinen et al.

(10) Patent No.: US 9,464,106 B2
(45) Date of Patent: Oct. 11, 2016

(54) OLIGONUCLEOTIDES USEFUL FOR DETECTING AND ANALYZING NUCLEIC ACIDS OF INTEREST

(75) Inventors: Sakari Kauppinen, Smørum (DK); Carsten Alsbo, Køge (DK); Peter S. Nielsen, Birkerød (DK); Daniel C. Jeffares, København N (DK); Tobias Mourier, København N (DK); Søren Mørk, Valby (DK); Peter Arctander, Askeby (DK); Niels Tommerup, Albertslund (DK); Niels Tolstrup, Klampenborg (DK); Henrik Vissing, Virum (DK); Søren Morgenthaler Echwald, Humlebaek (DK)

(73) Assignee: Exiqon A/S, Vedbaek (DK)

(*) Notice: Subject to any disclaimer, the term of this patent is extended or adjusted under 35 U.S.C. 154(b) by 0 days.

(21) Appl. No.: 13/295,615

(22) Filed: Nov. 14, 2011

(65) Prior Publication Data

US 2012/0157333 A1    Jun. 21, 2012

Related U.S. Application Data

(60) Continuation of application No. 11/643,615, filed on Dec. 21, 2006, now abandoned, which is a division of application No. 10/690,487, filed on Oct. 21, 2003, now abandoned.

(60) Provisional application No. 60/420,278, filed on Oct. 21, 2002.

(30) Foreign Application Priority Data

May 19, 2003   (DK) .................................. 2003 00752

(51) Int. Cl.
*C12Q 1/68* (2006.01)
*C12P 19/34* (2006.01)
*C07H 19/06* (2006.01)
*C07H 19/16* (2006.01)
*C07H 21/00* (2006.01)
*C07H 23/00* (2006.01)

(52) U.S. Cl.
CPC .............. *C07H 19/06* (2013.01); *C07H 19/16* (2013.01); *C07H 21/00* (2013.01); *C07H 23/00* (2013.01)

(58) Field of Classification Search
CPC ...... C07H 19/06; C07H 19/16; C07H 21/00; C07H 23/00
See application file for complete search history.

(56) References Cited

U.S. PATENT DOCUMENTS

| | | |
|---|---|---|
| 3,687,808 A | 8/1972 | Merigan et al. |
| 4,806,463 A | 2/1989 | Goodchild et al. |
| 4,889,818 A | 12/1989 | Gelfand et al. |
| 5,432,272 A | 7/1995 | Benner |
| 5,445,934 A | 8/1995 | Fodor et al. |
| 5,525,470 A | 6/1996 | Cohen et al. |
| 5,539,082 A | 7/1996 | Nielsen et al. |
| 5,643,766 A | 7/1997 | Scheele et al. |
| 5,714,331 A | 2/1998 | Buchardt et al. |
| 5,719,262 A | 2/1998 | Buchardt et al. |
| 5,738,993 A | 4/1998 | Fugono et al. |
| 5,744,305 A | 4/1998 | Fodor et al. |
| 5,800,992 A | 9/1998 | Fodor et al. |
| 5,874,229 A | 2/1999 | Mizutani et al. |
| 5,885,837 A | 3/1999 | Winkler et al. |
| 5,919,523 A | 7/1999 | Sundberg et al. |
| 5,945,334 A | 8/1999 | Besemer et al. |
| 5,989,165 A | 11/1999 | Giannelli et al. |
| 6,033,784 A | 3/2000 | Jacobsen et al. |
| 6,043,060 A | 3/2000 | Imanishi |
| 6,045,994 A | 4/2000 | Zabeau et al. |
| 6,117,635 A | 9/2000 | Nazarenko et al. |
| 6,156,501 A | 12/2000 | McGall et al. |
| 6,238,862 B1 | 5/2001 | McGall et al. |
| 6,239,273 B1 | 5/2001 | Pease et al. |
| 6,261,776 B1 | 7/2001 | Pirrung et al. |
| 6,268,490 B1 | 7/2001 | Imanishi et al. |
| 6,303,315 B1 | 10/2001 | Skouv |
| 6,309,823 B1 | 10/2001 | Cronin et al. |
| 6,309,831 B1 | 10/2001 | Goldberg et al. |
| 6,310,183 B1 | 10/2001 | Johannessen et al. |
| 6,316,198 B1 | 11/2001 | Skouv et al. |
| 6,329,143 B1 | 12/2001 | Stryer et al. |
| 6,344,316 B1 | 2/2002 | Lockhart et al. |
| 6,346,413 B1 | 2/2002 | Fodor et al. |
| 6,403,317 B1 | 6/2002 | Anderson |

(Continued)

FOREIGN PATENT DOCUMENTS

| | | |
|---|---|---|
| CA | 2380205 A2 | 3/2009 |
| CN | 101054576 A | 10/2007 |

(Continued)

OTHER PUBLICATIONS

Trojan J. et al. Proc. Natl. Acad. Sci. USA vol. 89, pp. 4874-4878, Jun. 1992.*
Singh S.K. et al. Chem. Commun., 1998 1247-1248.*
Reinhart B.J. et al. Nature, vol. 403, Feb. 24, 2000, pp. 901-906.*
Medhurst A.D. et al. Journal of Neuroscience Methods 98 (2000) 9-20.*
U.S. Appl. No. 13/295,615, Jun. 21, 2012, Kauppinen et al.
Abelson et al., "Sequence Variants in SLITRK1 are Associated with Tourette's Syndrome," *Science* 310: 317-320 (2005).

(Continued)

*Primary Examiner* — Stephen Kapushoc
(74) *Attorney, Agent, or Firm* — Clark & Elbing LLP

(57) ABSTRACT

The invention features improved nucleic acids and methods for expression profiling of mRNAs, identifying and profiling of particular mRNA splice variants, and detecting mutations, deletions, or duplications of particular exons or other splice variants, e.g., alterations associated with a disease such as cancer, in a nucleic acid sample, e.g., a biological sample or a patient sample.

2 Claims, 48 Drawing Sheets

(56) References Cited

U.S. PATENT DOCUMENTS

| | | |
|---|---|---|
| 6,403,320 B1 | 6/2002 | Read et al. |
| 6,403,957 B1 | 6/2002 | Fodor et al. |
| 6,406,844 B1 | 6/2002 | Pirrung et al. |
| 6,410,229 B1 | 6/2002 | Lockhart et al. |
| 6,440,739 B1 | 8/2002 | Bennett et al. |
| 6,706,476 B1 | 3/2004 | Thirstrup et al. |
| 7,217,805 B2 | 5/2007 | Imanishi et al. |
| 7,683,036 B2 | 3/2010 | Esau et al. |
| 2002/0068708 A1 | 6/2002 | Wengel et al. |
| 2002/0068709 A1 | 6/2002 | Orum et al. |
| 2002/0187476 A1 | 12/2002 | Koroulis et al. |
| 2002/0187485 A1 | 12/2002 | Jakobsen et al. |
| 2003/0077609 A1 | 4/2003 | Jakobsen et al. |
| 2003/0125241 A1 | 7/2003 | Wissenbach et al. |
| 2003/0134808 A1 | 7/2003 | Wengel |
| 2004/0137471 A1 | 7/2004 | Vickers et al. |
| 2004/0175732 A1 | 9/2004 | Rana |
| 2004/0235005 A1 | 11/2004 | Friedlander et al. |
| 2005/0059005 A1 | 3/2005 | Tuschl et al. |
| 2005/0196782 A1 | 9/2005 | Kiefer et al. |
| 2005/0221408 A1 | 10/2005 | Nalefski et al. |
| 2005/0266418 A1 | 12/2005 | Chen et al. |
| 2006/0014191 A1 | 1/2006 | Lao et al. |
| 2006/0094035 A1 | 5/2006 | Erlander et al. |
| 2006/0147924 A1 | 7/2006 | Ramsing et al. |
| 2006/0185027 A1 | 8/2006 | Bartel et al. |
| 2006/0265138 A1 | 11/2006 | Bowtell et al. |
| 2007/0065840 A1 | 3/2007 | Naguibneva et al. |
| 2007/0099196 A1 | 5/2007 | Kauppinen et al. |
| 2007/0105807 A1 | 5/2007 | Sazani et al. |
| 2007/0292878 A1 | 12/2007 | Raymond |
| 2009/0123912 A1 | 5/2009 | Raymond |

FOREIGN PATENT DOCUMENTS

| | | |
|---|---|---|
| CN | 101054580 A | 10/2007 |
| EP | 329822 B1 | 6/1994 |
| EP | 1072679 A2 | 1/2001 |
| EP | 1247815 A3 | 1/2003 |
| EP | 1201678 B1 | 9/2004 |
| EP | 0534858 B2 | 4/2005 |
| EP | 1222309 B1 | 12/2005 |
| EP | 1851336 B1 | 9/2010 |
| WO | WO-9712896 A1 | 4/1997 |
| WO | WO-9839352 A1 | 9/1998 |
| WO | WO-99/14266 A1 | 3/1999 |
| WO | WO-9914226 A2 | 3/1999 |
| WO | WO-0047599 A1 | 8/2000 |
| WO | WO-0056746 A2 | 9/2000 |
| WO | WO-0056748 A1 | 9/2000 |
| WO | WO-0066004 A1 | 11/2000 |
| WO | WO-0066604 A2 | 11/2000 |
| WO | WO-01/06004 A2 | 1/2001 |
| WO | WO-0100641 A1 | 1/2001 |
| WO | WO-0107455 A1 | 2/2001 |
| WO | WO-0125248 A2 | 4/2001 |
| WO | WO-0148190 A2 | 7/2001 |
| WO | WO-0181632 A1 | 11/2001 |
| WO | WO-02/057479 A2 | 7/2002 |
| WO | WO-02061387 A2 | 8/2002 |
| WO | WO-03020739 A2 | 3/2003 |
| WO | WO-2004/048511 A2 | 6/2004 |
| WO | WO-2004046160 A2 | 6/2004 |
| WO | WO-2004/057017 A2 | 7/2004 |
| WO | WO-2005/003318 A2 | 1/2005 |
| WO | WO-2005018534 A2 | 3/2005 |
| WO | WO-2005/040419 A1 | 5/2005 |
| WO | WO-2005098029 A2 | 10/2005 |
| WO | WO-2005111211 A2 | 11/2005 |
| WO | WO-2005116250 A2 | 12/2005 |
| WO | WO-2006/076025 A2 | 1/2006 |
| WO | WO-2006069584 A2 | 7/2006 |
| WO | WO-2006/081284 A2 | 8/2006 |
| WO | WO-2006085984 A2 | 8/2006 |
| WO | WO-2006/102309 A2 | 9/2006 |
| WO | WO-2006119266 A2 | 11/2006 |
| WO | WO-2007042899 A2 | 4/2007 |
| WO | WO-2008061537 A2 | 5/2008 |
| WO | WO-2008/074328 A3 | 6/2008 |
| WO | WO-2008/111908 A1 | 9/2008 |
| WO | WO-2008151639 A2 | 12/2008 |

OTHER PUBLICATIONS

Adams et al., "The Micro-Ribonucleic Acid (miRNA) miR-206 Targets the Human Estrogen Receptor-α (ERα) and Represses ERα Messenger Rna and Protein Expression in Breast Cancer Cell Lines," *Mol. Endocrinol.* 21: 1132-1147 (2007).

Alizadeh et al., "Distinct Types of Diffuse Large B-Cell Lymphoma Identified by Gene Expression Profiling," *Nature* 403: 503-511 (2000).

Bartel, "MicroRNAs: Genomics, Biogenesis, Mechanism, and Function," *Cell* 116: 281-297 (2004).

Beaumont et al., "Integrated Technology Platform for Fluorescence 2-D Difference Gel Electrophoresis," *Life Science News* 7: 1-3 (2001).

Bennasser et al., "HIV-1 Encoded Candidate Micro-RNAs and Their Cellular Targets," *Retrovirol.* 1: 43 (2004).

Berezikov et al., "Mammalian Mirtron Genes," *Mol. Cell* 28: 328-336 (2007).

Birmingham et al., "3' UTR Seed Matches, but not Overall Identity, are Associated with RNAi Off-Targets," *Nature Methods* 3: 199-204 (2006).

Bittner et al., "Molecular Classification of Cutaneous Malignant Melanoma by Gene Expression Profiling," *Nature* 406: 536-540 (2000).

Blower et al., "MicroRNA Expression Profiles for the NCI-60 Cancer Cell Panel," *Mol. Cancer Ther.* 6: 1483-1491 (2007).

Brummelkamp et al., "A System for Stable Expression of Short Interfering RNAs in Mammalian Cells," *Science* 296: 550-553 (2002).

Bustin, "Quantification of mRNA using Real-Time Reverse Transcription PCR (RT-PCR): Trends and Problems," *J. Mol. Endocrinol.* 29: 23-39 (2002).

Calin et al., "Human MicroRNA Genes are Frequently Located at Fragile Sites and Genomic Regions Involved in Cancers," *Proc. Natl. Acad. Sci. USA* 101: 2999-3004 (2004).

Calin et al., "MicroRNA Profiling Reveals Distinct Signatures in B Cell Chronic Lymphocytic Leukemias," *Proc. Natl. Acad. Sci. USA* 101: 11755-11760 (2004).

Calin et al., "A MicroRNA Signature Associated with Prognosis and Progression in Chronic Lymphocytic Leukemia," *New Engl. J. Med.* 353: 1793-1801 (2005).

Calin et al., "MicroRNA Signatures in Human Cancers," *Nat. Rev.* 6: 857-866 (2006).

Calin et al., "The Role of MicroRNA and Other Non-Coding RNA in the Pathogenesis of Chronic Lymphocytic Leukemia," *Best Pract. Res. Clin. Haematol.* 20: 425-437 (2007).

Cao et al., "A Functional Study of miR-124 in the Developing Neural Tube," *Genes Dev.* 21: 531-536 (2007).

Caruthers et al. "Chemical Synthesis and Biological Studies on Mutated Gene-control Regions," *Cold Spring Harbor Symp. Quant. Biol.* 47: 411-418 (1982).

Chan et al., "MicroRNA-21 is an Antiapoptotic Factor in Human Glioblastoma Cells," *Cancer Res.* 65: 6029-6033 (2005).

Christensen and Pedersen, "Intercalating Nucleic Acids Containing Insertions of 1-O-(1-Pyrenylmethyl)glycerol: Stabilisation of dsDNA and Discrimination of DNA Over RNA," *Nucleic Acids Res.* 30: 4918-4925 (2002).

Christofferson et al., "miR-200b Mediates Post-Transcriptional Repression of ZFHX1 B," *RNA* 13: 1172-1178 (2007).

Cui et al., "Prediction and Identification of Herpes Simplex Virus 1-Encoded MicroRNAs," *J. Virol.* 80: 5499-5508 (2006).

Database EMBL Accession No. HSA421732, created Dec. 11, 2001, last updated Jun. 11, 2003.

De Mesmaeker et al., "Backbone Modifications in Oligonucleotides and Peptide Nucleic Acid Systems," *Curr. Opin. Struct. Biol.* 5: 343-355 (1995).

(56) References Cited

OTHER PUBLICATIONS de Wildt et al., "Antibody Arrays for High-Throughput Screening of Antibody-Antigen Interactions," *Nat. Biotechnol.* 18: 989-994 (2000).
Dews et al., "Augmentation of Tumor Angiogenesis by a Myc-Activated microRNA Cluster," *Nat. Genet.* 38: 1060-1065 (2006).
Easow et al., "Isolation of MicroRNA Targets by miRNP Immunopurification," *RNA* 13: 1198-1204 (2007).
Ebert et al., "MicroRNA Sponges: Competitive Inhibitors of Small RNAs in Mammalian Cells," *Nat. Methods* 4: 721-726 (2007).
Eis et al., "Accumulation of miR-155 and BIC RNA in Human B cell Lymphomas," *Proc. Natl. Acad. Soc. U.S.A.* 102: 3627-3632 (2005).
Elbashir et al., "Duplexes of 21-Nucleotide RNAs Mediate RNA Interference in Cultured Mammalian Cells," *Nature* 411: 494-498 (2001).
Elbashir et al., "RNA Interference is Mediated by 21-and 22-Nucleotide RNAs," *Genes Dev.* 15: 188-200 (2001).
Esau et al., "miR-122 Regulation of Lipid Metabolism Revealed by In Vivo Antisense Targeting," *Cell Metab.* 3: 87-98 (2006).
Esquela-Kerscher and Slack, "Oncomirs—MicroRNAs With a Role in Cancer," *Nat. Rev.* 6: 259-269 (2006).
Felli et al., "MicroRNAs 221 and 222 Inhibit Normal Erythropoiesis and Erythroleukemic Cell Growth Via Kit Receptor Down-Modulation," *Proc. Natl. Sci. Acad. USA* 102: 18081-18086 (2005).
Frankel et al., "Programmed Cell Death 4 (PDCD4) Is an Important Functional Target of the MicroRNA *miR-21* in Breast Cancer Cells," *J. Biol. Chem.* 283: 1026-1033 (2008).
Galardi et al., "miR-221 and miR-222 Expression Affects the Proliferation Potential of Human Prostrate Carcinoma Cell Lines by Targeting p27Kip1," *J. Biol. Chem.* 282: 23716-23724 (2007).
Garzon et al., "MicroRNA Gene Expression During Retinoic Acid-Induced Differentiation of Human Acute Promyelocytic Leukemia," *Oncogene* 26: 4148-4157 (2007).
Goffeau et al., "Life with 6000 Genes," *Science* 274: 546, 563-567 (1996).
Golub et al., "Molecular Classification of Cancer: Class Discovery and Class Prediction by Gene Expression Monitoring," *Science* 286: 531-537 (1999).
Gramantieri et al., "Cyclin G1 Is a Target of miR-122a, a MicroRNA Frequently Down-Regulated in Human Hepatocellular Carcinoma," *Cancer Res.* 67: 6092-6099 (2007).
Griffiths-Jones et al., "miRBase: MicroRNA Sequences, Targets and Gene Nomenclature," *Nucleic Acids Res.* 34: D140-D144 (2006).
Grünweller et al., "Comparison of Different Antisense Strategies in Mammalian Cells Using Locked Nucleic Acids, 2'-*O*-methyl RNA, Phosphorothioates and Small Interfering RNA," *Nucleic Acids Res.* 31: 3185-3193 (2003).
Gupta et al., "Anti-Apoptotic Function of a microRNA Encoded by the HSV-1 Latency-Associated Transcript," *Nature* 442: 82-85 (2006).
Gygi et al., "Quantitative Analysis of Complex Protein Mixtures Using Isotope-coded Affinity Tags," *Nat. Biotechnol.* 17: 994-999 (1999).
Hariharan et al., "Targets for Human Encoded MicroRNAs in HIV Genes," *Biochem. Biophys. Res. Commun.* 337: 1214-1218 (2005).
Hayashita et al., "A Polycistronic MicroRNA Cluster, *miR-17-92*, is Overexpressed in Human Lung Cancers and Enhances Cell Proliferation," *Cancer Res.* 65: 9628-9632 (2005).
He et al., "A MicroRNA Polycistron as a Potential Human Oncogene," *Nature* 435: 828-833 (2005).
He et al., "The Role of MicroRNA Genes in Papillary Thyroid Carcinoma," *Proc. Natl. Acad. Sci. USA* 102: 19075-19080 (2005).
Hebert et al., "High Mobility Group A2 is a Target for miRNA-98 in Head and Neck Squamous Cell Carcinoma," *Mol. Cancer* 6: 5 (2007).
Hossain et al., "*Mir-17-5p* Regulates Breast Cancer Cell Proliferation by Inhibiting Translation of AIB1 mRNA," *Mol. Cell. Biol.* 26: 8191-8201 (2006).

Huesken et al., "Design of a Genome-wide siRNA Library Using an Artificial Neural Network," *Nat. Biotechnol.* 23: 995-1001, Supplementary Material (1 page) (2005).
Iwao et al., "Molecular Classification of Primary Breast Tumors Possessing Distinct Prognostic Properties," *Human Mol. Genet.* 11: 199-206 (2002).
Jackson et al., "Expression Profiling Reveals Off-Target Gene Regulation by RNAi," Nat. Biotechnol. 21: 635-637, Erratum (1 page), Supplementary Material (4 pages) (2003).
Jagla et al., "Sequence Characteristics of Functional siRNAs," *RNA* 11: 864-872 (2005).
Janowski et al., "Silencing Gene Expression by Targeting Chromosomal DNA with Antigene Peptide Nucleic Acids and Duplex RNAs," *Nat. Protocols* 1: 436-443 (2006).
Ji et al., "Enhanced Gene Silencing by the Application of Multiple Specific Small Interfering RNAs," *FEBS Lett.* 552: 247-252 (2003).
Ji et al., "MicroRNA Expression Signature and Antisense-Mediated Depletion Reveal an Essential Role of MicroRNA in Vascular Neointimal Lesion Formation," *Circ. Res.* 100: 15791588 (2007).
Johnson et al., "RAS Is Regulated by the Let-7 MicroRNA Family," *Cell* 120: 635-647 (2005).
Jopling et al., "Modulation of Hepatitis C Virus RNA Abundance by a Liver-Specific MicroRNA," *Science* 309: 1577-1581 (2005).
Kalota et al., "2'-Deoxy-2'-fluoro-β-D-arabinonucleic Acid (2'F-ANA) Modified Oligonucleotides (ON) Effect Highly Efficient, and Persistent, Gene Silencing," *Nucleic Acids Res.* 34: 451-461 (2006).
Karginov et al., "A Biochemical Approach to Identifying MicroRNA Targets," *Proc. NaNatl.Acad. Sci. U.S.A.* 104: 19291-19296 (2007).
Kato et al., "MicroRNA-192 in Diabetic Kidney Glomeruli and Its Function in TGF-β-Induced Collagen Expression Via Inhibition of E-box Repressors," *Proc. Natl. Acad. Sci. USA* 104: 3432-3437 (2007).
Kiriakidou et al., "A Combined Computational-Experimental Approach Predicts Human MicroRNA Targets," *Genes Dev.* 18: 1165-1178 (2004).
Kraynack et al., "Small Interfering RNAs Containing Full 2'-*O*-Methylribonucleotide-Modified Sense Strands Display Argonaute2/eIF2C2-Dependent Activity," *RNA* 12: 163-176 (2006).
Kroschwitz (Ed.), Concise Encyclopedia of Polymer Science and Engineering, John Wiley & Sons, pp. 858-866, 1990.
Krutzfeldt et al., "Silencing of MicroRNA In Vivo with 'Antagomirs,'" *Nature* 438: 685-689 (2005).
Lai, "Micro RNAs are Complementary to 3' UTR Sequence Motifs that Mediate Negative Post-Transcriptional Regulation," *Nat. Genet.* 30: 363-364 (2002).
Lander, "The New Genomics: Global Views of Biology," *Science* 274: 536-539 (1996).
Lecellier et al., "A Cellular MicroRNA Mediates Antiviral Defense in Human Cells," *Science* 308: 557-560 (2005).
Lee et al., "The Tumor Suppressor microRNA *let-7* Represses the HMGA2 Oncogene," *Genes Dev.* 21: 1025-1030 (2007).
Lewis et al., "Efficient Delivery of siRNA for Inhibition of Gene Expression in Postnatal Mice," *Nat. Genet.* 32: 107-108 (2002).
Lewis et al., "Conserved Seed Pairing, Often Flanked by Adenosines, Indicates that Thousands of Human Genes are MicroRNA Targets," *Cell* 120: 15-20 (2005).
Lim et al., "The microRNAs of *Caenorhabditis elegans,*" *Genes Dev.* 17: 991-1008 (2003).
Lin et al. "siRNA-Mediated Off-Target Gene Silencing Triggered by a 7 nt Complementation," *Nucleic Acids Res.* 33: 4527-4535 (2005).
Lind et al., "Structural Characteristics of 2'-*O*-(2-methoxyethyl)-Modified Nucleic Acids from Molecular Dynamics Simulations," *Nucleic Acids Res.* 26: 3694-3699 (1998).
Lu et al., "MicroRNA Expression Profiles Classify Human Cancers," *Nature* 435: 834-838 (2005).
MacBeath et al., "Printing Proteins as Microarrays for High-Throughput Function Determination," *Science* 289: 1760-1763 (2000).
Makeyev et al., "The MicroRNA miR-124 Promotes Neuronal Differentiation by Triggering Brain-Specific Alternative Pre-mRNA Splicing," *Mol. Cell* 27: 435-448 (2007).

(56) References Cited

OTHER PUBLICATIONS

Martin et al., "Applications of RNA Interference in Mammal an Systems", *Annu. Rev. Genomics Hum. Genet.* 8: 81-108, Supplementary Materia (2 pages) (2007).
Martin et al., "The Human Angiotensin II Type 1 Receptor +1166 A/C Polymorphism Attenuates MicroRNA-155 Binding," *J. Biol. Chem.* 282: 24262-24269 (2007).
Martinez et al., "Single-Stranded Antisense siRNAs Guide Target RNA Cleavage in RNAi," *Cell* 110: 563-574 (2002).
McCaffrey et al., "RNA Interference in Adult Mice," *Nature* 418: 38-39 (2002).
McManus et al., "Gene Silencing Using MicroRNA Designed Hairpins," *RNA* 8: 842-850 (2002).
Megraw et al., "miRGen: A Database for the Study of Animal MicroRNA Genomic Organization and Function," *Nucleic Acids Res.* 35: D149-D155 (2007).
Meng et al., Involvement of Human Micro-RNA in Growth and Response to Chemotherapy in Human Cholangiocarcinoma Cell Lines, *Gastroenterol.* 130: 2113-2129 (2006).
Meng et al., MicroRNA-21 Regulates Expression of the PTEN Tumor Suppressor Gene in Human Hepatocellular Cancer, *Gastroenterol.* 133: 647-658 (2007).
Naito et al., "siDirect: Highly Effective, Target-Specific siRNA Design Software for Mammalian RNA Interference," *Nucleic Acids Res.* 32: W124-129 (2004).
Nielson et al., "Sequence-Selective Recognition of DNA by Strand Displacement with a Thymine-Substituted Polyamide," *Science* 254: 1497-1500 (1991).
Ørum et al., "Locked Nucleic Acids: A Promising Molecular Family for Gene-Function Analysis and Antisense Drug Development," *Curr. Opin. Mol. Ther.* 3: 239-243 (2001).
Ozen et al., "Widespread Deregulation of MicroRNA Expression in Human Prostate Cancer," *Oncogene* 27: 1788-1793 (2008).
Paddison et al., "Short Hairpin RNAs (shRNAs) Induce Sequence-Specific Silencing in Mammalian Cells," *Genes Dev.* 16: 948-958 (2002).
Parker et al., "Argonaute: A Scaffold for the Function of Short Regulatory RNAs," *Trends Biochem. Sci.* 31: 622-630 (2006).
Pasquinelli et al., "Conservation of the Sequence and Temporal Expression of *let-7* Heterochronic Regulatory RNA," *Nature* 408: 86-89 (2000).
Pekarsky et al., "Tcl1 Expression in Chronic Lymphocytic Leukemia is Regulated by *miR-29* and *miR-181*," *Cancer Res.* 66: 11590-11593 (2006).
Petersen et al., "LNA: a Versatile Tool for the Therapeutics and Genomics," *Trends Biotechnol.* 21: 74-81 (2003).
Prashar et al., "Analysis of Differential Gene Expression by Display of 3' End Restriction Fragments of cDNAs," *Proc. Natl. Acad. Sci. U.S.A.* 93: 659-663 (1996).
Ramaswamy et al., "Multiclass Cancer Diagnosis Using Tumor Gene Expression Signatures," *Proc. Natl. Acad. Sci. U.S.A.* 98: 15149-15154 (2001).
Robins et al., "Incorporating Structure to Predict MicroRNA Targets," *Proc. NaNatl.Acad. Sci. U.S.A.* 102: 4006-4009 (2005).
Rooij et al., "Control of Stress-Dependent Cardiac Growth and Gene Expression by a MicroRNA," *Science* 316: 575-579 (2007).
Rooij et al., "MicroRNAs: Powerful New Regulators of Heart Disease and Provocative Therapeutic Targets," *J. Clin. Invest.* 117: 2369-2376 (2007).
Rubinson et al., "A Lentivirus-Based System to Functionally Silence Genes in Primary Mammalian Cells, Stem Cells and Transgenic Mice by RNA Interference," *Nat. Genet.* 33: 401-406, Supplementary Material (1 page) (2003).
Sætrom et al., "Distance Constraints Between MicroRNA Target Sites Dictate Efficacy and Cooperativity," *Nucleic Acids Res.* 35: 2333-2342 (2007).
Sagliocco et al., "Identification of Proteins of the Yeast Protein Map Using Genetically Manipulated Strains and Peptide-Mass Fingerprinting," *Yeast* 12: 1519-1533 (1996).

Scaria et al., "Host-Virus Interaction: A New Role for MicroRNAs," *Retrovirology.* 3: 68 (2006).
Shevchenko et al., "Linking Genome and Proteome by Mass Spectrometry: Large-Scale Identification of Yeast Proteins From Two Dimensional Gels," *Proc. Natl. Acad. Sci. U.S.A.* 93: 14440-14445 (1996).
Soifer et al., "MicroRNAs in Disease and Potential Therapeutic Applications," *Mol. Ther.* 15: 2070-2079 (2007).
Song et al., "RNA Interference Targeting Fas Protects Mice from Fulminant Hepatitis," *Nat. Medicine* 9: 347-351 (2003).
Sonkoly et al., "MicroRNAs: Novel Regulators Involved in the Pathogenesis of Psoriasis?" *PloS One* 2: e610 (2007).
Sørensen et al., "Gene Silencing by Systemic Delivery of Synthetic siRNAs in Adult Mice," *J. Mol. Biol.* 327: 761-766 (2003).
Stark et al., "Identification of *Drosophila* MicroRNA Targets," *PLoS Biol.* 1: 397-409 (2003).
Stern-Ginossar et al., "Host Immune System Gene Targeting by a Viral miRNA," *Science* 317: 376-381, Supplementary Material (2007).
Sui et al., "A DNA Vector-Based RNAi Technology to Suppress Gene Expression in Mammalian Cells," *Proc. Natl. Acad. Sci. U.S.A.* 99: 5515-5520 (2002).
Sylvestre et al., "An E2F/miR-20a Autoregulatory Feedback Loop," *J. Biol. Chem.* 282: 2135-2143 (2007).
Takamizawa et al., "Reduced Expression of the *let-7* MicroRNAs in Human Lung Cancers in Association with Shortened Postoperative Survival," *Cancer Res.* 64: 3753-3756 (2004).
Tiscornia et al., "A General Method for Gene Knockdown in Mice by Using Lentiviral Vectors Expressing Small Interfering RNA," *Proc. Natl. Acad. Sci. U.S.A.* 100: 1844-1848 (2003).
Tiscornia et al., "Design and Cloning of Lentiviral Vectors Expressing Small Interfering RNAs," *Nat. Protocols* 1: 234-240 (2006).
Tolstrup et al., "OligoDesign: Optimal Design of LNA (Locked Nucleic Acid) Oligonucleotide Capture Probes for Gene Expression Profiling," *Nucl. Acids Res.* 31: 3758-3762 (2003).
Tsuchiya et al., "MicroRNA Regulates the Expression of Human Cytochrome P450 1B1," *Cancer Res.* 66: 9090-9098 (2006).
Van Aerschot et al., "Improved Hybridisation Potential of Oligonucleotides Comprising *O*-Methylated Anhydrohexitol Nucleoside Congeners," *Nucleic Acids Res.* 29: 4187-4194 (2001).
Vatolin et al., "A Novel Method to Detect Functional MicroRNA Targets," *J. Mol. Biol.* 358: 983- 996 (2006).
Velculescu et al., "Serial Analysis of Gene Expression," *Science* 270: 484-487 (1995).
Verbeure et al., "RNase H Mediated Cleavage of RNA by Cyclohexene Nucleic Acid (CeNA)," *Nucleic Acids Res.* 29: 4941-4947 (2001).
Weiler et al., "Anti-miRNA Oligonucleotides (AMOs): Ammunition to Target miRNAs Implicated in Human Disease?" *Gene Ther.* 13: 1-7 (2005).
Welch et al., "MicroRNA-34a Functions as a Potential Tumor Suppressor by Inducing Apoptosis in Neuroblastoma Cells," *Oncogene* 26: 5017-5022 (2007).
Wienholds et al., "MicroRNA Expression in Zebrafish Embryonic Development," *Science* 309: 310-311, S1-S34 (Supporting Online Material) (2005).
Wightman et al., "Posttanscriptional Regulation of the Heterochronic Gene *lin-14* by *lin-4* Mediates Temporal Pattern Formation in *C. elegans*," *Cell* 75: 855-862 (1993).
Xia et al., "siRNA-mediated Gene Silencing In Vitro and In Vivo," *Nat. Biotech.* 20: 1006-1010 (2002).
Xiao et al., "Novel Approaches for Gene-Specific Interference Via Manipulating Actions of MicroRNAs: Examination on the Pacemaker Channel Genes *HCN2* and *HCN4*," *J. Cell. Physiol.* 212: 285-292 (2007).
Xu et al., "MicroRNA (miRNA) Transcriptome of Mouse Retina and Identification of a Sensory Organ-specific miRNA Cluster," *J. Biol. Chem.* 282: 25053-25066 (2007).
Yi et al., "Morphogenesis in Skin is Governed by Discrete Sets of Differentially Expressed MicroRNAs," *Nat. Genet.* 38: 356-362 (2006).

(56) References Cited

OTHER PUBLICATIONS

Yuan et al., "siRNA Selection Server: An Automated siRNA Oligonucleotide Prediction Server," *Nucleic Acids Res.* 32: W130-W134 (2004).
Zhu et al., "Global Analysis of Protein Activities Using Proteome Chips," *Science* 293: 2101-2105 (2001).
Zhu et al., "MicroRNA-21 Targets the Tumor Suppressor Gene Tropomyosin 1 (TPM1)," *J. Biol. Chem.* 282: 14328-14336 (2007).
Adams et al., "Hindered Dialkylamino Nucleoside Phosphite Reagents in the Synthesis of Two DNA 51-Mers," *J Am. Chem. Soc.* 105: 661-663 (1983).
Allawi et al., "Quantitation of MicroRNAs using a Modified Invader Assay," *RNA* 10:1153-1161 (2004).
Ambros, "MicroRNAs: Tiny Regulators with Great Potential," *Cell* 107: 823-826 (2001).
Ambros, "A Uniform System for MicroRNA Annotation," *RNA* 9: 277-279 (2003).
Ambros et al., "MicroRNA Pathways in Flies and Worms: Growth, Death, Fat, Stress, and Timing," *Cell* 113: 673-676 (2003).
Ambros, "The Functions of Animal MicroRNAs," *Nature* 431: 350-355 (2004).
Aravin et al., "The Small RNA Profile During *Drosophila melanogaster* Development," *Dev. Cell* 5: 337-350 (2003).
Bains et al., "Cardiac Actin is the Major Actin Gene Product in Skeletal Muscle Cell Differentiation In Vitro," *Mol. Cell. Biol.* 4: 1449-1453 (1984).
Barad et al., "MicroRNA Expression Detected by Oligonucleotide Microarrays: System Establishment and Expression Profiling in Human Tissues," *Genome Res.* 14: 2486-2494 (2004).
Beaucage et al., "Deoxynucleoside Phosphoramidites—A New Class of Key Intermediates for Deoxypolynucleotide Synthesis," *Tetrahedron Lett.* 22: 1859-1862 (1981).
Benton et al., "Screening λgt Recombinant Clones by Hybridization to Single Plaques In Situ," *Science* 196: 180-182 (1977).
Boutla et al., "Developmental Defects by Antisense-Mediated Inactivation of Micro-RNAs 2 and 13 in *Drosophila* and the Identification of Putative Target Genes," *Nucleic Acids Res.* 31: 4973-4980 (2003).
Brennecke et al., "*Bantam* Encodes a Developmentally Regulated MicroRNA that Controls Cell Proliferation and Regulates the Proapoptotic Gene *hid* in *Drosophila*," *Cell* 113: 25-36 (2003).
Buckingham, "Skeletal Muscle Formation in Vertebrates," *Curr. Opin. Genet. Dev.* 11: 440-448 (2001).
Calin et al., "Frequent Deletions and Down-Regulation of Micro-RNA Genes miR15 and miR16 at 13q14 in Chronic Lymphocytic Leukemia," *Proc. Natl. Acad. Sci. U.S.A.* 99: 15524-15529 (2002).
Carrington et al., "Role of MicroRNAs in Plant and Animal Development," *Science* 301: 336-338 (2003).
Caruthers, "Chemical Synthesis of DNA and DNA Analogues," *Acc. Chem. Res.* 24: 278-284 (1991).
Chargé et al., "Cellular and Molecular Regulation of Muscle Regeneration," *Physiol. Rev.* 84: 209-238 (2004).
Chen et al., "Cloning of Novel Orphan Receptor (GCNF) Expressed during Germ Cell Development," *Mol. Endocrinol.* 8: 1434-1444 (1994).
Chen, "A MicroRNA as a Translational Repressor of APETALA2 in Arabidopsis Flower Development," *Science* 303: 2022-2025 (2004).
Chen et al., "MicroRNAs Modulate Hematopoietic Lineage Differentiation," *Science* 303: 83-86 (2004).
Cook, "Medicinal Chemistry of Antisense Oligonucleotides-Future Opportunities," *Anticancer Drug Des.* 6: 585-607 (1991).
Croft et al., "ISIS, the Intron Information System, Reveals the High Frequency of Alternative Splicing in the Human Genome," *Nat Genet.* 24: 340-341 (2000).
Demidov, "PNA and LNA Throw Light on DNA," *Trends Biotechnol.* 21: 4-7 (2003).
DeNardi et al., "Type 2X-Myosin Heavy Chain Is Coded by a Muscle Fiber Type-Specific and Developmentally Regulated Gene," *J. Cell Biol.* 123: 823-835 (1993).
Dinsmore et al., "Embyronic Stem Cells Differentiated in Vitro as a Novel Source of Cells for Transplantation," *Cell Transplant* 5: 131-143 (1996).
Doench et al., "siRNAs Can Function as miRNAs," *Genes Dev.* 17: 438-442 (2003).
Dostie et al., "Numerous MicroRNPs in Neuronal Cells containing a Novel MicroRNAs," *RNA* 9: 180-186, 631-632 (2003).
Englisch et al., "Chemically Modified Oligonucleotides as Probes and Inhibitors," *Angewandte Chemie, Int. Edition* 30: 613-629 (1991).
Finnegan et al., "The Small RNA World," *J. Cell. Sci.* 116: 4689-4693 (2003).
Fire et al., "Potent and Specific Genetic Interference by Double-Stranded RNA in Caenorhabditis elegans," *Nature* 391: 806-811 (1998).
Freier et al., "The Ups and Downs of Nucleic Acid Duplex Stability: Structure-Stability Studies on Chemically-Modified Dna:Rna Duplexes," *Nucleic Acids Res.* 25: 4429-4443 (1997).
Fuchtbauer et al., "MyoD and Myogenin Are Coexpressed in Regenerating Skeletal Muscle of the Mouse," *Dev. Dyn.* 193: 34-39 (1992).
Gall et al., "Formation and Detection of RNA-DNA Hybrid Molecules in Cytological Preparations," *Proc. Natl. Acad. Sci. U.S.A.* 63: 378-383 (1969).
Gott, "Expanding Genome Capacity Via RNA Editing," *C. R. Biologies* 326: 901-908 (2003).
Grad et al., "Computational and Experimental Identification of C. elegans MicroRNAs," *Mol. Cell* 11: 1253-1263 (2003).
Grishok et al., "Genes and Mechanisms Related to RNA Interference Regulate Expression of the Small Temporal RNAs that Control C. elegans Developmental Timing," *Cell* 106: 23-34 (2001).
Grunstein et al., "Colony Hybridization: A Method for the Isolation of Cloned DNAs that Contain a Specific Gene," *Proc. Natl. Acad. Sci. U.S.A.* 72: 3961-3965 (1975).
Hakansson et al., "The Adenine Derivative of α—L-LNA (α—-L-ribo Configured Locked Nucleic Acid): Synthesis and High Affinity Hybridization towards DNA, RNA, LNA and α—L-LNA Complementary Sequences," *Bioorg. Med. Chem. Lett.* 11: 935-938 (2001).
Hakansson et al., "Convenient Syntheses of 7-Hydroxy-1-(hydroxymethyl)-3-(thymin-1-yl)-2,5-dioxabicyclo[2.2.1]heptanes:α—L-Ribo- and α—L-Xylo-Configured LNA Nucleosides," *J. Org. Chem.* 65: 5161-5166 (2000).
Hake, "MicroRNAs: A Role in Plant Development," *Curr. Biol.* 13: R851-R852 (2003).
Hosaka et al., "α1-Syntrophin-Deficient Skeletal Muscle Exhibits Hypertrophy and Aberrant Formation of Neuromusclular Junctions during Regeneration," *J. Cell. Biol.* 158: 1097-1107 (2002.).
Houbaviy et al., "Embryonic Stem Cell-Specific MicroRNAs," *Dev. Cell* 5: 351-358 (2003).
Hummelke et al., "Germ Cell Nuclear Factor is a Transcriptional Repressor Essential for Embryonic Development," *Front. Biosci.* 6: D1186-D1191 (2001).
Hutvágner et al., "A MicroRNA in a Multiple-Turnover RNAi Enzyme Complex," *Science* 297: 2056-2060 (2002).
Hutvágner et al., "Sequence-Specific Inhibition of Small RNA Function," *PLoS Biol.* 2: 465-475 (2004).
John et al., "Human MicroRNA Targets," *PLoS Biol.* 2: e363 (18 pages) (2004).
John et al., "RNA-DNA Hybrids at the Cytological Level," *Nature* 223: 582-587 (1969).
Juarez et al., "MicroRNA-Mediated Repression of *Rolled Leaf1* Specifies Maize Leaf Polarity," *Nature* 428: 84-88 (2004).
Kampa et al., "Novel RNAs Identified from an In-Depth Analysis of the Transcriptome of Human Chromosomes 21 and 22," *Genome Res.* 14: 331-342 (2004).
Ke et al., "MicroRNAs: Key Participants in Gene Regulatory Networks," *Curr. Opin. Chem. Biol.* 7: 516-523 (2003).
Kidner et al., "Spatially Restricted MicroRNA Directs Leaf Polarity through ARGONAUTE1," *Nature* 428: 81-84 (2004).
Kole et al., "Antisense Effects in the Cell Nucleus: Modification of Splicing," *Curr. Opin. Ther.* 3: 229-234 (2001).
Koshkin et al., "LNA (Locked Nucleic Acids): Synthesis of the Adenine, Cytosine, Guanine, 5-Methylcytosine Thymine and Uracil

(56) References Cited

OTHER PUBLICATIONS

Bicyclonucleoside Monomers, Oligomerisation, and Unprecedented Nucleic Acid Recognition," *Tetrahedron* 54: 3607-3630 (1998).
Koshkin et al., "LNA (Locked Nucleic Acid): An RNA Mimic Forming Exceedingly Stable LNA: LNA Duplexes," *J. Am. Chem. Soc.* 120: 13252-13253 (1998).
Koshkin et al., "A Simplified and Efficient Route to 2'-O, 4'-C-Methylene-Linked Bicyclic Ribonucleosides (Locked Nucleic Acid)," *J. Org. Chem.* 66. 8504-8512 (2001).
Krek et al., "Combinatorial MicroRNA Target Predictions," *Nat. Genet.* 37: 495-500 (2005).
Krichevsky et al., "A MicroRNA Array Reveals Extensive Regulation of MicroRNAs during Brain Development," *RNA* 9: 1274-1281 (2003).
Kumar et al., "The First Analogues of LNA (Locked Nucleic Acids): Phosphorothioate-LNA and 2'-Thio-LNA," *Bioorg. Med. Chem. Lett.* 8: 2219-2222 (1998).
Kurreck et al., "Design of Antisense Oligonucleotides Stabilized by Locked Nucleic Acids," *Nucleic Acids Res.* 30: 1911-1918 (2002).
Lagos-Quintana et al., "Identification of Novel Genes Coding for Small Expressed RNAs," *Science* 294: 853-858 and Supplemental Material (2001).
Lagos-Quintana et al., "Identification of Tissue-Specific MicroRNAs from Mouse," *Curr. Biol.* 12: 735-739 (2002).
Lagos-Quintana et al., "New MicroRNAs from Mouse and Human," *RNA* 9: 175-179 (2003).
Lander et al., "Initial Sequencing and Analysis of the Human Genome," *Nature* 409: 860-921 and Supplemental Material (2001).
Lee et al., "An Extensive Class of Small RNAs in *Caenorhabditis elegans*," *Science* 294: 862-864 (2001).
Lee et al., "The *C. Elegans* Heterochronic Gene *lin-4* Encodes Small RNAs with Antisense Complementarity to *lin-14*," *Cell* 75: 843-854 (1993).
Lee et al., "MicroRNA Maturation: Stepwise Processing and Subcellular Localization," *EMBO J.* 21: 4663-4670 (2002).
Lewis et al., "Prediction of Mammalian MicroRNA Targets," *Cell* 115: 787-798 (2003).
Lim et al., "Microarray Analysis Shows that Some MicroRNAs Downregulate Large Numbers of Target mRNAs," *Nature* 433: 769-773 (2005).
Lipardi et al., "RNAi as Random Degradative PCR: siRNA Primers Convert mRNA into dsRNAs that are Degraded to Generate New siRNAs," *Cell* 107: 297-307 (2001).
Liu et al., "An Oligonucleotide Microchip for Genome-Wide MicroRNA Profiling in Human and Mouse Tissues," *Proc. Natl. Acad. Sci. U.S.A.* 101: 9740-9744 (2004).
Mallory et al., "MicroRNAs: Something Important Between the Genes," *Curr. Opin. Plant Biol.* 7: 120-125 (2004).
Mansfield et al., "MicroRNA-Responsive 'Sensor' Transgenes Uncover Hox-Like and other Developmentally Regulated Patterns of Vertebrate MicroRNA Expression," *Nat. Genet.* 36: 1079-1083 (2004).
Mattick, "Non-Coding RNAs: The Architects of Eukaryotic Complexity," *EMBO Reports* 2: 986-991 (2001).
Meister el al., "Sequence-Specific Inhibition of MicroRNA- and siRNA-Induced RNA Silencing," *RNA* 10: 544-550 (2004).
Michael et al., "Reduced Accumulation of Specific MicroRNAs in Colorectal Neoplasia," *Mol. Cancer Res.* 1: 882-891 (2003).
Miska et al., "Microarray Analysis of MicroRNA Expression in the Developing Mammalian Brain," *Genome Biol.* 5: R68 (13 pages) (2004).
Morita et al., "2'-O, 4'-C-Ethylene-Bridged Nucleic Acids (ENA): Highly Nuclease-Resistant and Thermodynamically Stable Oligonucleotids for Antisense Drug," *Bioorg. Med. Chem. Lett.* 12: 73-76 (2002).
Moss, "MicroRNAs: Hidden in the Genome," *Curr. Biol.* 12: R138-R140 (2002).
Naguibneva et al., "An LNA-Based Loss-of-Function Assay for Micro-RNAs," *Biomed. Pharmacother.* 60: 633-638 (2006).
Nelson et al., "MiRNP:mRNA Association in Polyribosomes in a Human Nueronal Cell Line," *RNA* 10: 387-394 (2004).
Nelson et al., "The MicroRNA World: Small is Mighty," *Trends Biochem. Sci.* 28: 534-540 (2003).
Nykanen et al., "ATP Requirements and Small Interfering RNA Structure in the RNA Interference Pathway," *Cell* 107: 309-321 (2001).
Okazaki et al., "Analysis of the Mouse Transcriptome Based on Functional Annotation of 60,770 Full-Length cDNAs," *Nature* 420: 563-573 (2002).
Olsen et al., "The lin-4 Regulatory RNA Controls Developmental Timing in *Caenorhabditis elegans* by Blocking LIN-14 Protein Synthesis after the Initiation of Translation," *Dev. Biol.* 216: 671-680 (1999).
Patterson et al., "Hoxa11 and Hoxd11 Regulate Branching Morphogenesis of the Ureteric Bud in the Developing Kidney," *Development* 128: 2153-2161 (2001).
Paushkin et al., "The SMN Complex, an Assemblyosome of Ribonucleoproteins," *Curr. Opin. Cell Biol.* 14: 305-312 (2002).
Pfundheller et al., "Evaluation of Oligonucleotides Containing Two Novel 2'-O-Methyl Modified Nucleotide Monomers: A 3'-C-Allyl and a 2'-O, 3'-C-Linked Bicyclic Derivative," *Nucleosides Nucleotides* 18: 2017-2030 (1999).
Pillai et al., "Inhibition of Translational Initiation by Let-7 MicroRNA in Human Cells," *Science* 309: 1573-1576 (2005).
Polesskaya et al., "Wnt Signaling Induces the Myogenic Specification of Resident CD45+ Adult Stem Cells during Muscle Regeneration," *Cell* 113: 841-852 (2003).
Poy et al., "A Pancreatic Islet-Specific MicroRNA Regulates Insulin Secretion," *Nature* 432: 226-230 (2004).
Rehmsmeier et al., "Fast and Effective Prediction of MicroRNA/Target Duplexes," *RNA* 10: 1507-1517 (2004).
Reinhart et al., "MicroRNAs in Plants," *Genes Dev.* 16: 1616-1626, 2313 (2002).
Reinhart et al., "The 21-Nucleotide *let-7* RNA Regulates Developmental Timing in *Caenorhabditis elegans*," *Nature* 403: 901-906 (2000).
Sachidanandam et al., "A Map of Human Genome Sequence Variation Containing 1.42 Million Single Nucleotide Polymorphisms," *Nature* 409: 928-933 (2001).
Sanghvi, "Chapter 15: Heterocyclic Base Modificationis in Nucleic Acids and Their Applications in Antisense Oligonucleotides," In Antisense Research and Application, S. T. Crooke and L. Lebleu (Eds.), CRC Press (1993).
Schmittgen et al., "A High-Throughput Method to Monitor the Expression of microRNA Precursors," *Nucleic Acids Res.* 32: e43 (10 pages) (2004).
Schramke et al., "Hairpin RNAs and Retrotransposon LTRs Effect RNA and Chromatin-Based Gene Silencing," *Science* 301: 1069-1074 (2003).
Seale et al., "Adult Stem Cell Specification by Wnt Signaling in Muscle Regeneration," *Cell Cycle* 2: 418-419 (2003).
Seitz et al., "Imprinted microRNA Genes Transcribed Antisense to a Reciprocally Imprinted Retrotransposon-like Gene," *Nat. Genet.* 34: 261-262 (2003).
Sempere et al., "Expression Profiling of Mammalian microRNAs Uncovers a Subset of Brain-Expressed microRNAs with Possible Roles in Murine and Human Neuronal Differentiation," *Genome Biol.* 5: R13 (11 pages) (2004).
Sinha et al., "β-Cyanoethyl N,N-Dialkylamino/N-Morpholinomonochloro Phosphoamidites, New Phosphitylating Agents Facilitating Ease of Deprotection and Work-Up of Synthesized Oligonucleotides," *Tetrahedron Lett.* 24: 5843-5846 (1983).
Small et al., "Homeotic Transformations and Limb Defects in *Hox A11* Mutant Mice," *Genes Dev.* 7: 2318-2328 (1993).
Taghon et al., "Homeobox Gene Expression Profile in Human Hemaopoietic Multipotent Stem Cells and T-Cell Progenitors: Implications for Human T-Cell Development," *Leukemia* 17: 1157-1163 (2003).
Takahashi et al., "Expression Profiles of 39 HOX Genes in Normal Human Adult Organs and Anaplastic Thyroid Cancer Cell Lines by Quantitative Real-Time RT-PCR System," *Exp. Cell Res.* 293: 144-153 (2004).

(56) References Cited

OTHER PUBLICATIONS

Thomson et al., "A Custom Microarray Platform for Analysis of MicroRNA Gene Expression," *Nat. Methods* 1: 1-7 (2004).
Valoczi et al., "Sensitive and Specific Detection of MicroRNAs by Northern Blot Analysis using LNA-Modified Oligonucleotide Probes," *Nucleic Acids Res.* 32:e175 (7 pages) (2004).
Venter et al., "The Sequence of the Human Genome," *Science* 291: 1,1304-1351 (2001).
Verdel et al., "RNAi-Mediated Targeting of Heterochromatin by the RITS Complex," *Science* 303: 672-676 (2004).
Wahlestedt et al., "Potent and Nontoxic Antisense Oligonucleotides Containing Locked Nucleic Acids," *Proc. Nat. Acad. Sci. U.S.A.* 97: 5633-5638 (2000).
Wang et al., "Prediction and Identification of *Arabidopsis thaliana* microRNAs and the mRNA Targets," *Genome Biol.* 5: R65 (15 pp.) (2004).
Weiss et al., "Tribromoethanol (Avertin) as an Anaesthetic in Mice," *Lab Anim.* 33: 192-193 (1999).
Wong et al., "Most of the Human Genome is Transcribed," *Genome Res.* 11: 1975-1977 (2001).
Xu et al., "The *Drosophila* MircoRNA Mir-14 Suppresses Cell Death and Is Required for Normal Fat Metabolism," *Curr Biol.* 13: 790-795 (2003).
Yamamoto et al., "Coordinated Expression of *Hoxa-11* and *Hoxa-13* during Limb Muscle Patterning," *Development* 125: 1325-1335 (1998).
Yamamoto et al., "*Hoxa-11* and *Hoxa-13* are Involved in Repression of *MyoD* during Limb Muscle Development," *Dev. Growth Diff.* 45: 485-498 (2003).
Yekta et al., "MicroRNA-Directed Cleavage of *HOXB8* mRNA," *Science* 304: 594-596 and Supplemental Materials (2004).
Yelin et al., "Widespread Occurrence of Antisense Transcription in the Human Genome," *Nat. Biotechnol.* 21: 379-386 (2003).
Zeng et al., "Both Natural and Designed Micro RNAs Can Inhibit the Expression of Cognate mRNAs when Expressed in Human Cells," *Mol. Cell* 9: 1327-1333 (2002).
Zeng et al., "Sequence Requirements for Micro RNA Processing and Function in Human Cells," *RNA* 9: 112-123 (2003).
Zhang et al., "Human Dicer Preferentially Cleaves dsRNAs at their Termini without a Requirement for ATP," *EMBO J.* 21: 5875-5885 (2002).
Zhuang et al., "Helix-Loop-Helix Transcription Factors E12 and E47 Are Not Essential for Skeletal or Cardiac Myogenesis, Erythropoiesis, Chondrogenesis, or Neurogenesis," *Proc. Natl. Acad. Sci. U.S.A.* 89: 12132-12136 (1992).
Allawi et al., "Thermodynamics and NMR of Internal G•T Mismatches in DNA," *Biochemistry* 36: 10581-10594 (1997).
Beasley, "Mouse Neuroinvasive Phenotype of West Nile Virus Strains Varies Depending upon Virus Genotype," *Virology* 296: 17-23 (2002).
Beier et al., "Chemical Etiology of Nucleic Acid Structure: Comparing Pentopyranosly-(2'→ 4') Oligonucleotides with RNA," *Science* 283: 699-703 (1999).
Boudou et al., "Base Pairing of Anhydrohexitol Nucleosides with 2, 6-Diaminopurine, 5-Methylcytosine and Uracil as Base Moiety," *Nucleic Acids Res.* 27: 1450-1456 (1999).
Braasch et al., "Locked Nucleic Acid (LNA): Fine-Tuning the Recognition of DNA and RNA," *Chemistry and Biology* 8: 1-7 (2001).
Breslauer, "Extracting Thermodynamic Data from Equilibrium Melting Curves for Oligonucleotide Order-Disorder Transitions," *Meth. Enzymol.* 259: 221-242 (1995).
Bretner et al., "2-Thio Derivatives of dUrd and 5-Fluoro-dUrd and their 5'-Monophosphates: Synthesis, Interaction with Tumor Thymidylate Synthase, and in Vitro Antitumor Activity," *J. Med. Chem.* 36: 3611-3617 (1993).
Brown et al., "165 Nucleotides. Part XL. O2: 5'-CycloUridine and a Synthesis of isoCytidine," *J. Chem. Soc.* 868-872 (1957).

Causton et al., "Remodeling of Yeast Genome Expression in Response to Environmental Changes," *Mol. Biol. Cell* 12: 323-337 (2001).
Chang and Welch, "Iodination of 2'-Deoxycytidine and Related Substances," *J. Med. Chem.* 6: 428-430 (1963).
Chin, "On the Preparation and Utilization of Isolated and Purified Oligonucleotides," Katherine R. Everett Law Library, University of North Carolina, Chapel Hill, NC, Text Description of Contents (2002).
Christensen et al., "Stopped-Flow Kinetics of Locked Nucleic Acid (LNA)-Oligonucleotide Duplex Formation: Studies of LNA-DNA and DNA-DNA Interactions," *Biochem. J.* 354: 481-484 (2001).
Clark et al., "Genomewide Analysis of mRNA Processing in Yeast using Splicing-Specific Microarrays," *Science* 296: 907-910 (2002).
Cook, "Medicinal Chemistry of Antisenses Oligonucleotides—Future Opportunities," *Anti-Cancer Drug Design* 6: 585-607 (1991).
Crooke, "Therapeutic Applications of Oligonucleotides," *Annu. Rev. Pharmacol. Toxicol.* 32: 329-376 (1992).
Cusack et al., "Purines, Pyrimidines, and lmidzoles. Part XL.1 A New Synthesis of a D-Ribofuranosylamine Derivative and its use in the Synthesis of Pyrimidine and Imidazole Nucleosides," *J. Chem. Soc. Perkin* 116: 1720-1731 (1973).
Eschenmoser, "Chemical Etiology of Nucleic Acid Structure," *Science* 284: 2118-2124 (1999).
"Inaugural Splicing 2002 Concludes: Alternative Splicing May Make All the Difference in Discovering the Origin of Disease", IA Hope, Ed., C. Elegans—a practical approach, Oxford University Press, U.S.A. (1999) [http://www.exonhit.com/html/news/2002_09_25_splicing.htm].
Fathi et al., "Synthesis of 6-Substituted 2'-Deoxyguanosine Derivatives using Trifluoroacetic Anhydride in Pyridine," *Tetrahedron Letters* 31: 319-322 (1990).
Gao et al., "A Flexible Light-Directed DNA Chip Synthesis Gated by Deprotection using Solution Photogenerated Acids," *Nucleic Acid Research* 29: 4744-4750 (2001).
Gryaznov et al., "Stabilization of DNA:DNA and DNA:RNA Duplexes by Substitution of 2'-Deoxyadenosine with 2' Deoxy-2-Aminoadenosine," *Tetrahedron Letters* 35: 2489-2492 (1994).
Hakansson et al., "The Adenine Derivative of a-L-LNA (α-L-*ribo* Configured Locked Nucleic Acid): Synthesis and High-Affinity Hybridization Towards DNA, RNA, LNA, and α-L-LNA Complementary Sequences," *Bioorg. Med. Chem. Lett.* 11: 935-938 (2001).
Hakansson et al., "Convenient Syntheses of 7-Hydroxy-1-(hydroxymethyl)-3-(thymin-1yl)-2, 5-Dioxabicyclo[2.2.1]Heptanes: α-L-Ribo- and α-L-Xylo-Configured LNA Nucleosides," *J. Org. Chem.* 65: 5161-5166 (2000).
Hamamura et al., "Preparation of a Number of 5-Butylpyrimidine Nucleosides," *J. Med. Chem.* 15: 1061-1065 (1972).
Harrington et al., "Functional Domains within FEN-1 and RAD2 Define a Family of Structure-Specific Endonucleases: Implications for Nucleotide Excision Repair," *Genes Dev.* 8: 1344-1355 (1994).
Hill et al., "Genomic Analysis of Gene Expression in *C. elegans*," *Science* 290: 809-812 (2000).
Holstege et al., "Dissecting the Regulatory Circuitry of a Eukaryotic Genome," *Cell* 95: 717- 728 (1998).
Jeanpierre, "Human Satellites 2 and 3," *Annals of Genetics* 37: 163-171 (1994).
Kent et al., "Conservation, Regulation, Synteny, and Introns in a Large-Scale *C. briggsae-C. elegans* Genomic Alignment," *Genome Research* 10: 1115-1125 (2000).
Kent et al., "The Intronerator: Exploring Introns and Alternative Splicing in *Caenorhabditis elegans*," *Nucleic Acids Research* 28: 91-93 (2000).
Kokalj-Vokac et al., "Two-Color FISH Characterization of i (lq) and der(1;16) in Human Breast Cancer Cells," *Genes Chromosomes Cancer* 7: 8-14 (1993).
Kuimelis and Nambiar, "Synthesis of Oligodeoxynucleotides Containing 2-Thiopyrimidine Residues—a New Protection Scheme," *Nucleic Acid Res.* 22: 1429-1436 (1994).
Kumar et al., "The First Analogues of LNA (Locked Nucleic Acids): Phosphorothioate-LNA and 2'-Thio-LNA," *Bioorganic & Medicinal Chemistry Letters* 8: 2219-2222 (1998).

(56) References Cited

OTHER PUBLICATIONS

Kvaerno et al., "Investigation of Restricted Backbone Conformations as an Explanation for the Exceptional Thermal Stabilities of Duplexes Involving LNA (Locked Nucleic Acid): Synthesis and Evaluation of Abasic LNA," *Chem. Commun.* 657-658 (1999).
Kvaerno et al., "Synthesis of Abasic Locked Nucleic Acid and Two seco-LNA Derivatives and Evaluation of their Hybridization Properties Compared with their more Flexible DNA Counterparts," *J. Org. Chem.* 65: 5167-5176 (2000).
Kvaerno et al., "Novel Bicyclic Nucleoside Analogue (1 S, 5S, 6S)-6-Hydroxy-5-Hydroxymethyl-1-(uracil-1yl)-3, 8-Dioxabicyclo[3.2.1.] Octane: Synthesis and Incorporation into Oligodeoxynucleotides," *J. Org. Chem.* 66: 5498-5503 (2001).
Lakshman et al., "Facile Synthesis of O6-Alykyl-, O6-Aryl-, and Diaminopurine Nucleosides from 2'-Deoxyguanosine," *Org. Lett.* 2: 927-930 (2000).
Lykkesfeldt et al., "Human Breast Cancer Cell Lines Resistant to Pure Anti-Estrogens are Sensitive to Tamoxifen Treatment," *Int. J. Cancer* 61: 529-534 (1995).
Martin, "38. Ein Neuer Zugang zu 2'-O-Alkylribonucleosiden and Eigenschaften deren Oligonucleotide," *Helv. Chim. Acta* 78: 486-504 (1995).
Matray et al., "Selective and Stable DNA Base Pairing without Hydrogen Bonds," *J. Am. Chem. Soc.* 120: 6191-6192 (1998).
McBride et al., "Amidine Protecting Groups for Oligonucleotide Synthesis," *J. Am. Chem. Soc.* 108: 2040-2048 (1986).
McBride et al., "An Investigation of Several Deoxynucleoside Phosphoramidites Useful for Synthesizing Deoxyoligonucleotides," *Tetrahedron Letters* 24: 245-248 (1983).
Mesmaeker et al., "Backbone Modifications in Oligonucleotides and Peptide Nucleic Acid Systems," *Current Opinion in Structural Biology* 5: 343-355 (1995).
Morgan et al., "A More Efficient and Specific Strategy in the Ablation of mRNA in *Xenopus laevis* Using Mixtures of Antisense Oligos," *Nucleic Acids Res.* 21: 4615-4620 (1993).
Murante et al., "The Calf 5' to 3'-Exonuclease is also an Endonuclease with Both Activities Dependent on Primers Annealed Upstream of the Point of Cleavage," *J. Biol. Chem.* 269: 1191-1196 (1994).
Mutch et al., "Microarray Data Analysis: A Practical Approach for Selecting Differentially Expressed Genes," *Genome Biology* 2: preprint 0009.1-0009.29 (2001).
Nielsen et al., "Synthesis of 2'-O,3-C-linked Bicyclic Nucleosides and Bicyclic Oligonucleotides," *J. Chem Soc. Perkin Trans.* 1: 3423-3433 (1997).
Nielsen et al., "Solution Structure of an LNA Hybridized to DNA: NMR Study of the d(CT(L)GCT(L)T(L)CT(L)GC):d(GCAGAAGCAG) Duplex Containing Four Locked Nucleotides," *Bioconjug. Chem.* 11: 228-238 (2000).
Newton, C.R. and Graham, A., Ed., PCR, 2nd edition, Springer Verlag, New York, p. 24 (1997).
Obika et al., "Stability and Structural Features of the Duplexes Containing Nucleoside Analogues with a Fixed N-Type Conformation, 2'-O,4'-C-Methyleneribonucleosides," *Tetrahedron Letters* 39: 5401-5404 (1998).
Obika et al., "Synthesis of 2'-O,4'-C-Methyleneuridine and -Cytidine. Novel Bicyclic Nucleosides Having a Fixed C3 -endo Sugar Puckering," *Tetrahedron Letters* 38: 8735-8738 (1997).
Obika et al., "Synthesis of Conformationally Locked C-Nucleosides Having a 2, 5-Dioxabicyclo[2.2.1] Heptane Ring System," *Tetrahedron Letters* 41: 215-219 (2000).
Obika et al., "Triplex Formation by an Oligonucleotide Containing Conformationally Locked C-Nucleoside, 5-(2-O, 4-C-Methylene—β-D-Ribofuranosyl) Oxazole," *Tetrahedron Letters* 41: 221-224 (2000).
Pedersen et al., "Preparation of LNA Phosphoramidites," *Synthesis* 2002: 802-808 (2002).

Rajur et al., "The Synthesis of Oligodeoxynucleotides Containing 2-Thiothymine and 5-Methyl-4-Pyrimidinone Base Analogues," *Tetrahedron* 33: 6081-6084 (1992).
Saladino et al., "Transformations of Thiopyrimidine and Thiopurine Nucleosides Following Oxidation with Dimethydioxirane," *Tetrahedron Letters* 52: 6759-6780 (1996).
Samuel, "Host Genetic Variability and West Nile Virus Susceptibility," *Proc. Natl. Acad. Sci. U.S.A.* 99: 11555-11557 (2002).
SantaLucia, "A Unified View of Polymer, Dumbbell, and Oligonucleotide DNA Nearest-Neighbor Thermodynamics," *Proc. Natl. Acad. Sci. U.S.A.* 95: 1460-1465 (1998).
Shaw and Warrener, "32. Purines, Pyrimidines, and Glyoxalines. Part VII. New Sythesis of 2-Thiouracils and 2-Thiothymines," *J. Chem. Soc.* 153-156 (1958).
Silahtaroglu et al., "Not Para-, Not Peri-, But Centric Inversion of Chromosome 12," *J. Med. Genet.* 35: 682-684 (1998).
Singer et al., "*Escherichia Coli* Polymerase I Can Use O2-Methyldeoxythymidine or O4-Methyldeoxythymidine in Place of Deoxythymidine in Primed Poly(dA-dT)•Poly(dA-dT) Synthesis, *Proc. Natl. Acad. Sci. U.S.A.* 80: 4884-4888 (1983).
Singh et al., "LNA (Locked Nucleic Acids): Synthesis and High-Affinity Nucleic Acid Recognition," *Chem. Commun.* 455-456 (1998).
Singh et al., "Synthesis of Novel Bicyclo [2.2.1] Ribonucleosides: 2'-Amino- and 2'-Thio-LNA Monomeric Nucleosides," *J. Org. Chem.* 63: 6078-6079 (1998).
Sinha et al., "Polymer Support Oligonucleotide Synthesis XVIII1.2: Use of β Cyanoethyl-N, N-Dialkylamino-N-Morpholino Phosphoramidite of Deoxynucleosides for the Synthesis of DNA Fragments Simplifying Deprotection and Isolation of the Final Product," *Nucleic Acids Res.* 12: 4539-4557 (1984).
Sinha et al., "β Cyanoethyl N , N-Dialkylamino/N-Morpholinomonochloro Phosphoamidites, New Phosphitylating Agents Facilitating Ease of Deprotection and Work-Up of Synthesized Oligonucleotides," *Tetrahedron Letters* 24: 5843-5846 (1983).
Sonogashira et al., "A Convenient Synthesis of Acetylenes: Cataytic Substitutions of Acetylenic Hydrogen with Bromoalkenes, Iodoarenes, and Bromopyridines," *Tetrahedron Letters* 50: 4467-4470 (1975).
Tagarro et al., "Chromosomal Localization of Human Satellites 2 and 3 by a Fish Method using Oligonucleotides as Probes," *Human Genet.* 93: 383-388 (1994).
Tostensen et al., "Prediction of Melting Temperature for LNA (Locked Nucleic Acid) Modified Oligonucleotides," Bioinformatics 2002, Bergen, Norway, (Apr. 4-7, 2002). Poster.
Tostensen et al., "RNA Folding Transitions and Cooperativity," *J. Phys. Chem B.* 105: 1618-1630 (2001).
Uhlmann and Peyman, "Antisense Oligonucleotides: A New Theraputic Principle," *Chemical Reviews* 90: 543-584 (1990).
Van't Veer et al., "Gene Expression Profiling Predicts Clinical Outcome of Breast Cancer," *Nature* 415: 530-536 (2002).
Vorbruggen et al.,"Nucleoside Syntheses, XXII Nucleoside Synthesis with Trimethysilyl Triflate and Perchlorate as Catalysts," *Chem. Ber.* 114: 1234-1255 (1981).
Vorbruggen et al., "Nucleoside Syntheses, XXIII on the Mechanism of Nucleoside Synthesis," *Chem. Ber.* 114: 1256-1268 (1981).
Vorbruggen, "Some Recent Trends and Progress in Nucleoside Synthesis," *Acta Biochim. Pol.* 43: 25-36 (1996).
Woo et al., "G/C-Modified Oligodeoxynucleotides with Selective Complementarity: Synthesis and Hybridization Properties," *Nucleic Acids Res.* 24: 2470-2475 (1996).
Yamaguchi et al., "Synthesis of 4'-C-Ethynyl-β-D-*ribo*-Pentofuranosyl Pyrimidines," *Biosci. Biotechnol. Biochem.*, 63: 736-742 (1999).
Yeakley et al., "Profiling Alternative Splicing on Fiber-Optic Arrays," *Nature Biotechnology* 20: 353-358 (2002).
Zamecnik et al., "Inhibition of Rous Sarcoma Virus Replication and Cell Transformation by a Specific Oligodeoxynucleotide," *Proc. Natl. Acad. Sci. U.S.A.* 75: 280-284 (1978).
Rozen et al., "Primer3 on the WWW for General Users and for Biological Programmers," *Methods Mol. Biol.* 132: 365-386 (2000).
Deutsch and Long, "Intron-exon structures of eukaryotic model organisms," *Nucleic Acids Res.* 27: 3219-3228 (1999).

(56) References Cited

OTHER PUBLICATIONS

Hawkins, "A survey on intron and exon lengths," *Nucleic Acids Res.* 16: 9893-908 (1988).
Kornberg, "Chapter 14: Inhibitors of Replication DNA," *Replication 2nd Ed. University Science Books*, p. 450 (2005).
Lohse et al., "Double duplex invasion by peptide nucleic acid: a general principle for sequence-specific targeting of double-stranded DNA," *Proc. Natl. Acad. Sci. USA*. 96: 11804-11808 (1999).
"Nucleobase" http://en.wikipedia.org/wiki/Nucleobase.
Russell et al., "Extremely short 20-33 nucleotide introns are the standard length in Paramecium tetraurelia," *Nucleic Acids Res.* 22: 1221-1225 (1994).
Sakharkar et al., "Distributions of exons and introns in the human genome," *In Silico Biol.* 4: 387-393 (2004).
Suga et al., "Detection of intronlike sequences in the small subunit rDNA 3' region of Fusarium solani," Abstract only, *Mycological Res.* 104: 782-787 (2000).
Sun and Lee, "Stability of DNA Duplexes Containing Hypoxanthine (Inosine): Gas Versus Solution Phase and Biological Implications," *J Org Chem.* 75: 1848-1854 (2010).
Wendel et al., "Intron size and genome size in plants," *Mol Biol Evol.* 19: 2346-2352 (2002).
Taneja, "Foci of trinucleotide repeat transcripts in nuclei of myotonic dystrophy cells and tissues," *The Journal of Cell Biology*, 128: 995-1002 (1995).
Femino et. al., "Visualization of single RNA transcripts in situ," *Science*, 280: 585-590 (1998).
Chiang et al., "Filamin isogene expression during mouse myogenesis," *Developmental Dynamics*, 217: 99-108 (2000).
Steemers et al., "Screening unlabeled DNA targets with randomly ordered fiber-optic gene arrays," *Nat. Biotech.*, 18: 91-94 (2000).
Venkatesan et al., "Novel Phosphoramidite builfing blocks in synthesis and applications toward modified oligonucleotides," *Current Medical Chemistry*, 10: 1973-1991 (2003).
Pfeffer et al., "Cloning of small RNA molecules," in *Current Protocols in Molecular Biology*, 4: 26.4.1-26.4.18 (2003).
Raymond et al., "Simple, Quantitative Primer-Extension PCR Assay for Direct Monitoring of MicroRNAs and Short-Interfering RNAs," *RNA* 11: 1737-1744 (2005).
Brownie et al., "The elimination of primer-dimer accumulation in PCR." *Nucl. Acids Res.*, 25: 3235-3241 (1997).
Johnson et al., "Locked nucleic acid (LNA) single nucleotide polymorphism (SNP) genotype analysis and validation using real-time PCR," *Nucleic Acids Res.* 32: 1-9 (2004).
Latorra et al., "Enhanced allele-specific PCR discrimination in SNP genotyping using 3' locked nucleic acid (LNA) primers," *Hum Mutat.* 22: 79-85 (2003).
Latorra et al., "Design considerations and effects of LNA in PCR primers," *Mol Cell Probes.* 17: 253-259 (2003).
Lau et al. ."An abundant class of tiny RNAs with probable regulatory roles in Caenorhabditis elegans." *Science* 294: 858-862 (2001).
Lau et al., Supplementary Material (online), Oct. 26, 2001 (retrieved Nov. 7, 2008 from http://www.sciencemag.org/feature/data/lau1065062_SupMat.htm) (6 pages).

Echeverri et al., "Minimizing the risk of reporting false positives in large-scale RNAi screens.", *Nat Methods* 3: 777-779 (2006).
Croft et al., "ISIS, the Intron Information System, Reveals the High Frequency of Alternative Splicing in the Human Genome," Nature Genetics 24:340-341 (2000).
Barone et al., "Photolithographic synthesis of high-density oligonucleotide probe arrays," Nucleosides, Nucleotides & Nucleic Acids, 525-531, 2001.
Hacia et al., "Enhanced high density oligonucleotide array-based sequence analysis using modified nucleoside triphosphates," Nucleic Acids Res. vol. 26, No. 21, 4975-4982, 1998.
Darnell et al., "MicroRNA expression during Chick embryo development," *Developmental Dynamics* 235:3156-3165 (2006).
International Search Report for International Application No. PCT/DK03/00715, mailed Jul. 19, 2004 (5 pages).
Jacobsen et al., "Genotyping of the apolipoprotein B R3500Q mutation using immobilized locked nucleic acid capture probes," *Clin Chem.* 48:657-660 and Supplemental Figures (2 pages) (2002).
Kloosterman et al., "In situ detection of miRNAs in animal embryos using Lna-modified oligonucleotide probes," *Nature Methods* 3:27-29 and Supplemental Figures (1 page) (2006).
Ørum et al., "Detection of the factor V leiden mutation by direct allele-specific hybridization of PCR amplicons to photoimmobilized locked nucleic acids," *Clin Chem.* 45:1898-1905 (1999).
Plasterk, "MicroRNA involvment in embryo development," <http://www.exiqon.com/ls/Pages?Ronald-Plasterk.aspx>, retrieved May 27, 2013 (1 page).
Varkonyi-Gasic et al., "Protocol: a highly sensitive RT-PCR method for detection and quantification of microRNAs," *Plant Methods*. 3:1-12 (2007).
Roche Applied Science, "RealTime ready Universal ProbeLibrary: Redefining and revolutionizing real-time qPCR assays," Roche Diagnostics GmbH. 1-32 (2009).
Life Technologies. Manuals & Protocols, "S1 Nuclease," <https://www.lifetechnologies.com/search/support/supportSearchAction.action;hubblesession>, published on Mar. 7, 2001. Retreived on May 5, 2014. (4 pages).
Echwald et al., "LNA: Adding new functionality to PCR," *PCR Technology: Current innovations, Third Edition*. Tania Nolan, Stephen A. Bustin, 34 pages (2013).
Mouritzen et al., "ProbeLibrary: A new method for faster design and execution of quantitative real-time PCR," Nature Methods. 2(4):313-6 (2005).
Wenzel et al., "Library of Prefabricated Locked Nucleic Acid Hydrolysis Probes Facilitates Rapid Development of Reverse-Transcription Quantitative Real-Time PCR Assays for Detection of Novel Influenza A/H1N1/09 Virus," Clin Chem. 55(12):2218-2222 (2009).
Langer et al., "Enzymatic synthesis of biotin-labeled polynucleotides: novel nucleic acid affinity probes," Proc Natl Acad Sci U.S.A. 78(11):6633-7 (1981).
Ma et al., "Synthesis and evaluation of 9-O-substituted berberine derivatives containing azaaromatic terminal group as highly selective telomeric G-quadruplex stabilizing ligands," Bioorg Med Chem Lett. 19(13):3414-7 (2009).
Wetmur, "DNA probes: applications of the principles of nucleic acid hybridization," Crit Rev Biochem Mol Biol. 26(3-4):227-59 (1991).

\* cited by examiner

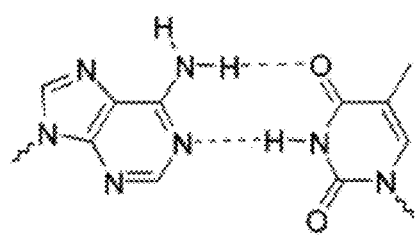 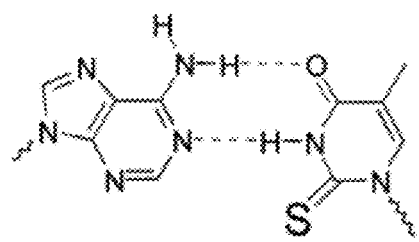
A - T    A - ²ˢT
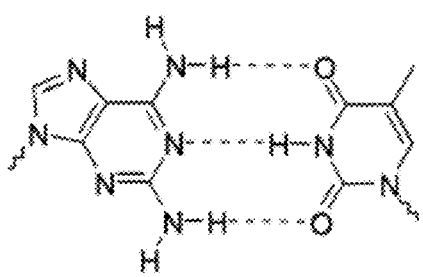 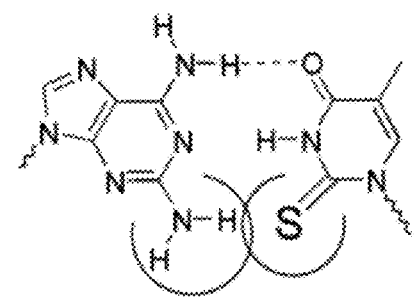
D - T    D - ²ˢT
Fig. 2

Fig. 4   A 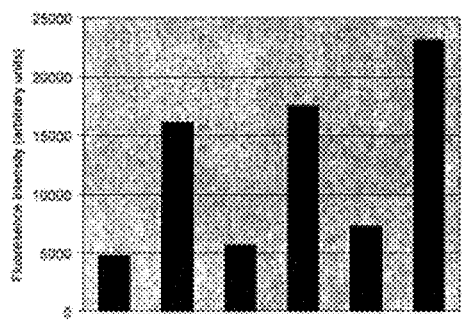   B 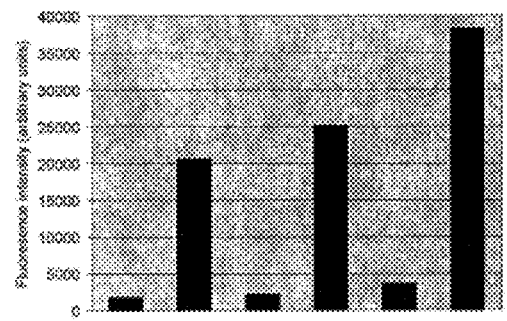
Fig. 5   A 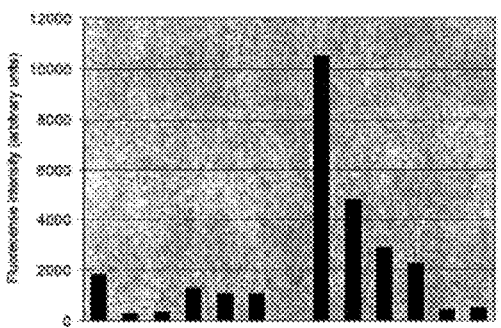   B 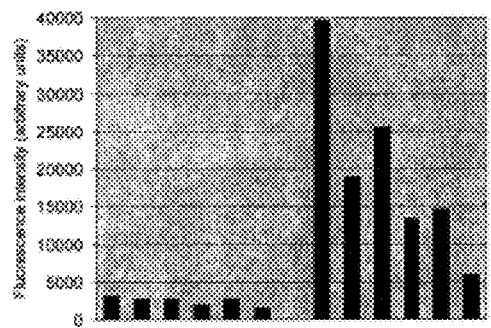

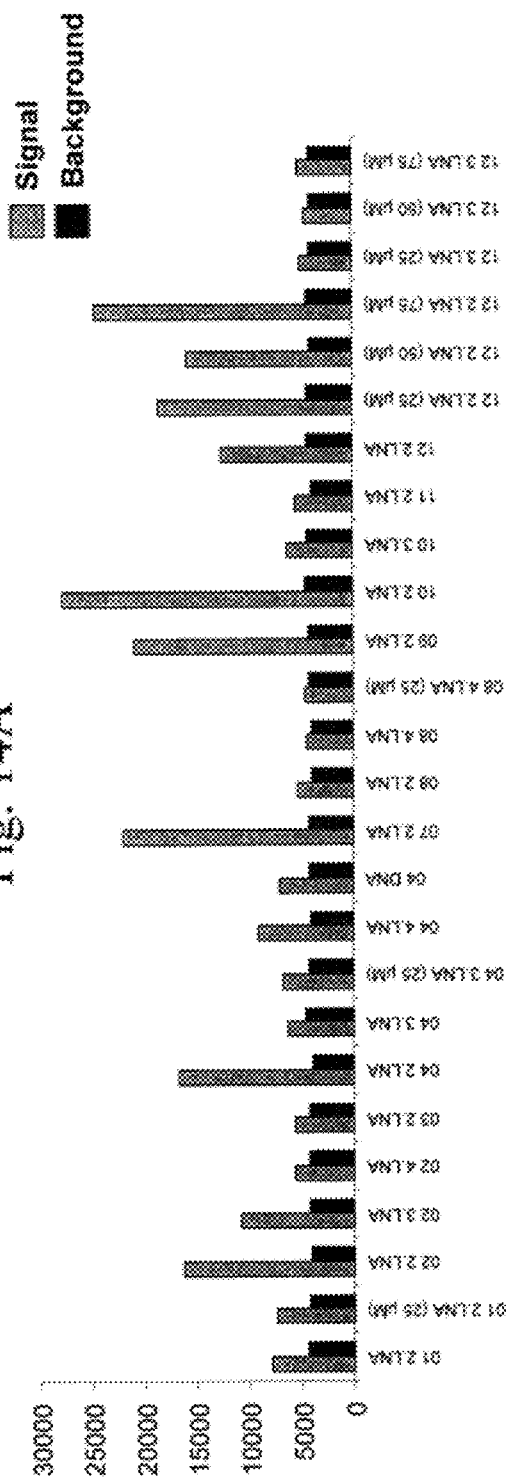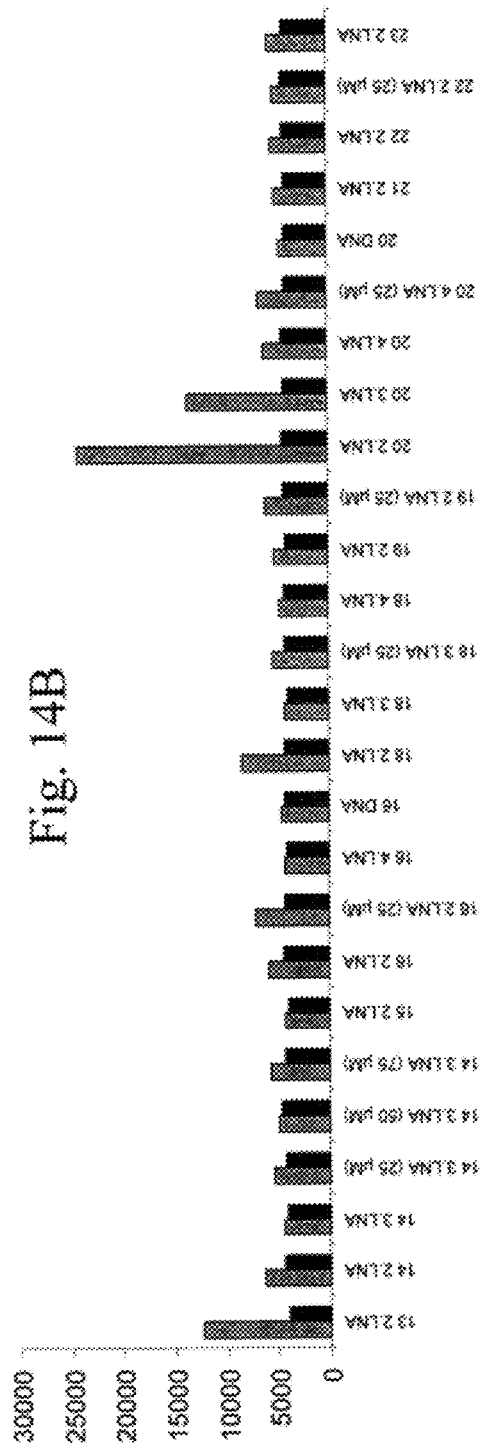

Fig. 17

| EQ No | Oligo Name | Sequence |
|---|---|---|
| 8253 | Menkes.02 5ONH2C6-DNA | tctgttgagggtatgacttgcaattccgtgtttggaccattgagcagca |
| 8254 | Menkes.02 5ONH2C6-4.LNA | TctgTtgaGggtAtgamCttgmCaatTccaGtgtTtggAccaTtgaGcagmCa |
| 8255 | Menkes.02 5ONH2C6-3.LNA | TctGttGagGgtAtgActTgcAatTccTgtGttTggAccAttGagmCagmCa |
| 8256 | Menkes.02 5ONH2C6-2.LNA | TcTgTtGaGgGtAtGamCtTgmCaAtTcmCtGtGtTGgAcmCaTtGaGcAgmCa |
| | | |
| 8258 | Menkes.04 5ONH2C6-DNA | agaaaagcaatagaggctgtatcacggaggctatatagagttagtatcac |
| 8259 | Menkes.04 5ONH2C6-4.LNA | AgaaAagcAataGaggmCtgtAtcamCcggGgctAtatAgagTtagTatcAc |
| 8260 | Menkes.04 5ONH2C6-3.LNA | AgaAaaGcaAtaGagGctGtaTcamCcgGggmCtaTatAgaGttAgtAtcAc |
| 8261 | Menkes.04 5ONH2C6-2.LNA | AgAaAaGcAaTaGaGgmCtGtAtmCamCcGgGgmCtAtAtAgAgTtAgTaTcAc |
| | | |
| 8263 | Menkes.06 5ONH2C6-DNA | gctgtatacaaccccccaatgatagcagagttcatccgagaacttggatt |
| 8264 | Menkes.06 5ONH2C6-4.LNA | GctgTtatAcaamCccmCaatGataGcagAgttmCatcmCgagAactTggaTt |
| 8265 | Menkes.06 5ONH2C6-3.LNA | GctGttAtamCaamCccmCcaAtgAtaGcaGagTtcAtcmCgaGaacCttGgaTt |
| 8266 | Menkes.06 5ONH2C6-2.LNA | GcTgTtAtAcAamCcmCcmCaAtGaTaGcAgAgTtmCaTcmCgAgAamCtTgGaTt |
| | | |
| 8268 | Menkes.08 5ONH2C6-DNA | tcttggtcaagaaggatcggtcagcaagtcactagatcataaacgaga |
| 8269 | Menkes.08 5ONH2C6-4.LNA | TctTggtmCaagAaggAtcgGtcaGcaaGtcamCttaGatcAtaaAcgaGa |
| 8270 | Menkes.08 5ONH2C6-3.LNA | TctTgGtcAagAagGatmCggTcaGcaAgtmCacTtaGatmCatAaamCgaGa |
| 8271 | Menkes.08 5ONH2C6-2.LNA | TcTtTgGtmCaAgAaGgAtmCgGtmCaGcAaGtmCamCtTaGaTcAtAaAcGaGa |
| | | |
| 8273 | Menkes.10 5ONH2C6-DNA | ttataaagcactgaagcataagacagcaaaatggacgtactgattgtgc |
| 8274 | Menkes.10 5ONH2C6-4.LNA | TtatAaagmCactGaagmCataAgacAgcaAataTggamCgtamCtgaTtgtGc |
| 8275 | Menkes.10 5ONH2C6-3.LNA | TtaTaaaAgcActGaaGcaTaaGacAgcAaaTatGgamCgtActGatTgtGc |
| 8276 | Menkes.10 5ONH2C6-2.LNA | TtAtAaAgmCamCtGaaGmCaTaAgAcAgmCaAaTaTgGamCgTamCtGaTtGtGc |
| | | |
| 8278 | Menkes.12 5ONH2C6-DNA | aacaagtggatgtggaacttgtacaacgtggagatatcattaaagtagtt |
| 8279 | Menkes.12 5ONH2C6-4.LNA | AacaAgtgGatgTggaActtGtacAacgTggaGataTcatTaaaGtagTt |
| 8280 | Menkes.12 5ONH2C6-3.LNA | AacAagTggAtgTggAacTtgTacAacGtgGagAtaTcaTtaAagTagTt |
| 8281 | Menkes.12 5ONH2C6-2.LNA | AamCaAgTgGaTgTgGaAcTtGtAcAamCgTgGaGaTaTcAtTaAaGtAgTt |
| | | |
| 8283 | Menkes.14 5ONH2C6-DNA | ccattgccacccctcttggtatggattgtaattgaattctgaatttgaa |
| 8284 | Menkes.14 5ONH2C6-4.LNA | mCcatTgccAcccTcttGgtaTggaTtgtAattGgaaTtctGaatTtgAa |
| 8285 | Menkes.14 5ONH2C6-3.LNA | mCcaTtgmCcamCccTctTggTatGgaTtgTaaTtgGatTtcTgaAttTgAa |
| 8286 | Menkes.14 5ONH2C6-2.LNA | mCcAtTgmCcAcmCcCTcTtGgTaTgGaTtGtAaTtGgAtTtmCtGaAtTtgAa |
| | | |
| 8288 | Menkes.16 5ONH2C6-DNA | ggtatttgataagactggaaccatactcacggaacccagtggtgaatc |
| 8289 | Menkes.16 5ONH2C6-4.LNA | GgtaTttgAtaaGactGgaamCcatTactmCacgGaacmCccaGtggTgaaTc |
| 8290 | Menkes.16 5ONH2C6-3.LNA | GgtAttTgaTaaGacTggAacmCatTacTcamCggAacmCccAgtGgtGaaTc |
| 8291 | Menkes.16 5ONH2C6-2.LNA | GgTaTtTgAtAaGamCtGgAamCcAtTamCtmCamCgGaAcmCcmCaGtGgTgAaTc |

Fig. 17 (continued)

| SQ No | Oligo Name | Sequence |
|---|---|---|
| 8293 | Menkes.18 5ONH2C6-DNA | attggtaaccgggagtggatgatagaaatggtcttgtcattaataacga |
| 8294 | Menkes.18 5ONH2C6-4.LNA | AttgGtaamCcggGagtGgatGatAgaaAtggTcttGtcaTtaaTaacGa |
| 8295 | Menkes.18 5ONH2C6-3.LNA | AttGgtAacmCcggGagTggAtgAttAgaAatGgtmCttGtcAttAatAacGa |
| 8296 | Menkes.18 5ONH2C6-2.LNA | AtTgGtAamCcGgGaGtGgAtGaTtAgAaAtGgTcTtGtmCaTtAaTaAcGa |
| | | |
| 8298 | Menkes.20 5ONH3C6-DNA | tggcacaggcacagatgtagccattgaagcagctgatgtggtttgataa |
| 8299 | Menkes.20 5ONH2C6-4.LNA | TggcAcagGcacAgatGtagmCcatTgaaGcagmCtgaTgtgGttTgatAa |
| 8300 | Menkes.20 5ONH2C6-3.LNA | TggmCacAggmCacAgaTgtAgcmCatTgaAgcAgcTgaTgtGgtTtGatAa |
| 8301 | Menkes.20 5ONH2C6-2.LNA | TgGcAcAgGcAcAgAtGtAgmCcAtTgAaGcAgmCtGaTgTgGtTtTgAtAa |

| SQ No. | Oligo Name | Sequence |
|---|---|---|
| 10573 | Menkes.01 5ONH2C6-2.LNA | GtGamCtTcTcmCgAtTgTgTgAgmCtTtGtTgGaGcmCtGcGtAcGtGgAtTt |
| 10574 | Menkes.03 5ONH2C6-2.LNA | TtTtAamCtGamCamCcTtGtTtmCtGamCtGtTamCgGcGamCamCtGamCtTtGcmCa |
| 10575 | Menkes.05 5ONH2C6-2.LNA | mCaTamCaGgTcAcTgGcAtGamCtTgmCgmCtTcmCtGtGtAgmCaAamCaTtGaAc |
| 10576 | Menkes.07 5ONH2C6-2.LNA | TgAgGgGaAtGamCgTgTgmCcTcmCtGcGtAcAtAaAaTaGaGtmCtAgTcTc |
| 10577 | Menkes.09 5ONH2C6-2.LNA | TgTaTtmCcTgTaAtGgGgmCtGaTgAcAtAtAtGaTgGtTaTgGamCcAcmCa |
| 10578 | Menkes.11 5ONH2C6-2.LNA | AcAamCaGaGgmCtmCtTgmCaAaGtTaAtTtmCamCtAcAaGcTamCaGaAgmCaAc |
| 10579 | Menkes.13 5ONH2C6-2.LNA | TtmCcAtTaAcmCaGaAcGgGbmCamCtGcTtAtmCtGcGcAamCamCaTgTtGgAg |
| 10580 | Menkes.14 5ONH2C6-2.LNA | mCcAtTgmCcAcmCcTcTtCgTaTgGaTtGtAaTtGgAtTtmCtGaAtTtTgAa |
| 10581 | Menkes.15 5ONH2C6-2.LNA | GaAamCgAtAaTamCgAtTtGcTtTcmCaAgmCcTcTaTcAcAgTtmCtGtTgmCa |
| 10582 | Menkes.17 5ONH2C6-2.LNA | AtGaAcAgTcAtmCaAcTtmCgTcTtmCcAtGaTbAtTgAtGcmCcAgAtmCtmCa |
| 10583 | Menkes.19 5ONH2C6-2.LNA | GtTcTgAtGamCtGgAgAcAamCaGtAaAamCaGcTaGaTcTaTtGcTtmCtmCa |
| 10584 | Menkes.21 5ONH2C6-2.LNA | TgGcAaGtAtTgAcTtAtmCaAgAaAgAcAgTcAaGaGgAtTcGgAtAaAt |
| 10585 | Menkes.23 5ONH2C6-2.LNA | GcmCtmCtAtAaAcTcAcTamCtGtmCtGaTaAamCgmCamCcmCtAaAcAgTgTtGt |
| 10706 | Menkes.22 5ONH2C6-2.LNA | mCtGgAtGgGaTcTgmCaGcAaTgGcTgmCtTcAtmCtGtTtmCtGtAgTamCtTt |

Abstract

Gene expression profiling using oligo micro arrays has become a central technology in pharmacogenomics and systems biology. Sensitivity and specificity are key elements in the development of oligo probes for micro arrays. A high sensitivity can be achieved by using LNA (Locked Nucleic Acid) modified oligos spotted onto a polymer slide. A high specificity can be reached through optimal oligo design.

The OligoDesign system features LNA modified oligonucleotide secondary structure prediction, LNA spiked oligo melting temperature prediction, genome wide cross hybridization prediction, secondary structure prediction of the target and recognition and filtering of the target in the genome. These features are determined for each possible probe of the query gene and presented to an artificial neural network. The probes are hereafter ranked according to the neural network prediction and the top scoring probes are returned.
The OligoDesign tools can be used freely at http://lnatools.com/.

LNA
- A novel
DNA analog

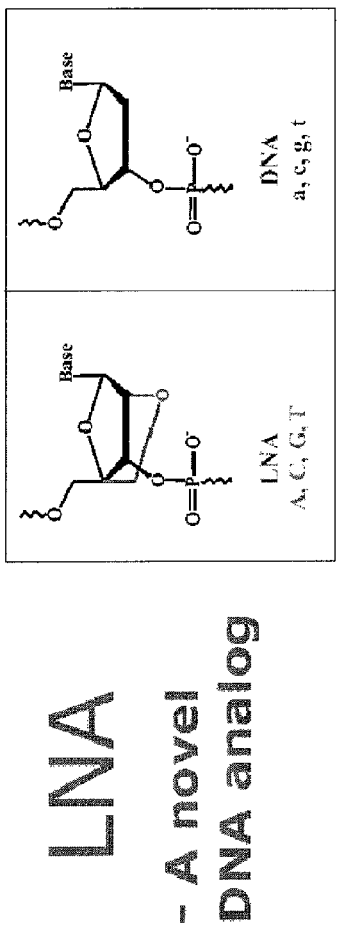

Locked Nucleic Acid is a novel chemical DNA analog, that can be substituted in DNA and RNA sequences. LNA obeys the Watson-Crick pairing rules, but have increased specificity and affinity in hybridization. Designing mixed LNA/DNA oligonucleotides facilitates a control of the melting properties of probes and primers, and an optimization of sequence discrimination at a given T.

Figure 19A

Cross hybridization

Possible cross hybridization to other genes can be detected from a blast search against the genome.

```
XxxXxxXxxXxxXxxXxxXxxXxx
    |||||||||||||||||||   18 matches
                          CHROMOSOME_III
    xxxxxxxxxxxxxxxxxxx    6 matches
                XXXXXX    CHROMOSOME_I
```

Secondary structure prediction

Based on Nussinov algorithm.
High scoring substructures detected only.
Scoring sheme derived from melting experiments with LNA modified oligonucleotides.

```
XxxXxxXxxXxxXxxXxxXxxXxxXxx
((((   )(.((    )).)))))
```

Secondary structure of an LNA spiked oligo.

Regions in the target gene with high secondary structure content are masked.

C. elegans heat shock Expression profile

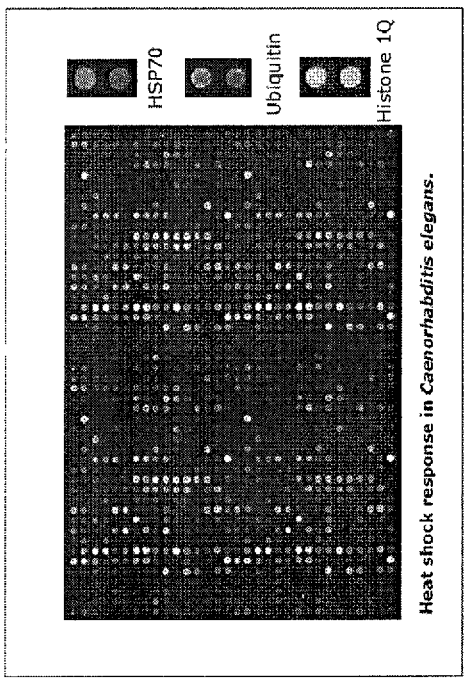

Heat shock response in *Caenorhabditis elegans*.

Key features:
- Comparative hybridization with Cy3 (standard) and Cy5 (heat treated) labelled cDNA from L4/adult *C. elegans* RNA
- Typical heat shock response for the HSP70 gene
- Expression of Ubiquitin is unaffected whereas expression of Histone 1Q is respressed

Conclusion

With the abillity to increase the melting temperature and affinity towards DNA it is possible to design LNA spiked oligos with balanced Tm for Micro Array Gene Expression Profiling.

The OligoDesign system selects unique oligos with high specificity towards the target, even Tm across the array slide and decreased secondary structure.

This ensures sensitivity and robustness and allows monitoration of gene expression otherwise not possible

Figure 19F

| Gene | Encoded protein | Functional categories | mRNA copies/cell | 1) Effect of heat shock 2) |
|---|---|---|---|---|
| ACT1 | Actin | cytoskeleton | 21 | none |
| GPD1 | Glycerol-3-phosphate dehydrogenase | glycerol metabolism | 7 | slightly induced |
| GUA1 | GMP synthase | purine metabolism | 8 | repressed |
| HAC1 | Transcription factor | unfolded protein response | 4 | none |
| HSP78 | Mitochondrial | protein folding | 1 | induced |
| RPP0 | 60S acidic ribosomal protein L10 | protein synthesis | 24 | none |
| SSA4 | Cytosolic HSP70 | ER and mitochondrial translocation | 1 | strongly induced |
| SWI5 | Transcription factor, regulates HO | cell cycle | 1 | slightly repressed |
| THI4 | Biosynthetic enzyme | thiamine biosynthesis | 1 | none |

Fig. 24

Constant Region      Variable region

Spliceforms:

Spliceform 1:

Spliceform 2:

or

Spliceform 1:

Spliceform 2:

OLIGONUCLEOTIDES USEFUL FOR DETECTING AND ANALYZING NUCLEIC ACIDS OF INTEREST

CROSS-REFERENCE TO RELATED APPLICATIONS

This application is a continuation of U.S. application Ser. No. 11/643,615, filed Dec. 21, 2006, which is a divisional of U.S. application Ser. No. 10/690,487, filed Oct. 21, 2003, which claims priority to U.S. Provisional Application No. 60/420,278, filed on Oct. 21, 2002 and Danish Application No. PA 2003 00752, filed on May 19, 2003, each of which is hereby incorporated by reference.

REFERENCE TO COMPUTER PROGRAM LISTING APPENDIX AND SEQUENCE LISTING

A computer program listing appendix with the files: 50287.007002_oligod.txt, 60 kB; 50287.007002_dyp.txt, 52 kB; 50287.007002_expression_array_param.txt, 3 kB; 50287.007002_tmprediction.txt, 3 kB; and 50287.007002_tmthermodynamic.txt, 47 kB, all created on Oct. 19, 2003, has been submitted via EFS-Web and is hereby incorporated by reference. The sequence listing, 50287.007003_SEQLIST.TXT, 203 kB, created on Dec. 20, 2006, is also submitted via EFS-Web and is hereby incorporated by reference.

BACKGROUND OF THE INVENTION

The invention relates to nucleic acids and methods for expression profiling of mRNAs, identifying and profiling of particular mRNA splice variants, and detecting mutations, deletions, or duplications of particular exons, e.g., alterations associated with a disease such as cancer, in a nucleic acid sample, e.g., a patient sample. The invention furthermore relates to methods for detecting nucleic acids by fluorescence in situ hybridization.

The field of the invention is oligonucleotides (e.g., oligonucleotide arrays) that are useful for detecting nucleic acids of interest and for detecting differences between nucleic acid samples (e.g, such as samples from a cancer patient and a healthy patient).

DNA chip technology utilizes miniaturized arrays of DNA molecules immobilized on solid surfaces for biochemical analyses. The power of DNA microarrays as experimental tools relies on the specific molecular recognition via complementary base-pairing, which makes them highly useful for massive parallel analyses. In the post-genomic era, microarray technology has thus become the method of choice for many hybridization-based assays, such as expression profiling, SNP detection, DNA re-sequencing, and genotyping on a genomic scale.

Expression microarrays are capable of profiling gene expression patterns of tens of thousands of genes in a single experiment. Hence, this technology provides a powerful tool for deciphering complex biological systems, and thereby greatly facilitates research in basic biology and living processes, as well as disease diagnostics, theranostics, and drug development. In a typical cell, the mRNAs are distributed in three frequency classes: (i) superprevalent (10-20% of the total mRNA mass); (ii) intermediate (40-45%); and (iii) low-abundant mRNAs (40-45%). It is therefore of utmost importance that the dynamic range and sensitivity of the expression arrays are optimal, especially when analyzing expression levels of messages or mRNA splice variants belonging to the low-abundant class.

The recent explosion of interest in DNA microarray technology has been sparked by two key innovations. The first was the use of non-porous solid support, such as glass or polymer as opposed to nylon or nitrocellulose filters, which has facilitated miniaturization and fluorescence-based detection. Roughly 20,000 cDNAs can be robotically spotted onto a microscope slide and hybridized with a double-labeled probe. The second was the development of methods for high-density spatial synthesis of oligonucleotides. The two key array technologies are outlined in the following.

Oligonucleotide Arrays

An efficient strategy for oligonucleotide microarray manufacturing involves DNA synthesis on solid surfaces using combinatorial chemistry. Most of the current technology is developed by Affymetrix and Rosetta Inpharmatics. Glass is currently preferred as the synthesis support because of its inert chemical properties and low level of intrinsic fluorescence as well as the ability to chemically derivatize the surface. Of the three approaches currently used to manufacture oligonucleotide arrays, the light-directed deprotection method is the most effective one in generating high density microchips. A single round of synthesis involves light-directed deprotection, followed by nucleotide coupling. Photolithographic masking is used to control the regions of the chip designated for illumination. Affymetrix uses a combination of photolithography and combinatorial chemistry to manufacture its GeneChip Arrays. Using technologies adapted from the semiconductor industry, GeneChip manufacturing begins with a 5-inch square quartz wafer. Initially the quartz is washed to ensure uniform hydroxylation across its surface. The wafer is placed in a bath of silane, which reacts with the hydroxyl groups of the quartz and forms a matrix of covalently linked molecules. The distance between these silane molecules determines the probes' packing density, allowing arrays to hold over 500,000 features within 1.28 square centimeters. The principal disadvantage of this method is that a significant amount of chip design work and cost is associated with the mask design. Once a set of masks has been made, a large number of chips can be produced at a reasonable cost. The current pricing of oligonucleotide arrays available from Affymetrix are in the range of 5-10 fold more expensive than cDNA microarrays.

DNA-DNA hybridization using oligonucleotide chips is clearly different from that of cDNA microarrays. Hybridizations involving oligos are much more sensitive to the GC content of individual heteroduplexes. In addition, single base mismatches have a pronounced effect on the hybridization reassociation of short oligos, and point mutations can thus be readily detected using oligo chips.

cDNA Microarrays cDNA microarrays containing large DNA segments such as cDNAs are generated by physically depositing small amounts of each DNA of interest onto known locations on glass surfaces. Two technologies for printing microarrays are (1) mechanical microspotting, and (2) ink-jetting. Mechanical microspotting has been extensively used at, e.g., Stanford University, and it utilizes pins or capillaries to deposit small quantities of DNA onto known addresses using motion control systems. Recent advances in microspotting technology using modern arraying robots allow for the preparation of 100 microarrays containing over 10,000 features in less than 12 hours. A DNA arrayer is relatively easy to set up, and the cost is usually low compared to on-chip oligoarrayers. cDNA microarrays are capable of profiling gene expression patterns of tens of thousands of genes in a single experiment. To compare the relative abundance of the arrayed gene sequences in two DNA or RNA samples, e.g., the total mRNA isolated from two different cell populations, the two samples are first labeled using two different fluorescent dyes such as Cy-3 and Cy-5. The labeled samples are mixed and hybridized to the clones on the array slide. After the hybridization, laser excitation of the incorporated, fluorescent target molecules yields an emission with a characteristic spectra, which is measured with a confocal laser scanner. The monochrome images from the scanner are imported to the software in which the images are pseudocolored and merged. Data from a single hybridization is viewed as a normalized ratio in which significant deviations from the ratio are indicative of either increased or decreased expression levels relative to the reference sample. Data from multiple experiments can be examined using any number of data mining tools.

Current Status of Array Technology

It has now become clear that cDNA microarrays, originally developed by Pat Brown and co-workers at the Stanford University, are sensitive, but may not be sufficiently specific with respect to, e.g., discrimination of homologous transcripts in gene families and alternatively spliced isoforms. On the other hand, the Affymetrix GeneChip system is specific, but may not be sensitive enough. This lack of sensitivity may explain why Affymetrix uses 16×26-mer perfect match capture probes together with 16×25-mer mismatch probes per transcript in its expression profiling chips resulting in enormous data sets in genome-wide arrays. Therefore, the functional genomics field is in the process of switching, as they run out of samples, from existing PCR-amplified cDNA fragment libraries for microarraying to custom longmer oligonucleotide arrays comprising transcript-specific oligonucleotide capture probes typically in the range of 30-mers to 80-mers, thus addressing both specificity and sensitivity.

Alternative Splicing

As the field of genomics research is shifting from the acquisition of genome sequences to high-throughput functional genomics, there is an increasing need to understand the dynamics within the genetic regulation as well as RNA and protein sequences in order to elucidate gene expression in all its complexity. A common feature for eukaryotic genes is that they are composed of protein-encoding exons and introns. Introns (intra-genic-regions) are non-coding DNA which interrupt the exons. Introns are characterized by being excised from the pre-mRNA molecule in RNA splicing, as the sequences on each side of the intron are spliced together. RNA splicing not only provides functional mRNA, but is also responsible for generating additional diversity. This phenomenon is called alternative splicing, which results in the production of different mRNAs from the same gene. The mRNAs that represent isoforms arising from a single gene can differ by the use of alternative exons or retention of an intron that disrupts two exons. This process often leads to different protein products that may have related or drastically different, even antagonistic, cellular functions. There is increasing evidence indicating that alternative splicing is very widespread (Croft et al. Nature Genetics, 2000). Recent studies have revealed that at least 60% of the roughly 35,000 genes in the human genome are alternatively spliced. Clearly, by combining different types of modifications and thus generating different possible combinations of transcripts of different genes, alternative splicing is a potent mechanism for generating protein diversity. Analysis of the spliceome, in turn, represents a novel approach to both functional genomics and pharmacogenomics.

Antisense Transcription in Eukaryotes

RNA-mediated gene regulation is widespread in higher eukaryotes and complex genetic phenomena like RNA interference, co-suppression, transgene silencing, imprinting, methylation, and possibly position-effect variegation and transvection, all involve intersecting pathways based on or connected to RNA signalling (Mattick 2001; EMBO reports 2, 11: 986-991). Recent studies indicate that antisense transcription is a very common phenomenon in the mouse and human genomes (Okazaki et al. 2002; Nature 420: 563-573; Yelin et al. 2003, Nature Biotechnol.). Thus, antisense modulation of gene expression in e.g. human cells may be a common regulatory mechanism. In light of this, the present invention provides novel tools, in which non-naturally occurring nucleic acids, such as LNA oligonucleotides, can be designed to silence or modulate the regulation of a given mRNA by non-coding antisense RNA, by designing a complementary sense LNA oligonucleotide for the regulatory antisense RNA. This has a high potential in target identification, target validation and therapeutic use of LNA oligonucleotides as modulating and silencing sense nucleic acid agents.

Misplaced Control of Alternative Splicing can Cause Disease

The detection of the detailed structure of all transcripts is an important goal for molecular characterization of a cell or tissue. Without the ability to detect and quantify the splice variants present in one tissue, the transcript content or the protein content cannot be described accurately. Molecular medical research shows that many cancers result in altered levels of splice variants, so an accurate method to detect and quantify these transcripts is required. Mutations that produce an aberrant splice form can also be the primary cause of such severe diseases such as spinal muscular dystrophy and cystic fibrosis.

Much of the study of human disease, indeed much of genetics is based upon the study of a few model organisms. The evolutionary stability of alternative splicing patterns and the degree to which splicing changes according to mutations and environmental and cellular conditions influence the relevance of these model systems. At present, there is little understanding of the rates at which alternative splicing patterns change, and the factors influencing these rates. Table 1 shows a set of genes that are known to be alternatively spliced and that are orthologs of known human disease genes.

TABLE 1

C. elegans disease orthologs that are known to be differentially spliced in C. elegans.

| Disease | C. elegans gene | BLAST E value |
| --- | --- | --- |
| brABL1 | M79.1A | 1.00E−162 |
| X-Linked Lymphoprol.-SH2D1A | M79.1A | 2.00E−58 |
| Cyclin Dep. Kinase 4-CDK4 | F18H3.5A | 1.00E−124 |
| HNPCC*-PMS2 | H12C20.2A | 1.00E−123 |
| Neurofibromatosis 2-NF2 | C01G8.5A | 5.00E−163 |
| Duchenne MD+-DMD | F32B4.3A | 0.00E+00 |
| Coffin-Lowry-RPS6KA3 | T01H8.1A | 2.00E−13 |
| Septooptic Dysplasia-HESX1 | Y113G7A.6A | 1.00E−152 |
| Non-Insulin Dep. Diabet.-PCSK1 | F11A6.1A | 1.00E−166 |
| Bartter's-SLC12A1 | Y37A1C.1A | 1.00E−167 |
| Gitelmans-SLC12A3 | Y37A1C.1A | 0.00E+00 |
| Hered. Spherocytosis-ANK1 | B0350.2A | 1.00E−09 |
| Darier-White-SERCA | K11D9.2A | 0.00E+00 |
| Spondyloepip. Dysp.-COL2A1 | F01G12.5A/let-2 | 9.00E−20 |

Previously, other microarray analyses have been performed with the aim of detecting either splicing of RNA transcripts per se in yeast, or of detecting putative exon skipping splicing events in rat tissues, but neither of these approaches had sufficient resolution to estimate quantities of splice variants, a factor that could be essential to an understanding of the changes in cell life cycle and disease.

Thus, improved methods are needed for nucleic acid amplification, hybridization, and classification. Desirable methods can distinguish between mRNA splice variants and quantitate the amount of each variant in a sample. Other desirable methods can detect differences in expressions patterns between patient nucleic acid samples and nucleic acid standards.

SUMMARY OF THE INVENTION

The present invention demonstrates the usefulness of LNA-modified oligonucleotides in the construction of highly specific and sensitive microarrays for expression profiling (e.g., mRNA splice variant detection) and comparative genomic hybridization. The invention provides novel technology platforms based on nucleic acids with LNA or other high affinity nucleotides for sensitive and specific assessment of alternative splicing using microarray technology. As opposed to high-density cDNA or DNA oligonucleotide microarrays, LNA microarrays are able to discriminate between highly homologous as well as differentially spliced transcripts. The invention furthermore provides methods for highly sensitive and specific nucleic acid detection by fluorescence in situ hybridization using LNA-modified oligonucleotides. The present methods greatly facilitate the analysis of gene expression patterns from a particular species, tissue, cell type. The analysis of the human spliceome provides important information for pharmacogenetics. Thus, the present methods are highly valuable in medical research and diagnostics as well as in drug development and toxicological studies.

In general, the invention features populations of high affinity nucleic acids that have duplex stabilizing properties and thus are useful for a variety of nucleic acid detection, amplification, and hybridization methods (e.g., expression or mRNA splice variant profiling). Some of these oligonucleotides contain novel nucleotides created by combining specialized synthetic nucleobases with an LNA backbone, thus creating high affinity oligonucleotides with specialized properties such as reduced sequence discrimination for the complementary strand or reduced ability to form intramolecular double stranded structures. The invention also provides improved methods for identifying nucleic acids in a sample and for classifying a nucleic acid sample by comparing its pattern of hybridization to an array to the corresponding pattern of hybridization of one or more standards to the array (e.g., comparative genomic hybridization).

Other desirable modified bases have decreased ability to self-anneal or to form duplexes with oligonucleotides containing one or more modified bases. The invention also provides arrays of nucleic acids containing these modified bases that have a decreased variance in melting temperature and/or an increased capture efficiency compared to naturally-occurring nucleic acids. These arrays as well as the oligonucleotides in solution can be used in a variety of applications for the detection, characterization, identification, and/or amplification of one or more target nucleic acids. These oligonucleotides and oligonucleotides of the invention in general can also be used for solution assays, such as homogeneous assays.

Merged Probes

In one aspect, the invention features a non-naturally-occurring nucleic acid with a melting temperature that is at least 3, 5, 8, 10, 12, 15, 20, 25, 30, 35, or 40° C. higher than that of the corresponding control nucleic acid with 2'-deoxynucleotides. The nucleic acid hybridizes to a first region within a first exon of a target nucleic acid and to a second region within a second exon of the target nucleic acid that is adjacent to the first exon.

In a related aspect, the invention provides a non-naturally-occurring nucleic acid with a melting temperature that is at least 3, 5, 8, 10, 12, 15, 20, 25, 30, 35, or 40° C. higher than that of the corresponding control nucleic acid with 2'-deoxynucleotides. The nucleic acid hybridizes to a first region within an exon of a target nucleic acid and to a second region within an intron of the target nucleic acid that is adjacent to the exon.

In another aspect, the invention features a non-naturally-occurring nucleic acid with a melting temperature that is at least 3, 5, 8, 10, 12, 15, 20, 25, 30, 35, or 40° C. higher than that of the corresponding control nucleic acid with 2'-deoxynucleotides. The nucleic acid hybridizes to a first region within a first intron of a target nucleic acid and to a second region within a second intron of the target nucleic acid that is adjacent to the first intron.

In yet another aspect, the invention provides a nucleic acid that is a non-naturally-occurring nucleic acid with a capture efficiency that is at least 10, 25, 50, 100, 150, 200, 500, 800, 1000, or 1200% greater than that of a corresponding control nucleic acid with 2'-deoxynucleotides at the temperature equal to the melting temperature of the nucleic acid. The nucleic acid hybridizes to a first region within a first exon of a target nucleic acid and to a second region within a second exon of the target nucleic acid that is adjacent to the first exon.

In a related aspect, the invention features a nucleic acid that is a non-naturally-occurring nucleic acid with a capture efficiency that is at least 10, 25, 50, 100, 150, 200, 500, 800, 1000, or 1200% greater than that of a corresponding control nucleic acid with 2'-deoxynucleotides at the temperature equal to the melting temperature of the nucleic acid. The nucleic acid hybridizes to a first region within an exon of a target nucleic acid and to a second region within an intron of the target nucleic acid that is adjacent to the exon.

In yet another aspect, the invention provides a nucleic acid that is a non-naturally-occurring nucleic acid with a capture efficiency that is at least 10, 25, 50, 100, 150, 200, 500, 800, 1000, or 1200% greater than that of a corresponding control nucleic acid with 2'-deoxynucleotides at the temperature equal to the melting temperature of the nucleic acid. The nucleic acid hybridizes to a first region within a first intron of a target nucleic acid and to a second region within a second intron of the target nucleic acid that is adjacent to the first intron.

In desirable embodiments, the nucleic acids of the invention featuring a non-naturally occurring nucleic acid exhibit increased duplex stability due to slower rates of dissociation of the nucleic acid complexes (the off-rate) (Christensen et al. 2001, Biochem. J. 354: 481-484).

In one aspect of the invention the structure of desirable adenosine, thymine, guanine and cytosine analogs are those disclosed in PCT Publication No. WO 97/12896, Formula 5, 6, 7, 8, 9, 10, 11, 12 and 13. These modified bases may be incorporated as part of an LNA, DNA, or RNA unit and used any of the oligomers of the invention.

In still another aspect, the invention features a nucleic acid that is an LNA (i.e., a nucleic acids with one or more LNA units) and that hybridizes to a first region within a first exon of a target nucleic acid and to a second region within a second exon of the target nucleic acid that is adjacent to the first exon.

In another aspect, the invention features a nucleic acid that is an LNA and that hybridizes to a first region within an exon of a target nucleic acid and to a second region within an intron of the target nucleic acid that is adjacent to the exon.

In one aspect, the invention provides nucleic acid that is an LNA and that hybridizes to a first region within a first intron of a target nucleic acid and to a second region within a second intron of the target nucleic acid that is adjacent to the first intron.

In desirable embodiments of any of the above aspects, the length of the segment of the nucleic acid hybridizing to the first region and the length of the segment of the nucleic acid hybridizing to the second region are between 3 and 50 nucleotides, 10 and 40 nucleotides, or 20 and 30 nucleotides, inclusive. The length of the segment of the nucleic acid hybridizing to the first region and the length of the segment of the nucleic acid hybridizing to the second region may be the same length or different lengths. Desirably, the nucleic acid containing LNA units are symmetrically spaced on both sides of a junction between either two exons, an exon and an intron, or two introns, or alternatively, the nucleic acid containing LNA units are spaced on both sides of a junction based on equalized duplex melting temperatures of the segments. Desirably, the nucleic acid has one or more LNA units within 5, 4, 3, 2, or 1 nucleotides of a junction between either two exons, an exon and an intron, or two introns.

In another aspect, the invention features a population of nucleic acids that includes one or more nucleic acids of any one of the above aspects.

Internal Probes

In another aspect, the invention features a non-naturally-occurring nucleic acid with a melting temperature that is at least 3, 5, 8, 10, 12, 15, 20, 25, 30, 35, or 40° C. higher than that of the corresponding control nucleic acid with 2'-deoxynucleotides. The nucleic acid hybridizes to only one exon or to only one intron of a target nucleic acid.

In a related aspect, the invention features a non-naturally-occurring nucleic acid with a capture efficiency that is at least 10, 25, 50, 100, 150, 200, 500, 800, 1000, or 1200% greater than that of a corresponding control nucleic acid with 2'-deoxynucleotides at the temperature equal to the melting temperature of the nucleic acid. The nucleic acid hybridizes to only one exon or to only one intron of a target nucleic acid.

In another aspect, the invention features a nucleic acid that is an LNA and that hybridizes to only one exon or to only one intron of a target nucleic acid.

In desirable embodiments of the above aspects for nucleic acids that hybridizes to only one exon or only one intron, the nucleic acid does not hybridize to both an exon and an intron.

In another aspect, the invention features a population of nucleic acids that includes one or more nucleic acids of any one of the above aspects.

Pharmaceutical Compositions and Nucleic Acid Populations

In another aspect, the invention features a pharmaceutical composition that includes one or more of the nucleic acids of the invention and a pharmaceutically acceptable carrier, such as one of the carriers described herein.

In another aspect, the invention features a population of two or more nucleic acids of the invention. The populations of nucleic acids of the invention may contain any number of unique molecules. For example, the population may contain as few as 10, $10^2$, $10^4$, or $10^5$ unique molecules or as many as $10^7$, $10^8$, $10^9$ or more unique molecules. In desirable embodiments, at least 1, 5, 10, 50, 100 or more of the polynucleotide sequences are a non-naturally-occurring sequence. Desirably, at least 20, 40, or 60% of the unique polynucleotide sequences are non-naturally-occurring sequences. Desirably, the nucleic acids are all the same length; however, some of the molecules may differ in length.

Desirable Embodiments of any of the Above Aspects

In desirable embodiments of any of the above aspects, the length of one or more nucleic acids (e.g., nucleic acids in a nucleic acid population of the invention) is between 15 and 150 nucleotides, 5 and 100 nucleotides, 20 and 80 nucleotides, or 30 and 60 nucleotides in length, inclusive. In particular embodiments, the nucleic acid is 6, 7, 8, 9, 10, 11, 12, 13, 14, 15, 16, 17, 18, 19, 20, 30, 40, 50 nucleotides or at least 60, 70, 80, 90, 100, 120, or 130 nucleotides in length. In additional embodiments, the nucleic acid is between 8 and 40 nucleotides, such as between 9 and 30, or 12 and 25, or 15 and 20 nucleotides. Desirably, at least 5, 10, 15, 20, 30, 40, 50, 60, or 70% of the nucleotides in the nucleic acid are LNA units. In desirable embodiments, every second nucleotide, every third, every fourth nucleotide, every fifth nucleotide, or every sixth nucleotide in the nucleic acid is an LNA unit. In various embodiments, (i) every second and every third nucleotide, (ii) every second and every fourth nucleotide, (iii) every second and every fifth nucleotide, (iv) every second and every sixth nucleotide, (v) every third and every fourth nucleotide, (vi) every third and every fifth nucleotide, (vii) every third and every sixth nucleotide, (viii) every fourth and every fifth nucleotide, (ix) every fourth and every sixth nucleotide, and/or (x) every fifth and every sixth nucleotide in the nucleic acid is an LNA unit. Desirably, every second, every third, and every fourth nucleotide in the nucleic acid is an LNA unit. In desirable embodiments, the nucleic acids of the invention have one or more of the following substitution patterns which is repeated throughout the nucleic acids: XxXx, xXxX, XxxXxx, xXxxXx, xxXxxX, XxxxXxxx, xXxxxXxx, xxXxxxXx, or xxxXxxxX in which "X" denotes an LNA unit and "x" denotes a DNA or RNA unit. In some embodiments, the nucleotides that are not LNA units are naturally-occurring DNA or RNA nucleotides.

In various embodiments, the nucleic acid comprises two or more contiguous LNA units. Desirably, the nucleic acid comprises at least 2, 3, 4, 5, 6, 7, or 8 contiguous LNA units. In desirable embodiments, the number of contiguous LNA units is between 5 and 20% or 10 and 15% of the total length of the nucleic acid. In a particular embodiment, 5 contiguous nucleotides of a 50-mer merged probe are LNA units. In one embodiment, the nucleic acid does not have greatly extended stretches of modified DNA or RNA residues, e.g. greater than about 4, 5, 6, 7, or 8 consecutive modified DNA or RNA residues. According to this embodiment, one or more non-modified DNA or RNA units are present after a consecutive stretch of about 3, 4, 5, 6, 7, or 8 modified nucleic acids.

Other desirable nucleic acids have an LNA substitution pattern that results in the formation of negligible secondary structure by the nucleic acids with itself. In one such embodiment, the nucleic acids do not form hairpins or do not form other secondary structures that would otherwise inhibit or prevent their binding to a target nucleic acid. Desirably, opposing nucleotides in a palindrome pair or opposing nucleotides in inverted repeats or in reverse complements are not both LNA units. In various embodiments, the nucleic acids in the first population form less than 3, 2, or 1 intramolecular base-pairs or base-pairs between two identical molecules. In desirable embodiments, the nucleic acid does not have LNA-5-nitroindole: LNA-5-nitroindole intramolecular base-pairs.

In other desirable embodiments, at least one LNA unit (e.g., at least 2, 3, 4, 5, 6, 7, 8, 9, or 10 LNA units) in the nucleic acid hybridizes to a first region within a first exon of a target nucleic acid and at least one LNA unit (e.g., at least 2, 3, 4, 5, 6, 7, 8, 9, or 10 LNA units) in the nucleic acid hybridizes to a second region within a second exon of the target nucleic acid that is adjacent to the first exon. The number of LNA units that bind to each region can be the same or different. In some embodiments, the 5' terminal nucleotide of the nucleic acid is or is not an LNA unit. Desirably, the 3' terminal nucleotide of the nucleic acid is not an LNA unit (e.g., the nucleic acid may contain a 3' terminal naturally-occurring nucleotide).

Desirably, the nucleic acid can distinguish between different nucleic acids (e.g., mRNA splice variants) that cannot be distinguished using a naturally-occurring control nucleic acid (e.g., a control nucleic acid that consists of only 2'-deoxynucleotides such as a control nucleic acid of the same length as the nucleic acid of the invention). Desirably, the hybridization intensity of the nucleic acid for an exon of interest is at least 2, 3, 4, 5, 6, or 10 fold greater than the hybridization intensity of the nucleic acid for another exon in the same target nucleic acid (e.g., mRNA) or in another nucleic acid. Desirably, the hybridization intensity of the nucleic acid for target nucleic acid is at least 2, 3, 4, 5, 6, or 10 fold greater than the hybridization intensity for a non-target nucleic acid with less than 99, 95, 90, 80, 70, or 60% sequence identity to the target nucleic acid.

Desirably, all of the nucleic acids of the population or all of the nucleic acids of a subpopulation of the population are the same length. In some embodiments, the population includes one or more nucleic acids of a different length. In some embodiments, longer nucleic acids contain one or more nucleotides with universal bases. For example, nucleotides with universal bases can be used to increase the thermal stability of nucleic acids that would otherwise have a thermal stability lower than some or all of the nucleic acids in the population. In some embodiments, one or more nucleic acids have a universal base located at the 5' or 3' terminus of the nucleic acid. In desirable embodiments, one or more (e.g., 2, 3, 4, 5, 6, or more) universal bases are located at the 5' and 3' termini of the nucleic acid. Desirably, all of the nucleic acids in the population have the same number of universal bases. Desirable universal bases include inosine, pyrene, 3-nitropyrrole, and 5-nitroindole.

In desirable embodiments, the nucleic acid has at least one LNA A or LNA T. In some embodiments, each nucleic acid has at least one LNA A or LNA T. Desirably, all of the adenine and thymine-containing nucleotides in the LNA are LNA A and LNA T, respectively. In some embodiments, a nucleic acid with a increased capture efficiency or melting temperature compared to a control nucleic acid has at least one LNA T or LNA C. In some embodiments, all of the thymine and cytosine-containing nucleotides in the LNA are LNA T and LNA C, respectively. In some embodiments, a nucleic acid with an increased specificity or decreased self-complementarity compared to a control nucleic acid has at least one LNA A or LNA C. In some embodiments, all of the adenine and cytosine-containing nucleotides in the LNA are LNA A and LNA C, respectively. Desirably, at least 10, 20, 25, 30, 40, 50, 60, 70, 80, 90, or 100% of the nucleic acids in the population have one or more LNA units.

In desirable embodiments, the LNA has at least one 2,6,-diaminopurine, 2-aminopurine, 2-thio-thymine, 2-thio-uracil, inosine, or hypoxanthine base. Desirably, the LNA has a nucleotide with a 2'O, 4'C-methylene linkage between the 2' and 4' position of a sugar moiety. In some embodiments, one or more nucleic acids in the first population are LNA/DNA, LNA/RNA, or LNA/DNA/RNA chimeras.

In desirable embodiments of any of the above aspects, the variance in the melting temperature of the population is at least 10, 20, 30, 40, 50, 60, or 70% less than the variance in the melting temperature of the corresponding control population of nucleic acids of the same length with 2'-deoxynucleotides (e.g., DNA nucleotides) instead of LNA units or other modified or non-naturally-occurring units. In desirable embodiments, the standard deviation in melting temperature is less than 10, 9.5, 9, 8.5, 8, 7.5, 7, 6.5, or 6. In certain embodiment, the range in melting temperatures for nucleic acids in the population is less than 70, 60, 50, 40, 30, or 20° C. Desirably, the variance in the melting temperature of the population is less than 59, 50, 40, 30, 25, 20, 15, 10, or 5° C.

In still other embodiments, the nucleic acids are covalently bonded to a solid support. Desirably, the nucleic acids are in a predefined arrangement. In various embodiments, the first population has at least 10; 100; 1,000; 5,000; 10,000; 100,000; or 1,000,000 different nucleic acids. Desirably, the nucleic acids in the population together hybridize to at least 10, 20, 30, 40, 50, 60, 70, 80, 90, 95, or 100% of the exons of a target nucleic acid. In desirable embodiments, the population includes nucleic acids that together hybridize to at least 10, 20, 30, 40, 50, 60, 70, 80, 90, 95, or 100% of the nucleic acids expressed by a particular cell or tissue. In some embodiments, the population includes nucleic acids that together hybridize to at least one exon from at least 1, 5, 10, 20, 25, 30, 40, 50, 60, 70, 80, 90, or 100% of the nucleic acid sequences expressed by a particular cell or tissue at a given point in time (e.g., an expression array with sequences corresponding to the sequences of mRNA molecules expressed by a particular cell type or a cell under a particular set of conditions). In some embodiments, the plurality of nucleic acids are used as PCR primers or FISH probes.

Desirable modified bases of the present invention when incorporated into the central position of a 9-mer oligonucleotide (all other eight residues or units being natural DNA or RNA units with natural bases) exhibit a $T_m$ difference equal to or less than about 15, 12, 10, 9, 8, 7, 6, 5, 4, 3 or 2° C. upon hybridizing to the four complementary oligonucleotide variants that are identical except for the unit corresponding to the LNA unit, where each variant has one of the natural bases uracil, cytosine, thymine, adenine or guanine. That is, the highest and the lowest $T_m$ (referred to herein as the $T_m$ differential) obtained with such four complementary sequences is 15, 12, 10, 9, 8, 7, 6, 5, 4, 3 or 2° C. or less.

Modified nucleic acid oligomers of the invention desirably contain at least one LNA unit, such as an LNA unit with a modified nucleobase. Modified nucleobases or nucleosidic bases desirably base-pair with adenine, guanine, cytosine, uracil, or thymine. Exemplary oligomers contain 2 to 100, 5 to 100, 4 to 50, 5 to 50, 5 to 30, or 8 to 15 nucleic acid units. In some embodiments, one or more LNA units with natural nucleobases are incorporated into the oligonucleotide at a distance from the LNA unit having a modified base of 1 to 6 (e.g., 1 to 4) bases. In certain embodiments, at least two LNA units with natural nucleobases are flanking an LNA unit having a modified base. Desirably, at least two LNA units independently are positioned at a distance from the LNA unit having the modified base of 1 to 6 (e.g., 1 to 4 bases).

Desirable modified nucleobases or nucleosidic bases for use in nucleic acid compositions of the invention include optionally substituted carbon alicyclic or carbocyclic aryl groups (i.e., only carbon ring members), particularly multi-ring carbocyclic aryl groups such as groups having 2, 3, 4, 5, 6, 7, or 8 linked, particularly fused carbocyclic aryl moieties. Optionally substituted pyrene is also desirable. Such nucleobases or nucleosidic bases can provide significant performance results, as demonstrated in the examples which follow. Heteroalicyclic and heteroaromatic nucleobases or nucleosidic bases also are suitable. In some embodiments, the carbocyclic moiety is linked to the 1'-position of the LNA unit through a linker (e.g., a branched or straight alkylene or alkenylene).

Desirable LNA units have a carbon or hetero alicyclic ring with four to six ring members, e.g. a furanose ring, or other alicyclic ring structures such as a cyclopentyl, cycloheptyl, tetrahydropyranyl, oxepanyl, tetrahydrothiophenyl, pyrrolidinyl, thianyl, thiepanyl, piperidinyl, and the like. In one aspect, at least one ring atom of the carbon or hetero alicyclic group is taken to form a further cyclic linkage to thereby provide a multi-cyclic group. The cyclic linkage may include one or more, typically two atoms, of the carbon or hetero alicyclic group. The cyclic linkage also may include one or more atoms that are substituents, but not ring members, of the carbon or hetero alicyclic group. Other desirable LNA units are compounds having a substituent on the 2'-position of the central sugar moiety (e.g., ribose or xylose), or derivatives thereof, which favors the C3'-endo conformation, commonly referred to as the North (or simply N for short) conformation. These LNA units include ENA (2'-O,4'-C-ethylene-bridged nucleic acids such as those disclosed in WO 00/47599) units as well as non-bridged riboses such as 2'-F or 2'-O-methyl.

For any of the above aspects, an exemplary control nucleic acid has β-D-2-deoxyribose instead of one or more bicyclic or sugar groups of a LNA unit or other modified or non-naturally-occurring units in a nucleic acid of the first population. In some embodiments, the nucleic acid or population of the invention and the control nucleic acid or population only have naturally-occurring nucleobases. If a nucleic acid in the nucleic acid or population of the invention has one or more non-naturally-occurring nucleobases, the capture efficiency of the corresponding control nucleic acid is calculated as the average capture efficiency for all of the nucleic acids that have either A, T, C, G or mC (methyl Cytosin) in each position corresponding to a non-naturally-occurring nucleobase in the nucleic acid in the first population.

Complex of Target Nucleic Acids and Nucleic Acid Probes

In one aspect, the invention features a complex of one or more target nucleic acids and nucleic acid of the invention (e.g., nucleic acid probes) in which one or more target nucleic acids are hybridized to a plurality of nucleic acids of the invention. Desirably, at least 2, 3, 4, 5, 6, 7, 10, 15, 20, 30, or 40 different target nucleic acids are hybridized. In some embodiments, the target nucleic acids are cDNA molecules reverse transcribed from a patient sample or cRNA molecules amplified from a patient sample using a T7 RNA polymerase-based linear amplification system or the like. The target nucleic acids are labeled prior to hybridization to the nucleic acids of invention.

Methods for Detecting or Amplifying Target Nucleic Acids

In one aspect, the invention features a method for detecting the presence of one or more target nucleic acids in a sample. This method involves incubating a nucleic acid sample with one or more nucleic acids of the invention under conditions that allow at least one target nucleic acid to hybridize to at least one of the nucleic acids of the invention. Desirably, hybridization is detected for at least 2, 3, 4, 5, 6, 8, 10, or 12 target nucleic acids. In some embodiments, the method further includes contacting the target nucleic acid with a second nucleic acid or a population of second nucleic acids that binds to a different region of the target molecule than the first nucleic acid. Desirably, the method further involves identifying one or more hybridized target nucleic acids and/or determining the amount of one or more hybridized target nucleic acids. In desirable embodiments, the method further includes determining the presence or absence of an mRNA splice variant of interest in the sample and/or determining the presence or absence of a mutation, deletion, and/or duplication of an exon of interest. In some embodiments, the mutation, deletion, and/or duplication is indicative of a disease, disorder, or condition, such as cancer.

In desirable embodiments of any of the above detection methods, at least 5, 10, 15, 20, 30, 40, 50, 80, 100, 150, 200, or more target nucleic acids hybridize to the nucleic acids of the invention. Desirably, the method is repeated under one or more different incubation conditions. In particular embodiments, the method is repeated at 1, 3, 5, 8, 10, 15, 20, 30, 40 or more different temperatures, cation concentrations (e.g., concentrations of monovalent cations such as $Na^+$ and $K^+$ or divalent cations such as $Mg^{2+}$ and $Ca^{2+}$), denaturants (e.g., hydrogen bond donors or acceptors that interfere with the hydrogen bonds keeping the base-pairs together such as formamide or urea). Desirably, the method also includes identifying the target nucleic acid hybridized to the nucleic acids of the invention and/or determining the amount of the target nucleic acid hybridized to the nucleic acids of the invention. In particular embodiments, the target nucleic acids are labeled with a fluorescent group. In certain embodiments, the labeling is repeated using different fluorescent groups (e.g., labelling for so-called dye-swap labeling experiments). In desirable embodiments, the determination of the amount of bound target nucleic acid involves one or more of the following: (i) adjusting for the varying intensity of the excitation light source used for detection of the hybridization, (ii) adjusting for photobleaching of the fluorescent group, and/or (iii) comparing the fluorescent intensity of the target nucleic acid(s) hybridized to the nucleic acids of the invention of nucleic acids to the fluorescent intensity of a different sample of nucleic acids hybridized to the nucleic acids of the invention (e.g., a different sample hybridized to the same population of nucleic acids of the invention on the same or a different solid support such as the same chip or a different chip). Desirably, this comparison in fluorescent intensity involves adjusting for a difference in the amount of the nucleic acids of the invention used for hybridization to each sample and/or adjusting for a difference in the buffer (e.g., a difference in $Mg^{2+}$ concentration) used for hybridization to each sample or scaling for different labeling efficiencies with different fluorochromes.

Desirably, the target nucleic acids are cDNA molecules reverse transcribed from a patient sample or cRNA molecules amplified using a T7 RNA polymerase-based linear amplification system or the like from a patient sample. In particular embodiments, the sample has nucleic acids that are amplified using one or more primers specific for an exon of a target nucleic acid, and the method involves determining the presence or absence of an mRNA splice variant with the exon in the sample. Desirably, one or more of the primers are specific for an exon or exon-exon junction of a pathogen of interest, and the method involves determining the presence or absence of a nucleic acid with the exon in the sample.

In a desirable embodiment, the nucleic acids of the invention are covalently bonded to a solid support by reaction of a nucleoside phosphoramidite with an activated solid support, and subsequent reaction of a nucleoside phosphoramide with an activated nucleotide or nucleic acid bound to the solid support. In some embodiments, the solid support or the growing nucleic acid bound to the solid support is activated by illumination, a photogenerated acid, or electric current.

In another aspect, the invention features a method for amplifying a target nucleic acid molecule. The method involves (a) incubating a first nucleic acid of the invention with a target nucleic acid under conditions that allow the first nucleic acid to bind the target nucleic acid; and (b) extending the first nucleic acid with the target nucleic acid as a template. Desirably, the method further involves contacting the target nucleic acid with a second nucleic acid (e.g., a second nucleic acid of the invention) that binds to a different region of the target nucleic acid than the first nucleic acid. In various embodiments, the sequence of the target nucleic acid is known or unknown.

In one aspect, the invention features a method of detecting a nucleic acid of a pathogen (e.g., a nucleic acid in a sample such as a blood or urine sample from a mammal). This method involves contacting a nucleic acid probe of the invention (e.g., a probe specific for an exon or a mRNA from a particular pathogen or family of pathogens) with a nucleic acid sample under conditions that allow the probe to hybridize to at least one nucleic acid in the sample. The probe is desirably at least 60, 70, 80, 90, 95, or 100% complementary to a nucleic acid of a pathogen (e.g., a bacteria, virus, or yeast such as any of the pathogens described herein). Hybridization between the probe and a nucleic acid in the sample is detected, indicating that the sample contains the corresponding nucleic acid from a pathogen. In some embodiments, the method is used to determine what strain of a pathogen has infected a mammal (e.g., a human) by determining whether a particular nucleic acid is present in the sample. In other embodiments, the probe has a universal base in a position corresponding to a nucleotide that varies among different strains of a pathogen, and thus the probe detects the presence of a nucleic acid from any of a multiple of pathogenic strains.

Methods for Classifying Nucleic Acids Samples

In one aspect, the invention features a method for classifying a test nucleic acid sample including target nucleic acids. This method involves (a) incubating a test nucleic acid sample with a one or more nucleic acids of the invention under conditions that allow at least one of the nucleic acids in the test sample to hybridize to at least one nucleic acid of the invention, (b) detecting a hybridization pattern of the test nucleic acid sample, and (c) comparing the hybridization pattern to a hybridization pattern of a first nucleic acid standard, whereby the comparison indicates whether or not the test sample has the same classification as the first standard. Desirably, the method also includes comparing a hybridization pattern of the test nucleic acid sample to a hybridization pattern of a second standard. In various embodiments, a hybridization pattern of the test nucleic acid sample is compared to at least 3, 4, 5, 8, 10, 15, 20, 30, 40, or more standards.

Desirably, the method also includes identifying the hybridized target nucleic acid and/or determining the amount of hybridized target nucleic acid. In particular embodiments, the target nucleic acids are labeled with a fluorescent group. Desirably, the first nucleic acid standard is labeled with a different fluorescent group. The fluorescence of the target nucleic acids and the first nucleic acid standard can be detected simultaneously or sequentially.

In desirable embodiments, the method further includes determining the presence or absence of an mRNA splice variant of interest in the sample and/or determining the presence or absence of a mutation, deletion, and/or duplication of an exon of interest. In some embodiments, the mutation, deletion, and/or duplication is indicative of a disease, disorder, or condition, such as cancer.

In desirable embodiments, the determination of the amount of bound target nucleic acid involves one or more of the following: (i) adjusting for the varying intensity of the excitation light source used for detection of the hybridization, (ii) adjusting for photobleaching of the fluorescent group, and/or (iii) comparing the fluorescent intensity of the target nucleic acid(s) hybridized to the nucleic acids of the invention to the fluorescent intensity of a different sample of nucleic acids hybridized to the nucleic acids of the invention (e.g., a different sample hybridized to same set of nucleic acids of the invention on the same or a different solid support such as the same chip or a different chip). Desirably, this comparison in fluorescent intensity involves adjusting for a difference in the amount of the plurality used for hybridization to each sample and/or adjusting for a difference in the buffer (e.g., a difference in $Mg^{2+}$ concentration) used for hybridization to each sample.

Desirably, the nucleic acids in the population together hybridize to at least 10, 20, 30, 40, 50, 60, 70, 80, 90, 95, or 100% of the exons of a target nucleic acid. In desirable embodiments, the population includes nucleic acids that together hybridize to at least 10, 20, 30, 40, 50, 60, 70, 80, 90, 95, or 100% of the nucleic acids expressed by a particular cell or tissue. In some embodiments, the population includes nucleic acids that together hybridize to at least one exon from at least 1, 5, 10, 20, 25, 30, 40, 50, 60, 70, 80, 90, or 100% of the nucleic acid sequences expressed by a particular cell or tissue at a given point in time (e.g., an expression array with sequences corresponding to the sequences of mRNA molecules expressed by a particular cell type or a cell under a particular set of conditions). Desirably, the method further includes using a nucleic acid or a region of a nucleic acid that is present in a first test sample but not present in a first standard or not present in a second test sample as a probe or primer for the detection, amplification, or characterization of the nucleic acid.

In desirable embodiments of any of the above methods, at least 5, 10, 15, 20, 30, 40, 50, 80, 100, 150, 200, or more target nucleic acids hybridize to the nucleic acids of the invention. Desirably, the method is repeated under one or more different incubation or hybridization conditions. In particular embodiments, the method is repeated at 1, 3, 5, 8, 10, 15, 20, 30, 40 or more different temperatures, cation concentrations (e.g., concentration of monovalent cations such as $Na^+$ and $K^+$ or divalent cations such as $Mg^{2+}$ and $Ca^2$); denaturants (e.g., hydrogen bond donors or acceptors that interfere with the hydrogen bonds keeping the base-pairs together such as formamide or urea).

In particular embodiments, the sample has nucleic acids that are amplified using one or more primers specific for an exon of a target nucleic acid, and the method involves determining the presence or absence of an mRNA splice variant with the exon in the sample. Desirably, one or more of the primers are specific for an exon or exon-exon junction of a pathogen of interest, and the method involves determining the presence or absence of a nucleic acid with the exon in the sample.

Desirably, the comparison of the hybridization pattern of a patient nucleic acid sample to that of one or more standards is used to determine whether or not a patient has a particular disease, disorder, condition, or infection or an increased risk for a particular disease, disorder, condition, or infection. In some embodiments, the comparison is used to determine what pathogen has infected a patient and to select a therapeutic for the treatment of the patient. Desirably, the comparison is used to select a therapeutic for the treatment or prevention of a disease or disorder in the patient. In yet other embodiments, the comparison is used to include or exclude the patient from a group in a clinical trial. Desirably, the comparison is used to compare the expression of nucleic acids (e.g., mRNA splice forms associated with toxicity) in the presence and absence of a candidate compound (e.g., a lead compound for drug development). In other embodiments, the comparison is used to determine differences in expression of nucleic acids (e.g., mRNA splice variants) under particular conditions (e.g., under different environmental stress conditions) or at different developmental time points. In particular embodiments, the expression of one or more members from a particular enzyme class (e.g., protein kinase splice variants) is measured.

In a desirable embodiment, the nucleic acids of the invention are covalently bonded to a solid support by reaction of a nucleoside phosphoramidite with an activated solid support, and subsequent reaction of a nucleoside phosphoramide with an activated nucleotide or nucleic acid bound to the solid support. In some embodiments, the solid support or the growing nucleic acid bound to the solid support is activated by illumination, a photogenerated acid, or electric current.

The use of a variety of different monomers in the nucleic acids of the invention offers a means to "fine tune" the chemical, physical, biological, pharmacokinetic, and pharmacological properties of the nucleic acids thereby facilitating improvement in their safety and efficacy profiles when used as a therapeutic drug.

Applications for the Nucleic Acids of the Invention

In another aspect, the invention features the use of one or more nucleic acids of the invention for the detection, amplification, or classification of a nucleic acid of interest or a population of nucleic acids of interest.

In another aspect, the invention features the use of one or more nucleic acids of the invention for alternative mRNA splice variant detection, expression profiling, comparative genomic hybridization, or real-time PCR. In exemplary real-time PCR applications, the nucleic acids are used to determine the amount of one or more target nucleic acids (e.g., mRNA splice variants) in a sample. In particular embodiments, fluorescently labeled RT-PCR products from the amplification of a test nucleic acid sample are hybridized to a population of nucleic acids of the invention. Desirably, the amount of one or more RT-PCR products is measured to determine the amount of the corresponding nucleic acid in the initial sample.

In yet another aspect, the invention features the use of a nucleic of the invention as a PCR primer or FISH probe.

Methods for Selecting a Population of Nucleic Acid

In one aspect, the invention features a method of selecting a nucleic acid for a population of nucleic acids. This method involves (a) determining the melting temperature of a nucleic acid of the invention, determining the ability of the nucleic acid to self-anneal, determining the ability of the nucleic acid to hybridize to one or more exons or introns of a target nucleic acid, and/or determining the ability of the nucleic acid to hybridize to a non-target nucleic acid, and (b) selecting the nucleic acid for inclusion or exclusion from the population based on the determination in step (a). In desirable embodiments, step (a) is performed for at least 2, 3, 4, 5, 6, 10, 20, 50, 100, 200, 500, 1,000, 5,000 or more nucleic acids, and a subset of the nucleic acids are selected for inclusion in the population based on the determination in step (a). Desirably, the nucleic acids with the highest melting temperatures and/or ability to hybridize to one or more exons or introns of a target nucleic acid are selected. Desirably, the nucleic acids with the lowest ability to self-anneal and/or hybridize to a non-target nucleic acid are selected.

Databases with Hybridization Patterns of Nucleic Acids Samples and/or Standards

The invention also features a variety of databases. These databases are useful for storing the information obtained in any of the methods of the invention. These databases may also be used in the diagnosis of disease or an increased risk for a disease or in the selection of a desirable therapeutic for a particular patient or class of patients.

Accordingly, in one such aspect, the invention provides an electronic database including at least 1, 10, $10^2$, $10^3$, $5 \times 10^3$, $10^4$, $10^5$, $10^6$, $10^7$, $10^8$, or $10^9$ records of a nucleic acid of interest or a population of nucleic acids of interest (e.g., one or more nucleic acids in a standard or in a test nucleic acid sample) correlated to records of its hybridization pattern to a plurality of nucleic acids of the invention under one or more incubation conditions (e.g., one or more temperatures, denaturant concentrations, or salt concentrations).

In another aspect, the invention features computer including the database of the above aspect and a user interface (i) capable of displaying a hybridization pattern for a nucleic acid of interest or a population of nucleic acids of interest whose record is stored in the computer or (ii) capable of displaying a nucleic acid of interest (e.g., displaying the polynucleotide sequence or another identifying characteristic of the nucleic acid of interest) or a population of nucleic acids of interest that produces a hybridization pattern whose record is stored in the computer.

Methods for Silencing a Target Nucleic Acid in a Cell or Animal

One method for inhibiting specific gene expression involves the use of antisense or double stranded oligonucleotides, which are complementary to a specific target messenger RNA (mRNA) sequence, such as a specific mRNA splice variant. Of special interest are oligonucleotides with a modified backbone (such as LNA or phosphorothioate) that are not readily degraded by endonucleases in the target cells.

In one aspect, the invention features the use of a nucleic acid of the invention for the manufacture of a pharmaceutical composition for treatment of a disease curable by an antisense or RNAi technology.

In one aspect, the invention provides a method for inhibiting the expression of a target nucleic acid in a cell. The method involves introducing into the cell a nucleic acid of the invention in an amount sufficient to specifically attenuate expression of the target nucleic acid. The introduced nucleic acid has a nucleotide sequence that is essentially complementary to a region of desirably at least 20 nucleotides of the target nucleic acid. Desirably, the cell is in a mammal.

In a related aspect, the invention provides a method for preventing, stabilizing, or treating a disease, disorder, or condition associated with a target nucleic acid in a mammal. This method involves introducing into the mammal a nucleic acid of the invention in an amount sufficient to specifically attenuate expression of the target nucleic acid, wherein the introduced nucleic acid has a nucleotide sequence that is essentially complementary to a region of desirably at least 20 nucleotides of the target nucleic acid.

In another aspect, the invention provides a method for preventing, stabilizing, or treating a pathogenic infection in a mammal by introducing into the mammal a nucleic acid of the invention in an amount sufficient to specifically attenuate expression of a target nucleic acid of a pathogen. The introduced nucleic acid has a nucleotide sequence that is essentially complementary to a region of desirably at least 20 nucleotides of the target nucleic acid.

In desirable embodiments of the therapeutic methods of the above aspects, the mammal is a human. In some embodiments, the introduced nucleic acid is single stranded or double stranded.

With respect to the therapeutic methods of the invention, it is not intended that the administration of nucleic acids to a mammal be limited to a particular mode of administration, dosage, or frequency of dosing; the present invention contemplates all modes of administration, including oral, intraperitoneal, intramuscular, intravenous, intraarticular, intralesional, subcutaneous, or any other route sufficient to provide a dose adequate to prevent or treat a disease (e.g., a disease associated with the expression of a target nucleic acid that is silenced with a nucleic acid of the invention). One or more nucleic acids may be administered to the mammal in a single dose or multiple doses. When multiple doses are administered, the doses may be separated from one another by, for example, one week, one month, one year, or ten years. It is to be understood that, for any particular subject, specific dosage regimes should be adjusted over time according to the individual need and the professional judgment of the person administering or supervising the administration of the compositions.

Exemplary mammals that can be treated using the methods of the invention include humans, primates such as monkeys, animals of veterinary interest (e.g., cows, sheep, goats, buffalos, and horses), and domestic pets (e.g., dogs and cats). Exemplary cells in which one or more target genes can be silenced using the methods of the invention include invertebrate, plant, bacteria, yeast, and vertebrate (e.g., mammalian or human) cells.

Optimum dosages for gene silencing applications may vary depending on the relative potency of individual oligonucleotides, and can generally be estimated based on $EC_{50}$ values found to be effective in in vitro and in vivo animal models. In general, dosage is from 0.001 µg to 100 g per kg of body weight (e.g., 0.001 µg/kg to 1 g/kg), and may be given once or more daily, weekly, monthly or yearly, or even once every 2 to 20 years (U.S. Pat. No. 6,440,739). Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.001 ug to 100 g per kg of body weight (e.g., 0.001 µg/kg to 1 g/kg), once or more daily, to once every 20 years. If desired, conventional treatments may be used in combination with the nucleic acids of the present invention.

Suitable carriers include, but are not limited to, saline, buffered saline, dextrose, water, glycerol, ethanol, and combinations thereof. The composition can be adapted for the mode of administration and can be in the form of, for example, a pill, tablet, capsule, spray, powder, or liquid. In some embodiments, the pharmaceutical composition contains one or more pharmaceutically acceptable additives suitable for the selected route and mode of administration. These compositions may be administered by, without limitation, any parenteral route including intravenous, intraarterial, intramuscular, subcutaneous, intradermal, intraperitoneal, intrathecal, as well as topically, orally, and by mucosal routes of delivery such as intranasal, inhalation, rectal, vaginal, buccal, and sublingual. In some embodiments, the pharmaceutical compositions of the invention are prepared for administration to vertebrate (e.g., mammalian) subjects in the form of liquids, including sterile, non-pyrogenic liquids for injection, emulsions, powders, aerosols, tablets, capsules, enteric coated tablets, or suppositories.

Exemplary Oligomers of the Invention and Methods for Synthesizing them

In desirable embodiments, the invention features a method of synthesizing a nucleic acid. This method involves synthesizing a 2-thio-uridine nucleoside or nucleotide of formula IV using a compound of formula VIII, IX, X, XI, or XII as shown below. The nucleoside, nucleoside phosphoramidite, or nucleotide is incorporated into a nucleic acid of the invention.

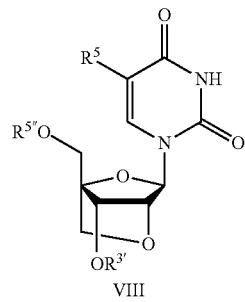

VIII

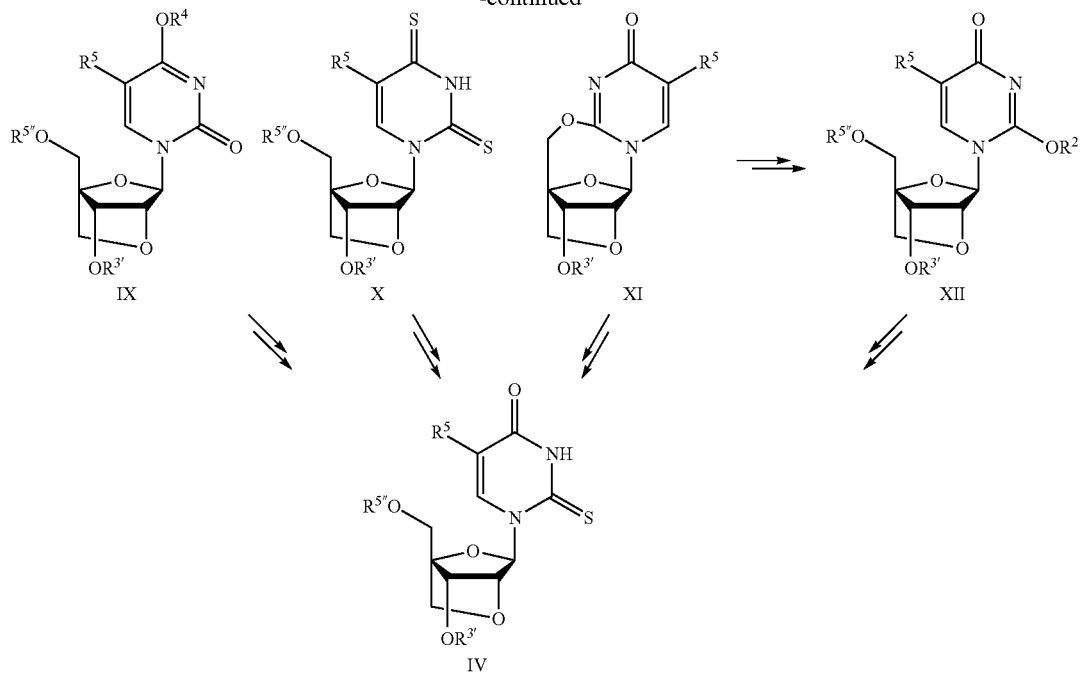

In a particular embodiment, nucleobase thiolation is performed on the O2 position of compound XI to form compound IV. In another embodiment, sulphurization on both O2 and O4 in compound VIII generates a 2,4-dithio-uridine nucleoside or nucleotide of formula X which is converted into compound IV. In yet another embodiment, a cyclic ether of formula XI is transferred into compound IV or a 2-O-alkyl-uridine nucleoside or nucleotide of formula XII through reaction with the 5' position. In other embodiments, a 2-O-alkyl-uridine nucleoside or nucleotide of formula XII is generated by direct alkylation of a uridine nucleoside or nucleotide of formula VIII.

In desirable embodiments $R^4$ and $R^2$ are each independently alkyl (e.g., methyl or ethyl), acyl (e.g., acetyl or benzoyl), or any appropriate protecting group such as silyl, 4,4'-dimethoxytrityl, monomethoxytrityl, or trityl(triphenylmethyl). $R^{5''}$ is any appropriate protecting group such as silyl, 4,4'-dimethoxytrityl, monomethoxytrityl, trityl(triphenylmethyl), acetyl, benzoyl, or benzyl. In desirable embodiments, $R^5$ is hydrogen, alkyl (e.g., methyl or ethyl), 1-propynyl, thiazol-2-yl, pyridine-2-yl, thien-2-yl, imidazol-2-yl, (4/5-methyl)-thiazol-2-yl, 3-(iodoacetamido)propyl, 4-[N,N-bis(3-aminopropyl)amino]butyl), or halo (e.g., chloro, bromo, iodo, fluoro).

The group —$OR^{3'}$ in the formulas IV, VIII, IX, X, XI, and XII is any of the groups listed for $R^3$ or $R^{3'}$ in formula Ia or formula Ib or listed for $R^3$ or $R^{3*}$ in formula IIa, Scheme A, or Scheme B, or the group —$OR^{3'}$ or $R^{3'}$ in the formulas IV, VIII, IX, X, XI, and XII is selected from the group consisting of H, —OH, $P(O(CH_2)_2CN)N(iPr)_2$, $P(O(CH_2)_2CN)N(iPr)_2$, phosphate, phosphorothioate, phosphorodithioate, phosphoramidate, phosphoroselenoate, phosphorodiselenoate, alkylphosphotriester, methyl phosphonate, halo (e.g., chloro, fluoro, iodo, or bromo), optionally substituted aryl, (e.g., phenyl or benzyl), alkyl (e.g, methyl or ethyl), alkoxy (e.g., methoxy), acyl (e.g., acetyl or benzoyl), aroyl, aralkyl, hydroxy, hydroxyalkyl, alkoxy, aryloxy, aralkoxy, nitro, cyano, carboxy, alkoxycarbonyl, aryloxycarbonyl, aralkoxycarbonyl, acylamino, aroylamine, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, amidino, amino, carbamoyl, sulfamoyl, alkene, alkyne, protecting groups (e.g., silyl, 4,4'-dimethoxytrityl, monomethoxytrityl, or trityl(triphenylmethyl)), linkers (e.g., a linker containing an amine, ethylene glycol, quinone such as anthraquinone), detectable labels (e.g., radiolabels or fluorescent labels), and biotin.

The group —$OR^{5'}$ in the formulas IV, and VIII, IX, X, and XII is any of the groups listed for $R^5$ or $R^{5'}$ in formula Ia or formula Ib or listed for $R^5$ or $R^{5*}$ in formula IIa, Scheme A, or Scheme B, or the group —$OR^{5'}$ or $R^{5'}$ in the formulas IV, and VIII, IX, X, and XII is selected from the group consisting of H, —OH, $P(O(CH_2)_2CN)N(iPr)_2$, $P(O(CH_2)_2CN)N(iPr)_2$, phosphate, phosphorothioate, phosphorodithioate, phosphoramidate, phosphoroselenoate, phosphorodiselenoate, alkylphosphotriester, methyl phosphonate, halo (e.g., chloro, fluoro, iodo, or bromo), optionally substituted aryl, (e.g., phenyl or benzyl), alkyl (e.g, methyl or ethyl), alkoxy (e.g., methoxy), acyl (e.g. acetyl or benzoyl), aroyl, aralkyl, hydroxy, hydroxyalkyl, alkoxy, aryloxy, aralkoxy, nitro, cyano, carboxy, alkoxycarbonyl, aryloxycarbonyl, aralkoxycarbonyl, acylamino, aroylamine, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, amidino, amino, carbamoyl, sulfamoyl, alkene, alkyne, protecting groups (e.g., silyl, 4,4'-dimethoxytrityl, monomethoxytrityl, or trityl(triphenylmethyl)), linkers (e.g., a linker containing an amine, ethylene glycol, quinone such as anthraquinone), detectable labels (e.g., radiolabels or fluorescent labels), and biotin.

In yet another aspect, the invention features a method of synthesizing a nucleic acid. This method involves synthesizing a 2-thiopyrimidine nucleoside or nucleotide of formula IV using a compound of formula III or compounds of the formula I, II, and III as shown below. The nucleoside, nucleoside phosphoramidite, or nucleotide is incorporated into a nucleic acid of the invention.

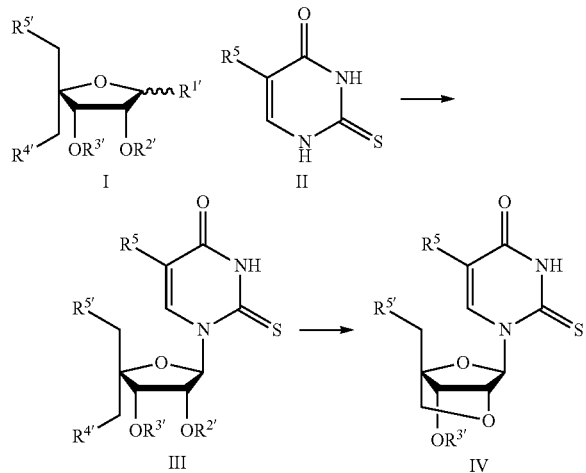

In some embodiments, lewis acid-catalyzed condensation of a substituted sugar of formula I and a substituted 2-thio-uracil of formula II results in a substituted 2-thio-uridine nucleoside or nucleotide of the formula III. In some embodiments, a compound of formula III is converted into a LNA 2-thiouridine nucleoside or nucleotide of formula IV.

In desirable embodiments $R^4$ and $R^5$ are, e.g., methanesulfonyloxy, p-toluenesulfonyloxy, or any appropriate protecting group such as silyl, 4,4'-dimethoxytrityl, monomethoxytrityl, trityl(triphenylmethyl), acetyl, benzoyl, or benzyl, $R^1$ is, e.g., acetyl, benzoyl, alkoxy (e.g., methoxy). $R^2$ is, e.g., acetyl or benzoyl, and $R^3$ is any appropriate protecting group such as silyl, 4,4'-dimethoxytrityl, monomethoxytrityl, trityl(triphenylmethyl), acetyl, or benzoyl. In desirable embodiments, $R^5$ is hydrogen, alkyl (e.g. methyl or ethyl), 1-propynyl, thiazol-2-yl, pyridine-2-yl, thien-2-yl, imidazol-2-yl, (4/5-methyl)-thiazol-2-yl, 3-(iodoacetamido)propyl, 4-[N,N-bis(3-aminopropyl)amino]butyl), or halo (e.g., chloro, bromo, iodo, fluoro).

The group —$OR^{3'}$ in the formulas I, III, and IV is any of the groups listed for $R^3$ or $R^{3'}$ in formula Ia or formula Ib or listed for $R^3$ or $R^{3*}$ in formula IIa, Scheme A, or Scheme B, or the group —$OR^{3'}$ or $R^{3'}$ in the formulas I, III, and IV is selected from the group consisting of H, —OH, P(O(CH$_2$)$_2$CN)N(iPr)$_2$, phosphate, phosphorothioate, phosphorodithioate, phosphoramidate, phosphoroselenoate, phosphorodiselenoate, alkylphosphotriester, methyl phosphonate, halo (e.g., chloro, fluoro, iodo, or bromo), optionally substituted aryl, (e.g., phenyl or benzyl), alkyl (e.g., methyl or ethyl), alkoxy (e.g., methoxy), acyl (e.g. acetyl or benzoyl), aroyl, aralkyl, hydroxy, hydroxyalkyl, alkoxy, aryloxy, aralkoxy, nitro, cyano, carboxy, alkoxycarbonyl, aryloxycarbonyl, aralkoxycarbonyl, acylamino, aroylamine, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, amidino, amino, carbamoyl, sulfamoyl, alkene, alkyne, protecting groups (e.g., silyl, 4,4'-dimethoxytrityl, monomethoxytrityl, or trityl (triphenylmethyl)), linkers (e.g., a linker containing an amine, ethylene glycol, quinone such as anthraquinone), detectable labels (e.g., radiolabels or fluorescent labels), and biotin.

The group $R^{5'}$ in the formulas I, III, and IV is any of the groups listed for $R^5$ or $R^{5'}$ in formula Ia or formula Ib or listed for $R^5$ or $R^{5*}$ in formula IIa, Scheme A, or Scheme B, or $R^{5'}$ in the formulas I, III, and IV is selected from the group consisting of H, —OH, P(O(CH$_2$)$_2$CN)N(iPr)$_2$, phosphate, phosphorothioate, phosphorodithioate, phosphoramidate, phosphoroselenoate, phosphorodiselenoate, alkylphosphotriester, methyl phosphonate, halo (e.g., chloro, fluoro, iodo, or bromo), optionally substituted aryl, (e.g., phenyl or benzyl), alkyl (e.g, methyl or ethyl), alkoxy (e.g., methoxy), acyl (e.g. acetyl or benzoyl), aroyl, aralkyl, hydroxy, hydroxyalkyl, alkoxy, aryloxy, aralkoxy, nitro, cyano, carboxy, alkoxycarbonyl, aryloxycarbonyl, aralkoxycarbonyl, acylamino, aroylamine, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, amidino, amino, carbamoyl, sulfamoyl, alkene, alkyne, protecting groups (e.g., silyl, 4,4'-dimethoxytrityl, monomethoxytrityl, or trityl(triphenylmethyl)), linkers (e.g., a linker containing an amine, ethylene glycol, quinone such as anthraquinone), detectable labels (e.g., radiolabels or fluorescent labels), and biotin.

In still another aspect, the invention features a method of synthesizing a nucleic acid. This method involves synthesizing a 2-thiopyrimidine nucleoside or nucleotide of formula IV using a compound of formula VII, compounds of the formula V, VI, and VII, or compounds of the formula I, V, VI, and VII as shown below. The nucleoside, nucleoside phosphoramidite, or nucleotide is incorporated into a nucleic acid of the invention.

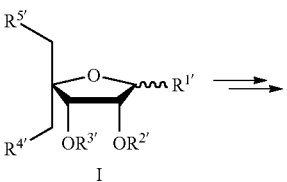

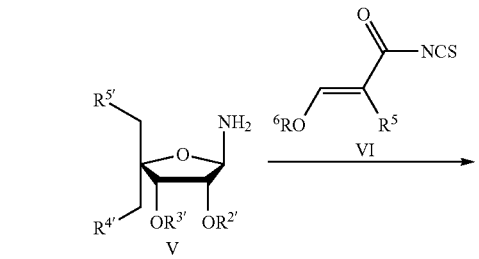

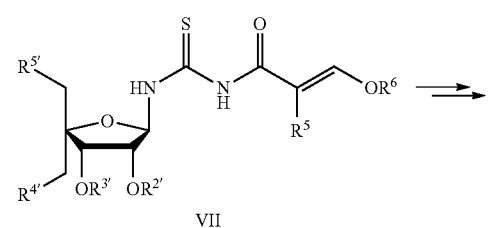

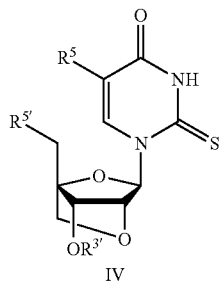

IV

In some embodiments, a 2-thio-uridine nucleoside or nucleotide of the formula IV is synthesized through ring-synthesis of the nucleobase by reaction of an amino sugar of the formula V and a substituted isothiocyanate of the formula VI.

In desirable embodiments, $R^{4'}$ and $R^{5'}$ are each independently, e.g., methanesulfonyloxy, p-toluenesulfonyloxy, or any appropriate protecting group such as silyl, 4,4'-dimethoxytrityl, monomethoxytrityl, trityl(triphenylmethyl), acetyl, benzoyl, or benzyl. $R^{1'}$ is, e.g., acetyl or benzoyl or alkoxy (e.g., methoxy), and $R^{2'}$ is, e.g., acetyl or benzoyl, $R^{3'}$ is any appropriate protecting group such as silyl, 4,4'-dimethoxytrityl, monomethoxytrityl, trityl(triphenylmethyl), acetyl, or benzoyl. $R^5$ are $R^6$ each independently, e.g., hydrogen or alkyl (e.g. methyl or ethyl). $R^6$ can also be, e.g., an appropriate protecting group such as silyl, 4,4'-dimethoxytrityl, monomethoxytrityl, or trityl(triphenylmethyl). In desirable embodiments, $R^5$ is hydrogen or methyl, and $R^6$ is methyl or ethyl.

The group —$OR^{3'}$ in the formulas I, V, VII, and IV is any of the groups listed for $R^3$ or $R^{3'}$ in formula Ia or formula Ib or listed for $R^3$ or $R^{3*}$ in formula IIa, Scheme A, or Scheme B, or the group —$OR^{3'}$ or $R^{3'}$ in the formulas I, V, VII, and IV is selected from the group consisting of H, —OH, $P(O(CH_2)_2CN)N(iPr)_2$, phosphate, phosphorothioate, phosphorodithioate, phosphoramidate, phosphoroselenoate, phosphorodiselenoate, alkylphosphotriester, methyl phosphonate, halo (e.g., chloro, fluoro, iodo, or bromo), optionally substituted aryl, (e.g., phenyl or benzyl), alkyl (e.g, methyl or ethyl), alkoxy (e.g., methoxy), acyl (e.g. acetyl or benzoyl), aroyl, aralkyl, hydroxy, hydroxyalkyl, alkoxy, aryloxy, aralkoxy, nitro, cyano, carboxy, alkoxycarbonyl, aryloxycarbonyl, aralkoxycarbonyl, acylamino, aroylamine, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, amidino, amino, carbamoyl, sulfamoyl, alkene, alkyne, protecting groups (e.g., silyl, 4,4'-dimethoxytrityl, monomethoxytrityl, or trityl (triphenylmethyl)), linkers (e.g., a linker containing an amine, ethylene glycol, quinone such as anthraquinone), detectable labels (e.g., radiolabels or fluorescent labels), and biotin.

$R^{5'}$ in the formulas I, V, VII, and IV is any of the groups listed for $R^5$ or $R^{5'}$ in formula Ia or formula Ib or listed for $R^5$ or $R^{5*}$ in formula IIa, Scheme A, or Scheme B, or $R^{5'}$ in the formulas I, V, VII, and IV is selected from the group consisting of H, —OH, $P(O(CH_2)_2CN)N(iPr)_2$, phosphate, phosphorothioate, phosphorodithioate, phosphoramidate, phosphoroselenoate, phosphorodiselenoate, alkylphosphotriester, methyl phosphonate, halo (e.g., chloro, fluoro, iodo, or bromo), optionally substituted aryl, (e.g., phenyl or benzyl), alkyl (e.g, methyl or ethyl), alkoxy (e.g., methoxy), acyl (e.g. acetyl or benzoyl), aroyl, aralkyl, hydroxy, hydroxyalkyl, alkoxy, aryloxy, aralkoxy, nitro, cyano, carboxy, alkoxycarbonyl, aryloxycarbonyl, aralkoxycarbonyl, acylamino, aroylamine, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, amidino, amino, carbamoyl, sulfamoyl, alkene, alkyne, protecting groups (e.g., silyl, 4,4'-dimethoxytrityl, monomethoxytrityl, or trityl(triphenylmethyl)), linkers (e.g., a linker containing an amine, ethylene glycol, quinone such as anthraquinone), detectable labels (e.g., radiolabels or fluorescent labels), and biotin.

In another aspect, the invention features a method of synthesizing a nucleic acid. This method involves synthesizing a 2-thiopyrimidine nucleoside as shown below. In desirable embodiments, the method further comprises reacting one or both compounds of the formula 4 with a phosphodiamidite (e.g., 2-cyanoethyl tetraisopropylphosphorodiamidite) to produce the corresponding nucleoside phosphoramidite. The nucleoside, nucleoside phosphoramidite, or nucleotide is incorporated into a nucleic acid of the invention.

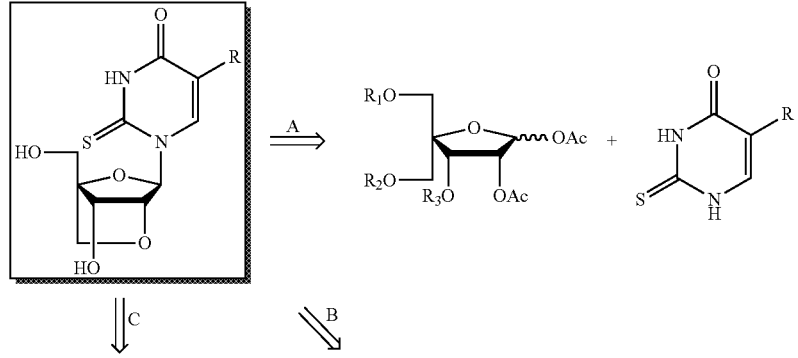

-continued

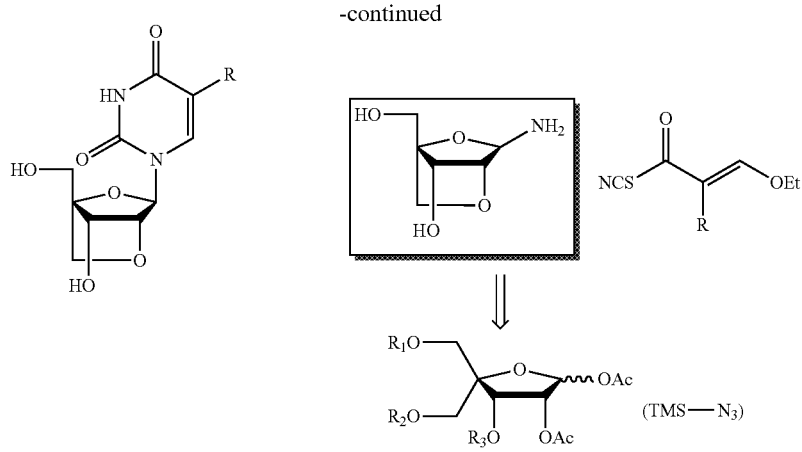

In some embodiments, a glycosyl-donor is coupled to a nucleobase as shown in pathway A. In other embodiments, ring synthesis of the nucleobase is performed as show in pathway B. In still other embodiments, LNA-T diol is modified as shown in pathway C.

4 as shown below. The nucleoside, nucleoside phosphoramidite, or nucleotide is incorporated into a nucleic acid of the invention. This method can also be performed using any other appropriate protecting groups instead of Bn (benzyl), Ac (acetyl), or Ms (methansulfonyl).

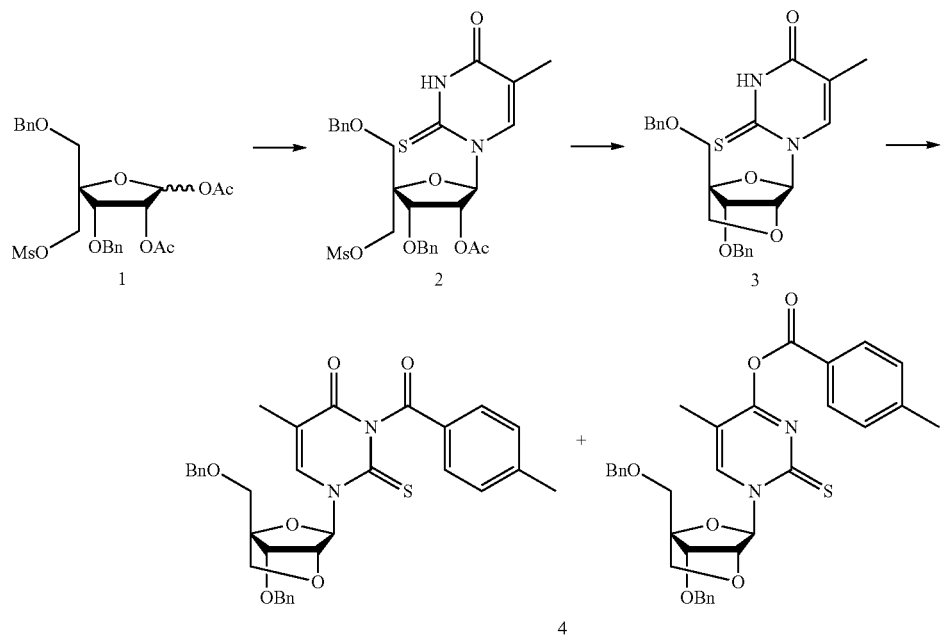

In desirable embodiments, R is hydrogen, methyl, 1-propynyl, thiazol-2-yl, pyridine-2-yl, thien-2-yl, imidazol-2-yl, (4/5-methyl)-thiazol-2-yl, 3-(iodoacetamido)propyl, 4-[N,N-bis(3-aminopropyl)amino]butyl, or halo (e.g., chloro, bromo, iodo, fluoro). Desirably, $R_1$, $R_2$, and $R_3$ are each any appropriate protecting group such as acetyl, benzyl, silyl, 4,4'-dimethoxytrityl, monomethoxytrityl, or trityl(triphenylmethyl).

In another aspect, the invention features a method of synthesizing a nucleic acid. This method involves synthesizing a 2-thiopyrimidine nucleoside or nucleotide of formula 4 using a compound of formula 3, compounds of the formula 2 and 3, or compounds of the formula 1, 2, and In desirable embodiments, the method further comprises reacting one or both compounds of the formula 4 with a phosphodiamidite (e.g., 2-cyanoethyl tetraisopropylphosphorodiamidite) to produce the corresponding nucleoside phosphoramidite.

In another aspect, the invention features a method of synthesizing a nucleic acid. This method involves synthesizing a nucleoside or nucleotide of formula 10 or 11 using a compound of any one of the formula 6-9, compounds of the formula 5 and any one of the formulas 6-9, or compounds of the formula 4, 5, and any one of the formulas 6-9 as shown below. The nucleoside, nucleoside phosphoramidite, or nucleotide is incorporated into a nucleic acid of the invention. This method can also be performed using any other appropriate protecting groups instead of DMT, Bn, Ac, or Ms.

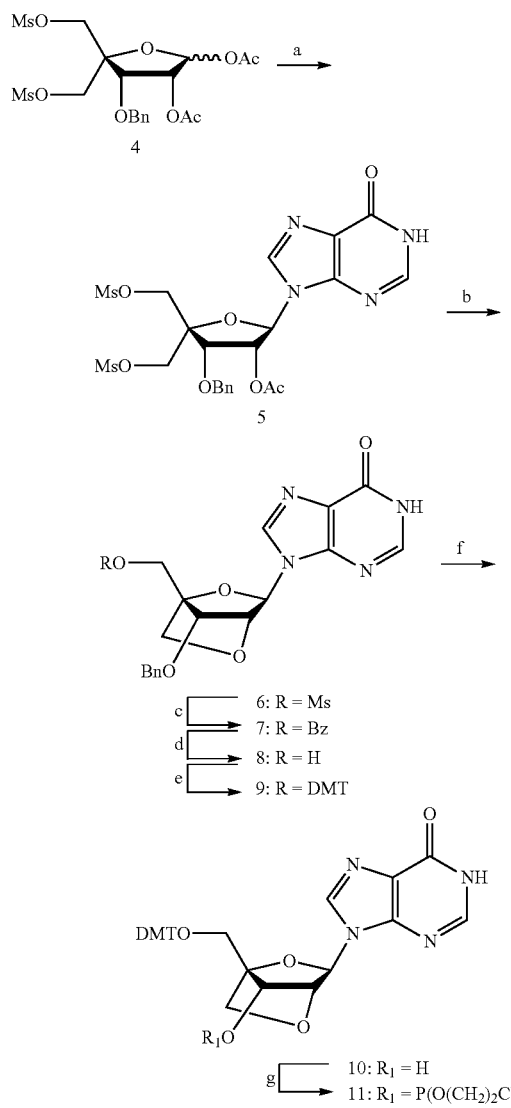

In some embodiments, a compound of formula 4 is used as a glycosyl donor in a coupling reaction with silylated hypoxanthine to form a compound of the formula 5. In certain embodiments, a compound of the formula 5 is used in a ring closing reaction to form a compound of the formula 6. Desirably, deprotection of the 5'-hydroxy group of compound 6 is performed by displacing the 5'-O-mesyl group with sodium benzoate to produce a compound of the formula 7 that is converted into a compound of the formula 8 after saponification of the 5'-benzoate. In some embodiments, compound 8 is converted to a DMT-protected compound 9 prior to debenzylation of the 3'-O-hydroxy group. In desirable embodiments, a phosphoramidite of the formula 11 is generated by phosphitylation of a nucleoside of the formula 10.

In desirable embodiments, the $R_1$ is H or $P(O(CH_2)_2CN)N(iPr)_2$. In other embodiments, the group $R_1$ or $—OR_1$ is any of the groups listed for $R^3$ or $R^{3'}$ in formula Ia or formula Ib or listed for $R^3$ or $R^{3*}$ in formula IIa, Scheme A, or Scheme B, or the group $—OR_1$ or $R_1$ is selected from the group consisting of $—OH$, $P(O(CH_2)_2CN)N(iPr)_2$, phosphate, phosphorothioate, phosphorodithioate, phosphoramidate, phosphoroselenoate, phosphorodiselenoate, alkylphosphotriester, methyl phosphonate, halo (e.g., chloro, fluoro, iodo, or bromo), optionally substituted aryl, (e.g., phenyl or benzyl), alkyl (e.g, methyl or ethyl), alkoxy (e.g., methoxy), acyl (e.g. acetyl or benzoyl), aroyl, aralkyl, hydroxy, hydroxyalkyl, alkoxy, aryloxy, aralkoxy, nitro, cyano, carboxy, alkoxycarbonyl, aryloxycarbonyl, aralkoxycarbonyl, acylamino, aroylamine, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, amidino, amino, carbamoyl, sulfamoyl, alkene, alkyne, protecting groups (e.g., silyl, 4,4'-dimethoxytrityl, monomethoxytrityl, or trityl(triphenylmethyl)), linkers (e.g., a linker containing an amine, ethylene glycol, quinone such as anthraquinone), detectable labels (e.g., radiolabels or fluorescent labels), and biotin.

In another aspect, the invention features a method of synthesizing a nucleic acid. This method involves synthesizing a nucleoside or nucleotide of formula 20 or 21 as shown below, in which compound 4 is the same sugar shown in the above aspect. The nucleoside, nucleoside phosphoramidite, or nucleotide is incorporated into a nucleic acid of the invention. This method can also be performed using any other appropriate protecting groups instead of DMT, Bn, Bz (benzoyl), Ac, or Ms. Additionally, the method can be performed with any other halogen (e.g., fluoro or bromo) instead of chloro.

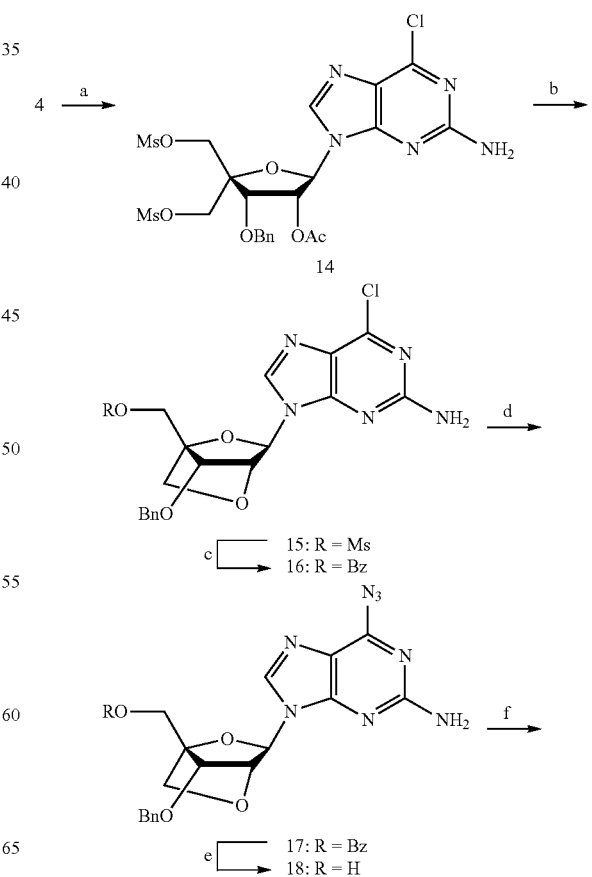

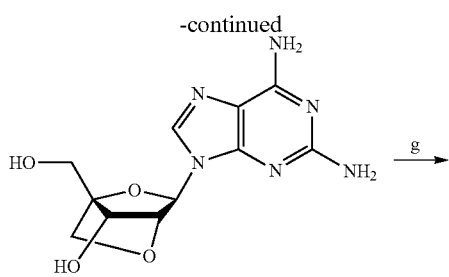

19

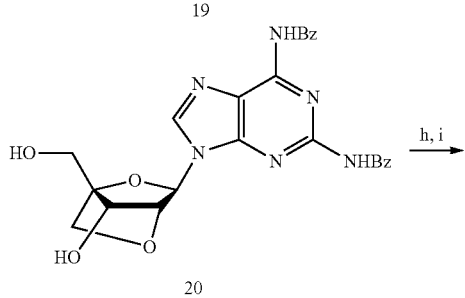

20

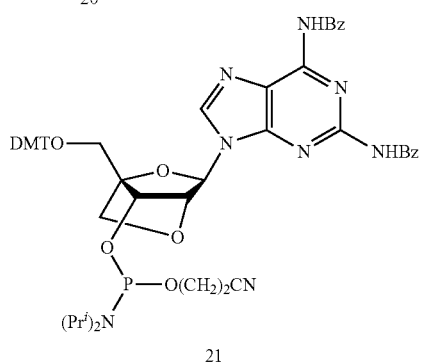

21 alkene, alkyne, protecting groups (e.g., silyl, 4,4'-dimethoxytrityl, monomethoxytrityl, or trityl(triphenylmethyl)), linkers (e.g., a linker containing an amine, ethylene glycol, quinone such as anthraquinone), detectable labels (e.g., radiolabels or fluorescent labels), and biotin.

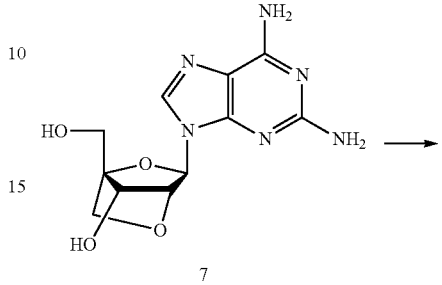

7

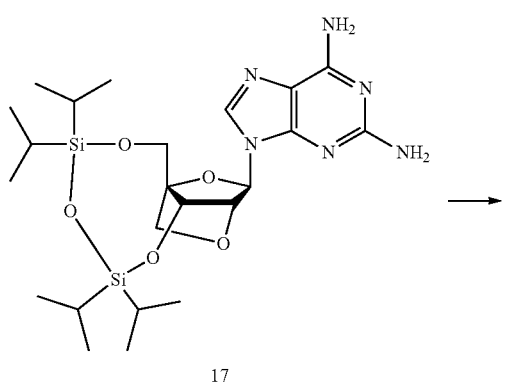

17

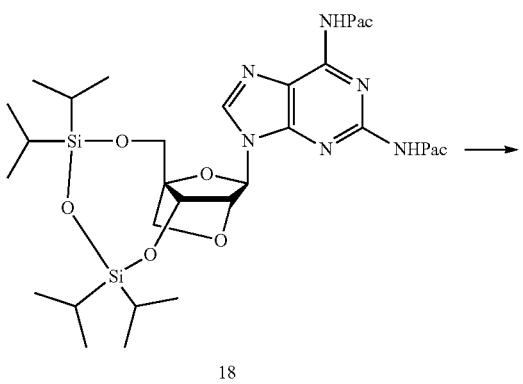

18

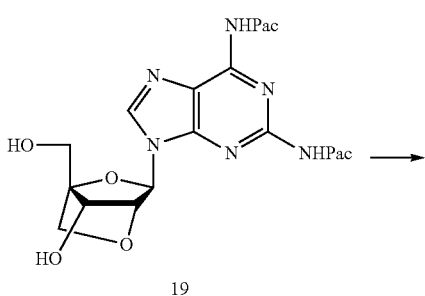

19

In desirable embodiments to promote the ring closing reaction, a solution of compound 14 in aqueous 1,4-dioxane is treated with sodium hydroxide to give a bicyclic compound 15. In some embodiments, sodium benzoate is used for displacement of 5'-mesylate of compound 15 to give compound 16. In some embodiments, compound 17 is formed by reaction of compound 16 with sodium azide. In some embodiments, compound 18 is produced by saponification of the 5'-benzoate of compound 17. In certain embodiments, hydrogenation of compound 18 produces compound 19. In certain embodiments, the peracelation method is used to benzolylate the 2- and 6-amino groups of compound 19, yielding 20, which is desirably converted into the phosphoramidite compound 21.

In a related aspect, the invention features a derivative of a compound of the formula 20 or 21 as described in the above aspect in which 3'-OH or —OP(O(CH$_2$)$_2$CN)N(iPr)$_2$ group is replaced by any other group is selected from the group consisting of phosphorothioate, phosphorodithioate, phosphoramidate, phosphoroselenoate, phosphorodiselenoate, alkylphosphotriester, methyl phosphonate, halo (e.g., chloro, fluoro, iodo, or bromo), optionally substituted aryl, (e.g., phenyl or benzyl), alkyl (e.g, methyl or ethyl), alkoxy (e.g., methoxy), acyl (e.g. acetyl or benzoyl), aroyl, aralkyl, hydroxy, hydroxyalkyl, alkoxy, aryloxy, aralkoxy, nitro, cyano, carboxy, alkoxycarbonyl, aryloxycarbonyl, aralkoxycarbonyl, acylamino, aroylamine, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, amidino, amino, carbamoyl, sulfamoyl,

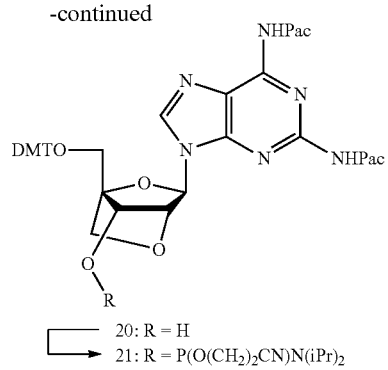

20: R = H
21: R = P(O(CH$_2$)$_2$CN)N(iPr)$_2$

In yet another aspect, the invention features a method of synthesizing a nucleic acid. This method involves synthesizing a nucleoside or nucleotide of formula 20 or 21 as shown below. The nucleoside, nucleoside phosphoramidite, or nucleotide is incorporated into a nucleic acid of the invention. This method can also be performed using any other appropriate protecting groups instead of DMT.

In some embodiments, compound 17 is formed by reaction of compound 7 with 1,3-dichloro-1,1,3,3-tetraisopropyldisiloxane. Desirably, compound 18 is formed by reaction of compound 17 with phenoxyacetic anhydride. In some embodiments, compound 19 is generated by reaction of compound 18 with acid. Desirably, compound 20 is produced by reacting compound 19 with DMT-Cl. In desirably embodiments, compound 20 is reacted with 2-cyanoethyl tetraisopropylphosphorodiamidite to give the phosphoramidite 21.

In desirable embodiments, the R is H or P(O(CH$_2$)$_2$CN)N(iPr)$_2$. In other embodiments, the R or —OR is any of the groups listed for R$^3$ or R$^{3'}$ in formula Ia or formula Ib or listed for R$^3$ or R$^{3*}$ in formula IIa, Scheme A, or Scheme B, or the group —OR or R is selected from the group consisting of —OH, P(O(CH$_2$)$_2$CN)N(iPr)$_2$, phosphate, phosphorothioate, phosphorodithioate, phosphoramidate, phosphoroselenoate, phosphorodiselenoate, alkylphosphotriester, methyl phosphonate, halo (e.g., chloro, fluoro, iodo, or bromo), optionally substituted aryl, (e.g., phenyl or benzyl), alkyl (e.g, methyl or ethyl), alkoxy (e.g., methoxy), acyl (e.g. acetyl or benzoyl), aroyl, aralkyl, hydroxy, hydroxyalkyl, alkoxy, aryloxy, aralkoxy, nitro, cyano, carboxy, alkoxycarbonyl, aryloxycarbonyl, aralkoxycarbonyl, acylamino, aroylamine, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, amidino, amino, carbamoyl, sulfamoyl, alkene, alkyne, protecting groups (e.g., silyl, 4,4'-dimethoxytrityl, monomethoxytrityl, or trityl(triphenylmethyl)), linkers (e.g., a linker containing an amine, ethylene glycol, quinone such as anthraquinone), detectable labels (e.g., radiolabels or fluorescent labels), and biotin.

In yet another aspect, the invention features a method of synthesizing a nucleic acid. This method involves synthesizing a nucleoside or nucleotide of formula 24 or 25 as shown below. The nucleoside, nucleoside phosphoramidite, or nucleotide is incorporated into a nucleic acid of the invention. This method can also be performed using any other appropriate protecting groups instead of Bz, Bn, and DMT. Additionally, the method can be performed with any other halogen (e.g., fluoro or bromo) instead of chloro.

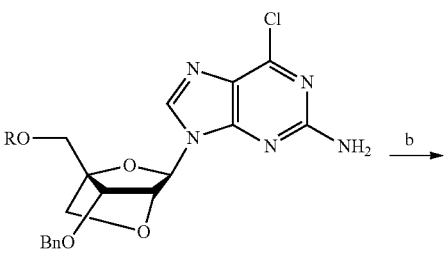

a [ 16: R = Bz
    22: R = H

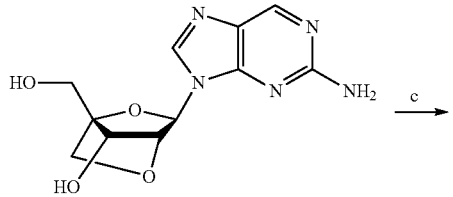

23

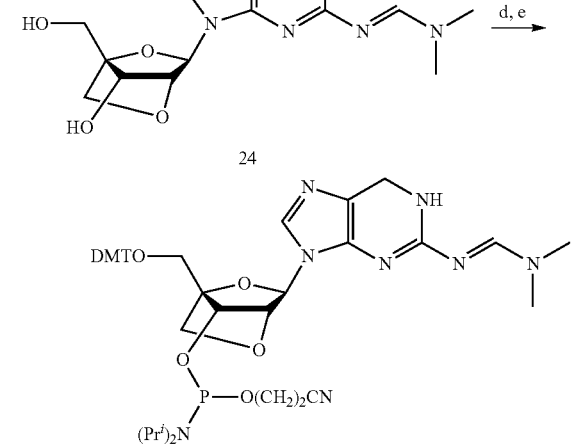

25

In some embodiments, the compound 16 is formed from compounds 4, 14, and 15 as illustrated in an aspect above. Desirably, the 5'-O-benzoyl group of compound 16 is hydrolyzed by aqueous sodium hydroxyde to give compound 22. Compound 23 is desirably produced by incubation of compound 22 in the presence of paladium hydroxide and ammonium formate. Desirably, the 2-amine of compound 23 is selectively protected with an amidine group after treatment with N,N-dimethylformamide dimethyl acetal to yield compound 24. In some embodiments, the diol 24 is 5'-O-DMT protected and 3'-O-phosphitylated produce the phosphoramidite LNA-2AP compound 25.

In some embodiments, compound 25 has one of the following groups instead of the P(O(CH$_2$)$_2$CN)N(iPr)$_2$ group: any of the groups listed for R$^3$ or R$^{3'}$ in formula Ia or formula Ib or listed for R$^3$ or R$^{3*}$ in formula IIa, Scheme A, or Scheme B, or a group selected from the group consisting of —OH, phosphate, phosphorothioate, phosphorodithioate, phosphoramidate, phosphoroselenoate, phosphorodiselenoate, alkylphosphotriester, methyl phosphonate, halo (e.g., chloro, fluoro, iodo, or bromo), optionally substituted aryl, (e.g., phenyl or benzyl), alkyl (e.g, methyl or ethyl), alkoxy (e.g., methoxy), acyl (e.g. acetyl or benzoyl), aroyl, aralkyl, hydroxy, hydroxyalkyl, alkoxy, aryloxy, aralkoxy, nitro, cyano, carboxy, alkoxycarbonyl, aryloxycarbonyl, aralkoxycarbonyl, acylamino, aroylamine, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, amidino, amino, carbamoyl, sulfamoyl, alkene, alkyne, protecting groups (e.g., silyl, 4,4'-dimethoxytrityl, monomethoxytrityl, or trityl(triphenylmethyl)), linkers (e.g., a linker containing an amine, ethylene glycol, quinone such as anthraquinone), detectable labels (e.g., radiolabels or fluorescent labels), and biotin.

In another aspect, the invention features a nucleic acid of the invention that includes a compound of the formula 6pC or the product of a compound of the formula 6pC treated with ammonia as described herein. In a related aspect, the invention features a method of synthesizing a nucleic acid that involves performing one or more of the steps described herein for the synthesis of a compound of the formula 6pC or the product of a compound of the formula 6pC treated with ammonia.

In yet another aspect, the invention features a method of synthesizing a nucleic acid. This method involves one or more of any of the nucleosides or nucleotides of the invention with (i) any other nucleoside or nucleotide of the invention, (ii) any other nucleoside or nucleotide of formula Ia, formula Ib, formula IIa, Scheme A, or Scheme B, and/or (iii) any naturally-occurring nucleoside or nucleotide. Desirably, the method involves reacting one or more nucleoside phosphoramidites of any of the above aspects with a nucleotide or nucleic acid.

Methods for Synthesis of Nucleic Acids on a Solid Support

In another aspect, the invention provides a method for the synthesis of a population of nucleic acids (e.g., a population of nucleic acids of the invention) on a solid support. This method involves the reaction of a plurality of nucleoside phosphoramidites with an activated solid support (e.g., a solid support with an activated linker) and the subsequent reaction of a plurality of nucleoside phosphoramidites with activated nucleotides or nucleic acids bound to the solid support.

In some embodiments of any of the above aspects, the solid support or the growing nucleic acid bound to the solid support is activated by illumination, a photogenerated acid, or electric current. In desirable embodiments, one or more spots or regions (e.g., a region with an area of less than 1 cm$^2$, 0.1 cm$^2$, 0.01 cm$^2$, 1 mm$^2$, or 0.1 mm$^2$ that desirably contains one particular nucleic acid monomer or oligomer) on the solid support are irradiated to produce a photogenerated acid that removes the 5'-OH protecting group of one or more nucleic acid monomers or oligomers to which a nucleotide is subsequently added. In other embodiments, an electric current is applied to one or more spots or regions (e.g., a region with an area of less than 1 cm$^2$, 0.1 cm$^2$, 0.01 cm$^2$, 1 mm$^2$, or 0.1 mm$^2$ that desirably contains one particular nucleic acid monomer or oligomer) on the solid support to remove an electrochemically sensitive protecting group of one or more nucleic acid monomers or oligomers to which a nucleotide is subsequently added. In still other embodiments, one or more spots or regions (e.g., a region with an area of less than 1 cm$^2$, 0.1 cm$^2$, 0.01 cm$^2$, 1 mm$^2$, or 0.1 mm$^2$ that desirably contains one particular nucleic acid monomer or oligomer) on the solid support are irradiated to remove a photosensitive protecting group of one or more nucleic acid monomers or oligomers to which a nucleotide is subsequently added. In various embodiments, the solid support (e.g., chip, coverslip, microscope glass slide, quartz, or silicon) is less than 1, 0.5, 0.1. or 0.05 mm thick.

Methods for the Synthesis of Nucleic Acids

In another aspect, the invention features a method of reacting a population of nucleic acids of the invention with one or more nucleic acids. This method involves incubating an immobilized population of nucleic acids of the invention with a solution that includes one or more probes (e.g., at least 2, 3, 4, 5, 10, 15, 20, 30, 40, 50, 60, 80, 100, or 150 different nucleic acids) and one or more target nucleic acids (e.g., at least 2, 3, 4, 5, 10, 15, 20, 30, 40, 50, 60, 80, 100, or 150 different target nucleic acids). The incubation is performed in the presence of a ligase under conditions that allow the ligase to covalently react one or more immobilized nucleic acids with one or more nucleic acid probes in solution that hybridize to the same target nucleic acid. Desirably, at least 2, 5, 10, 15, 20, 30, 40, 50, 80, or 100 pairs of immobilized nucleic acids and nucleic acid probes are ligated. In various embodiments, the incubation occurs between 15 and 45° C., such as between 20 and 40° C. or between 25 and 35° C.

Desirable Embodiments of any of the Aspects of the Invention

In other embodiments of any of various aspects of the invention, a nucleic acid probe or primer specifically hybridizes to a target nucleic acid but does not substantially hybridize to non-target molecules, which include other nucleic acids in a cell or biological sample having a sequence that is less than 99, 95, 90, 80, or 70% identical or complementary to that of the target nucleic acid. Desirably, the amount of the these non-target molecules hybridized to, or associated with, the nucleic acid probe or primer, as measured using standard assays, is 2-fold, desirably 5-fold, more desirably 10-fold, and most desirably 50-fold lower than the amount of the target nucleic acid hybridized to, or associated with, the nucleic acid probe or primer. In other embodiments, the amount of a target nucleic acid hybridized to, or associated with, the nucleic acid probe or primer, as measured using standard assays, is 2-fold, desirably 5-fold, more desirably 10-fold, and most desirably 50-fold greater than the amount of a control nucleic acid hybridized to, or associated with, the nucleic acid probe or primer. In certain embodiments, the nucleic acid probe or primer is substantially complementary (e.g., at least 80, 90, 95, 98, or 100% complementary) to a target nucleic acid or a group of target nucleic acids from a cell. In other embodiments, the probe or primer is homologous to multiple RNA or DNA molecules, such as RNA or DNA molecules from the same gene family. In other embodiments, the probe or primer is homologous to a large number of RNA or DNA molecules. In desirable embodiments, the probe or primer binds to nucleic acids which have polynucleotide sequences that differ in sequence at a position that corresponds to the position of a universal base in the probe or primer. Examples of control nucleic acids include nucleic acids with a random sequence or nucleic acids known to have little, if any, affinity for the nucleic acid probe or primer. In some embodiments, the target nucleic acid is an RNA, DNA, or cDNA molecule.

Desirably, the association constant ($K_a$) of the nucleic acid toward a complementary target molecule is higher than the association constant of the complementary strands of the double stranded target molecule. In some desirable embodiments, the melting temperature of a duplex between the nucleic acid and a complementary target molecule is higher than the melting temperature of the complementary strands of the double stranded target molecule.

In some embodiments, the LNA-pyrene is in a position corresponding to the position of a non-base (e.g., a unit without a base) in another nucleic acid, such as a target nucleic acid. Incorporation of pyrene in a DNA strand that is hybridized against the four natural bases decreases the $T_m$ by -4.5° C. to -6.8° C.; however, incorporation of pyrene in a DNA strand in a position opposite a non-base only decreases the $T_m$ by -2.3° C. to -4.6° C., most likely due to the better accommodation of the pyrene in the B-type duplex (Matray and Kool, J. Am. Chem. Soc. 120, 6191, 1998). Thus, incorporation on LNA-pyrene into a nucleic acid in a position opposite a non-base (e.g., a unit without a base or a unit with a small group such as a noncyclic group instead of a base) in a target nucleic acid may also minimize any potential decrease in $T_m$ due to the pyrene substitution.

In various embodiments, the number of molecules in the plurality of nucleic acids of the invention is at least 2, 4, 5, 6, 7, 8, or 10-fold greater than the number of molecules in the test nucleic acid sample. In some embodiments, a LNA is a triplex-forming oligonucleotide.

In desirable embodiments of any of the aspects of the invention, the target nucleic acids (e.g., cDNA molecules reverse transcribed from a patient sample or cRNA molecules amplified from a patient sample using a T7 RNA polymerase-based amplification system or the like) are fragmented using an enzyme such as a uracil-DNA glycosylase (e.g., *E. coli* uracil-DNA glycosylase) or using chemical hydrolysis such as alkaline hydrolysis. In various embodiments, the average size of the fragmented nucleic acids is between 300 and 50 nucleic acids, such as approximately 300, 200, 100, or 50 nucleotides.

Advantages

The present invention has a variety of advantages related to nucleic acid analysis methods. The ability to equalize melting temperatures of a series of nucleic acids is generally applicable and desirable in all situations where more than one sequence is used simultaneously (e.g. DNA arrays with more than one capture probe, PCR and especially multiplex PCR, homogeneous assays such as Taqman and Molecular beacon). Sample preparation of specific sequences (e.g., DNA or RNA extraction using capture probes on filters or magnetic beads) is another area where melting temperature equalization of specific probe sequences is useful.

For example, the invention provides high affinity nucleotides (e.g., LNA and other high affinity nucleotides with a modified base and/or backbone) that can be used, e.g., arrays of the invention. In particular, the nucleic acids of the invention containing LNA units exhibited a surprising ability to discriminate between different mRNA splice variants compared to naturally-occurring nucleic acids. If desired, universal bases can be added as part of flanking regions in capture probes (e.g., probes of an array) to stabilize hybridization with high affinity nucleotides in the capture probes. Replacement of one or more DNA-t nucleotides with LNA-T and/or replacement of one or more DNA-a nucleotides with LNA-A reduces the variability of melting temperatures for capture probes of similar length but different GC and AT content by desirably at least 10, 20, 30, 40 or 50%. Additionally, replacement of one or more DNA-t nucleotides with LNA-T and/or replacement of one or more DNA-c with LNA-C increases the stability of a large number of capture probes, while desirably avoiding self-complementary sequences with LNA:LNA base-pairs within a capture probe that would otherwise reduce or eliminate the binding of target molecules to the probe. Although a general T and C substitution may not reduce the variability of melting temperatures of the probes, this substitution increases the melting temperature and binding efficiency of many capture probes that contain these two nucleotides.

The invention also provides a general substitution algorithm for enhancement of the hybridization signal of a test nucleic acid sample by inclusion of high affinity monomers (e.g., LNA and other high affinity nucleotides with a modified base and/or backbone) in the array. This method increases the stability and binding affinity of capture probes while avoiding substitutions in positions that may form self-complementary base-pairs which may otherwise inhibit binding to a target molecule. The substitution algorithm is broadly useful for specialized arrays, as well as for PCR primers and FISH probes.

Other features and advantages of the invention will be apparent from the following detailed description.

Definitions

When used herein, the term "LNA" (Locked Nucleoside Analogues) refers to nucleoside analogues (e.g., bicyclic nucleoside analogues, e.g., as disclosed in WO 9914226) either incorporated in an oligonucleotide or as a discrete chemical species (e.g., LNA nucleoside and LNA nucleotide). Furthermore, the term "LNA" includes the compounds as described in the present specificatiion including the compounds described in Example 17.

The term "monomeric LNA" may, e.g., refer to the monomers LNA A, LNA T, LNA C, or any other LNA monomers.

By "LNA unit" is meant an individual LNA monomer (e.g., an LNA nucleoside or LNA nucleotide) or an oligomer (e.g., an oligonucleotide or nucleic acid) that includes at least one LNA monomer. LNA units as disclosed in WO 99/14226 are in general particularly desirable modified nucleic acids for incorporation into an oligonucleotide of the invention. Additionally, the nucleic acids may be modified at either the 3' and/or 5' end by any type of modification known in the art. For example, either or both ends may be capped with a protecting group, attached to a flexible linking group, attached to a reactive group to aid in attachment to the substrate surface, etc. Desirable LNA units and their method of synthesis also are disclosed in WO 0056746, WO 0056748, WO 0066604, Morita et al., Bioorg. Med. Chem. Lett. 12(1):73-76, 2002; Hakansson et al., Bioorg. Med. Chem. Lett. 11(7):935-938, 2001; Koshkin et al., J. Org. Chem. 66(25):8504-8512, 2001; Kvaerno et al., J. Org. Chem. 66(16):5498-5503, 2001; Hakansson et al., J. Org. Chem. 65(17):5161-5166, 2000; Kvaerno et al., J. Org. Chem. 65(17):5167-5176, 2000; Pfundheller et al., Nucleosides Nucleotides 18(9):2017-2030, 1999; and Kumar et al., Bioorg. Med. Chem. Lett. 8(16):2219-2222, 1998.

By "LNA modified oligonucleotide" is meant a oligonucleotide comprising at least one LNA monomeric unit of the general scheme A, described infra, having the below described illustrative examples of modifications:

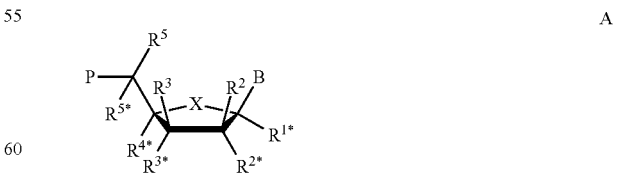

A wherein X is selected from —O—, —S—, —N($R^N$)—, —C($R^6R^{6*}$)—, —O—C($R^7R^{7*}$)—, —C($R^6R^{6*}$)—O—, —S—C($R^7R^{7*}$)—, —C($R^6R^{6*}$)—S—, —N($R^{N*}$)—C($R^7R^{7*}$)—, —C($R^6R^{6*}$)—N($R^{N*}$)—, and —C($R^6R^{6*}$)—C($R^7R^{7*}$).

B is selected from a modified base as discussed above e.g. an optionally substituted carbocyclic aryl such as optionally substituted pyrene or optionally substituted pyrenylmethylglycerol, or an optionally substituted heteroalicylic or optionally substituted heteroaromatic such as optionally substituted pyridyloxazole, optionally substituted pyrrole, optionally substituted diazole or optionally substituted triazole moieties; hydrogen, hydroxy, optionally substituted $C_{1-4}$-alkoxy, optionally substituted $C_{1-4}$-alkyl, optionally substituted $C_{1-4}$-acyloxy, nucleobases, DNA intercalators, photochemically active groups, thermochemically active groups, chelating groups, reporter groups, and ligands.

P designates the radical position for an internucleoside linkage to a succeeding monomer, or a 5'-terminal group, such internucleoside linkage or 5'-terminal group optionally including the substituent $R^5$. One of the substituents $R^2$, $R^{2*}$, $R^3$, and $R^{3*}$ is a group P* which designates an internucleoside linkage to a preceding monomer, or a 2'/3'-terminal group. The substituents of $R^{1*}$, $R^{4*}$, $R^5$, $R^{5*}$, $R^6$, $R^{6*}$, $R^7$, $R^{7*}$, $R^N$, and the ones of $R^2$, $R^{2*}$, $R^3$, and $R^{3*}$ not designating P* each designates a biradical comprising about 1-8 groups/atoms selected from —C($R^aR^b$)—, —C($R^a$)=C($R^a$)—, —C($R^a$)=N—, —C($R^a$)—O—, —O—, —Si($R^a$)$_2$—, —C($R^a$)—S—, —S—, —SO$_2$—, —C($R^a$)—N($R^b$)—, —N($R^a$)—, and >C=Q, wherein Q is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, hetero-aryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyeamino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents $R^a$ and $R^b$ together may designate optionally substituted methylene (=CH$_2$), and wherein two non-geminal or geminal substituents selected from $R^a$, $R^b$, and any of the substituents $R^{1*}$, $R^2$, $R^{2*}$, $R^3$, $R^{3*}$, $R^{4*}$, $R^5$, $R^{5*}$, $R^6$ and $R^{6*}$, $R^7$, and $R^{7*}$ which are present and not involved in P, P* or the biradical(s) together may form an associated biradical selected from biradicals of the same kind as defined before; the pair(s) of non-geminal substituents thereby forming a mono- or bicyclic entity together with (i) the atoms to which said non-geminal substituents are bound and (ii) any intervening atoms.

Each of the substituents $R^{1*}$, $R^2$, $R^{2*}$, $R^3$, $R^{4*}$, $R^5$, $R^{5*}$, $R^6$ and $R^{6*}$, $R^7$, and $R^{7*}$ which are present and not involved in P, P* or the biradical(s), is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene, or together may form a spiro biradical consisting of a 1-5 carbon atom(s) alkylene chain which is optionally interrupted and/or terminated by one or more heteroatoms/groups selected from —O—, —S—, and —(NR$^N$)— where $R^N$ is selected from hydrogen and $C_{1-4}$-alkyl, and where two adjacent (non-geminal) substituents may designate an additional bond resulting in a double bond; and $R^{N*}$, when present and not involved in a biradical, is selected from hydrogen and $C_{1-4}$-alkyl; and basic salts and acid addition salts thereof.

Exemplary 5', 3', and/or 2' terminal groups include —H, —OH, halo (e.g., chloro, fluoro, iodo, or bromo), optionally substituted aryl, (e.g., phenyl or benzyl), alkyl (e.g, methyl or ethyl), alkoxy (e.g., methoxy), acyl (e.g. acetyl or benzoyl), aroyl, aralkyl, hydroxy, hydroxyalkyl, alkoxy, aryloxy, aralkoxy, nitro, cyano, carboxy, alkoxycarbonyl, aryloxycarbonyl, aralkoxycarbonyl, acylamino, aroylamine, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, amidino, amino, carbamoyl, sulfamoyl, alkene, alkyne, protecting groups (e.g., silyl, 4,4'-dimethoxytrityl, monomethoxytrityl, or trityl (triphenylmethyl)), linkers (e.g., a linker containing an amine, ethylene glycol, quinone such as anthraquinone), detectable labels (e.g., radiolabels or fluorescent labels), and biotin.

It is understood that references herein to a nucleic acid unit, nucleic acid residue, LNA unit, or similar term are inclusive of both individual nucleoside units and nucleotide units and nucleoside units and nucleotide units within an oligonucleotide.

A "modified base" or other similar term refers to a composition (e.g., a non-naturally occurring nucleobase or nucleosidic base) which can pair with a natural base (e.g., adenine, guanine, cytosine, uracil, and/or thymine) and/or can pair with a non-naturally occurring nucleobase or nucleosidic base. Desirably, the modified base provides a $T_m$ differential of 15, 12, 10, 8, 6, 4, or 2° C. or less as described herein. Exemplary modified bases are described in EP 1 072 679 and WO 97/12896.

By "nucleobase" is meant the naturally occurring nucleobases adenine (A), guanine (G), cytosine (C), thymine (T) and uracil (U) as well as non-naturally occurring nucleobases such as xanthine, diaminopurine, 8-oxo-$N^6$-methyladenine, 7-deazaxanthine, 7-deazaguanine, $N^4$,$N^4$-ethanocytosin, $N^6$,$N^6$-ethano-2,6-diaminopurine, 5-methylcytosine (mC), 5-($C^3$-$C^6$)-alkynyl-cytosine, 5-fluorouracil, 5-bromouracil, pseudoisocytosine, 2-hydroxy-5-methyl-4-triazolopyridin, isocytosine, isoguanine, inosine and the "non-naturally occurring" nucleobases described in Benner et al., U.S. Pat. No. 5,432,272 and Susan M. Freier and Karl-Heinz Altmann, Nucleic Acids Research, 1997, vol. 25, pp 4429-4443. The term "nucleobase" thus includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., Angewandte Chemie, International Edition, 1991, 30, 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). The term "nucleosidic base" or "base unit" is further intended to include compounds such as heterocyclic compounds that can serve like nucleobases including certain "universal bases" that are not nucleosidic bases in the most classical sense but serve as nucleosidic bases. Especially mentioned as universal bases are 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

As described herein, various groups of an LNA unit may be optionally substituted. A "substituted" group such as a nucleobase or nucleosidic base and the like may be substituted by other than hydrogen at one or more available positions, typically 1 to 3 or 4 positions, by one or more suitable groups such as those disclosed herein. Suitable groups that may be present on a "substituted" group include e.g. halogen such as fluoro, chloro, bromo and iodo; cyano; hydroxyl; nitro; azido; alkanoyl such as a $C_{1-6}$ alkanoyl group such as acyl and the like; carboxamido; alkyl groups including those groups having 1 to about 12 carbon atoms, or 1, 2, 3, 4, 5, or 6 carbon atoms; alkenyl and alkynyl groups including groups having one or more unsaturated linkages and from 2 to 12 carbon, or 2, 3, 4, 5 or 6 carbon atoms; alkoxy groups including those having one or more oxygen linkages and from 1 to about 12 carbon atoms, or 1, 2, 3, 4, 5 or 6 carbon atoms; aryloxy such as phenoxy; alkylthio groups including those moieties having one or more thioether linkages and from 1 to about 12 carbon atoms, or 1, 2, 3, 4, 5 or 6 carbon atoms; alkylsulfinyl groups including those moieties having one or more sulfinyl linkages and from 1 to about 12 carbon atoms, or 1, 2, 3, 4, 5, or 6 carbon atoms; alkylsulfonyl groups including those moieties having one or more sulfonyl linkages and from 1 to about 12 carbon atoms, or 1, 2, 3, 4, 5, or 6 carbon atoms; aminoalkyl groups such as groups having one or more N atoms and from 1 to about 12 carbon atoms, or 1, 2, 3, 4, 5 or 6 carbon atoms; carbocyclic aryl having 6 or more carbons; aralkyl having 1 to 3 separate or fused rings and from 6 to about 18 carbon ring atoms, with benzyl being a desirable group; aralkoxy having 1 to 3 separate or fused rings and from 6 to about 18 carbon ring atoms, with O-benzyl being a desirable group; or a heteroaromatic or heteroalicyclic group having 1 to 3 separate or fused rings with 3 to about 8 members per ring and one or more N, O or S atoms, e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl.

By "oxy-LNA monomer or unit" is meant any nucleoside or nucleotide which contains an oxygen atom in a 2'-4' linkage.

A "non-oxy-LNA" monomer or unit is broadly defined as any nucleoside or nucleotide which does not contain an oxygen atom in a 2'-4'-linkage. Examples of non-oxy-LNA monomers include 2'-deoxynucleotides (DNA) or nucleotides (RNA) or any analogues of these monomers which are not oxy-LNA, such as for example the thio-LNA and amino-LNA described herein with respect to formula Ia and in Singh et al. J. Org. Chem. 1998, 6, 6078-9, and the derivatives described in Susan M. Freier and Karl-Heinz Altmann, Nucleic Acids Research, 1997, vol 25, pp 4429-4443.

By "universal base" is meant a naturally-occurring or desirably a non-naturally occurring compound or moiety that can pair with a natural base (e.g., adenine, guanine, cytosine, uracil, and/or thymine), and that has a $T_m$ differential of 15, 12, 10, 8, 6, 4, or 2° C. or less as described herein.

By "oligonucleotide," "oligomer," or "oligo" is meant a successive chain of monomers (e.g., glycosides of heterocyclic bases) connected via internucleoside linkages. The linkage between two successive monomers in the oligo consist of 2 to 4, desirably 3, groups/atoms selected from —$CH_2$—, —O—, —S—, —$NR^H$—, >C=O, >C=$NR^H$, >C=S, —$Si(R'')_2$—, —SO—, —$S(O)_2$—, —$P(O)_2$—, —$PO(BH_3)$—, —P(O,S)—, —$P(S)_2$—, —PO(R'')—, —PO($OCH_3$)—, and —PO($NHR^H$)—, where $R^H$ is selected from hydrogen and $C_{1-4}$-alkyl, and R'' is selected from $C_{1-6}$-alkyl and phenyl. Illustrative examples of such linkages are —$CH_2$—$CH_2$—$CH_2$—, —$CH_2$—CO—$CH_2$—, —$CH_2$—CHOH—$CH_2$—, —O—$CH_2$—O—, —O—$CH_2$—$CH_2$—, —O—$CH_2$—CH= (including $R^5$ when used as a linkage to a succeeding monomer), —$CH_2$—$CH_2$—O—, —$NR^H$—$CH_2$—$CH_2$—, —$CH_2$—$CH_2$—$NR^H$—, —$CH_2$—$NR^H$—$CH_2$—, —O—$CH_2$—$CH_2$—$NR^H$—, —$NR^H$—CO—O—, —$NR^H$—CO—$NR^H$—, —$NR^H$—CS—$NR^H$—, —$NR^H$—C(=$NR^H$)—$NR^H$—, —$NR^H$—CO—$CH_2$—$NR^H$—, —O—CO—O—, —O—CO—$CH_2$—O—, —O—$CH_2$—CO—O—, —$CH_2$—CO—$NR^H$—, —O—CO—$NR^H$—, —$NR^H$—CO—$CH_2$—, —O—$CH_2$—CO—$NR^H$—, —O—$CH_2$—$CH_2$—$NR^H$—, —CH=N—O—, —$CH_2$—$NR^H$—O—, —$CH_2$—O—N= (including $R^5$ when used as a linkage to a succeeding monomer), —$CH_2$—O—$NR^H$—, —CO—$NR^H$—$CH_2$—, —$CH_2$—$NR^H$—O—, —$CH_2$—$NR^H$—CO—, —O—$NR^H$—$CH_2$—, —O—$NR^H$—, —O—$CH_2$—S—, —S—$CH_2$—O—, —$CH_2$—$CH_2$—S—, —O—$CH_2$—$CH_2$—S—, —S—$CH_2$—CH= (including $R^5$ when used as a linkage to a succeeding monomer), —S—$CH_2$—$CH_2$—, —S—$CH_2$—$CH_2$—O—, —S—$CH_2$—$CH_2$—S—, —$CH_2$—S—$CH_2$—, —$CH_2$—SO—$CH_2$—, —$CH_2$—$SO_2$—$CH_2$—, —O—SO—O—, —O—$S(O)_2$—O—, —O—$S(O)_2$—$CH_2$—, —O—$S(O)_2$—$NR^H$—, —$NR^H$—$S(O)_2$—$CH_2$—, —O—$S(O)_2$—$CH_2$—, —O—$P(O)_2$—O—, —O—P(O,S)—O—, —O—$P(S)_2$—O—, —S—$P(O)_2$—O—, —S—P(O,S)—O—, —S—$P(S)_2$—O—, —O—$P(O)_2$—S—, —O—P(O,S)—S—, —O—$P(S)_2$—S—, —S—$P(O)_2$—S—, —S—P(O,S)—S—, —S—$P(S)_2$—S—, —O—PO(R'')—O—, —O—PO($OCH_3$)—O—, —O—PO($OCH_2CH_3$)—O—, —O—PO($OCH_2CH_2S$—R)—O—, —O—PO($BH_3$)—O—, —O—PO($NHR^N$)—O—, —O—$P(O)_2$—$NR^H$—, —$NR^H$—$P(O)_2$—O—, —O—P(O,$NR^H$)—O—, —$CH_2$—$P(O)_2$—O—, —O—$P(O)_2$—$CH_2$—, and —O—$Si(R'')_2$—O—; among which —$CH_2$—CO—$NR^H$—, —$CH_2$—$NR^H$—O—, —S—$CH_2$—O—, —O—$P(O)_2$—O—, —O—P(O,S)—O—, —O—$P(S)_2$—O—, —$NR^H$—P(O)_2—O—, —O—P(O,$NR^H$)—O—, —O—PO(R'')—O—, —O—PO($CH_3$)—O—, and —O—PO($NHR^N$)—O—, where $R^H$ is selected form hydrogen and $C_{1-4}$-alkyl, and R'' is selected from $C_{1-6}$-alkyl and phenyl, are especially desirable. Further illustrative examples are given in Mesmaeker et. al., Current Opinion in Structural Biology 1995, 5, 343-355 and Susan M. Freier and Karl-Heinz Altmann, Nucleic Acids Research, 1997, vol 25, pp 4429-4443. The left-hand side of the internucleoside linkage is bound to the 5-membered ring as substituent P* at the 3'-position, whereas the right-hand side is bound to the 5'-position of a preceding monomer.

By "succeeding monomer" is meant the neighboring monomer in the 5'-terminal direction, and by "preceding monomer" is meant the neighboring monomer in the 3'-terminal direction.

By "LNA spiked oligo" is meant an oligonucleotide, such as a DNA oligonucleotide, wherein at least one unit (and preferably not all units) has been substituted by the corresponding LNA nucleoside monomer.

The term "$T_m$" is used in reference to the "melting temperature." The melting temperature is the temperature at which 50% of a population of double-stranded nucleic acid molecules becomes dissociated into single strands. The equation for calculating the $T_m$ of nucleic acids is well-known in the art. The $T_m$ of a hybrid nucleic acid is often estimated using a formula adopted from hybridization assays in 1 M salt, and commonly used for calculating $T_m$ for PCR primers: $T_m$=[(number of A+T)×2° C.+(number of G+C)×4° C.]. C. R. Newton et al. PCR, 2nd Ed., Springer-Verlag (New York: 1997), p. 24. This formula was found to be inaccurate for primers longer that 20 nucleotides. Id. Other more sophisticated computations exist in the art which take structural as well as sequence characteristics into account for the calculation of $T_m$. A calculated $T_m$ is merely an estimate; the optimum temperature is commonly determined empirically.

A nucleic acid compound that has a $T_m$ differential of a specified amount (e.g., less than 15, 12, 10, 8, 6, 4, 2, or 1° C.) means the nucleic acid exhibits that specified $T_m$ differential when incorporated into a specified 9-mer oligonucleotide with respect to the four complementary variants, as defined immediately below.

Unless otherwise indicated, a $T_m$ differential provided by a particular modified base is calculated by the following protocol (steps a) through d)):

a) incorporating the modified base of interest into the following oligonucleotide 5'-d(GTGAMATGC), wherein M is the modified base;

b) mixing $1.5 \times 10^{-6}$M of the oligonucleotide having incorporated therein the modified base with each of $1.5 \times 10^{-6}$M of the four oligonucleotides having the sequence 3'-d(CACTYTACG), wherein Y is A, C, G, T, respectively, in a buffer of 10 mM sodium phosphate, 100 mM sodium chloride, 0.1 mM EDTA, pH 7.0;

c) allowing the oligonucleotides to hybridize; and d) detecting the $T_m$ for each of the four hybridized nucleotides by heating the hybridized nucleotides and observing the temperature at which the maximum of the first derivative of the melting curve recorded at a wavelength of 260 nm is obtained.

Unless otherwise indicated, a $T_m$ differential for a particular modified base is determined by subtracting the highest $T_m$ value determined in steps a) through d) immediately above from the lowest $T_m$ value determined by steps a) through d) immediately above.

By "variance in $T_m$" is meant the variance in the values of the melting temperatures for a population of nucleic acids. The $T_m$ for each nucleic acid is determined by experimentally measuring or computationally predicting the temperature at which 50% of a population double-stranded molecules with the sequence of the nucleic acid becomes dissociated into single strands. For a nucleic acid with only A, T, C, G, and/or U bases, the $T_m$ is the temperature at which 50% of a population of 100% complementary double-stranded molecules with the sequence of the nucleic acid becomes dissociated into single strands. For determining the $T_m$ variance when a nucleic acid has one or more nucleobases other than A, T, C, G, or U, the $T_m$ of this "modified" nucleic acid is approximated by determining the $T_m$ for each possible double stranded molecule in which one strand is the modified nucleic acid and the other strand has either A, T, C, or G in each position corresponding to a nucleobase other than A, T, C, G, or U in the modified nucleic acid. For example, if the modified nucleic acid has the sequence XMX in which X is 0, 1, or more A, T, C, G, or U bases and M is any other nucleobase or nucleosidic base, the $T_m$ is calculated for each possible double stranded molecule in which one strand is XMX and the other strand is X'YX' in which X' is the base complementary to the corresponding X base and Y is either A, T, C, or G. The average is then calculated for the $T_m$ values for each possible double stranded molecule (i.e., four possible duplexes per modified nucleobase or nucleoside base in the modified nucleic acid) and used as the approximate $T_m$ value for the modified nucleic acid.

By "capture efficiency" is meant the amount of target nucleic acid(s) bound to a particular nucleic acid or a population of nucleic acids. Standard methods can be used to calculate the capture efficiency by measuring the amount of bound target nucleic acid(s) and/or measuring the amount of unbound target nucleic acid(s). The capture efficiency of a nucleic acid or nucleic acid population of the invention is typically compared to the capture efficiency of a control nucleic acid or nucleic acid population under the same incubation conditions (e.g., using same buffer and temperature).

For example, a control nucleic acid may have β-D-2-deoxyribose instead of one or more bicyclic or sugar groups of a LNA unit or other modified or non-naturally-occurring units in a nucleic acid of the invention. In some embodiments, the nucleic acid of the invention and the control nucleic acid only have naturally-occurring nucleobases. If a nucleic acid of the invention has one or more non-naturally-occurring nucleobases, the capture efficiency of the corresponding control nucleic acid is calculated as the average capture efficiency for all of the nucleic acids that have either A, T, C, or G in each position corresponding to a non-naturally-occurring nucleobase in the nucleic acid of the invention.

Monomers are referred to as being "complementary" if they contain nucleobases that can form hydrogen bonds according to Watson-Crick base-pairing rules (e.g., G with C, A with T, or A with U) or other hydrogen bonding motifs such as for example diaminopurine with T, inosine with C, and pseudoisocytosine with G.

By "substantially complementarity" is meant having a sequence that is at least 60, 70, 80, 90, 95, or 100% complementary to that of another sequence. Sequence complementarity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications.

The term "homology" refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous."

When used in reference to a double-stranded nucleic acid sequence such as a cDNA or genomic clone, the term "substantially homologous" refers to a probe that can hybridize to a strand of the double-stranded nucleic acid sequence under conditions of low stringency, e.g. using a hybridization buffer comprising 20% formamide in 0.8M saline/0.08M sodium citrate (SSC) buffer at a temperature of 37° C. and remaining bound when subject to washing once with that SSC buffer at 37° C.

When used in reference to a single-stranded nucleic acid sequence, the term "substantially homologous" refers to a probe that can hybridize to (i.e., is the complement of) the single-stranded nucleic acid template sequence under conditions of low stringency, e.g. using a hybridization buffer comprising 20% formamide in 0.8M saline/0.08M sodium citrate (SSC) buffer at a temperature of 37° C. and remaining bound when subject to washing once with that SSC buffer at 37° C.

By "internal probe" is meant a nucleic acid (e.g., a probe or primer) that hybridizes to either only one exon or only one intron of a nucleic acid (e.g., mRNA). The internal probe may hybridize to the 5' end of the exon or intron, the 3' end of the exon or intron, or between the 5' end and the 3' end of the exon or intron. Desirably, the internal probe is at least 90, 95, 96, 97, 98, 99, or 100% identical to the corresponding region of a target nucleic acid.

By "merged probe" is meant a nucleic acid (e.g., a probe or primer) that hybridizes to more than one exon and/or intron of a nucleic acid (e.g., mRNA). Desirably, the merged probe hybridizes to two consecutive exons (e.g., exons in a mature mRNA transcript that may or may not be consecutive in the corresponding DNA molecule). In another desirable embodiment, the merged probe hybridizes to an exon and the consecutive intron. In desirable embodiments, the merged probe hybridizes to the same number of nucleotides in each exon or to the same number of nucleotides in the exon and intron. In various embodiments, the length of the region of the merged probe that hybridizes to one exon differs by less than 60, 40, 20, 10, or 5% from the length of the region of the merged probe that hybridizes to the other exon or to the intron. Desirably, the merged probe is at least 90, 95, 96, 97, 98, 99, or 100% identical to the corresponding region of a target nucleic acid.

By "poly-$T_{20}$ tail" is meant a DNA polymer consisting of 20 DNA-t units added by polymerase chain reaction as a tail to a nucleic acid sequence, which is subsequently cloned in a plasmid vector allowing in vitro synthesis of poly$(A)_{20}$ polyadenylated RNA.

By "mixmer" or "mixmer probe" is meant a nucleic acid (e.g., a probe or primer) that contains at least one LNA unit and at least one RNA or DNA unit (e.g., a naturally-occurring RNA or DNA unit).

By "corresponding unmodified reference nucleobase" is meant a nucleobase that is not part of an LNA unit and is in the same orientation as the nucleobase in an LNA unit.

By "mutation" is meant an alteration in a naturally-occurring or reference nucleic acid sequence, such as an insertion, deletion, frameshift mutation, silent mutation, nonsense mutation, or missense mutation. Desirably, the amino acid sequence encoded by the nucleic acid sequence has at least one amino acid alteration from a naturally-occurring sequence.

By "selecting" is meant substantially partitioning a molecule from other molecules in a population. Desirably, the partitioning provides at least a 2-fold, desirably, a 30-fold, more desirably, a 100-fold, and most desirably, a 1,000-fold enrichment of a desired molecule relative to undesired molecules in a population following the selection step. The selection step may be repeated a number of times, and different types of selection steps may be combined in a given approach. The population desirably contains at least $10^9$ molecules, more desirably at least $10^{11}$, $10^{13}$, or $10^{14}$ molecules and, most desirably, at least $10^{15}$ molecules.

By a "population" is meant more than one nucleic acid. A "population" according to the invention desirably means more than $10^1$, $10^2$, $10^3$, or $10^4$ different molecules.

By "photochemically active groups" is meant compounds which are able to undergo chemical reactions upon irradiation with light. Illustrative examples of functional groups are quinones, especially 6-methyl-1,4-naphtoquinone, anthraquinone, naphtoquinone, and 1,4-dimethyl-anthraquinone, diazirines, aromatic azides, benzophenones, psoralens, diazo compounds, and diazirino compounds.

By "thermochemically reactive group" is meant a functional group which is able to undergo thermochemically-induced covalent bond formation with other groups. Illustrative examples of functional parts of thermochemically reactive groups are carboxylic acids, carboxylic acid esters such as activated esters, carboxylic acid halides such as acid fluorides, acid chlorides, acid bromide, acid iodides, carboxylic acid azides, carboxylic acid hydrazides, sulfonic acids, sulfonic acid esters, sulfonic acid halides, semicarbazides, thiosemicarbazides, aldehydes, ketones, primary alcohols, secondary alcohols, tertiary alcohols, phenols, alkyl halides, thiols, disulphides, primary amines, secondary amines, tertiary amines, hydrazines, epoxides, maleimides, and boronic acid derivatives.

By "chelating group" is meant a molecule that contains more than one binding site and frequently binds to another molecule, atom, or ion through more than one binding site at the same time. Examples of functional parts of chelating groups are iminodiacetic acid, nitrilotriacetic acid, ethylenediamine tetraacetic acid (EDTA), and aminophosphonic acid.

By "reporter group" is meant a group which is detectable either by itself or as a part of an detection series. Examples of functional parts of reporter groups are biotin, digoxigenin, fluorescent groups (e.g., groups which are able to absorb electromagnetic radiation, e.g. light or X-rays, of a certain wavelength, and which subsequently reemit the energy absorbed as radiation of longer wavelength; such as dansyl (5-dimethylamino)-1-naphthalenesulfonyl), DOXYL (N-oxyl-4,4-dimethyloxazolidine), PROXYL (N-oxyl-2,2,5, 5-tetramethylpyrrolidine), TEMPO(N-oxyl-2,2,6,6-tetramethylpiperidine), dinitrophenyl, acridines, coumarins, Cy3 and Cy5 (trademarks for Biological Detection Systems, Inc.), erythrosine, coumaric acid, umbelliferone, Texas red, rhodamine, tetramethyl rhodamine, Rox, 7-nitrobenzo-2-oxa-1-diazole (NBD), pyrene, fluorescein, Europium, Ruthenium, Samarium, and other rare earth metals), radioisotopic labels, chemiluminescence labels (i.e., labels that are detectable via the emission of light during a chemical reaction), spin labels (a free radical e.g., substituted organic nitroxides) or other paramagnetic probes (e.g., $Cu^{2+}$ or $Mg^{2+}$) bound to a biological molecule being detectable by the use of electron spin resonance spectroscopy), enzymes (such as peroxidases, alkaline phosphatases, β-galactosidases, and glycose oxidases), antigens, antibodies, haptens (e.g., groups which are able to combine with an antibody, but which cannot initiate an immune response by itself, such as peptides and steroid hormones), carrier systems for cell membrane penetration, fatty acid units, steroid moieties (cholesteryl), vitamin A, vitamin D, vitamin E, folic acid peptides for specific receptors, groups for mediating endocytose, epidermal growth factor (EGF), bradykinin, and platelet derived growth factor (PDGF). Especially desirable groups are biotin, fluorescein, Texas Red, rhodamine, dinitrophenyl, digoxigenin, Ruthenium, Europium, Cy5, and Cy3.

By "ligand" is meant a compound which binds. Ligands can comprise functional groups such as aromatic groups (such as benzene, pyridine, naphthalene, anthracene, and phenanthrene), heteroaromatic groups (such as thiophene, furan, tetrahydrofuran, pyridine, dioxane, and pyrimidine), carboxylic acids, carboxylic acid esters, carboxylic acid halides, carboxylic acid azides, carboxylic acid hydrazides, sulfonic acids, sulfonic acid esters, sulfonic acid halides, semicarbazides, thiosemicarbazides, aldehydes, ketones, primary alcohols, secondary alcohols, tertiary alcohols, phenols, alkyl halides, thiols, disulphides, primary amines, secondary amines, tertiary amines, hydrazines, epoxides, maleimides, $C_1$-$C_{20}$ alkyl groups optionally interrupted or terminated with one or more heteroatoms such as oxygen atoms, nitrogen atoms, and/or sulphur atoms, optionally containing aromatic or mono/polyunsaturated hydrocarbons, polyoxyethylene such as polyethylene glycol, oligo/polyamides such as poly-α-alanine, polyglycine, polylysine, peptides, oligo/polysaccharides, oligo/polyphosphates, toxins, antibiotics, cell poisons, and steroids. "Affinity ligands" include functional groups or biomolecules that have a specific affinity for sites on particular proteins, antibodies, poly- and oligosaccharides, and other biomolecules.

It should be understood that the above-mentioned specific examples under DNA intercalators, photochemically active groups, thermochemically active groups, chelating groups, reporter groups, and ligands correspond to the "active/functional" part of the groups in question. For the person skilled in the art it is furthermore clear that DNA intercalators, photochemically active groups, thermochemically active groups, chelating groups, reporter groups, and ligands are typically represented in the form M-K- where M is the "active/functional" part of the group in question and where K is a spacer through which the "active/functional" part is attached to the 5- or 6-membered ring. Thus, it should be understood that the group B, in the case where B is selected from DNA intercalators, photochemically active groups, thermochemically active groups, chelating groups, reporter groups, and ligands, has the form M-K-, where M is the "active/functional" part of the DNA intercalator, photochemically active group, thermochemically active group, chelating group, reporter group, and ligand, respectively, and where K is an optional spacer comprising 1-50 atoms, desirably 1-30 atoms, in particular 1-15 atoms, between the 5- or 6-membered ring and the "active/functional" part.

By "spacer" is meant a thermochemically and photochemically non-active distance-making group and is used to join two or more different moieties of the types defined above. Spacers are selected on the basis of a variety of characteristics including their hydrophobicity, hydrophilicity, molecular flexibility and length (e.g., Hermanson et. al., "Immobilized Affinity Ligand Techniques," Academic Press, San Diego, Calif. (1992). Generally, the length of the spacers is less than or about 400 Å, in some applications desirably less than 100 Å. The spacer, thus, comprises a chain of carbon atoms optionally interrupted or terminated with one or more heteroatoms, such as oxygen atoms, nitrogen atoms, and/or sulphur atoms. Thus, the spacer K may comprise one or more amide, ester, amino, ether, and/or thioether functionalities, and optionally aromatic or mono/polyunsaturated hydrocarbons, polyoxyethylene such as polyethylene glycol, oligo/polyamides such as poly-α-alanine, polyglycine, polylysine, peptides, oligosaccharides, or oligo/polyphosphates. Moreover the spacer may consist of combined units thereof. The length of the spacer may vary, taking into consideration the desired or necessary positioning and spatial orientation of the "active/functional" part of the group in question in relation to the 5- or 6-membered ring. In particularl embodiments, the spacer includes a chemically cleavable group. Examples of such chemically cleavable groups include disulphide groups cleavable under reductive conditions and peptide fragments cleavable by peptidases.

By "target nucleic acid" or "nucleic acid target" is meant a particular nucleic acid sequence of interest. Thus, the "target" can exist in the presence of other nucleic acid molecules or within a larger nucleic acid molecule.

By "solid support" is meant any rigid or semi-rigid material to which a nucleic acid binds or is directly or indirectly attached. The support can be any porous or non-porous water insoluble material, including without limitation, membranes, filters, chips, slides, wafers, fibers, magnetic or nonmagnetic beads, gels, tubing, strips, plates, rods, polymers, particles, microparticles, capillaries, and the like. The support can have a variety of surface forms, such as wells, trenches, pins, channels and pores.

By an "array" is meant a fixed pattern of at least two different immobilized nucleic acids on a solid support. Desirably, the array includes at least $10^2$, more desirably, at least $10^3$, and, most desirably, at least $10^4$ different nucleic acids.

By "antisense nucleic acid" is meant a nucleic acid, regardless of length, that is complementary to a coding strand or mRNA of interest. In some embodiments, the antisense molecule inhibits the expression of only one nucleic acid, and in other embodiments, the antisense molecule inhibits the expression of more than one nucleic acid. Desirably, the antisense nucleic acid decreases the expression or biological activity of a nucleic and or encoded protein by at least 20, 40, 50, 60, 70, 80, 90, 95, or 100%. An antisense molecule can be introduced, e.g., to an individual cell or to whole animals, for example, it may be introduced systemically via the bloodstream. Desirably, a region of the antisense nucleic acid or the entire antisense nucleic acid is at least 70, 80, 90, 95, 98, or 100% complementary to a coding sequence, regulatory region (5' or 3' untranslated region), or an mRNA of interest. Desirably, the region of complementarity includes at least 5, 10, 20, 30, 50, 75, 100, 200, 500, 1000, 2000 or 5000 nucleotides or includes all of the nucleotides in the antisense nucleic acid.

In some embodiments, the antisense molecule is less than 200, 150, 100, 75, 50, or 25 nucleotides in length. In other embodiments, the antisense molecule is less than 50,000; 10,000; 5,000; or 2,000 nucleotides in length. In certain embodiments, the antisense molecule is at least 200, 300, 500, 1000, or 5000 nucleotides in length. In some embodiments, the number of nucleotides in the antisense molecule is contained in one of the following ranges: 5-15 nucleotides, 16-20 nucleotides, 21-25 nucleotides, 26-35 nucleotides, 36-45 nucleotides, 46-60 nucleotides, 61-80 nucleotides, 81-100 nucleotides, 101-150 nucleotides, or 151-200 nucleotides, inclusive. In addition, the antisense molecule may contain a sequence that is less than a full-length sequence or may contain a full-length sequence.

By "double stranded nucleic acid" is meant a nucleic acid containing a region of two or more nucleotides that are in a double stranded conformation. In various embodiments, the double stranded nucleic acids consist entirely of LNA units or a mixture of LNA units, ribonucleotides, and/or deoxynucleotides. The double stranded nucleic acid may be a single molecule with a region of self-complementarity such that nucleotides in one segment of the molecule base-pair with nucleotides in another segment of the molecule. Alternatively, the double stranded nucleic acid may include two different strands that have a region of complementarity to each other. Desirably, the regions of complementarity are at least 70, 80, 90, 95, 98, or 100% identical. Desirably, the region of the double stranded nucleic acid that is present in a double stranded conformation includes at least 5, 10, 20, 30, 50, 75, 100, 200, 500, 1000, 2000 or 5000 nucleotides or includes all of the nucleotides in the double stranded nucleic acid. Desirable double stranded nucleic acid molecules have a strand or region that is at least 70, 80, 90, 95, 98, or 100% identical to a coding region or a regulatory sequence (e.g., a transcription factor binding site, a promoter, or a 5' or 3' untranslated region) of a nucleic acid of interest. In some embodiments, the double stranded nucleic acid is less than 200, 150, 100, 75, 50, or 25 nucleotides in length. In other embodiments, the double stranded nucleic acid is less than 50,000; 10,000; 5,000; or 2,000 nucleotides in length. In certain embodiments, the double stranded nucleic acid is at least 200, 300, 500, 1000, or 5000 nucleotides in length. In some embodiments, the number of nucleotides in the double stranded nucleic acid is contained in one of the following ranges: 5-15 nucleotides, 16-20 nucleotides, 21-25 nucleotides, 26-35 nucleotides, 36-45 nucleotides, 46-60 nucleotides, 61-80 nucleotides, 81-100 nucleotides, 101-150 nucleotides, or 151-200 nucleotides, inclusive. In addition, the double stranded nucleic acid may contain a sequence that is less than a full-length sequence or may contain a full-length sequence.

In some embodiments, the double stranded nucleic acid inhibits the expression of only one nucleic acid, and in other embodiments, the double stranded nucleic acid molecule inhibits the expression of more than one nucleic acid. Desirably, the nucleic acid decreases the expression or biological activity of a nucleic acid of interest or a protein encoded by a nucleic acid of interest by at least 20, 40, 50, 60, 70, 80, 90, 95, or 100%. A double stranded nucleic acid can be introduced, e.g., to an individual cell or to whole animals, for example, it may be introduced systemically via the bloodstream.

In various embodiments, the double stranded nucleic acid or antisense molecule includes one or more LNA nucleotides, one or more universal bases, and/or one or more modified nucleotides in which the 2' position in the sugar (e.g., ribose or xylose) contains a halogen (such as fluorine group) or contains an alkoxy group (such as a methoxy group) which increases the half-life of the double stranded nucleic acid or antisense molecule in vitro or in vivo compared to the corresponding double stranded nucleic acid or antisense molecule in which the corresponding 2' position contains a hydrogen or an hydroxyl group. In yet other embodiments, the double stranded nucleic acid or antisense molecule includes one or more linkages between adjacent nucleotides other than a naturally-occurring phosphodiester linkage. Examples of such linkages include phosphoramide, phosphorothioate, and phosphorodithioate linkages. Desirably, the double stranded or antisense molecule is purified.

By "purified" is meant separated from other components that naturally accompany it. Typically, a factor is substantially pure when it is at least 50%, by weight, free from proteins, antibodies, and naturally-occurring organic molecules with which it is naturally associated. Desirably, the factor is at least 75%, more desirably, at least 90%, and most desirably, at least 99%, by weight, pure. A substantially pure factor may be obtained by chemical synthesis, separation of the factor from natural sources, or production of the factor in a recombinant host cell that does not naturally produce the factor. Nucleic acids and proteins may be purified by one skilled in the art using standard techniques such as those described by Ausubel et al. (Current Protocols in Molecular Biology, John Wiley & Sons, New York, 2000). The factor is desirably at least 2, 5, or 10 times as pure as the starting material, as measured using polyacrylamide gel electrophoresis, column chromatography, optical density, HPLC analysis, or western analysis (Ausubel et al., supra). Desirable methods of purification include immunoprecipitation, column chromatography such as immunoaffinity chromatography, magnetic bead immunoaffinity purification, and panning with a plate-bound antibody.

By "treating, stabilizing, or preventing a disease, disorder, or condition" is meant preventing or delaying an initial or subsequent occurrence of a disease, disorder, or condition; increasing the disease-free survival time between the disappearance of a condition and its reoccurrence; stabilizing or reducing an adverse symptom associated with a condition; or inhibiting or stabilizing the progression of a condition. Desirably, at least 20, 40, 60, 80, 90, or 95% of the treated subjects have a complete remission in which all evidence of the disease disappears. In another desirable embodiment, the length of time a patient survives after being diagnosed with a condition and treated with a nucleic acid of the invention is at least 20, 40, 60, 80, 100, 200, or even 500% greater than (i) the average amount of time an untreated patient survives or (ii) the average amount of time a patient treated with another therapy survives.

By "treating, stabilizing, or preventing cancer" is meant causing a reduction in the size of a tumor, slowing or preventing an increase in the size of a tumor, increasing the disease-free survival time between the disappearance of a tumor and its reappearance, preventing an initial or subsequent occurrence of a tumor, or reducing an adverse symptom associated with a tumor. In one desirable embodiment, the number of cancerous cells surviving the treatment is at least 20, 40, 60, 80, or 100% lower than the initial number of cancerous cells, as measured using any standard assay. Desirably, the decrease in the number of cancerous cells induced by administration of a nucleic acid of the invention (e.g., a nucleic acid with substantial complementarily to a nucleic acid associated with cancer such as an oncogene) is at least 2, 5, 10, 20, or 50-fold greater than the decrease in the number of non-cancerous cells. In yet another desirable embodiment, the number of cancerous cells present after administration of a nucleic acid of the invention is at least 2, 5, 10, 20, or 50-fold lower than the number of cancerous cells present prior to the administration of the compound or after administration of a buffer control. Desirably, the methods of the present invention result in a decrease of 20, 40, 60, 80, or 100% in the size of a tumor as determined using standard methods. Desirably, at least 20, 40, 60, 80, 90, or 95% of the treated subjects have a complete remission in which all evidence of the cancer disappears. Desirably, the cancer does not reappear or reappears after at least 5, 10, 15, or 20 years.

Exemplary cancers that can be treated, stabilized, or prevented using the above methods include prostate cancers, breast cancers, ovarian cancers, pancreatic cancers, gastric cancers, bladder cancers, salivary gland carcinomas, gastrointestinal cancers, lung cancers, colon cancers, melanomas, brain tumors, leukemias, lymphomas, and carcinomas. Benign tumors may also be treated or prevented using the methods and nucleic acids of the present invention.

By "infection" is meant the invasion of a host animal by a pathogen (e.g., a bacteria, yeast, or virus). For example, the infection may include the excessive growth of a pathogen that is normally present in or on the body of an animal or growth of a pathogen that is not normally present in or on the animal. More generally, an infection can be any situation in which the presence of a pathogen population(s) is damaging to a host. Thus, an animal is "suffering" from an infection when an excessive amount of a pathogen population is present in or on the animal's body, or when the presence of a pathogen population(s) is damaging the cells or other tissue of the animal. In one embodiment, the number of a particular genus or species of pathogen is at least 2, 4, 6, or 8 times the number normally found in the animal.

A bacterial infection may be due to gram positive and/or gram negative bacteria. In desirable embodiments, the bacterial infection is due to one or more of the following bacteria: Chlamydophila pneumoniae, C. psittaci, C. abortus, Chlamydia trachomatis, Simkania negevensis, Parachlamydia acanthamoebae, Pseudomonas aeruginosa, P. alcaligenes, P. chlororaphis, P. fluorescens, P. luteola, P. mendocina, P. monteilii, P. oryzihabitans, P. pertocinogena, P. pseudalcaligenes, P. putida, P. stutzeri, Burkholderia cepacia, Aeromonas hydrophilia, Escherichia coli, Citrobacter freundii, Salmonella typhimurium, S. typhi, S. paratyphi, S. enteritidis, Shigella dysenteriae, S. flexneri, S. sonnei, Enterobacter cloacae, E. aerogenes, Klebsiella pneumoniae, K. oxytoca, Serratia marcescens, Francisella tularensis, Morganella morganii, Proteus mirabilis, Proteus vulgaris, Providencia alcalifaciens, P. rettgeri, P. stuartii, Acinetobacter calcoaceticus, A. haemolyticus, Yersinia enterocolitica, Y. pestis, Y. pseudotuberculosis, Y. intermedia, Bordetella pertussis, B. parapertussis, B. bronchiseptica, Haemophilus influenzae, H. parainfluenzae, H. haemolyticus, H. parahaemolyticus, H. ducreyi, Pasteurella multocida, P. haemolytica, Branhamella catarrhalis, Helicobacter pylori, Campylobacter fetus, C. jejuni, C. coli, Borrelia burgdorferi, V. cholerae, V. parahaemolyticus, Legionella pneumophila, Listeria monocytogenes, Neisseria gonorrhea, N. meningitidis, Kingella dentrificans, K kingae, K. oralis, Moraxella catarrhalis, M. atlantae, M. lacunata, M. nonliquefaciens, M. osloensis, M. phenylpyruvica, Gardnerella vaginalis, Bacteroides fragilis, Bacteroides distasonis, Bacteroides 3452A homology group, Bacteroides vulgatus, B. ovalus, B. thetaiotaomicron, B. uniformis, B. eggerthii, B. splanchnicus, Clostridium difficile, Mycobacterium tuberculosis, M avium, M intracellulare, M leprae, C. diphtheriae, C. ulcerans, C. accolens, C. afermentans, C. amycolatum, C. argentorense, C. auris, C. bovis, C. confusum, C. coyleae, C. durum, C. falsenii, C. glucuronolyticum, C. imitans, C. jeikeium, C. kutscheri, C. kroppenstedtii, C. lipophilum, C. macginleyi, C. matruchoti, C. mucifaciens, C. pilosum, C. propinquum, C. renale, C. riegelii, C. sanguinis, C. singulare, C. striatum, C. sundsvallense, C. thomssenii, C. urealyticum, C. xerosis, Streptococcus pneumoniae, S. agalactiae, S. pyogenes, Enterococcus avium, E. casselifavus, E. cecorum, E. dispar, E. durans, E. faecalis, E. faecium, E. flavescens, E. gallinarum, E. hirae, E. malodoratus, E. mundtii, E. pseudoavium, E. raffinosus, E. solitarius, Staphylococcus aureus, S. epidermidis, S. saprophyticus, S. intermedius, S. hyicus, S. haemolyticus, S. hominis, and/or S. saccharolyticus. Desirably, a nucleic acid is administered in an amount sufficient to prevent, stabilize, or inhibit the growth of a pathogenic bacteria or to kill the bacteria.

In various embodiments, the viral infection relevant to the methods of the invention is an infection by one or more of the following viruses: West Nile virus (e.g., Samuel, "Host genetic variability and West Nile virus susceptibility," Proc. Natl. Acad. Sci. USA Aug. 21, 2002; Beasley, Virology 296:17-23, 2002), Hepatitis, picornarirus, polio, HIV, coxsachie, herpes (e.g., zoster, simplex, EBV, or CMV), adenovirus, retrovius, falvi, pox, rhabdovirus, picorna virus (e.g., coxsachie, entero, hoof and mouth, polio, or rhinovirus), St. Louis encephalitis, Epstein-Barr, myxovirus, JC, coxsakievirus B, togavirus, measles, paramyxovirus, echovirus, bunyavirus, cytomegalovirus, varicella-zoster, mumps, equine encephalitis, lymphocytic choriomeningitis, rabies, simian virus 40, polyoma virus, parvovirus, papilloma virus, primate adenovirus, and/or BK.

By "mammal in need of treatment" is meant a mammal in which a disease, disorder, or condition is treated, stabilized, or prevented by the administration of a nucleic acid of the invention.

Other aspects and embodiments of the invention are in the detailed description and claims below. Additionally, other nucleic acids and methods described in U.S. Ser. No. 10/105, 639 (Jakobsen et al., "Modified Oligonucleotides and Uses Thereof") or U.S. Ser. No. 60/410,061 (Ramsing et al., "Populations of Oligonucleotides with Duplex Stabilizing Properties and Uses Thereof") which are hereby incorporated by reference, can be used in the present invention.

BRIEF DESCRIPTION OF THE DRAWINGS

FIG. 2 illustrates the chemical structures of Selective Binding Complementary (SBC) nucleotides.

FIGS. 4A and 4B show the sensitivity of 50-mer LNA capture probes compared to 50-mer DNA capture probes. SW15-specific 50-mer DNA oligonucleotides (green bars) and 50-mer capture probes with an LNA nucleotide incorporated at every third nucleotide position (red bars) were printed at the oligo concentration indicated below. The slides were hybridized at 65° C. in 3×SSC (FIG. 4A) and at 70° C. in 3×SSC (FIG. 4B).

FIGS. 5A and 5B show the specificity of 40-mer LNA capture probes (red bars) compared to DNA capture probes (green bars). The hybridizations were carried out at 65° C. in 3×SSC. Bars 1 and 7 represent perfectly matched duplexes, bars 2 and 8, 3, and 9, 4 and 10, 5 and 11, and 6 and 12 represent duplexes with 1, 2, 3, 4, 5 mismatches, respectively. The in vitro RNA used was SW15 in FIG. 5A and TH14 in FIG. 5B.

FIG. 14 is a bar graph of the signal intensities of a patient DNA sample hybridized to an array of the invention. The names of the probes in FIGS. 14 and 17 match, although the numbers used in FIG. 14 are abbreviated, e.g., probe No. 10580 Menkes.14 50NH2C6-2.LNA in FIG. 17 corresponds to the second probe counted from the left "14.2" LNA in the lower graph of FIG. 14.

FIG. 17 is a table of comparative genome hybridization (CGH) capture probe sequences (SEQ ID NOs: 108-161, in sequential order).

Figure 19E:
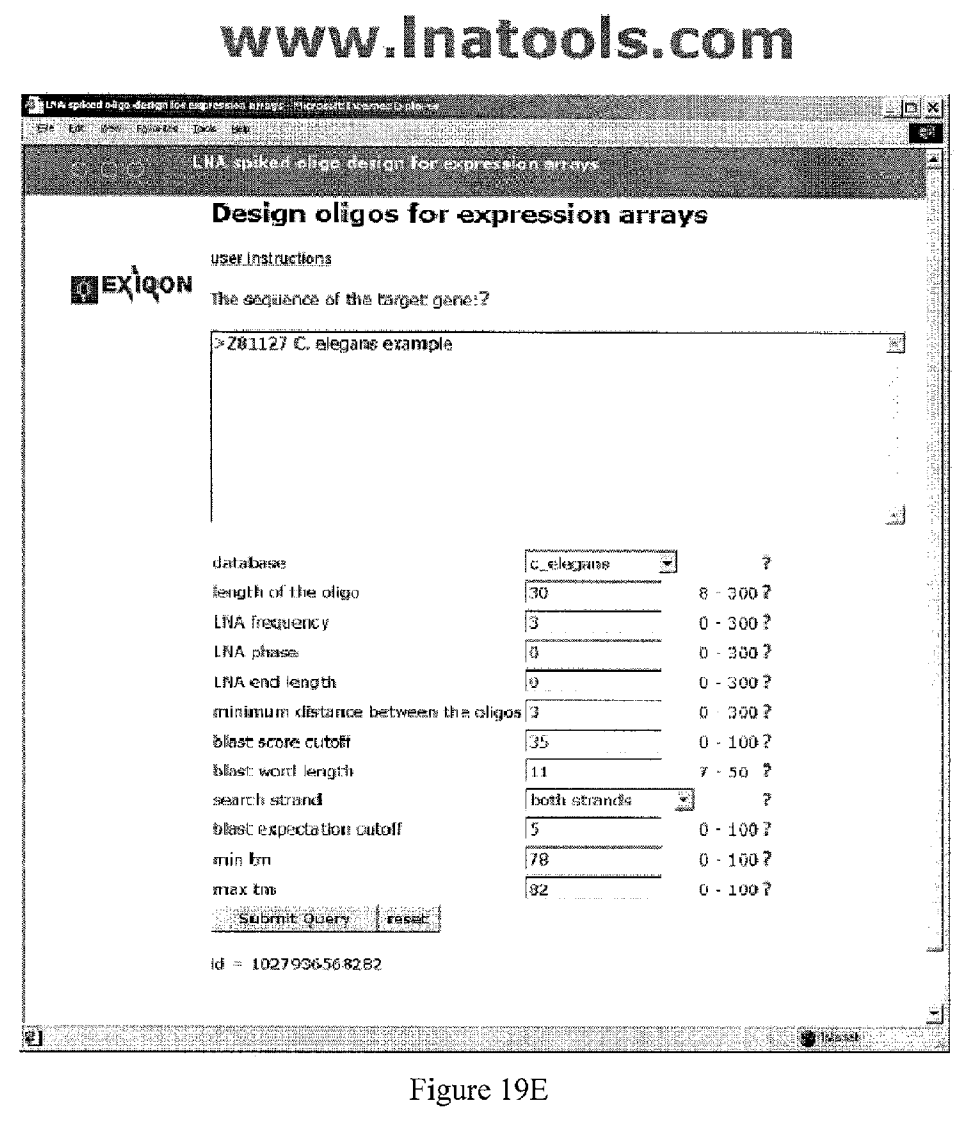

FIGS. 19A-19F are a schematic illustration of the OligoDesign software of the invention.

FIG. 24 is a table of exemplary target nucleic acids (Holstege et al. (1998) (Cell 95, 717-728, and Causton et al. (2001) Mol. Biol. Cell 12, 323-337).

FIGS. 36b and 36d demonstrate the improved mismatch discrimination with the 50-mer LNA probes by increasing the hybridization temperature from 65° C. to 70° C. hybridized with Cy3-labelled cDNA from 10 μg C. elegans total RNA spiked with yeast b) SWI5 RNA and d) THI4 RNA.

DETAILED DESCRIPTION OF THE INVENTION

Detection and Analysis of mRNA Splice Variants

Figure 9:
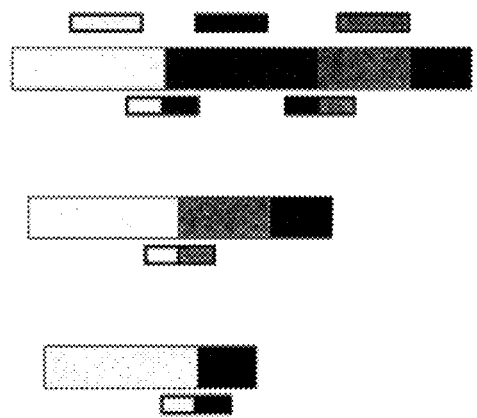
FIG. 9 illustrates the LNA exon-exon junction (merged) probe concept.

Alternative splicing is the process by which different mature messenger RNAs are produced from the same pre-mRNA. Because the mRNA composition of a given cell determines the proteins present in a cell, this process is an important aspect of a cells gene expression profile. Current investigations of transcriptomes (i.e., the total complexity of RNA transcripts produced by an organism) indicate that at least 50-60% of the genes of complex eukaryotes produce more than one splice variant. The present invention provides a novel method for detecting and quantifying the levels of splice variants in complex mRNA pools using LNA discriminating probes and high-throughput LNA oligonucleotide microarray technology. The detection concept which uses internal LNA exon probes and/or splice-variant specific exon-exon junction or exon-intron or intron-exon (so-called merged) probes is depicted in FIG. 9.

Internal, exon-specific (or intron-specific) LNA oligonucleotide probes are designed and used to detect the relative levels of a given exon (or intron) in complex mRNA pools using oligonucleotide microarray technology or similar techniques. Exon-exon LNA junction probes are designed for multiple or all possible exon-exon combinations or exon-intron combinations. The LNA discriminating probes are highly specific and superior compared to DNA oligonucleotides due to the higher $\Delta$Tm of LNA probes. These probes can be used to determine the sequential order of each sub-element (i.e., exon structure or exon-intron structure) in a given alternatively spliced mRNA isoform, thus giving the exact composition of the mRNA. Subsequently, the ratios of each splice variant can be quantified using the combined readouts from both internal and merged LNA probes and control probes. The invention is applicable both in single fluor (single channel) or comparative two-fluor (two channel) microarray hybridizations.

Several "artificial," alternatively spliced mRNA molecules may be constructed in an in vitro transcription vector for the production of clean IVT RNA. Both internal and junction-specific LNA oligonucleotide capture probes are designed, synthesized, and spotted onto, e.g., Exiqon's polymer microarray platform. The resulting splice-specific microarray is used to validate the LNA discriminating probe concept by spiking the in vitro RNAs individually as well as in different ratios into a complex RNA background for fluorochrome-labelling and array hybridization.

The internal and merged probes of the invention can also be used in any standard method for the analysis of mRNA splice variants (see, for example, Yeakley et al., Nature Biotechnology 20:353-358, 2002; Clark et al., Science 296: 907-910, 2002; Mutch et al., Genome Biology 2(12):preprint00009.1-0009.31, 2001).

Exemplary Applications of Internal and/or Merged Probes

The internal and/or merged probes of the invention can also be used for gene expression profiling of alternative splice variants, oligonucleotide expression microarrays, real-time PCR, and profiling of alternatively spliced mRNAs using microtiterplate assays or fiber-optic arrays.

Detection and characterization of alternative splicing is particularly useful for the study and treatment of human disease (exonhit website, "Inaugural Splicing 2002 Concludes: Alternative Splicing May Make All the Difference in Discovering the Origin of Disease). In particular, RNA splicing is now widely recognized as a means to generate protein diversity. Alternative splicing is a key mechanism for regulating gene expression, and any mutation or defect in its regulation can impact considerably cell functions. Therefore, it is likely to be an important source of novel gene and protein targets implicated in human pathology. Industry has long recognized the need for innovative discovery technologies that focuses on the origin of disease for the development of novel diagnostics and therapeutics.

In particular, there are many examples of human pathologies caused by alterations in normal patterns of alternative RNA splicing. Because a large number of human genes undergo alternative splicing, the protein isoforms that result from this process represent a major source of targets for commercial development of therapies and diagnostics. In particular, splicing processes play a significant role in the onset and development of cardiovascular, muscular, CNS diseases, and cancer. Early evidence indicates the origin of many diseases can be identified by examining alternative splicing—which leads to the point of intervention for discovering future generations of drugs. The study of splicing enables the discovery of new mechanisms underlying disease progression.

Comparative Genomic Hybridization

Comparative Genomic Hybridization (CGH) is a powerful technology for detection of unbalanced chromosome rearrangements and holds much promise for screening and identification of interstitial submicroscopic rearrangements that otherwise cannot be detected using classical cytogenetic or FISH technologies. The adaptation of CGH onto an oligo microarray platform allows detection of small single exon deletion/duplications on a genome wide scale. There is a strong need for developing microarrays that can detect, e.g., single exon aberrations. This detection can be achieved by employing LNA mixmer oligos as capture probes for individual exons in selected genes.

A model system for these methods is the Menkes loci. Menkes disease is a lethal-X linked recessive disorder associated with copper metabolism disturbance leading to death in early childhood. The Menkes locus has been mapped to Xq13. The gene spans about 150 kb genomic region, contains 23 exons, and encodes a 8.5 kb gene transcript. The gene for Menkes disease (now designated as ATP7A) encodes a 1500 amino acid membrane-bound Cu-binding P-type ATPase (ATP7A). The 8.5 kb transcript is expressed in all tissues from normal individuals (though only trace amounts are present in liver), but is diminished or absent in Menkes disease patients. Several different kinds of mutations, like chromosome aberrations, point mutations and partial gene deletions affecting ATP7A have been identified in MD patients. 50-mer capture probes with LNA spiked in every second, third, and fourth position have been designed for every exon (23 exons) representing ATP7A, using the OligoDesign software tool, described herein. The C6-amino-linked capture probes were spotted onto Immobilizer slides and hybridized with patient samples with Cy3 fluorescent dye and a known reference genomic sample with Cy5. After mixing equal amounts of the labelled DNA, the probe is hybridized it to array. The ratio of Cy5 signal to Cy3 for each clone indicates differences in chromosome/DNA material. For example, the Cy5 signal is higher than Cy3 if the patient genome has a deletion, and is lower if there is duplication. In regions that are unchanged, the Cy5:Cy3 ratio is 1:1. These methods can be used to analyze a number of well-characterized Menkes patients with a range of partial deletions of ATP7A.

LNA oligonucleotide-based CGH makes it possible to assess a large number of chromosomal aberrations that are being screen for in the cytogenetic clinic. In contrast, standard FISH analysis typically only detects large chromosomal rearrangements. In desirable embodiments, an array that contains a series of overlapping probes is used to detect a chromosomal deletion in a nucleic acid sample, such as a patient sample.

Clinical Diagnostics

Clinical diagnosis is a key element in healthcare management and point-of-care. A large number of analyses in the hospitals are based on the use of robust, cost efficient, sensitive and highly specific diagnostic tests. Thus, the diagnosis of various diseases is performed with a high selectivity and reliability, resulting in confirmation of medical diagnosis, choice of therapy and follow-up treatment as well as prevention. In addition to its importance in the quality of healthcare provided to patients, clinical diagnosis also contributes to the control of healthcare costs. The field of clinical diagnostics involves analyzing biological fluid samples (blood, urine, etc.) or biopsies collected from patients in order to establish the diagnosis of diseases, whether of infectious, metabolic, endocrine or cancerous origin. Medical analysis of infectious diseases involves testing and identifying the micro-organisms causing the infection e.g. testing for and identifying a micro-organism in blood and determining its susceptibility to antibiotics or detecting an antigen-antibody reaction produced as a response to an attack by a micro-organism in the human body, e.g. testing for antibodies for the diagnosis of hepatitis. The accurate diagnosis of metabolic and endocrine diseases and cancers, resulting in a disease phenotype with a bodily imbalance, involves the measurement of diagnostic substances or elements present in the biological fluids or biopsies. These substances are examined and results are interpreted with reference to known normal values.

Use of Diagnostic Kits in Microbiological Control

The pharmaceutical, cosmetics and agri-food industries are being confronted with increasingly strict quality standards. Thus, the purpose of industrial microbiological control testing is to detect and measure the presence of potentially pathogenic microbial contaminants throughout the manufacturing process from raw materials to the finished products, as well as in the production environment. The obtained results are subsequently compared to the current regulatory guidelines and industry standards.

Application of Molecular Biological Techniques to In Vitro Diagnostics

Recently, several different molecular biological techniques have been used successfully in accurate quantification of RNA levels in clinical diagnosis as well as in microbiological control. The applications are wide-ranging and include methods for quantification of the regulation and expression of drug resistance markers in tumour cells, monitoring of the responses to chemotherapy, measuring the biodistribution and transcription of gene-encoded therapeutics, molecular assessment of the tumor stage in a given cancer, detecting circulating tumor cells in cancer patients and detection of bacterial and viral pathogens. The reverse transcription polymerase chain reaction (RT-PCR) is the most sensitive method for the detection of mRNA, including low abundant mRNAs, often obtained from limited tissue samples in clinical diagnostics. The application of fluorescence techniques to RT-PCR combined with suitable instrumentation has led to development of quantitative RT-PCR methods, combining amplification, detection and quantification in a closed system avoid from contamination and with minimized hands-on time. The two most commonly used quantitative RT-PCR techniques are the Taqman RT-PCR assay (ABI, Foster City, USA) and the Lightcycler assay (Roche, USA). A third method applied to detection and quantification of RNA levels is real-time nucleic acid sequence based amplification (NASBA) combined with molecular beacon detection molecules. NASBA is a singe-step isothermal RNA-specific amplification method that amplifies mRNA in a double stranded DNA environment, and this method has recently proven useful in the detection of various mRNAs and in the detection of both viral and bacterial RNA in clinical samples. Finally, the recent explosion in microarray technology holds the promise of using microarrays in clinical diagnostics. For example van't Veer et al. (Nature 2002: 415, 31) describe the successful use of microarrays in obtaining digital mRNA signatures from breast tumors and the use of these signatures in the precise prediction of the clinical outcome of breast cancer in patients.

The success of exploiting molecular biological techniques in diagnostics and diagnostic kits depends on continuous optimization of the technologies and the development of new robust and cost-effective technology platforms for producing accurate, reproducible and valid clinical data. Locked nucleic acid (LNA) oligonucleotides constitute a novel class of bicyclic RNA analogs having an exceptionally high affinity and specificity toward their complementary DNA and RNA target molecules. Besides increased thermal stability, LNA-containing oligonucleotides show significantly increased mismatch discrimination, and allow full control of the melting temperature across microarray hybridizations. The LNA chemistry is completely compatible with conventional DNA phosphoramidite chemistry and thus LNA substituted oligonucleotides can be designed to optimize performance. LNA oligonucleotides would be well-suited for large-scale clinical studies providing highly accurate genotyping by direct competitive hybridization of two allele-specific LNA probes to e.g. microarrays of immobilized patient amplicons. In addition, the use of LNA substituted oligonucleotides would increase both sensitivity and specificity in detection and quantification of mRNA levels in clinical samples, either by quantitative RT-PCR, quantitative NASBA or oligonucleotide microarrays, compared with DNA probes. Application of LNA oligonucleotides into diagnostic kits would thus significantly enhance their performance. Finally, the use of LNA substituted oligonucleotides would increase the sensititity and specificity in the detection of alternatively spliced mRNA isoforms and non-coding RNAs either by homogeneous assays (Taqman assay, Lightcycler assay, NASBA) or by oligonucleotide microarrays in a massive parallel analysis setup.

Optimized Nucleic Acids of the Invention

Decreasing the variation in melting temperatures ($T_m$) of a population of nucleic acids allows the nucleic acids to hybridize to target molecules under similar binding conditions, thereby simplifying the simultaneous hybridization of multiple nucleic acids. Similar melting temperatures also allow the same hybridization conditions to be used for multiple experiments, which is particularly useful for assays involving hybridization to nucleic acids of varying "AT" content. For example, current methods often require less stringent conditions for hybridization of nucleic acids with high "AT" content compared to nucleic acids with low "AT" content. Due to this variation in hybridization stringency, current methods may require significant trial and error to optimize the hybridization conditions for each experiment.

To overcome limitations in current nucleic acid hybridization and/or amplification techniques, we have developed populations of nucleic acid probes or primers with minimal variation in melting temperature (U.S. Ser. No. 60/410,061). For example, the unique properties of LNA nucleotide analogs increase their binding affinity for DNA and RNA. The stability of duplexes can generally be ranked as follows: DNA:DNA<DNA:RNA<RNA:RNA≤LNA:DNA<LNA: RNA<LNA:LNA. The DNA:DNA duplex is thus the least stable and the LNA:LNA duplex the most stable. The affinity of the LNA nucleotides A and T corresponds approximately to the affinity of DNA G and C to their complementary bases. General substitution of one or more A and T nucleotides with LNA A and LNA T in DNA oligonucleotides is therefore a simple way of equalizing differences in $T_m$. Furthermore, the mean melting temperature is increased significantly, which is often important for shorter oligonucleotides. For example, predictions of melting temperature of all possible 9-mer oligonucleotides have shown that the mean temperature increases from 39.7° C. to 59.3° C. by substituting all DNA A and T nucleotides with LNA A and T nucleotides. The variance in $T_m$ of all 9-mers furthermore decreases from 59.6° C. for DNA oligonucleotides to only 4.7° C. for the LNA substituted oligonucleotides. The estimations are based on the latest LNA $T_m$ prediction algorithms such as those disclosed herein, which have a variance of 6-7° C.

If desired, the capture efficiency of one or more nucleic acids can be increased by including any of the high affinity nucleotides (e.g., LNA units) described herein within the nucleic acids. The examples herein also provide algorithms for optimizing the substitution patterns of the nucleic acids to minimize self-complementarity that may otherwise inhibit the binding of the nucleic acids to target molecules.

For various applications of the nucleic acids and arrays of the invention, LNA A and LNA T substitutions are made to equalize the melting temperatures of the nucleic acids. In other embodiments, LNA A and LNA C substitutions are made to minimize self-complementarity and to increase specificity. LNA C and LNA T substitutions also minimize self-complementarity. Additionally, oligonucleotides containing LNA C and LNA T are desirable because these modified nucleotides are easy to synthesis and are especially useful for applications such as antisense technology in which minimizing cost is especially desirable.

The following non-limiting examples are illustrative of the invention. All documents mentioned herein are incorporated herein by reference in their entirety. In the following Examples, compound reference numbers designate the compound as shown in Scheme 1 and 2 herein.

EXAMPLE 1

The Use of LNA-Modified Oligonucleotides in Microarrays Provide Significantly Improved Sensitivity and Specificity in Expression Profiling This example demonstrates the advantages of using LNA oligonucleotide microarrays in gene expression profiling experiments. Capture probes for the *Saccharomyces cerevisiae* genes SWI5 (YDR146C) and THI4 (YGR144W) were designed as 50-mer standard DNA and different LNA/DNA "mixmer" oligonucleotides (i.e., oligonucleotides containing both LNA and DNA nucleotides) respectively, for comparison (Table 2). In addition, 40-mer oligonucleotides were designed as truncated versions of the 50-mer capture probes (Table 2). The specificity of the LNA oligoarrays was addressed by introducing 1-5 consecutive mismatches positioned in the middle of 40-mer LNA/DNA mixmer capture probes with LNA in every fourth position. To assess the sensitivity of DNA versus LNA capture probes in complex hybridization mixtures, in vitro synthesized yeast RNA for either SWI5 or THI4 was spiked into *Caenorhabditis elegans* total RNA for cDNA target synthesis. These experiments are described further below.

Cultivation of *Caenorhabditis elegans* Worms

Mixed stage *C. elegans* cultures were grown according to standard methods. Samples were harvested by centrifugation at 3,000×g, suspended in RNA Later storage buffer (Ambion, USA), and immediately frozen in liquid nitrogen.

RNA Extraction

RNA was extracted from the worm samples using the FastRNA® Kit, GREEN (Q-BIO) essentially according to the suppliers' instructions.

In vitro RNA Synthesis

Amplification of the yeast genes was performed using standard PCR with yeast genomic DNA as the template. In the first step, a forward primer containing a restriction enzyme site and a reverse primer containing a universal linker sequence were used. In the second PCR reaction, the reverse primer was exchanged with a nested primer containing a poly-T20 tail and a restriction enzyme site. The DNA fragments were ligated into the pTRIamp18 vector (Ambion, USA) using the Quick Ligation Kit (New England Biolabs, USA) according to the supplier's instructions and transformed into *E. coli* DH-5α by standard methods. The PCR clones were sequenced using M13 forward and M13 reverse primers on an ABI 377 (Applied Biosystems, USA). Synthesis of in vitro RNA was carried out using the MEGAscript™ T7 Kit (Ambion, USA) according to the manufacturer's instructions.

Design and Synthesis of the LNA Capture Probes

To design the capture probes, regions with unique mRNA sequence of the selected target genes were identified. The optimal 50-mer oligonucleotide sequences with respect to $T_m$, self-complementarity, and secondary structure were selected. LNA modifications were incorporated to increase affinity and specificity.

Printing of the LNA Microarrays

The microarrays were printed on Immobilizer™ MicroArray Slides (Exiqon, Denmark) using the Biochip One Arrayer from Packard Biochip technologies (Packard, USA). The arrays were printed with a spot volume of 2×300 pl of a 10 µM capture probe solution. Four replicas of the capture probes were printed on each slide.

Synthesis of Fluorochrome Labelled First Strand cDNA from Total RNA

Ten ng of *S. cerevisiae* in vitro synthesized RNA (either SWI5 or THI4) was combined with 10 µg of *C. elegans* total RNA and 5 µg oligo dT primer (T20VN) in an RNase free, pre-siliconized 1.5 mL tube, and the final volume was adjusted with DEPC-water to 8 µL. The reaction mixture was heated at +70° C. for 10 minutes, quenched on ice for 5 minutes, and spun for 20 seconds, followed by addition of 1 µL SUPERase-In™ (20 U/µL, RNAse inhibitor, Ambion, USA), 4 µL 5×RTase buffer (Invitrogen, USA), 2 µL, 0.1 M DTT (Invitrogen, USA), 1 µL dNTP (20 mM dATP, dGTP, dTTP; 0.4 mM dCTP in DEPC-water, Amersham Pharmacia Biotech, USA), and 3 µL Cy3™-dCTP or Cy5™-dCTP (Amersham Pharmacia Biotech, USA). First strand cDNA synthesis was carried out by adding 1 µL of Superscript™ II (Invitrogen, 200 U/mL), mixing, and incubating the reaction mixture for one hour at 42° C. An additional 1 µL of Superscript™ II was added, and the cDNA synthesis reaction mixture was incubated for an additional one hour at 42° C.; the reaction was stopped by heating at 70° C. for 5 minutes, and quenching on ice for 2 minutes. The RNA was hydrolyzed by adding 3 µL of 0.5 M NaOH, and incubating at 70° C. for 15 minutes. The samples were neutralized by adding 3 µL of 0.5 M HCl, and purified by adding 450 µL 1×TE buffer, pH 7.5 to the neutralized sample and transferring the samples onto a Microcon-30 concentrator. The samples were centrifuged at 14000×g in a microcentrifuge for ~8 minutes, the flow-through was discarded and the washing step was repeated twice by refilling the filter with 450 µl 1×TE buffer and by spinning for ~12 minutes. Centrifugation was continued until the volume was reduced to 5 µL, and finally the labelled cDNA probe was eluted by inverting the Microcon-30 tube and spinning at 1000×g for 3 minutes.

Hybridization with Fluorochrome-Labelled cDNA

The arrays were hybridized overnight using the following protocol. The Cy3™ or Cy5™-labelled cDNA samples were combined in one tube followed by addition of 3 µL 20×SSC (3×SSC final), 0.5 µL 1 M HEPES, pH 7.0 (25 mM final), 25 µg yeast tRNA (1.25 µg/µL final), 10 µg PolyA blocker (0.5 µg/µL final), 0.6 µL 10% SDS (0.3% final), and DEPC-treated water to 20 µL final volume. The labelled cDNA target sample was filtered in a Millipore 0.22 micron spin column according to the manufacturer's instructions (Millipore, USA), and the probe was denatured by incubating the reaction at 100° C. for 2 minutes. The sample was cooled at 20-25° C. for 5 minutes by spinning at maximum speed in a microcentrifuge. A LifterSlip (Erie Scientific Company, USA) was carefully placed on top of the microarray spotted on Immobilizer™ MicroArray Slide, and the hybridization mixture was applied to the array from the side. An aliquot of 30 µL of 3×SSC was added to both ends of the hybridization chamber, and the Immobilizer™ MicroArray Slide was placed in the hybridization chamber. The chamber was sealed watertight and incubated at 65° C. for 16-18 hours submerged in a water bath. After hybridization, the slide was removed carefully from the hybridization chamber and washed using the following protocol. The Lifterslip coverslip was washed off in 2×SSC, pH 7.0 containing 0.1% SDS at room temperature for one minute, followed by washing of the microarrays subsequently in 1.0×SSC, pH 7.0 at room temperature for one minute, and then in 0.2×SSC, pH 7.0 at room temperature for one minute. Finally, the slides were washed for 5 seconds in 0.05×SSC, pH 7.0. The slides were then dried by centrifugation in a swinging bucket rotor at approximately 600 rpm for 5 minutes.

Data Analysis

Following washing and drying, the slides were scanned using a ScanArray 4000XL scanner (Perkin-Elmer Life Sciences, USA), and the array data were processed using the GenePix™ Pro 4.0 software package (Axon, USA).

Results

Incorporation of LNA nucleotides at every third nucleotide position in standard 50-mer expression array oligonucleoitde capture probes resulted in a 3-fold increase in fluorescence intensity levels, when hybridized under standard stringency conditions (FIGS. 4A and 4B). When the hybridization temperature is increased from 65° C. to 70° C., the capture of the SWI5 spike mRNA by LNA 50-mer oligos is increased by 8-fold relative to the DNA controls. Thus, it can clearly be concluded that oligonucleotides containing LNA units are more sensitive in expression profiling compared to oligonucleotides containing only DNA units. The specificity of 40-mer LNA/DNA mixmer capture probes in the discrimination of highly homologous target sequences was addressed by introducing 1-5 consecutive mismatches in the middle of SWI5 and THI4 capture oligos together with the corresponding DNA controls. As demonstrated in FIGS. 5A and 5B, the LNA-spiked (LNA modification at every fourth nucleotide position) 40-mer triple mismatch oligos showed a 3-fold signal intensity decrease relative to the perfectly matched duplexes, whereas the corresponding 40-mer standard DNA capture probes did not form duplexes under standard hybridization stringency. Further, the 40-mer perfect match LNA capture probes showed a 5-fold to 14-fold increase in the intensity levels compared to DNA oligonucleotides under standard hybridization conditions. Capture probes of other lengths and/or with other LNA substitution patterns can be used similarly.

TABLE 2

DNA and LNA-modified SWI5 (YDR146C) and THI4 (YGR144W) oligonucleotide capture probes.

| Oligo Name | Sequence |
|---|---|
| YDR146C-40 | acggggattatggtttcgccaatgaaaactaatcaaaggt |
| YDR146C-40_mt1 | acggggattatggtttcgcctatgaaaactaatcaaaggt |
| YDR146C-40_mt2 | acggggattatggtttcgcgtatgaaaactaatcaaaggt |
| YDR146C-40_mt3 | acggggattatggtttcgggtatgaaaactaatcaaaggt |
| YDR146C-40_mt4 | acggggattatggtttcgggtttgaaaactaatcaaaggt |
| YDR146C-40_mt5 | acggggattatggtttcgggttagaaaactaatcaaaggt |
| YDR146C-40_LNA4 | acGgggAttaTggtTtcgmCcaaTgaaAactAatcAaagGt |
| YDR146C-40_LNA4_mt1 | acGgggAttaTggtTtcgmCctaTgaaAactAatcAaagGt |
| YDR146C-40_LNA4_mt2 | acGgggAttaTggtTtcgmCgtaTgaaAactAatcAaagGt |
| YDR146C-40_LNA4_mt3 | acGgggAttaTggtTtcgGgtaTgaaAactAatcAaagGt |
| YDR146C-40_LNA4_mt4 | acGgggAttaTggtTtcgGgttTgaaAactAatcAaagGt |
| YDR146C-40_LNA4_mt5 | acGgggAttaTggtTtcgGgttAgaaAactAatcAaagGt |
| YDR146C-50 | tgggaatggaacggggattatggtttcgccaatgaaaactaatcaaaggt |
| YDR146C-50_mt1 | tgggaatggaacggggattatggtatcgccaatgaaaactaatcaaaggt |
| YDR146C-50_mt2 | tgggaatggaacggggattatggtaacgccaatgaaaactaatcaaaggt |
| YDR146C-50_mt3 | tgggaatggaacggggattatggtaaggccaatgaaaactaatcaaaggt |
| YDR146C-50_mt4 | tgggaatggaacggggattatggaaaggccaatgaaaactaatcaaaggt |
| YDR146C-50_mt5 | tgggaatggaacggggattatggaaagcccaatgaaaactaatcaaaggt |
| YDR146C-50_LNA2 | TgGgAaTgGaAcGgGgAtTaTgGtTtmCgmCcAaTgAaAamCtAaTcAaAgGt |
| YDR146C-50_LNA3 | TggGaaTggAacGggGatTatGgtTtcGccAatGaaAacTaaTcAaagGt |
| YDR146C-50_LNA4 | TgggAatgGaacGgggAttaTggtTtcgmCcaaTgaaAactAatcAaagGt |
| YDR146C-50_LNA5 | TgggaAtggaAcgggGattaTggttTcgccAatgaAaactAatcAaaggt |
| YDR146C-50_LNA6 | TgggaaTggaacGgggatTatggtTtcgccAatgaaAactaaTcaaagGt |
| YDR146C-50_LNA3_mt1 | TggGaaTggAacGggGatTatGgtAtcGccAatGaaAacTaaTcAaagGt |
| YDR146C-50_LNA3_mt2 | TggGaaTggAacGggGatTatGgtAacGccAatGaaAacTaaTcAaagGt |
| YDR146C-50_LNA3_mt3 | TggGaaTggAacGggGatTatGgtAagGccAatGaaAacTaaTcAaagGt |
| YDR146C-50_LNA3_mt4 | TggGaaTggAacGggGatTatGgaAagGccAatGaaAacTaaTcAaagGt |
| YDR146C-50_LNA3_mt5 | TggGaaTggAacGggGatTatGgaAagmCccAatGaaAacTaaTcAaagGt |
| YGR144W-40 | ttgctgaactggatggattaaaccgtatgggtccaacttt |
| YGR144W-40_mt1 | ttgctgaactggatggatttaaccgtatgggtccaacttt |
| YGR144W-40_mt2 | ttgctgaactggatggatataaccgtatgggtccaacttt |
| YGR144W-40_mt3 | ttgctgaactggatggatattaccgtatgggtccaacttt |

TABLE 2-continued

DNA and LNA-modified SWI5 (YDR146C) and THI4 (YGR144W) oligonucleotide capture probes.

| Oligo Name | Sequence |
| --- | --- |
| YGR144W-40_mt4 | ttgctgaactggatggatatttccgtatgggtccaacttt |
| YGR144W-40_mt5 | ttgctgaactggatggatatttgcgtatgggtccaacttt |
| YGR144W-40_LNA4 | ttGctgAactGgatGgatTaaamCcgtAtggGtccAactTt |
| YGR144W-40_LNA4_mt1 | ttGctgAactGgatGgatTtaamCcgtAtggGtccAactTt |
| YGR144W-40_LNA4_mt2 | ttGctgAactGgatGgatAtaamCcgtAtggGtccAactTt |
| YGR144W-40_LNA4_mt3 | ttGctgAactGgatGgatAttamCcgtAtggGtccAactTt |
| YGR144W-40_LNA4_mt4 | ttGctgAactGgatGgatAtttmCcgtAtggGtccAactTt |
| YGR144W-40_LNA4_mt5 | ttGctgAactGgatGgatAtttGcgtAtggGtccAactTt |
| YGR144W-50 | ggtatggaagttgctgaactggatggattaaaccgtatgggtccaacttt |
| YGR144W-50_mt1 | ggtatggaagttgctgaactggatcgattaaaccgtatgggtccaacttt |
| YGR144W-50_mt2 | ggtatggaagttgctgaactggatccattaaaccgtatgggtccaacttt |
| YGR144W-50_mt3 | ggtatggaagttgctgaactggaaccattaaaccgtatgggtccaacttt |
| YGR144W-50_mt4 | ggtatggaagttgctgaactggaacctttaaaccgtatgggtccaacttt |
| YGR144W-50_mt5 | ggtatggaagttgctgaactggaacctataaaccgtatgggtccaacttt |
| YGR144W-50_LNA3 | GgtAtgGaaGttGctGaamCtgGatGgaTtaAacmCgtAtgGgtmCcaActTt |
| YGR144W-50_LNA3_mt1 | GgtAtgGaaGttGctGaamCtgGatmCgaTtaAacmCgtAtgGgtmCcaActTt |
| YGR144W-50_LNA3_mt2 | GgtAtgGaaGttGctGaamCtgGatmCcaTtaAacmCgtAtgGgtmCcaActTt |
| YGR144W-50_LNA3_mt3 | GgtAtgGaaGttGctGaamCtgGaamCcaTtaAacmCgtAtgGgtmCcaActTt |
| YGR144W-50_LNA3_mt4 | GgtAtgGaaGttGctGaamCtgGaamCctTtaAacmCgtAtgGgtmCcaActTt |
| YGR144W-50_LNA3_mt5 | GgtAtgGaaGttGctGaamCtgGaamCctAtaAacmCgtAtgGgtmCcaActTt |

LNA modifications are depicted by uppercase letters in the sequence,
mt denotes the number of mismatches (bolded) in the center of the oligonucleotide with respect to its target cDNA (mRNA), and
"mC" denotes LNA methyl cytosine.
(SEQ ID NOs: 1-52, in sequential order)

EXAMPLE 2

Detection of Alternative Splice Isoforms Using Exon-Specific, Internal LNA Capture Probes in the Caenorhabditis elegans Gene Let-2

Capture Probe Design
Finding the Regions of Interest

From the database "intronerator" (W. Jim Kent and Al M. Zahler, "The Intronerator: exploring introns and alternative splicing in C. elegans," Nucleic Acids Research Jan. 1, 2000; 28(1):91-93 and "Conservation, Regulation, Synteny, and Introns in a Large-scale C. briggsae-C. elegans Genomic Alignment" in Genome Research August, 2000; 10(8):1115-1125) as well as scientific literature, the C. elegans Let-2 gene encoding type IV collagen was found according to the following criteria. The generation of mature mRNA desirably involves either complete exon or intron skipping. ESTs (expressed sequence tags) desirably indicate different isoforms. If ESTs were only different from the gene annotation(s), this could simply mean that the prediction is wrong, and nothing more. Desirably, there are different EST splice indications in different developmental stages. Two gene prediction algorithms (e.g., GeneFinder and Genie) desirably agree upon the number of genes in a coding segment. Exons of interest (e.g., exons being skipped and their flanking exons) in the C. elegans gene T01D3.3 desirably exceed 70 base-pairs. Other genes of interest may be selected using one or more of the above criteria or using other criteria, such as the medical relevance of the gene.

Determining Melting Temperatures and Palindromic Properties of the C. elegans Let-2 Gene/Exons 8, 9, 10, and 11-Specific Capture Probes The script PICK70 (which was kindly provided by Jingchun Zhu from the Joe DeRisi Laboratory and which is publicly available) was used to run a sliding 50 base-pair window across the regions in which an oligonucleotide capture probe should be designed. The output data were saved for later.

Determining the Uniqueness of the Regions

All regions were compared using a publicly available BLAST program to the complete set of annotated transcripts from the C. elegans genome downloaded from NCBI. For each region a list with the location of all BLAST hits was made.

Choice of Desirable $T_m$ for Capture Probes

From the PICK70 output, the distribution of melting temperatures for all possible oligonucleotides was collected.

As these centered around approximately 80° C., this temperature was chosen as the desirable temperature.

For each region, an oligonucleotide with a palindromic value below 100 (default value in PICK70, value based on Smith-Waterman algorithm) and with a melting temperature closest to 80° C. was picked. The location of the oligonucleotide within the region was then compared to the list made using the above BLAST search. If the oligonucleotide did not coincide with a BLAST hit exceeding around 25 (consecutive) base-pairs, this oligonucleotide sequence was chosen as a 50-mer capture probe. Otherwise, a new oligo sequence was picked from the PICK70 output.

Checking Probe Sequences

The selected 50-mer oligonucleotide sequences were "BLASTed" against the C. elegans transcripts again, as described above.

Accounting for the Introns

The oligonucleotide sequences were "BLASTed" against the complete C. elegans genome. The matches were run against a list made from the GenBank reports of the complete genome, indexing whether positions in the genome were genic or intergenic.

It was checked to determine whether new hits to genic regions appeared (compared to the initial BLAST search using the PICK70 output). If this was not case, the oligonucleotide sequences were selected for capture probe synthesis.

Design of the LNA-Modified Capture Probes

For the LNA-modified oligonucleotide capture probes, every fourth DNA nucleotide was substituted with an LNA nucleotide, as shown in Table 3. The oligonucleotides were synthesized with an anthraquinone (AQ) moiety at the 5'-end of each oligonucleotide (e.g., as described in allowed U.S. Ser. No. 09/611,833), followed by a hexaethyleneglycol tetramer linker region and the LNA/DNA mixmer capture oligonucleotide sequence.

TABLE 3

C. elegans let-2 gene/exons 8, 9, 10, and 11-specific capture probes (SEQ ID NOs: 53-56, in sequential order)

Sequence (LNA = uppercase, Capture probe DNA = lowercase letters)

CE42.08-0HEG4 GgctGgatmCcccAggaAaccmCaggAatcGgaaGc
atTggamCcaaAaggAg

CE42.09-0HEG4 mCaccGgatmCcggmCtcaAttgTcggAcctmCgcg
GaaamCcctGgagAaaaGg

CE42.10-0HEG4 TccgmCcagGcccAatcGcctmCcacmCatgTcca
AgggAaccAttaTcggTc

CE42.11-0HEG4 GagcmCaggAgagGgagGtcaAcgcGgttAcccAgga
AatgGaggActcTc

Strains and Growth Conditions

C. elegans wild-type strain (Bristol-N2) was maintained on nematode growth medium (NG) plates seeded with Escherichia coli strain OP50 at 20° C., and the eggs and L1 larvae were prepared as described in Hope, I. A. (ed.) "C. elegans—A Practical Approach", Oxford University Press 1999. The samples were immediately flash frozen in liquid $N_2$ and stored at −80° C. until RNA isolation.

Isolation of Total RNA

A 100 µl aliquot of packed C. elegans worms from a L1 larvae population was homogenized using the FastPrep Bio101 from Kern-En-Tee for 1 minute at speed 6 followed by isolation of total RNA from the extracts using the FastPrep Bio101 kit (Kem-En-Tec) according to the manufacturer's instructions. A 50 µl aliquot of packed C. elegans eggs was homogenized in lysis buffer (RNeasy total RNA purification kit, QIAGEN) containing quartz sand for 3 minutes using a Pellet Pestle Motor followed by isolation of total RNA according to the manufacturer's manual.

The eluted total RNA from worms (L1 larvae) as well as eggs was ethanol precipitated for 24 hours at −20° C. by addition of 2.5 volumes of 96% EtOH and 0.1 volume of 3M Na-acetate, pH 5.2 (Ambion, USA), followed by centrifugation of the total RNA sample for 30 minutes at 13200 rpm. The total RNA pellet was air-dried and redissolved in 6 µl (worms) or 2.5 µl (eggs) of diethylpyrocarbonate (DEPC)-treated water (Ambion, USA) and stored at −80° C.

Reverse Transcription (RT)-PCR

Total RNA (1.5 µg) from eggs or 1 µg total RNA from worms (L1 larvae) were mixed with 5 µg oligo(dT) 12-18 primer (Amersham Pharmacia Biotech, USA) and 0.5 µg of random hexamers, $pd(N)_6$ (Amersham Pharmacia Biotech, USA) and DEPC-treated water to a final volume of 7 µl. The mixture was heated at 70° C. for 10 minutes, quenched on ice for 5 minutes, followed by addition of 20 units of Superasin RNase inhibitor (Ambion, USA), 4 µl of 5× Superscript buffer (Life Technologies, USA), 2 µl of 100 mM DTT, 1 µl of dNTP solution (20 mM each dATP, dGTP, dTTP and dCTP, Amersham Pharmacia Biotech, USA), and 3 µl of DEPC-treated water.

The primers were pre-annealed at 37° C. for 5 minutes, followed by addition of 400 units of Superscipt II reverse transcriptase (Invitrogen, USA). First strand cDNA synthesis was carried out at 37° C. for 30 minutes, followed by 2 hours at 42° C., and the reaction was stopped by incubation at 70° C. for 5 minutes, followed by incubation on ice for 5 minutes.

Unincorporated dNTPs were removed by gel filtration using MicroSpin S-400 HR columns as described below. The column was pre-spun for 1 minute at 735×g in a 1.5 ml tube, and the column was placed in a new 1.5 ml tube. The cDNA sample was slowly applied to the top center of the resin and spun at 735×g for 2 minutes. The eluate was collected. The volume of the eluate was adjusted to 50 µl with TE-buffer pH 7.0 before being used as the template for linear PCR. Four µl template (RT from eggs or worms) was combined with 1 µl dNTP solution (10 mM each dATP, dGTP, dTTP and dCTP, Amersham Phamacia Biotech, USA), 1 µl of each primer (20 µM CE42.07 sense: gatcgaattcctccaggagagaagggagatg (SEQ ID NO: 57), and CE42.12 antisense: 5' gatcaagcttatctcttcctgggtatccagctt (SEQ ID NO: 58)), 5 µl 10× AmpliTaq Gold Polymerase buffer, 5 µl 25 mM $MgCl_2$, 0.5 µl AmpliTaq Gold DNA polymerase (5 U/µl, Applied Biosystems), 2 µl Cy3-dCTP (Amersham Phamacia Biotech, USA) (eggs) or 2 µl Cy5-dCTP (Amersham Pharmacia Biotech, USA) (worms), and 31.5 µl DEPC-treated water to a final volume of 50 µl. The PCR reactions were carried out using the following program: 95° C. for 5 minutes followed by 30 cycles of PCR using the following cycling program (denaturation at 95° C. for 45 seconds, annealing at 60° C. for 30 seconds, and extension at 72° C. for 1 minute) followed by a final extension step at 72° C. for 10 minutes and incubation on ice for 5 minutes.

Purification of the PCR amplicons from eggs as well as worms was performed using a Qiaquick PCR purification kit (QIAGEN) according to the manufacturer's instructions.

Fluorochrome-Labeling of the Let-2 cDNA Fragments Using Primer Extension

Four (4) μl template (RT from eggs or worms) was combined with 1 μl dNTP solution (10 mM each dATP, dGTP, dTTP and dCTP, Amersham Phamacia Biotech, USA), 1 μl of each primer (20 μM CE42.12 antisense 5' gatcaagcttatctcttcctgggtatccagctt (SEQ ID NO: 58)), 5 μl 10× AmpliTaq Gold Polymerase buffer, 5 μl 25 mM MgCl$_2$, 0.5 μl AmpliTaq Gold DNA polymerase (5 U/μl, Applied Biosystems), 2 μl Cy3-dCTP (Amersham Phamacia Biotech, USA) (eggs) or 2 μl Cy5-dCTP (Amersham Phamacia Biotech, USA) (worms), and 31.5 μl DEPC-treated water to a final volume of 50 μl. The PCR reactions were carried out using the following program: 95° C. for 5 minutes followed by 30 cycles of PCR using the following cycling program (denaturation at 95° C. for 45 seconds annealing at 60° C. for 30 seconds extension at 72° C. for 1 minute) followed by a final extension step at 72° C. for 10 minutes and incubation on ice for 5 minutes.

Purification of the PCR amplicons from eggs as well as worms were performed using a Qiaquick PCR purification kit (QIAGEN) according to the manufacturer's instructions. Unincorporated dNTP nucleotides were removed by gel filtration using MicroSpin S-400 HR columns as described above before the eluted, fluorochrome-labelled DNA fragments were stored at −20° C. in the dark until microarray hybridization.

Printing and Coupling of the *C. elegans* Let-2 Exon 8-11 Microarrays

The *C. elegans* gene Let-2/exon 8-11 capture probes were synthesized with a 5' anthraquinone (AQ)-modification, followed by a hexaethyleneglycol-4 (HEG4) linker (Table 3). The capture probes were first diluted to a 10 μM final concentration in 100 mM Na-phosphate buffer pH 7.0 and spotted on Euray COP microarray slides using the Biochip Arrayer One (Packard Biochip Technologies) with a spot volume of 300 pl and 300 μm between the spots.

The capture probes were immobilized onto the microarray slide by UV irradiation in a Stratalinker for 90 seconds at full power (Stratagene, USA). Non-immobilized capture probe oligonucleotides were removed from the slides by washing the slides for ½ hour in 30% acetone before rising in milli-Q H$_2$O. After washing, the slides were centrifuged at 800 rpm for 2 minutes and stored in a slide box until microarray hybridization.

Comparative Hybridization of the *C. elegans* Microarrays and Post-Hybridization Washes The slides were hybridized with 2.5 μl of the Cy3-labelled and 2.5 μl of the Cy5-labelled target preparation from eggs and worms, respectively, as described above (see "Reverse transcription (RT)-PCR" section) in 25 μl of hybridization solution, containing 25 mM HEPES, pH 7.0, 3×SSC, 0.3% SDS, and 25 μg of yeast tRNA. The target probe was filtered in a Millipore 0.22 micron spin column (Ultrafree-MC, Millipore, USA), denatured by incubation at 100° C. for 5 minutes, cooled at room temperature for 5 minutes, and then carefully applied onto the prepared microarray. One-third of a cover slip was laid over the microarray, and the hybridization was performed for 16-18 hours at 65° C. in a hybridization chamber (DieTech, model Joe deRisi, USA).

Following hybridization, the slides were washed sequentially by plunging gently in 2×SSC/0.1% SDS at room temperature until the cover slip falls off into the washing solution, then in 1×SSC pH 7.0 (150 mM NaCl, 15 mM Sodium Citrate) at room temperature for 1 minute, then in 0.2×SSC, pH 7.0 (30 mM NaCl, 3 mM Sodium Citrate) at room temperature for 1 minute, and finally in 0.05×SSC (7.5 mM NaCl, 0.75 mM Sodium Citrate) for 5 seconds, followed by drying of the slides by spinning at 500 rpm for 5 minutes. The slides were stored in a slide box in the dark until scanning.

Microarray Data Analysis

Figure 6:
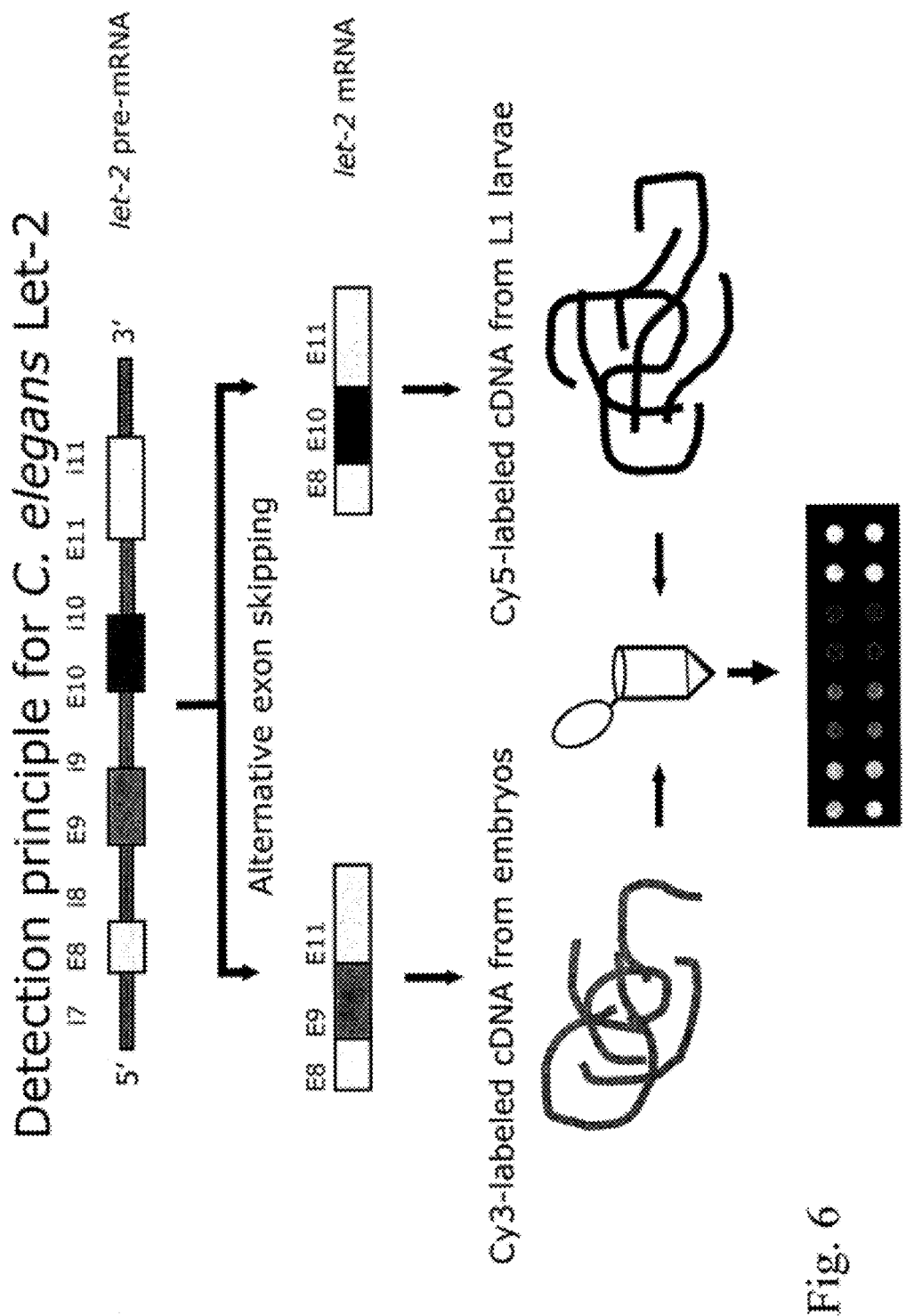
FIG. 6 shows the detection principle for alternative exon skipping in the C. elegans let-2 gene using LNA oligonucleotide capture probes and comparative expression profiling.
Figure 7:
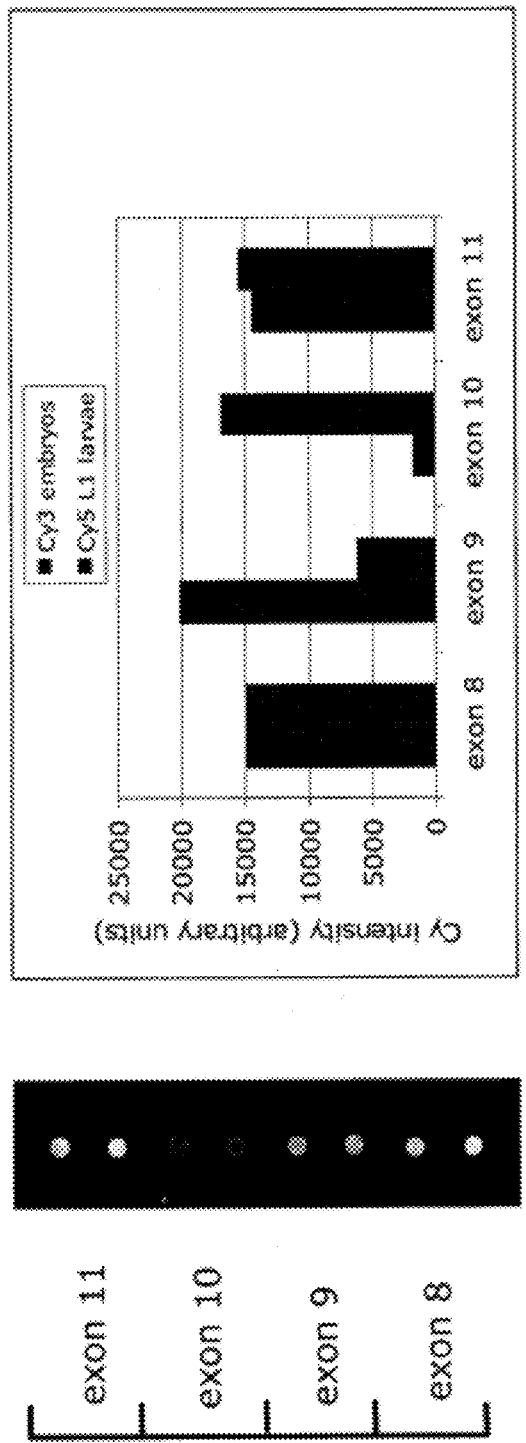
FIG. 7 shows the detection of alternative splicing of C. elegans Let-2 exon 9 and 10 using LNA-modified capture probes.

The *C. elegans* let-2 gene microarray was scanned in an ArrayWoRx Scanner (Applied Precision, USA) using an exposure time of 5 seconds, resolution of 5.0, and high (high level) sensitivity. The hybridization data were analyzed using the ArrayVision image analysis software package 5.1 (IMAGING Research Inc., USA). The detection principle for alternative exon skipping the *C. elegans* let-2 gene is shown in FIG. 6. As demonstrated in FIG. 7, analysis of the comparative hybridization data from the *C. elegans* Let-2 exon 8-11 array demonstrates detection of alternative exon skipping of the let-2 exon 9 (eggs) and exon 10 (L1 larvae) using LNA-modified 50-mer capture probes. Capture probes of other lengths and/or with other LNA substitution patterns can be used similarly.

EXAMPLE 3

Improved Sensitivity in the Specific Detection of the *C. elegans* Gene T01D3.3 Exon 4 Using LNA-Modified Oligonucleotide Capture Probes Capture Probe Design: The design method of exon-specific capture probes for the *C. elegans* gene T01D3.3 exon 4 has been described in example 2.

Design of the LNA-modified Capture Probes: For the LNA-spiked oligonucleotide capture probes, every fourth DNA nucleotide was substituted with an LNA nucleotide, as shown in Table 4.

TABLE 4

| *C. elegans* gene T01D3.3/exon 4-specific capture probes. (SEQ ID NOs: 59-68, in sequential order) ||
|---|---|
| Capture probes | Sequence (LNA = uppercase, DNA = lowercase letters) |
| CEgene26.04-70 | ggctggaacagaagtttgttggtgcgtga caaggtatggaagaagattatccggaaaa gaaagcaaagac |
| CEgene26.04-50 | ggctggaacagaagtttgttggtgcgtgacaa ggtatggaagaagattat |
| CEgene26.04-40 | ggctggaacagaagtttgttggtgcgtgacaa ggtatgga |
| CEgene26.04-30 | gaacagaagtttgttggtgcgtgacaaggt |
| CEgene26.04-50HEG2 | GgctGgaamCagaAgttTgttGgtgm CgtgAcaaGgtaTggaAgaaGattAt |
| CEgene26.04-50HEG4 | GgctGgaamCagaAgttTgttGgtgm CgtgAcaaGgtaTggaAgaaGattAt |
| CEgene26.04-40HEG2 | GgctGgaamCagaAgttTgttGgtgm CgtgAcaaGgtaTgga |
| CEgene26.04-40HEG4 | GgctGgaamCagaAgttTgttGgtgm CgtgAcaaGgtaTgga |
| CEgene26.04-30HEG2 | GaacAgaaGtttGttgGtgcGtgamCaagGt |
| CEgene26.04-30HEG4 | GaacAgaaGtttGttgGtgcGtgamCaagGt |

Cultivation of *Caenorhabditis elegans* Worms

Mixed stage *C. elegans* cultures were grown according to standard methods. Samples were harvested by centrifugation at 3000×g, suspended in RNA Later (Ambion, USA), and immediately frozen in liquid nitrogen.

mRNA Isolation from *C. elegans* Mixed Stages Worms

Poly(A)+RNA was isolated from the worm samples using the Pick-Pen (Bio-Nobile, Finland) Starter kit combined with the KingFisher mRNA purification kit (ThermoLabsystems, Finland) according to the manufacturer's instructions. The yield was 1-2 μg poly(A)+RNA from approximately 50 mg of *C. elegans* worms.

Synthesis of Fluorochrome Labelled First Strand cDNA from *C. elegans* mRNA

One μg of *C. elegans* poly(A)+RNA was combined with 2 μg oligo dT primer (T20VN) in an RNase free, pre-siliconized 1.5 mL tube, and the final volume was adjusted with DEPC-water to 8 μL. The reaction mixture was heated at +70° C. for 10 minutes, quenched on ice 5 minutes, spun for 20 seconds, followed by addition of 1 μL SUPERase-In™ (20 U/μL, RNAse inhibitor, Ambion, USA), 4 μL 5×RTase buffer (Invitrogen, USA), 2 μL 0.1 M DTT (Invitrogen, USA), 1 μL dNTP (20 mM dATP, dGTP, dTTP; 4 mM dCTP in DEPC-water, Amersham Pharmacia Biotech, USA), and 3 μL Cy3™-dCTP (Amersham Pharmacia Biotech, USA). First strand cDNA synthesis was carried out by adding 1 μL of Superscript™ II (Invitrogen, 200 U/mL), mixing, and incubating the reaction mixture for one hour at 42° C. An additional 1 μL of Superscript™ II was added and the cDNA synthesis reaction mixture was incubated for an additional one hour at 42° C.; the reaction was stopped by heating at 70° C. for 5 minutes, and quenching on ice for 2 minutes. The RNA was hydrolyzed by adding 3 μL of 0.5 M NaOH and incubating at 70° C. for 15 minutes. The samples were neutralized by adding 3 μL of 0.5 M HCl and purified by adding 450 μL 1×TE buffer, pH 7.5 to the neutralized sample and transferring the samples onto a Microcon-30 concentrator. The samples were centrifuged at 14000×g in a microcentrifuge for ~8 minutes, the flow-through was discarded, and the washing step was repeated twice by refilling the filter with 450 μl 1×TE buffer and by spinning for ~12 minutes. Centrifugation was continued until the volume was reduced to 5 μL, and finally the labelled cDNA probe was eluted by inverting the Microcon-30 tube and spinning at 1000×g for 3 minutes.

Printing and Coupling of the *C. elegans* Microarrays

The *C. elegans* gene T01D3.3/exon 4 capture probes were synthesized with a 5' anthraquinone (AQ)-modification, followed by either a hexaethyleneglycol-2 or a hexaethyleneglycol-4 (HEG2/HEG4) linker (Table 4). The capture probes were first diluted to a 10 μM final concentration in 100 mM Na-phosphate buffer pH 7.0, followed by a two-fold dilution series (10 μM, 5 μM, 2.5 μM, 1.25 μM, 0.625 μM, 0.31 μM, and 0.155 μM) and spotted on Exiqon's polycarbonate microarray slides using the Biochip Arrayer One (Packard Biochip Technologies, USA) with a spot volume of 3×300 pl and 400 μm between the spots. The capture probes were immobilized onto the microarray slide by UV irradiation in a Stratalinker for 90 seconds at full power (Stratagene, USA). Non-immobilized capture probe oligonucleotides were removed from the slides by washing the slides for 24 hours in milli-Q H$_2$O. After washing, the slides were dried in an oven at 37° C. for 30 minutes and stored in a slide box until microarray hybridization.

Hybridization with Cy3-Labelled cDNA

The arrays were hybridized overnight using the following protocol. The Cy3™-labelled cDNA sample was combined with 3 μL 20×SSC (3×SSC final), 0.5 μL 1 M HEPES, pH 7.0 (25 mM final), 25 μg yeast tRNA (1.25 μg/μL final), 10 μg PolyA blocker (0.5 μg/μL final), 0.6 μL 10% SDS (0.3% final), and DEPC-treated water to 20 μL final volume. The labelled cDNA target sample was filtered in a Millipore 0.22 micron spin column according to the manufacturer's instructions (Millipore, USA), and the probe was denatured by incubating the reaction at 100° C. for 2 minutes. The sample was cooled at 20-25° C. for 5 minutes by spinning at maxium speed in a microcentrifuge, and then carefully applied on top of the microarray. A cover slip was laid over the microarray and the hybridization was performed for 16 hours at 63° C. in a hybridization chamber (Corning, USA) submerged in a water bath, with an aliquot of 30 μL of 3×SSC added to both ends of the hybridization chamber to prevent evaporation. After hybridization, the slide was removed carefully from the hybridization chamber and washed using the following protocol. The coverslip was washed off in 2×SSC, pH 7.0 containing 0.1% SDS at room temperature for one minute, followed by washing of the microarrays subsequently in 1.0×SSC, pH 7.0 at room temperature for one minute, and then in 0.2×SSC, pH 7.0 at room temperature for one minute. Finally, the slides were washed for 5 seconds in 0.05×SSC, pH 7.0. The slides were then dried by centrifugation in a swinging bucket rotor at approximately 600 rpm for 5 minutes.

Microarray Data Analysis

Figure 8A:
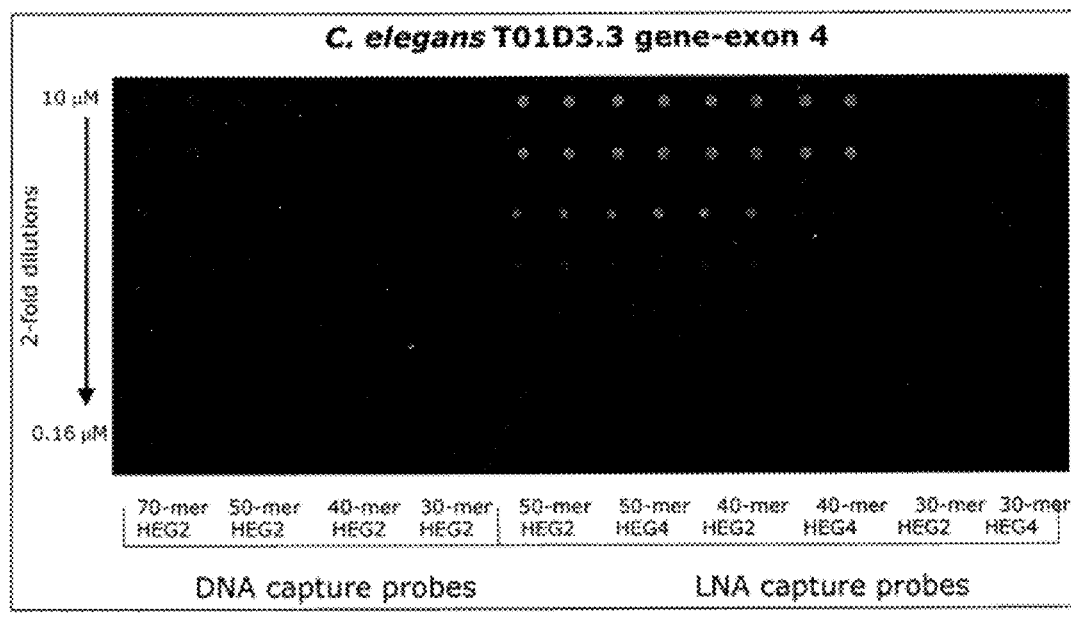
FIGS. 8A and 8B show the comparison of DNA and LNA-modified oligonucleotide capture probes in the specific capture of the C. elegans T01D3.3 mRNA, exon 4.
Figure 8B:
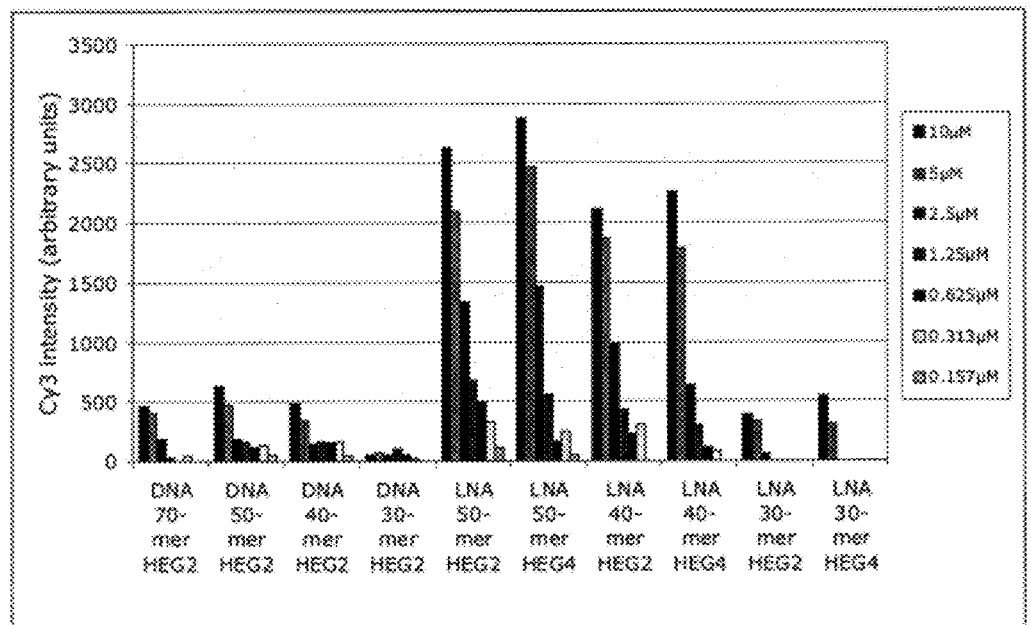

The *C. elegans* gene T01D3.3 exon 4 array was scanned in an ArrayWoRx Scanner (Applied Precision, USA) using an exposure time of 5 seconds, resolution of 5.0, and high (high level) sensitivity. The hybridization data were analyzed using the ArrayVision image analysis software package 5.1 (IMAGING Research Inc., USA). As shown in FIGS. 8A and 8B, analysis of the hybridization data from the *C. elegans* gene 26/T01D3.3 exon 4 array demonstrates that the use of LNA-modified capture probes for the *C. elegans* T01D3.3 exon results in 5-fold increased sensitivity in exon 4 capture compared to the corresponding DNA oligonucleotide capture probe controls printed on the same microarray. Capture probes of other lengths and/or with other LNA substitution patterns can be used similarly.

EXAMPLE 4

Assessment of Capture Probe Specificity for the *C. elegans* Gene T01D3.3 Exons 4 and 5 Using Synthetic Antisense Target Oligos Capture probe design: Exon-specific capture probes for the *C. elegans* gene T01D3.3 exons 4 and 5 were designed as described in Example 2.

Design of the LNA-modified capture probes: For the LNA-spiked oligonucleotide capture probes, every fourth DNA nucleotide was substituted with an LNA nucleotide, as shown in Table 5: *C. elegans* gene T01D3.3/exons 4 and 5-specific capture probes and synthetic target oligonucleotides.

TABLE 5

| | Sequence (LNA = uppercase, DNA = lowercase letters) | SEQ ID NO: |
|---|---|---|
| Capture probes | | |
| CEgene26.04-70 | ggctggaacagaagtttgttggtgcgtgacaaggtatggaagaagattatccggaaaagaaagcaaagac | 59 |
| CEgene26.05-70 | tatgtggcgcgaatgagcaatattcagcatgtttctcctcttgtcaaccatcatgtcaagatccttcaac | 69 |
| CEgene26.04-50 | ggctggaacagaagtttgttggtgcgtgacaaggtatggaagaagattat | 60 |
| CEgene26.05-50 | tatgtggcgcgaatgagcaatattcagcatgtttctcctcttgtcaacca | 70 |
| CEgene26.04-40 | ggctggaacagaagtttgttggtgcgtgacaaggtatgga | 61 |
| CEgene26.05-40 | tatgtggcgcgaatgagcaatattcagcatgtttctcctc | 72 |
| CEgene26.04-30 | gaacagaagtttgttggtgcgtgacaaggt | 62 |
| CEgene26.05-30 | tatgtggcgcgaatgagcaatattcagcat | 72 |
| CEgene26.04-50HEG2 | GgctGgaamCagaAgttTgttGgtgmCgtgAcaaGgtaTggaAgaaGattAt | 63 |
| CEgene26.04-50HEG4 | GgctGgaamCagaAgttTgttGgtgmCgtgAcaaGgtaTggaAgaaGattAt | 64 |
| CEgene26.05-50HEG2 | TatgTggcGcgaAtgaGcaaTattmCagcAtgtTtctmCctcTtgtmCaacmCa | 73 |
| CEgene26.05-50HEG4 | TatgTggcGcgaAtgaGcaaTattmCagcAtgtTtctmCctcTtgtmCaacmCa | 74 |
| CEgene26.04-40HEG2 | GgctGgaamCagaAgttTgttGgtgmCgtgAcaaGgtaTgga | 65 |
| CEgene26.04-40HEG4 | GgctGgaamCagaAgttTgttGgtgmCgtgAcaaGgtaTgga | 66 |
| CEgene26.05-40HEG2 | TatgTggcGcgaAtgaGcaaTattmCagcAtgtTtctmCctc | 75 |
| CEgene26.05-40HEG4 | TatgTggcGcgaAtgaGcaaTattmCagcAtgtTtctmCctc | 76 |
| CEgene26.04-30HEG2 | GaacAgaaGtttGttgGtgcGtgamCaagGt | 67 |
| CEgene26.04-30HEG4 | GaacAgaaGtttGttgGtgcGtgamCaagGt | 68 |
| CEgene26.05-30HEG2 | TatgTggcGcgaAtgaGcaaTattmCagcAt | 77 |
| CEgene26.05-30HEG4 | TatgTggcGcgaAtgaGcaaTattmCagcAt | 78 |
| Target oligos | | |
| CEgene26.04-biotarget | accttgtcacgcaccaacaaacttctgttc | 79 |
| CEgene26.05-biotarget | atgctgaatattgctcattcgcgccacata | 80 |

Printing and Coupling of the *C. elegans* Gene T01D3.3/Exon 4-5 Microarrays

The *C. elegans* gene T01D3.3/exon 4-5 capture probes were synthesized with a 5' anthraquinone (AQ)-modification, followed by either a hexaethyleneglycol-2 or a hexaethyleneglycol-4 (HEG2/HEG4) linker (Table 5). The capture probes were first diluted to a 10 µM final concentration in 100 mM Na-phosphate buffer pH 7.0, followed by a two-fold dilution series (10 µM, 5 µM, 2.5 µM, 1.25 µM, 0.625 µM, 0.31, µM, and 0.155 µM) and spotted on Euray polycarbonate microarray slides using the Biochip Arrayer One (Packard Biochip Technologies) with a spot volume of 3×300 pl and 400 µm between the spots. The capture probes were immobilized onto the microarray slide by UV irradiation in a Stratalinker for 90 seconds at full power (Stratagene, USA). Non-immobilized capture probe oligonucleotides were removed from the slides by washing the slides for 24 hours in milli-Q H$_2$O. After washing, the slides were dried in an oven at 37° C. for 30 minutes, and stored in a slide box until microarray hybridization.

Hybridization of the *C. elegans* Microarrays and Post-Hybridization Washes

The slides were hybridized with a high (saturated) concentration of 1 µM of each gene T01D3.3, exon 4 or 5 target oligo (Table 5) in 50 µl of hybridization solution, containing 25 mM HEPES, pH 7.0, 3×SSC, 0.22% SDS, and 0.8 µg/µl of poly(A) blocker. The target probes were filtered in a Millipore 0.45 micron spin column (Ultrafree-MC, Millipore, USA), denatured by incubation at 100° C. for 2 minutes, cooled at room temperature for 5 minutes, and then carefully applied onto the prepared microarray. One-half of a cover slip was laid over the microarray, and the hybridization was performed for 16-18 hours at 63° C. in a hybridization chamber (Corning, USA).

Following hybridization, the slides were washed sequentially by plunging gently in 1×SSCT (150 mM NaCl, 15 mM Sodium Citrate+Tween 20) at room temperature for one minute, then in 0.2×SSCT (30 mM NaCl, 3 mM Sodium Citrate+Tween 20) at room temperature for one minute, and finally in Milli Q water, followed by drying of the slides in an oven at 37° C. for 30 minutes. The slides were Cy5 labelled using a Cy5-straptavidin target. Thirty µl of a Cy5-streptavidin (2 µg/ml in 1×SSCT) were carefully applied onto the hybridized microarray and incubated one hour at room temperature before an additional washing step were performed in 1×SSCT (150 mM NaCl, 15 mM Sodium Citrate+Tween 20) at room temperature for one minute, then in 0.2×SSCT (30 mM NaCl, 3 mM Sodium Citrate+Tween 20) at room temperature for one minute, and finally in Milli Q water. Following washing, the slides were drying in an oven at 37° C. for 30 minutes and stored in a slide box in the dark until scanning.

Microarray Data Analysis

Figure 10A:
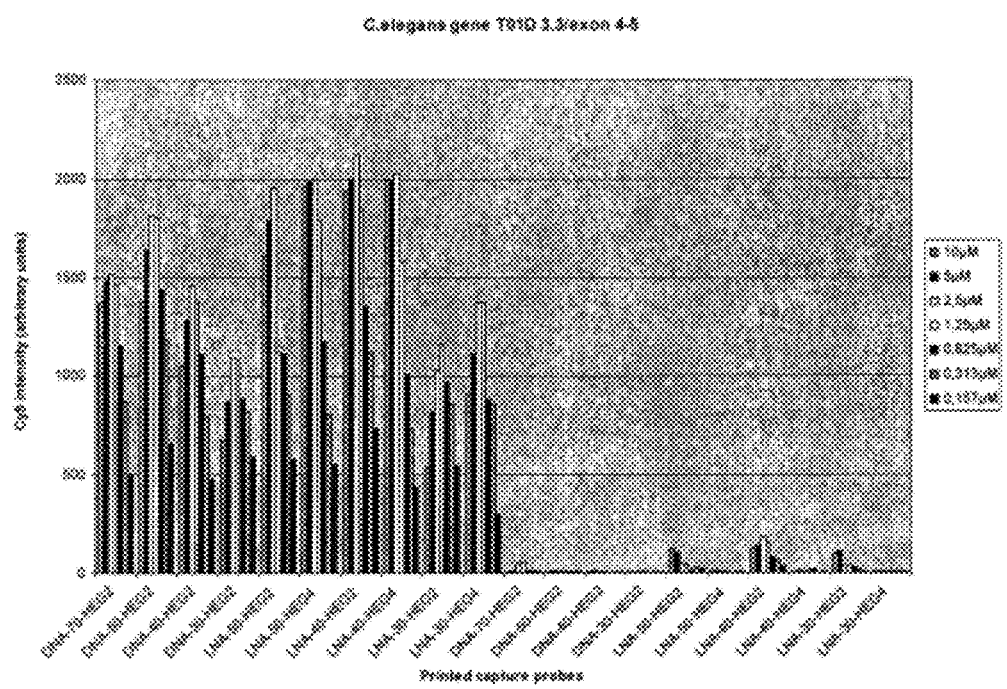
FIGS. 10A and 10B show the capture probe specificity for the C. elegans T01D3.3 mRNA, exon 4 (FIG. 10A) and exon 5 (FIG. 10B) as validated by short complementary target oligonucleotides.
Figure 10B:
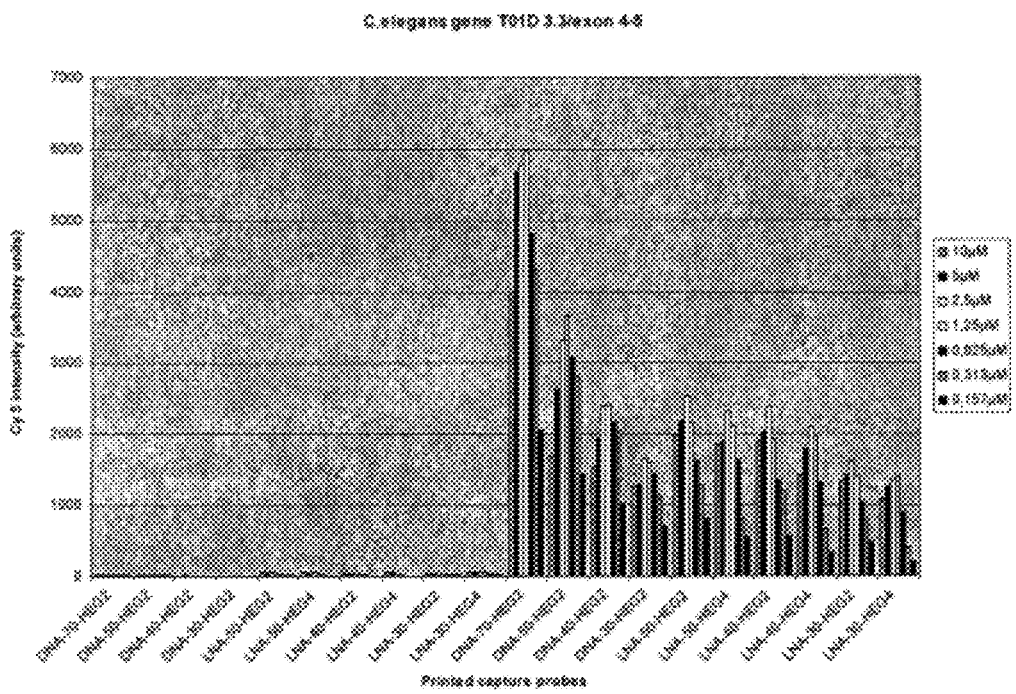

The *C. elegans* gene T01D3.3 exon 4-5 microarray was scanned in an ArrayWoRx Scanner (Applied Precision, USA) using an exposure time of 5 seconds, resolution of 5.0, and high (high level) sensitivity. The hybridization data were analyzed using the ArrayVision image analysis software package 5.1 (IMAGING Research Inc., USA). As shown in FIGS. 10A and 10B, analysis of the hybridization data from the *C. elegans* gene 26/T01D3.3 array demonstrates that both the DNA as well as the LNA capture probes for the *C. elegans* T01D3.3 exons 4 (FIG. 10A) and exon 5 (FIG. 10B), respectively are highly specific with a very low level of cross-hybridization between their respective target oligonucleotides. The exon-specific design of the oligonucleotide capture probes is thus validated. Capture probes of other lengths and/or with other LNA substitution patterns can be used similarly.

EXAMPLE 5

Detection of Alternatively Spliced Isoforms Using Internal Exon-Specific, and Exon-Exon Junction-Specific (Merged) LNA-Modified Capture Probes Oligonucleotide Design for Microarrays.

Methods for designing exon-specific internal oligonucleotide capture probes has been described in Example 2.

Design of the LNA-Modified Capture Probes

For the LNA-modified oligonucleotide capture probes, every third DNA nucleotide was substituted with an LNA nucleotide. The probes designed to capture the junction of the recombinant splice variants were designed with LNA modifications in a block of five consecutive LNAs nucleotides, two on the 5' side of the splice junction and three on the 3' side of the splice junction. All capture probes are shown in Table 6.

TABLE 6

Internal, exon-specific and merged, exon-exon junction specific oligonucleotide capture probes. (SEQ ID NOs: 81-96, in sequential order)

| Capture probes | Sequence (LNA = uppercase, DNA lowercase letters) |
| --- | --- |
| gene78.01a | cctgaaagtagatttgttatttccgaaacgccttctcccgttcttaagtc |
| gene78.01b | catataccacaaatagtccctcaaaaatcacaagaaaactcacaacactg |
| gene78.03a | gatttgcagcggtggtaaaaagtatgaaaacgtggtaattaaaaggtctc |
| gene78.03b | ccaatgaaaactaatcaaaggtaaacgtggatcccatggcaattcccggg |
| gene78.m01INS3 | caacactgcccagaggttcaatcgatccgatgatcctaatgaaggcgccc |
| gene78.mINS303 | gtccagtatcgtccatcatagtatcgataaatatgtgaaggaaatgcctg |
| gene78.m01INS4 | caacactgcccagaggttcaatcgatgtgtgataggatcagtgttcaggg |
| gene78.mINS403 | gaaggcgaaggagactgctaatatcgataaatatgtgaaggaaatgcctg |
| gene78.01a_50_LNA3 | mCctGaaAgtAgaTttGttAttTccGaaAcgmCctTctmCccGttmCttAagTc |
| gene78.01b_50_LNA3 | mCatAtamCcamCaaAtaGtcmCctmCaaAaaTcamCaaGaaAacTcamCaamCacTg |
| gene78.03a_50_LNA3 | GatTtgmCagmCggTggTaaAaaGtaTgaAaamCgtGgtAatTaaAagGtcTc |
| gene78.03b_50_LNA3 | mCcaAtgAaaActAatmCaaAggTaaAcgTggAtcmCcaTggmCaaTtcmCcgGg |
| gene78.m01INS3_50_block | caacactgcccagaggttcaatcGATmCmCgatgatcctaatgaaggcgccc |
| gene78.mINS303_50_block | gtccagtatcgtccatcatAGTATcgataaatatgtgaaggaaatgcctg |
| gene78.m01INS4_50_block | caacactgcccagaggttcaatcGATGTgtgataggatcagtgttcaggg |
| gene78.mINS403_50_block | gaaggcgaaggagactgctAATATcgataaatatgtgaaggaaatgcctg |

Printing and Coupling of the Splice Isoform-Specific Microarrays

The splice variant capture probes were synthesized with a 5' anthraquinone (AQ)-modification, followed by a hexaethyleneglycol-2 (HEG2) linker. The capture probes were first diluted to a 20 µM final concentration in 100 mM Na-phosphate buffer pH 7.0, and spotted on the Immobilizer polymer microarray slides (Exiqon, Denmark) using the Biochip Arrayer One (Packard Biochip Technologies, USA) with a spot volume of 2×300 pl and 300 µm between the spots. The capture probes were immobilized onto the microarray slide by UV irradiation in a Stratalinker with 2300 µjoules (Stratagene, USA). Non-immobilized capture probe oligonucleotides were removed from the slides by washing the slides two times 15 minutes in 1×SSC. After washing, the slides were dried by centrifugation at 1000×g for 2 minutes, and stored in a slide box until microarray hybridization.

Construction of Splice Variant Vectors

The recombinant splice variant constructs were cloned into the Triamp18 vector (Ambion, USA). The constructs were sequenced to confirm their construction. The plasmid clones were transformed into *E. coli* XL10-Gold (Stratagene, USA).

Triamp18/SWI5 Vector Construct

Genomic DNA was prepared from a wild-type standard laboratory strain of *Saccharomyces cerevisiae* using the Nucleon MiY DNA extraction kit (Amersham Biosciences, USA) according to the supplier's instructions. Amplification of the partial yeast gene was performed using standard PCR with yeast genomic DNA as the template. In the first step of amplification, a forward primer containing a restriction enzyme site and a reverse primer containing a universal linker sequence were used. In this step, 20 base-pairs were added to the 3'-end of the amplicon, next to the stop codon. In the second step of amplification, the reverse primer was exchanged with a nested primer containing a poly-$T_{20}$ tail and a restriction enzyme site. The SWI5 amplicon contains 730 bp of the SW15 ORF plus a 20 bp universal linker sequence and a poly-$A_{20}$ tail. The PCR primers used were YDR146C-For-EcoRI (acgtgaattcaaatacagacaatgaagga-gatga) (SEQ ID NO: 97), YDR146C-Rev-Uni (gatc-cccgggaattgccatgttacctttgattagttttcattggc (SEQ ID NO: 98)), and Uni-polyT-BamHI (acgtggatcctttttttttttttttttttgatc-cccgggaattgccatg (SEQ ID NO: 99)).

The PCR amplicon was cleaved with the restriction enzymes EcoRI and BamHI. The DNA fragment was ligated into the pTRIamp18 vector (Ambion, USA) using the Quick Ligation Kit (New England Biolabs, USA) according to the supplier's instructions and transformed into *E. coli* DH-5α by standard methods.

Construction of the Recombinant Splice Variant #1 (Triamp18/swi5-Rubisco)

The *Arabidopsis thaliana* Rubisco small subunit ssu2b gene fragment (gi17064721) was amplified from genomic DNA using primers named DJ 305 (5'-ACTATGATGGAC-GATACTGGAC-3' (SEQ ID NO: 100)) and DJ 306 (5'-ATTGGATCGATCCGATGATCCTAATGAAGGC-3' (SEQ ID NO: 101)), containing ClaI restriction site linkers. The purified PCR fragment was digested with ClaI and then cloned into the swi5 (gI:7839148) vector at the unique ClaI site (atcgat) giving each insert a flanking sequence from the original yeast SWI5 insert (named exon01 and exon 03, FIG. 11). The product was inserted in the reverse orientation, so that the insert sequence is as follows:

(SEQ ID NO: 102)
AtcgatCCGATGATCCTAATGAAGGCGCCCGGGTACTCCTTCTTGCA

TTCTTCAACTTCCTTCAACACTTGAGCGGAGTCGGTGCATCCGAA

CAATGGAAGCTTCCACATTGTCCAGTATCGTCCATCATAGTatcgat.

Nucleotide sequence analysis revealed a difference between the sequence of *A. thaliana* rubisco expected from the GenBank database and that obtained from all sequenced constructs and PCR products. Position 30 in the Rubisco insert is "C" rather than the expected "A." This SNP was probably created by PCR. None of the oligonucleotide capture probes used in the example cover this region. The Rubisco sequence in Genbank is TCCTAAT-GAAGGCGCCA (SEQ ID NO: 103), and the sequence obtained from the plasmid contruct is TCCTAAT-GAAGGCGCCC (SEQ ID NO: 104).

Construction of the Recombinant Splice Variant #2 (Triamp18/swi5-Lea)

The *Arabidopsis thaliana* Lea gene (gi1526423) was amplified from genomic DNA with primers named DJ 307 (5'-GGAATTATCGATGTGTGATAGGATCAGTGT-TCAG-3' (SEQ ID NO: 105)), and DJ 308 (5'-AATTG-GATCGATATTAGCAGTCTCCTTCGCC-3' (SEQ ID NO: 106)), including the ClaI linker sites as above. The PCR fragment was digested with ClaI cloned into the yeast SWI5 IVT construct as above at the unique ClaI site.

The fragment was inserted in the forward orientation, resulting in the following insert sequence:

(SEQ ID NO: 107)
atcgatGTGTGATAGGTTCAGTGTTCAGGGCTGTCCAAGGAACGTATG

AGCATGCGAGAGACGCTGTAGTTGGAAAAACCCACGAAGCGGCT

GAGTCTACCAAAGAAGGAGCTCAGATAGCTTCAGAGAAAGCGGTT

GGAGCAAAGGACGCAACCGTCGAGAAAGCTAAGGAAACCGCTGA

TTATACTGCGGAGAAGGTGGGTGAGTATAAAGACTATACGGTTGAT

AAAGCTAAAGAGGCTAAGGACACAACTGCAGAGAAGGCGAAGGA

GACTGCTAATatcgat.

In vitro RNA Preparation from Splice Variant Vectors

In vitro RNA from the splice variants were made using the MEGAscript™ high yield transcription kit according to the manufacturer's instructions (Ambion, USA). The yield of IVT RNA was quantified at a Nanodrop spectrophotometer (Nanodrop Technologies, USA, FIG. 11).

Isolation of Total RNA from *C. elegans*

*C. elegans* wild-type strain (Bristol-N2) was maintained on nematode growth medium (NG) plates seeded with *Escherichia coli* strain OP50 at 20° C., and the mixed stages of the nematode were prepared as described by Hope (ed.) ("*C. elegans*—A Practical Approach", Oxford University Press 1999). The samples were immediately flash frozen in liquid $N_2$ and stored at −80° C. until RNA isolation.

A 100 µl aliquot of packed *C. elegans* worms from a mixed stage population was homogenized using the Fast-Prep Bio101 from Kem-En-Tec for one minute, speed 6 followed by isolation of total RNA from the extracts using the FastPrep Bio101 kit (Kem-En-Tec) according to the manufacturer's instructions.

The eluted total RNA was ethanol precipitated for 24 hours at −20° C. by addition of 2.5 volumes of 96% EtOH and 0.1 volume of 3M Na-acetate, pH 5.2 (Ambion, USA), followed by centrifugation of the total RNA sample for 30 minutes at 13200 rpm. The total RNA pellet was air-dried and redissolved in 10 μl of diethylpyrocarbonate (DEPC)-treated water (Ambion, USA) and stored at −80° C.

Fluorochrome-Labelling of the Target

Ten (10) μg total RNA from *C. elegans* and 1 ng of in vitro RNA from Splice variant #1 were combined with 5 μg anchored oligo(dT$_{20}$) primer and DEPC-treated water to a final volume of 8 μl. The mixture was heated at 70° C. for 10 minutes, quenched on ice for 5 minutes, followed by addition of 20 units of Superasin RNase inhibitor (Ambion, USA), 1 μl dNTP solution (10 mM each dATP, dGTP, dTTP and 0.4 mM dCTP, and 3 μl Cy5-dCTP, Amersham Biosciensces, USA), 4 μl 5×RTase buffer (Invitrogen), 2 μl 0.1 mM DTT (Invitrogen), 400 units of Superscript II reverse transcriptase (Invitrogen, USA), and DEPC-treated water to 20 μl final volume.

A parallel set-up was made with 10 μg total RNA from *C. elegans* and 1 ng of in vitro RNA from Splice variant #2, labelling with Cy3-dCTP. Both cDNA syntheses were carried out at 42° C. for 2 hours, and the reactions were stopped by incubation at 70° C. for 5 minutes, followed by incubation on ice for 5 minutes.

Unincorporated dNTPs were removed by gel filtration using MicroSpin S-400 HR columns as described below. The column was pre-spun for one minute at 1500×g in a 1.5 ml tube, and the column was placed in a new 1.5 ml tube. The cDNA sample was slowly applied to the top center of the resin and spun 1500-×g for 2 minutes. The eluate was collected. RNA was degraded by adding 3 μl of 0.5 M NaOH. The solution was mixed well and incubated at 70° C. for 15 minutes. The solution was neutralized by adding 3 μl of 0.5 M HCl and mixed well. Then, 450 μl 1×TE, pH 7.5 was added to the neutralized sample, and the sample was transferred onto a Microcon-30 concentrator (prior to use, 500 μl 1×TE was spun through the column to remove residual glycerol). The samples were spun at 14000×g in a micro centrifuge for 12 minutes, and the volume was checked. Spinning was continued until the volume was reduced to 5 μl. The labelled cDNA probe was eluted by inverting the Microcon-30 tube and spinning at 1000×g for 3 minutes. The Microcon filter was checked for proper elution.

Comparative Hybridization of the Splice Variant Microarrays and Post-Hybridization Washes The Cy3 and Cy5-labelled cDNA samples, respectively, were combined in one tube. The following was added: 3.75 μl 20×SSC (3×SSC final, pass through 0.22 μfilter prior to use to remove particulates), yeast tRNA (1 μg/μl final), 0.625 μl 1 M HEPES, pH 7.0 (25 mM final, pass through 0.22 μfilter prior to use to remove particulates), 0.75 μl 10% SDS (0.3% final), and DEPC-water to 25 μl final volume. The labelled cDNA target sample was filtered in Millipore 0.22 μfilter spin column (Ultrafree-MC, Millipore, USA) according to the manufacturer's instructions, followed by incubation of the reaction mixture at 100° C. for 2-5 minutes. The cDNA probes were cooled at room temperature for 2-5 minutes by spinning at maxium speed in a microcentrifuge. A LifterSlip (Erie Scientific Company, USA) was carefully placed on top of the microarray spotted on Immobilizer™ MicroArray Slide, and the hybridization mixture was applied to the array from the side. An aliquot of 30 μL of 3×SSC was added to both ends of the hybridization chamber, and the Immobilizer™ MicroArray Slide was placed in the hybridization chamber (DieTech, USA). The chamber was sealed watertight and incubated at 65° C. for 16-18 hours submerged in a water bath. After hybridization, the slide was removed carefully from the hybridization chamber and washed using the following protocol.

The slides were washed sequentially by plunging gently in 2×SSC/0.1% SDS at room temperature until the cover slip falls of into the washing solution, then in 1×SSC pH 7.0 (150 mM NaCl, 15 mM Sodium Citrate) at room temperature for one minute, then in 0.2×SSC, pH 7.0 (30 mM NaCl, 3 mM Sodium Citrate) at room temperature for one minute, and finally in 0.05×SSC (7.5 mM NaCl, 0.75 mM Sodium Citrate) for 5 seconds, followed by drying of the slides by spinning at 1000×g for 2 minutes. The slides were stored in a slide box in the dark until scanning.

Microarray Data Analysis

The splice variant microarray was scanned in a ScanArray 4000XL confocal laser scanner (Packard Instruments, USA). The hybridization data were analyzed using the GenePix Pro 4.01 microarray analysis software (Axon, USA).

In the data analysis, the experimental variation in the labelling efficiency between the two fluorescent dyes was normalized (scaled) as follows. The average signal intensities from the "exon1" and "exon3" internal capture probes (Table 6), were used to calculate normalization factor of 2.75. This factor was multiplied to the signal intensity values from the Cy-3 target.

Figure 12A:
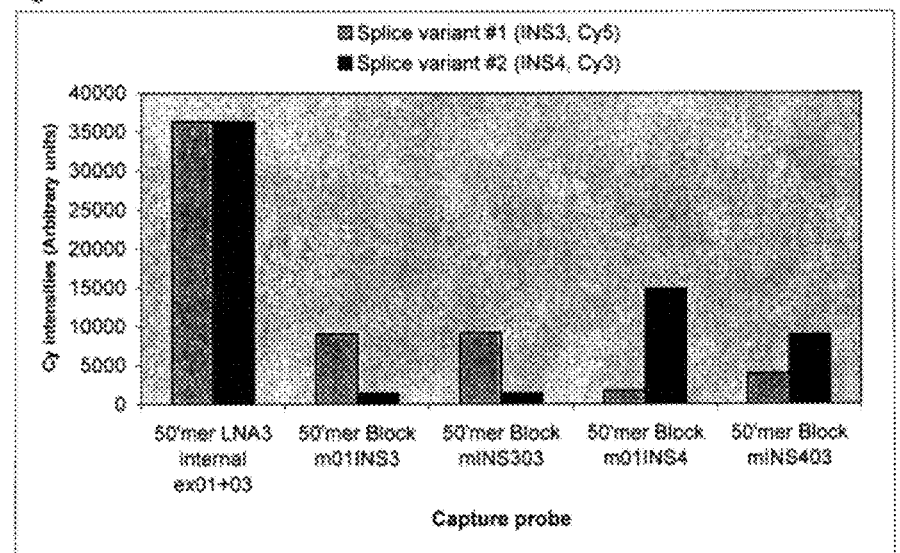
FIGS. 12A (LNA probes) and 12B (DNA control probes) show the detection of splice variant #1 and #2, respectively using merged capture probes in a comparative, two-color hybridization.
Figure 12B:
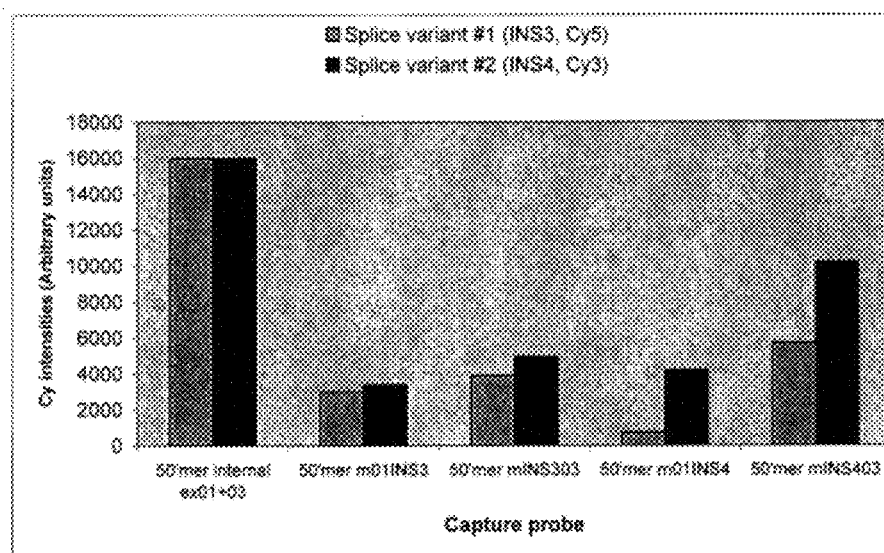

Analysis of the data from the specific detection of the two recombinant splice variants in a complex RNA pool demonstrates that the merged capture probes containing a LNA block have significantly higher signals and a very low level of cross-hybridization, compared to the DNA capture probes (FIGS. 12A and 12B). In addition, the specific detection of the two artificial splice variants #1 and #2 is validated with the results from LNA-modified oligonucleotide capture probes. Capture probes of other lengths and/or with other LNA substitution patterns can be used similarly. In contrast, the corresponding DNA oligonucleotide capture probes fail to detect splice variant #1 (FIG. 12B).

EXAMPLE 6

The Use of LNA-Modified Oligonucleotides in Microarrays Provides Significantly Improved Sensitivity in Expression Profiling This example demonstrates the advantages of using LNA oligonucleotide microarrays in gene expression profiling experiments. Capture probes for the *Saccharomyces cerevisiae* gene SWI5 (YDR146C) were designed as 50-mer standard DNA and two different LNA-modified oligonucleotides with LNA substitutions at every second or every third nucleotide position, respectively, for comparison (Table 7). To assess the sensitivity of DNA versus LNA capture probes, hybridizations with different amounts of biotin-labelled antisense oligonucleotides in a 10-fold dilution series were performed.

Design and Synthesis of the LNA Capture Probes

To design capture probes, regions with unique mRNA sequence of the selected target genes were identified. Optimized 50-mer oligonucleotide sequences with respect to $T_m$, self-complementarity, and secondary structure were selected. LNA modifications were incorporated to increase affinity and specificity. The biotin-labelled antisense DNA target oligonucleotide corresponds to the reverse complement sequence.

Printing of the LNA Microarrays

The microarrays were printed on Immobilizer™ MicroArray Slides (Exiqon, Denmark) using the Biochip One Arrayer from Packard Biochip technologies (Packard, USA). The arrays were printed with a spot volume of 2×300 pl of a 10 μM (final concentration) capture probe dilution. Four replicas of the capture probes were printed on each slide Hybridization with Biotin-Labelled Antisense Oligonucleotide The arrays were hybridized overnight using the following protocol. The desired amount of biotin-labelled oligonucleotide was combined in one tube followed by addition of 3 μL 20×SSC (3×SSC final), 0.5 μL 1 M HEPES, pH 7.0 (25 mM final), 25 μg yeast tRNA (1.25 μg/μL final), 0.6 μL 10% SDS (0.3% final), and DEPC-treated water to 20 μL final volume. The biotin-labelled target sample was filtered in a Millipore 0.22 micron spin column according to the manufacturer's instructions (Millipore, USA), and the probe was denatured by incubating the reaction at 100° C. for 2 minutes. The sample was cooled at 20-25° C. for 5 minutes by spinning at maxium speed in a microcentrifuge. A LifterSlip (Erie Scientific Company, USA) was carefully placed on top of the microarray spotted on Immobilizer™ MicroArray Slide, and the hybridization mixture was applied to the array from the side. An aliquot of 30 μL of 3×SSC was added to both ends of the hybridization chamber, and the Immobilizer™ MicroArray Slide was placed in the hybridization chamber. The chamber was sealed watertight and incubated at 65° C. for 16-18 hours submerged in a water bath. After hybridization, the slide was removed carefully from the hybridization chamber and washed using the following protocol. The Lifterslip coverslip was washed off in 2×SSC, pH 7.0 containing 0.1% SDS at room temperature for 1 minute, followed by washing of the microarrays subsequently in 1.0×SSC, pH 7.0 at room temperature for 1 minute, and then in 0.2×SSC, pH 7.0 at room temperature for 1 minute. Finally, the slides were washed for 5 seconds in 0.05×SSC, pH 7.0. The slides were then dried by centrifugation in a swinging bucket rotor at approximately 200 G for 2 minutes. To visualize the biotin containing duplexes, an aliquot of 40 μL of the 2 μg/ml streptavidin-Cy3 in 1×SSC+0.05% Tween solution was applied to the slide as described for the hybridization mixture above. The slide was incubated in a humidified chamber for 1 hour at room temperature. The coverslip was washed off in 1×SSC+0.05% Tween for 1 minute, followed by wash in 0.2×SSC+0.05% Tween for 1 minute and then 10 seconds in MilliQ-water. The slide was dried by centrifugation in a swinging bucket rotor for 2 minutes at 200 G.

Data Analysis

Following washing and drying, the slides were scanned using a ScanArray 4000XL scanner (Perkin-Elmer Life Sciences, USA), and the array data were processed using the GenePix™ Pro 4.0 software package (Axon, USA).

Results

Figure 13:
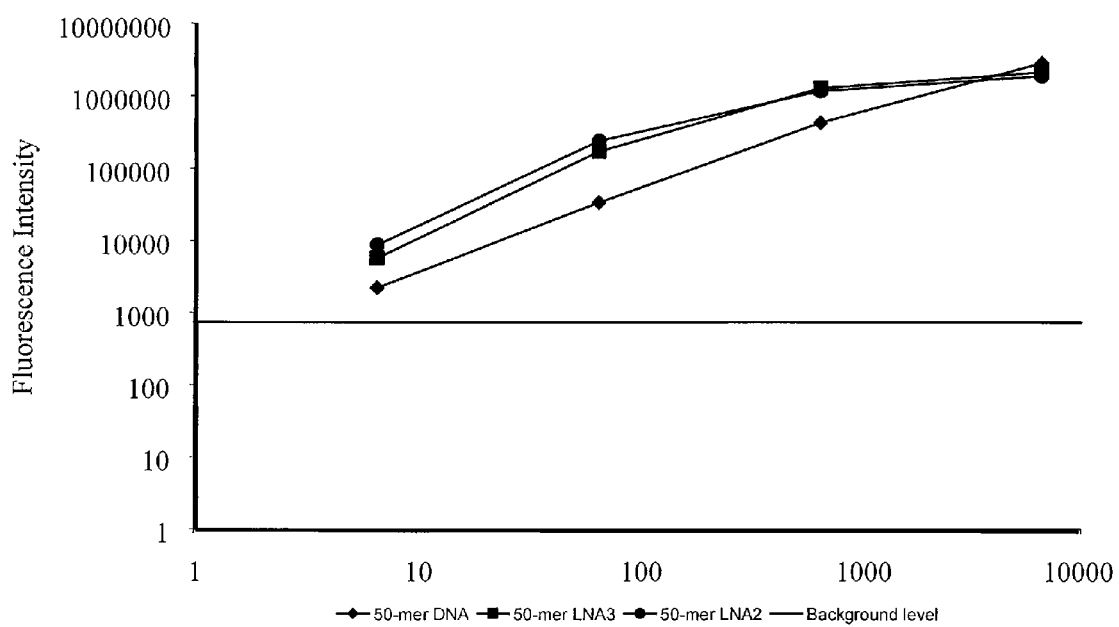
FIG. 13 shows the sensitivity of 50-mer LNA capture probes compared to 50-mer DNA capture probes. SWI5-specific 50-mer DNA oligonucleotides and 50-mer capture probes with an LNA nucleotide incorporated at every second (LNA2) or third (LNA3) nucleotide position. The slides were hybridized at 65° C. in 3×SSC.

Incorporation of LNA nucleotides at every second or third nucleotide position in standard 50-mer expression array oligonucleotide capture probes results in a 2-7-fold increase in fluorescence intensity levels using an unsaturated target concentration and hybridizing under standard stringency conditions (FIG. 13). Thus, it can clearly be concluded that the LNA oligonucleotides are more sensitive in expression profiling compared to DNA oligonucleotides.

TABLE 7

DNA and LNA-modified SWI5 (YDR146C) oligonucleotide capture probes. LNA modifications are depicted by uppercase letters in the sequence; "mC" denotes LNA methyl cytosine.

| Oligo Name | Sequence |
| --- | --- |
| YDR146C-50 | tgggaatggaacggggattatggtttcgccaat gaaaactaatcaaaggt (SEQ ID NO: 13) |
| YDR146C-50_LNA2 | TgGgAaTgGaAcGgGgAtTaTgGtTtmCgmCcA aTgAaAamCtAaTcAaAgGt (SEQ ID NO: 19) |
| YDR146C-50_LNA3 | TggGaaTggAacGggGatTatGgtTtcGccAat GaaAacTaaTcaAagGt (SEQ ID NO: 13) |

EXAMPLE 7

The Use of LNA-modified Oligonucleotides in Microarrays Provides Significantly Improved Sensitivity in Comparative Genome Hybridization (CGH)

This example demonstrates the advantages of using LNA oligonucleotide microarrays in Comparative Genome Hybridization (CGH) experiments. Capture probes for all 23 exons of the Menkes gene (ATP7A) were designed as 50-mer standard DNA and different LNA/DNA mixmer oligonucleotides, respectively, for comparison (FIG. 17). The C6-amino-linked capture probes were applied to Immobilizer slides and hybridized with patient DNA samples labelled with a Cy3 fluorescent dye.

Design and Synthesis of the LNA Capture Probes

To design the capture probes, regions comprising individual exons of the Menkes gene were identified. The optimal 50-mer oligonucleotide sequences with respect to $T_m$, self-complementarity, and secondary structure were selected for each exon. LNA modifications were incorporated to increase affinity and specificity. A software tool "OligoDesign", which automatically designs capture probes that are optimized for sequence specificity, $T_m$, self-complementarity, secondary structure, and LNA modifications was used for oligonucleotide design.

Results

Figure 15:
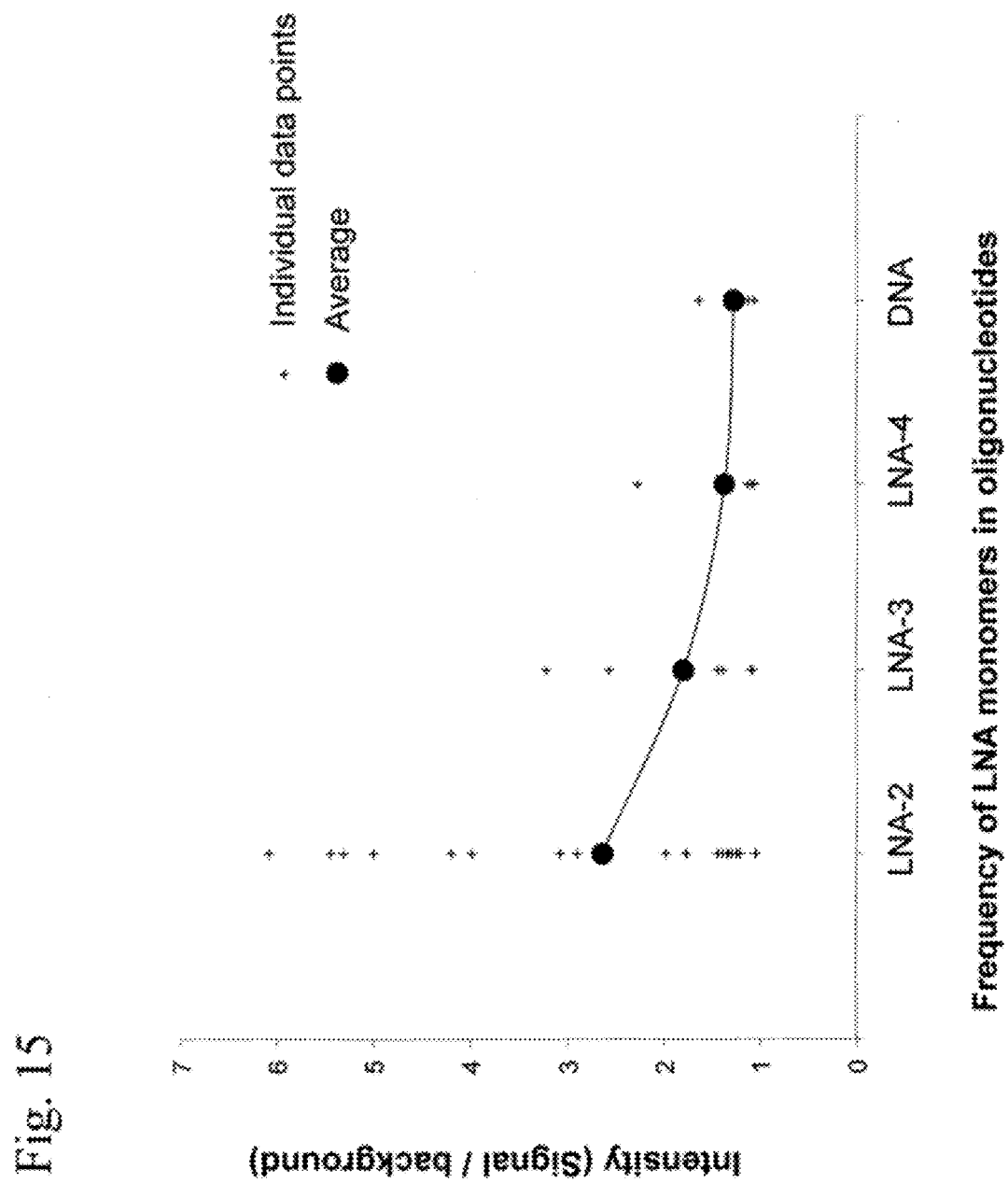
FIG. 15 is a graph comparing the spot intensity for probes of the invention with different LNA substitution patterns.
Figure 16:
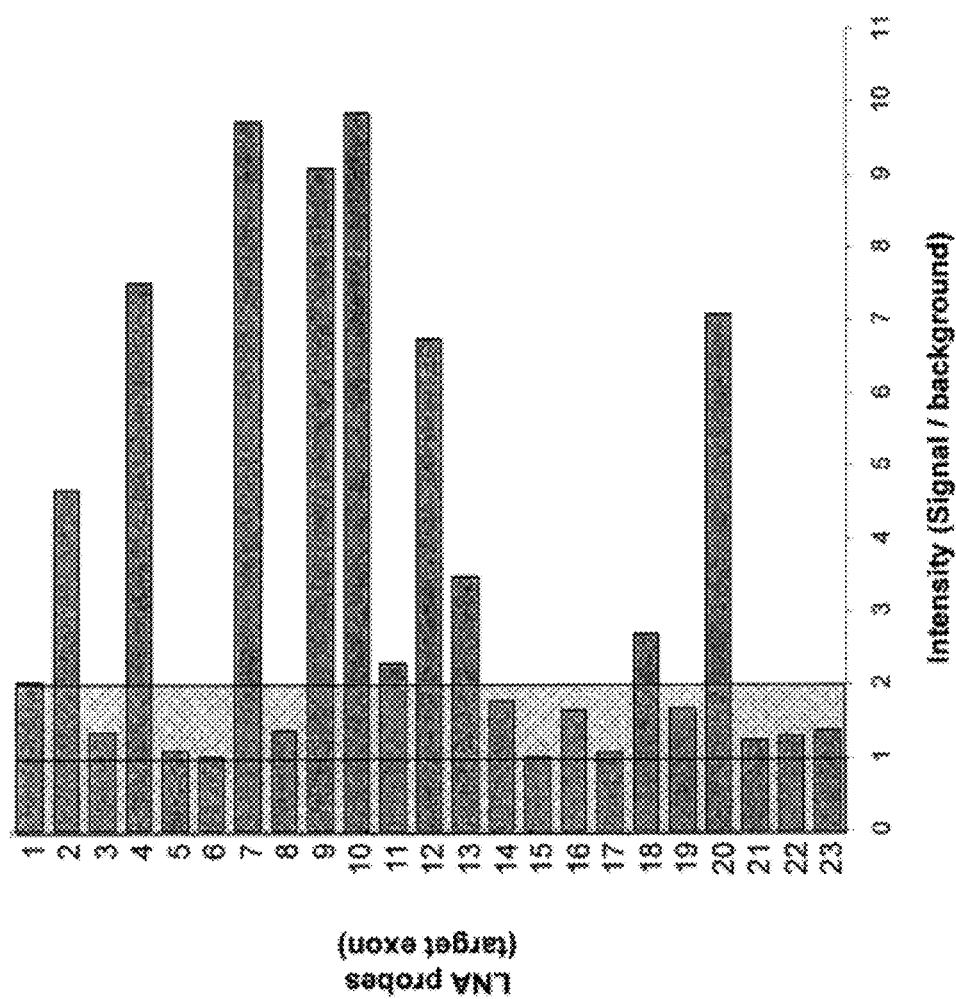
FIG. 16 is a bar graph of the spot intensity for LNA probes for different exons.
Figure 18:
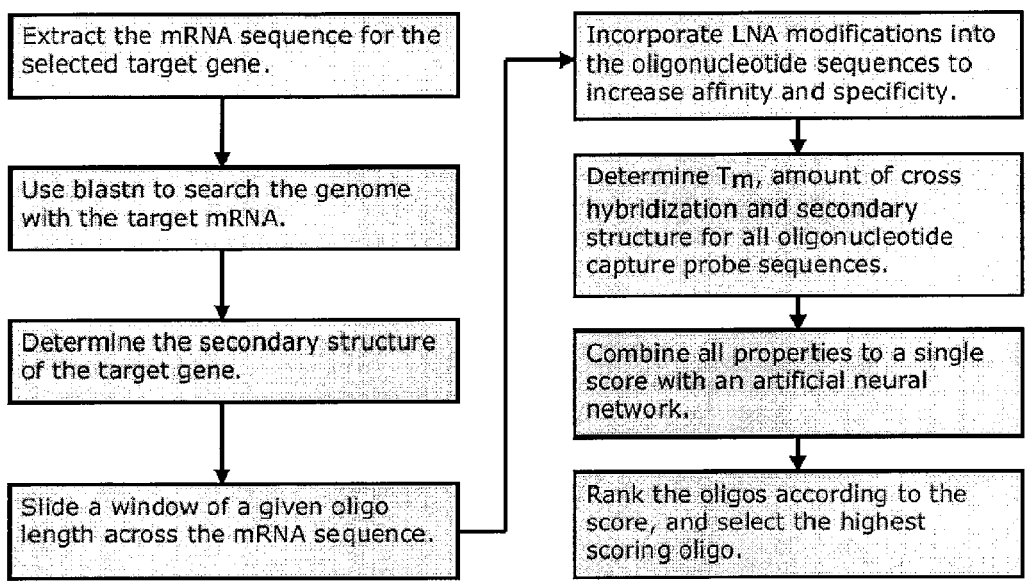
FIG. 18 is a flow chart of the steps of oligo design software of the invention. The OligoDesign software features LNA modified oligonucleotide secondary structure prediction, LNA spiked oligonucleotide melting temperature prediction, genome wide cross hybridization prediction, secondary structure prediction of the target, and recognition and filtering of the target in the genome. These features are determined for each possible probe of the query gene and presented to an artificial neural network. The probes are then ranked according to the neural network prediction and the top scoring probes are returned.
Figure 19B:
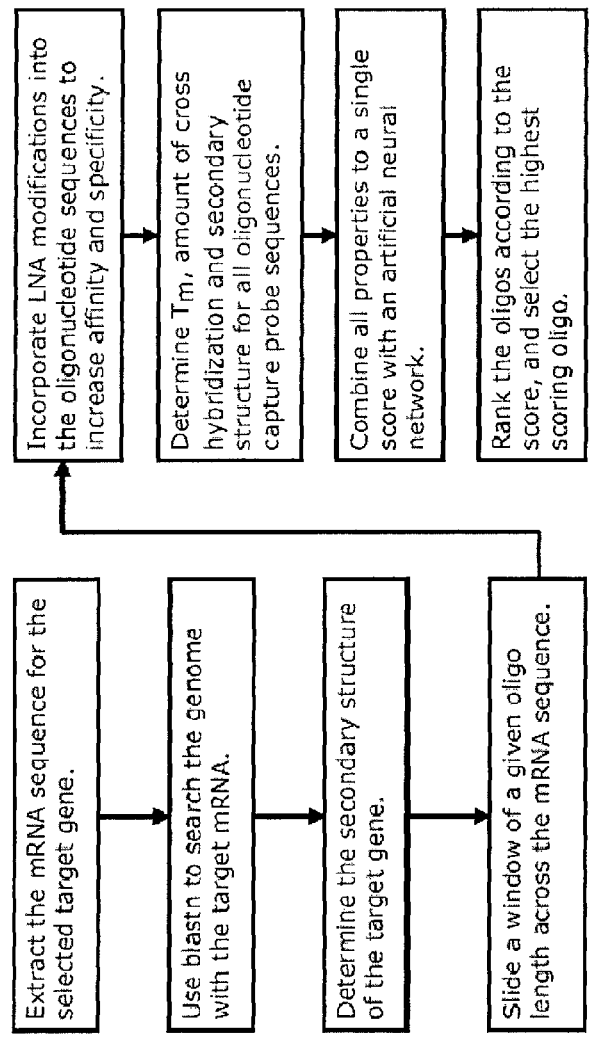
Figure 19D:
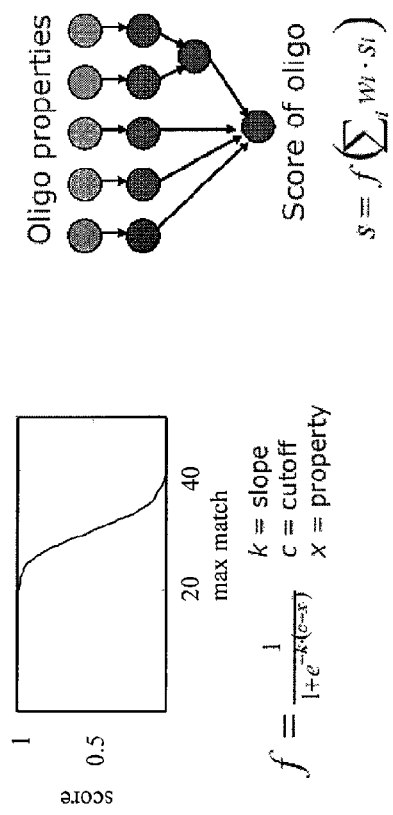
Figure 20:
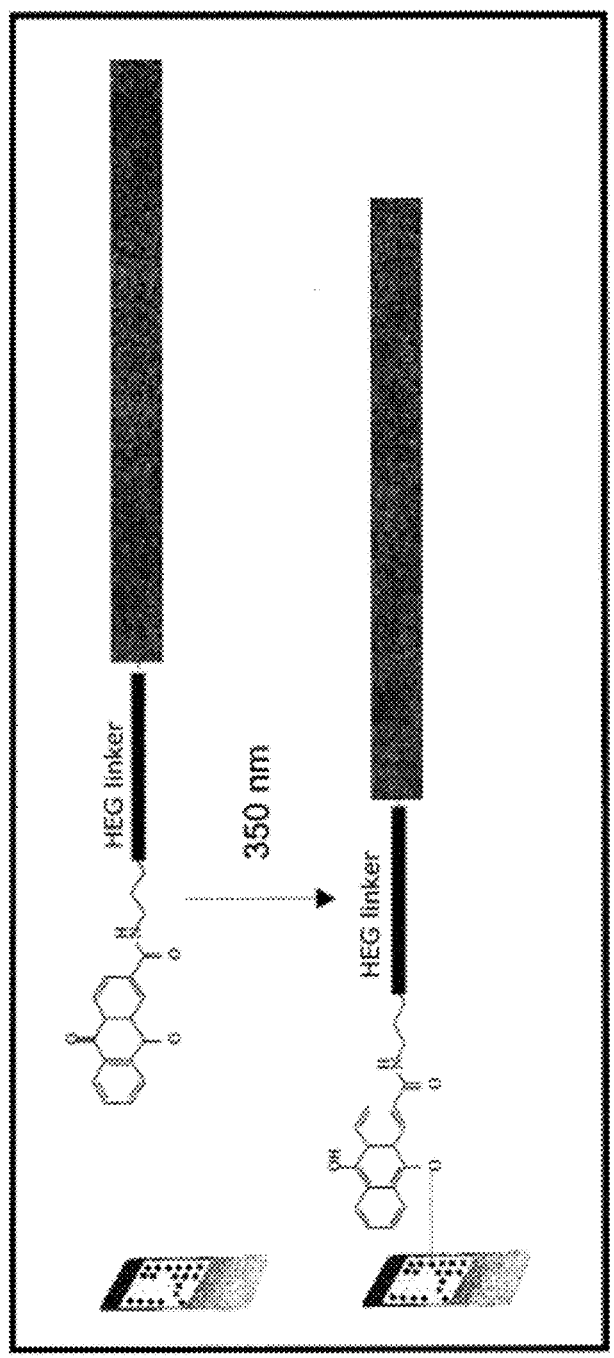
FIG. 20 illustrates photo-activated immobilization of nucleic acids of the invention, which enables polarized coupling of anthraquinone (AQ)-linked LNA oligonucleotides onto the polymer surface. No pretreatment of the slide is needed. A covalent bond is formed between the oligonucleotide and the polymer using a UV source, e.g. Stratalinker.
Figure 21:
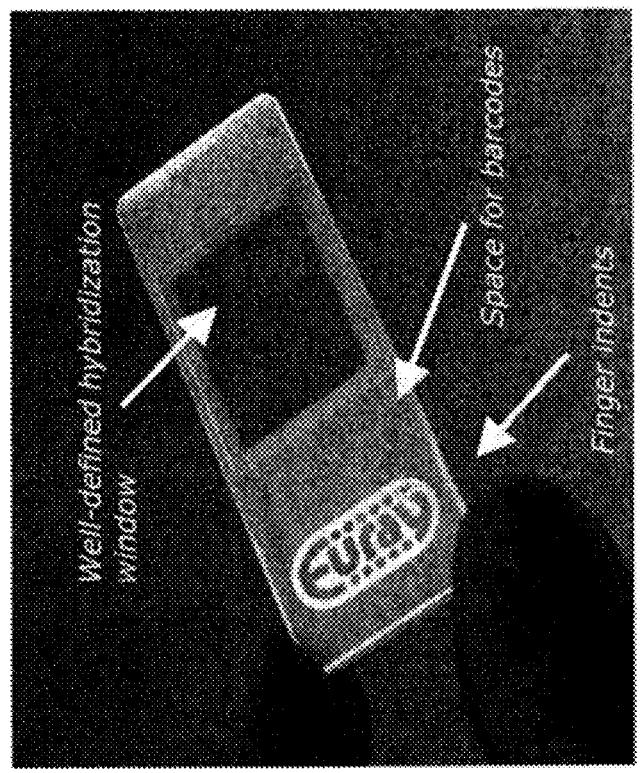
FIG. 21 illustrates an injection-molded polymer slide. Finger indents ease slide handling. The slide has a well-defined printing and hybridization window, frosted surface for identification and orientation, and space for barcodes.
Figure 22:
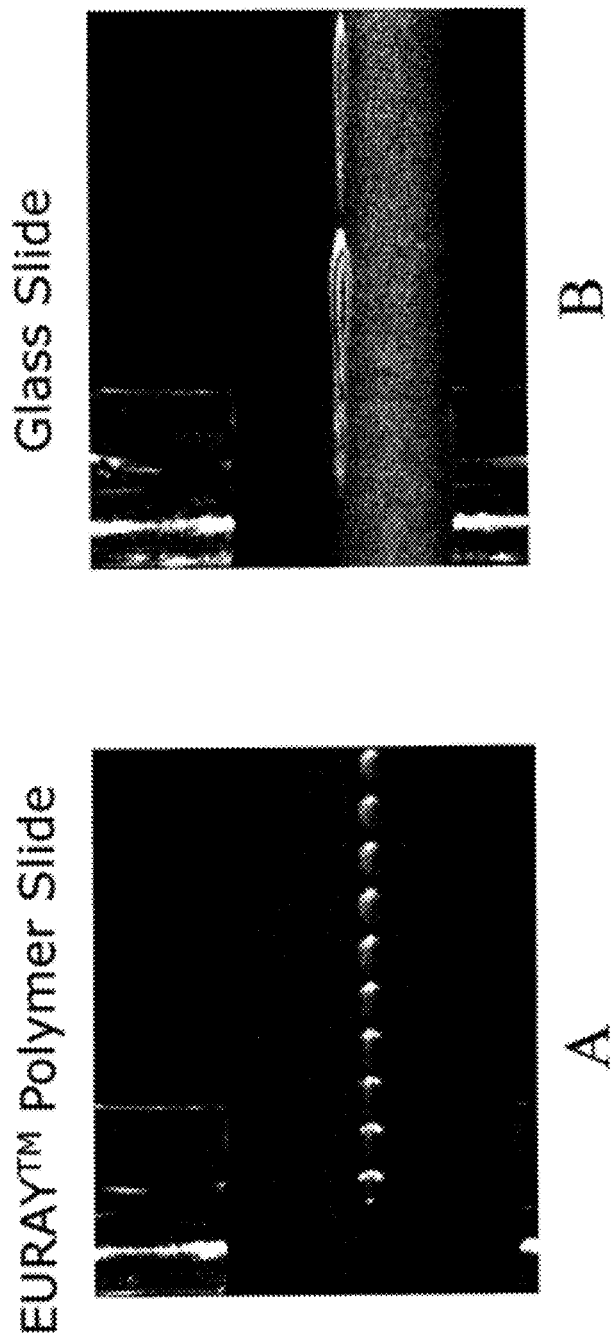
FIG. 22 illustrates spot quality on different slides that can be used to immobilize nucleic acids of the invention. The hydrophobic slide surface ensures that extremely homogenous spots are generated when hydrophilic spotting solution is applied to the surface. A high spot quality is obtained on the Immobilizer™ polymer slide compared to a glass slide when using a spot-to-spot distance of 150 μM. The high-quality arrays simplify downstream image analyses.
Figure 23:
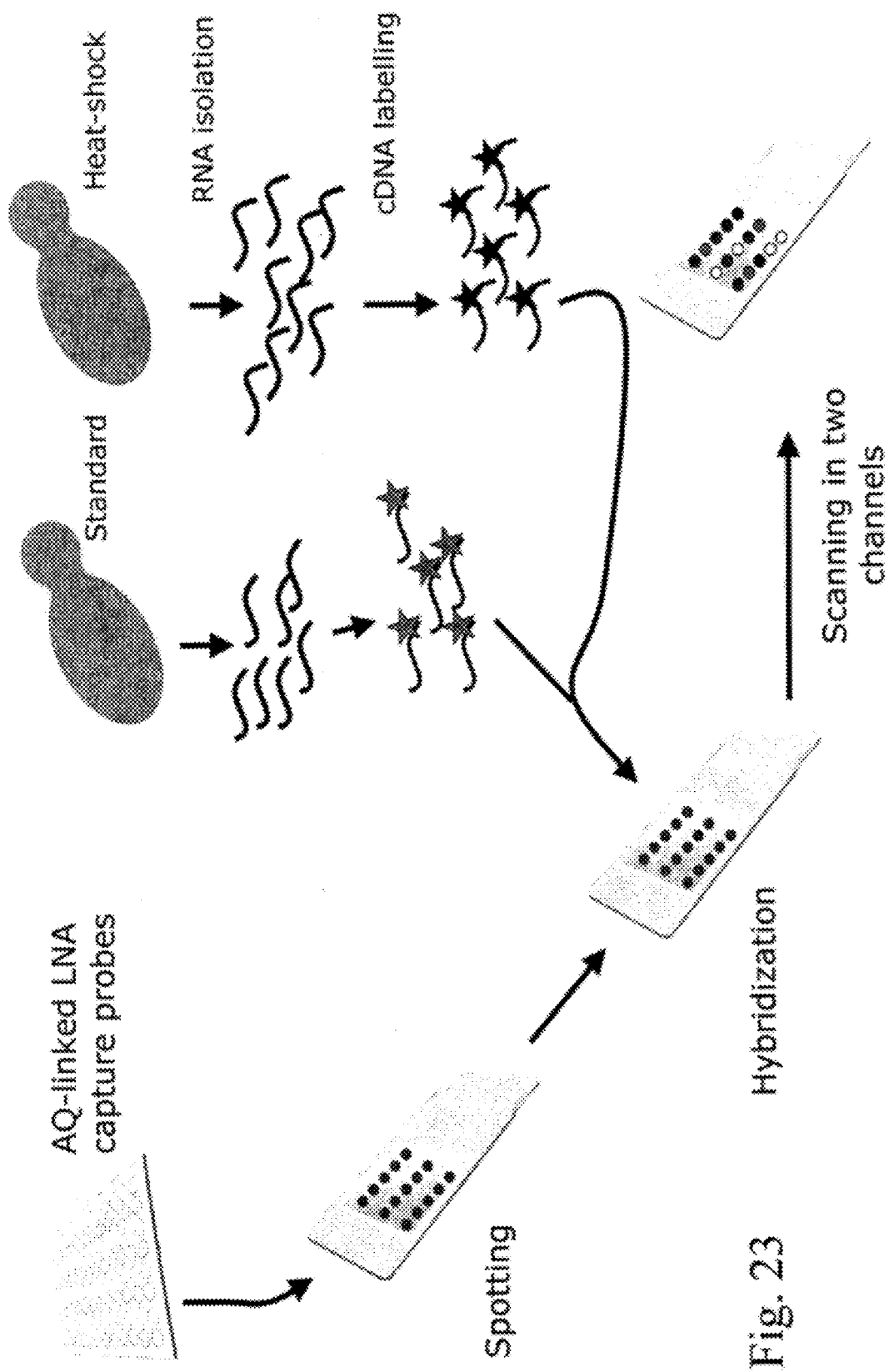
FIG. 23 is a schematic illustration of a method of the invention.
Figure 25:
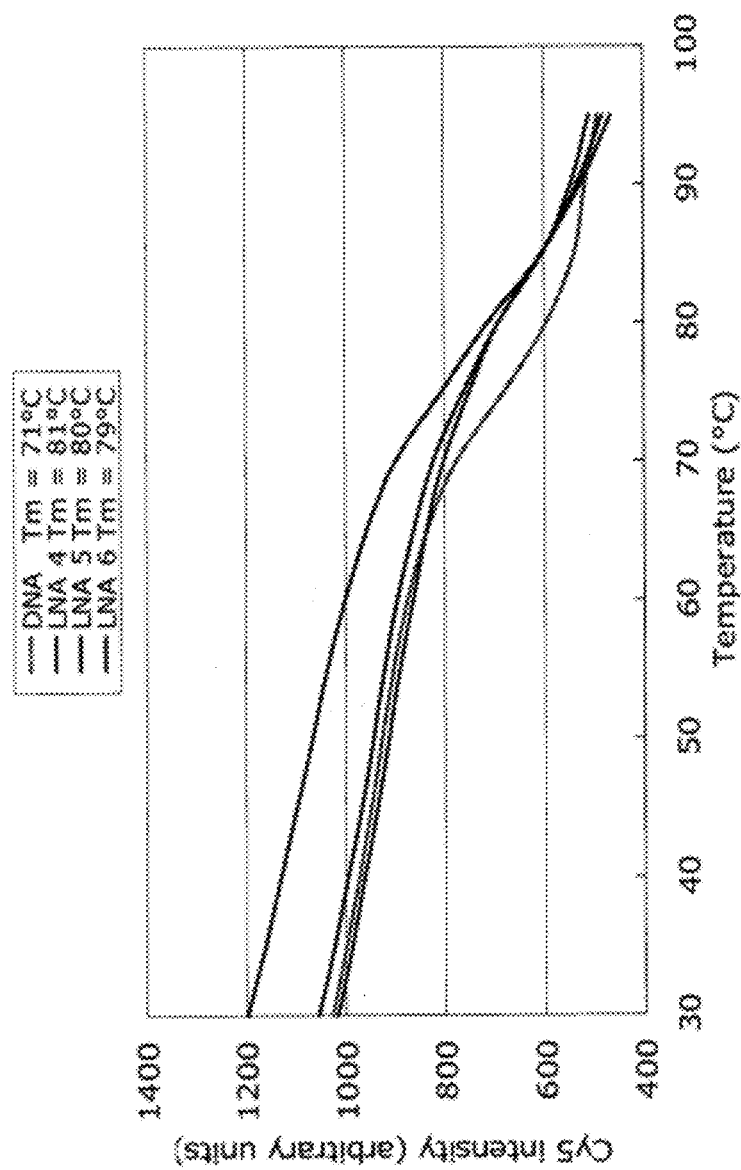
FIG. 25 is a graph of Cy5 intensity. Yeast actin 1-specific 50-mer capture probes were synthesized as DNA and DNA/LNA mixmer oligonucleotides. LNA-substituted mixmer capture probes contain an LNA at every $4^{th}$, $5^{th}$, and $6^{th}$ nucleotide position (LNA_4, LNA_5, LNA_6). On-chip melting profiles demonstrate a 8-10° C. increase in $T_m$ obtained with LNA capture probes.
Figure 26A:
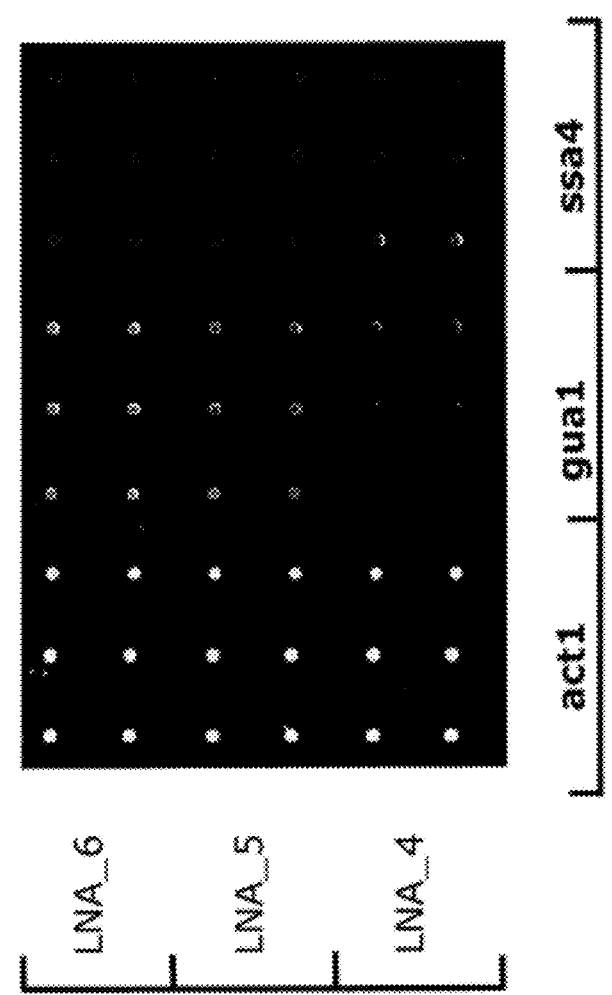
FIG. 26A illustrates the heat-shock response in yeast. The array was hybridized with Cy3-labeled standard and Cy5-labelled heat-shock yeast cDNA.
Figure 26B:
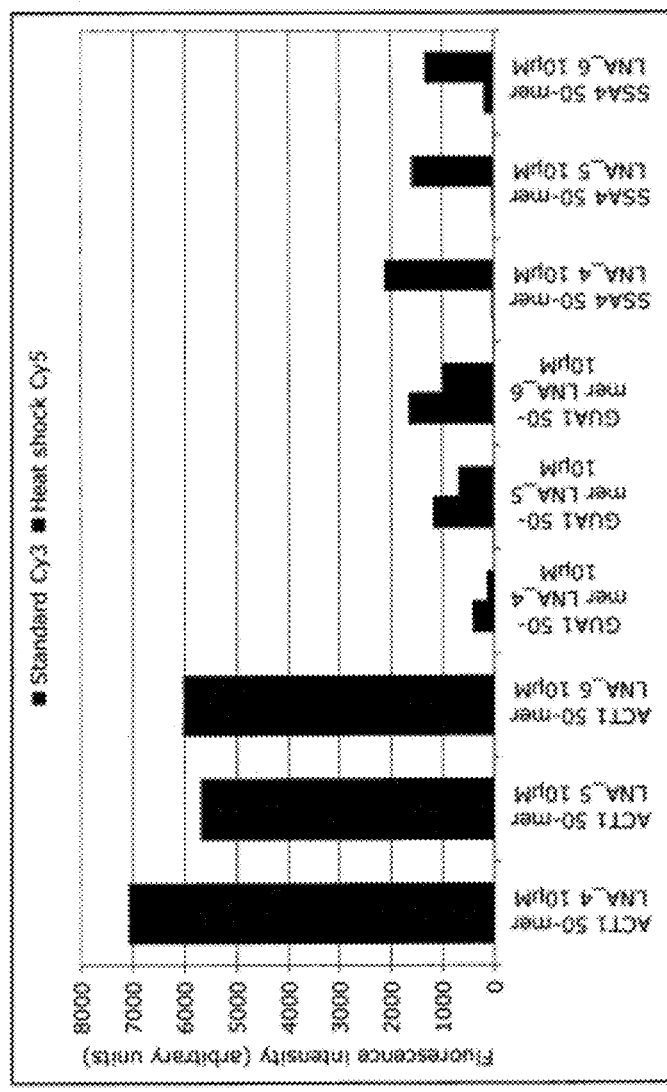
FIG. 26B also illustrates the heat-shock response in yeast. The microarray data were normalized using yeast actin 1. The ssa4 gene encoding heat shock protein HSP70 is up-regulated over 2-fold. Expression of the gual gene is down-regulated.
Figure 27A:
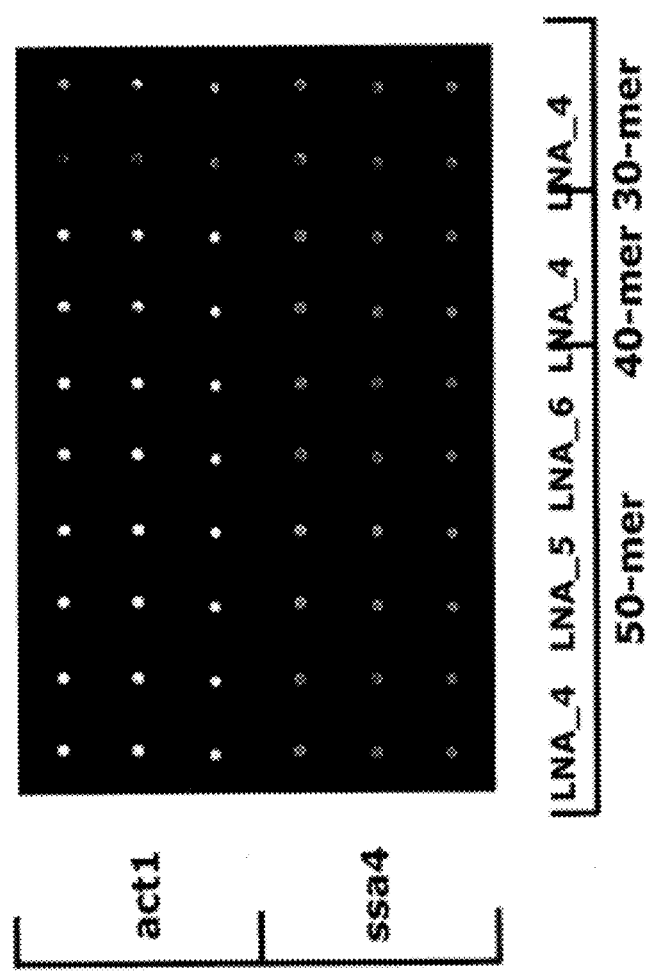
FIG. 27A compares expression of wild-type and ssa4 mutant yeast. The array was hybridized with Cy3-labeled wild-type and Cy5-labelled ssa4 mutant yeast cDNA.
Figure 27B:
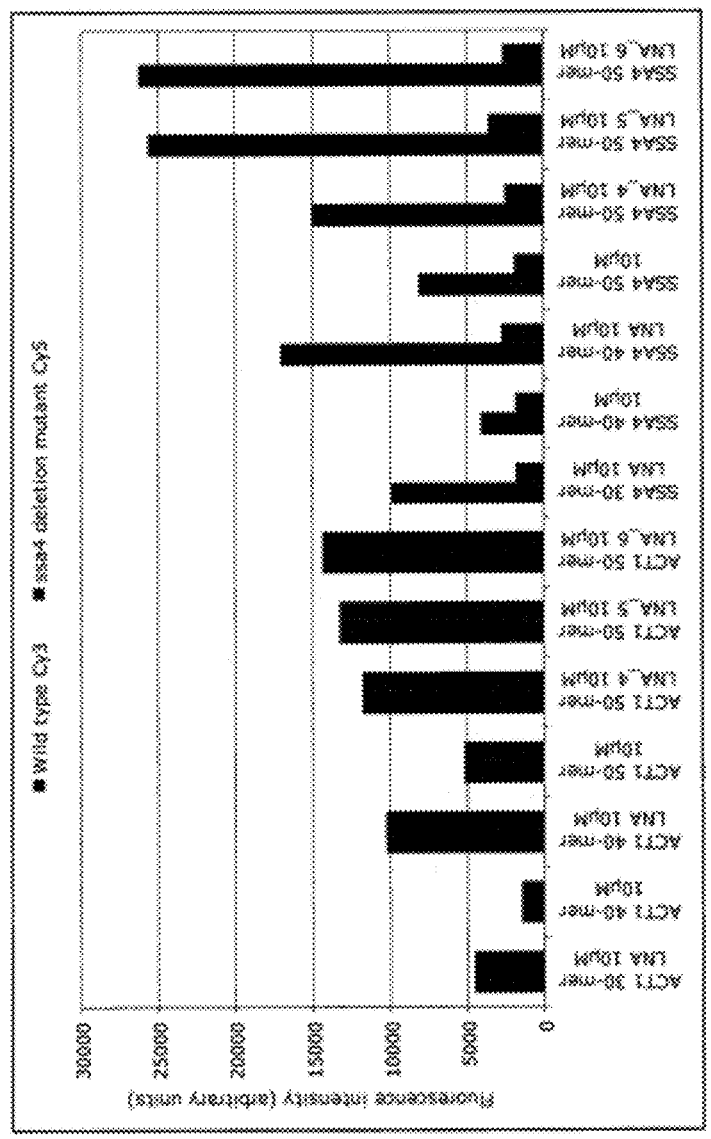
FIG. 27B also compares wild-type and ssa4 yeast. The hybridization data were normalized using yeast actin 1. ssa4 is detected in the wild-type yeast strain, but not in the ssa4 knock-out strain.
Figure 28:
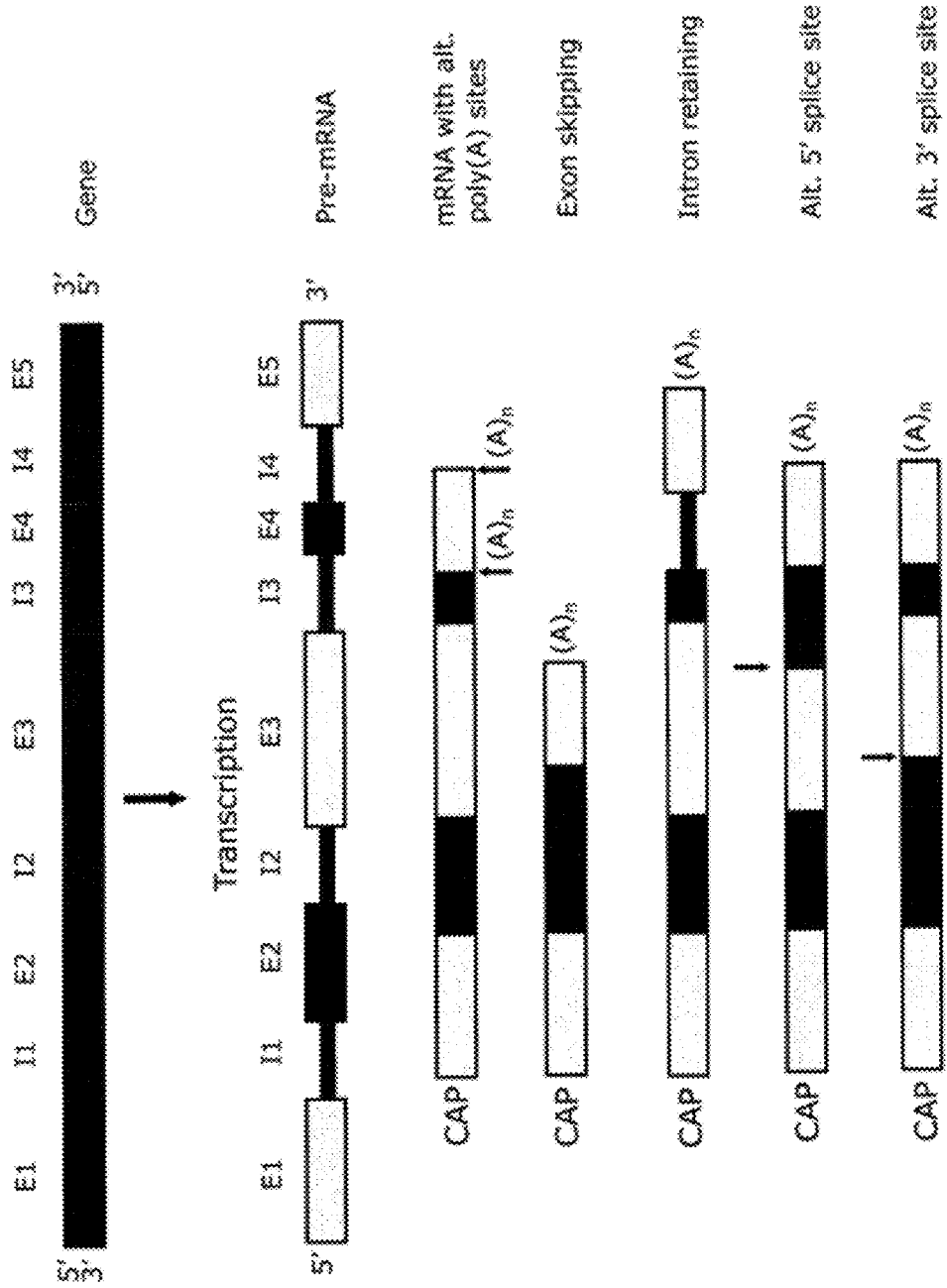
FIG. 28 illustrates mRNA splicing.

Fluorescent Cy3 labelled patient genomic DNA was hybridized to microarrays spotted with the CGH capture probes listed in FIG. 17. Compared to DNA capture probes, capture probes with LNA in every second position (LNA-2) had a significantly better capture rate of non-amplified labelled genomic patient DNA as shown in FIGS. 14-16. Capture probes of other lengths and/or with other LNA substitution patterns can be used similarly.

EXAMPLE 8

Expression Profiling of Stress and Toxicity in *Caenorhabditis elegans* Using LNA Oligonucleotide Microarrays This example demonstrates the use of the *C. elegans* LNA tox oligoarray in gene expression profiling experiments in the nematode *Caenorhabditis elegans*. The *C. elegans* tox oligoarray monitors the expression of a selection of 110 genes relevant for general stress response and for the metabolism of toxic compounds. Two different capture probes for each of these target genes were designed and included in the LNA tox array. In addition, the *C. elegans* LNA tox oligoarray contained capture probes providing control for cDNA synthesis efficiency and the developmental stage of the nematode. Capture probes for constitutively expressed genes for data set normalization were also included on the *C. elegans* LNA tox oligoarray.

Cultivation of *C. elegans* Worms

For all cultures, the sample was divided into two, and one half of the sample was used as the control, the other was used as the treated sample. Worm samples were harvested and sucrose cleaned by standard methods. For heat shock treatment, the heat shock sample was added to S-media preheated to 33° C. in a 1 L flask suspended in a water bath at 33° C., the other sample was added to a 1 L flask with S-media at 25° C. Both samples were shaken at approximately 100 rpm for an hour. For Lansoprazole treatment, 0.5 mL of 10 mg/mL Lansoprazole (Sigma) in DMSO was added to each 500 mL volume of S-media culture after 28 hours of growth from L1. At the same time, 0.5 mL of DMSO was added to the control. Incubation was for 24 hours. Samples were then harvested by centrifugation at 3000×g suspended in RNALater™ (Ambion) and immediately frozen in liquid nitrogen.

RNA Extraction

RNA was extracted from the worm samples using the FastRNA® Kit, GREEN (Q-BIO) essentially according to the suppliers' instructions.

Design and Synthesis of the LNA Capture Probes

To design the capture probes, regions with unique mRNA sequence of the selected target genes were identified. The optimal 50-mer oligonucleotide sequences with respect to $T_m$, self-complementarity, and secondary structure were selected. LNA modifications were incorporated to increase affinity and specificity.

Printing of the LNA Microarrays

The microarrays were printed on Immobilizer™ MicroArray Slides (Exiqon, Denmark) using the Biochip One Arrayer from Packard Biochip technologies (Packard, USA). The arrays were printed with a spot volume of 2×300 pl of a 10 µM capture probe solution. Four replicas of the capture probes were printed on each slide.

Synthesis of Fluorochrome Labelled First Strand cDNA from Total RNA

15 µg of *C. elegans* total RNA was combined with 5 µg oligo dT primer (T20VN) in an RNase free, pre-siliconized 1.5 mL tube, and the final volume was adjusted with DEPC-water to 8 µL. The reaction mixture was heated at +70° C. for 10 minutes, quenched on ice 5 minutes, spin 20 seconds, followed by addition of 1 µL SUPERase-In™ (20 U/µL, Ambion, USA), 4 µL 5×RTase buffer (Invitrogen, USA), 2 µL 0.1 M DTT (Invitrogen, USA), 1 µL dNTP (20 mM dATP, dGTP, dTTP; 0.4 mM dCTP in DEPC-water, Amersham Pharmacia Biotech, USA), and 3 µL Cy3™-dCTP or Cy5™-dCTP (Amersham Pharmacia Biotech, USA). First strand cDNA synthesis was carried out by adding 1 µL of Superscript™ II (Invitrogen, 200 U/mL), mixing, and incubating the reaction mixture for 1 hour at 42° C. An additional 1 µL of Superscript™ II was added, and the cDNA synthesis reaction mixture was incubated for an additional 1 hour at 42° C.; the reaction was stopped by heating at 70° C. for 5 minutes, and quenching on ice for 2 minutes. The RNA was hydrolyzed by adding 3 µL of 0.5 M NaOH, and incubating at 70° C. for 15 minutes. The samples were neutralized by adding 3 µL of 0.5 M HCl, and purified by adding 450 µL 1×TE buffer, pH 7.5 to the neutralized sample and transferring the samples onto a Microcon-30 concentrator. The samples were centrifuged at 14000×g in a microcentrifuge for ~8 minutes, the flow-through was discarded, and the washing step was repeated twice by refilling the filter with 450 µl 1×TE buffer and by spinning for ~12 minutes. Centrifugation was continued until the volume was reduced to 5 µL, and finally the labelled cDNA probe was eluted by inverting the Microcon-30 tube and spinning at 1000×g for 3 minutes.

Hybridization with Fluorochrome-Labelled cDNA

The arrays were hybridized overnight using the following protocol. The Cy3™ and Cy5™-labelled cDNA samples were combined in one tube followed by addition of 3 µL 20×SSC (3×SSC final), 0.5 µL 1 M HEPES, pH 7.0 (25 mM final), 25 µg yeast tRNA (1.25 µg/µL final), 0.64 µL 10% SDS (0.3% final), and DEPC-treated water to 20 µL final volume. The labelled cDNA target sample was filtered in a Millipore 0.22 micron spin column according to the manufacturer's instructions (Millipore, USA), and the probe was denatured by incubating the reaction at 100° C. for 2 minutes. The sample was cooled at 20-25° C. for 5 minutes by spinning at maximum speed in a microcentrifuge. A LifterSlip (Erie Scientific Company, USA) was carefully placed on top of the microarray spotted on Immobilizer™ MicroArray Slide, and the hybridization mixture was applied to the array from the side. An aliquot of 30 µL of 3×SSC was added to both ends of the hybridization chamber, and the Immobilizer™ MicroArray Slide was placed in the hybridization chamber. The chamber was sealed watertight and incubated at 65° C. for 16-18 hours submerged in a water bath. After hybridisation, the slide was removed carefully from the hybridization chamber and washed using the following protocol. The Lifterslip coverslip was washed off in 2×SSC, pH 7.0 containing 0.1% SDS at room temperature for 1 minute, followed by washing of the microarrays subsequently in 1.0×SSC, pH 7.0 at room temperature for 1 minute, and then in 0.2×SSC, pH 7.0 at room temperature for 1 minute. Finally, the slides were washed for 5 seconds in 0.05×SSC, pH 7.0. The slides were then dried by centrifugation in a swinging bucket rotor at approximately 200 G for 2 minutes. The slide was then ready for scanning.

Data Analysis

Following washing and drying, the slides were scanned using a ScanArray 4000XL scanner (Perkin-Elmer Life Sciences, USA), and the array data were processed using the GenePix™ Pro 4.0 software package (Axon, USA). The data in each image was normalized so that the ratio of means of all of the features is equal to 1.

Results

Use of LNA-modified oligonucleotide capture probes in the *C. elegans* LNA tox oligoarray clearly allows the identification of distinct expression profiles for *C. elegans* genes relevant for general stress response and for the metabolism of toxic compounds.

TABLE 12

Expression profiling using LNA Oligonucleotide Microarrays.

| Protein name (clone name) | Heat shock | Lansoprazole |
| --- | --- | --- |
| HSP70 (F44E5.4/5) | 4.11 | nd |
| CYP37A (F01D5.9) | nd | 0.98 |
| Ubiquitin (M7.1) | 0.16 | −0.12 |
| Histone 1Q (C01B10.5) | −1.49 | nd |
| HSP90 (C47E8.5) | nd | −1.17 |

Log2 transformed fold of changes for five selected genes in the two expression profiling experiments.

TABLE 13

LNA-modified oligonucleotide capture probes.

| Oligo Name | Sequence |
|---|---|
| CEABC_C34G6.4_u293_LNA3 | TgcmCatTgcAcgGgcActTgtTcgAtcTccTtcTgtTttActTttGgaTg |
| CEABC_C34G6.4_u375_LNA3 | TcaTtcTagGatTgcmCagAtgGttAtgAtamCtcAtgTcgGagAgaAagGa |
| CEABC_F57C12.4_u15_LNA3 | mCcaAtgTtgTttAatTggTtgTaaTgtmCttGatGacmCtgmCatAatmCatAt |
| CEABC_F57C12.4_u480_LNA3 | mCacAagAtcmCtgTgtTgtTctmCcgGaamCaaTgaAaaTgaActTagAtcmCa |
| CEABC_F57C12.5_u111_LNA3 | TacTtgTtcTcgAcaAagGttGtgTagmCcgAgtTtgAcamCtcmCgaAgaAa |
| CEABC_F57C12.5_u444_LNA3 | TgaActTggAtcmCctTctTtgmCatTtaGcgAtgAtcAaaTttGggAagmCg |
| CEABC_K08E7.9_d8_LNA3 | TcaTtaAttTtgTgtAgcTttmCttTctmCgaTttTtgmCacGatmCttTccmCc |
| CEABC_K08E7.9_u51_LNA3 | AggGtgmCctActAcaAacTgamCccAaaAgcAgaTgamCcgAgaAgaAatAa |
| CEABC_Y39D8C.1_u37_LNA3 | AttGaaAgcGacGcgGaaAgtGccAtgTatTtcTaaTttTgtTttmCttTa |
| CEABC_Y39D8C.1_u422_LNA3 | TtgTcaGcaTatmCaaGagTagAtaTggAagTggAtamCacTctGctAatmCc |
| CEADH_H24K24.3a_d3_LNA3 | mCacmCttAttGcgTtcAatTttTgtTtcmCacmCtamCtamCtamCgaAtamCgtTg |
| CEADH_H24K24.3a_u50_LNA3 | TcamCaaGggAgaGagTctGcgGtcGgtGctGgcGttmCgaGaaAatAtaAc |
| CEAPEX_R09B3.1_u191_LNA3 | mCatGcaTccmCgamCgaGaaGaaGtamCtcAttTtgGagTtaTctGgcGaaTt |
| CEAPEX_R09B3.1_u37_LNA3 | GacmCatGctmCcgGtcGtcAtgmCaaAtcGacTtcTaaAttGctTctGatTa |
| CEAPO_C35D10.9_u15_LNA3 | TtgmCatGctGttAaaAccTatmCgtGtamCaaTatTgcmCtgTatAttmCccmCt |
| CEAPO_C35D10.9_u609_LNA3 | TggmCacAgcTtaAtAcaAatTggAaaGtcGagGatTagTcgGtgTtgAa |
| CEAPO_C48D1.2_u176_LNA3 | GacAcamCgcAaaGgaTatGgaTgtTgtTgaGctGctGacTgaAgtmCaaTa |
| CEAPO_C48D1.2_u23_LNA3 | AgcAcgAaamCtcTgcmCgtmCtaAaaTtcActmCgtGatTcaTtgmCccAatTg |
| CEAPO_F20C5.1_u453_LNA3 | AtgGtcAtamCtcTaaAatGggmCagAacTtcAacmCaaAtcAttmCtcGtcAg |
| CEAPO_F20C5.1_u96_LNA3 | AacmCcgAgcTtgmCcgmCaaAgtGcaAgaAaaTtaTagAacGaaTgaAacAg |
| CEATPase_B0365.3_u31_LNA3 | GgaTggGtcGagmCgtGagAccTacTacTaaAgaAcaGctTgtGaaTctTt |
| CEATPase_B0365.3_u386_LNA3 | mCaamCgtTctmCgaTtcmCtamCggAcaAgaAtgGacmCtaTgcmCaamCagAaaGa |
| CEATPase_C17H12.14_u356_LNA3 | TgcTcgTtaTccAgcTatTttGaaGggActTgtmCatGcaAggActTctTc |
| CEATPase_C17H12.14_u89_LNA3 | mCcgTttAgaGctTatTgcTaamCcaGatTgtmCccAcaAgtmCagAacAgcTc |
| CEATPase_F55F3.3_u215_LNA3 | TgamCggAcgmCtamCtamCccAtaTgtAttTgtTccAtcTtamCcaGcaAccAa |
| CEATPase_F55F3.3_u275_LNA3 | AgcTacTtcAttmCgamCaaGgaAcaTctmCggAaaAgtmCaaGtamCatmCccGg |
| CEATPase_Y49A3A.2_u103_LNA3 | AaaTtcAagGatmCcaGttGccGatGgtGaaGccAagAttmCgcAagGatTa |
| CEATPase_Y49A3A.2_u272_LNA3 | mCgaTcgTttmCtgmCccAttmCtamCaaGacTgtmCggTatGctmCaaGaaTatGa |
| CECALR_Y38A10A.5_u238_LNA3 | TcaGgaAcgAtcTttGacAacAttAtcAtcAccGacTctGttGagGagGc |
| CECALR_Y38A10A.5_u296_LNA3 | TgaActmCtamCtcTtaTgaAagmCtgGggAgcmCatmCggAttmCgaTttGtgGc |
| CECAT_Y54G11A.5b_u137_LNA3 | GaamCttTgcAggGccGctmCggGgaAtgTcaTgaTttmCatTatTaaGggAa |
| CECAT_Y54G11A.5b_u189_LNA3 | GtcAatTctGggAgaAggTgtTggAtamCcgGggmCtcGggAgaGaaTgtGc |
| CECC_C03D6.3_u275_LNA3 | AtgTaaAgaAggAatGctTccmCgaAtgGatTggAtaTttAttTgtmCcaGa |
| CECC_C03D6.3_u430_LNA3 | GgamCcgAaaTttGtgmCagmCatGtcGgamCacGaaAttGatGgtmCtcAttTt |
| CECC_C07G2.3_d9_LNA3 | mCagAcamCgaAggTtamCgaTagAtaAccAtcTctmCaaAgtmCtaTcgAccTc |
| CECC_C07G2.3_u44_LNA3 | mCgamCgaTgtGcgTgtTccTgamCgaTgaAagAatGggAtaTtaAgaAaamCc |
| CECC_Y46G5A.2_u331_LNA3 | TtgTgcTccAtcGctGctmCcgmCttAcaGacTtgAcaAcgmCtcAccTttGc |
| CECC_Y46G5A.2_u385_LNA3 | AatGagmCggTtgTgcmCgtGtgAcgTcamCttmCgtmCacAgtGttGctmCtamCt |

TABLE 13-continued

LNA-modified oligonucleotide capture probes.

| Oligo Name | Sequence |
|---|---|
| CECoA_C29F3.1_u316_LNA3 | AaaTtgAcamCcaAtcAaaTctGtcTcaTctmCctGagGacmCgtmCaamCttmCg |
| CECoA_C29F3.1_u392_LNA3 | AatmCttTgtGtamCggAgaTggGgcAaaAggmCagmCaaGaaAgtAaamCcaAg |
| CECoA_F08A8.4_u1094_LNA3 | AggAcaAggGgcActActGgcAcaGgcTttGatTatTgcAgtGagAtaTt |
| CECoA_F08A8.4_u1260_LNA3 | TtaAtgGagGtgAcaAtgGgtTccTtgGatTcgAtaAatTccGagTgcmCc |
| CECoA_F59F4.1_u109_LNA3 | GctmCttmCtcmCagTggGctmCaaAatAgtmCaamCtcAacAgaTcgGaaGttmCt |
| CECoA_F59F4.1_u424_LNA3 | AaaGctTcgAgaTggmCacGttmCgtmCtgTatmCtcGtgAagAacTtaTtgmCa |
| CECoA_Y25C1A.13_u115_LNA3 | GatTcgmCtgAacTttAtcAagAcgTggAatAtgAgcmCagmCtcmCtgTcgAc |
| CECoA_Y25C1A.13_u451_LNA3 | GatmCttAtcAccGcgTgcGatAttmCgaGtaGctTcamCagGatGcgAttTt |
| CECOL_C27H5.5_u493_LNA3 | GgaAagGaaGgaTccAttmCtcAgcTctGcamCttmCcamCcaTcaGagmCcaTg |
| CECOL_C27H5.5_u680_LNA3 | TggAtamCaaGgaGggAtcTggmCagTggTggAtcTggAagTggTggAtaTg |
| CECOQ_ZC395.2_u199_LNA3 | TtgAaaGaamCtcmCttGccGacGatmCctGaaAcamCacAaaGaaTtgmCtgAa |
| CECOQ_ZC395.2_u400_LNA3 | AtgTggGatGagGagAaaGaamCatTtaGatAcaAtgGaaAgaTtaGctGc |
| CECRYZ_F39B2.3_u171_LNA3 | AggmCtgAgcTctTggActTtgGcaTcaAcaTtgTctmCatTctTgaAggAa |
| CECRYZ_F39B2.3_u222_LNA3 | TtaTggTtamCagAagGagmCtgTttAcgGtgTagmCatTggGaaTgtmCttmCc |
| CECyclin_R02F2.1a_u24_LNA3 | mCacTtcAacmCaamCtcmCgtGttAatmCaaGcaAgcmCgcmCacmCatmCtaAtgAg |
| CECyclin_R02F2.1a_u312_LNA3 | TctmCatTgcTcgTcgAggmCtamCcaAcaAacActGgcAatAccmCaaTtaAt |
| CECyclin_ZC168.4_u203_LNA3 | TaaGaaAgtmCatTgaGgaTgcTgtmCgcTttGctmCgcmCgaAgtmCtcGtaTa |
| CECyclin_ZC168.4_u273_LNA3 | AagTtcAtcmCtgTtgAcgGaaTcgAggmCggAgaAtgmCtgTatmCggTcaTt |
| CECYP_B0213.15_u133_LNA3 | AcaGgaAatAtgAttTtgGatTtcGatTttGaaTcgGttGgtGctGccmCc |
| CECYP_B0213.15_u202_LNA3 | GctGagmCtgTatTtgGctAgtGaaAtgTgtGttTttGatActTtaAatGa |
| CECYP_B0304.3_u38_LNA3 | AcgAggTttGgaTcamCaaTcaGaaTtcTgtGaaAtaAgcGttTttTggGa |
| CECYP_B0304.3_u89_LNA3 | AgtTctmCggTctAacAgtGtcTccmCgtTgaAtaTtcTtgTaaAatmCacAc |
| CECYP_C03G6.14_u706_LNA3 | AtgAccActmCaaAatActGctAaaAgaTttGcaGcgGcaGaaGccGttAa |
| CECYP_C03G6.14_u768_LNA3 | TtgAtaTggmCtgTacmCtgTatGgtTttTgaGgamCgtTttTtaGgaGtcGa |
| CECYP_C03G6.15_d9_LNA3 | AttTatTcaTtcAtcmCatGtaAacTgtAtaTttTgaAttTgtGttGtaAa |
| CECYP_C03G6.15_u148_LNA3 | GccAaaGcaGaaTtgTatTtgAtcTtcGgtAacmCttmCtcmCttmCgcTacAa |
| CECYP_C06B3.3_u102_LNA3 | AttTtgAatmCttmCtgGgaAaaTgcmCatmCcamCtcGagAaamCcgTtcmCgtTt |
| CECYP_C06B3.3_u474_LNA3 | mCtaAcgGagGatmCtcGccAatTatmCttTgaGagAcaAaamCtgAaamCtcmCt |
| CECYP_C12D5.7_u399_LNA3 | AtcTagTccmCaaTgaAtcTccmCacAtgmCtgTtamCtcGtgAtgTtcAacTc |
| CECYP_C12D5.7_u65_LNA3 | TttTgcTttmCatmCgcAaaAgcTcaAgaTtamCacAtgTcaGgtmCaaGccAa |
| CECYP_C45H4.17_u27_LNA3 | mCcgmCgamCttTaaAgaGaaGatmCatAaaTttGcaTtgTttTttGttTgtAt |
| CECYP_C45H4.17_u598_LNA3 | mCgaGggTgaTtcGgaGacTttmCagTaaTgtmCcaActTtcAaaTgtTtgmCa |
| CECYP_C45H4.2_u110_LNA3 | TagAtamCaaGatAcaTccmCtcAaaAgaAggmCctAccGtcAatGgcmCaaAg |
| CECYP_C45H4.2_u429_LNA3 | TcaAcgmCgtmCtaTaaAtgAatmCacAacGagGtaTcaAcaTtcTccmCccTg |
| CECYP_C49C8.4_u363_LNA3 | AtgmCtgAtgTtgAaaTtgmCtgGctAccGtaTtcmCaaAagAtamCtgTaaTc |
| CECYP_C49C8.4_u883_LNA3 | AtgAatmCcaTggmCttGgamCatmCtcmCcgTttTtcAagGgaTatAaaAatGt |
| CECYP_C49G7.8_d6_LNA3 | AtgmCaamCgaAttAgtGaaAaaTtcAtcmCtgGaaTaaAaaAtaAttmCtaAa |

TABLE 13-continued

LNA-modified oligonucleotide capture probes.

| Oligo Name | Sequence |
|---|---|
| CECYP_C49G7.8_u795_LNA3 | AtcGctAcgAcaAtcTtttmCcgAtgmCctTcgAagTtttmCgaAagmCttTctmCt |
| CECYP_F01D5.9_u374_LNA3 | GagGtcGgtGgaGgaGgaAgtGgaAatTgamCggmCaaAatmCctGccmCaaGg |
| CECYP_F01D5.9_u46_LNA3 | mCccTctTtgGgaTttmCcamCtcAagTttActGttmCggmCagmCagTgaTatAa |
| CECYP_F08F3.7_u25_LNA3 | GagTtgGttmCcamCagAatGctTagGacGttTaaAttmCgtmCacAaamCttTt |
| CECYP_F08F3.7_u401_LNA3 | mCaaTatGgtTccmCatTttAgcAacTcaTatGaamCacAgaAgaTgtmCctTg |
| CECYP_F14F7.2_u397_LNA3 | GaaAaaGgcGtcGacAttTtaTgtGacAcgTggAcamCttmCacTatGacAa |
| CECYP_F14F7.2_u68_LNA3 | TaaTtgAatTacGggTctTttGtamCatAttAatTttAgtAtamCttTgtGa |
| CECYP_F42A9.5_u435_LNA3 | AtaTcaAtgmCaamCtaTtaAtgAatmCacAacGtcTtgmCcaAtcTtcTccmCg |
| CECYP_F42A9.5_u55_LNA3 | GgaGtgActAtgAaaGcaAagAgtTacmCgaTtgAaamCtgAaaGacAgamCa |
| CECYP_K07C6.3_u3_LNA3 | AatmCttTaaTgaTaaTttAtgGgaTctGtaTtttmCtcTtttmCtgTcaAtaAa |
| CECYP_K07C6.3_u354_LNA3 | AtgAgcmCcamCaaAtgTaaAagGatAcgAgaTtgAttmCggGaamCagTcaTg |
| CECYP_K07C6.4_u118_LNA3 | AtcmCtgmCgaTatGacAttAagmCcamCatGgtTctGaamCctTcaAcaGaaGa |
| CECYP_K07C6.4_u87_LNA3 | mCtgAacmCttmCaamCagAagAtaAacTtcmCgtAtaGcgmCtgGaaAaamCtcmCt |
| CECYP_K07C6.5_u7_LNA3 | AttTaaAggAatTcamCagmCtcAaaAaaTaaTaamCtamCcgGttmCagAgaTt |
| CECYP_K07C6.5_u99_LNA3 | AatTtgAgcmCacAtgGcaAgtTatmCaamCagAggAgamCaaTgcmCgtAcaGt |
| CECYP_K09A11.3_u362_LNA3 | TgamCatTctActTaaAggGaaGaaAatAccAacTggTacmCctTgtAttTg |
| CECYP_K09A11.3_u48_LNA3 | TcamCcamCaaAgcmCatAcaTatGcgAgcTagTtcmCtcAggmCtgmCttAaamCc |
| CECYP_K09A11.4_u238_LNA3 | TtcGacAaaActAttTtgGaaAgaAcaAtcmCcaTtcAgtGtcGgcAaamCg |
| CECYP_K09A11.4_u68_LNA3 | TctGacAacAaaGccAtamCacGtgmCcgActAatTccAcaAtcAgcTagAa |
| CECYP_K09D9.2_u151_LNA3 | TtgGcaAaaGcaGaaTtgTatTtaAtcTttGgaAacmCtcmCttmCttmCgcTa |
| CECYP_K09D9.2_u866_LNA3 | TgaAtcTttmCaaActTatmCacTccTttTaaTacTacmCgtTccTgtTtgGa |
| CECYP_T10B9.10_u410_LNA | AttGagAttGtaTccAttGgcGtcTctTgtTcamCaaTcgAaaAtgTctmCa |
| CECYP_T10B9.10_u56_LNA | AacTgcTacTatTgcGccAtcAagTgtGctGctmCaaActTaaAtcmCagGt |
| CECYP_T10B9.7_u102_LNA3 | TtgAgamCagGaaAtaAgamCtaGaaTtcmCttTgaAacTggTggGaaGtgmCt |
| CECYP_T10B9.7_u267_LNA3 | AagAtgTcaAagAatTcaAgcmCagAacGatGgtmCcamCcgAcgAgcmCatTa |
| CECYP_T19B10.1_u100_LNA3 | AttGaamCcaActmCtgAaaTatAatGacAcaAaamCcaTgtmCtgGaaGtgGt |
| CECYP_T19B10.1_u319_LNA3 | GgcAatGtgAcaAtaTctmCcaAtgGttmCttmCacAgcAatmCatmCacGtgTt |
| CECYP_Y49C4A.9_u121_LNA3 | mCtaTtcAatmCgaTatTttAtcAcamCcaTccAgtGctGgamCctmCcaTcaTt |
| CECYP_Y49C4A.9_u413_LNA3 | GtcTcaGagAtgTgtAaaTttActTccmCtgmCaaTttGttTcamCgcAacTa |
| CECYP_ZK177.5_u394_LNA3 | TtcmCgaAtgTttmCcaAttGggActGaaGttTcaAgaGtcAccmCagAaaAa |
| CECYP_ZK177.5_u445_LNA3 | GatmCcaGcaTctTccAagmCttAcaTtcmCtcmCgtGctTgtAtcAagGaaAc |
| CEDAO_C47A10.5_d9_LNA3 | TttGaaAacmCtgTttTatTatTaaAatAgaTaaTtgAttAgtTctGtamCg |
| CEDAO_C47A10.5_u269_LNA3 | AtamCgtTgcActGcaTccGgcTatGagGgaGccAaaAatmCttAggGgaGt |
| CEDC_C01A2.3_u373_LNA3 | GcamCttmCcaTtcAtcTctGcaGctActAtgGctTtgGtgAcaAaaGttGg |
| CEDC_C01A2.3_u96_LNA4 | mCcgTccAaaAgaAtgmCcaTctmCacAagTctTgaAatmCttAtaAagGtaGt |
| CEDC_C34F6.1_u301_LNA3 | GagGgaTcaAcaGtaAccTcgTgcGgtAttGacAagGgaTgtmCcgGaaGg |
| CEDC_C34F6.1_u450_LNA3 | GatGgtTctTcgAtcGcaAacAaaAcaGatGtgmCtcmCatTtamCatAcgGa |
| CEDC_F33D11.3_u126_LNA3 | AtgGagAaaAtgGatmCtgAtgGagTtgmCagGaaGtgAtgGagmCtcmCagGa |

TABLE 13-continued

LNA-modified oligonucleotide capture probes.

| Oligo Name | Sequence |
| --- | --- |
| CEDC_F33D11.3_u14_LNA3 | TgaAtcTccAtaAatTatTcaAtgTttmCcaAatAttTaaTttAtcAatTg |
| CEDC_F46E10.2_u392_LNA3 | GctmCaamCacGgtAggAtcmCtaTggAacmCgtmCggAggAgcAggmCctmCggAg |
| CEDC_F46E10.2_u54_LNA3 | mCgtGacAacmCtcTtaTttAttTctGtaAaamCtgAttmCgcmCaaActTttGt |
| CEDC_F56G4.2_u382_LNA3 | GaaGctTtcAaamCcaAatGagTtcmCttmCccGgaAtcmCcaAagAatAccAa |
| CEDC_F56G4.2_u82_LNA3 | AcaAtgAaaAgaGagGatGgaAagGaaAtcGaaGtcTctGttmCttGacGa |
| CEDC_M162.2_u103_LNA3 | GatGagGtamCatAacTttGtgTgcAgtTatAggmCcaTctAcaGtamCctGc |
| CEDC_M162.2_u480_LNA3 | TtcmCatmCatmCacTaamCcgAttGtcmCtgAcaTtgAtgGccAaamCcaGggAa |
| CEDC_R10E4.11_u274_LNA3 | TcamCatTatmCgaAcaAgtActAgtAagmCatGctGtgAtgGagTgcmCgcTa |
| CEDC_R10E4.11_u397_LNA3 | mCacGgaGatmCacGacAtcAaaGcgGatTgcTtaGagTgtGgaAacmCgtmCt |
| CEDC_T04C9.1_u321_LNA3 | ActAtcTacGtgGcamCgtTggActmCatmCatmCgaTggGaamCgamCgtAtaAg |
| CEDC_T04C9.1_u64_LNA3 | TctmCtgGccAgtTcamCttTgtGatmCaaTctmCagAttmCgtmCcamCacAagAt |
| CEDC_W02A2.3_u32_LNA3 | mCtamCttmCcgmCaaGaaGgcmCcgTcgTttmCtaAtcGatmCgaAcaTctmCacAc |
| CEDC_W02A2.3_u374_LNA3 | AtgGatGatmCgamCccActTgcmCacTgamCccAcaAtcmCcgmCacTcamCtamCc |
| CEDC_W05G11.3_u153_LNA3 | AagAcgGagAggmCtgGagAgaAcgGtamCcgAtgGagAgcmCagGaamCtgAt |
| CEDC_W05G11.3_u51_LNA3 | mCcamCccAggAggAggGatAcaAgaGaaGaaAgtAcaGatTctmCcaActAa |
| CEDC_ZK863.5_u256_LNA3 | AgtTtcAcamCttmCttTttGccGttTtgGttmCccGttAtcAatmCcaTtgAt |
| CEDC_ZK863.5_u324_LNA3 | mCttTtaTatTctmCatmCaaTttGttTccTacTtgGtcAgcTgaGgaTcgTt |
| CEEPHX_Y55B1BR.4_u161_LNA3 | TtcGgcAcaAatGgaGcaAaaGtaTcgTggTtaTtgTgaTgcGatTatTc |
| CEEPHX_Y55B1BR.4_u93_LNA3 | mCtamCtaTgaAtgAgcTcamCtgGacTcaTttAtcAacTcgAgtmCaaAagmCc |
| CEER_18S_u388_LNA3 | GttGgcGaaTctTcgGgtTcgTatAacTtcTtaGagGgaTaaGcgGtgTt |
| CEER_18S_u82_LNA3 | GaamCtgAttmCgaGaaGagTggGgamCtgTcgmCttmCgaGgtTtaAcgActTc |
| CEER_26S_u342_LNA3 | TgtTatTgcGaaAgtAatmCctGctTagTacGagAggAacAgcGggTtcAa |
| CEER_26S_u38_LNA3 | TgcAtamCgamCttGgtmCtcTtgGtcAagGtgTtgTatTcaGtaGagmCagTc |
| CEFOXO_R13H8.1b_u331_LNA3 | TgtGctmCagAatmCcamCttmCttmCgaAatmCcaAttGtgmCcaAgcActAacTt |
| CEFOXO_R13H8.1b_u393_LNA3 | TtaAgamCggAacmCaaTtgmCtcmCacmCacmCatmCatAccAcgAgtTgaAcaGt |
| CEGAPDH_K10B3.7_u21_LNA3 | AcaTtgmCtamCcaAggmCctAagmCcgmCttmCaaAttmCtcTaaGtcTgaAatGa |
| CEGAPDH_K10B3.7_u727_LNA3 | GttGagTccAccGgaGtcTtcAccAccAtcGagAagGccAatGctmCacTt |
| CEGBA_F11E6.1a_u232_LNA3 | AgtAaaTtcmCttmCcamCgtGgaTctActmCgtGtgTtcAcaAagAtcGagGg |
| CEGBA_F11E6.1a_u451_LNA3 | GgtmCcaAtaAtgGgaGacTggTtcmCgcGcaGaaAgtTatGcaGatGatAt |
| CEGLU_C02A12.1_u264_LNA3 | AgaAaamCttmCgtTggAccmCtgmCtaAggAgaAgtAttTcaAgcTtcTgaGc |
| CEGLU_C02A12.1_u55_LNA3 | GagmCacmCcgAagmCtcAagmCcaTatTtgGaaAcaAgamCcaTacTctTcaAa |
| CEGLU_C46F11.2_u271_LNA3 | GttAccmCtcTacAaaTctmCgcTtcAatmCcaAtgTtgTtcGcaGtcAccAa |
| CEGLU_C46F11.2_u45_LNA3 | mCcgAagAgcTcgTtamCtaTgcGagGagGtgTgaAgcmCggAatAatTttTt |
| CEGLU_F26E4.12_u109_LNA3 | AagTtcTtgGttGgamCgcGatGggAaaAttAtcAagAgaTttGgamCcaAc |
| CEGLU_F26E4.12_u480_LNA3 | AcgAttTcaAcgTcaAaaAtgmCtaAtgGtgAtgAcgTgtmCacTttmCggAt |
| CEGLU_R07B1.4_u166_LNA3 | AccTggGttGatGttTttGcgGctGaaAgtTtcTccAagmCtcAttGatTa |
| CEGLU_R07B1.4_u38_LNA3 | GaaGtamCgtmCtcmCcaAagAaaAgcTacmCccAgcTtaAggmCatTgcAcaAt |
| CEGLU_T09A12.2_u220_LNA3 | GcgmCcaGatAtgTatTcaAagAtcGagGtaAatGgtmCagAacActmCatmCc |

TABLE 13-continued

LNA-modified oligonucleotide capture probes.

| Oligo Name | Sequence |
|---|---|
| CEGLU_T09A12.2_u335_LNA3 | AatmCtamCagGgaAaaAggAttTcgAgtTgcmCgcGttTccAtgmCaaTcaAt |
| CEGLU_T28A11.11_u299_LNA3 | AgaTggmCaaAgaAgcAtamCatAacTgaAacTctTccmCggGgaGctActAc |
| CEGLU_T28A11.11_u54_LNA3 | TgaAtaAacGggmCcgAacTaaAtcmCatTcgTcaGtgGaaAtgGgaAacAa |
| CEGPD_B0035.5_u256_LNA3 | GtcmCgtmCttmCctGatGctTatGaamCgcmCtaTttmCtcGaaGtaTtcAtgGg |
| CEGPD_B0035.5_u478_LNA3 | TgtGgaAaaGctmCtcAacGagAagAaaGcaGaaGttmCgtAtamCaaTtcAa |
| CEHSP_C09B8.6_d8_LNA3 | AtaTcgmCcgmCctGctTccTcamCcaAccmCgaAtaAcgmCaamCaaAaamCttTa |
| CEHSP_C09B8.6_u286_LNA3 | AagAgcmCcamCtcAtcAagGatGaaAgtGatGgaAagActmCttmCgtmCtcAg |
| CEHSP_C12C8.1_u127_LNA3 | mCaaGatAttTtaAcaAaaAtgmCatmCaamCaaGaaGccmCaaTcaGgtTccGg |
| CEHSP_C12C8.1_u1531_LNA3 | mCttGggmCatTctGtamCggGatGctGtcAttActGtgmCctGcaTatTttAa |
| CEHSP_C47E8.5_u310_LNA3 | AagAgmCatmCtcGaaAtcAacmCcaGacmCacGctAtcAtgAagAcamCttmCg |
| CEHSP_C47E8.5_u361_LNA3 | AtgAaaGctmCaaGctmCttmCgtGatTccTctActAtgGgaTacAtgGccGc |
| CEHSP_F26D10.3_u276_LNA3 | TtaAgcAgamCcaTtgAggAcgAgaAgcTcaAggAtaAgaTcaGccmCagAa |
| CEHSP_F26D10.3_u397_LNA3 | mCgtmCttTccAagGatGacAttGaamCgcAtgGtcAacGaaGctGagAaaTa |
| CEHSP_F43D9.4_u169_LNA3 | GtcGacTtgGctmCacAtcmCacAccGtcAtcAacAagGaaGgamCagAtgAc |
| CEHSP_F43D9.4_u275_LNA3 | mCaaTctTgaGggAcamCgtTctmCacmCatTgaGggAcamCcamCgaGgtmCaaGa |
| CEHSP_F44E5.4/5_u123_LNA3 | TcamCtaAaaTgcAccAatmCtgGacAatmCttmCgmCttmCgmCtgGatGcgmCt |
| CEHSP_F44E5.4/5_u380_LNA3 | TcaTgaAgcTaaAcaAttmCgaAaaGgaAgaTggTgaAcaAcgGgaAcgTg |
| CEHSP_F52E1.7_u175_LNA3 | AagTatAacmCttmCcaAcaGggGtcmCgtmCcaGaamCaaAtcAagTccGaaTt |
| CEHSP_F52E1.7_u448_LNA3 | TttAacmCatGgcmCgcAgaTtcTtcGatGacGtcGacTttGatmCgcmCacAt |
| CEHSP_F54D5.8_u252_LNA3 | GcgTcgAaaAgaTctmCccTgaAgtmCtgmCatTgamCtgGccTtgAtaTtaTg |
| CEHSP_F54D5.8_u318_LNA3 | AcaTagTctTcgTcaTcaAggAtAagcmCacAccmCgaAatTcaAgcGagAg |
| CEHUS_H26D21.1_u117_LNA3 | TcgmCcaAcamCtcGgamCacGtgmCcaAaaTgaAtaTcaTctmCaaAtcGaaTg |
| CEHUS_H26D21.1_u478_LNA3 | GtcGaaGttAgaAatmCcaGaaGccGatAttGttTctmCatmCaaAttmCcaAt |
| CEMRE_ZC302.1_u169_LNA3 | ActActmCgtGgaAgaTccAatAaaGttGttTcaAcgmCgamCaaAtcGatTc |
| CEMRE_ZC302.1_u292_LNA3 | GgcAgtGaaGatGaaGtgGcaAatTctGatGaaGaaAtgGgaAgcAgtAt |
| CEMTL_T08G5.10_d127_LNA3 | TtgTcaAcgAccAgaAgcAaaAatTatGggAatmCgcGatAaaAttmCaaGg |
| CEMTL_T08G5.10_u45_LNA3 | GatGcaAgtGtgmCcaAactGcgAatGtgmCtcAggmCtgmCtcAttAatTtgAa |
| CENAP_D2096.8_u356_LNA3 | GacGatAtgTtcGatTtcmCcaGgaGagGacGgtGatGatGtgTcaGacTt |
| CENAP_D2096.8_u70_LNA3 | GacGatAtgTtcGatTtcmCcaGgaGagGacGgtGatGatGtgTcaGacTt |
| CEPAI_F56D12.5_u241_LNA3 | GagGtcGtcGtaAtcmCacAagGctmCcaAgaAagmCaaGtgmCtcGacAttTc |
| CEPAI_F56D12.5_u301_LNA3 | GatActTttGgcAagmCtcGttmCcaAtcAagAagGagGtcAtcmCcaGatmCg |
| CEPDI_C07A12.4_u28_LNA3 | GatGagGagGgamCacAccGagmCtcTaaAtcmCacAttmCcaAtamCagTtcAa |
| CEPDI_C07A12.4_u433_LNA3 | mCttAtgTccGaaGatAtcmCcaGagGatTggGacAagAacmCcaGtcAagAt |
| CEPDI_C14B1.1_u119_LNA3 | TacmCccAgtmCgamCtaTgaTggAgamCagAaamCctmCgaGaaGttmCgaAgaAt |
| CEPDI_C14B1.1_u358_LNA3 | mCtcGtcGccTccAacTtcAacGaaAttGccmCttGatGaaAccAagActGt |
| CEPGK_T03F1.3_d9_LNA3 | TtcTatTgtTtaTtcmCttGccmCaaTagTgtAttTgtAttTatTctTtcTc |
| CEPGK_T03F1.3_u424_LNA3 | mCaaAtcmCatmCtcmCcaGtgGatTtcGtcAttGctGacAagTtcGccGagGa |

TABLE 13-continued

LNA-modified oligonucleotide capture probes.

| Oligo Name | Sequence |
| --- | --- |
| CEPON_E01A2.7_u223_LNA3 | GttTctGatTcgAcamCttTatGgamCcaTctmCaaGttmCtgmCgaGttTctTt |
| CEPON_E01A2.7_u79_LNA3 | GggAaamCaaAtgAttGttGgtAcaGtaGccmCgcmCctGctAttmCacTgtGa |
| CEPPGB_F13D12.6_u44_LNA3 | mCgaGcamCatmCatmCcaAtcGttmCctGttmCaamCaaGgcmCttmCtaAtcGttAg |
| CEPPGB_F13D12.6_u440_LNA3 | TgaTgaGagmCccAgtAacmCaaTtaTttGaamCcgTcaGgaTgtGcgTaaGg |
| CEPPS_T14G10.1_d2_LNA3 | mCgtmCtaAtcGaaGaaGggGatmCgtGggmCaaTcaTaamCtaAttAacmCttmCa |
| CEPPS_T14G10.1_u240_LNA3 | mCaaTggmCtcmCagGtcTttmCtgmCtcTtcAtaTacTtcmCatTccGagTtgmCt |
| CEPRDX_R07E5.2_u405_LNA3 | GttmCtcTtgGagmCtgAagTtgTcgmCgtGctmCgtGtgAttmCtcActTctmCt |
| CEPRDX_R07E5.2_u42_LNA3 | TcgmCtamCcaGcaAggAatActTcaAcaAggTcaAcaAgtGatmCacAcaGa |
| CEPYC_D2023.2_u256_LNA3 | AagGaaAttGtaActmCgcmCcaAgaGctmCtcmCcaGgtGtcmCgtGgamCatAt |
| CEPYC_D2023.2_u427_LNA3 | TtgActGgaTtgGagAttGcgGaaGaaGttGatGttGaaAtcGagAgtGg |
| CERAD_F10G7.4_u169_LNA3 | GccAagTctmCaaGcaAtaAgtGttGatmCaaTcaGagmCcaTacGgaGagAt |
| CERAD_F10G7.4_u267_LNA3 | AtaTtgAgamCttmCggGacAagmCggActTctmCatmCtgTcamCagmCaamCtgmCc |
| CERAD_F32A11.2_u250_LNA3 | GatmCcgmCagAgaAtcGagTatTtcmCtcTcgAgamCccAtgGatAtcAacTg |
| CERAD_F32A11.2_u380_LNA3 | TccGttAagAagmCtcActGgaAaaAcamCacGgcTcgAacGaaAttGgaAt |
| CERAD_T04H1.4_u274_LNA3 | AatTtgGatGagAgcAaaGtgGaaGgaAtgGctAtcGttTtgGcaGatAt |
| CERAD_T04H1.4_u375_LNA3 | GtgmCtgGtcAaaAaaTgcTtgmCttmCgtTgcTtaTtcGcaTtgmCacTcgmCa |
| CERAD_W06D4.6_u325_LNA3 | mCttmCgaGaamCtcTtcAagTtgGaaTcaAcaGtgGcaTcgGatAcamCatGa |
| CERAD_W06D4.6_u34_LNA3 | GtgmCctTctGaaGccGaaGaaAcGacGatTagTtaAatGttTccAagTt |
| CERAD_Y116A8C.13_u289_LNA3 | GatAaaAtcGatAgcGacGacGatGagGaaGccGatGatGagGagmCtcGa |
| CERAD_Y116A8C.13_u59_LNA3 | GcaGgtGgaTacGgaTgtGgaGctGacTttTgcGttTtaTcaAgaAtcTc |
| CERAD_Y39A1A.23_u221_LNA3 | TccmCgtAgaAgtAgaAatGctAgaAgaAccTgaAcaAgaAgaTcaAgaAa |
| CERAD_Y39A1A.23_u276_LNA3 | TgcAagAtgTcaGtaTtgAaamCaaTtcmCtgTagAgamCccmCcgAagAaaAt |
| CERAD_Y41C4A.14_u509_LNA3 | AgtmCtcGtaTccGggAatGttTcaGccTgtGaaAatGctTgtTgaAgamCg |
| CERAD_Y41C4A.14_u731_LNA3 | mCttmCaaAacmCgtmCgcTttTaaGgaTacAggAacGtgGcamCgcTtcmCgaGg |
| CERAD_Y43C5A.6_u131_LNA3 | mCagAttGtamCctTcgAaaAggAaaAggAgaGaaTcgmCgtmCgcAaaAatGg |
| CERAD_Y43C5A.6_u429_LNA3 | TgaTggmCttTgaTtaTtcGagmCagGagmCaaTgaTgtmCcgAgaGtcGttAt |
| CERFC_F31E3.3_u128_LNA3 | mCaaTgamCgaGaaTatTggAgtAatGggGaaActGgtTgcGacTtgmCgaAa |
| CERFC_F31E3.3_u55_LNA3 | TtgGaaAacAatmCtcmCtcGacTttmCtgmCtcActmCttmCgtGaaActAtcmCa |
| CERPL_K11H12.2_d1_LNA3 | TctTgtTatTttAttTtgTttTggGctTgtTccGaaAatGaaAtgGttGt |
| CERPL_K11H12.2_u172_LNA3 | mCaaTggAtcAccAagmCcaGttmCacAagmCacmCgtGagmCaaAgaGgamCtcAc |
| CERT_F36A4.7_u1396_LNA3 | mCttTgtGatGtgAtgActGcgAagGgamCacTtgAtgGctAttAcgAgamCa |
| CERT_F36A4.7_u2302_LNA3 | GagmCcaGctActmCagAtgAcamCtcAacAcgTtcmCatTatGcaGgaGttTc |
| CERT_F36A4.7_u289_LNA3 | TacActmCcaTccTcgmCcgAcaTacAatmCcaAcaTctmCcamCgcGgaTtcTc |
| CERT_F36A4.7_u2919_LNA3 | AtgGagAagAtgGttTggAtgGaaTgtGggTtgAgaAtcAgaAtaTgcmCg |
| CERT_F36A4.7_u4269_LNA3 | AacmCggGatAccGtgTcgAacGtcAcaTgaAagAtgGcgAtaTaaTcgTc |
| CERT_F36A4.7_u5485_LNA3 | GagGagAttAaamCgcAtgTcaGtgGctmCatGtcGagTttmCcaGaaGtcTa |
| CESLC_F52F12.1a_u249_LNA3 | AgaTatTgcmCtcTacTtaTcaTggGccTgaTggmCttTgtmCtgmCcgGtaTt |

TABLE 13-continued

LNA-modified oligonucleotide capture probes.

| Oligo Name | Sequence |
|---|---|
| CESLC_F52F12.1a_u76_LNA3 | GaaTctmCaamCcamCttmCtgGaamCccmCatAcamCcaAtgGatAgaAgamCggAg |
| CESLC_K11G9.5_u400_LNA3 | GttGttmCttTtttTccGtgAtcTtttTcaTgtTtaTgtmCtgAacGtgGcaGg |
| CESLC_K11G9.5_u462_LNA3 | GacTcgTtgGtgTctTgcTagGatGtcTtgGgtTcaTtcmCtcAatmCgtTg |
| CESLC_Y32F6B.1_u179_LNA3 | GtamCtgGgcTcgAggGctGaaActAatmCgaAgaAgaAacTccAgaAgaTa |
| CESLC_Y32F6B.1_u280_LNA3 | GgaTcaTgcTctGttTacGacActGatGagTtaAgaGtcAgamCtgmCacGt |
| CESLC_Y37A1C.1a_u104_LNA3 | mCgaTggTtcTtcTcgTctAtcAtaTcgGggTagTtgmCcgAagTgtTgaAa |
| CESLC_Y37A1C.1a_u404_LNA3 | mCaaAtcGaamCtgGtaTaaAggAggAccGacGgaGacGaaTttGaamCgaGa |
| CESLC_Y70G10A.3_u383_LNA3 | AttmCgaTcaAagAacTctGgcTctmCggmCgtTaamCtgGacAttTgtTcgTc |
| CESLC_Y70G10A.3_u46_LNA3 | mCtcmCccGagmCagGcgAttAttmCacGctAgtTatGctmCaaAtgTgaTctGt |
| CESOD_C15F1.7_u435_LNA3 | mCcgGtamCtaTctGgaTcamCacAgaAgtmCcgAaaAtgAccAggmCagTtaTt |
| CESOD_C15F1.7_u9_LNA3 | mCccAgtGacTacmCtgAatmCgcGtcTctGaaTctmCcamCacAatTccTacTa |
| CESOD_F10D11.1_u326_LNA3 | GgaGttGctmCacmCgcAatTaaGagmCgamCttmCggAtcTctGgaTaaTctTc |
| CESOD_F10D11.1_u477_LNA3 | AaaTtgAggAaaAgcTtcAcgAggmCggTctmCcaAagGaaAcgTcaAagAa |
| CESULT_EEED8.2_u316_LNA3 | mCaaTcgTacmCatGaaAgaAgtTggAagmCcamCgtGcaAgaGaaGaaAtcmCa |
| CESULT_EEED8.2_u82_LNA3 | AagAagAttmCctGacmCagAgaGacTcamCgtGctTacmCcaAgaAgcAtcTa |
| CESULT_Y113G7A.11_u252_LNA3 | AgcAttGgtGgaAatAcgAaaTggmCatGggAagAgaAacmCccTctmCaaTt |
| CESULT_Y113G7A.11_u96_LNA3 | mCtgGttAcgGtaGtgTatGgtmCccTgtmCctmCtcAgaAtgmCaaAtaTgtmCg |
| CESULT_Y67A10A.4_u108_LNA3 | TctAcgTcgAtgGaaAgmCcgAttTaamCaaTcaAagmCcaAcaAcgmCagTt |
| CESULT_Y67A10A.4_u327_LNA3 | GgaAagGtgmCcaAaaAgtTgamCagmCaaTtgGagGatmCttAttmCatTgcmCa |
| CETOPO_K12D12.1_u398_LNA3 | AgaTgaTgaTgaAgtTccTgcAaaGaaGccTgcTccAgcGaaGaaAgcTg |
| CETOPO_K12D12.1_u449_LNA3 | AaaAccTcgTacTggAaaAggAgcTgcGaaAgcGgaAgtTatmCgaTttGt |
| CETOPO_M01E5.5b_u256_LNA3 | GagAagGccmCagAagAagTacGacAgamCtgAagGagmCagTtgAaaAagTt |
| CETOPO_M01E5.5b_u429_LNA3 | TtcTgtmCatAcaAtcGtgmCtaAtcGgcAggTtgmCgaTccTttGtaAccAt |
| CEUbi_F25B5.4_u186_LNA3 | AagmCttmCggAcamCcaTtgAgaAtgTcaAagmCcaAaaTccAggAtaAggAg |
| CEUbi_F25B5.4_u2_LNA3 | AatmCgaAccmCatmCaaTtcActmCgtTatTccTccTcgAtcTccGttmCaaGt |
| CEUbi_F29B9.6_u145_LNA3 | mCtgAacmCatmCcaAatAttGaaGatmCcaGctmCagGctGaaGccTatmCagAt |
| CEUbi_F29B9.6_u230_LNA3 | mCgtGtgmCttAtcTctTctGgaTgaAaamCaaGgaTtgGaaGccGtcAatmCt |
| CEUbi_M7.1_u239_LNA3 | mCggAagmCatmCtgmCctTgamCatTctmCcgTtcGcaGtgGtcGccGgcTctG |
| CEUbi_M7.1_u53_LNA3 | AaaGtamCgcTatGtgAggAggmCtaAcamCcaTtcAtaTaaGaamCgcAgcmCa |
| CEUGT_F39G3.1_u40_LNA3 | TgtTgcmCgtAgaAgaGagActAaaActAagAacGatTgaTtgAagGtcTg |
| CEUGT_F39G3.1_u466_LNA3 | TacAatTctTtgmCagGaaGcaAtaTccGccGgaGtcmCccmCttAtcActAt |
| CEUGT_M88.1_u480_LNA3 | mCtcAcgGagGttAtaAttmCtaTgcAggAggmCaaTttmCgmCtgGagTtcmCa |
| CEUGT_M88.1_u72_LNA3 | AccGttTcaTgaGagmCtgTaaTcaGgtGttGttTctGtaAaaAgtGtgAa |
| YAL009W_u145_LNA3 | GtgGatGtgAaaTtaGtcmCtcAacmCccAgaGcaTttAgtGcaGagAttAg |
| YAL009W_u341_LNA3 | GcaGttTaaTgtGaaGctAgtTaaAgtAcaGtcTacGtgGgamCgaGaaAt |
| YAL059W_u262_LNA3 | AttGccAagTccAttTctmCgtGccAagTacAttmCaaAatAcaAgaAagGc |
| YAL059W_u51_LNA3 | AgamCtcmCtamCaaAtaGatTcgGtgTccTgcmCagAcgAtgTtgAagAatAg |
| YER109C_u109_LNA3 | TtgAagTttGggAatAttGgtAtgGttGaaGacmCaaGgamCcgGatTacGa |

TABLE 13-continued

LNA-modified oligonucleotide capture probes.

| Oligo Name | Sequence |
|---|---|
| YER109C_u436_LNA3 | GagGcgmCaaGtaGgcAatGatTcaAgaAgtAgtAaaGgcAatmCgtAacAc |
| YHR152W_u128_LNA3 | TgaGcamCaaAgtTaaGatGttmCggAaaGaaAaaGaaAgtmCaaTccTatGa |
| YHR152W_u510_LNA3 | mCaaGtgAccAatmCagmCacGcamCggmCttmCcaTccTcaAgamCtgAtaTtamCc |
| YKL130C_u211_LNA3 | AttAaaTgcGcaGatGagGacGgaAcgAatAtcGgaGaaActGatAatAt |
| YKL130C_u85_LNA3 | GatGgtAagmCtgAgcGccTtgGacGaaGaaTttGatGttGtcGctActAa |
| YKL178C_u199_LNA3 | TacGtcAcgmCaaGgamCagAgcTttGacGacGaaAtaTcamCttGgaGgaTt |
| YKL178C_u367_LNA3 | TctmCccTgtGtaGgtAcamCcaAtaTcamCaaGcgmCatTtcTatGtcGacTa |
| YLR443W_u179_LNA3 | TgcTaamCacmCagTttAgamCcaTggAaaTccmCacmCgcAaaTatAagmCaaTg |
| YLR443W_u86_LNA3 | GcaGgamCatAagAttmCcgGtcAagmCaamCgamCagTgaAgaAagTatGcaAa |
| YOR092W_u251_LNA3 | mCcgTctAgtGaaAgcGggAtgGctAaaTtgGgaAaamCgamCaaGatGttAt |
| YOR092W_u82_LNA3 | GatGctTcaAtaTccTttGatGgtmCgtTagTttAccAttTttGgtGtcTt |
| YPL263C_u132_LNA3 | CatTtgAgtTatGtgAagAccGttGgtGggAaaGaaGagAtcAggTg |
| YPL263C_u257_LNA3 | GtcTtgGctAccAcamCccAaaAccGttmCgaAacTttAagAgcAttmCtamCt |

LNA modifications are depicted by uppercase letters in the sequence;
"mC" denotes LNA methyl cytosine.
(SEQ ID NOs: 162-437, in sequential order)

EXAMPLE 9

Performance Analysis of LNA Oligonucleotide Capture Probes Designed to Detect Ratios of Splice Variants in mRNA Pools Oligonucleotide Design for Microarrays The methods for designing exon-specific internal oligonucleotide capture probes are described above.

Design of the LNA-Modified Capture Probes

For the internal LNA-modified oligonucleotide capture probes, every third DNA nucleotide was substituted with an LNA nucleotide. The probes designed to capture the junction of the recombinant splice variants were designed with LNA modifications in a block of five consecutive LNAs nucleotides, two on the 5' side of the splice junction and three on the 3' side of the splice junction. All capture probes are shown in Table 14.

TABLE 14

Internal, exon-specific and merged, exon-exon junction specific oligonucleotide capture probes used in this example.
(SEQ ID NOs: 89-96, in sequential order)

| Capture probes | Sequence (LNA = uppercase, DNA lowercase letters) |
|---|---|
| gene78.01a_50_LNA3 | mCctGaaAgtAgaTttGttAttTccGaaAcgmCctTctmCccGttmCttAagTc |
| gene78.01b_50_LNA3 | mCatAtamCcamCaaAtaGtcmCctmCaaAaaTcamCaaGaaAacTcamCaamCacTg |

TABLE 14-continued

Internal, exon-specific and merged, exon-exon junction specific oligonucleotide capture probes used in this example.
(SEQ ID NOs: 89-96, in sequential order)

| Capture probes | Sequence (LNA = uppercase, DNA lowercase letters) |
|---|---|
| gene78.03a_50_LNA3 | GatTtgmCagmCggTggTaaAaaGtaTgaAaamCgtGgtAatTaaAagGtcTc |
| gene78.03b_50_LNA3 | mCcaAtgAaaActAatmCaaAggTaaAcgTggAtcmCcaTggmCaaTtcmCcgGg |
| gene78.m01INS3_50_block | caacactgcccagaggttcaatcGATmCmCgatgatcctaatgaaggcgccc |
| gene78.mINS303_50_block | gtccagtatcgtccatcatAGTATcgataaatatgtgaaggaaatgcctg |
| gene78.m01INS4_50_block | caacactgcccagaggttcaatcGATGTgtgataggatcagtgttcaggg |
| gene78.mINS403_50_block | gaaggcgaaggagactgctAATATcgataaatatgtgaaggaaatgcctg |

Printing and Coupling of the Splice Isoform-Specific Microarrays

The splice variant capture probes were synthesized with a 5' anthraquinone (AQ)-modification, followed by a hexaethyleneglycol-2 (HEG2) linker. The capture probes were first diluted to a 20 μM final concentration in 100 mM Na-phosphate buffer pH 7.0, and spotted on the Immobilizer polymer microarray slides (Exiqon, Denmark) using the Biochip Arrayer One (Packard Biochip Technologies, USA)

with a spot volume of 2×300 pl and 300 µm between the spots. The capture probes were immobilized onto the microarray slide by UV irradiation in a Stratalinker with 2300 µjoules (Stratagene, USA). Non-immobilized capture probe oligonucleotides were removed from the slides by washing the slides two times 15 minutes in 1×SSC. After washing, the slides were dried by centrifugation at 1000×g for 2 minutes, and stored in a slide box until microarray hybridization.

Construction of Splice Variant Vectors

The recombinant splice variant constructs were cloned into the Triamp18 vector (Ambion, USA). The constructs were sequenced to confirm their construction. The plasmid clones were transformed into *E. coli* XL10-Gold (Stratagene, USA).

Triamp18/SWI5 Vector Construct

Genomic DNA was prepared from a wild type standard laboratory strain of *Saccharomyces cerevisiae* using the Nucleon MiY DNA extraction kit (Amersham Biosciences, USA) according to the supplier's instructions. Amplification of the partial yeast gene was performed using standard PCR using yeast genomic DNA as template. In the first step of amplification, a forward primer containing a restriction enzyme site and a reverse primer containing a universal linker sequence were used. In this step, 20 bp was added to the 3'-end of the amplicon, next to the stop codon. In the second step of amplification, the reverse primer was exchanged with a nested primer containing a poly-$T_{20}$ tail and a restriction enzyme site. The SWI5 amplicon contains 730 bp of the SWI5 ORF plus 20 bp universal linker sequence and a poly-$A_{20}$ tail.

The PCR primers used were;

YDR146C-For-EcoRI:
(SEQ ID NO: 97)
acgtgaattcaaatacagacaatgaaggagatga

YDR146C-Rev-Uni:
(SEQ ID NO: 98)
gatcccgggaattgccatgttacctttgattagttttcattggc

Uni-polyT-BamHI:
(SEQ ID NO: 99)
acgtggatccttttttttttttttttttttgatcccgggaattgccat
g, The PCR amplicon was cut with the restriction enzymes, EcoRI+BamHI. The DNA fragment was ligated into the pTRIamp18 vector (Ambion, USA) using the Quick Ligation Kit (New England Biolabs, USA) according to the supplier's instructions and transformed into *E. coli* DH-5α by standard methods.

Construction of the Recombinant Splice Variant #1 (Triamp18/swi5-rubisco)

The *Arabidopsis thaliana* Rubisco small subunit ssu2b gene fragment (gi17064721) was amplified from genomic DNA by primers named DJ 305 5'-ACTATGATGGACGATACTGGAC-3' (SEQ ID NO: 100) and DJ 306 5'-ATTGGATCGATCCGATGATCCTAATGAAGGC-3' (SEQ ID NO: 101), containing ClaI restriction site linkers. The purified PCR fragment was digested with ClaI and then cloned into the swi5 (gI:7839148) vector at the unique ClaI site (atcgat) giving each insert a flanking sequence from the original yeast SWI5 insert (named exon01 and exon 03, FIG. 11). The product was inserted in the reverse orientation, so that the insert sequence is:

(SEQ ID NO: 102)
atcgatCCGATGATCCTAATGAAGGCGCCCGGGTACTCCTTCTTGCATTC

TTCAACTTCCTTCAACACTTGAGCGGAGTCGGTGCATCCGAACAATGGAA

GCTTCCACATTGTCCAGTATCGTCCATCATAGTatcgat

Nucleotide sequence analysis revealed a difference between the sequence of *A. thaliana* rubisco expected from the GenBank database and that obtained from all sequenced constructs and PCR products. Position 30 in the Rubisco insert is "C" rather than the expected "A". This SNP was probably created by PCR. None of the oligonucleotide capture probes used in the example cover this region. Rubisco sequence in genbank is TCCTAATGAAGGCGCCA (SEQ ID NO: 103). The sequence obtained from the plasmid contruct is TCCTAATGAAGGCGCCC (SEQ ID NO: 104).

Construction of the Recombinant Splice Variant #2 (Triamp18/swi5-Lea)

The *Arabidopsis thaliana* Lea gene (gi1526423) was amplified from genomic DNA with primers named DJ 307 5'-GGAATTATCGATGTGTGATAGGATCAGTGTTCAG-3' (SEQ ID NO: 105) and DJ 308 5'-AATTGGATCGATATTAGCAGTCTCCTTCGCC-3' (SEQ ID NO: 106) including the ClaI linker sites as above. The PCR fragment was digested with ClaI cloned into the yeast SWI5 IVT construct as above at the unique ClaI site. The fragment was inserted in the forward orientation, resulting in the following insert sequence:

(SEQ ID NO: 107)
atcgatGTGTGATAGGTTCAGTGTTCAGGGCTGTCCAAGGAACGTATGAG

CATGCGAGAGACGCTGTAGTTGGAAAAACCCACGAAGCGGCTGAGTCTAC

CAAAGAAGGAGCTCAGATAGCTTCAGAGAAAGCGGTTGGAGCAAAGGACG

CAACCGTCGAGAAAGCTAAGGAAACCGCTGATTATACTGCGGAGAAGGTG

GGTGAGTATAAAGACTATACGGTTGATAAAGCTAAAGAGGCTAAGGACAC

AACTGCAGAGAAGGCGAAGGAGACTGCTAATatcgat.

Preparation of Target

In vitro RNA Preparation from Splice Variant Vectors

In vitro RNA from the splice variants were made using the MEGAscript™ high yield transcription kit according to the manufacturer's instructions (Ambion, USA). The yield of IVT RNA was quantified at a Nanodrop spectrophotometer (Nanodrop Technologies, USA).

Isolation of Total RNA from *C. elegans*

*C. elegans* wild-type strain (Bristol-N2) was maintained on nematode growth medium (NG) plates seeded with *Escherichia coli* strain OP50 at 20° C., and the mixed stages of the nematode were prepared as described in Hope, I. A. (ed.) "*C. elegans*—A Practical Approach", Oxford University Press 1999. The samples were immediately flash frozen in liquid $N_2$ and stored at −80° C. until RNA isolation.

A 100 µl aliquot of packed *C. elegans* worms from a mixed stage population was homogenized using the Fast-Prep Bio101 from Kern-En-Tec for 1 minute, speed 6 followed by isolation of total RNA from the extracts using the FastPrep Bio101 kit (Kem-En-Tec) according to the manufacturer's instructions. The eluted total RNA was ethanol precipitated for 24 hours at −20° C. by addition of 2.5 volumes of 96% EtOH and 0.1 volume of 3M Na-acetate, pH 5.2 (Ambion, USA), followed by centrifugation of the total RNA sample for 30 minutes at 13200 rpm. The total RNA pellet was air-dried and redissolved in 10 µl of diethylpyrocarbonate (DEPC)-treated water (Ambion, USA) and stored at −80° C.

Fluorochrome-Labelling of the Target

The following fluorochrome-labelled cDNA targets were synthesized to test the performance of 'merged' probes that span exon borders. Synthetic RNAs corresponding to the splice variant #1 (exon01-INS3-exon03 (1-INS3-3) and splice variant #2 (exon01-INS4-exon03 (1-INS3-3) were spiked into 10 µg of C. elegans reference total RNA sample in two different ratios. The first target pool (KU007) contained 10 ng of splice variant #1 (1-INS3-3) transcript and 2 ng of variant #2 (1-INS4-3) transcript, a ratio of 5:1. The second target pool (KU008) contained 2 ng variant #1 (1-INS3-3) transcript and 10 ng of splice variant #2 (1-INS4-3) transcript, a ratio of 1:5. Both mRNA pools were combined in separate labeling reactions with 5 µg anchored oligo(dT$_{20}$) primer and DEPC-treated water to a final volume of 8 µl. The mixture was heated at 70° C. for 10 minutes, quenched on ice for 5 minutes, followed by addition of 20 units of Superasin RNase inhibitor (Ambion, USA), 1 µl dNTP solution (10 mM each dATP, dGTP, dTTP and 0.4 mM dCTP, and 3 µl Cy5-dCTP, Amersham Biosciensces, USA), 4 µl 5× RTase buffer (Invitrogen), 2 µl 0.1 mM DTT (Invitrogen), 400 units of Superscript II reverse transcriptase (Invitrogen, USA) and DEPC-treated water to 20 µl final volume. Background hybridization to merged capture probes was monitored in both hybridizations using the other fuor channel with 10 µg of C. elegans reference RNA alone labeled with Cy3-dCTP, according to the labeling method described above for the splice variant spikes. All four cDNA syntheses were carried out at 42° C. for 2 hours, and the reaction was stopped by incubation at 70° C. for 5 minutes, followed by incubation on ice for 5 minutes.

Unincorporated dNTPs were removed by gel filtration using MicroSpin S-400 HR columns as described below. The column was pre-spun for 1 minute at 1500×g in a 1.5 ml tube, and the column was placed in a new 1.5 ml tube. The cDNA sample was slowly to the top center of the resin, spun 1500-×g for 2 minutes, and the eluate was collected. The RNA was hydrolyzed by adding 3 µl of 0.5 M NaOH, mixing, and incubating at 70° C. for 15 minutes. The samples were neutralized by adding 3 µl of 0.5 M HCl and mixing, followed by addition of 450 µl 1×TE, pH 7.5 to the neutralized sample and transfer onto a Microcon-30 concentrator (prior to use, 500 µl 1×TE was spun through the column to remove residual glycerol). The samples were centrifuged at 14000-×g in a microcentrifuge for 12 minutes. Spinning was continued until volume was reduced to 5 µl. The labelled cDNA probes were eluted by inverting the Microcon-30 tube and spinning at 1000-×g for 3 minutes.

Microarray Hybridization

The fluorochrome-labelled cDNA samples, respectively, were combined (the two different ratios separately). The following were added: 3.75 µl 20×SSC (3×SSC final, which was passed through a 0.22 µfilter prior to use to remove particulates) yeast tRNA (1 µg/µl final) 0.625 µl 1 M HEPES, pH 7.0 (25 mM final, which was passed through 0.22 µfilter prior to use to remove particulates) 0.75 µl 10% SDS (0.3% final) and DEPC-water to 25 µl final volume. The labelled cDNA target samples were filtered in Millipore 0.22 µfilter spin column (Ultrafree-MC, Millipore, USA) according to the manufacturer's instructions, followed by incubation of the reaction mixture at 100° C. for 2-5 minutes. The cDNA probes were cooled at room temp for 2-5 minutes by spinning at maximum speed in a microcentrifuge. A LifterSlip (Erie Scientific Company, USA) was carefully placed on top of the microarray spotted on Immobilizer™ MicroArray Slide, and the hybridization mixture was applied to the array from the side. An aliquot of 30 µL of 3×SSC was added to both ends of the hybridization chamber, and the Immobilizer™ MicroArray Slide was placed in the hybridization chamber (DieTech, USA). The chamber was sealed watertight and incubated at 65° C. for 16-18 hours submerged in a water bath. After hybridization, the slide was removed carefully from the hybridization chamber and washed using the following protocol. The slides were washed sequentially by plunging gently in 2×SSC/0.1% SDS at room temperature until the cover slip falls off into the washing solution, then in 1×SSC pH 7.0 (150 mM NaCl, 15 mM Sodium Citrate) at room temperature for 1 minute, then in 0.2×SSC, pH 7.0 (30 mM NaCl, 3 mM Sodium Citrate) at room temperature for 1 minute, and finally in 0.05×SSC (7.5 mM NaCl, 0.75 mM Sodium Citrate) for 5 seconds, followed by drying of the slides by spinning at 1000×g for 2 minutes. The slides were stored in a slide box in the dark until scanning.

Microarray Data Analysis

The splice variant microarray was scanned in a ScanArray 4000XL confocal laser scanner (Packard Instruments, USA). The hybridization data were analysed using the GenePix Pro 4.01 microarray analysis software (Axon, USA). Only the Cy5 (650 nm) data were examined as both hybridizations produced comparable, and acceptably low, signal from the C. elegans reference RNA alone (Cy3 channel).

Normalization

Data was normalized so that it could be compared between hybridizations. Both hybridizations contained the same amount of RNA from synthetic exons 01 and exons 03 (10+2 ng), so signal from the capture probes designed to internal regions of these exons is expected to be equal. The ratio of raw Cy5 signal between the two different labeled cDNA target pools, designated as KU007 and KU008 hybridizations, for each probe corresponding to either of these exons was calculated, that is for each probe i we calculated the ratio probeiKU007/probeiKU008). The average of all of these ratios was used as the normalization ratio.

Expectations of Normalized Data

To reflect the proportions of RNA spiked into the hybridization, the ratio of signal in hybridization KU007/KU008 should be 5 for probes designed to exon junctions of the INS3 splice variant #1 and 0.2 for probes corresponding to 1-INS4 splice variant #2. Data was log$_2$ transformed: log$_2$(5)=+2.32, log$_2$(0.2)=−2.32. The merged probe corresponding to the exon 01-exon 03 border desirably produces a consistently low value that is desirably independent of which transcript was more abundant, i.e., log$_2$(ratio)=0.

Array Results

Results are summarized in Table 15. 50-mer capture probes containing LNA in a block spanning exon-exon junctions were consistent in producing the expected ratios.

TABLE 15

LNA 50-mer block probes are most consistent in producing overall data closest to expected ratios.

| Capture probe | Expected ratio (log2) | Observed ratio (log2) with merged LNA block capture probes |
|---|---|---|
| gene78.m0103 | 0.00 | −0.24 |
| gene78.m01INS3 | 2.32 | 2.93 |
| gene78.m01INS4 | −2.32 | −2.39 |
| gene78.mINS303 | 2.32 | 3.11 |
| gene78.mINS403 | −2.32 | −0.86 |

EXAMPLE 10

Improved Signal-to-Noise Ratios Using LNA Oligonucleotide Capture Probes Combined with cDNA Target Fragmentation with the *E. coli* Uracil-DNA Glycosylase Capture Probe Design The capture probes were designed to a 602-nucleotide sequence in the 3'-region of the Yeast (*S. cerevisiae*) 70 kDa heat shock protein (SSA4) gene. The 602-base pair sequence is shown in Table 16. For the LNA-spiked oligonucleotide capture probes, every third DNA nucleotide was substituted with a LNA nucleotide. All capture probes are shown in Table 17.

TABLE 16

Six hundred and two (602) base pair sequence stretch of the *S. cerevisiae* ssa4 gene. Then underlined segments indicate the position of the capture probes. First underline is equal to capture probe YER103W-554, second underline is equal to capture probe YER103W-492 and so forth.

(SEQ ID NO: 438)
ggtgaaaggacaaggacaaaagacaacaatctactgggtaaatttgagttgagcggtattccacccgctccaagaggcgtaccac aaattgaagttacatttgatatcgatgcaaatggtattctgaacgtatctgccgttgaaaaaggtactggtaaatctaacaagat tacaattactaacgataagggaagattatcgaaggaagatatcgataaaatggttgctgaggcagaaaagttcaaggccgaagat gaacaagaagctcaacgtgttcaagctaagaatcagctagaatcgtacgcgtttactttgaaaaattctgtgagcgaaaataact tcaaggagaaggtgggtgaagaggatgccaggaaattggaagccgccgcccaagatgctataaattggttagatgcttcgcaagc ggcctccaccgaggaatacaaggaaaggcaaaaggaactagaaggtgttgcaaacccattatgagtaaattttacggagctgca ggtggtgccccaggagcaggcccagttccgggtgctggagcaggccccactggagcaccagacaacggcccaacggttgaagagg ttgattag

TABLE 17

| Capture probes for the SSA4 tile array. (SEQ ID NOs: 439-464, in sequential order) | |
|---|---|
| Oligo Name | Sequence |
| YER103W-1-DNA | gccccactggagcaccagacaacggcccaacggttgaagaggttgattag |
| YER103W-38-DNA | gccccaggagcaggcccagttccgggtgctggagcaggccccactggagc |
| YER103W-73-DNA | ccattatgagtaaattttacggagctgcaggtggtgccccaggagcaggc |
| YER103W-92-DNA | ctagaaggtgttgcaaacccattatgagtaaattttacggagctgcagg |
| YER103W-127-DNA | cctccaccgaggaatacaaggaaaggcaaaaggaactagaaggtgttgca |
| YER103W-200-DNA | ggtgaagaggatgccaggaaattggaagccgccgcccaagatgctataaa |
| YER103W-245-DNA | actttgaaaaattctgtgagcgaaaataacttcaaggagaaggtgggtga |
| YER103W-272-DNA | aagaatcagctagaatcgtacgcgtttactttgaaaaattctgtgagcga |
| YER103W-336-DNA | aatggttgctgaggcagaaaagttcaaggccgaagatgaacaagaagctc |
| YER103W-393-DNA | taacaagattacaattactaacgataagggaagattatcgaaggaagata |
| YER103W-447-DNA | cgatgcaaatggtattctgaacgtatctgccgttgaaaaaggtactggta |
| YER103W-492-DNA | acccgctccaagaggcgtaccacaaattgaagttacatttgatatcgatg |
| YER103W-554-DNA | ggtgaaaggacaaggacaaaagacaacaatctactgggtaaatttgagtt |

TABLE 17-continued

Capture probes for the SSA4 tile array. (SEQ ID NOs: 439-464, in sequential order)

| Oligo Name | Sequence |
|---|---|
| YER103W-1-LNA1 | GccmCcamCtgGagmCacmCagAcaAcgGccmCaamCggTtgAagAggTtgAttAg |
| YER103W-38-LNA1 | GccmCcaGgaGcaGgcmCcaGttmCcgGgtGctGgaGcaGgcmCccActGgaGc |
| YER103W-73-LNA1 | mCcaTtaTgaGtaAatTttAcgGagmCtgmCagGtgGtgmCccmCagGagmCagGc |
| YER103W-92-LNA1 | mCtaGaaGgtGttGcaAacmCccAttAtgAgtAaaTttTacGgaGctGcaGg |
| YER103W-127-LNA1 | mCctmCcamCcgAggAatAcaAggAaaGgcAaaAggAacTagAagGtgTtgmCa |
| YER103W-200-LNA1 | GgtGaaGagGatGccAggAaaTtgGaaGccGccGccmCaaGatGctAtaAa |
| YER103W-245-LNA1 | ActTtgAaaAatTctGtgAgcGaaAatAacTtcAagGagAagGtgGgtGa |
| YER103W-272-LNA1 | AagAatmCagmCtaGaaTcgTacGcgTttActTtgAaaAatTctGtgAgcGa |
| YER103W-336-LNA1 | AatGgtTgcTgaGgcAgaAaaGttmCaaGgcmCgaAgaTgaAcaAgaAgcTc |
| YER103W-393-LNA1 | TaamCaaGatTacAatTacTaamCgaTaaGggAagAttAtcGaaGgaAgaTa |
| YER103W-447-LNA1 | mCgaTgcAaaTggTatTctGaamCgtAtcTgcmCgtTgaAaaAggTacTggTa |
| YER103W-492-LNA1 | AccmCgcTccAagAggmCgtAccAcaAatTgaAgtTacAttTgaTatmCgaTg |
| YER103W-554-LNA1 | GgtGaaAggAcaAggAcaAaaGacAacAatmCtamCtgGgtAaaTttGagTt |
| Control capture probes | |
| YFL039C-50 | acaagaatacgacgaaagtggtccatctatcgttcaccacaagtgtttct (SEQ ID NO: 465) |
| YFL039C-50_LNA3 | AcaAgaAtamCgamCgaAagTggTccAtcTatmCgtTcamCcamCaaGtgTttmCt (SEQ ID NO: 466) |
| YDR146C-50 | Tgggaatggaacggggattatggtttcgccaatgaaaactaatcaaaggt (SEQ ID NO: 13) |
| YDR146C-50_LNA3 | TggGaaTggAacGggGatTatGgtTtcGccAatGaaAacTaaTcaAagGt (SEQ ID NO: 20) |

Printing and Coupling of the Yeast SSA4 Tile Microarrays

The SSA4 capture probes were synthesized with a 5' anthraquinone (AQ)-modification, followed by a hexaethyleneglycol-2 (HEG2) linker. The capture probes (Table 17) were first diluted to a 20 µM final concentration in 100 mM Na-phosphate buffer pH 7.0, and spotted on the Immobilizer microarray slides (Exiqon, Denmark) using the Biochip Arrayer One (Packard Biochip Technologies) with a spot volume of 2×300 pl and 400 µm between the spots. The capture probes were immobilized onto the microarray slide by UV irradiation in a Stratalinker with 2300 µjoules (Stratagene, USA). Non-immobilized capture probe oligonucleotides were removed from the slides by washing the slides two times 15 minutes in 1×SSC. After washing, the slides were dried by centrifugation at 1000×g for 2 minutes, and stored in a slide box until microarray hybridization.

Yeast Cultures

Saccharomyces cerevisiae wild-type (BY4741, MATa; his3Δ1; leu2Δ0; met15Δ0; ura3Δ0) and Δssa4 (MATa; his3Δ1; leu2Δ0; met15Δ0; ura3Δ0; YER103w::kanMX4) mutant strains (EUROSCARF) were grown in YPD at 30° C. until the $A_{600}$ density of the cultures reached 0.8. Half of the cultures were collected by centrifugation and resuspended in one volume of 40° C. preheated YPD. Incubation was continued for an additional 30 minutes at 30° C. or 40° C. for the standard and heat-shocked cultures, respectively. Cells were harvested by centrifugation and stored at −80° C.

RNA Extraction

Total RNA was extracted using the FastRNA Kit-RED (BIO 101) according to suppliers' instructions. The quantity and quality of the RNA preparations were examined by standard spectrophotometry on a NanoDrop ND-1000 (USA) and by gel electrophoresis. Only high quality RNA preparations were used for microarray analyses.

Fluorochrome-Labelling of the Target

A total of seven cDNA assay mixtures were produced; each with ten (10) µg total RNA from wt and combined with 5 µg anchored oligo(dT$_{20}$) primer and DEPC-treated water to a final volume of 8 µl. The mixtures were heated at 70° C. for 10 minutes, quenched on ice for 5 minutes, followed by addition of 20 units of Superasin RNase inhibitor (Ambion, USA), 3 µl Cy3-dCTP (Amersham Biosciences), 10 mM final concentration of dATP and dGTP, 4 µl 5×RTase buffer (Invitrogen), 2 µl 0.1 mM DTT (Invitrogen), 400 units of Superscript II reverse transcriptase (Invitrogen, USA), dUTP and dTTP accordingly to Table 18, and DEPC-treated water to 20 µl final volume. A parallel set-up was made with 10 µg total RNA from Δssa4 for target cDNA labelling with Cy5-dCTP. All cDNA syntheses were carried out at 42° C. for 2 hours, and the reaction was stopped by incubation at 70° C. for 5 minutes, followed by incubation on ice for 5 minutes. Each cDNA pool (except the unfragmented control pool) was incubated at 37° C. for 2 hours with 2 units of Uracil-DNA Glycosylase (UDG, New England Biolabs, USA) and by addition of 2.4 µl (1× final concentration in the reaction mixture) of UDG reaction buffer. The enzyme was heat-inactivated at 95° C. for 10 minutes. Unincorporated dNTPs were removed by gel filtration using MicroSpin S-400 HR columns as described in Example 9.

TABLE 18 dUTP and dTTP ratios in cDNA target labelling.

| Assay # | Final conc. dUTP | Final conc. dTTP |
|---|---|---|
| 1 | 0.5 | 0 |
| 2 | 0.25 | 0.25 |
| 3 | 0.125 | 0.375 |
| 4 | 0.05 | 0.45 |
| 5 | 0.025 | 0.475 |
| 6 | 0.0125 | 0.4875 |
| 7 | 0 | 0.5 |

Figure 29:
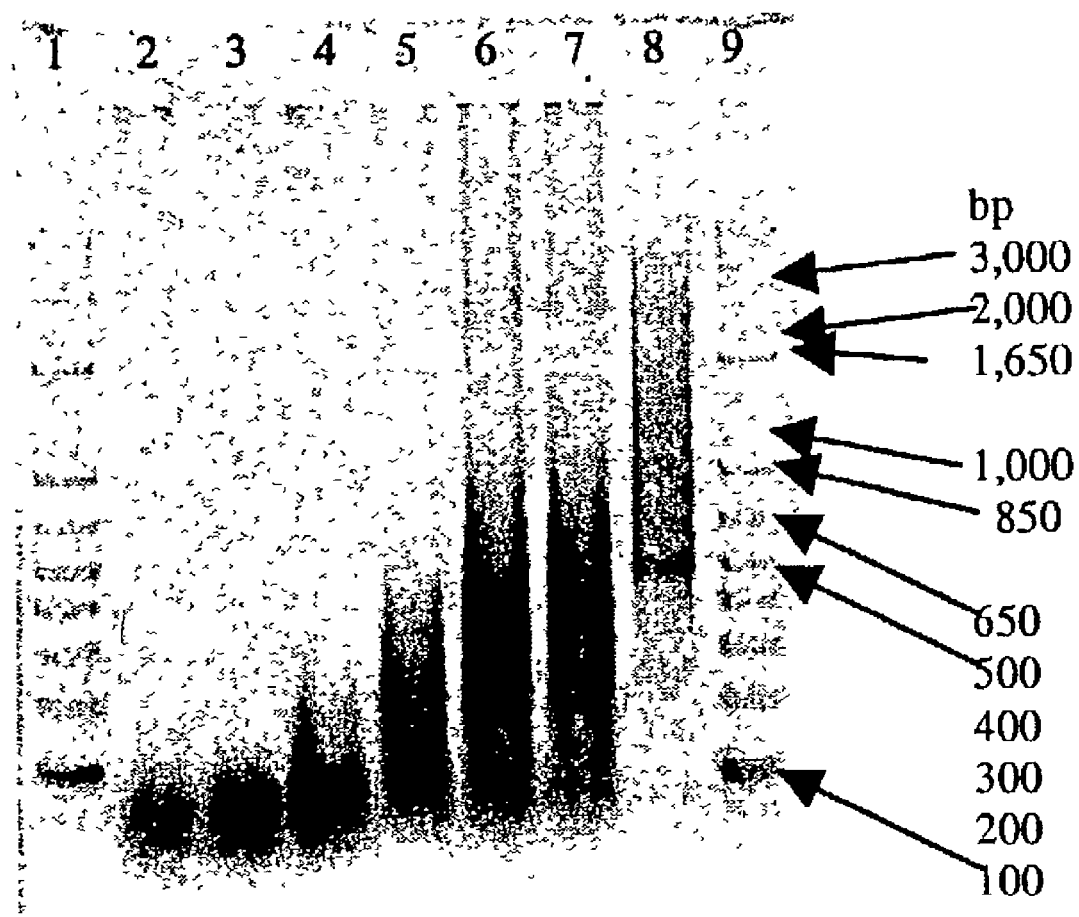
FIG. 29 is a picture showing gel electrophoresis of fragmented cDNA from the yeast wild-type strain. The molecular marker (lane 1 and 9) is from Life technologies, USA. Lanes 2-8 represents the UDG-fragmented cDNA 1-7 according to the different dUTP/dTTP ratios in Table 18.

Gel Electrophoresis of the cDNA Target Pools 0.5 µl of each of the seven fragmented cDNA pools were analysed on a 2% agarose-gel. The data show that the cDNA is fragmented linearly with respect to the concentration of dUTP used in the synthesis. FIG. 29 shows the gel electrophoresis of fragmented cDNA from the yeast wild-type strain.

Comparative Hybridization of the SSA4 Tile Array with Fluorochrome-Labelled Wild-Type and Δssa4 cDNA Target Pools and Post-Hybridization Washes The fluorochrome-labelled cDNA samples, respectively, were combined (the different UDG-fragmented samples separately). The following were added: 3.75 µl 20×SSC (3×SSC final, pass through 0.22 µfilter prior to use to remove particulates) yeast tRNA (1 µg/µl final) 0.625 µl 1 M HEPES, pH 7.0 (25 mM final, pass through 0.22 µfilter prior to use to remove particulates) 0.75 µl 10% SDS (0.3% final) and DEPC-water to 25 µl final volume. The labelled cDNA target samples were filtered in Millipore 0.22 µfilter spin column (Ultrafree-MC, Millipore, USA) according to the manufacturer's instructions, followed by incubation of the reaction mixture at 100° C. for 2-5 minutes. The cDNA probes were cooled at room temp for 2-5 minutes by spinning at maximum speed in a microcentrifuge. A Lifter-Slip (Erie Scientific Company, USA) was carefully placed on top of the SSA4 microarrays spotted on Immobilizer™ MicroArray Slide, and the hybridization mixture was applied to the array from the side. An aliquot of 30 µL of 3×SSC was added to both ends of the hybridization chamber, and the slide was placed in the hybridization chamber (DieTech, USA). The chamber was sealed watertight and incubated at 65° C. for 16-18 hours submerged in a water bath. After hybridization, the slide was removed carefully from the hybridization chamber and washed using the following protocol. The slides were washed sequentially by plunging gently in 2×SSC/0.1% SDS at room temperature until the cover slip falls of into the washing solution, then in 1×SSC pH 7.0 (150 mM NaCl, 15 mM Sodium Citrate) at room temperature for 1 minute, then in 0.2×SSC, pH 7.0 (30 mM NaCl, 3 mM Sodium Citrate) at room temperature for 1 minute, and finally in 0.05×SSC (7.5 mM NaCl, 0.75 mM Sodium Citrate) for 5 seconds, followed by drying of the slides by spinning at 1000×g for 2 minutes. The slides were stored in a slide box in the dark until scanning.

Microarray Data Analysis

The slides were scanned in a ScanArray 4000XL confocal laser scanner (Packard Instruments, USA). The hybridization data were analysed using the GenePix Pro 4.01 microarray analysis software (Axon, USA).

Figure 30:
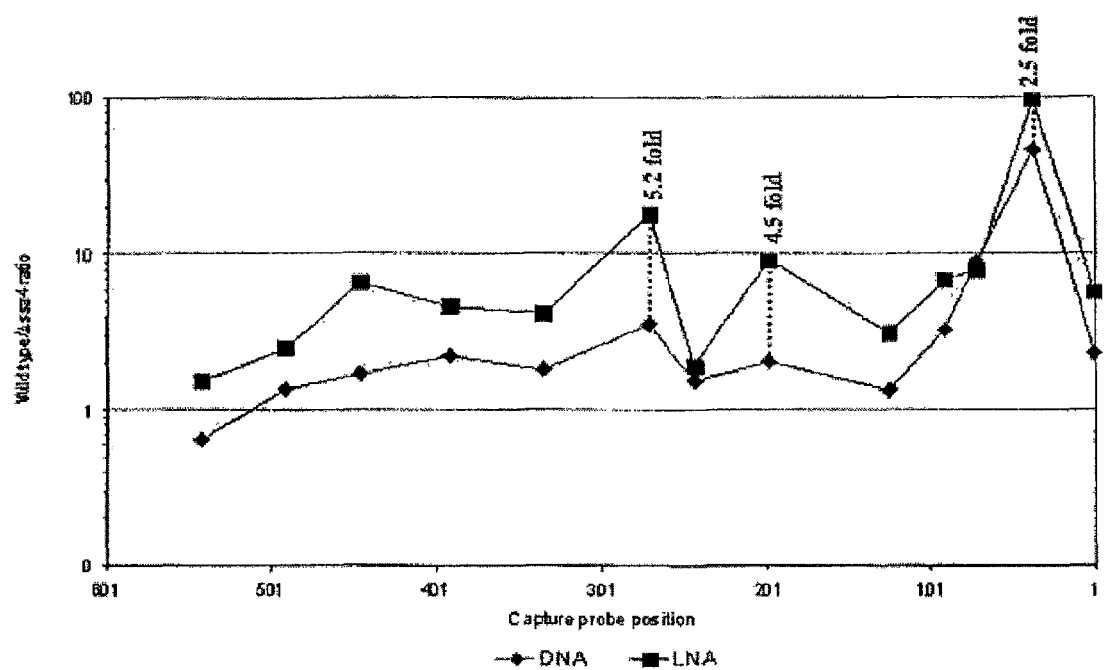
FIG. 30 is a graph of the log ratios of the normalized fluorescence intensities from the wild-type yeast strain (signal) and those from the Δssa4 yeast strain (noise) as a function of capture probe position in the 3' region of the SSA4 mRNA.

In the data analysis, the differences in labelling efficiency between the two fluorescent dyes were scaled by using an internal normalization approach. The average signal intensities from the control capture probes (Table 17) were used to calculate the normalization factor. This factor was multiplied to the signal intensity values from the Cy-3 target. Analysis of the data demonstrates that capture probes with LNA in every third position have up to 5.2 fold higher signal-to-noise ratios, compared to the DNA capture probes (FIG. 30).

EXAMPLE 11

Interpretation of Splice Array Data Using LNA Discriminating Probes

This example illustrates the interpretation of microarray analysis of alternative mRNA splicing. Different LNA capture probe design types are formalized, and the expression constant Ø is introduced as a measurement of alternative splicing.

Introduction

The eukaryotic pre-mRNA is the subject of Splicing and Alternative Splicing, hence sequences refer to RNA sequences, Original sequence refers to pre-mRNA, and splice forms refer to mRNA sequences. The splicing is conducted by a cellular machinery named the spliceosome. The terms exons and introns can be used to refer to regions of pre-RNA sequences (or more specifically a single splice form). It is noted that a part of the corresponding DNA/pre-mRNA sequence that is an exon (not excised) in one splice form can potentially be absent in another splice form (e.g., partly absent in exon truncation and completely absent in exon skipping). Thus, the terms "constant regions" and "variable regions" (see below) are useful for characterizing the process of identifying different splice forms.

Figure 31:
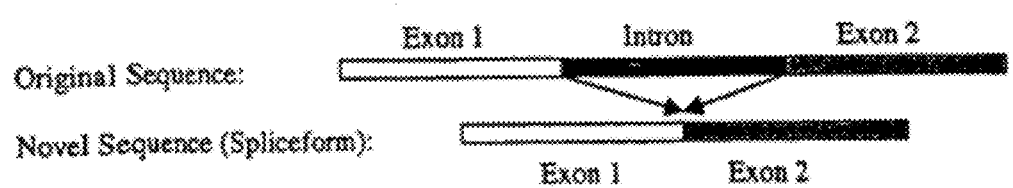
FIG. 31 is a schematic illustration of mRNA splicing.
Figure 32:
FIG. 32 is a schematic illustration of alternative mRNA splicing.

Splicing can be defined as the production of a new sequence via the excision of part(s) of an original sequence (FIG. 31). Alternative splicing can be defined as the production of more than one novel sequence via the excision of different parts of the original sequence. When comparing two different splice forms, they can be divided into a constant region that is shared by both sequences and a variable region by which the two splice forms differ (FIG. 32).

Alternative splicing can be categorized in terms of (i) whether or not the variable region is flanked by a single constant region or surrounded by two constant regions, (ii) the size of the variable region (e.g., exon skipping/intron retention vs. extension and truncation) [(intron/exon) 5' and 3'], and (iii) the number of variable regions (and hence the number of splice forms).

Capture Probe Design

Figure 33:
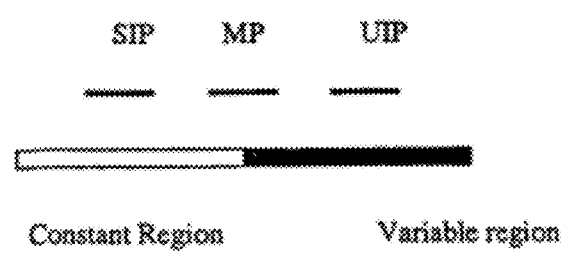
FIG. 33 is a schematic illustration of probes of the invention.
Figure 34:
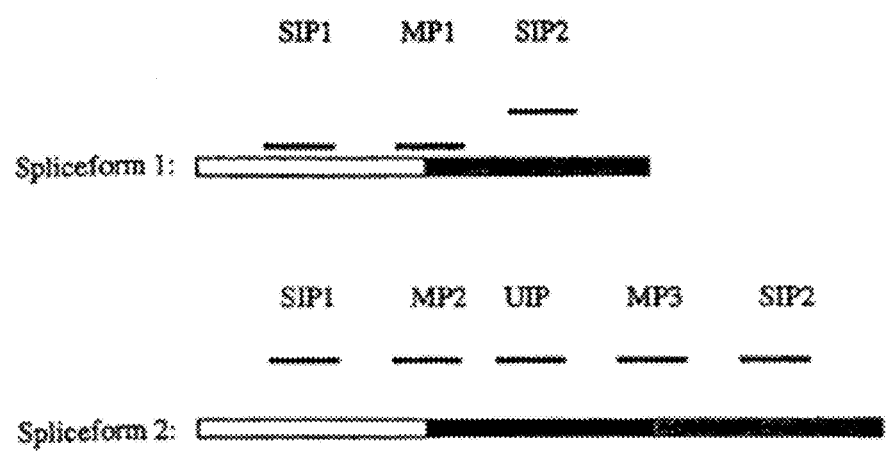
FIG. 34 is a schematic illustration of probes of the invention.

Capture Probe design can be divided into 3 distinct types according to their position: Merged Probes (MP) or Junction Probes, Unique Internal Probes (UIP), and Shared Internal Probes (SIP) (FIG. 33). Considering the case of a single variable region surrounded by constant regions, there are several different possible capture probe positions for each type (FIG. 34).

Data Interpretation

The aim of the analyses can be to determine (i) whether a given original sequence is subject to alternative splicing (i.e., whether there is more than one splice form present), and (ii) whether there is a difference in alternative splicing of the original sequence between two biological samples (i.e., whether the proportions between the two splice forms differ between biological samples). The analysis can also be used for data validation.

Possible biases in the microarray platform include (a) noise in terms of non-specific binding and subsequent false signal, (b) differences in dye labeling efficiency, (c) differences in capture probe affinity, (d) differences in sample conditions (e.g., number of cells, and amount of RNA), and (e) differences in reverse transcriptase efficiency of different splice forms. Biases can be corrected for by various means of normalization and/or standardization.

Data Analysis

In order to analyze the expression of the different splice forms, the expression constant Ø is introduced. Ø denotes the relation between the proportions of the signals (capture probes a and b) between the labeled extracts from biological samples (labeled with Cy5 & Cy3). That is, $$(Cy5a/Cy3a) = (Cy5b/Cy3b) * \emptyset \text{ or,}$$

$$\emptyset = (Cy5a/Cy3a)/(Cy5b/Cy3b)$$
$$= (Cy5a * Cy3b)/(Cy5b * Cy3a) \text{ and,}$$

$$\emptyset = (Cy5a/Cy5b)/(Cy3a/Cy3b)$$
$$= (Cy5a * Cy3b)/(Cy3a * Cy5b)$$
$$= (Cy5a * Cy3b)/(Cy5b * Cy3a) \text{ [same as above]}$$

Considering normalization due to different biases and given a sample normalization factor S due to differences between the samples in terms of amounts of RNA, RT-efficiency, dye properties, etc. and a probe normalization factor P due to differences in probes in terms of affinity, position in target sequence, etc., the following equations apply.

For two probes: a and b, a*P=b
For two samples Cy5 & Cy3, Cy5*S=Cy3,
Thus, considering two probes from two samples the signals are:
  Cy5a*P*S
  Cy5b*S
  Cy3a*P
  Cy3b
With respect to Ø:

$$\emptyset = (Cy5a * P * S)/(Cy3a * P)]/[(Cy5b * S)/(Cy3b)]$$
$$= (Cy5a * P * S * Cy3b)/(Cy3a * P * Cy5b * S)$$
$$= (Cy5a * Cy3b * P * S)/(Cy3a * Cy5b * P * S)$$
$$= (Cy5a * Cy3b)/(Cy3a * Cy5b) * (P * S)/(P * S)$$
$$= (Cy5a * Cy3b)/(Cy3a * Cy5b) * 1$$
$$= (Cy5a * Cy3b)/(Cy3a * Cy5b) \text{ [same as without normalization]}$$

Note that the calculation of Ø is not affected by the normalization factors S and P, hence it is not necessary to normalize the array data when interpreting alternative splice arrays with the use of the Expression constant Ø.

Properties of Ø

If Ø=1, there is no difference in the proportions of the targets of capture probes a and b in the two samples. Even in the case of alternative splicing, it is not possible to determine whether there is more than a single splice form present using this particular method. If Ø≠1, there is a difference in the proportions of the targets of capture probes a and b in the two samples, thus there is a difference in splice pattern and therefore there must be more than one splice form present.

Comparing Ø's

Ø can be compared between different transcripts to determine whether they have correlated expression, and Ø's from sets of capture probes from the same transcript (different probes) can be averaged.

Example

Considering a simple example of a single large variable region surrounded by constant regions using a combination of a Merged Probe and a Shared Internal Probe. Calculating Ø of a single splice form can be performed using the following equation:

$$\emptyset = (Cy5MP * Cy3SIP)/(Cy3MP * Cy5SIP)$$

If Ø=1, there is no difference in the proportions of the targets of capture probes a and b in the two samples, and it may not be possible to determine whether multiple splice forms are present using this particular method. If Ø≠1, there is a difference in the proportions of the targets of capture probes a and b, thus there is a difference in splice pattern and therefore there must be more than one splice form present.

Conclusions

It is possible to infer difference in expression level of two capture probe targets from two tissues when one is comparing the proportions of signals from one capture probe with the proportion of signals from the other probe. In contrast, single signals may be subject to biases from normalizations and standardizations for each probe and sample.

EXAMPLE 12

Exemplary Microarrays

The nucleic acid arrays of the invention can be generated by standard methods for either synthesis of nucleic acid probes that are then bonded to a solid support or synthesis of the nucleic acid probes on a solid support (e.g., by sequential addition of nucleotides to a reactive group on the solid support). In desirable methods for on-chip synthesis of the capture probes, photogenerated acids are produced in light-irradiate sites of the chip and used to deprotect the 5'-OH group of nucleic acid monomers and oligomers (e.g., to remove an acid-labile protecting group such as 5'-O-DMT) to which a nucleotide is to be added (Gao et al., Nucleic Acid Research 29:4744-4750, 2001). Standard methods can also be used to label the nucleic acids in a test sample with, e.g., a fluorescent label, incubate the labeled nucleic acid sample with the array, and remove any unbound or weakly bound test nucleic acids from the array. Exemplary methods are described, for example, in U.S. Pat. Nos. 6,410,229; 6,406,844; 6,403,957; 6,403,320; 6,403,317; 6,346,413; 6,344,316; 6,329,143; 6,310,189; 6,309,831; 6,309,823; 6,261,776; 6,239,273; 6,238,862; 6,156,501; 5,945,334; 5,919,523; 5,889,165; 5,885,837; 5,744,305; 5,445,934; 5,800,9927; and 5,874,219.

In an exemplary method for synthesis of an array, capture probes were immobilized using AQ technology with a HEG5 linker (U.S. Pat. No. 6,033,784) onto an Immobilizer™ slide. An exemplary chip consists of 288 spots in four replicates (i.e., 1152 spots) with a pitch of 250 µm, and an exemplary hybridization buffer is 5×SSCT (i.e., 750 mM NaCl, 75 mM Sodium Citrate, pH 7.2, 0.05% Tween) and 10 mM $MgCl_2$. An exemplary target is a 45-mer oligonucleotide with Cy5 at the 5' end and with a final concentration in the hybridization solution of 1 µM.

Hybridization was performed with 200 µL hybridization solution in a hybridization chamber created by attaching a CoverWell™ gasket to the Immobilizer slide. The incubation was conducted overnight at 4° C. After hybridization, the hybridization solution was removed, and the chamber was flushed with 3×1.0 mL hybridization buffer described above without any target nucleic acid. A coverWell™ chamber was then filled with 200 µL hybridization solution without target. The slide was observed with a Zeiss Axioplan 2 epifluorescence microscope with a 5×Fluar objective and a Cy5 filterset from OMEGA. The temperature of the microscope stage was controlled with a Peltier element. Thirty-five images at each temperature were acquired automatically with a Photometrics camera, automated shutter, and motorized microscope stage. The images were acquired, stitched together, calibrated and stored in stack by the software package "MetaVue"

Arrays can be generated using capture probes of any desired length (e.g., arrays of pentamers, hexamers, or heptamers.) In various embodiments, 1, 2, 3, 4, 5, 6, 7, 8, or more nucleotides of the probes are LNA nucleotides. Desirably, at least 1, 2, 3, 5, 7, 9, or all of the A and T nucleotides in the probes are LNA A and LNA T nucleotides. LNA nucleotides can be placed in any position of the capture probe, such as at the 5' terminus, between the 5' and 3' termini, or at the 3' terminus. LNA nucleotides may be consecutive or may be separated by one or more other nucleotides. The microarrays can be used to analyze target nucleic acids of any "AT" or "GC" content, and are especially useful for analyzing nucleic acids with high "AT" content because of the increased affinity of the microarrays of the present invention for such nucleic acids compared to traditional microarrays. Desirably, the array has at least 100, 200, 300, 400, 500, 600, 800, 1000, 2000, 5000, 8000, 10000, 15000, 20000, or more different probes. If desired, nucleotides with a universal base can be included in the capture probes to increase the $T_m$ of the capture probes (e.g., capture probes of less than 7, 6, 5, or 4 nucleotides). Exemplary "non-discriminatory" nucleotides include inosine, random nucleotides, 5 nitro-indole, LNA, inosine, and LNA 2-aminopurine. In desirable embodiments, 1, 2, 3, 4, 5, or more nucleotides with a universal base are located at the 5' and/or 3' termini of the capture probes.

EXAMPLE 13

Exemplary Application of Nucleic Acids of the Invention

An exemplary application of these methods includes comparing hybridization patterns of cDNA or cRNA from a patient sample to classify early-tumors or detect an infection or a diseased state. The microarrays of the invention may also be used as a general tool to analyze the PCR products generated by amplification of a test sample with PCR primers for one or more nucleic acids of interest. For example, PCR primers can be used to amplify nucleic acids with a particular exon or exon-exon combination, and then the PCR products can be identified and/or quantified using a microarray of the invention. For identification of splice variants, PCR primers to specific exons can be used to amplify nucleic acids that are then applied to a microarray for detection and/or quantification as described herein. To detect microbial pathogens, species-specific PCR primers (e.g., primers specific for an exon whose sequence differs among species) can be used to amplify nucleic acids in a sample for subsequent analysis using a microarray. For example, the hybridization pattern of the PCR products to the array can be used to distinguish between different bacteria, viruses, or yeast and even between different strains of the same pathogenic species. In particular embodiments, the array is used to determine whether a patient sample contains a bacteria strain that is known to be resistant or susceptible to particular antibiotics or contains a virus or yeast strain known to be resistant or susceptible to certain drugs. Changes in product composition or raw material origin can also be detected using a microarray. The arrays can also be used to determine the composition of mRNA cocktails.

Exemplary environmental microbiology applications of these arrays include identification of major rRNA types in contaminated soil samples and classification of microbial isolates. These rRNA amplificates are formed from rRNA by rtPCR or from the rDNA gene by conventional PCR. Numerous general and selective primers for different groups of organisms have been published. Most frequently an almost full length amplificate of the 16S rDNA gene is used (e.g., the primers 26F and 1492R). For purifying rRNA from a soil sample, standard methods such as one or more commercial extraction kits from companies such as QIA-GEN ("Rneasy", Q-biogene "RNA PLUS," or "Total RNA safe" can be used.

EXAMPLE 14

Methods for Minimizing the Variance in Melting Temperatures in Nucleic Acid Populations of the Invention Any simultaneous use of more than one primer or probe is made difficult because the involved primers or probes must work under the same conditions. An indication of whether or not two or more primers or probes will work under the same conditions is the relative $T_{ms}$ at which the hybridized oligonucleotides dissociate. In cases where probes are applied for specific detection of homologous sequences such as splice variants, the $\Delta T_m$ is of importance. $\Delta T_m$ expresses the difference between $T_m$ of the match and the $T_m$ of the mismatch hybridizations. Generally, the larger $\Delta T_m$ obtained, the more specific detection of the sequence of interest. In addition, a large $\Delta T_m$ facilitates more probes to be used simultaneously and in this way a higher degree of multiplexity can be applied.

High affinity nucleotide analogs such a LNA can be also be used universally to equalize the melting properties of oligonucleotides with different AT and CG content. The increased affinity of LNA adenosine and LNA thymidine corresponds approximately to the normal affinity of DNA guanine and DNA cytosine. An overall substitution of all DNA-A and DNA-T with LNA-A and LNA-T results in melting properties that are nearly sequence independent but only depend on the length of the oligonucleotide. This may be important for design of oligonucleotide probes used in large multiplex analysis. The effect of LNA A and T substitutions has been evaluated by predicting the Tm value of all possible 9-mer oligonucleotides with different universal substitutions. The distribution of the 262,000 $T_m$-values exhibits a very homogeneous $T_m$ value for universally LNA A and T substituted oligonucleotides. The standard deviation of the melting temperature for all 9-mers drops from 7.7° C. for pure DNA to only 2.2° C. for LNA A and T substituted oligonucleotides. This equalizing effect may also be utilized for photomediated on-chip synthesis of oligonucleotides.

It is often difficult to design probes and primers with the same range of melting temperature due to the variance in A/T and G/C content of the probing sites. Highly A/T rich regions typically give lower $T_m$ values. Furthermore, if single mismatches are to be resolved, G/T mismatches are known to contribute little to $\Delta T_m$. As discussed above, the use of LNA is a desirable way to solve problems related to multiplex use of primers and probes. LNA offers the possibility to adjust $T_m$ and increase the $\Delta T_m$ at the same time. LNA increases $T_m$ with 4-8° C./substitution and increases $\Delta T_m$ in many cases (Table 9).

TABLE 9

Demonstration of LNA controlled increase of $T_m$ and $\Delta T_m$.

| $T_m$ of LNA:DNA Duplexes | Perfect match 3'-ACGACCAC-5' | Single mismatch 3'-ACGGCCAC-5' | $\Delta T_m$ |
|---|---|---|---|
| LNA 8-mer 5'-TGC<u>T</u>GGTG-3' | 71° C. | 45° C. | 26° C. |
| DNA 8-mer 5'-TGC<u>T</u>GGTG-3' | 35° C. | 25° C. | 10° C. |

As LNA can be mixed with DNA during standard oligonucleotide synthesis, LNA can be placed at optimal positions in probes in order to adjust $T_m$. The specificity of PCR may also be enhanced by the use of LNA in primers, or probes, and this facilitates a higher degree of multiplexity. By incorporation of LNA, the $T_m$ of the primers or probes can be adjusted to work at the same temperature. Amplification or hybridization is more specific when LNA is included in primers or probes. This is due to the LNA increased $\Delta T_m$, which relates to higher specificity. Once $\Delta T_m$ of the primers or probes is high, more primers or probes can potentially be brought to work together.

Prediction of $T_m$

LNA can be used to enhance any experiment that is based on hybridization. The series of algorithms described herein have been developed to predict the optimal use of LNA. Melting properties of 129 different LNA substituted capture probes hybridized described herein to their corresponding DNA targets were measured in solution using UV-spectrophotometry. The data set was divided into a training set with 90 oligonucleotides and a test set with 39 oligonucleotides. The training set was used for training of both linear regression models and neural networks. Neural networks trained with nearest neighbour information, length, and DNA/LNA neighbour effect are efficient for prediction of $T_m$ with the given set of data.

Applications of the Normalization of Thermal Stability by LNA A and T Nucleotide Substitutions All assays in which DNA/RNA hybridization is conducted may benefit from the use of LNA in terms of increased specificity and quality. Exemplary uses include sequencing, primer extension assays, PCR amplification, such as multiplex PCR, allele specific PR amplification, molecular beacons, (e.g., nucleic acids be multiplexed with one colour based on multiple $T_m$'s), Taq-man probes, in situ hybridization probes (e.g., chromosomal and bacterial 16S rRNA probes), capture probes to the mRNA poly-A tail, capture probes for microarray detection of SNPs, capture probes for expression microarrays (sensitivity increased 5-8 times), and capture probes for assessment of alternative mRNA splicing.

EXAMPLE 15

Exemplary Methods for the Prediction of Melting Temperatures for Nucleic Acid Populations of the Invention LNA units have different melting properties than DNA and RNA nucleotides. Until recently, thermodynamical models for melting temperature prediction have existed for DNA and RNA only, but not for LNA. Now a $T_m$ prediction model for LNA/DNA mixed oligonucleotides has been developed (John SantaLucia, Jr. (1998) Proc. Natl. Acad. Sci. 95 1460-1465 and Tøstesen et al. "Prediction of Melting Temperature for LNA (Locked Nucleic Acid) Modified Oligonucleotides" Bioinformatics 2002, Bergen, Norway Apr. 4-7 2002). The $T_m$ prediction tool is available on-line at the Exiqon website (www.LNA-Tm.com and http://www.exiqon.com/Poster/Tmpred-ET-view.pdf).

Numerous applications in molecular biology are based on the ability of DNA and RNA to hybridize in a temperature dependent manner (e.g. the microarray techniques, PCR reactions and blotting techniques). The melting properties of nucleic acid duplexes, in particular the melting temperature $T_m$, are crucial for optimal design of such experiments. $T_m$ is usually computed using a two-state thermodynamical model (Breslauer, Meth. Enzymol., 259:221-242, 1995). Several different groups have estimated model parameters for nearest neighbors in the sequence based on experimental data (for a review see SantaLucia, Proc. Natl. Acad. Sci., 95:1460-1465, 1998).

The model described herein predicts the $T_m$ of duplexes of mixed LNA/DNA oligonucleotides hybridized to their complementary DNA strands. DNA monomers are denoted with lowercase letters, and LNA monomers are denoted with uppercase letters, e.g., there are eight types of monomers in the mixed strand: a, c, g, t, A, C, G and T. The model is based on the formula (SantaLucia, 1998, supra; Allawi et al., Biochemistry 36:10581-10594, 1997).

$$T_m = \frac{\Delta H}{\Delta S + R \cdot \ln(C - C_m/2) + 0.368(L-1)\ln[\text{Na}^+]},$$

in which the salt concentration [Na+] enters as an entropic correction together with the oligonucleotide concentrations. R is the gas constant, C and $C_m$ are the concentrations of the two strands where $C \geq C_m$, and L is the length of the strands. For self-complementary sequences, $C-C_m/2$ is replaced by the total strand concentration $C_T$ and a symmetry correction of −1.4 cal/k·mol is added to $\Delta S$ (SantaLucia, 1998, supra).

The LNA model differs from SantaLucia's DNA model in the way the changes in enthalpy $\Delta H$ and entropy $\Delta S$ are calculated. As in SantaLucia's model, they depend on nearest neighbor sequence information and special contributions for the terminal base-pairs in the two ends of the duplex. However, with eight types of monomers (LNA and DNA) the increased number of nearest neighbor combinations requires more model parameters to be determined and hence more data.

Parameter Reduction

Usually $\Delta H$ and $\Delta S$ are calculated as a sum of contributions from all nearest neighbor pairs in the sequence. The inclusion of LNA doubles the number of monomer types and quadruples the number of possible nearest neighbor pairs. Parameter reduction strategies are used for matching the model complexity to limited data sets. A strategy for reducing model complexity is to sum ΔH from single base-pair contributions, which do not take the influence of adjacent nucleotides into account. However, nearest neighbor contributions are added as a correction term to the single base-pair contributions.

Another strategy is to use hierarchically reduced monomer alphabets. Here, similar monomers are identified with the same letter. A four-letter alphabet, {w,s,W,S}, defines classes according to binding strength: w={a,t}, s={c,g}, W={A,T} and S={C,G}. The smallest alphabet, {D,L}, simply identifies the monomer type: DNA or LNA. As an example, the sequence GcTAAcTt can be written as SsW-WWsWw or as LDLLLDLD.

The principle is to split ΔH and ΔS into contributions that depend on different levels of detail of the sequence. The fine levels of detail require many parameters to be determined, while the coarse levels need fewer parameters. The more detailed contributions can then be treated as minor corrections, thus effectively reducing the total number of model parameters.

Training

Model parameters were determined using data from melting experiments on hundreds of oligonucleotides. The oligonucleotides were random sequences with lengths between 8 and 20 and a percentage of LNA between 20 and 70. Melting curves were obtained using a Perkin-Elmer UV λ-40 spectrophotometer, but only the $T_m$ values were used for modeling. Model parameters were adjusted using a gradient descent algorithm that minimizes the error function $$E = \sum_{\substack{data \\ set}} \frac{1}{N}(T_m^{pred} - T_m^{exp})^2,$$

i.e., the distance between predicted and experimental $T_m$ values. Many different models were trained in this way and their performance was evaluated on test sets distinct from the training data. Seven reliable models were chosen and combined to form the committee model implemented at the Exiqon website (www.LNA-Tm.com.)

Machine Learning and Thermodynamics

The aim of this work has been to estimate $T_m$ values as accurately as possible. To this end, a machine learning approach has been adopted in which the prediction of the physical ΔH and ΔS quantities is less important. The parameters of this model may be inaccurate as thermodynamic quantities. First, the gradient descent algorithm produces a broad ensemble of models in which the ΔH and ΔS parameters can vary substantially, while maintaining an accuracy in the predicted $T_m$. Second, the thermodynamic meaning of ΔH and ΔS is based on a two-state assumption, which may not be realistic in every case. Even short oligonucleotides can form different secondary structures or melt through multiple-state transitions (Tøstesen et al., J. Phys. Chem. B. 105:1618-1630, 2001). Third, the use of an optical instrument instead of a calorimetric instrument (DSC) introduces an error in the measured ΔH and ΔS. Nevertheless, the uncertain thermodynamic interpretation of the ΔH and ΔS model parameters does not imply that the $T_m$ prediction model is unreliable.

Results

The $T_m$ prediction model has been tested on two data sets that were not used during the training process. One set consisted of pure DNA oligonucleotides without LNA monomers and had a standard deviation of the residuals (SEP) of 1.57 degrees. The other set consisted of mixed oligonucleotides with both LNA and DNA and had a SEP of 5.25 degrees. The difference in prediction accuracy between the two types of oligonucleotides suggests that $T_m$ prediction of mixed strands is a more complex task than Tm prediction of pure DNA. This is possibly due to irregularities in the duplex helical structure induced by the LNA monomers (Nielsen et al., Bioconjug. Chem. 11:228-238, 2000). The obtained prediction accuracy is in both cases adequate for most biological applications. In conclusion, the reduced nearest neighbor model implemented at the Exiqon website can predict $T_m$ surprisingly well for both types of oligonucleotides. This indicates that the parameter reduction strategy is applicable for other types of modified oligonucleotides.

EXAMPLE 16A

Algorithm to Optimize the Substitution Pattern of Nucleic Acids of the Invention High affinity nucleotides such as LNA and other nucleotides that are conformationally restricted to prefer the C3'-endo conformation or nucleotides with a modified backbone and/or nucleobase stabilize a double helix configuration. As these effects are generally additive, the most stable duplex between a high affinity capture oligonucleotide and an unmodified target oligonucleotide should generally arise when all nucleotides in the capture probe or primer are replaced by their high affinity analogue. The most stable duplex should thus be formed between a fully modified LNA capture probe and the corresponding DNA/RNA target molecule. Such a fully modified capture probe should be more efficient in capturing target molecules, and the resulting duplex is more thermally stable.

However, many high affinity nucleotides (e.g., as LNA) have an even higher affinity for other high affinity nucleotides (e.g., as LNA) than for DNA/RNA. A fully modified capture probe may thus form duplexes with itself, or if it is long enough, internal hairpins that are even more stable than duplexes with the desired target molecule. Probes with even a small inverse repeat segment where all constituent positions are substituted with high affinity nucleotides may bind to itself and be unable to bind the target. Thus, a sequence dependent substitution pattern is desirably used to avoid substitutions in positions that may form self-complementary base-pairs.

For example, a computer algorithm can be used to automatically determine the optimal substitution pattern for any given capture probe sequence according to the following two criteria. First, the difference between the stability of (i) the duplex formed between the capture probe and the target molecule and (ii) the best possible duplex between two capture probes should be above a certain threshold. If this is not possible, then the substitution pattern with the largest possible difference is chosen. Second, the capture probe should contain as many substitutions as possible in order to bind as much target as possible at any given temperature and to increase the thermal stability of the formed duplex. Alternatively, the second criterion is substituted with the following alternative criterion to obtain capture probes with similar thermal stability. The number and position of capture probe substitutions should be adjusted so that all the duplexes between capture probes and targets have a similar thermal stability (i.e., $T_m$ equalization).

For oligonucleotide capture probes such, incomplete matches between target and capture probe are likely to be a reproducible feature of the recorded biosignatures. For short probes, the second criterion for increasing thermal stability is more desirable that the alternative second criterion for $T_m$ equalization. For long capture probes and PCR primers, the second alternative criterion is desirably used since $T_m$ equalization is desirable for these probes and primers.

An exemplary algorithm works as follows. For each nucleotide sequence in an array of length n, all possible substitution patterns, i.e., $2^n$ different sequences are evaluated. Each evaluation consist of estimating the energetic stability of the duplex between the substituted capture sequence and a perfect match unmodified target ("target duplex") and the energetic stability of the most stable duplex that can be formed between two substituted capture probes themselves ("self duplex").

The energetic stability estimate for a duplex may be calculated, e.g., using a Smith-Waterman algorithm with the following scoring matrix.
Gap initiation penalty: −8
Gap continuation penalty: −50

|   | a  | c  | g  | t  | A  | C  | G  | T  |
|---|----|----|----|----|----|----|----|----|
| a | −2 |    |    |    |    |    |    |    |
| c | −2 | −2 |    |    |    |    |    |    |
| g | −2 | 3  | −2 |    |    |    |    |    |
| t | 2  | −2 | 1  | −2 |    |    |    |    |
| A | −3 | −3 | −3 | 4  | −3 |    |    |    |
| C | −3 | −3 | 6  | −3 | −3 | −3 |    |    |
| G | −3 | 6  | −3 | 2  | −3 | 9  | −3 |    |
| T | 4  | −3 | 2  | −3 | 6  | −3 | 3  | −3 |

This scoring matrix was partly based on the best parameter fit to a large (over 1000) number of melting curves of different DNA and LNA containing duplexes and partly by visual scoring of test capture probe efficiency. If desired, this scoring matrix may be optimized by optimizing the parameter fit as well as increasing or optimizing the dataset used to obtain these parameters.

As an example of these calculations, the heptamer sequence ATGCAGA in which each position can be either an LNA or a DNA nucleotide is used. The target duplex formed between a fully modified capture probes with this sequence and its unmodified target receive a score of 34 as illustrated below.

```
Capture sequence:  A-T-G-C-A-G-A
                   | | | | | | |
Target sequence:   t-a-c-g-t-c-t
Score:             4+4+6+6+4+6+4 = 34
```

The most stable self duplex that can be formed between two modified capture probes has an almost equivalent energetic stability with a score of 30 as illustrated below.

```
Capture sequence:  A-T-G-C-A-G-A
                   |   | |   |
Target sequence:   A-G-A-C-G-T-A
Score:                +6+9+9+6    = 30
```

Thus, the capture probe efficiency of a fully modified probe is likely reduced by its propensity to form a stable duplex with itself. In contrast, by choosing a slightly different substitution pattern, ATGcaGA in which capital letters represent LNA nucleotides, the stability of the target duplex is reduced slightly from 34 to 29.

```
Capture sequence:  A-T-G-c-a-G-A
                   | | | | | | |
Target sequence:   t-a-c-g-t-c-t
Score:             4+4+6+3+2+6+4 = 29
```

However, the most stable self complementary duplex that can be formed is reduced much more from 30 to 20, as illustrated below.

```
Capture sequence:  A-T-G-c-a-G-A
                   |     | |
Target sequence:   A-G-a-c-G-T-A
Score:                +4+6+6+4    = 20
```

The difference between the stability of the desired target duplex and the undesired self duplex can be further increased by using the capture sequence AtgcaGA where the target duplex has a score of 24.

```
Capture sequence:  A-t-g-c-a-G-A
                   | | | | | | |
Target sequence:   t-a-c-g-t-c-t
Score:             4+2+3+3+2+6+4 = 24
```

Whereas the score of the self duplex is only 10, as shown below.

```
Capture sequence:  A-t-g-c-a-G-A
                   |   |   |
Target sequence:   A-G-a-c-g-t-A
Score:                +2+3+3+2    = 10
```

The additional destabilization of the self duplex is generally not required if the difference in stability between the target duplex and self duplex is above a threshold of 25% of the target duplex stability, as illustrated below.

Discrimination for ATGCAGA=(34−30)/
 34=12%<threshold (25%)

Discrimination for ATGcaGA=(29−20)/
 29=31%≥threshold (25%)

Discrimination for ATGCAGA=(24−10)/
 24=58%≥threshold (25%)

Thus, ATCcaGA is the substitution pattern with the highest degree of substitution for which the stability of the target duplex is adequately more stable than the stability of the best self duplex (e.g., above 25%).

This algorithm can be used to determine desirable substitution patterns for any size capture probe or any given probe sequence. The following simple design rules may also be applied for probe design, especially for short probes. The best self alignment for the corresponding DNA capture probe in the sequence is determined using a simple Smith-Waterman scoring matrix of:

|   | a  | c  | g  | t  |
|---|----|----|----|----|
| a | −2 |    |    |    |
| c | −2 | −2 |    |    |
| g | −2 | 3  | −2 |    |
| t | 2  | −2 | 1  | −2 |

Additionally, all possible positions in the sequence are substituted, with the exception of desirably avoiding the substitution of both bases of a self-complementary base-pair. The most stable self duplex thus does not contain any LNA:LNA base-pairs but only LNA:DNA basepairs.

EXAMPLE 16B

Computer Code for a Preferred Software Program of the Invention

Exemplary programs are provided in the Computer Program Listing Appendix submitted on compact disc herewith. The oligod program (50287.007002_oligod.txt) takes a gene sequence as input and returns sequences for LNA spiked oligonucleotides. The dyp program (50287.007002_dyp.txt) is used by oligod to predict the secondary structure and self annealing properties of the oligonucleotides. The expression_array_param file (50287.007002_expression_array-_param.txt) contains parameters used by the oligod program. 50287.007002_tmprediction.txt contains code for a $T_m$ prediction program, and 50287.007002_tmthermodynamic.txt contains code for a $T_m$ thermodynamic model.

Exemplary Computer

Figure 35:
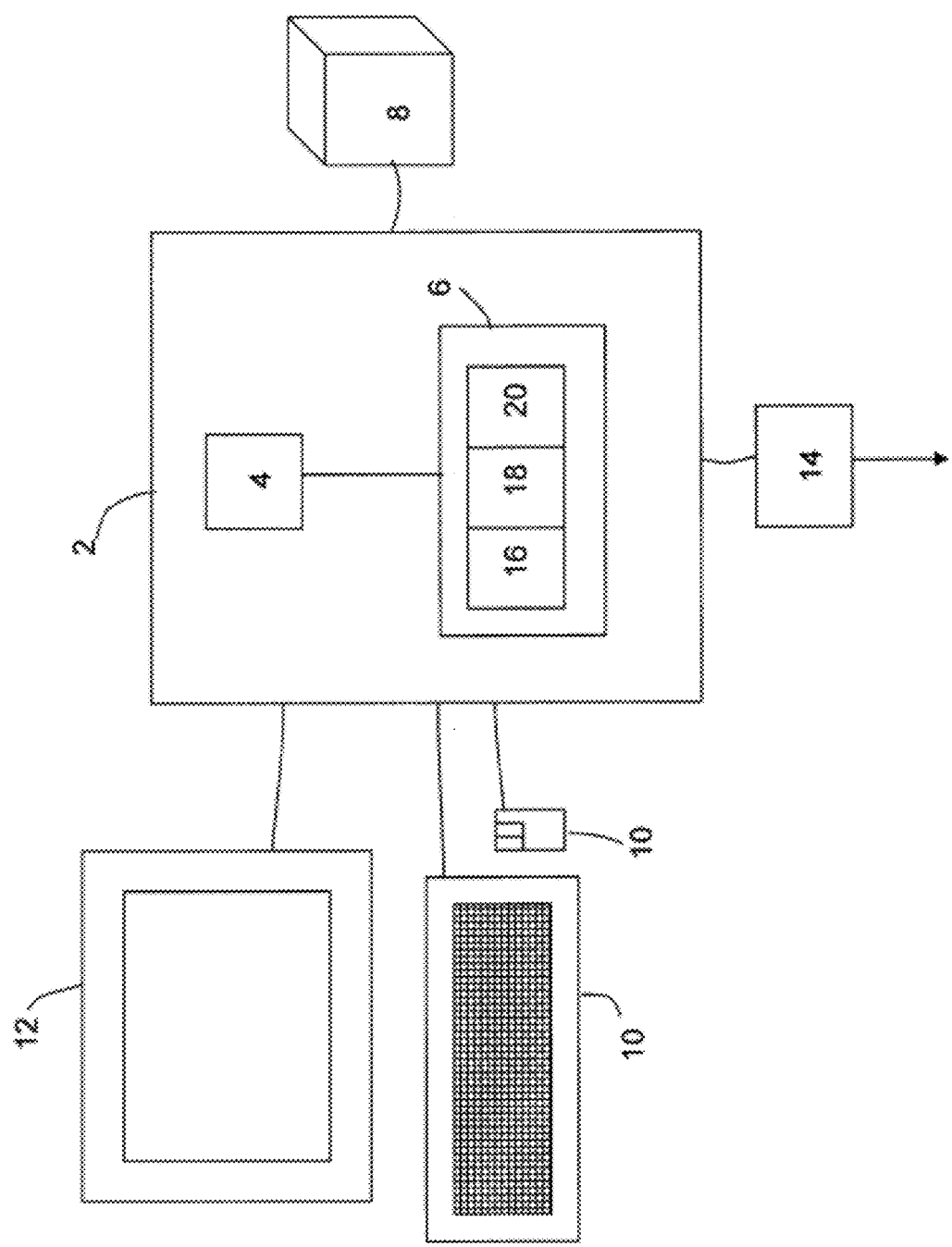
FIG. 35 illustrates an exemplary computer for use in the methods of the invention.

Any of the methods described herein may be implemented using virtually any computer. FIG. 35 shows such an exemplary computer system. Computer system 2 includes internal and external components. The internal components include a processor 4 coupled to a memory 6. The external components include a mass-storage device 8, e.g., a hard disk drive, user input devices 10, e.g., a keyboard and a mouse, a display 12, e.g., a monitor, and usually, a network link 14 capable of connecting the computer system to other computers to allow sharing of data and processing tasks. Programs are loaded into the memory 6 of this system 2 during operation. These programs include an operating system 16, e.g., Microsoft Windows, which manages the computer system, software 18 that encodes common languages and functions to assist programs that implement the methods of this invention, and software 20 that encodes the methods of the invention in a procedural language or symbolic package. Languages that can be used to program the methods include, without limitation, Visual C/C++ from Microsoft. In preferred applications, the methods of the invention are programmed in mathematical software packages that allow symbolic entry of equations and high-level specification of processing, including algorithms used in the execution of the programs, thereby freeing a user of the need to program procedurally individual equations or algorithms. An exemplary mathematical software package useful for this purpose is Matlab from Mathworks (Natick, Mass.). Using the Matlab software, one can also apply the Parallel Virtual Machine (PVM) module and Message Passing Interface (MPI), which supports processing on multiple processors. This implementation of PVM and MPI with the methods herein is accomplished using methods known in the art. Alternatively, the software or a portion thereof is encoded in dedicated circuitry by methods known in the art.

EXAMPLE 17

Exemplary Locked Nucleic Acids (LNA)

As disclosed in WO 99/14226, LNA are DNA analogues that form DNA- or RNA-heteroduplexes with exceptionally high thermal stability. LNA units include bicyclic compounds as shown immediately below where ENA refers to 2'O,4'C-ethylene-bridged nucleic acids:

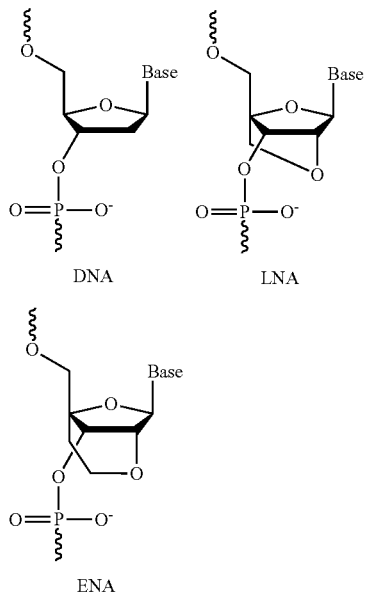

References herein to Locked Nucleoside Analogues, LNA units, LNA monomers, or similar terms are inclusive of such compounds as disclosed in WO 99/14226, WO 00/56746, WO 00/56748, and WO 00/66604.

Desirable LNA monomers and oligomers share some chemical properties of DNA and RNA; they are water soluble, can be separated by agarose gel electrophoresis, and can be ethanol precipitated.

Desirable LNA monomers and oligonucleotide units include nucleoside units having a 2'-4' cyclic linkage, as described in the International Patent Application WO 99/14226 and WO 0056746, WO 0056748, and WO 0066604. Desirable LNA monomers structures are exemplified in the formulae Ia and Ib below. In formula Ia the configuration of the furanose is denoted D-β, and in formula Ib the configuration is denoted L-α. Configurations which are composed of mixtures of the two, e.g. D-β and L-α, are also included.

Ia

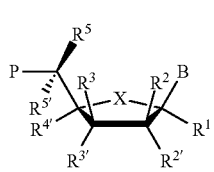

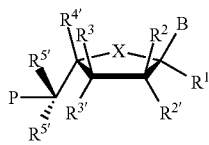

Ib

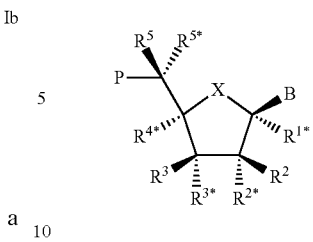

IIa

In Ia and Ib, X is oxygen, sulfur and carbon; B is a universal or modified base (particularly non-natural occurring base) e.g. pyrene and pyridyloxazole derivatives, pyrenyl, pyrenylmethylglycerol moieties, all of which may be optionally substituted. Other desirable universal bases include, pyrrole, diazole or triazole moieties, all of which may be optionally substituted, and other groups e.g. modified adenine, cytosine, 5-methylcytosine, isocytosine, pseudoisocytosine, guanine, thymine, uracil, 5-bromouracil, 5-propynyluracil, 5-propyny-6-fluoroluracil, 5-methylthiazoleuracil, 6-aminopurine, 2-aminopurine, inosine, diaminopurine, 7-propyne-7-deazaadenine, 7-propyne-7-deazaguanine. $R^1$, $R^2$ or $R^{2'}$, $R^3$ or $R^{3'}$, $R^5$ and $R^{5'}$ are hydrogen, methyl, ethyl, propyl, propynyl, aminoalkyl, methoxy, propoxy, methoxy-ethoxy, fluoro, or chloro.

P designates the radical position for an internucleoside linkage to a succeeding monomer, or a 5'-terminal group, $R^3$ or $R^{3'}$ is an internucleoside linkage to a preceding monomer, or a 3'-terminal group. The internucleotide linkage may be a phosphate, phosphorothioate, phosphorodithioate, phosphoramidate, phosphoroselenoate, phosphorodiselenoate, alkylphosphotriester, or methyl phosphonate. The internucleotide linkage may also contain non-phosphorous linkers, hydroxylamine derivatives (e.g. —$CH_2$—$NCH_3$—O—$CH_2$—), hydrazine derivatives, e.g. —$CH_2$—$NCH_3$—$NCH_3$—$CH_2$—, amid derivatives, e.g. —$CH_2$—CO—NH—$CH_2$—NH—CO—$CH_2$—. In Ia, $R^{4'}$ and $R^{2'}$ together designate —$CH_2$—O—, —$CH_2$—S—, —$CH_2$—NH—, —$CH_2$—NMe-, —$CH_2$—$CH_2$—O—, —$CH_2$—$CH_2$—S—, —$CH_2$—$CH_2$—NH—, or —$CH_2$—$CH_2$—NMe- where the oxygen, sulfur or nitrogen, respectively, is attached to the 2'-position. In Formula Ib, $R^{4'}$ and $R^2$ together designate —$CH_2$—O—, —$CH_2$—S—, —$CH_2$—NH—, —$CH_2$—NMe-, —$CH_2$—$CH_2$—O—, —$CH_2$—$CH_2$—S—, —$CH_2$—$CH_2$—NH—,or —$CH_2$—$CH_2$—NMe- where the oxygen, sulphur or nitrogen, respectively, is attached to the 2-position ($R^2$ configuration).

Desirable LNA monomer structures are structures in which X is oxygen (Formula Ia and Ib); B is a universal base such as pyrene; $R^1$, $R^2$ or $R^{2'}$, $R^3$ or $R^{3'}$, $R^5$ and $R^{5'}$ are hydrogen; P is a phosphate, phosphorothioate, phosphorodithioate, phosphoramidate, and methyl phosphornates; $R^3$ or $R^{3'}$ is an internucleoside linkage to a preceding monomer, or a 3'-terminal group. In Formula Ia, $R^{4'}$ and $R^{2'}$ together designate —$CH_2$—O—, —$CH_2$—S—, —$CH_2$—NH—, —$CH_2$—NMe-, —$CH_2$—$CH_2$—O—, —$CH_2$—$CH_2$—S—, —$CH_2$—$CH_2$—NH—,or —$CH_2$—$CH_2$—NMe- where the oxygen, sulphur or nitrogen, respectively, is attached to the 2'-position, and in Formula Ib, $R^{4'}$ and $R^2$ together designate —$CH_2$—O—, —$CH_2$—S—, —$CH_2$—NH—, —$CH_2$—NMe-, —$CH_2$—$CH_2$—O—, —$CH_2$—$CH_2$—S—, —$CH_2$—$CH_2$—NH—, or —$CH_2$—$CH_2$—NMe- where the oxygen, sulphur or nitrogen, respectively, is attached to the 2'-position in the $R^2$ configuration.

Particularly desirable LNA monomer for incorporation into an oligonucleotide of the invention include those of the following formula IIa wherein X oxygen, sulfur, nitrogen, substituted nitrogen, carbon and substituted carbon, and desirably is oxygen; B is a modified base as discussed above e.g. an optionally substituted carbocyclic aryl such as optionally substituted pyrene or optionally substituted pyrenylmethylglycerol, or an optionally substituted heteroalicylic or optionally substituted heteroaromatic such as optionally substituted pyridyloxazole. Other desirable universal bases include, pyrrole, diazole or triazole moieties, all of which may be optionally substituted; $R^{1*}$, $R^2$, $R^3$, $R^5$ and $R^{5*}$ are hydrogen; P designates the radical position for an internucleoside linkage to a succeeding monomer, or a 5'-terminal group, $R^{3*}$ is an internucleoside linkage to a preceding monomer, or a 3'-terminal group; and $R^{2*}$ and $R^{4*}$ together designate —O—$CH_2$— or —$CH_2$—$CH_2$—O— where the oxygen is attached in the 2'-position, or a linkage of —$(CH_2)_n$— where n is 2, 3 or 4, desirably 2, or a linkage of —S—$CH_2$— or —NH—$CH_2$—.

LNA units of formula IIa where $R^{2*}$ and $R^{4*}$ contain oxygen are sometimes referred to herein as "oxy-LNA"; units of formula IIa where $R^{2*}$ and $R^{4*}$ contain sulfur are sometimes referred to herein as "thio-LNA"; and units of formula IIa where $R^{2*}$ and $R^{4*}$ contain nitrogen are sometimes referred to herein as "amino-LNA". For many applications, oxy-LNA units are desirable modified nucleic acid units of oligonucleotides of the invention.

Particularly desirable LNA monomers for use in oligonucleotides of the invention are 2'-deoxyribonucleotides, ribonucleotides, and analogues thereof that are modified at the 2'-position in the ribose, such as 2"-O-methyl, 2'-fluoro, 2'-trifluoromethyl, 2'-O-(2-methoxyethyl), 2'-O-aminopropyl, 2'-O-dimethylamino-oxyethyl, 2'-O-fluoroethyl or 2"-O-propenyl, and analogues wherein the modification involves both the 2' and 3' position, desirably such analogues wherein the modifications links the 2'- and 3'-position in the ribose, such as those described in Nielsen et al., J. Chem. Soc., Perkin Trans. 1, 1997, 3423-33, and in WO 99/14226, and analogues wherein the modification involves both the 2'- and 4'-position, desirably such analogues wherein the modifications links the 2'- and 4'-position in the ribose, such as analogues having a —$CH_2$—S— or a —$CH_2$—NH— or a —$CH_2$—NMe- bridge (see Singh et al. J. Org. Chem. 1998, 6, 6078-9). Although LNA monomers having the β-D-ribo configuration are often the most applicable, other configurations also are suitable for purposes of the invention. Of particular use are α-L-ribo, the β-D-xylo and the α-L-xylo configurations (see Beier et al., Science, 1999, 283, 699 and Eschenmoser, Science, 1999, 284, 2118), in particular those having a 2'-4'-$CH_2$—S—, —$CH_2$—NH—, —$CH_2$—O— or —$CH_2$—NMe- bridge.

In another desirable embodiment, LNA modified oligonucleotides used in this invention comprises oligonucleotides containing at least one LNA monomeric unit of the general scheme A above, wherein X, B, P are defined as above. One of the substituents $R^2$, $R^{2*}$, $R^3$, and $R^{3*}$ is a group P* which designates an internucleoside linkage to a preceding monomer, or a 2'/3'-terminal group. Two of the substituents of $R^{1*}$, $R^2$, $R^{2*}$, $R^3$, $R^{4*}$, $R^5$, $R^{5*}$, $R^6$, $R^{6*}$, $R^7$, and $R^{7*}$ when taken together designate a biradical structure selected from $-(CR^*R^*)_r$-M-$(CR^*R^*)_s-$, $-(CR^*R^*)_r$-M-$(CR^*R^*)_s$-M-, -M-$(CR^*R^*)_{r+s}$-M-, -M-$(CR^*R^*)_r$-M-$(CR^*R^*)_s-$, $-(CR^*R^*)_{r+s}-$, -M-, -M-M-, wherein each M is independently selected from $-O-$, $-S-$, $-Si(R^*)_2-$, $-N(R^*)-$, $>C=O$, $-C(=O)-N(R^*)-$, and $-N(R^*)-C(=O)-$. Each $R^*$ and $R^{1(1*)}$-$R^{7(7*)}$, which are not involved in the biradical, are independently selected from hydrogen, halogen, azido, cyano, nitro, hydroxy, mercapto, amino, mono- or di($C_{1-6}$-alkyl)amino, optionally substituted $C_{1-6}$-alkoxy, optionally substituted $C_{1-6}$-alkyl, DNA intercalators, photochemically active groups, thermochemically active groups, chelating groups, reporter groups, and ligands, and/or two adjacent (non-geminal) $R^*$ may together designate a double bond, and each of r and s is 0-4 with the proviso that the sum r+s is 1-5.

Examples of LNA units are shown scheme B:

Scheme B

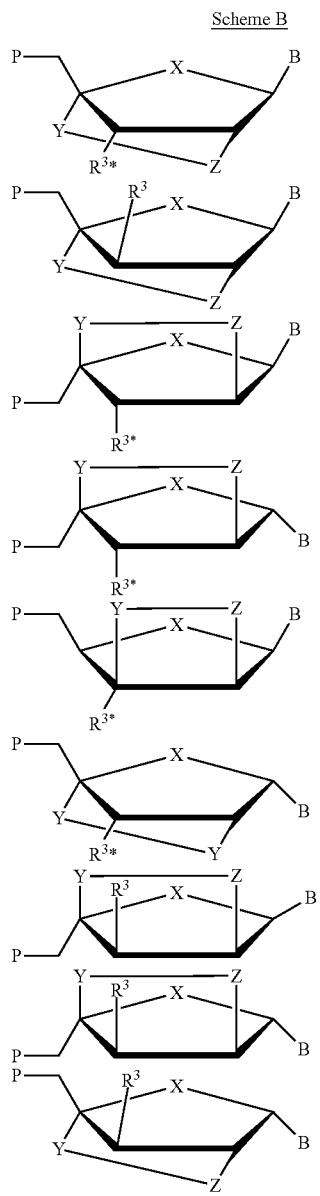

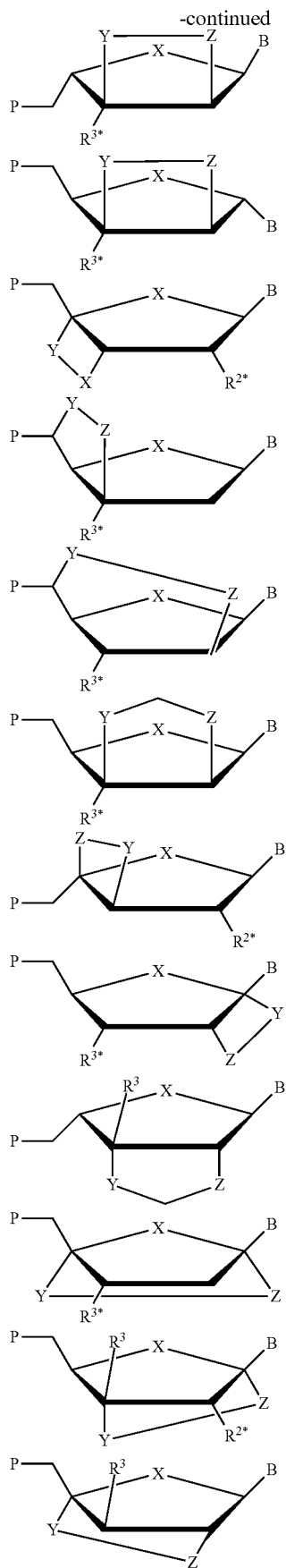

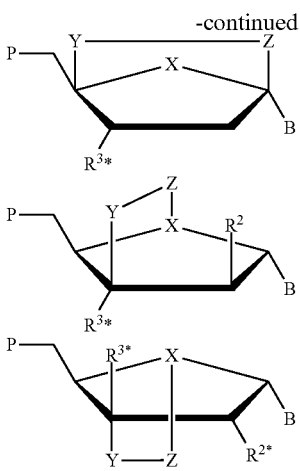

wherein the groups, X and B are defined as above. P designates the radical position for an internucleoside linkage to a succeeding monomer, nucleoside such as an L-nucleoside, or a 5'-terminal group, such internucleoside linkage or 5'-terminal group optionally including the substituent $R^5$. One of the substituents $R^2$, $R^{2*}$, $R^3$, and $R^{3*}$ is a group P* which designates an internucleoside linkage to a preceding monomer, or a 2'/3'-terminal group.

Desirable nucleosides are L-nucleosides such as for example, derived dinucleoside monophosphates. The nucleoside can be comprised of either a beta-D, a beta-L or an alpha-L nucleoside. Desirable nucleosides may be linked as dimers wherein at least one of the nucleosides is a beta-L or alpha-L. B may also designate the pyrimidine bases cytosine, 5-methyl-cytosine, thymine, uracil, or 5-fluorouridine (5-FUdR) other 5-halo compounds, or the purine bases, adenosine, guanosine or inosine.

Figure 1:
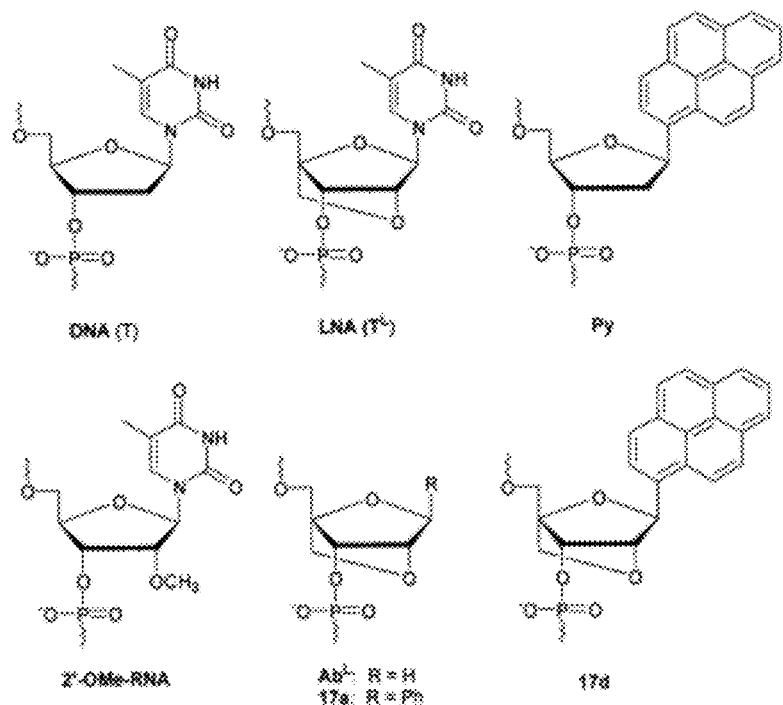
FIG. 1 shows the structures of selected nucleotide monomers: DNA (T), LNA ($T^L$), pyrene DNA (Py), 2'-OMe-RNA [2'-OMe(T)], abasic LNA ($Ab^L$), phenyl LNA (17a), and pyrenyl LNA (17d).

As discussed above, a variety of LNA units may be employed in the monomers and oligomers of the invention including bicyclic and tricyclic DNA or RNA having a 2'-4' or 2'-3' sugar linkages; 2'-O,4'-C-methylene-β-D-ribofuranosyl moiety, known to adopt a locked C3'-endo RNA-like furanose conformation. Illustrative modified structures that may be included in oligonucleotides of the invention are shown in FIG. 1. Other nucleic acid units that may be included in an oligonucleotide of the invention may comprise T-deoxy-2'-fluoro ribonucleotides; 2'-O-methyl ribonucleotides; 2'-O-methoxyethyl ribonucleotides; peptide nucleic acids; 5-propynyl pyrimidine ribonucleotides; 7-deazapurine ribonucleotides; 2,6-diaminopurine ribonucleotides; and 2-thio-pyrimidine ribonucleotides, and nucleotides with other sugar groups (e.g. xylose).

Oligonucleotides containing LNA are readily synthesized by standard phosphoramidite chemistry. The flexibility of the phosphoramidite synthesis approach further facilitates the easy production of LNA oligos carrying all types of standard linkers, fluorophores and reporter groups.

EXAMPLE 18

Selective Binding Complementary (SBC) Nucleotides

Selective Binding Complementary (SBC) nucleotides are unable to form stable hybrids with each other, yet are able to form stable, sequence-specific hybrids with complementary unmodified strands of nucleic acids. Thus, the reduced ability of SBC oligonucleotides to form intramolecular hydrogen bond base-pairs between regions of substantially complementary sequence causes a reduced level of secondary structure. Self-complementarity is an important issue in nucleic acid technologies as reported for DNA, PNA and LNA, and in different biological applications especially in the field of homogeneous assays. LNA:LNA duplexes are the most thermally stable nucleic acid type duplex system known, making the reduction of self-complementarity even more important.

Figure 3:
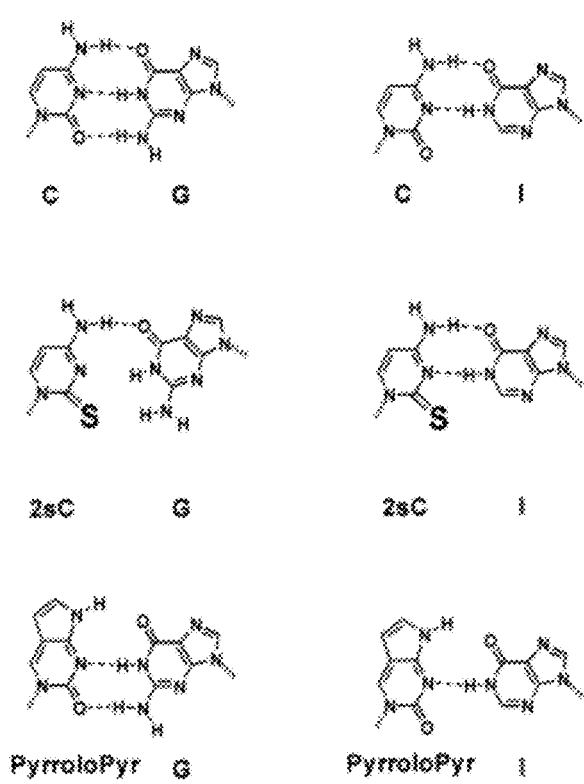
FIG. 3 shows the base-pairing between modified bases and naturally-occurring nucleotides. These modified bases may be incorporated as part of an LNA, DNA, or RNA unit and used any of the oligomers of the invention.

Exemplary SBC oligonucleotides contain 2-amino-A (D) and $^{2S}$T incorporated in the same oligonucleotide as replacements of A and T, respectively. The SBC name refers to the fact that D and $^{2S}$T form a destabilised base-pair compared to the A-T base-pair, but D-T and $^{2S}$T-A base-pairs are normally more stable than the original A-T base-pair. Exemplary SBC-G nucleotides include inosine or LNA-inosine, and exemplary SBC-C nucleotides include PyrroloPyr, LNA-PyrroloPyr, $^{2S}$C, and LNA-$^{2S}$C (FIG. 3). Other exemplary SBC nucleotides are shown in FIGS. 2 and 3. If desired, SBC nucleotides may be incorporated into the nucleic acids and arrays of the invention, using standard methods.

The systems disclosed herein can provide significant nucleic acid probes for universal hybridization. In particular, universal hybridization can be accomplished with a conformationally restricted monomer, including a desirable pyrene LNA monomer. Universal hybridization behavior also can be accomplished in an RNA context. Additionally, the binding affinity of probes for universal hybridization can be increased by the introduction of high affinity monomers without compromising the base-pairing selectivity of bases neighboring the universal base.

Incorporation of one or more modified nucleobases or nucleosidic bases into an oligonucleotide can provide significant advantages. Among other things, LNA oligonucleotides can often self-hybridize, rather than hybridize to another oligonucleotide. Use of one or more modified bases with the LNA units can modulate the propensity of the oligonucleotide to form double stranded structures with other oligonucleotides containing modified nucleobases including internal duplex formation, thereby inhibiting undesired self-hybridization.

EXAMPLE 19

Exemplary Methods for Synthesizing LNA-2-Thiopyrimidine Nucleosides and Nucleotides 2-Thiopyrimidine nucleosides can be prepared in several ways as described below. For example, the 2-thiouridine-nucleosides (IV) can be synthesized from a substituted uridine nucleoside (VIII) as described in the scheme below. By protection of the O4-position (IX) on the nucleobase thionation can be performed, O2 position, which results in the 2-thio-uridine nucleoside (IV). Performing sulphurisation on both O2 and O4 results in 2,4-dithio-uridine nucleoside (X) which may be transformed into the 2-thio-uridine nucleoside (IV) (Saladino et. al., Tetrahedron, 1996, 52, 6759). Another way is to generate a cyclic ether (XI) through reaction with the 5' position this product can then be transformed to the 2-thio-uridine nucleoside (IV) or the 2-O-alkyl-uridine nucleoside (XII). The 2-O-alkyl-uridine nucleoside (XII) can also be generated by direct alkylation of the uridine nucleoside (VIII). Treatment of the 2-O-alkyl-uridine nucleoside (XII) can also be transformed into the 2-thio-uridine nucleoside (Brown et. al., J. Chem. Soc. 1957, 868; Singer, et. al., Proc. Natl. Acad. Sci. USA, 1983, 80, 4884; Rajur and McLaughlin, Tetrahedron Lett., 1992, 33, 6081).

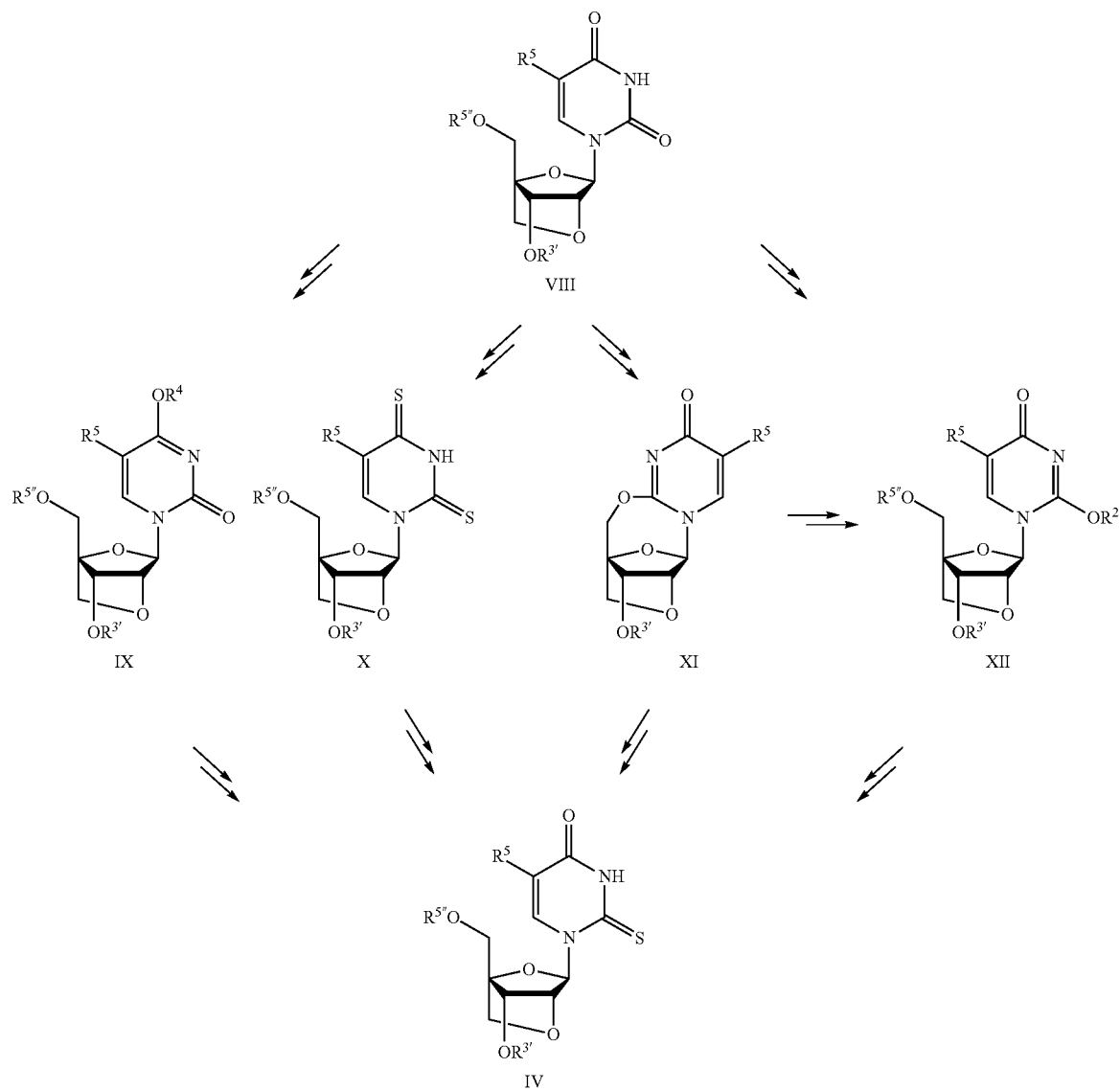

In another method, lewis acid-catalyzed condensation of a properly substituted sugar (I) and a substituted 2-thio-uracil (II) can result in a substituted 2-thio-uridine nucleoside of the structure (III) which by further synthetic manipulations can be transformed into the LNA 2-thiouridine nucleoside (IV) (Hamamura et. al., Moffatt, J. Med. Chem., 1972, 15, 1061; Bretner et. al., J. Med. Chem., 1993, 36, 3611).

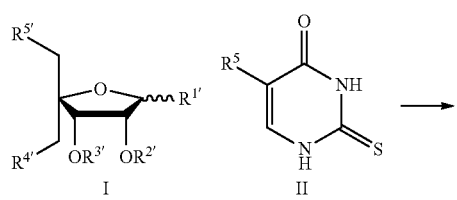

-continued

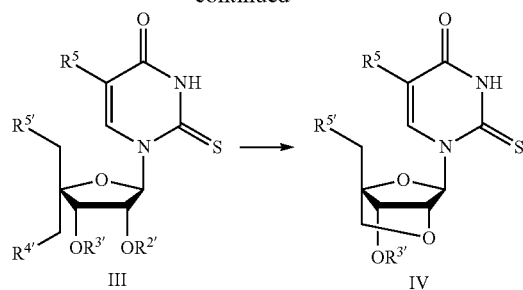

Using a properly substituted amino-sugar (V), a 2-thio-uridine nucleoside can be synthesized through ring-synthesis of the nucleobase by reaction of the amino sugar (V) and an substituted isothiocyanate (VI), yielding the substituted LNA 2-thio-uracil nucleoside (VI) (Shaw and Warrener, J. Chem. Soc. 1957, 153; Cusack et al., J. Chem. Soc. Perkin 1, 1973, 1721).

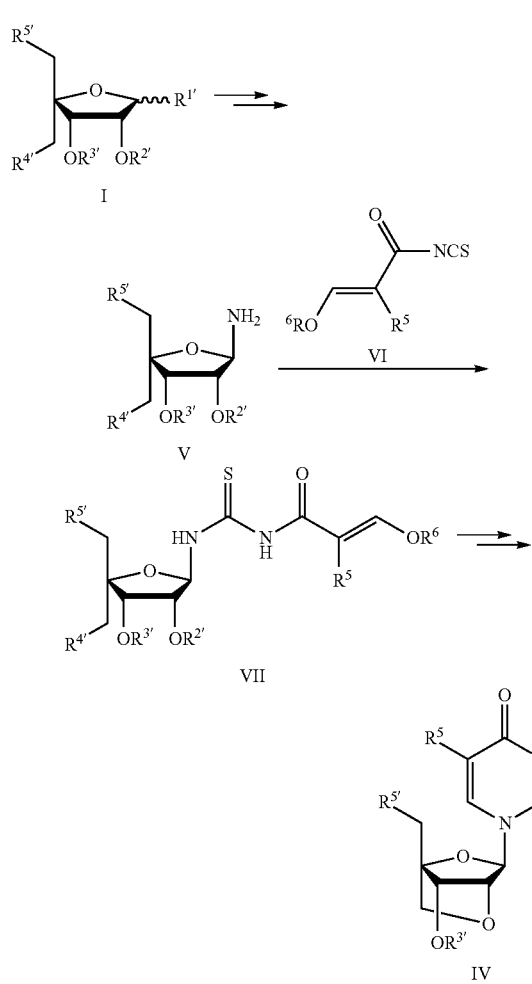

EXAMPLE 20

Exemplary Methods for Synthesizing $^{2s}$T-LNA

Three different strategies for synthesis of $^{2s}$T-LNA are outlined in the Summary of the Invention section. Strategy A involves coupling a glycosyl-donor and a nucleobase, using standard methodology for synthesis of existing LNA monomers. Strategy B involves ring synthesis of the nucleobase. This strategy is desirable because the availability of 1-amino-LNA enables introduction of a variety of new nucleobases. Strategy C includes modification of T-LNA; the easy synthesis of LNA-T diol makes this an attractive pathway.

In a desirable embodiment, $^{2s}$T-LNA is synthesized as illustrated in the scheme below.

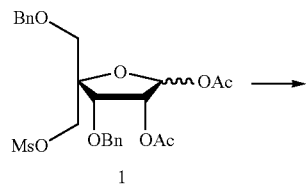

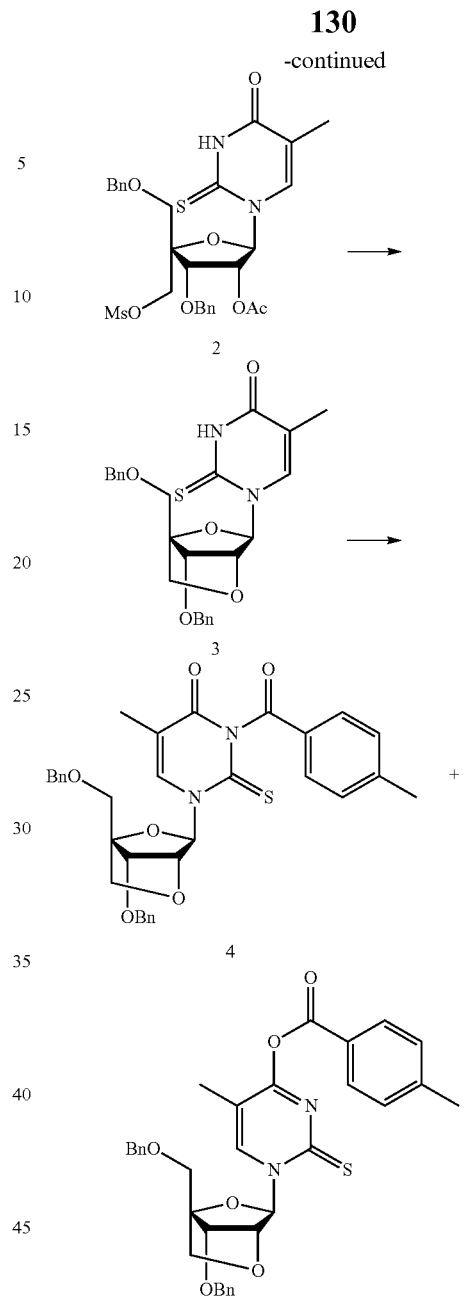

In particular, the known coupling sugar 1,2-di-O-acetyl-3,5 di-O-benzyl, 4-C-mesyloxymethyl, α,β-D-ribofuranose 1 was coupled with the nucleobase 2-thio-thymidine in a Vorbruggen type reaction. Thus, the nucleobase was silylated and condensed with the sugar using SnCl$_4$ as catalyst to promote the reaction affording nucleoside 2. Mass spectrometry and NMR subsequently identified the isolated product as the desired one. NMR data were compared with published data of a 2-thio-thymindine derivative (Kuimelis and Nambiar, Nucleic Acid Res., 1994, 22, 1429-1436) in order to validate the correct attachment point of the nucleobase.

Subsequently, a base mediated ring-closing reaction afforded the di-benzylated LNA derivative 3 in 77% yield. The signals in the $^1$H-NMR spectrum of the compound appeared as singlets, thus proving that the cyclization had occurred to give the LNA skeleton, in which the 1'-H and 2'-H are perpendicular to each other causing the $^3J_{1',2'}$ to be 0 Hz. MALDI mass spectrometry was likewise used for the identification of the compound.

The LNA derivative was protected at the nucleobase with the toluoyl protective group to give 4. This group is well known for the protection of 2-thio-thymidine derivatives, (Kuimelis and Nambiar, Nucleic Acid Res., 1994, 22, 1429-1436). The protection of the nucleobase occurs at both the N-3 and the O-4 position and hence the compound is isolated as a mixture of two compounds. NMR shows that the ratio of the two isomers in the isolated mixture is 2:1.

These methods are described further below.

1-(2-O-acetyl-3-O,5-O-dibenzyl,4-C-mesyloxymethyl-β-D-ribofuranosyl)-2-thio-thymine (2)

1,2-di-O-acetyl-3,5di-O-dibenzyl,4-C-mesyloxymethyl, α,β-D-ribofuranose (1, 2.0 g, 3.83 mmol) and 2-thio-thymine (552 mg, 3.89 mmol) were co-evaporated with anhydrous acetonitrile (100 ml) and redissolved in anhydrous acetonitrile (80 ml), N,O-bistrimethylsilylacetamide (1.5, 5.85 mmol) was added, and the reaction was stirred at 80° C. for one hour. The mixture was cooled to 0° C., SnCl$_4$ (0.9 ml, 7.66 mmol) was added, and the reaction was left to stir for 24 hours. The reaction mixture was diluted with EtOAc and washed with NaHCO$_3$ and subsequently with water. The organic phase was dried (Na$_2$SO$_4$) and evaporated to dryness. The product was purified using column chromatography, giving the thio-thymidine derivative 2 (1.1 g, 1.82 mmol, 40%) as a white foam. R$_f$ (10% THF/dichloromethane): 0.75.

MALDI-MS: 627 (M+Na) $^{13}$C-NMR (CDCl$_3$): δ=174.40, 169.29, 159.89, 136.13, 136.51, 136.05, 128.62, 128.56, 128.41, 128.29, 128.07, 127.89, 12767, 116.18, 91.41, 86.21, 75.59, 75.31, 74.46, 74.22, 73.61, 69.25, 69.04, 37.52, 20.62, 11.91

(1R,3R,4R,7S)-7-(benzyloxy)-1-(benzyloxymethyl)-3-(2-thiothymidine)-2,5-dioxabicyclo[2.2.1]heptane (3)

1-(2-O-acetyl-3-O,5-O-dibenzyl,4-C-mesyloxymethyl-β-D-ribofuranosyl)-2-thiothymine (2, 630 mg, 1.04 mmol) was dissolved in dioxane (15 ml) and water (8 ml), and aqueous NaOH (2M, 5 ml) was added, and the reaction was left to stir at room temperature for one hour. The yellow solution was neutralized with HCl (1 M, 6 ml) affording a precipitation. The mixture was diluted with dichloromethane and ethyl acetate causing an emulsion. After separation, the aqueous phase extracted with ethyl acetate, and the combined organic phase was dried (Na$_2$SO$_4$) and evaporated to dryness. The compound was purified by column chromatography (0-2, then 5% THF/dichloromethane), giving the ring closed compound 3 as a white foam (370 mg, 0.79 mmol, 77%). R$_f$ (2% MeOH/dichloromethane): 0.23.

MALDI-MS: 488 (M+Na) $^{13}$C-NMR (CDCl$_3$): δ=173.14, 160.39, 137.20, 136.63, 136.00, 128.46, 128.34, 128.02, 127.66, 115.52, 90.29, 87.77, 77.39, 75.26, 73.77, 72.07, 71.70, 64.15, 30.17, 12.33

$^1$H-NMR (CDCl$_3$): δ=9.87 (s, 1H), 7.69 (d, 1.1 Hz, 1H), 7.26-7.37 (m, 10H), 6.13 (s, 1H), 4.84 (s, 1H), 4.66 (d, J=11.3 Hz, 1H), 4.61 (s, 2H), 4.52 (d, J=11.5 Hz, 1H), 4.04 (d, J=7.7 Hz, 1H), 3.93 (s, 1H), 3.88 (d, J=11.0 Hz, 1H), 3.82 (d, J=7.7 Hz, 1H), 3.82 (d, J=10.8 Hz, 1H), 1.59 (d, J=1.1 Hz, 3H)

(1R,3R,4R,7S)-7-(benzyloxy)-1-(benzyloxymethyl)-3-(2-thio-N3/O4-toluoyl-thymidine)-2,5-dioxabicyclo[2.2.1]heptane (4)

(1R,3R,4R,7S)-7-(benzyloxy)-1-(benzyloxymethyl)-3-(2-thiothymidine)-2,5-dioxabicyclo[2.2.1]heptane (3, 290 mg, 0.62 mmol) was dissolved in anhydrous pyridine and diisopropylethylamine (0.2 ml, 1.15 mmol), toluoyl chloride (0.25 ml, 1.89 mmol) was added, and the reaction mixture was stirred at room temperature for three hours. After completion, the reaction mixture was diluted with dichloromethane, and the reaction was quenched by addition of water. The phases were separated, and the organic phase was dried (Na$_2$SO$_4$) and evaporate to dryness. The residue was co-evaporated with toluene. The product was purified by column chromatography (0-1% MeOH/dichloromethane) to give nucleoside 4 as a white foam (320 mg, 0.55 mmol, 89%). R$_f$ (2% MeOH/dichloromethane): 0.78.

MALDI-MS: 606 (M+Na) $^{13}$C-NMR (CDCl$_3$): δ=171.98, 168.30, 160.30, 145.92, 145.82, 137.22, 136.65, 135.98, 130.39, 130.27, 129.85, 129.50, 128.51, 128.41, 128.08, 127.73, 115.11, 90.10, 87.81, 76.01, 75.80, 75.39, 75.01, 73.83, 72.19, 72.09, 71.74, 64.15, 21.75, 12.40.

EXAMPLE 21

Exemplary Methods for Synthesizing LNA-I, LNA-D, and LNA-2AP

2'-O,4'-C-methylene linked (LNA) nucleosides containing hypoxanthine (or inosine) (LNA-I), 2,6-diaminopurine (LNA-D), and 2-aminopurine (LNA-2AP) nucleobases were efficiently prepared via convergent syntheses. The nucleosides were converted into phosphoramidite monomers and incorporated into LNA oligonucleotides using an automated phosphoramidite method. The complexing properties of oligonucleotides containing these LNA nucleosides were assessed against perfect and singly mismatch DNA.

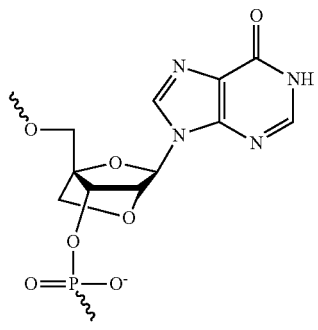

LNA-I

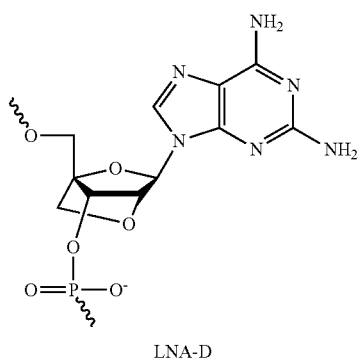

LNA-D

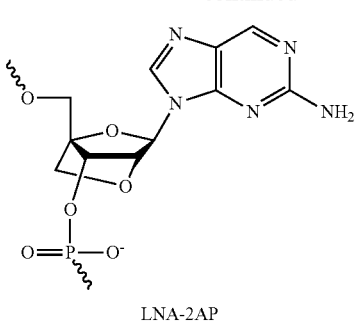

LNA-2AP

Hypoxantine, the base found in the nucleotides inosine and deoxyinosine, is considered as a guanine analogue in nucleic acids.

Oligonucleotides containing 2,6-diaminopurine replacements for adenines are expected to bind more strongly to their complementary sequences especially as part of A-type helixes due to the potential formation of three hydrogen bounds with thymine or uracil. The reported effect of 2,6-diaminopurine deoxyriboside (D) on the stability of polynucleotide duplexes reaches, on average, about 1.5° C. per modification. Higher stabilization effects for mismatches were observed for D nucleosides involved in formation of duplexes prone to form A-type helixes. LNA D and LNA 2'-OMe-D are expected to have increased stabilization and mismatch discrimination. LNA can be used in combination with 2-thio-T for construction of selectively binding complementary oligonucleotides. Taking into consideration the extremely high stability of LNA:LNA duplexes, this approach might be very useful for constructing of LNA containing capture probes and antisense reagents including drugs.

2-Aminopurine (2-AP) is a fluorescent nucleobase (emission at 363 nm), which is useful for probing nucleic acids structure and dynamics and for hybridizing with thymine in Watson-crick geometry. LNA-I, LNA-D, and/or LNA-2AP may be used in the nucleic acids of the present invention, e.g., to increase the priming efficiency of DNA oligonucleotides in PCR experiments and to construct selectively binding complementary agents.

Synthesis of LNA-I

The convergent method adopted for preparation of LNA monomers (Koshkin et al., J. Org. Chem. 66:8504, 2001) was successfully applied for syntheses of the modified LNA nucleotides 1-3. The synthetic route to LNA-I phosphoramidite 11 is depicted in the scheme below. The previously described 4-C-branched furanose 4 (Koshkin et al., supra) was used as a glycosyl donor in coupling reaction with silylated hypoxantine by the method of Vorbrüggen et al. (Vorbrüggen et al., Chem. Ber. 114:1234, 1981; Vorbrüggen et al., Chem. Ber. 114:1256, 1981; and Vorbrügen, Acta Biochim. Pol., 43:25, 1996). The reaction resulted in high yield formation of desired β-configurated nucleoside derivative 5. However, analogous to the coupling reaction of 4 with protected guanines, the formation of undesired N-7 isomer (ratio of N-9/N-7=4:1) was also detected. The mixture of the isomers was used for the ring closing reaction and protected LNA nucleoside 6 was isolated in 68% yield as a crystalline compound. The correct structure of the isolated isomer was confirmed later by chemical conversion of LNA-I into LNA-A nucleoside (vide infra). Deprotection of the 5'-hydroxy group of 6 was accomplished via two-step procedure developed for the syntheses of other LNA nucleosides (Koshkin et al., supra). First, 5'-O-mesyl group was displaced by sodium benzoate to produce nucleoside 7. The latter was converted into 5'-hydroxy derivative 8 after saponification of the 5'-benzoate. Direct removal of the 3'-O-benzyl group from compound 8 was unsuccessful under the conditions tested due to a solubility problem. Therefore, compound 8 was converted to DMT-protected nucleoside 9 prior to catalytic debenzylation of the 3'-β-hydroxy group. The phosphoramidite 11 was finally afforded via standard phosphitylation (McBride et al., Tetrahedron Lett. 24:245, 1983; Sinha et al., Tetrahedron Lett. 24:5843, 1983; and Sinha et al., Nucleic Acids Res. 12:4539, 1984) of the nucleoside 10. In order to verify the correct orientation of the glycoside bond (N-9 isomer) in synthesized LNA-I nucleoside, compound 7 was successfully converted into the known LNA-A derivative 13 (Koshkin et al., supra) (Scheme 2). Thus, a treatment of 7 with phosphoryl chloride according to the procedure reported by Martin (Helv. Chim. Acta 78:486, 1995) resulted in a high yield formation of 6-chloropurine derivative 12. The adenosine derivative 13 was derived from 12 after reaction with ammonia.

Exemplary Analytical Data

Data for compound 8 includes the following: mp 302-305° C. (dec). $^1$H NMR (DMSO-$d_6$): δ 8.16, (s, 1H), 8.06 (s, 1H), 7.30-7.20 (m, 5H), 5.95 (s, 1H), 4.69 (s, 1H), 4.63 (s, 2H), 4.28 (s, 1H), 3.95 (d, J=7.7, 1H), 3.83 (m, 3H). $^{13}$C NMR (DMSO-$d_6$): δ 156.6, 147.3, 146.1, 137.9, 137.3, 128.3, 127.6, 127.5, 124.5, 88.2, 85.4, 77.0, 72.1, 71.3, 56.7. MALDI-MS m/z: (M+H)$^+$. Anal. Calcd for $C_{18}H_{18}N_4O_5 \cdot 5/12H_2O$: C, 57.21; H, 5.02; N, 14.82. Found: C, 57.47; H, 4.95; N, 14.17.

Analysis of compound 11 indicated that $^{31}$P NMR (DMSO-$d_6$): δ 148.90.

Scheme for Synthesis of LNA-I$^a$

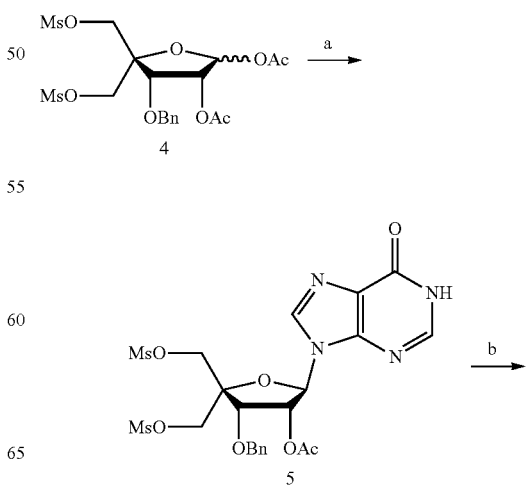

Scheme for Synthesis of LNA-G

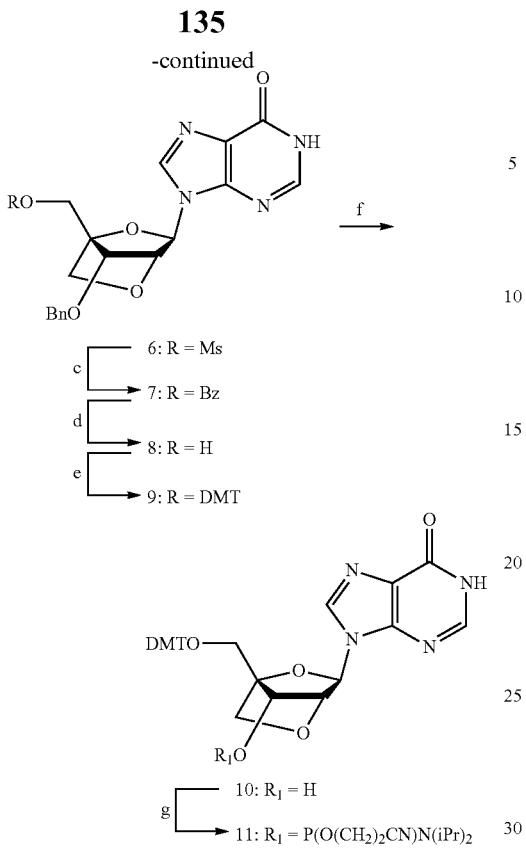

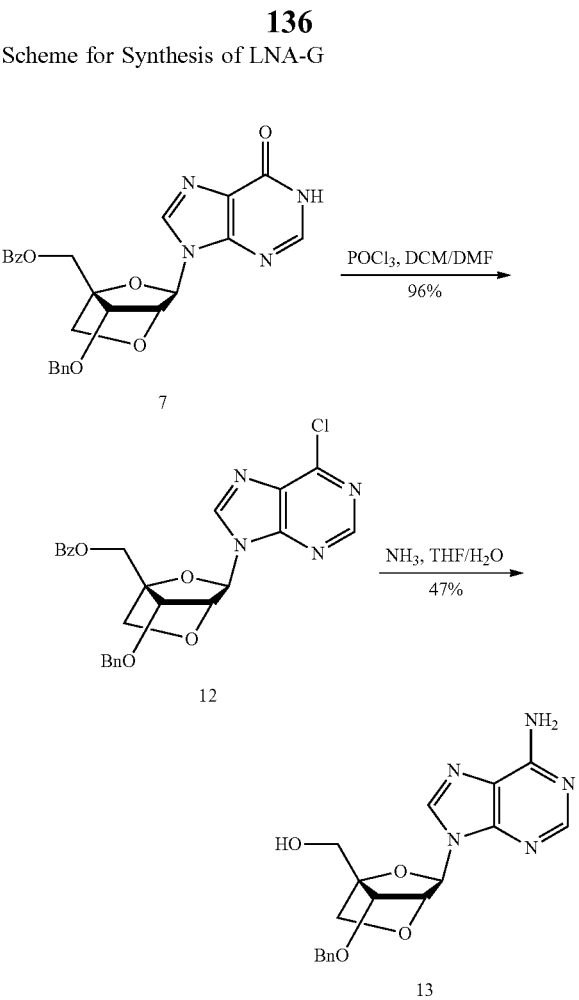

*a* Keys: (a) hypoxantine, BSA, TMSOTf, 1,2-dichloromethane; 93%; (b) NaOH, THF, EtOH, H$_2$O; 69%; (c) NaOBz, DMSO; 76%; (d) NaOH, THF, MeOH, H$_2$O; 85%; (e) DMT—Cl, pyridine; 92%; (f) Pd/C, HCO$_2$NH$_4$; 77%; (g) 2-cyanoethyl-N,N-diisopropyl-phosphoramidochloridite, DIPEA, DMF; 75%.

Exemplary Experimental Conditions (1R,3R,4R,7S)-7-(2-Cyanoethoxy(diisopropylamino)phosphinoxy)-1-(4,4'-dimethoxytrityloxymethyl)-3-(hyroxanthin-9-yl)-dioxabicyclo[2.2.1]heptane (11)

Compound 10 (530 mg, 0.90 mmol, described previously, (see for example, WO 00/56746) was dissolved in anhydrous EtOAc (5 mL) and cooled in an ice-bath. DIPEA (0.47 mL, 2.7 mmol) and (250 µL, 1.1 mmol) were added under intensive stirring. Formation of insoluble material was observed, and CH$_2$Cl$_2$ (3 mL) was added to produce a clear solution. More 2-cyanoethyl-N,N-diisopropylphosphoramidochloridite (200 µL, 0.88 mmol) was added after one hour, and the mixture was stirred overnight. EtOAc (30 mL) was added, the mixture was washed with sat. NaHCO$_3$ (2×50 mL), brine (50 mL), dried (Na$_2$SO$_4$), and concentrated to a solid residue. Purification by silica gel HPLC (1-5% MeOH/ CH$_2$Cl$_2$ v/v, containing 0.1% of pyridine) gave compound 11 (495 mg, 75%) as a white solid material. $^{31}$P NMR (DMSO-d$_6$): δ 148.90.

Synthesis of LNA-D

Taking advantage of a high availability of the natural deoxy- and riboguanosines, a number of effective methods were developed for their conversion into 2,6-diaminopurine (D) nucleosides (Fathi et al., Tetrahedron Lett. 31:319, 1990; Gryaznov et al., Tetrahedron Lett., 35:2489, 1994; and Lakshman et al., Org. Lett., 2:927, 2000). However, the production of LNA-G nucleoside is a multi-step synthetic procedure.

For the synthesis of LNA-D nucleoside, a novel synthesis method was developed that employed a common convergent scheme, related to the strategy used earlier for the synthesis of its anhydrohexitol counterpart (Boudou et al., Nucleic Acids Res. 27:1450, 1999). In particular, a properly protected carbohydrate unit was conjugated with 6-chloro-2-aminopurine to give a stable 6-chloro intermediate derivative (scheme below) which was further converted into desired diaminopurine nucleoside.

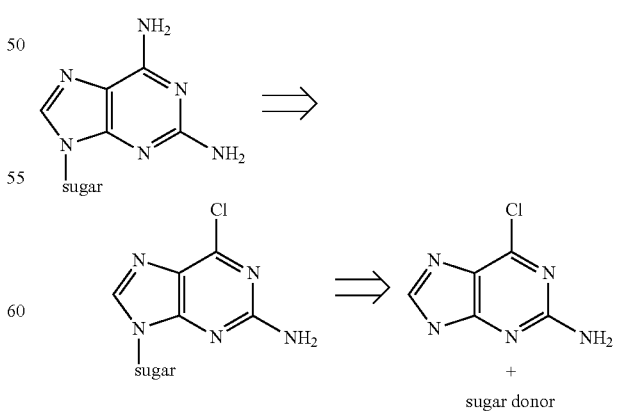

Thus, it was shown that glycosylation of 2-chloro-6-aminopurine with compound 4 resulted in highly stereoselective formation of the nucleoside derivative 14. To promote the ring closing reaction, a solution of 14 in aqueous 1,4-dioxane was treated with 10-fold excess of sodium

Synthesis of LNA-D[a]

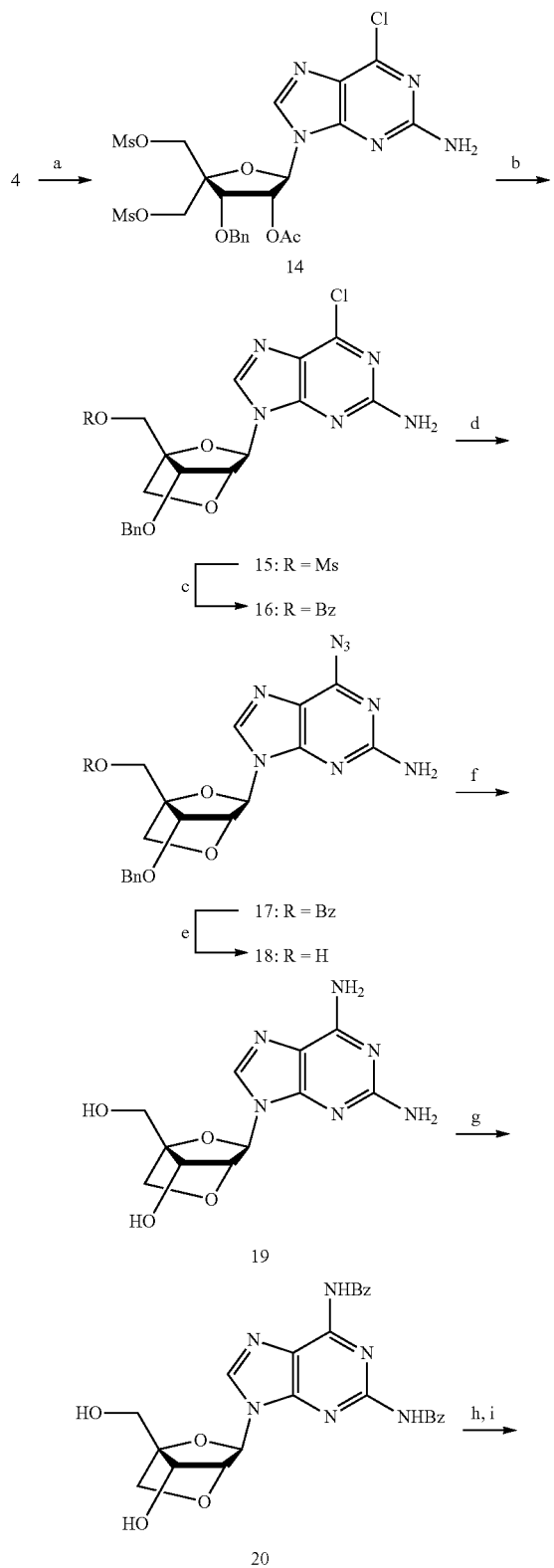

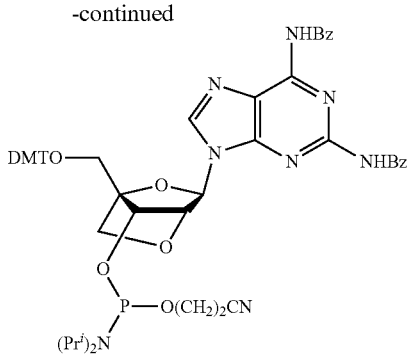

[a] Keys: (a) 2-chloro-6-aminopurine, BSA, TMSOTf, 1,2-dichloromethane; 90%; (b) NaOH, 1,4-dioxane, H$_2$O; 87%; (c) NaOBz, DMF; (d) NaN$_3$, DMSO; (e) NaOH, EtOH; 79% (three steps); (f) 10% Pd/C, HCO$_2$NH$_4$, MeOH, H$_2$O; 84%; (g) 1. BzCl, pyridine; 2. NaOH, EtOH, pyridine; 62%; (h) DMT—Cl, pyridine; 80%; (i) 2-cyanoethyl-N,N-diisopropylphosphoramidochloridite, DIPEA, DMF; 74%.

hydroxide to give bicyclic compound 15 in 87% yield. The standard reaction with sodium benzoate in hot DMF was then successfully applied for displacement of 5'-mesylate of 15. Notably, this reaction proceeded in very selective manner and no side products originating from the modification of the nucleobase were detected. The desired compound 16 was precipitated from the reaction mixture after addition of water. In order to introduce the 6-amino group into nucleobase structure, intermediate 6-azido derivative 17 was synthesized via reaction of 16 with sodium azide. The nucleoside derivative 18 was isolated as a crystalline compound after saponification of the 5'-benzoate of 17. Subsequent catalytic hydrogenation of 18 on palladium hydroxide resulted in simultaneous reduction of 6-azido and 3'-benzyl groups to give LNA-D diol 19 after crystallization from water. By the use of peracelation method, 2- and 6-amino groups of 19 were benzoylated at the next step to give the nucleobase protected derivative 20, which was in the standard way further converted into phosphoramidite monomer 21. This phosphoramidite has been produced in a quantity of 0.5 grams.

Exemplary Analytical Data

Data for compound 19 includes the following: $^1$H NMR (DMSO-d$_6$): δ 7.81 (s, 1H), 6.78 (br s, 2H), 5.91 (br s, 2H), 5.71 (s, 1H), 5.66 (br s, 1H), 5.04 (br s, 1H), 4.31 (s, 1H), 4.20 (s, 1H), 3.90 (d, J=7.7 Hz, 1H), 3.77 (m, 2H), 3.73 (d, J=7.7 Hz, 1H). $^{13}$C NMR (DMSO-d$_6$): δ 160.5, 156.2, 150.9, 134.2, 113.4, 88.3, 85.0, 79.3, 71.5, 70.0, 56.8. MALDI-MS m/z: 295.0 (M+H)$^+$. Anal. Calcd for C$_{11}$H$_{14}$N$_6$O$_4$·1.5H$_2$O: C, 41.12; H, 5.33; N, 26.15. Found: C, 41.24; H, 5.19; N, 25.80.

The $^{31}$P NMR (DMSO-d$_6$) spectrum for compound 24 contained signals at δ 149.19 and 148.98.

Data for compound 23 includes the following: crystallized from MeOH. mp. 227.5-229° C. (dec). $^1$H NMR (DMSO-d$_6$): δ 8.60 (s, 1H), 8.15 (s, 1H), 6.64 (br s, 2H), 5.82 (s, 1H), 5.71 (br s, 1H), 5.04 (br s, 1H), 4.40 (s, 1H), 4.21 (s, 1H), 3.92 (d, J=7.7 Hz, 1H), 3.79 (m, 2H), 3.75 (d, J=7.7 Hz, 1H). $^{13}$C NMR (DMSO-d$_6$): δ 160.6, 152.0, 149.4, 139.3, 127.1, 88.6, 84.8, 79.1, 71.6, 70.2, 56.8. MALDI-MS m/z: 334.7 (M+H)$^+$.

For protected compound 23, the $^{31}$P NMR (DMSO-d$_6$) spectrum has a signal at 148.93 and 148.85.

Exemplary Experimental Conditions

(1S,3R,4R,7S)-3-(2-amino-6-chloropurin-9-yl)-7-benzyloxy-1-methanesulfonoxymethyl-2,5-dioxabicyclo[2.2.1]heptane (15)

To a solution of compound 14 (40 g, 64.5 mmol) in 1,4-dioxane (300 mL) was added 1 M NaOH (350 mL). The mixture was stirred for one hour at 0° C., neutralized with AcOH (40 mL), and washed with $CH_2Cl_2$ (2×200 mL). The combined organic layers were dried ($Na_2SO_4$) and concentrated under reduced pressure. The solid residue was purified by silica gel flash chromatography to give compound 15 (27.1 g, 87%) as a white solid material. $^1$H NMR ($CDCl_3$): δ 7.84 (s, 1H), 7.32-7.26 (m, 5H), 5.91 (s, 1H), 4.73 (s, 1H), 4.66 (d, J=11.7 Hz, 1H), 4.61 (d, J=11.7 Hz, 1H), 4.59 (s, 2H), 4.31 (s, 1H), 4.18 (d, J=8.0 Hz, 2H), 3.99 (d, J=7.9 Hz, 1H), 3.05 (s, 3H). $^{13}$C NMR ($CDCl_3$) δ 158.9, 152.2, 151.4, 139.1, 136.4, 128.4, 128.2, 127.7, 125.3, 86.5, 85.2, 77.2, 76.8, 72.4, 72.1, 64.0, 37.7. MALDI-MS m/z 482.1 $[M+H]^+$.

(1S,3R,4R,7S)-3-(2-amino-6-chloropurin-9-yl)-1-benzoyloxymethyl-7-benzyloxy-2,5-dioxabicyclo[2.2.1]heptane (16)

A mixture of sodium benzoate (7.78 g, 54 mmol) and compound 15 13 g, 27 mmol) was suspended in anhydrous DMF (150 mL) and stirred for two hours at 105° C. Ice-cold water (500 mL) was added to the solution under intensive stirring. The precipitate was filtered off, washed with water, and dried in vacuo. The intermediate product 16 (8 g) was used for ext step without further purification. Analytical sample was additionally purified by silica gel HPLC (0-2% MeOH/$CH_2Cl_2$ v/v). $^1$H NMR ($CDCl_3$) δ 7.98-7.95 (m, 2H), 7.79 (s, 1H), 7.62-7.58 (m, 1H), 7.48-7.44 (m, 2H), 7.24 (m, 5H), 5.93 (s, 1H), 4.80 (d, J=12.6 Hz, 1H), 4.77 (s, 1H), 4.67 (d, J=11.9 Hz, 1H), 4.65 (d, J=12.6 Hz, 1H), 4.56 (d, J=11.9 Hz, 1H), 4.27 (d, J=8.0 Hz, 1H), 4.25 (s, 1H), 4.08 (d, J=7.9 Hz, 1H). $^{13}$C NMR ($CDCl_3$) δ 165.7, 158.8, 152.1, 151.3, 138.9, 136.4, 133.4, 129.4, 129.0, 128.5, 128.4, 128.2, 127.6, 125.4, 86.4, 85.7, 77.2, 76.7, 72.5, 72.3, 59.5. MALDI-MS m/z 508.0 $[M+H]^+$.

(1S,3R,4R,7S)-3-(2-amino-6-azidopurin-9-yl)-7-benzyloxy-1-hydroxymethyl-2,5-dioxabicyclo[2.2.1]heptane (18)

All the amount of compound 16 from the previous experiment was dissolved in anhydrous DMSO (100 mL) and $NaN_3$ (5.4 g, 83 mmol) was added. The mixture was stirred for two hours at 100° C. and cooled to room temperature. Water (400 ml) was added, and the mixture was stirred for 30 minutes at 0° C. (ice-bath) to give a yellowish precipitate 17. The precipitate was filtered off, washed with water, and dissolved in THF (25 mL). 2M NaOH (30 mL) was then added to the solution, and after 15 minutes of stirring the mixture was neutralized with AcOH (4 mL). The mixture was concentrated to approximately ½ of its volume and cooled in an ice-bath. The title compound was collected by filtration, washed with cold water, and dried in vacuo.

Yield: 8.8 g (79% from 15). $^1$H NMR (DMSO-$d_6$) δ 8.53 (br s, 2H), 8.23 (s, 1H), 7.31-7.26 (m, 5H), 6.00 (s, 1H), 5.26 (t, J=5.7 Hz, 1H), 4.76 (s, 1H), 4.64 (s, 1H), 4.31 (s, 1H), 3.99 (d, J=7.9 Hz, 1H), 3.88-3.85 (m, 3H). $^{13}$C NMR (DMSO-$d_6$) δ 146.0, 144.0, 143.8, 137.9, 137.0, 128.3, 127.7, 127.6, 112.3, 88.3, 85.6, 77.1, 77.0, 72.2, 71.4, 56.8. MALDI-MS m/z 384.7 $[M+H]^+$ for 2,6-diaminopurine product, 410.5 $[M+H]^+$. Anal. Calcd for $C_{18}H_{18}N_8O_4$: C, 52.68; H, 4.42; N, 27.30. Found: C, 52.62; H, 4.36; N, 26.94.

(1S,3R,4R,7S)-3-(2,6-Diaminopurin-9-yl)-7-hydroxy-1-hydroxymethyl-2,5-dioxabicyclo[2.2.1]heptane (19)

To a suspension of compound 18 (8 g, 19.5 mmol) in MeOH (100 mL) were added Pd(OH)$_2$/C (20%, 5.5 g) and HCO$_2$NH$_4$(3 g). The mixture was refluxed for 30 minutes and more HCO$_2$NH$_4$ (3 g) was added. After refluxing for further 30 minutes, the catalyst was filtered off and washed with boiling MeOH/H$_2$O (1/1 v/v, 200 mL). The combined filtrates were concentrated to approximately 100 mL and cooled in an ice-bath. The precipitate was filtered off, washed with ice-cold H$_2$O and dried in vacuo to give compound 19 (5.4 g, 94%) as a white solid material. $^1$H NMR (DMSO-$d_6$): δ 7.81 (s, 1H), 6.78 (br s, 2H), 5.91 (br s, 2H), 5.71 (s, 1H), 5.66 (br s, 1H), 5.04 (br s, 1H), 4.31 (s, 1H), 4.20 (s, 1H), 3.90 (d, J=7.7 Hz, 1H), 3.77 (m, 2H), 3.73 (d, J=7.7 Hz, 1H). $^{13}$C NMR (DMSO-$d_6$) δ 160.5, 156.2, 150.9, 134.2, 113.4, 88.3, 85.0, 79.3, 71.5, 70.0, 56.8. MALDI-MS m/z: 295.0 $(M+H)^+$. Anal. Calcd for $C_{11}H_{14}N_6O_4 \cdot 1.5H_2O$: C, 41.12; H, 5.33; N, 26.15. Found: C, 41.24; H, 5.19; N, 25.80.

(1S,3R,4R,7S)-3-(2,6-Di-(N-benzoylamino)purin-9-yl)-7-hydroxy-1-hydroxymethyl-2,5-dioxabicyclo[2.2.1]heptane (20)

A solution of compound 19 (0.5 g, 1.7 mmol) in anhydrous pyridine (20 mL) was cooled in an ice-bath and benzoyl chloride (1.5 mL, 12.9 mmol) was added under intensive stirring. The mixture was allowed to warm to room temperature and was stirred overnight. Ethanol (20 mL) and 2 M NaOH (20 mL) were added, and the mixture was stirred for an additional hour. EtOAc (75 mL) was added and the solution was washed with water (2×50 mL). The combined aqueous layers were washed with $CH_2Cl_2$ (2×50 mL). The combined organic phases were dried ($Na_2SO_4$) and concentrated under reduced pressure to a solid residue. The residue was suspended in Et$_2$O (75 mL, under refluxing for 30 minutes) and cooled in an ice-bath. The product was collected by filtration, washed with cold Et$_2$O, and dried in vacuo to give compound 20 (530 mg, 62%) as a slightly yellow solid material.

(1R,3R,4R,7S)-3-(2,6-Di-(N-benzoylamino)purin-9-yl)-1-(4,4'-dimethoxytrityloxymethyl)-7-hydroxy-2,5-dioxabicyclo[2.2.1]heptane (21)

Compound 20 (530 mg, 1.06 mmol) was co-evaporated with anhydrous pyridine (2×20 mL) and dissolved in anhydrous piridine (10 mL). DMT-Cl (600 mg, 1.77 mmol) was added, and the solution was stirred overnight at rt. The mixture was diluted with EtOAc (100 mL), washed with saturated NaHCO$_3$ (100 mL) and brine (50 mL). Organic layer was dried over Na$_2$SO$_4$ and concentrated under reduced pressure. Purification by silica gel HPLC (20-100% EtOAc/hexane v/v, containing 0.1% of pyridine) gave compound 21 (670 mg, 79%) as a white solid material.

$^1$H NMR (CD$_3$OD): δ 8.41 (s, 1H), 8.15-8.03 (m, 4H), 7.71-7.22 (m, 15H), 6.92-6.86 (m, 4H), 6.23 (s, 1H), 4.77 (s, 1H), 4.62 (s, 1H), 4.03 (d, J=7.9 Hz, 1H), 3.99 (d, J=7.9 Hz, 1H), 3.79 (s, 6H), 3.67 (d, J=10.9 Hz, 1H), 3.54 (d, J=10.8

Hz, 1H). MALDI-MS m/z: 826 (M+Na)⁺. Anal. Calcd for $C_{46}H_{40}N_6O_8 \cdot H_2O$: C, 67.14; H, 5.14; N, 10.21. Found: C, 67.24; H, 4.97; N, 10.11.

(1R,3R,4R,7S)-7-(2-Cyanoethoxy(diisopropylamino)phosphinoxy)-3-(2,6-di-(N-benzoylamino)purin-9-yl)-1-(4,4'-dimethoxytrityloxymethyl)-2,5-dioxabicyclo[2.2.1]heptane (21)

To a stirred solution of compound 20 (640 mg, 0.8 mmol) in anhydrous DMF (5 mL) were added DIPEA (420 L, 2.4 mmol) and 2-cyanoethyl-N,N-diisopropylphosphoramidochloridite (300 μL, 1.2 mmol). The mixture was stirred for 1.5 hours at room temperature, diluted with EtOAc (100 mL), and washed with saturated $NaHCO_3$ (2×100 mL) and brine (50 mL). Organic layer was dried ($Na_2SO_4$) and concentrated under reduced pressure to give a yellow solid residue. Purification by silica gel HPLC (20-100% EtOAc/hexene containing 0.1% of pyridine) gave compound 21 (590 mg, 74%) as a white solid material. ³¹P NMR (DMSO-$d_6$) δ 149.19, 148.98.

Synthesis of Pac-Protected LNA-D Amidite

The following scheme illustrates a method for synthesizing a Pac-protected version of LNA-D amidite.

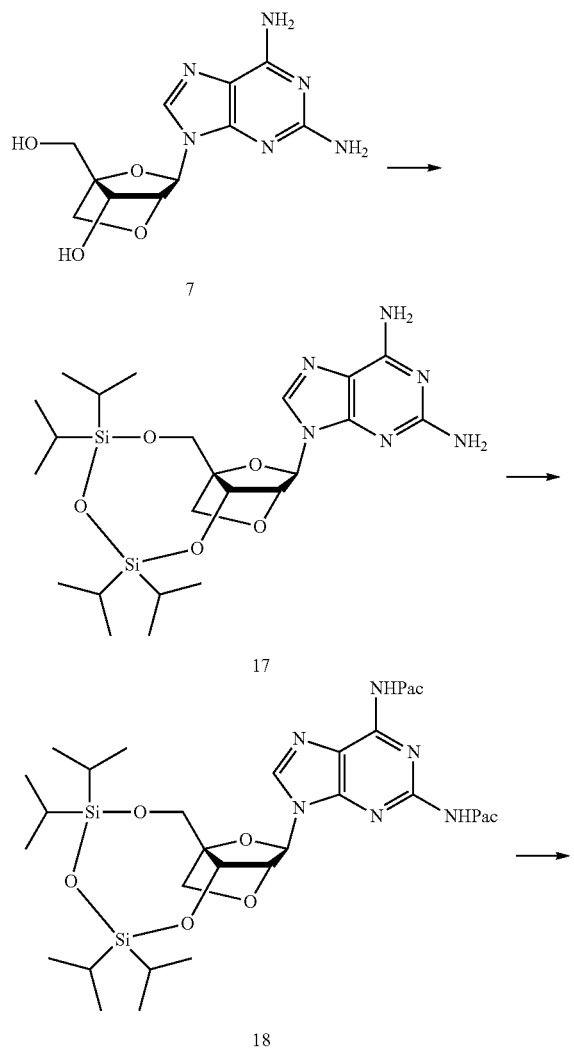

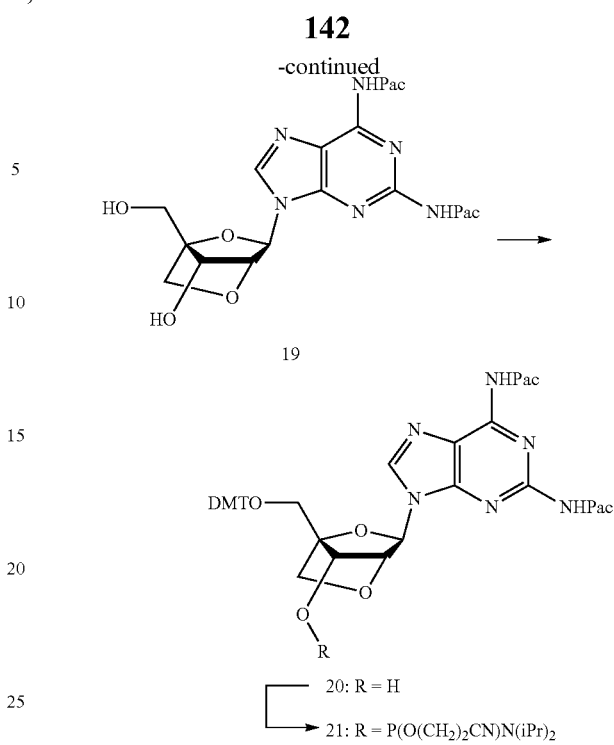

Compound 17

Compound 7 (1 g, 3.39 mmol) was co-evaporated with anhydrous DMF (2×10 mL) and dissolved in DMF (10 mL). Imidazole (0.69 g, 10.17 mmol) and 1,3-dichloro-1,1,3,3-tetraisopropyldisiloxane (1.4 mL, 4.37 mmol) were added, and the mixture was stirred overnight. $H_2O$ (100 mL) was added under intensive stirring to precipitate nucleoside material. The precipitate was filtered off, washed with $H_2O$, and dried in vacuo. Crystallization from ethanol gave compound 17 (1.15 g, 63%) as a white solid material. MALDI-MS: m/z 537.3 (M+H)⁺.

Compound 18

To a solution of compound 17 (1.15 g, 2.14 mmol) in anhydrous pyridine (5 mL) was added phenoxyacetic anhydride (2 g, 7.0 mmol) and the mixture was stirred for four hours. EtOAc (100 mL) was added, and the solution was washed with sat. $NaHCO_3$ (2×100 mL), brine (50 mL), dried ($Na_2SO_4$), and concentrated to a solid residue. Purification by silica gel HPLC (50-100% v/v EtOAc/hexane) gave compound 18 (1.65 g, 95%) as a white solid material. MALDI-MS: m/z 827.3 (M+Na)⁺.

(1S,3R,4R,7S)-3-(2,6-Di-(N-phenoxyacetylamino)purin-9-yl)-7-hydroxy-1-hydroxymethyl-2,5-dioxabicyclo[2.2.1]heptane (19)

To a solution of compound 18 (0.96 g, 1.19 mmol) in anhydrous THF (10 mL) was added $Et_3N \cdot 3HF$ (0.2 mL) and the mixture was stirred overnight at room temperature. The formed precipitate was collected by filtration and washed with THF (5 mL) and pentane (5 mL) to give after drying compound 19 (650 mg, 97%) as a white solid material. MALDI-MS: m/z 563.0 (M+H)⁺.

(1R,3R,4R,7S)-3-(2,6-Di-(N-phenoxyacetylamino)-purin-9-yl)-1-(4,4'-dimethoxytrityloxymethyl)-7-hydroxy-2,5-dioxabicyclo[2.2.1]heptane (20)

To a solution of compound 19 (650 mg, 1.15 mmol) was added DMT-Cl (500 mg, 1.48 mmol). The mixture was stirred for five hours, diluted with EtOAc (100 mL), and washed with sat. NaHCO$_3$ (2×100 mL). The organic layer was dried and concentrated to a solid residue. Crystallization from EtOAc gave compound 20 (810 mg, 81%) as a white solid material.

(1R,3R,4R,7S)-7-(2-Cyanoethoxy(diisopropylamino)phosphinoxy)-3-(2,6-di-(N-phenoxyacetylamino)-purin-9-yl)-1-(4,4'-dimethoxytrityloxymethyl)-2,5-dioxabicyclo[2.2.1]heptane (21)

To a solution of compound 20 (800 mg, 0.92 mmol) in anhydrous DMF (10 mL) were added 0.75 M solution of DCI in EtOAc (0.7 mL) and 2-cyanoethyl tetraisopropylphosphorodiamidite (0.32 mL, 1.01 mmol). The mixture was stirred at room temperature overnight and EtOAc (75 mL) was added. The resulting solution was washed with sat. NaHCO$_3$ and brine, dried and concentrated to a solid residue. Purification by silica gel HPLC (30-100% v/v EtOAc/hexane, containing 0.1% of pyridine) gave phosphoramidite 21 (550 mg, 56%) as a white solid material.

$^{31}$P NMR (DMSO-d$_6$): δ 149.08, 148.8.

Synthesis of LNA-2AP

The intermediate derivative 16 was also used for the synthesis of LNA-2AP nucleoside. First, the 5'-O-benzoyl group of 16 was hydrolyzed by aqueous sodium hydroxide to give the nucleoside derivative 22 in 72% yield. The conditions of catalytic transfer hydrogenation usually used for removal of the 3'-O-benzyl group turned out to be suitable for complete dechlorination of the nucleobase of 22. Thus, totally deprotected LNA-2AP nucleoside 23 was afforded in high yield after refluxing of the methanolic solution of 22 in the presence of paladium hydroxide and ammonium formate. The 2-amine of 23 was selectively protected with an amidine group after treatment with N,N-dimethylformamide dimethyl acetal. The resulting diol 24 was then 5'-O-DMT protected and 3'-O-phosphitylated to yield the desired phosphoramidite LNA-2AP monomer 25 (McBride et al., J. Am. Chem. Soc. 108:2040, 1986).

Synthesis of LNA-2AP$^a$

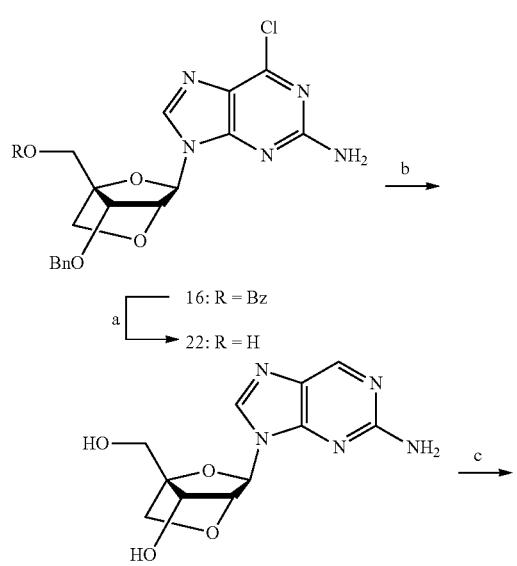

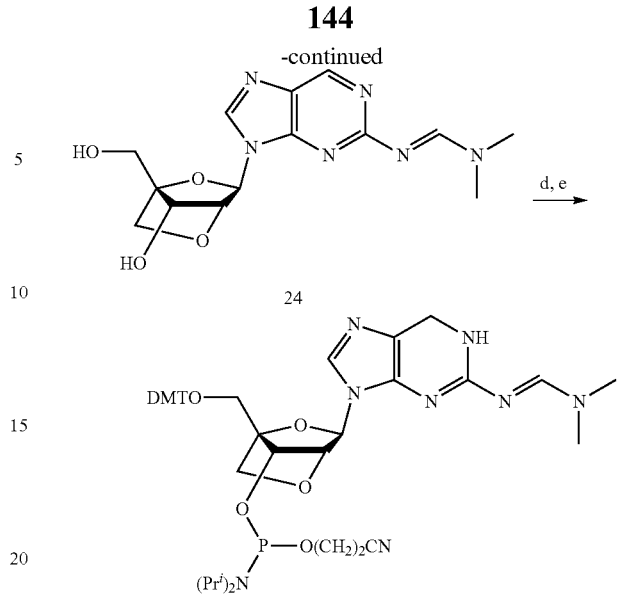

$^a$ Keys: (a) NaOH, 1,4-dioxane, H$_2$O; 72%; (b) 20% Pd(OH)$_2$/C, HCO$_2$NH$_4$, MeOH, H$_2$O; 89%; (c) N,N-dimethylformamide dimethyl acetal, DMF; (d) DMT—Cl, pyridine; 87% (two steps); (e) 2-cyanoethyl-N,N-diisopropylphosphoramidochloridite, DIPEA, DMF; 64%.

Exemplary Experimental Conditions (1S,3R,4R,7S)-3-(2-amino-6-chloropurin-9-yl)-7-benzyloxy-1-hydroxymethyl-2,5-dioxabicyclo[2.2.1]heptane (22)

To a solution of compound 16 (3 g, 5.92 mmol) in 1,4-dioxane (20 mL) was added 2 M NaOH (20 mL) and the mixture was stirred for one hour. AcOH (3 mL) was added, and the solvents were removed under reduced pressure. The solid residue was re-dissolved in 20% MeOH/EtAc (50 mL), washed with NaHCO$_3$ (2×50 mL), dried (Na$_2$SO$_4$) and concentrated to a solid residue. The residue was purified by silica gel column chromatography (1-2% MeOH/EtAc v/v) to give compound 22 (1.72 g, 72%) as a white solid material.

(1S,3R,4R,7S)-3-(2-aminopurin-9-yl)-7-hydroxy-1-hydroxymethyl-2,5-dioxabicyclo[2.2.1]heptane (23)

To a solution of compound 22 (0.72 g, 1.79 mmol) in MeOH/dioxane (1/1 v/v) were added Pd(OH)$_2$/C (20%, 0.5 g) and HCO$_2$NH$_4$ (1.5 g, 23.8 mmol). The mixture was stirred under refluxing for 30 minutes and cooled to room temperature. The catalyst was filtered off and washed with MeOH. The combined filtrates were concentrated under reduced pressure to yield compound 23 (0.44 g, 89%) as a white solid material. Analytical sample was crystallized from MeOH. mp. 227.5-229° C. (dec). $^1$H NMR (DMSO-d$_6$): δ 8.60 (s, 1H), 8.15 (s, 1H), 6.64 (br s, 2H), 5.82 (s, 1H), 5.71 (br s, 1H), 5.04 (br s, 1H), 4.40 (s, 1H), 4.21 (s, 1H), 3.92 (d, J=7.7 Hz, 1H), 3.79 (m, 2H), 3.75 (d, J=7.7 Hz, 1H). $^{13}$C NMR (DMSO-d$_6$): δ 160.6, 152.0, 149.4, 139.3, 127.1, 88.6, 84.8, 79.1, 71.6, 70.2, 56.8.

(1R,3R,4R,7S)-1-(4,4'-dimethoxytrityloxymethyl)-3-(2-N-(dimethylaminomethylidene)aminopurin-9-yl)-7-hydroxy-2,5-dioxabicyclo[2.2.1]heptane (5' DMT protected version of 24)

Compound 23 (0.4 g, 1.43 mmol) was co-evaporated with anhydrous DMF (10 mL) and dissolved in DMF (15 mL).

N,N-Dimethylformamide dimethylacetal (0.8 mL) was added and the solution was stirred for three days at room temperature. Water (5 mL) was added, and the solvents were removed under reduced pressure. The solid residue was co-evaporated with anhydrous pyridine (2×10 mL) and dissolved in anhydrous pyridine (5 mL). DMT-Cl (0.7 g, 2.1 mmol) was added, the solution was stirred for four hours, diluted with EtOAc (50 mL), and washed with NaHCO$_3$(2× 50 mL) and brine (50 mL). Organic layer was dried (Na$_2$SO$_4$) and concentrated to a yellow solid residue. Purification by silica gel HPLC (1-6% MeOH/CH$_2$Cl$_2$ v/v, containing 0.1% of pyridine) gave the 5' DMT protected version of compound 24 (0.87 g, 87%) as a white solid material.

(1R,3R,4R,7S)-7-(2-Cyanoethoxy(diisopropylamino)phosphinoxy)-1-(4,4'-dimethoxytrityloxymethyl)-3-(2-N-(dimethylaminomethylidene)aminopurin-9-yl)-2,5-dioxabicyclo[2.2.1]heptane (25)

The 5' DMT protected version of compound 24 (0.5 g, 0.79 mmol) was dissolved in anhydrous DMF (10 mL) and DIPEA (350 μL) and 2-cyanoethyl-N,N-diisopropylphosphoramidochloridite (250 μl) were added. The mixture was stirred for one hour, diluted with EtOAc (50 mL), washed with saturated NaHCO$_3$ (2×100 mL) and brine (50 mL), dried (Na$_2$SO$_4$), and concentrated to a solid residue. Purification by silica gel HPLC (0-3% MeOH/CH$_2$Cl$_2$ v/v, containing 0.1% of pyridine) gave compound 25 (0.42 g, 64%) as a white solid material. $^{31}$P NMR (DMSO-d$_6$) δ 148.93, 148.85.

Synthesis of Oligomers

Along with previously described LNA phosphoramidites (Koshkin et al., supra; and Pedersen et al., Synthesis p. 802, 2002), the phosphoramidite monomers 11, 21, and 25 were successfully applied for automated oligonucleotide synthesis (Caruthers, Acc. Chem. Res. 24:278, 1991) to produce the LNA oligomers depicted in Table 9. Oligonucleotide syntheses were performed on a 0.2 μmol scale using an Expedite synthesizer (Applied Biosystems) with the recommended commercial reagents. Standard protocols for DNA synthesis were used, except that the coupling time was extended to 5 minutes and the oxidation time was extended to 30 second cycles. Deprotection of the oligonucleotides were performed by treatment with concentrated ammonium hydroxide for five hours at 60° C. After that, the LNA-D containing oligonucleotides were additionally treated with AMA (concentrated ammonium hydroxide/40% aqueous MeNH$_2$; 1/1 v/v) for one hour at 60° C. All the synthesized oligonucleotides were purified by RP-HPLC, and their structures were verified by MALDI-TOF mass spectra.

The complexing properties of oligonucleotides containing new LNA monomers 1-3 were assessed. Comparative binding data from an 8-mer LNA sequence is shown in Table 9 as the melting temperatures against complementary single stranded DNA. An exemplary sequence for this comparison is GACATAGG, which is the central part of a capture probe used for SNP detection in GlueIV57-7asA (A:a mismatch position). The thermal stabilities of reference DNA duplexes (entries 1-7, Table 9) can be directly compared with their LNA counterparts (entries 8-14). The hybridizing ability of all LNA 8-mers is superior to that of isosequencial DNA oligonucleotides. The average melting temperatures of DNA and LNA 8-mers against complementary DNAs typically differ by about 40° C. The replacement of one internal LNA-A nucleotide by LNA-D resulted in the further stabilization of the complementary duplex (i.e., compare entries 8 and 11) by 6.2° C. Interestingly, the analogous replacement made in an DNA octamer destabilized the corresponding duplex by 0.5° C. (i.e., entries 1 and 4). D-nucleosides may facilitate a B to A helix transition, because the A-type structure of an LNA:DNA duplex is more suitable for effective D:t pairing. This stabilizing effect is expected to be even more pronounced for LNA:RNA duplexes, which can be very useful for construction of antisense or other gene-silencing reagents. The mismatch discrimination ability of the D-nucleoside was also studied (entry 11). In comparison to LNA-A (entry 8) D-nucleoside demonstrated remarkable increased mismatch discrimination against DNA-g nucleoside.

TABLE 9

Melting temperatures (Tm) of the complementary DNA-DNA and LNA-DNA duplexes. $^a$Modified monomers (LNA are in CAPITALs): I = inosine; D = 2,6-diaminopurine; X = 2-aminopurine.

| | Oligonucleotide | Tm (±0.5° C.) of the duplexes with complementary deoxynucleotide | | | |
|---|---|---|---|---|---|
| Entry | structure | 3'-ctgtatcc | 3'-ctgaatcc | 3'-ctggatcc | 3'-ctgcatcc |
| 1 | 5'-gacatagg | 23.8 | <10 | <10 | <10 |
| 2 | 5'-gacttagg | <10 | 22.6 | <10 | <10 |
| 3 | 5'-gacgtagg | <10 | <10 | <10 | 25.0 |
| 4 | 5'-gacdtagg | 23.3 | <10 | <10 | <10 |
| 5 | 5'-gdcdtdgg | 33.4 | <10 | <10 | 17.7 |
| 6 | 5'-gacitagg | <10 | <10 | <10 | 20.9 |
| 7 | 5'-gacxtagg | <10 | <10 | <10 | <10 |
| 8 | 5'-GACATAGG | 61.6 | 38.2 | 43.4 | 40.6 |
| 9 | 5'-GACTTAGG | 28.0 | 60.7 | 36.4 | 23.5 |
| 10 | 5'-GACGTAGG | 55.0 | 32$^b$ | 41$^b$ | 70.9 |

TABLE 9-continued

Melting temperatures (Tm) of the complementary DNA-DNA and LNA-DNA duplexes. <sup>a</sup>Modified monomers (LNA are in CAPITALs): I = inosine; D = 2,6-diaminopurine; X = 2-aminopurine.

| Entry | Oligonucleotide structure | Tm (±0.5° C.) of the duplexes with complementary deoxynucleotide | | | |
|---|---|---|---|---|---|
| | | 3'-ctgtatcc | 3'-ctgaatcc | 3'-ctggatcc | 3'-ctgcatcc |
| 11 | 5'-GACDTAGG | 67.8 | 42.2 | 41.4 | 52.4 |
| 12 | 5'-GDCDTDGG | 78.3 | 55.9 | 54.7 | 63.8 |
| 13 | 5'-GACITAGG | 53.1 | 48.2 | 43.0 | 59.9 |
| 14 | 5'-GACXTAGG | 60.8 | 45.5 | 44.0 | 53.9 |

<sup>a</sup>The melting temperatures (Tm values) were obtained as a maxima of the first derivative of the corresponding melting curves (optical density at 260 nm versus temperature). Concentration of the duplexes: 2.5 µM. Buffer: 0.1M NaCl; 10 mM Na-phosphate (pH 7.0); 1 mM EDTA.
<sup>b</sup>Low cooperativity of transitions (accuracy ±1° C.).

TABLE 10

The mismatch discrimination effect of the chimeric LNA-DNA 12-mers containing LNA-A or LNA-D nucleosides against the point of mutation.

| The structure of LNA-DNA oligonucleotide | Tm (±0.5° C.) of the complementary duplexes with DNA oligonucleotides (ΔTm between singly mismatched and perfect duplexes) | |
|---|---|---|
| | HNFas128A-2 | |
| | caacatcccaca (SEQ ID NO: 467) | caacaacccaca (SEQ ID NO: 468) |
| tGtggGATGttg (SEQ ID NO: 469) | 61.0 | 45.9 (-15.1) |
| tGtggGDTGttg (SEQ ID NO: 470) | 65.5 | 49.7 (-15.8) |
| | Gluc53as-A | |
| | aagagtccagtg (SEQ ID NO: 471) | aagaggccagtg (SEQ ID NO: 472) |
| cAmCtgGAmCtctt (SEQ ID NO: 473) | 61.5 | 50.6 (-10.9) |
| cAmCtgGDmCtctt (SEQ ID NO: 474) | 65.3 | 45.4 (-19.9) |

<sup>a</sup>Concentration of duplexes: 2 µM; Buffer: see Table 9.

TABLE 11

Melting temperatures of the LNA and DNA duplexes (LNAs are CAPITALIZED) containing 2-thio-deoxythymidine (s) and diaminopurineriboside (d). See Table 9 for experimental conditions.

| oligo structure | T<sub>m</sub> (±0.5° C.) of complementary duplexes with | | | | |
|---|---|---|---|---|---|
| | 3'-ctgtatcc | 3'-ctgsatcc | 3'-CTGsATCC | 3'-CTGtATCC | 3'-CTGTATCC |
| 5'-gacatagg | 23.8 | 27 | 54.4 | 49.4 | 54.6 |
| 5'-gacdtagg | 23.3 | <6 | 45.4 | 55.2 | 60.5 |
| 5'-GACATAGG | 61.6 | 64.6 | 87* | 88 | 88 |
| 5'-GACDTAGG | 67.8 | 59.4 | 80 | >90 | >90 |

*T<sub>m</sub> values in the shaded cells were measured in low salt buffers (1 mM Na-phosphate, pH 7.0). Low cooperativity of the transitions was observed (accuracy ±1.5° C.)

EXAMPLE 22

Exemplary Methods for Synthesizing LNA-PyrroloPyr-SBC-C

The furanopyrimidine phosphoramidite 6pC used for incorporation of the pyrroloC analogue can be synthesized from LNA-U through a series of reactions as illustrated below and in FIG. 6. Starting from LNA-U 1pC iodine can be introduced on the 5 position on the nucleobase (Chang and Welch, J. Med. Chem. 1963, 6, 428). This compound can be used in a Sonogashira type palladium coupling reaction (Sonogashira, Tohda and Hagihara, Tetrahedron Lett. 1975, 4467) resulting in the 5-ethynyl-LNA-U 3pC. The 5-ethynyl-LNA-U 3pC can be transformed to the furanopyrimidie LNA analogue 4pC when reacted with CuI, and then transformed into the DMT-protected phosphoramidite 6pC (Woo, Meyer, and Gamper, Nucleic Acids Res., 1996, 24, 2470). LNA-PyrroloPyr-SBC-C is formed when 6pC or an oligonucleotide containing 6pC is deprotected with ammonia.

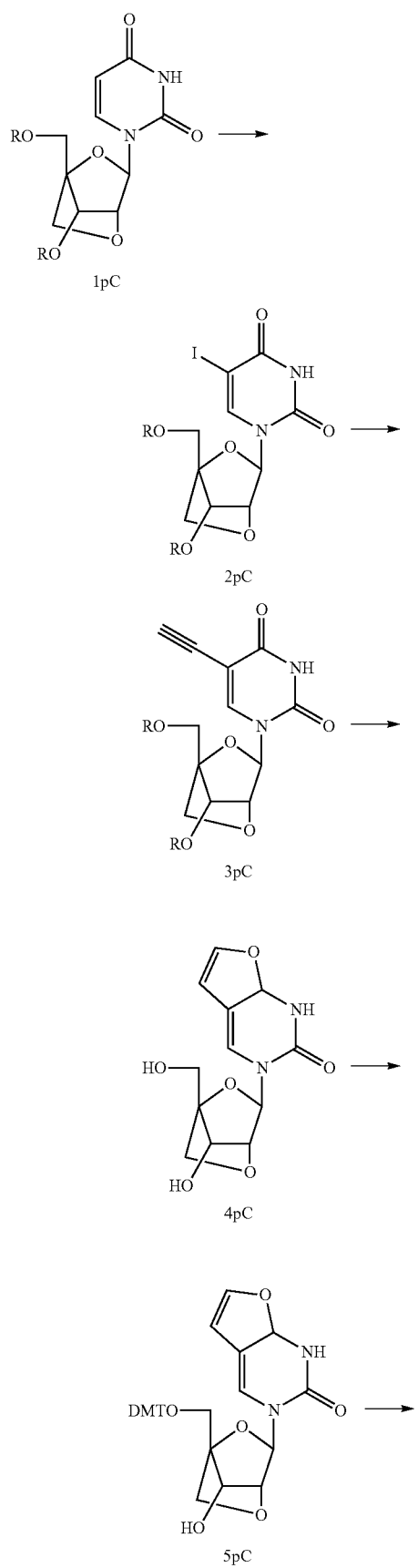

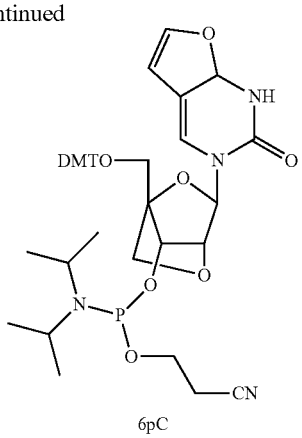

EXAMPLE 23

Exemplary Modified Bases Such as Universal Bases

Desirable modified bases are covalently linked to the 1'-position of a furanosyl ring, particularly to the 1'-position of a 2',4'-linked furanosyl ring, especially to the 1'-position of a 2'-O,4'-C-methylene-beta-D-ribofuranosyl ring.

As discussed above, other desirable modified bases contain one or more carbon alicyclic or carbocyclic aryl units, i.e. non-aromatic or aromatic cyclic units that contain only carbon atoms as ring members. Modified bases that contain carbocyclic aryl groups are generally desirable, particularly a moiety that contains multiple linked aromatic groups, particularly groups that contain fused rings. That is, optionally substituted polynuclear aromatic groups are especially desirable such as optionally substituted naphthyl, optionally substituted anthracenyl, optionally substituted phenanthrenyl, optionally substituted pyrenyl, optionally substituted chrysenyl, optionally substituted benzanthracenyl, optionally substituted dibenzanthracenyl, optionally substituted benzopyrenyl, with substituted or unsubstituted pyrenyl being particularly desirable.

Without being bound by any theory, it is believed that such carbon alicyclic and/or carbocyclic aryl modified bases can increase hydrophobic interaction with neighboring bases of an oligonucleotide. Those interactions can enhance the stability of a hybridized oligo pair, without necessity of interactions between bases of the distinct oligos of the hybridized pair.

Again without being bound by any theory, it is further believed that such hydrophobic interactions can be particularly favored by platelike stacking of neighboring bases, i.e. intercalation. Such intercalation will be promoted if the base comprises a moiety with a relatively planar extended structure, such as provided by an aromatic group, particularly a carbocyclic aryl group having multiple fused rings. This is indicated by the increases in $T_m$ values exhibited by oligos having LNA units with pyrenyl nucleobases relative to comparable oligos having LNA units with naphthyl nucleobases.

Modified bases that contain one or more heteroalicyclic or heteroaromatic groups also are suitable for use in LNA units, particularly such non-aromatic and aromatic groups that contains one or more N, O or S atoms as ring members, particularly at least one sulfur atom, and from 5 to about 8 ring members. Also desirable is a nucleo base that contains two or more fused rings, where at least one of the rings is a heteroalicyclic or heteroaromatic group containing 1, 2, or 3 N, O, or S atoms as ring members.

In general, desirable are modified bases that contain 2, 3, 4, 5, 6, 7 or 8 fused rings, which may be carbon alicyclic, heteroalicyclic, carbocyclic aryl and/or heteroaromatic; more desirably modified bases that contain 3, 4, 5, or 6 fused rings, which may be carbon alicyclic, heteroalicyclic, carbocyclic aryl and/or heteroaromatic, and desirably the fused rings are each aromatic, particularly carbocyclic aryl.

In some embodiments, the base is not an optionally substituted oxazole, optionally substituted imidazole, or optionally substituted isoxazole modified base.

Other suitable modified bases for use in LNA units in accordance with the invention include optionally substituted pyridyloxazole, optionally substituted pyrenylmethylglycerol, optionally substituted pyrrole, optionally substituted diazole and optionally substituted triazole groups.

Desirable modified bases of the present invention when incorporated into an oligonucleotide containing all LNA units or a mixture of LNA and DNA or RNA units will exhibit substantially constant $T_m$ values upon hybridization with a complementary oligonucleotide, irrespective of the bases present on the complementary oligonucleotide.

In some embodiments, one or more of the common RNA or commonly used derivatives thereof, such as 2'-O-methyl, 2'-fluoro, 2'-allyl, and 2'-O-methoxyethoxy derivatives are combined with at least one nucleotide with a universal base to generate an oligonucleotide having between five to 100 nucleotides.

Modified nucleic acid compounds may comprise a variety of nucleic acid units e.g. nucleoside and/or nucleotide units. As discussed above, an LNA nucleic acid unit has a carbon or hetero alicyclic ring with four to six ring members, e.g. a furanose ring, or other alicyclic ring structures such as a cyclopentyl, cycloheptyl, tetrahydropyranyl, oxepanyl, tetrahydrothiophenyl, pyrrolidinyl, thianyl, thiepanyl, piperidinyl, and the like.

In an aspect of the invention, at least one ring atom of the carbon or hetero alicyclic group is taken to form a further cyclic linkage to thereby provide a multi-cyclic group. The cyclic linkage may include one or more, typically two atoms, of the carbon or hetero alicyclic group. The cyclic linkage also may include one or more atoms that are substituents, but not ring members, of the carbon or hetero alicyclic group.

Unless indicated otherwise, an alicyclic group as referred to herein is inclusive of group having all carbon ring members as well as groups having one or more hetero atom (e.g. N, O, S or Se) ring members. The disclosure of the group as a "carbon or hetero alicyclic group" further indicates that the alicyclic group may contain all carbon ring members (i.e. a carbon alicyclic) or may contain one or more hetero atom ring members (i.e. a hetero alicyclic). Alicyclic groups are understood not to be aromatic, and typically are fully saturated within the ring (i.e. no endocyclic multiple bonds).

Desirably, the alicyclic ring is a hetero alicyclic, i.e. the alicyclic group has one or more hetero atoms ring members, typically one or two hetero atom ring members such as O, N, S or Se, with oxygen being often desirable.

The one or more cyclic linkages of an alicyclic group may be comprised completely of carbon atoms, or generally more desirable, one or more hetero atoms such as O, S, N or Se, desirably oxygen for at least some embodiments. The cyclic linkage will typically contain one or two or three hetero atoms, more typically one or two hetero atoms in a single cyclic linkage.

The one or more cyclic linkages of a nucleic acid compound of the invention can have a number of alternative configurations and/or configurations. For instance, cyclic linkages of nucleic acid compounds of the invention will include at least one alicyclic ring atom. The cyclic linkage may be disubstituted to a single alicyclic atom, or two adjacent or non-adjacent alicyclic ring atoms may be included in a cyclic linkage. Still further, a cyclic linkage may include a single alicyclic ring atom, and a further atom that is a substituent but not a ring member of the alicyclic group.

For instance, as discussed above, if the alicyclic group is a furanosyl-type ring, desirable cyclic linkages include the following: C-1', C-2'; C-2', C-3'; C-2', C-4'; or a C-2', C-5' linkage.

A cyclic linkage will typically comprise, in addition to the one or more alicyclic group ring atoms, 2 to 6 atoms in addition to the alicyclic ring members, more typically 3 or 4 atoms in addition to the alicyclic ring member(s).

The alicyclic group atoms that are incorporated into a cyclic linkage are typically carbon atoms, but hetero atoms such as nitrogen of the alicyclic group also may be incorporated into a cyclic linkage.

Specifically desirable modified nucleic acids for use oligonucleotides of the invention include locked nucleic acids as disclosed in WO99/14226 (which include bicyclic and tricyclic DNA or RNA having a 2'-4' or 2'-3' sugar linkages); 2'-deoxy-2'-fluoro ribonucleotides; 2'-O-methyl ribonucleotides; 2'-O-methoxyethyl ribonucleotides; peptide nucleic acids; 5-propynyl pyrimidine ribonucleotides; 7-deazapurine ribonucleotides; 2,6-diaminopurine ribonucleotides; and 2-thio-pyrimidine ribonucleotides.

LNA units as disclosed in WO 99/14226 are in general particularly desirable modified nucleic acids for incorporation into an oligonucleotide of the invention. Additionally, the nucleic acids may be modified at either the 3' and/or 5' end by any type of modification known in the art. For example, either or both ends may be capped with a protecting group, attached to a flexible linking group, attached to a reactive group to aid in attachment to the substrate surface, etc. Desirable LNA units also are disclosed in WO 0056746, WO 0056748, and WO 0066604.

Desirable syntheses of pyrene-LNA monomers is shown in the following Schemes 1 and 2. In the below Schemes 1 and 2, the compound reference numerals are also referred to in the examples below.

Scheme 1

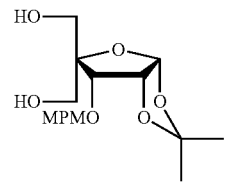

-continued

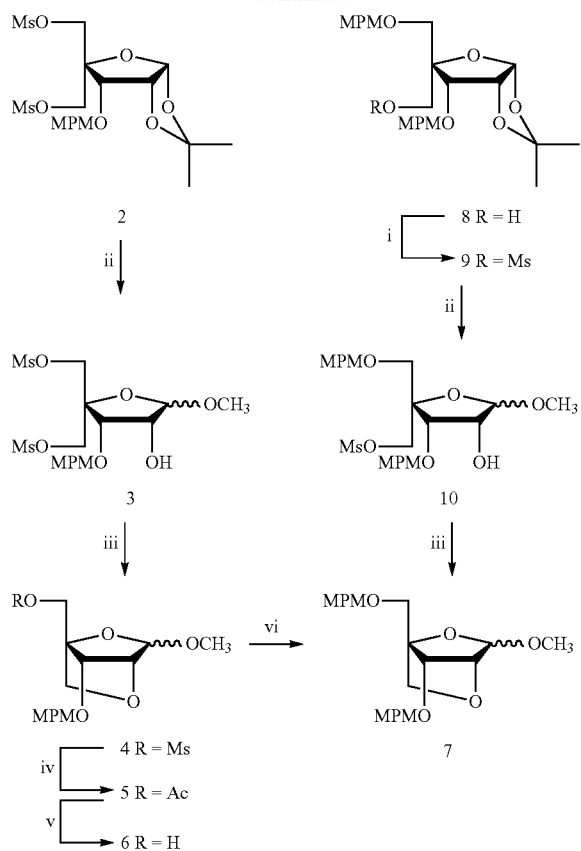

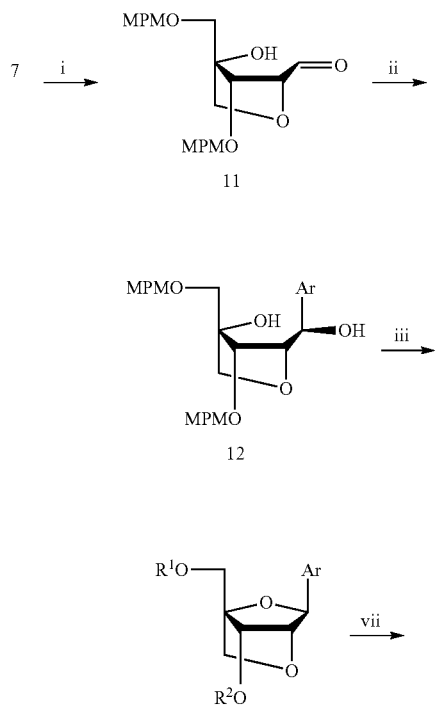

Scheme 2

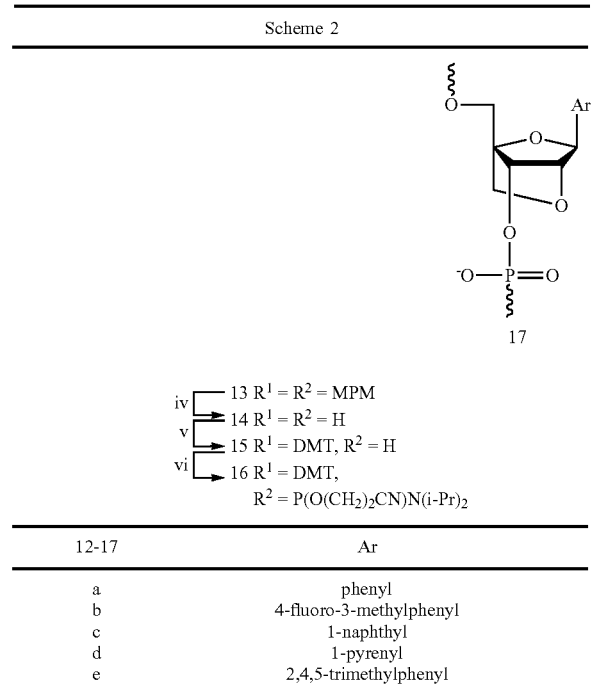

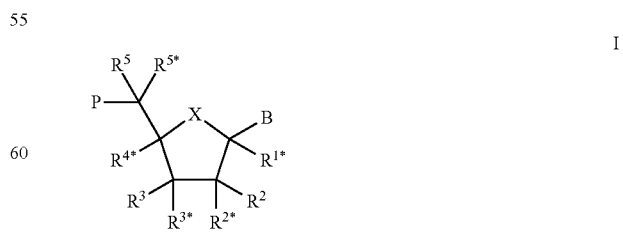

| 12-17 | Ar |
|---|---|
| a | phenyl |
| b | 4-fluoro-3-methylphenyl |
| c | 1-naphthyl |
| d | 1-pyrenyl |
| e | 2,4,5-trimethylphenyl |

A wide variety of modified nucleic acids may be employed, including those that have 2'-modification of hydroxyl, 2'-O-methyl, 2'-fluoro, 2'-trifluoromethyl, 2'-O-(2-methoxyethyl), 2'-O-aminopropyl, 2'-O-dimethylamino-oxyethyl, 2'-O-fluoroethyl or 2'-O-propenyl. The nucleic acid may further include a 3' modification, desirably where the 2'- and 3'-position of the ribose group is linked. The nucleic acid also may contain a modification at the 4'-position, desirably where the 2'- and 4'-positions of the ribose group are linked such as by a 2'-4' link of $-CH_2-S-$, $-CH_2-NH-$, or $-CH_2-NMe-$ bridge.

The nucleotide also may have a variety of configurations such as α-D-ribo, β-D-xylo, or α-L-xylo configuration.

The internucleoside linkages of the units of oligos of the invention may be natural phosphorodiester linkages, or other linkages such as $-O-P(O)_2-O-$, $-O-P(O,S)-O-$, $-O-P(S)_2-O-$, $-NR^H-P(O)_2-O-$, $-O-P(O,NR^H)-O-$, $-O-PO(R'')-O-$, $-O-PO(CH_3)-O-$, and $-O-PO(NHR^N)-O-$, where $R^H$ is selected from hydrogen and $C_{1-4}$-alkyl, and R" is selected from $C_{1-6}$-alkyl and phenyl.

A further desirable group of modified nucleic acids for incorporation into oligomers of the invention include those of the following formula:

I wherein X is $-O-$; B is a modified base as discussed above e.g. an optionally substituted carbocyclic aryl such as optionally substituted pyrene or optionally substituted pyrenylmethylglycerol, or an optionally substituted heteroalicylic or optionally substituted heteroaromatic such as optionally substituted pyridyloxazole. Other desirable universal bases include, pyrrole, diazole or triazole moieties, all of which may be optionally substituted. $R^{1*}$ is hydrogen.

P designates the radical position for an internucleoside linkage to a succeeding monomer, or a 5'-terminal group, such internucleoside linkage or 5'-terminal group optionally including the substituent $R^5$, $R^5$ being hydrogen or included in an internucleoside linkage. $R^{3*}$ is a group P* which designates an internucleoside linkage to a preceding monomer, or a 3'-terminal group. One or two pairs of non-geminal substituents selected from the present substituents of $R^2$, $R^{2*}$, $R^3$, $R^{4*}$, may designate a biradical consisting of 1-4 groups/atoms selected from —C($R^a R^b$)—, —C($R^a$)=C ($R^a$)—, —C($R^a$)=N—, —O—, —S—, —SO$_2$—, —N($R^a$)—, and >C=Z. Z is selected from —O—, —S—, and —N($R^a$)—, and $R^a$ and $R^b$ each is independently selected from hydrogen, optionally substituted $C_{1-6}$-alkyl, optionally substituted $C_{2-6}$-alkenyl, hydroxy, $C_{1-6}$-alkoxy, $C_{2-6}$-alkenyloxy, carboxy, $C_{1-6}$-alkoxycarbonyl, $C_{1-6}$-alkylcarbonyl, formyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, photochemically active groups, thermochemically active groups, chelating groups, reporter groups, and ligands, the possible pair of non-geminal substituents thereby forming a monocyclic entity together with (i) the atoms to which the non-geminal substituents are bound and (ii) any intervening atoms; and each of the substituents $R^2$, $R^{2*}$, $R^3$, $R^{4*}$ which are present and not involved in the possible biradical is independently selected from hydrogen, optionally substituted $C_{1-6}$-alkyl, optionally substituted $C_{2-6}$-alkenyl, hydroxy, $C_{1-6}$-alkoxy, $C_{2-6}$-alkenyloxy, carboxy, $C_{1-6}$-alkoxycarbonyl, $C_{1-6}$-alkylcarbonyl, formyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, photochemically active groups, thermochemically active groups, chelating groups, reporter groups, and ligands; and basic salts and acid addition salts thereof.

Modified nucleobases and nucleosidic bases may comprise a cyclic unit (e.g. a carbocyclic unit such as pyrenyl) that is joined to a nucleic unit, such as a 1'-position of furasonyl ring through a linker, such as a straight of branched chain alkylene or alkenylene group. Alkylene groups suitably having from 1 (i.e. —CH$_2$—) to about 12 carbon atoms, more typically 1 to about 8 carbon atoms, still more typically 1 to about 6 carbon atoms. Alkenylene groups suitably have one, two or three carbon-carbon double bounds and from 2 to 12 carbon atoms, more typically 2 to 8 carbon atoms, still more typically 2 to 6 carbon atoms.

EXAMPLE 24

Exemplary Nucleic Acid Monomers and Oligomers

Desirable LNA units include those that contain a furanosyl-type ring and one or more of the following linkages: C-1', C-2'; C-2', C-3'; C-2', C-4'; or a C-2', C-5' linkage. A C-2', C-4' is particularly desirable. In another aspect of the invention, desirable LNA units are compounds having a substituent on the 2'-position of the central sugar moiety (e.g., ribose or xylose), or derivatives thereof, which favors the C3'-endo conformation, commonly referred to as the North (or simply N for short) conformation. Desirable LNA In various embodiments, the oligonucleotide has at least one LNA unit with a modified base as disclosed herein. Suitable oligonucleotides also may contain natural DNA or RNA units (e.g., nucleotides) with natural bases, as well as LNA units that contain natural bases. Furthermore, the oligonucleotides of the invention also may contain modified DNA or RNA, such as 2'-O-methyl RNA, with natural or modified nucleobases (e.g., pyrene). Desirable oligonucleotides contain at least one of and desirably both of 1) one or more DNA or RNA units (e.g., nucleotides) with natural bases, and 2) one or more LNA units with natural bases, in addition to LNA units with a modified base. In other embodiments, the nucleic acid does not contain a modified base.

Oligonucleotides of the invention desirably contain at least 50 percent or more, more desirably 55, 60, 65, or 70 percent or more of non-modified or natural DNA or RNA units (e.g., nucleotides) or units other than LNA units based on the total number of units or residues of the oligo. A non-modified nucleic acid as referred to herein means that the nucleic acid upon incorporation into a 10-mer oligomer will not increase the $T_m$ of the oligomer in excess of 1° C. or 2° C. More desirably, the non-modified nucleic acid unit (e.g., nucleotide) is a substantially or completely "natural" nucleic acid, i.e. containing a non-modified base of uracil, cytosine, 5-methyl-cytosine, thymine, adenine or guanine and a non-modified pentose sugar unit of β-D-ribose (in the case of RNA) or β-D-2-deoxyribose (in the case of DNA).

Oligonucleotides of the invention suitably may contain only a single modified (i.e. LNA) nucleic acid unit, but desirably an oligonucleotide will contain 2, 3, 4 or 5 or more modified nucleic acid units. Typically desirable is where an oligonucleotide contains from about 5 to about 40 or 45 percent modified (LNA) nucleic acid units, based on total units of the oligo, more desirably where the oligonucleotide contains from about 5 or 10 percent to about 20, 25, 30 or 35 percent modified nucleic acid units, based on total units of the oligo.

Typical oligonucleotides that contain one or more LNA units with a modified base as disclosed herein suitably contain from 3 or 4 to about 200 nucleic acid repeat units, with at least one unit being an LNA unit with a modified base, more typically from about 3 or 4 to about 5, 6, 7, 8, 9, 10, 15, 20, 30, 40, 50, 60, 70, 80, 90, 100, 110, 120, 130, 140 or 150 nucleic acid units, with 1, 2, 3, 4, 5, 6, 7, 8, 9, or 10 LNA units with a modified base being present.

As discussed above, particularly desirable oligonucleotides contain a non-modified DNA or RNA unit at the 3' terminus and a modified DNA or RNA unit at one position upstream from (generally referred to hereing as the −1 or penultimate position) the 3' terminal non-modified nucleic acid unit. In some embodiments, the modified base is at the 3' terminal position of a nucleic acid primer, such as a primer for the detection of a single nucleotide polymorphism. Other particularly desirable nucleic acids have an LNA unit with or without a modified base in the 5' and/or 3' terminal position.

Also desirable are oligonucleotides that do not have an extended stretches of modified DNA or RNA units, e.g. greater than about 4, 5 or 6 consecutive modified DNA or RNA units. That is, desirably one or more non-modified DNA or RNA will be present after a consecutive stretch of about 3, 4 or 5 modified nucleic acids.

Generally desirable are oligonucleotides that contain a mixture of LNA units that have non-modified or natural nucleobases (i.e., adenine, guanine, cytosine, 5-methyl-cytosine, uracil, or thymine) and LNA units that have modified bases as disclosed herein.

Particularly desirable oligonucleotides of the invention include those where an LNA unit with a modified base is interposed between two LNA units each having non-modified or natural bases (adenine, guanine, cytosine, 5-methyl-cytosine, uracil, or thymine. The LNA "flanking" units with natural base moieties may be directly adjacent to the LNA with modified base moiety, or desirably is within 2, 3, 4 or 5 nucleic acid units of the LNA unit with modified base. Nucleic acid units that may be spaced between an LNA unit with a modified base and an LNA unit with natural nucleobasis suitably are DNA and/or RNA and/or alkyl-modified RNA/DNA units, typically with natural base moieties, although the DNA and or RNA units also may contain modified base moieties.

The oligonucleotides of the present invention are comprised of at least about one universal base. Oligonucleotides of the present can also be comprised, for exmple, of between about one to six 2'-Ome-RNA unit, at least about two LNA units and at least about one LNA pyrene unit.

EXAMPLE 25

Exemplary Target Nucleic Acids

In the practice of the present invention, target genes may be suitably single-stranded or double-stranded DNA or RNA; however, single-stranded DNA or RNA targets are desirable. It is understood that the target to which the nucleic acids of the invention are directed include allelic forms of the targeted gene and the corresponding mRNAs including splice variants. There is substantial guidance in the literature for selecting particular sequences for nucleic acids with LNA or other high affinity nucleotides given a knowledge of the sequence of the target polynucleotide, e.g., Peyman and Ulmann, *Chemical Reviews*, 90:543-584, 1990; Crooke, *Ann. Rev. Pharmacol. Toxicol.*, 32:329-376 (1992); and Zamecnik and Stephenson, *Proc. Natl. Acad. Sci.*, 75:280-284 (1974). Desirable mRNA targets include the 5' cap site, tRNA primer binding site, the initiation codon site, the mRNA donor splice site, and the mRNA acceptor splice site, e.g., Goodchild et al., U.S. Pat. No. 4,806,463.

EXAMPLE 26

Exemplary Applications of Present Methods

The chimeric oligos of the present invention are highly suitable for a variety of diagnostic purposes such as for the isolation, purification, amplification, detection, identification, quantification, or capture of nucleic acids such as DNA, mRNA or non-protein coding cellular RNAs, such as tRNA, rRNA, snRNA and scRNA, or synthetic nucleic acids, in vivo or in vitro.

The oligomer can comprise a photochemically active group, a thermochemically active group, a chelating group, a reporter group, or a ligand that facilitates the direct or indirect detection of the oligomer or the immobilization of the oligomer onto a solid support. Such group are typically attached to the oligo when it is intended as a probe for in situ hybridization, in Southern hybridization, Dot blot hybridization, reverse Dot blot hybridization, or in Northern hybridization.

When the photochemically active group, the thermochemically active group, the chelating group, the reporter group, or the ligand includes a spacer (K), the spacer may suitably comprise a chemically cleavable group.

An additional object of the present invention is to provide oligonucleotides which combines an increased ability to discriminate between complementary and mismatched targets with the ability to act as substrates for nucleic acid active enzymes such as for example DNA and RNA polymerases, ligases, phosphatases. Such oligonucleotides may be used for instance as primers for sequencing nucleic acids and as primers in any of the several well known amplification reactions, such as the PCR reaction.

Introduction of LNA monomers with natural bases into either DNA, RNA, or pure LNA oligonucleotides can result in extremely high thermal stability of duplexes with complementary DNA or RNA, while at the same time obeying the Watson-Crick base-pairing rules. In general, the thermal stability of heteroduplexes is increased 3-8° C. per LNA monomer in the duplex. Oligonucleotides containing LNA can be designed to be substrates for polymerases (e.g., Taq polymerase), and PCR based on LNA primers is more discriminatory towards single base mutations in the template DNA compared to normal DNA-primers (e.g., allele specific PCR). Furthermore, very short LNA oligos (e.g. 5-mers or 8-mers) which have high $T_m$'s when compared to similar DNA oligos can be used as highly specific catching probes with outstanding discriminatory power towards single base mutations (e.g., SNP detection).

LNA oligonucleotides are capable of hybridizing with double-stranded DNA target molecules as well as RNA secondary structures by strand invasion as well as of specifically blocking a wide selection of enzymatic reactions such as, digestion of double-stranded DNA by restriction endonucleases; and digestion of DNA and RNA with deoxyribonucleases and ribonucleases, respectively.

In a further aspect, oligonucleotides of the invention may be used to construct new affinity pairs with exhibit enhanced specificity towards each other. The affinity constants can easily be adjusted over a wide range and a vast number of affinity pairs can be designed and synthesized. One part of the affinity pair can be attached to the molecule of interest (e.g. proteins, amplicons, enzymes, polysaccharides, antibodies, haptens, peptides, etc.) by standard methods, while the other part of the affinity pair can be attached to e.g. a solid support such as beads, membranes, micro-titer plates, sticks, tubes, etc. The solid support may be chosen from a wide range of polymer materials such as for instance polypropylene, polystyrene, polycarbonate or polyethylene. The affinity pairs may be used in selective isolation, purification, capture and detection of a diversity of the target molecules.

Oligonucleotides of the invention also may be employed as probes in the purification, isolation and detection of for instance pathogenic organisms such as viral, bacteria and fungi etc. Oligonucleotides of the invention also may be used as generic tools for the purification, isolation, amplification and detection of nucleic acids from groups of related species such as for instance rRNA from gram-positive or gram negative bacteria, fungi, mammalian cells etc.

Oligonucleotides of the invention also may be employed as an aptamer in molecular diagnostics, e.g. in RNA mediated catalytic processes, in specific binding of antibiotics, drugs, amino acids, peptides, structural proteins, protein receptors, protein enzymes, saccharides, polysaccharides, biological cofactors, nucleic acids, or triphosphates or in the separation of enantiomers from racemic mixtures by stereospecific binding.

Oligonucleotides of the invention also may be used for labeling of cells, e.g. in methods wherein the label allows the cells to be separated from unlabelled cells.

Oligonucleotides also may be conjugated to a compound selected from proteins, amplicons, enzymes, polysaccharides, antibodies, haptens, and peptides.

Kits are also provided containing one or more oligonucleotides of the invention for the isolation, purification, amplification, detection, identification, quantification, or capture of natural or synthetic nucleic acids. The kit typically will contain a reaction body, e.g. a slide or biochip. One or more oligonucleotides of the invention may be suitably immobilized on such a reaction body.

The invention also provides methods for using kits of the invention for carrying out a variety of bioassays, e.g. for diagnostic purposes. Any type of assay wherein one component is immobilized may be carried out using the substrate platforms of the invention. Bioassays utilizing an immobilized component are well known in the art. Examples of assays utilizing an immobilized component include for example, immunoassays, analysis of protein-protein interactions, analysis of protein-nucleic acid interactions, analysis of nucleic acid-nucleic acid interactions, receptor binding assays, enzyme assays, phosphorylation assays, diagnostic assays for determination of disease state, genetic profiling for drug compatibility analysis, and SNP detection (U.S. Pat. Nos. 6,316,198; 6,303,315).

Identification of a nucleic acid sequence capable of binding to a biomolecule of interest can be achieved by immobilizing a library of nucleic acids onto the substrate surface so that each unique nucleic acid was located at a defined position to form an array. The array would then be exposed to the biomolecule under conditions which favored binding of the biomolecule to the nucleic acids. Non-specifically binding biomolecules could be washed away using mild to stringent buffer conditions depending on the level of specificity of binding desired. The nucleic acid array would then be analyzed to determine which nucleic acid sequences bound to the biomolecule. Desirably the biomolecules would carry a fluorescent tag for use in detection of the location of the bound nucleic acids.

Oligonucleotides of the invention can be employed in a wide range of applications, particularly those applications involving a hybridization reaction. Oligonucleotides also may be used in DNA sequencing aiming at improved throughput in large-scale, shotgun genome sequencing projects, improved throughput in capillary DNA sequencing (e.g. ABI prism 3700) as well as at an improved method for 1) sequencing large, tandemly repeated genomic regions, 2) closing gaps in genome sequencing projects and 3) sequencing of GC-rich templates. In DNA sequencing, oligonucleotide sequencing primers are combined with LNA enhancer elements for the read-through of GC-rich and/or tandemly repeated genomic regions, which often present many challenges for genome sequencing projects. LNA may increase the specificity of certain sequencing primers and thus facilitate selection of a particular version of a repeated sequence and possibly also use strand invasion to open up recalcitrant GC rich sequences.

The incorporation of one or more universal nucleosides into the oligomer makes bonding to unknown bases possible and allows the oligonucleotide to match ambiguous or unknown nucleic acid sequences.

As discussed above, oligonucleotides of the invention may be used for therapeutic applications, e.g. as an antisense, antigene or ribozyme or double stranded nucleic acid therapeutic agents. In these therapeutic methods, one or more oligonucleotides of the invention is administered as desired to a patient suffering from or susceptible the targeted disease or disorder, e.g. a viral infection.

In an exemplary in vitro method for measuring the ability of a nucleic acid of the invention to silence a target gene, cells are cultured in standard medium supplemented with 1% fetal calf serum as previously described (Lykkesfeld et al., Int. J. Cancer 61:529-534, 1995). At the start of the experiment cells are approximately 40% confluent. The serum containing medium is removed and replaced with serum-free medium. Transfection is performed using, e.g., Lipofectin (GibcoBRL cat. No 18292-011) diluted 40× in medium without serum and combined with the oligo to a concentration of 750 nM oligo, 0.8 ug/ml Lipofectin. Then, the medium is removed from the cells and replaced with the medium containing oligo-Lipofectin complex. The cells are incubated at 37° C. for 6 hours, rinsed once with medium without serum and incubated for a further 18 hours in DME/F12 with 1% FCS at 37° C. Standard methods are used to measure the level of mRNA or protein encoded by the target gene to measure the level of gene silencing.

It is also contemplated that information on the structures assumed by a target nucleic acid may be used in the design of the probes, such that regions that are known or suspected to be involved in folding may be chosen as hybridization sites. Such an approach will reduce the number of probes that are likely to be needed to distinguish between targets of interest.

There are many methods used to obtain structural information involving nucleic acids, including the use of chemicals that are sensitive to the nucleic acid structure, such as phenanthroline/copper, EDTA-$Fe^{2+}$, cisplatin, ethylnitrosourea, dimethylpyrocarbonate, hydrazine, dimethyl sulfate, and bisulfite. Enzymatic probing using structure-specific nucleases from a variety of sources, such as the Cleavase™ enzymes (Third Wave Technologies, Inc., Madison, Wis.), Taq DNA polymerase, *E. coli* DNA polymerase I, and eukaryotic structure-specific endonucleases (e.g., human, murine and *Xenopus* XPG enzymes, yeast RAD2 enzymes), murine FEN-1 endonucleases (Harrington and Lieber, Genes and Develop., 3:1344 [1994]) and calf thymus 5' to 3' exonuclease (Murante et al., J. Biol. Chem., 269:1191 [1994]). In addition, enzymes having 3' nuclease activity such as members of the family of DNA repair endonucleases (e.g., the RrpI enzyme from *Drosophila melanogaster*, the yeast RAD1/RAD10 complex and *E. coli* Exo III), are also suitable for examining the structures of nucleic acids.

If analysis of structure as a step in probe selection is to be used for a segment of nucleic acid for which no information is available concerning regions likely to form secondary structures, the sites of structure-induced modification or cleavage must be identified. It is most convenient if the modification or cleavage can be done under partially reactive conditions (i.e., such that in the population of molecules in a test sample, each individual will receive only one or a few cuts or modifications). When the sample is analyzed as a whole, each reactive site should be represented, and all the sites may be thus identified. Using a Cleavase Fragment Length Polymorphism™ cleavage reaction as an example, when the partial cleavage products of an end labeled nucleic acid fragment are resolved by size (e.g., by electrophoresis), the result is a ladder of bands indicating the site of each cleavage, measured from the labeled end. Similar analysis can be done for chemical modifications that block DNA synthesis; extension of a primer on molecules that have been partially modified will yield a nested set of termination products. Determining the sites of cleavage/modification may be done with some degree of accuracy by comparing the products to size markers (e.g., commercially available fragments of DNA for size comparison) but a more accurate measure is to create a DNA sequencing ladder for the same segment of nucleic acid to resolve alongside the test sample. This allows rapid identification of the precise site of cleavage or modification.

EXAMPLE 27

General Reaction Conditions for Synthesis of Some Compounds of the Invention Reactions were conducted under an atmosphere of nitrogen when anhydrous solvents were used. All reactions were monitored by thin-layer chromatography (TLC) using EM reagent plates with fluorescence indicator ($SiO_2$-60, F-254). The compounds were visualized under UV light and by spraying with a mixture of 5% aqueous sulfuric acid and ethanol followed by heating. Silica gel 60 (particle size 0.040-0.063 mm, Merck) was used for flash column chromatography. NMR spectra were recorded at 300 MHz for $^1$H NMR, 75.5 MHz for $^{13}$C NMR and 121.5 MHz for $^{31}$P NMR on a Varian Unity 300 spectrometer. δ-Values are in ppm relative to tetramethyl silane as internal standard ($^1$H and $^{13}$C NMR) and relative to 85% $H_3PO_4$ as external standard ($^{31}$P NMR). Coupling constants are given in Hertz. The assignments, when given, are tentative, and the assignments of methylene protons, when given, may be interchanged. Bicyclic compounds are named according to the Von Bayer nomenclature. Fast atom bombardment mass spectra (FAB-MS) were recorded in positive ion mode on a Kratos MS50TC spectrometer. The composition of the oligonucleotides were verified by MALDI-MS on a Micromass T of Spec E mass spectrometer using a matrix of diammonium citrate and 2,6-dihydroxyacetophenone.

EXAMPLE 28

Synthesis of 1,2-O-Isopropylidene-5-O-methanesulfonyl-4-C-methanesulfonyloxymethyl-3-O-(p-methoxybenzyl)-α-D-ribofuranose [Compound 2 in Scheme 1 above]

Mesyl chloride (8.6 g, 7.5 mmol) was dropwise added to a stirred solution of 4-C-hydroxymethyl-1,2-O-isopropylidene-3-O-p-methoxybenzyl-α-D-ribofuranose [R. Yamaguchi, T. Imanishi, S. Kohgo, H. Horie and H. Ohrui, *Biosci. Biotechnol. Biochem.*, 1999, 63, 736] (1, 10.0 g, 29.4 mmol) in anhydrous pyridine (30 cm$^3$) and the reaction mixture was stirred overnight at room temperature. The mixture was evaporated to dryness under reduced pressure to give a residue which was co-evaporated with toluene (2×25 cm$^3$), dissolved in $CH_2Cl_2$ (200 cm$^3$) and washed successively with saturated aqueous $NaHCO_3$ (2×100 cm$^3$) and brine (50 cm$^3$). The organic phase was dried ($Na_2SO_4$), filtered and evaporated to dryness under reduced pressure. The colorless viscous oil obtained was purified by column chromatography [0.5-1% (v/v) MeOH in $CH_2Cl_2$ as eluent], followed by crystallization from MeOH to give furanose 2 as a white solid material (13.6 g, 93%); $R_f$ 0.57 ($CH_2Cl_2$/MeOH 95:5, v/v); $δ_H$ (CDCl$_3$) 7.30 (2 H, d, J 8.7), 6.90 (2 H, d, J 8.5), 5.78 (1 H, d, J 3.7), 4.86 (1 H, d, J 12.0), 4.70 (1 H, d, J 11.4), 4.62 (1 H, dd, J 5.0 and 3.8), 4.50 (1 H, d, J 11.1), 4.39 (1 H, d, J 12.3), 4.31 (1 H, d, J 11.0), 4.17 (1 H, d, J 5.1), 4.11 (1 H, d, J 11.0), 3.81 (3 H, s), 3.07 (3 H, s), 2.99 (3 H, s), 1.68 (3 H, s), 1.34 (3 H, s); $δ_c$ (CDCl$_3$) 159.8, 129.9, 128.8, 114.1, 114.0, 104.5, 83.2, 78.0, 77.9, 72.6, 69.6, 68.8, 55.4, 38.1, 37.5, 26.3, 25.7.

EXAMPLE 29

Synthesis of Methyl 5-O-methanesulfonyl-4-C-methanesulfonyloxymethyl-3-O-(p-methoxybenzyl)-D-ribofuranoside [Compound 3 in Scheme 1 above]

A suspension of furanoside 2 (13.5 g, 27.2 mmol) in a mixture of $H_2O$ (45 cm$^3$) and 15% HCl in MeOH (450 cm$^3$, w/w) was stirred at room temperature for 72 h. The mixture was carefully neutralized by addition of saturated aqueous $NaHCO_3$ (100 cm$^3$) followed by $NaHCO_3$ (s) whereupon the mixture was evaporated to dryness under reduced pressure. $H_2O$ (100 cm$^3$) was added, and extraction was performed with EtOAc (3×100 cm$^3$). The combined organic phase was washed with brine (100 cm$^3$), dried ($Na_2SO_4$), filtered and then evaporated to dryness under reduced pressure. The residue was coevaporated with toluene (2×25 cm$^3$) and purified by column chromatography [1-2% (v/v) MeOH in $CH_2Cl_2$] to give furanoside 3 as an anomeric mixture (clear oil, 11.0 g, 86%, ratio between anomers ca. 6:1); $R_f$ 0.39, 0.33 ($CH_2Cl_2$/MeOH 95:5, v/v); $δ_H$ (CDCl$_3$, major anomer only) 7.28 (2 H, d, J 8.4), 6.91 (2 H, d, J 8.9), 4.87 (1 H, s), 4.62 (1 H, d, J 11.4), 4.53 (1 H, d, J 11.2), 4.41 (2 H, s), 4.31 (1 H, d, J 9.8), 4.24 (1 H, d, J 4.6), 4.06 (1 H, d, J 10.0), 3.98 (1 H, br s), 3.81 (3 H, s), 3.33 (3 H, s), 3.06 (3 H, s), 3.03 (3 H, s); $δ_c$ (CDCl$_3$, major anomer only) 160.0, 130.1, 128.5, 114.3, 107.8, 81.7, 81.2, 73.8, 73.6, 69.7, 69.6, 55.5, 55.4, 37.5, 37.4.

EXAMPLE 30

Synthesis of (1R,3RS,4R,7S)-1-Methanesulfonyloxymethyl-3-methoxy-7-(p-methoxybenzyloxy)-2,5-dioxabicyclo[2.2.1]heptane [Compound 4 in Scheme 1 above]

To a stirred solution of the anomeric mixture of Compound 3 (10.9 g, 23.2 mmol) in anhydrous DMF (50 cm$^3$) at 0° C. was during 10 min added sodium hydride (2.28 g of a 60% suspension in mineral oil (w/w), 95.2 mmol) and the mixture was stirred for 12 h at room temperature. Ice-cold $H_2O$ (200 cm$^3$) was slowly added and extraction was performed using EtOAc (3×200 cm$^3$). The combined organic phase was washed successively with saturated aqueous $NaHCO_3$ (2×100 cm$^3$) and brine (50 cm$^3$), dried ($Na_2SO_4$), filtered and evaporated to dryness under reduced pressure. The residue was purified by column chromatography [0.5-1% (v/v) MeOH in $CH_2Cl_2$] to give first the major isomer (6.42 g, 74%) and then [1.5% (v/v) MeOH in $CH_2Cl_2$] the minor isomer (1.13 g, 13%), both as clear oils; $R_f$ 0.56, 0.45 ($CH_2Cl_2$/MeOH 95:5, v/v); $δ_H$ (CDCl$_3$, major isomer) 7.16 (2 H, d, J 8.8), 6.74 (2 H, d, J 8.4), 4.65 (1 H, s), 4.42-4.32 (4 H, m), 3.95-3.94 (2 H, m), 3.84 (1 H, d, J 7.4), 3.66 (3 H, s), 3.54 (1 H, d, J 7.4), 3.21 (3 H, s), 2.90 (3 H, s); $δ_c$ (CDCl$_3$, major isomer) 159.6, 129.5, 129.3, 114.0, 105.3, 83.2, 78.6, 77.2, 72.1, 71.8, 66.3, 55.6, 55.4, 37.8; $δ_H$ (CDCl$_3$, minor isomer) 7.27 (2 H, d, J 8.9), 6.89 (2 H, d, J 8.6), 4.99 (1 H, s), 4.63-4.39 (4 H, m), 4.19 (1 H, s), 4.10-3.94 (2 H, m), 3.91 (1 H, s), 3.81 (3 H, s), 3.47 (3 H, s), 3.05 (3 H, s); $δ_c$ (CDCl$_3$, minor isomer) 159.7, 129.6, 129.5, 114.1, 104.4, 86.4, 79.3, 77.1, 72.3, 71.9, 66.2, 56.4, 55.4, 37.7.

EXAMPLE 31

Synthesis of (1R,4R,7S)-1-Acetoxymethyl-3-methoxy-7-(p-methoxybenzyloxy)-2,5-dioxabicyclo[2.2.1]heptane [Compound 5 in Scheme 1]

To a stirred solution of furanoside 4 (major isomer, 6.36 g, 17.0 mmol) in dioxane (25 cm³) was added 18-crown-6 (9.0 g, 34.1 mmol) and KOAc (8.4 g, 85.6 mmol). The stirred mixture was heated under refluxed for 12 h and subsequently evaporated to dryness under reduced pressure. The residue was dissolved in $CH_2Cl_2$ (100 cm³) and washing was performed, successively, with saturated aqueous $NaHCO_3$ (2×50 cm³) and brine (50 cm³). The separated organic phase was dried ($Na_2SO_4$), filtered and evaporated to dryness under reduced pressure. The residue was purified by column chromatography [1% (v/v) MeOH in $CH_2Cl_2$] to give furanoside 5 as a white solid material (one anomer, 5.23 g, 91%); $R_f$ 0.63 ($CH_2Cl_2$/MeOH 95:5, v/v); $\delta_H$ (CDCl₃) 7.27-7.24 (2 H, m), 6.90-6.87 (2 H, m), 4.79 (1 H, s), 4.61 (1 H, d, J 11.0), 4.49 (2 H, m), 4.28 (1 H, d, J 11.0), 4.04 (3 H, m), 3.80 (3 H, s), 3.68 (1 H, m), 3.36 (3 H, s), 2.06 (3 H, s); $\delta_c$ (CDCl₃) 170.7, 159.5, 129.5, 129.4, 113.9, 105.1, 83.3, 78.9, 77.2, 72.0, 71.9, 61.0, 55.4, 55.3, 20.8.

EXAMPLE 32

Synthesis of (1S,4R,7S)-1-Hydroxymethyl-3-methoxy-7-(p-methoxybenzyloxy)-2,5-dioxabicyclo[2.2.1]heptane [Compound 6 in Scheme 1]

A solution of furanoside 5 (one anomer, 5.16 g, 15.3 mmol) in saturated methanolic ammonia (200 cm³) was stirred at room temperature for 48 h. The reaction mixture was evaporated to dryness under reduced pressure, coevaporated with toluene (2×50 cm³), and the residue purified by column chromatography [2-3% (v/v) MeOH in $CH_2Cl_2$] to give furanoside 6 as a white solid material (one anomer, 3.98 g, 88%); $R_f$ 0.43 ($CH_2Cl_2$/MeOH 95:5, v/v); $\delta_H$ (CDCl₃) 7.27 (2 H, d, J 8.6), 6.88 (2 H, d, J 8.9), 4.79 (1 H, s), 4.59 (1 H, d, J 11.3), 4.53 (1 H, d, J 11.4), 4.09 (2 H, s), 3.97 (1 H, d, J 7.5), 3.86 (2 H, br s), 3.80 (3 H, s), 3.75-3.62 (2 H, m), 3.37 (3 H, s); $\delta_c$ (CDCl₃) 159.4, 129.7, 129.3, 113.9, 105.2, 85.6, 78.3, 77.4, 71.9, 71.8, 58.8, 55.5, 55.3.

EXAMPLE 33

(1S,4R,7S)-3-Methoxy-7-(p-methoxybenzyloxy)-1-(p-methoxybenzyloxymethyl)-2,5-dioxabicyclo[2.2.1]heptane [Compound 7 in Scheme 1]

To a stirred solution of furanoside 6 (one anomer, 3.94 g, 13.3 mmol) in anhydrous DMF (50 cm³) at 0° C. was added a suspension of NaH [60% in mineral oil (w/w), 1.46 g, 60.8 mmol] followed by dropwise addition of p-methoxybenzyl chloride (2.74 g, 17.5 mmol). The mixture was allowed to warm to room temperature and stirring was continued for another 4 h whereupon ice-cold $H_2O$ (50 cm³) was dropwise added. The mixture was extracted with $CH_2Cl_2$ (3×100 cm³) and the combined organic phase was washed with brine (100 cm³), dried ($Na_2SO_4$), filtered, evaporated to dryness under reduced pressure and coevaporated with toluene (3×50 cm³). The residue (4.71 g) tentatively assigned as a mixture of 7 and aldehyde 11 was used in the preparation of 11 (see below) without further purification.

EXAMPLE 34

4-C-Methanesulfonyloxymethyl-3,5-di-O-(p-methoxybenzyl)-1,2-O-isopropylidene-α-D-ribofuranose [Compound 9 in Scheme 1]

4-C-Hydroxymethyl-3,5-di-O-(p-methoxybenzyl)-1,2-O-isopropylidene-α-D-ribofuranose [R. Yamaguchi, T. Imanishi, S. Kohgo, H. Horie and H. Ohrui, *Biosci. Biotechnol. Biochem.*, 1999, 63, 736] (8, 3.2 g, 6.95 mmol) was mesylated using MsCl (2.00 g, 17.5 mmol) and pyridine (10 cm³) following the procedure described for 2. After work-up, the colorless viscous oil was purified by column chromatography [1% (v/v) MeOH in $CH_2Cl_2$] to give derivative 9 in 89% yield (3.17 g) as a clear oil; $R_f$ 0.45 ($CH_2Cl_2$/MeOH 98:2, v/v); $\delta_H$ (CDCl₃) 7.22 (2 H, d, J 8.9), 7.18 (2 H, d, J 8.7), 6.86 (4 H, d, J 8.3), 5.76 (1 H, d, J 3.8), 4.83 (1 H, d, J 12.0), 4.64 (1 H, d, J 11.6), 4.59 (1 H, m), 4.49-4.35 (4 H, m), 4.24 (1 H, d, J 5.3), 3.80 (6 H, s), 3.56 (1 H, d, J 10.5), 3.45 (1 H, d, J 10.5), 3.06 (3 H, s), 1.67 (3 H, s), 1.33 (3 H, s); $\delta_c$ (CDCl₃) 159.6, 159.4, 129.9, 129.8, 129.7, 129.5, 129.4, 129.3, 114.0, 113.9, 113.8, 113.7, 113.6, 104.5, 84.9, 78.6, 78.1, 73.4, 72.4, 71.0, 69.9, 55.3, 38.0, 26.4, 25.9.

EXAMPLE 35

Methyl 4-C-methanesulfonyloxymethyl-3,5-di-O-(p-methoxybenzyl)-D-ribofuranose [Compound 10 in Scheme 1]

Methanolysis of furanoside 9 (3.1 g, 5.76 mmol) was performed using a mixture of a solution of 15% HCl in MeOH (w/w, 120 cm³) and $H_2O$ (12 cm³) following the procedure described for the synthesis of 3. After work-up, the crude product was purified by column chromatography [0.5-1% (v/v) MeOH in $CH_2Cl_2$] to give the major anomer of 10 (1.71 g, 58%) and [1-1.5% (v/v) MeOH in $CH_2Cl_2$] the minor anomer of 10 (0.47 g, 16%), both as clear oils; $R_f$ 0.31, 0.24 ($CH_2Cl_2$/MeOH 98:2, v/v); $\delta_c$ (major anomer, CDCl₃) 159.8, 159.5, 129.9, 129.8, 129.6, 129.5, 129.0, 114.2, 114.1, 114.0, 113.9, 107.9, 84.7, 79.9, 74.2, 73.5, 73.5, 70.2, 64.4, 55.6, 55.4, 37.4.

EXAMPLE 36

Alternative preparation of Compound 7 in Scheme 1

Ring closure of furanoside 10 (major anomer, 1.68 g, 3.28 mmol) was achieved using NaH (60% suspension in mineral oil (w/w), 0.32 g, 13.1 mmol) in anhydrous DMF (10 cm³) following the procedure described for the synthesis of 4 to give a crude product tentatively assigned as a mixture of furanoside 7 and aldehyde 11 (see below) (1.13 g).

EXAMPLE 37

(2R,3S,4S)-4-Hydroxy-3-(p-methoxybenzyloxy)-4-(p-methoxybenzyloxymethyl)-tetrahydrofuran-2-carbaldehyde [Compound 11 in Scheme 1]

A solution of crude furanoside 7 (as a mixture with 11 as prepared as described above, 5.80 g) in 80% glacial acetic acid (100 cm³) was stirred at 50° C. for 4 h. The solvent was distilled off under reduced pressure and the residue was successively coevaporated with absolute ethanol (3×25 cm³) and toluene (2×25 cm³) and purified by column chromatography [4-5% (v/v) MeOH in CH$_2$Cl$_2$] to give aldehyde 11 as a colorless oil (4.60 g); R$_f$ 0.37 (CH$_2$Cl$_2$/MeOH 95:5, v/v); δ$_H$ (CDCl$_3$) 9.64 (1H, br s), 7.27-7.17 (4 H, m), 6.87-6.84 (4 H, m), 4.59 (1 H, d, J 11.6), 4.51-4.41 (2 H, m), 4.35 (1 H, s), 3.92-3.90 (2 H, m), 3.79 (6 H, s), 3.77-3.68 (3 H, m), 3.55 (2 H, br s); δ$_c$ (CDCl$_3$) 203.6, 159.5, 159.4, 129.7, 129.6, 129.5, 129.2, 114.0, 113.9, 113.8, 87.3, 86.7, 81.0, 75.1, 73.4, 71.6, 67.6, 55.3.

EXAMPLE 38

General Procedure for the Reaction of Aryl Magnesium Bromides with Aldehyde 11 to Give Compounds 12a-e in Scheme 2

A solution of aldehyde 11 (Scheme 2) in anhydrous THF (10 cm$^3$) was added dropwise during 5 min to a stirred solution of the aryl magnesium bromide dissolved in anhydrous THF at 0° C. The mixture was allowed to heat to room temperature and stirred for 12 h. The mixture was evaporated to dryness under reduced pressure and the residue diluted with CH$_2$Cl$_2$ and washed several times with saturated aqueous NH$_4$Cl. The organic phase was dried (Na$_2$SO$_4$), filtered, and evaporated to dryness under reduced pressure. Column chromatography of the crude product obtained afforded the compounds 12a-e as shown in Scheme 2.

EXAMPLE 38a

Synthesis of (2S,3S,4S)-4-Hydroxy-2-[(R)-hydroxy (phenyl)methyl]-4-(p-methoxybenzyloxy)-3-(p-methoxybenzyloxymethyl)tetrahydrofuran [Compound 12a of Scheme 2]

Grignard reaction of phenylmagnesium bromide (1.0 M solution in THF, 14.2 cm$^3$, 14.2 mmol) with aldehyde 11 (515 mg, 1.28 mmol) afforded 12a as shown in Scheme 2. The crude product was purified by column chromatography [4% (v/v) MeOH in CH$_2$Cl$_2$] to give tetrahydrofuran 12a (540 mg, 88%) as a colorless oil; R$_f$ 0.34 (CH$_2$Cl$_2$/MeOH 95:5, v/v); δ$_H$ (CDCl$_3$) 7.40-7.19 (7 H, m), 6.91-6.73 (6 H, m), 4.73 (1 H, d, J 6.4), 4.48 (2 H, s), 4.08 (2 H, s), 3.88 (1 H, d, J 9.4), 3.79 (1 H, m), 3.78 (3 H, s), 3.76 (3 H, s), 3.75-3.69 (2 H, m), 3.50 (1 H, d, J 9.4), 3.45 (1 H, s), 3.42 (1 H, br s), 3.26 (1 H, br s); δ$_c$ (CDCl$_3$) 159.5, 159.3, 140.7, 129.7, 129.6, 129.5, 129.2, 128.5, 128.0, 127.3, 113.9, 113.8, 113.7, 89.4, 84.6, 81.8, 75.3, 74.7, 73.5, 71.6, 69.3, 55.3; m/z (FAB) 503 [M+Na]$^+$, 479 [M−H]$^+$, 461 [M−H−H$_2$O]$^+$.

EXAMPLE 38b

Synthesis of (2S,3S,4S)-4-Hydroxy-2-[(R)-hydroxy (4-fluoro-3-methylphenyl)-methyl]-4-(p-methoxybenzyloxy)-3-(p-methoxybenzyloxymethyl)tetrahydrofuran [Compound 12b of Scheme 2]

Grignard reaction of 4-fluoro-3-methylphenylmagnesium bromide (1.0 M solution in THF, 15.0 cm$^3$, 15.0 mmol) with aldehyde 11 (603 mg, 1.5 mmol) afforded 12b as shown in Scheme 2. The crude product was purified by column chromatography [4-5% (v/v) MeOH in CH$_2$Cl$_2$] to give tetrahydrofuran 12b (611 mg, 85%) as a colorless oil; R$_f$ 0.34 (CH$_2$Cl$_2$/MeOH 95:5, v/v); δ$_H$ (CDCl$_3$) 7.24-7.12 (5 H, m), 6.98-6.84 (5 H, m), 6.77 (1 H, d, J 8.5), 4.65 (1 H, dd, J 2.8 and 6.4), 4.49 (2 H, s), 4.15 (2 H, s), 4.01 (1 H, dd, J 2.3 and 6.5), 3.87 (1 H, d, J 9.3), 3.79 (3 H, s), 3.78 (3 H, s), 3.76-3.68 (2 H, m), 3.52 (1 H, s), 3.47 (1 H, d, J 10.3), 3.42 (1 H, d, J 2.9), 3.22 (1 H, s), 2.24 (3 H, d, J 0.8); δ$_c$ (CDCl$_3$) 162.7, 159.5, 159.4, 136.2, 136.1, 130.3, 130.2, 129.7, 129.6, 129.5, 129.4, 129.1, 126.1, 126.0, 115.1, 114.8, 114.0, 113.9, 113.8, 89.3, 84.5, 81.8, 75.3, 74.0, 73.5, 71.7, 69.2, 55.4, 55.3, 14.7 (d, J 3.9); m/z (FAB) 535 [M+Na]$^+$, 511 [M−H]$^+$, 493 [M−H−H$_2$O]$^+$.

EXAMPLE 38c

Synthesis of (2S,3S,4S)-4-Hydroxy-2-[(R)-hydroxy (1-naphtyl)methyl]-4-(p-methoxybenzyloxy)-3-(p-methoxybenzyloxymethyl)tetrahydrofuran [Compound 12c of Scheme 2]

1-Bromonaphthalene (1.55 g, 7.5 mmol) was added to a stirred mixture of magnesium turnings (182 mg, 7.5 mmol) and iodine (10 mg) in THF (10 cm$^3$). The mixture was stirred at 40° C. for 1 h whereupon it was allowed to cool to room temperature. A solution of aldehyde 11 (603 mg, 1.5 mmol) in THF (10 cm$^3$) was added slowly and the reaction mixture was stirred for 12 h. The crude product was purified by column chromatography [4-5% (v/v) MeOH in CH$_2$Cl$_2$] to give tetrahydrofuran 12c (756 mg, 95%) as a colorless oil; R$_f$ 0.35 (CH$_2$Cl$_2$/MeOH 95:5, v/v); δ$_H$ (CDCl$_3$) 8.08 (1 H, m), 7.86 (1 H, m), 7.79 (1 H, d, J 8.2), 7.72 (1 H, d, J 7.2), 7.49-7.44 (3 H, m), 7.18 (2 H, d, J 8.4), 6.84 (2 H, d, J 8.6), 6.74 (2 H, d, J 8.7), 6.68 (2 H, d, J 8.8), 5.52 (1 H, dd, J 3.7 and 5.6), 4.45 (2 H, s), 4.34 (1 H, dd, J 2.5 and 5.9), 4.03 (1 H, d, J 11.0), 3.96 (1 H, d, J 11.0), 3.93 (1 H, d, J 9.5), 3.80 (1 H, d, J 9.3), 3.77 (3 H, s), 3.75 (1 H, d, J 2.6), 3.72 (3 H, s), 3.68 (1 H, d, J 9.3), 3.56 (1 H, d, J 3.7), 3.49 (1 H, d, J 9.3), 3.34 (1 H, s); δ$_c$ (CDCl$_3$) 159.5, 159.3, 136.3, 134.0, 131.0, 129.7, 129.6, 129.5, 129.4, 129.0, 128.6, 128.2, 125.6, 125.5, 123.5, 114.0, 113.8, 113.7, 88.7, 84.7, 81.9, 75.5, 73.5, 71.7, 71.3, 69.3, 55.4, 55.3; m/z (FAB) 553 [M+Na]$^+$, 529 [M−H]$^+$, 511 [M−H−H$_2$O]$^+$.

EXAMPLE 38d (2S,3S,4S)-4-Hydroxy-2-[(R)-hydroxy(1-pyrenyl) methyl]-4-(p-methoxybenzyloxy)-3-(p-methoxybenzyloxymethyl)tetrahydrofuran [Compound 12d of Scheme 2]

Tetrahydrofuran 12d was synthesized from aldehyde 11 (515 mg, 1.28 mmol), 1-bromopyrene (1.0 g, 3.56 mmol), magnesium turnings (155 mg, 6.4 mmol), iodine (10 mg) and THF (20 cm$^3$) following the procedure described for synthesis of compound 12c. The crude product was purified by column chromatography [3-4% (v/v) MeOH in CH$_2$Cl$_2$] to give tetrahydrofuran 12d (690 mg, 89%) as a pale yellow solid; R$_f$ 0.35 (CH$_2$Cl$_2$/MeOH 95:5, v/v); δ$_H$ (CDCl$_3$) 8.23 (2 H, d, J 8.4 and 9.2), 8.19-8.13 (3 H, m), 8.05-7.99 (4 H, m), 7.14 (2 H, d, J 8.8), 6.82 (2 H, d, J 9.0), 6.30 (2 H, d, J 8.7), 6.20 (2 H, d, J 8.6), 5.87 (1 H, d, J 7.2), 4.43 (2 H, s), 4.41 (1 H, m), 4.01 (1 H, d, J 9.4), 3.91 (1 H, d, J 11.8), 3.86 (1 H, d, J 9.2), 3.77 (1 H, d, J 1.9), 3.76 (3 H, s), 3.70-3.64 (3 H, m), 3.52-3.45 (1 H, m), 3.44 (3 H, s); δ$_c$ (CDCl$_3$) 159.5, 158.9, 133.9, 131.4, 131.1, 130.7, 129.7, 129.5, 129.2, 128.9, 128.5, 127.8, 127.7, 127.5, 126.0, 125.5, 125.3, 125.2, 125.1, 125.0, 124.9, 122.9, 113.9, 113.3, 89.5, 83.5, 82.0, 75.7, 73.4, 71.3, 71.0, 69.3, 55.3, 55.0; m/z (MALDI) 627 [M+Na]$^+$, 609 [M$^+$+Na−H$_2$O]$^+$.

EXAMPLE 38e (2S,3S,4S)-4-Hydroxy-2-[(R)-hydroxy(2,4,5-trimethylphenyl)methyl]-4-(p-methoxybenzyloxy)-3-(p-methoxybenzyloxymethyl)tetrahydrofuran [Compound 12e of Scheme 2]

Tetrahydrofuran 12e was synthesized from aldehyde 11 (515 mg, 1.28 mmol), 1-bromo-2,4,5-trimethylbenzene (1.28 g, 6.4 mmol), magnesium turnings (155 mg, 6.4 mmol), iodine (10 mg) and THF (20 cm$^3$) following the procedure described for synthesis of compound 12c. The crude product was purified by column chromatography [3-4% (v/v) MeOH in $CH_2Cl_2$] to give tetrahydrofuran 12e (589 mg, 88%) as a colorless oil; $R_f$ 0.34 ($CH_2Cl_2$/MeOH 95:5, v/v); $\delta_H$ ($CDCl_3$) 7.25 (2 H, d, J 8.7), 7.21 (2 H, d, J 8.9), 6.90 (1 H, s), 6.87 (1 H, s), 6.85 (2 H, d, J 8.9), 6.76 (2 H, d, J 8.7), 4.95 (1 H, dd, J 3.6 and 5.9), 4.48 (2 H, s), 4.18-4.08 (3 H, m), 3.89 (1 H, d, J 9.6), 3.80 (1 H, m), 3.79 (3 H, s), 3.77 (3 H, s), 3.71 (1 H, d, J 9.2), 3.64 (1 H, d, J 2.6), 3.51 (1 H, d, J 9.4), 3.24 (1 H, s), 3.18 (1 H, d, J 3.4), 2.25 (3 H, s), 2.22 (3 H, s), 2.21 (3 H, s); $\delta_c$ ($CDCl_3$) 159.5, 159.3, 136.0, 135.8, 134.2, 132.5, 132.0, 129.8, 129.7, 129.6, 129.5, 128.5, 113.9, 113.8, 88.6, 84.7, 81.7, 75.4, 73.5, 71.7, 70.9, 69.4, 55.3, 19.5, 19.4, 19.0; m/z (FAB) 545 [M+Na]$^+$, 521 [M–H]$^+$, 503 [M–H–$H_2O$]$^+$.

EXAMPLE 39

General Procedure for the Cyclization of 12a-e to Give Compounds 13a-e as Shown in Scheme 2

N,N,N',N'-Tetramethylazodicarboxamide (TMAD) was added in one portion to a stirred solution of the compounds 12a-e as shown in Scheme 2 and tributylphosphine in benzene at 0° C. The mixture was stirred for 12 h at room temperature whereupon it was diluted with diethyl ether (50 cm$^3$). The organic phase was washed successively with saturated aqueous $NH_4Cl$ (2×20 cm$^3$) and brine (25 cm$^3$), dried ($Na_2SO_4$), filtered and evaporated to dryness under reduced pressure. The crude product obtained was purified by column chromatography [1.5-2% (v/v) MeOH in $CH_2Cl_2$] to give compounds 13a-e as shown in Scheme 2.

EXAMPLE 39a (1S,3S,4R,7S)-7-(p-Methoxybenzyloxy)-1-(p-methoxybenzyloxymethyl)-3-phenyl-2,5-dioxabicyclo[2.2.1]heptane [Compound 13a of Scheme 2]

Cyclization of compound 12a (540 mg, 1.13 mmol) in the presence of TMAD (310 mg, 1.8 mmol), $PBu_3$ (364 mg, 1.8 mmol) and benzene (10 cm$^3$) followed by the general work-up procedure and column chromatography afforded compound 13a as a colorless oil (400 mg, 77%); $R_f$ 0.51 ($CH_2Cl_2$/MeOH 98:2, v/v); $\delta_H$ ($CDCl_3$) 7.36-7.33 (7 H, m), 7.10 (2 H, d, J 8.3), 6.88 (2 H, d, J 8.7), 6.78 (2 H, d, J 8.7), 5.17 (1 H, s, H-3), 4.59 (2 H, br s, —$CH_2$ (MPM)), 4.43 (1 H, d, J 11.3, —$CH_2$ (MPM)), 4.34 (1 H, d, J 11.3, —$CH_2$ (MPM)), 4.19 (1 H, s, H-4), 4.09 (1 H, d, J 7.7, H-6), 4.06 (1 H, d, J 7.7, H-6), 4.01 (1 H, s, H-7), 3.82-3.77 (5 H, m, —$C_1$—$CH_2$—O—, $OCH_3$), 3.76 (3 H, s, —$OCH_3$); $\delta_c$ ($CDCl_3$) 159.4, 159.3, 139.4 (C-1'), 130.3, 129.7, 129.5, 129.3, 128.5, 127.5, 125.4, 113.9, 113.8, 85.9 (C-1), 84.1 (C-3), 81.1 (C-4), 77.4 (C-7), 73.7 (—$CH_2$ (MPM)), 73.4 (C-6), 71.8 (—$CH_2$ (MPM)), 66.3 (—$C_1$—$CH_2$—O—), 55.4 (—$OCH_3$), 55.3 (—$OCH_3$); m/z (FAB) 467 [M+Na–$H_2O$]$^+$, 461 [M–H]$^+$.

EXAMPLE 39b (1S,3S,4R,7S)-3-(4-Fluoro-3-methylphenyl)-7-(p-methoxybenzyloxy)-1-(p-methoxybenzyloxymethyl)-2,5-dioxabicyclo[2.2.1]heptane [Compound 13b of Scheme 2]

Cyclization of compound 12b (550 mg, 1.08 mmol) in the presence of TMAD (275 mg, 1.6 mmol), $PBu_3$ (325 mg, 1.6 mmol) and benzene (10 cm$^3$) followed by the general work-up procedure and column chromatography afforded compound 13b as a colorless oil (445 mg, 84%); $R_f$ 0.52 ($CH_2Cl_2$/MeOH 98:2, v/v); $\delta_H$ ($CDCl_3$) 7.28 (2 H, d, J 8.7), 7.11 (2 H, d, J 8.6), 7.08-7.09 (2 H, m, H-2' and H-6'), 6.94 (1 H, dd, J 8.5 and 9.2, H-5'), 6.88 (2 H, d, J 8.6), 6.79 (2 H, d, J 8.4), 5.08 (1 H, s, H-3), 4.62-4.55 (2 H, m, —$CH_2$ (MPM)), 4.45 (1 H, d, J 11.1, —$CH_2$ (MPM)), 4.36 (1 H, d, J 11.6, —$CH_2$ (MPM)), 4.13 (1 H, s, H-4), 4.07, 4.03 (1 H each, 2d, J 7.6 each, H-6), 3.99 (1 H, s, H-7), 3.81 (2 H, m, —$C_1$—$CH_2$—O—), 3.80 (3 H, s, —$OCH_3$), 3.77 (3H, s, —$OCH_3$), 2.23 (3 H, d, J 1.6, Ar—$CH_3$); $\delta^c$ ($CDCl_3$) 162.3 (C-4'), 159.4, 159.3, 134.8, 134.7, 130.3, 129.6, 129.5, 129.2, 128.5, 128.4, 128.3, 124.2, 115.1, 114.8, 113.9, 113.8, 85.9 (C-1), 83.5 (C-3), 81.0 (C-4), 77.1 (C-7), 73.6 (—$CH_2$ (MPM)), 73.4 (C-6), 71.8 (—$CH_2$ (MPM)), 66.2 (—$C_1$—$CH_2$—O—), 55.4 (—$OCH_3$), 55.3 (—$OCH_3$), 14.7 (d, J 3.3, Ar—$CH_3$); m/z (FAB) 494 [M]$^+$, 493 [M–H]$^+$.

EXAMPLE 39c (1S,3S,4R,7S)-7-(p-Methoxybenzyloxy)-1-(p-methoxybenzyloxymethyl)-3-(1-naphthyl)-2,5-dioxabicyclo[2.2.1]heptane [Compound 13c of Scheme 2]

Cyclization of compound 12c (700 mg, 1.32 mmol) in the presence of TMAD (345 mg, 2.0 mmol), $PBu_3$ (405 mg, 2.0 mmol) and benzene (15 cm$^3$) followed by the general work-up procedure and column chromatography afforded compound 13c as a colorless oil (526 mg, 78%); $R_f$ 0.53 ($CH_2Cl_2$/MeOH 98:2, v/v); $\delta_H$ ($CDCl_3$) 7.91-7.86 (2 H, m), 7.78 (1 H, d, J 8.2), 7.73 (1 H, d, J 7.1), 7.53-7.46 (3 H, m), 7.32 (2 H, d, J 8.7), 7.04 (2 H, d, J 8.7), 6.90 (2 H, d, J 8.3), 6.71 (2 H, d, J 8.6), 5.79 (1 H, s, H-3), 4.67-4.61 (2 H, m, —$CH_2$ (MPM)), 4.43 (1 H, s, H-4), 4.38 (1 H, d, J 11.2, —$CH_2$ (MPM)), 4.27 (1 H, d, J 10.9, —$CH_2$ (MPM)), 4.16 (2 H, br s, H-6), 4.08 (1 H, s, H-7), 3.91, 3.87 (1 H each, 2d, J 11.0 each, —$C_1$—$CH_2$—O—), 3.81 (3 H, s, —$OCH_3$), 3.72 (3 H, s, —$OCH_3$); $\delta_c$ ($CDCl_3$) 159.3, 134.6 (C-1'), 133.5, 130.3, 129.8, 129.7, 129.4, 129.3, 128.9, 128.1, 126.4, 125.8, 125.6, 123.8, 122.7, 113.9, 113.7, 85.7 (C-1), 82.3 (C-3), 79.9 (C-4), 78.2 (C-7), 73.7 (—$OCH_2$ (MPM)), 73.5 (C-6), 71.8 (—$OCH_2$ (MPM)), 66.3 (—$C_1$—$CH_2$—O—), 55.4 (—$OCH_3$), 55.3 (—$OCH_3$); m/z (FAB) 512 [M]$^+$, 511 [M–H]$^+$.

EXAMPLE 39d (1S,3S,4R,7S)-7-(p-Methoxybenzyloxy)-1-(p-methoxybenzyloxymethyl)-3-(1-pyrenyl)-2,5-dioxabicyclo[2.2.1]heptane [Compound 13d of Scheme 2]

Cyclization of compound 12d (650 mg, 1.08 mmol) in the presence of TMAD (275 mg, 1.6 mmol), $PBu_3$ (325 mg, 1.6 mmol) and benzene (10 cm³) followed by the general work-up procedure and column chromatography afforded compound 13d as a pale yellow solid (496 mg, 79%); $R_f$ 0.53 (CH$_2$Cl$_2$/MeOH 98:2, v/v); $\delta_H$ (CDCl$_3$) 8.29 (1 H, d, J 8.2), 8.18-8.12 (5 H, m), 8.08-8.01 (2 H, m), 7.96 (1 H, d, J 7.5), 7.35 (2 H, d, J 8.5), 6.97 (2 H, d, J 8.9), 6.92 (2 H, d, J 8.8), 6.60 (2 H, d, J 8.8), 6.09 (1 H, s, H-3), 4.71-4.65 (2 H, m, —CH$_2$ (MPM)), 4.49 (1 H, s, H-4), 4.34 (1 H, d, J 11.4, —CH$_2$ (MPM)), 4.23 (1 H, d, J 11.1, —CH$_2$ (MPM)), 4.25 (1 H, d, J 7.6, H-6), 4.21 (1 H, d, J 7.8, H-6), 4.16 (1 H, s, H-7), 3.95-3.94 (2 H, m, —C$_1$—CH$_2$—O—), 3.81 (3 H, s, —OCH$_3$), 3.59 (3 H, s, —OCH$_3$); $\delta_c$ (CDCl$_3$) 159.4, 159.3, 132.2 (C-1'), 131.4, 130.8, 130.7, 130.4, 129.5, 129.4, 128.0, 127.5, 127.4, 126.9, 126.1, 125.6, 125.4, 124.9, 124.8, 124.7, 123.6, 122.0, 113.9, 113.7, 85.9 (C-1), 82.7 (C-3), 80.6 (C-4), 77.9 (C-7), 73.9 (—OCH$_2$ (MPM)), 73.5 (C-6), 71.8 (—OCH$_2$ (MPM)), 66.3 (—C$_1$—CH$_2$—O—), 55.4 (—OCH$_3$), 55.2 (—OCH$_3$); m/z (FAB) 587 [M+H]$^+$, 586 [M]$^+$.

EXAMPLE 39e (1S,3S,4R,7S)-7-(p-Methoxybenzyloxy)-1-(p-methoxybenzyloxymethyl)-3-(2,4,5-trimethylphenyl)-2,5-dioxa bicyclo[2.2.1]heptane [Compound 13e of Scheme 2]

Cyclization of compound 12e (550 mg, 1.05 mmol) in the presence of TMAD (275 mg, 1.6 mmol), PBu$_3$ (325 mg, 1.6 mmol) and benzene (10 cm³) followed by the general work-up procedure and column chromatography afforded compound 13e as a colorless oil (425 mg, 80%); $R_f$ 0.52 (CH$_2$Cl$_2$/MeOH 98:2, v/v); $\delta_H$ (CDCl$_3$) 7.30 (2 H, d, J 9.0), 7.24 (1 H, s, H-6'), 7.13 (2 H, d, J 8.9), 6.89 (1 H, s, H-3'), 6.88 (2 H, d, J 8.8), 6.79 (2 H, d, J 8.6), 5.18 (1 H, s, H-3), 4.64-4.57 (2 H, m, —CH$_2$ (MPM)), 4.46 (1 H, d, J 11.2, —CH$_2$ (MPM)), 4.36 (1 H, d, J 11.5, —CH$_2$ (MPM)), 4.18 (1 H, s, H-4), 4.14 (1 H, s, H-7), 4.09 (1 H, d, J 7.9, H-6), 4.04 (1 H, d, J 7.7, H-6), 3.86 (2 H, s, —C$_1$—CH$_2$—O—), 3.80 (3 H, s, —OCH$_3$), 3.76 (3 H, s, —OCH$_3$), 2.21 (6 H, s, 2×Ar—CH$_3$), 2.17 (3 H, s, Ar—CH$_3$); $\delta_c$ (CDCl$_3$) 159.4, 159.3, 135.5 (C-1'), 134.4, 134.0, 131.7, 131.3, 130.5, 129.9, 129.4, 129.2, 127.2, 113.9, 113.8, 85.6 (C-1), 82.4 (C-3), 79.4 (C-4), 77.6 (C-7), 73.5 (—OCH$_2$ (MPM)), 73.4 (C-6), 71.8 (—OCH$_2$ (MPM)), 66.3 (—C$_1$—CH$_2$—O—), 55.4 (—OCH$_3$), 55.3 (—OCH$_3$), 19.5 (—CH$_3$), 19.3 (—CH$_3$), 18.4 (—CH$_3$); m/z (FAB) 504 [M]$^+$, 503 µM–H]$^+$.

EXAMPLE 40

General Procedure for the Oxidative Removal of the P-Methoxybenzyl Groups to give Compounds 14a-e as shown in Scheme 2

To a stirred solution of Compound 13a-e in CH$_2$Cl$_2$ (containing a small amount of H$_2$O) at room temperature, was added 2,3-dichloro-5,6-dicyanoquinone (DDQ) which resulted in an immediate appearance of a deep greenish-black color which slowly faded into pale brownish-yellow. The reaction mixture was vigorously stirred at room temperature for 4 h. The precipitate was removed by filtration through a short pad of silica gel and washed with EtOAc. The combined filtrate was washed, successively, with saturated aqueous NaHCO$_3$ (2×25 cm³) and brine (25 cm³). The separated organic phase was dried (Na$_2$SO$_4$), filtered and evaporated to dryness under reduced pressure. The crude product obtained was purified by column chromatography [4-5% (v/v) MeOH in CH$_2$Cl$_2$] to give compounds 14a-e.

EXAMPLE 40a (1S,3S,4R,7S)-7-Hydroxy-1-hydroxymethyl-3-phenyl-2,5-dioxabicyclo[2.2.1]-heptane [Compound 14a of Scheme 2]

Compound 13a (400 mg, 0.86 mmol) was treated with DDQ (600 mg, 2.63 mmol) in a mixture of CH$_2$Cl$_2$ (10 cm³) and H$_2$O (0.5 cm³). After the general work-up procedure and column chromatography, compound 14a was obtained as a white solid material (128 mg, 66%); $R_f$ 0.30 (CH$_2$Cl$_2$/MeOH 9:1, v/v); $\delta_H$ ((CD$_3$)$_2$CO/CD$_3$OD; (CD$_3$)$_2$CO was added to the compound followed by addition of CD$_3$OD until a clear solution appeared) 7.40-7.22 (5 H, m), 4.99 (1 H, s), 4.09 (1 H, s), 4.04 (1 H, s), 4.01 (1 H, d, J 7.7), 3.86 (1 H, d, J 7.7), 3.90 (2 H, br s), 3.77 (2 H, br s); $\delta_c$ ((CD$_3$)$_2$CO/CD$_3$OD; (CD$_3$)$_2$CO was added to the compound followed by addition of CD$_3$OD until a clear solution appeared) 140.0, 128.2, 127.2, 125.4, 87.2, 83.7, 83.5, 72.3, 70.2, 58.4; m/z (FAB) 223 [M+H]$^+$.

EXAMPLE 40b (1S,3S,4R,7S)-3-(4-Fluoro-3-methylphenyl)-7-hydroxy-1-hydroxymethyl-2,5-dioxabicyclo[2.2.1] heptane [Compound 14b of Scheme 2]

Compound 13b (400 mg, 0.81 mmol) was treated with DDQ (570 mg, 2.5 mmol) in a mixture of CH$_2$Cl$_2$ (10 cm³) and H$_2$O (0.5 cm³). After the general work-up procedure and column chromatography, compound 14b was obtained as a white solid material (137 mg, 67%); $R_f$ 0.31 (CH$_2$Cl$_2$/MeOH 9:1, v/v); $\delta_H$ (CD$_3$OD) 7.23 (1 H, d, J 8.1), 7.19 (1 H, m), 6.99 (1 H, dd, J 8.5 and 9.3), 4.99 (1 H, s), 4.09 (1 H, s), 4.06 (1 H, s), 4.03 (1 H, d, J 7.6), 3.93-3.91 (3 H, m), 2.25 (3 H, d, J 1.4); $\delta_c$ (CD$_3$OD) 161.9 (d, J 243.3), 136.4 (d, J 3.4), 129.6 (d, J 5.0), 126.1 (d, J 22.8), 125.5 (d, J 8.0), 115.7 (d, J 22.9), 88.5, 85.0, 84.3, 73.5, 71.3, 59.4, 14.5 (d, J 3.7); m/z (FAB) 255 [M+H]$^+$.

EXAMPLE 40c (1S,3S,4R,7S)-7-Hydroxy-1-hydroxymethyl-3-(1-naphthyl)-2,5-dioxabicyclo-[2.2.1]heptane [Compound 14b of Scheme 2]

Compound 13c (475 mg, 0.93 mmol) was treated with DDQ (600 mg, 2.63 mmol) in a mixture of CH$_2$Cl$_2$ (10 cm³) and H$_2$O (0.5 cm³). After the general work-up procedure and column chromatography, compound 14c was obtained as a white solid material (170 mg, 67%); $R_f$ 0.31 (CH$_2$Cl$_2$/MeOH 9:1, v/v); $\delta_H$ (CDCl$_3$/CD$_3$OD; CD$_3$OD was added to the compound followed by addition of CDCl$_3$ until a clear solution appeared) 7.94-7.86 (2 H, m), 7.80-7.74 (2 H, m), 7.55-7.46 (3 H, m), 5.74 (1 H, s), 4.56 (2 H, br s), 4.37 (1 H, s), 4.24 (1 H, s), 4.17-4.11 (2 H, m), 4.04 (2 H, br s); $\delta_c$ (CDCl$_3$/CD$_3$OD; CD$_3$OD was added to the compound followed by addition of CDCl$_3$ until a clear solution appeared 134.7, 134.0, 130.2, 129.3, 128.6, 126.8, 126.2, 125.8, 123.8, 122.8, 87.4, 83.1, 82.2, 73.1, 71.5, 59.0; m/z (FAB) 273 [M+H]$^+$, 272 [M]$^+$.

EXAMPLE 40d (1S,3S,4R,7S)-7-Hydroxy-1-hydroxymethyl-3-(1-pyrenyl)-2,5-dioxabicyclo-[2.2.1]heptane [Compound 14d of Scheme 2]

Compound 13d (411 mg, 0.7 mmol) was treated with DDQ (570 mg, 2.5 mmol) in a mixture of $CH_2Cl_2$ (10 cm$^3$) and $H_2O$ (0.5 cm$^3$). After the general work-up procedure and column chromatography, compound 14d was obtained as a white solid material (182 mg, 75%); $R_f$ 0.32 ($CH_2Cl_2$/MeOH 9:1, v/v); $\delta_H$ ($CDCl_3$/$CD_3OD$; $CD_3OD$ was added to the compound followed by addition of $CDCl_3$ until a clear solution appeared) 8.32 (1 H, d, J 7.8), 8.23-8.18 (5 H, m), 8.06 (2 H, br s), 8.01 (1 H, d, J 7.6), 6.06 (1H, s), 4.47 (1 H, s), 4.36 (1 H, s), 4.27-4.18 (2 H, m), 4.10 (2 H, br s); $\delta_c$ ($CDCl_3$/$CD_3OD$) 132.2, 131.0, 128.5, 127.8, 127.3, 126.5, 125.9, 125.7, 125.1, 123.6, 122.1, 87.7, 83.7, 82.6, 73.1, 71.4, 58.9; m/z (FAB) 347 [M+H]$^+$, 346 [M]$^+$.

EXAMPLE 40e (1S,3S,4R,7S)-7-Hydroxy-1-hydroxymethyl-3-(2,4,5-trimethylphenyl)-2,5-dioxabicyclo[2.2.1]heptane [Compound 14e of Scheme 2]

Compound 13e (355 mg, 0.7 mmol) was treated with DDQ (570 mg, 2.5 mmol) in a mixture of $CH_2Cl_2$ (10 cm$^3$) and $H_2O$ (0.5 cm$^3$). After the general usual work-up procedure and column chromatography, compound 14e was obtained as a white solid material (120 mg, 65%); $R_f$ 0.31 ($CH_2Cl_2$/MeOH 9:1, v/v); $\delta_H$ ($CDCl_3$/$CD_3OD$; $CD_3OD$ was added to the compound followed by addition of $CDCl_3$ until a clear solution appeared) 7.23 (1 H, s), 6.92 (1 H, s), 5.14 (1 H, s), 4.26 (1 H, s), 4.10 (1 H, s), 4.08, (1 H, d, J 7.7), 4.00-3.95 (3 H, m), 2.23 (6 H, s), 2.21 (1 H, s); ($CDCl_3$/$CD_3OD$; $CD_3OD$ was added to the compound followed by addition of $CDCl_3$ until a clear solution appeared) 135.6, 133.9, 133.8, 131.7, 131.2, 126.6, 86.6, 82.1, 81.9, 72.3, 70.6, 58.5, 19.2, 19.0, 18.1; m/z (FAB) 265 [M+H]$^+$, 264 [M]$^+$.

EXAMPLE 41

General Procedure for Dimethoxytritylation of Compounds 14a-e to Give Compounds 15a-e as Shown in Scheme 2

4,4'-Dimethoxytrityl chloride (DMTC1) was added in one portion to a stirred solution of compound 14a-e in anhydrous pyridine. After stirring the mixture at room temperature for 4 h, methanol (0.2 cm$^3$) was added and the resulting mixture was evaporated to dryness under reduced pressure. The residue was coevaporated with anhydrous $CH_3CN$ (2×5 cm$^3$) and anhydrous toluene (2×5 cm$^3$) and then dissolved in $CH_2Cl_2$ (20 cm$^3$, traces of acid removed by filtration through a short pad of basic alumina). The resulting solution was washed, successively, with saturated aqueous $NaHCO_3$ (2×10 cm$^3$) and brine (10 cm$^3$). The separated organic phase was dried ($Na_2SO_4$), filtered and evaporated to dryness under reduced pressure. The crude product obtained was purified by column chromatography [0.25-0.50% (v/v) MeOH in $CH_2Cl_2$, containing 0.5% $Et_3N$] affording compounds 15a-e.

EXAMPLE 41a (1R,3S,4R,7S)-1-(4,4'-Dimethoxytrityloxymethyl)-7-hydroxy-3-phenyl-2,5-dioxabicyclo[2.2.1]heptane [Compound 15a of Scheme 2]

Dimethoxytritylation of compound 14a (108 mg, 0.49 mmol) using DMTCl (214 mg, 0.63 mmol) in anhydrous pyridine (2 cm$^3$) followed by the general work-up procedure and column chromatography afforded compound 15a as a white solid material (180 mg, 71%); $R_f$ 0.31 ($CH_2Cl_2$/MeOH 98:2, v/v); $\delta_H$ ($CDCl_3$) 7.66-7.21 (14 H, m), 6.84 (4 H, d, J 8.8), 5.19 (1 H, s), 4.29 (1 H, s), 4.13 (1 H, s), 4.07 (1 H, d, J 8.4), 4.01 (1 H, d, J 8.3), 3.78 (6 H, s), 3.55 (1 H, d, J 10.2), 3.50 (1 H, d, J 10.7), 2.73 (1 H, br s); $\delta_c$ ($CDCl_3$) 158.6, 149.8, 144.9, 139.4, 136.2, 135.9, 135.8, 130.3, 130.2, 128.5, 128.3, 128.0, 127.6, 126.9, 125.4, 123.9, 113.3, 86.4, 86.0, 83.8, 83.4, 73.0, 71.6, 60.2, 55.3; m/z (FAB) 525 [M+H]$^+$, 524 [M]$^+$.

EXAMPLE 41b (1R,3S,4R,7S)-1-(4,4'-Dimethoxytrityloxymethyl)-3-(4-fluoro-3-methylphenyl)-7-hydroxy-2,5-dioxabicyclo[2.2.1]heptane [Compound 15b of Scheme 2]

Dimethoxytritylation of compound 14b (95 mg, 0.38 mmol) using DMTCl (129 mg, 0.42 mmol) in anhydrous pyridine (2 cm$^3$) followed by the general work-up procedure and column chromatography afforded compound 15b as a white solid material (126 mg, 61%); $R_f$ 0.32 ($CH_2Cl_2$/MeOH 98:2, v/v); $\delta_H$ ($CDCl_3$) 7.53-7.15 (11 H, m), 6.97 (1 H, dd, J 8.7 and 8.9), 6.84 (4H, d, J 8.8), 5.11 (1 H, s), 4.26 (1 H, d, J 3.9), 4.08 (1 H, s), 4.03 (1 H, d, J 8.0), 3.95 (1 H, d, J 8.0), 3.78 (6 H, s), 3.54 (1 H, d, J 10.5), 3.47 (1 H, d, J 10.1), 2.26 (3 H, d, J 1.5), 2.08 (1 H, br s); $\delta_c$ ($CDCl_3$) 160.8 (d, J 244.1), 158.7, 144.9, 135.9, 134.7, 134.6, 130.3, 130.2, 130.1, 128.5, 128.4, 128.3, 128.0, 127.0, 125.2, 124.9, 124.4, 124.3, 115.2, 114.9, 113.4, 86.5, 86.0, 83.7, 83.0, 72.9, 71.7, 60.1, 55.3, 14.8 (d, J 3.1); m/z (FAB) 556 [M]$^+$.

EXAMPLE 41c 1R,3S,4R,7S)-1-(4,4'-Dimethoxytrityloxymethyl)-7-hydroxy-3-(1-naphthyl)-2,5-dioxabicyclo[2.2.1]heptane [Compound 15c of Scheme 2]

Dimethoxytritylation of compound 14c (125 mg, 0.46 mmol) using DMTCl (170 mg, 0.5 mmol) in anhydrous pyridine (2 cm$^3$) followed by the general work-up procedure and column chromatography afforded compound 15c as a white solid material (158 mg, 60%); $R_f$ 0.35 ($CH_2Cl_2$/MeOH 98:2, v/v); $\delta_H$ ($CDCl_3$) 7.95-7.86 (3 H, m), 7.79 (1 H, d, J 8.3), 7.58-7.41 (9 H, m), 7.35-7.23 (3 H, m), 6.86 (4 H, d, J 8.8), 5.80 (1 H, s), 4.36 (1 H, s), 4.32 (1 H, d, J 6.5), 4.17 (1 H, d, J 8.3), 4.06 (1 H, d, J 8.0), 3.78 (6 H, s), 3.62-3.56 (2 H, m), 2.00 (1 H, d, J 6.6); $\delta_c$ ($CDCl_3$) 158.7, 144.9, 136.0, 135.9, 134.5, 133.6, 130.3, 129.8, 129.0, 128.3, 128.2, 128.1, 127.0, 126.5, 125.9, 125.6, 123.9, 122.6, 113.4, 86.6, 85.7, 82.5, 81.7, 73.1, 72.6, 60.2, 55.3; m/z (FAB) 575 [M+H]$^+$, 574 [M]$^+$.

EXAMPLE 41d (1R,3S,4R,7S)-1-(4,4'-Dimethoxytrityloxymethyl)-7-hydroxy-3-(1-pyrenyl)-2,5-dioxabicyclo[2.2.1]heptane [Compound 15d of Scheme 2]

Dimethoxytritylation of the compound 14d (130 mg, 0.38 mmol) using DMTCl (140 mg, 0.42 mmol) in anhydrous pyridine (2 cm³) followed by the general work-up procedure and column chromatography afforded compound 15d as a white solid material (147 mg, 61%); $R_f$ 0.37 (CH₂Cl₂/MeOH 98:2, v/v); $\delta_H$ (CDCl₃) 8.46 (1 H, d, J 8.0), 8.19-8.00 (7 H, m), 7.61 (2 H, dd, J 1.6 and 7.4), 7.48 (4 H, d, J 8.3), 7.35 (2 H, dd, J 7.2 and 7.5), 7.25 (1 H, m), 7.15 (1 H, m), 6.88 (4 H, d, J 9.0), 6.10 (1 H, s), 4.46 (1 H, s), 4.43 (1 H, br s), 4.25 (1 H, d, J 8.1), 4.12 (1 H, d, J 8.1), 3.79 (6H, s), 3.71-3.63 (2 H, m), 2.22 (1 H, br s); $\delta_c$ (CDCl₃) 158.7, 149.8, 144.9, 136.1, 136.0, 135.9, 132.1, 131.4, 130.9, 130.6, 130.3, 130.2, 129.2, 129.1, 128.4, 128.3, 128.2, 128.1, 127.5, 127.4, 127.0, 126.9, 126.2, 125.5, 125.4, 124.9, 124.8, 124.7, 123.8, 123.7, 121.9, 113.4, 86.6, 86.1, 83.2, 82.2, 73.2, 72.4, 60.3, 55.3; m/z (FAB) 649 [M+H]⁺, 648 [M]⁺.

EXAMPLE 41e (1R,3S,4R,7S)-1-(4,4'-Dimethoxytrityloxymethyl)-7-hydroxy-3-(2,4,5-trimethylphenyl)-2,5-dioxabicyclo[2.2.1]heptane [Compound 15e of Scheme 2]

Dimethoxytritylation of compound 14e (80 mg, 0.3 mmol) using DMTCl (113 mg, 0.33 mmol) in anhydrous pyridine (2 cm³) followed by the general work-up procedure and column chromatography afforded compound 15e as a white solid material (134 mg, 78%); $R_f$ 0.32 (CH₂Cl₂/MeOH 98:2, v/v); $\delta_H$ (CDCl₃) 7.55 (2 H, d, J 7.9), 7.45-7.42 (4 H, m), 7.32-7.21 (4 H, m), 6.93 (1 H, s), 6.84 (4 H, d, J 8.2), 5.20 (1 H, s), 4.40 (1 H, s), 4.08 (1 H, s), 4.04 (1 H, d, J 8.3), 3.95 (1 H, d, J 8.2), 3.78 (6 H, s), 3.56 (1 H, d, J 10.5), 3.47 (1 H, d, J 10.2), 2.24 (3 H, s), 2.22 (3 H, s), 2.19 (3 H, s); $\delta_c$ (CDCl₃) 158.6, 145.0, 136.0, 135.7, 134.4, 134.2, 131.8, 131.3, 130.3, 130.2, 128.3, 128.0, 127.2, 126.9, 113.3, 86.4, 85.7, 82.1, 81.8, 73.0, 71.8, 60.2, 55.3, 19.6, 19.3, 18.4; m/z (FAB) 567 [M+H]⁺, 566 [M]⁺.

EXAMPLE 42

General Procedure for Synthesis of the Phosphoramidite Derivatives 16a-e as Shown in Scheme 2

2-Cyanoethyl N,N'-diisopropylphosphoramidochloridite was added dropwise to a stirred solution of nucleoside 15a-e and N,N'-diisopropylethylamine (DIPEA) in anhydrous CH₂Cl₂ at room temperature. After stirring the mixture at room temperature for 6 h, methanol (0.2 cm³) was added and the resulting mixture diluted with EtOAc (20 cm³, containing 0.5% Et₃N, v/v). The organic phase was washed, successively, with saturated a. NaHCO₃ (2×10 cm³) and brine (10 cm³). The separated organic phase was dried (Na₂SO₄), filtered and evaporated to dryness under reduced pressure. The residue obtained was purified by column chromatography [25-30% (v/v) EtOAc in n-hexane containing 0.5% Et₃N] to give the amidites 16a-e.

EXAMPLE 42a

Synthesis of (1R,3S,4R,7S)-7-[2-Cyanoethoxy(diisopropylamino) phosphinoxy]-1-(4,4'-dimethoxytrityloxymethyl)-3-phenyl-2,5-dioxabicyclo[2.2.1]heptane [Compound 16a of Scheme 2]

Treatment of compound 15a (170 mg, 0.32 mmol) with 2-cyanoethyl N,N'-diisopropylphosphoramidochloridite (85 mg, 0.36 mmol) in the presence of DIPEA (0.4 cm³) and anhydrous CH₂Cl₂ (2.0 cm³) followed by the general work-up procedure and column chromatography afforded phosphoramidite 16a as a white solid material (155 mg, 66%); $R_f$ 0.45, 0.41 (CH₂Cl₂/MeOH 98:2, v/v); $\delta_p$ (CDCl₃) 149.3, 148.9.

EXAMPLE 42b (1R,3S,4R,7S)-7-[2-Cyanoethoxy(diisopropylamino) phosphinoxy]-1-(4,4'-dimethoxytrityloxymethyl)-3-(4-fluoro-3-methylphenyl)-2,5-dioxabicyclo[2.2.1]heptane [Compound 16b of Scheme 2]

Treatment of compound 15b (95 mg, 0.17 mmol) with 2-cyanoethyl N,N'-diisopropylphosphoramidochloridite (53 mg, 0.22 mmol) in the presence of DIPEA (0.3 cm³) and anhydrous CH₂Cl₂ (2.0 cm³) followed by the general work-up procedure and column chromatography afforded phosphoramidite 16b as a white solid material (85 mg, 66%); $R_f$ 0.45, 0.41 (CH₂Cl₂/MeOH 98:2, v/v); $\delta_p$ (CDCl₃) 149.3, 148.8.

EXAMPLE 42c

Synthesis of (1R,3S,4R,7S)-7-[2-Cyanoethoxy(diisopropylamino)phosphinoxy]-1-(4,4'-dimethoxytrityloxymethyl)-3-(1-naphthyl)-2,5-dioxabicyclo[2.2.1]heptane [Compound 16c of Scheme 2]

Treatment of compound 5c (158 mg, 0.28 mmol) with 2-cyanoethyl N,N'-diisopropylphosphoramidochloridite (75.7 mg, 0.32 mmol) in the presence of DIPEA (0.4 cm³) and anhydrous CH₂Cl₂ (2.0 cm³) followed by the general work-up procedure and column chromatography afforded phosphoramidite 16c as a white solid material (127 mg, 60%); $R_f$ 0.47, 0.44 (CH₂Cl₂/MeOH 98:2, v/v); $\delta_p$ (CDCl₃) 149.2, 149.1.

EXAMPLE 42d

Synthesis of (1R,3S,4R,7S)-7-[2-Cyanoethoxy(diisopropylamino) phosphinoxy]-1-(4,4'-dimethoxytrityloxymethyl)-3-(1-pyrenyl)-2,5-dioxabicyclo[2.2.1]heptane [Compound 16d of Scheme 2]

Treatment of compound 15d (140 mg, 0.22 mmol) with 2-cyanoethyl N,N'-diisopropylphosphoramidochloridite (64 mg, 0.27 mmol) in the presence of DIPEA (0.3 cm³) and anhydrous CH₂Cl₂ (2.0 cm³) followed by the general work-up procedure and column chromatography afforded phosphoramidite 16d as a white solid material (124 mg, 68%); $R_f$ 0.51, 0.47 (CH₂Cl₂/MeOH 98:2, v/v); $\delta_p$ (CDCl₃) 149.4, 149.1.

EXAMPLE 42e

Synthesis of (1R,3S,4R,7S)-7-[2-Cyanoethoxy(diisopropylamino) phosphinoxy]-1-(4,4'-dimethoxytrityloxymethyl)-3-(2,4,5-trimethylphenyl)-2,5-dioxabicyclo[2.2.1]heptane [Compound 16e of Scheme 2]

Treatment of compound 15e (130 mg, 0.23 mmol) with 2-cyanoethyl N,N'-diisopropylphosphoramidochloridite (64 mg, 0.27 mmol) in the presence of DIPEA (0.3 cm³) and anhydrous CH₂Cl₂ (2.0 cm³) followed by the general work-up procedure and column chromatography afforded phosphoramidite 16e as a white solid material (111 mg, 63%); $R_f$ 0.44, 0.42 (CH$_2$Cl$_2$/MeOH 98:2, v/v); $\delta_p$ (CDCl$_3$) 149.0.

EXAMPLE 43

Synthesis, Deprotection and Purification of Oligonucleotides

All oligomers were prepared using the phosphoramidite approach on a Biosearch 8750 DNA synthesizer in 0.2 µmol scale on CPG solid supports (BioGenex). The stepwise coupling efficiencies for phosphoramidites 16a-c (10 min coupling time) and phosphoramidites 16d and 16e (20 min coupling time) were >96% and for unmodified deoxynucleoside and ribonucleoside phosphoramidites (with standard coupling time) generally >99%, in all cases using 1H-tetrazole as activator. After standard deprotection and cleavage from the solid support using 32% aqueous ammonia (12 h, 55° C.), the oligomers were purified by precipitation from ethanol. The composition of the oligomers were verified by MALDI-MS analysis and the purity (>80%) by capillary gel electrophoresis. Selected MALDI-MS data ([M−H]$^-$; found/calcd.: ON3 2731/2733; ON4 2857/2857; ON6 3094/3093).

EXAMPLE 44

Thermal Denaturation Studies

The thermal denaturation experiments were performed on a Perkin-Elmer UV/VIS spectrometer fitted with a PTP-6 Peltier temperature-programming element using a medium salt buffer solution (10 mM sodium phosphate, 100 mM sodium chloride, 0.1 mM EDTA, pH 7.0). Concentrations of 1.5 mM of the two complementary strands were used assuming identical extinction coefficients for modified and unmodified oligonucleotides. The absorbance was monitored at 260 nm while raising the temperature at a rate of 1° C. per min. The melting temperatures ($T_m$ values) of the duplexes were determined as the maximum of the first derivatives of the melting curves obtained.

EXAMPLE 45

Synthesis of Compounds 16a-16e and Oligomers Containing Monomers 17a-17e

LNA containing the derivatives 17a-17e (FIG. 1, Scheme 1, Scheme 2), were synthesized, all based on the LNA-type 2'-O,4'-C-methylene-β-D-ribofuranosyl moiety which is known to adopt a locked C3'-endo RNA-like furanose conformation [S. Obika, D. Nanbu, Y. Hari, K. Morio, Y. In, T. Ishida, and T. Imanishi, Tetrahedron Lett., 1997, 38, 8735; S. K. Singh, P. Nielsen, A. A. Koshkin and J. Wengel, Chem. Commun., 1998, 455; A. A. Koshkin, S. K. Singh, P. Nielsen, V. K. Rajwanshi, R. Kumar, M. Meldgaard, C. E. Olsen and J. Wengel, Tetrahedron, 1998, 54, 3607; S. Obika, D. Nanbu, Y. Hari, J. Andoh, K. Morio, T. Doi and T. Imanishi, Tetrahedron Lett., 1998, 39, 5401]. The syntheses of the phosphoramidite building blocks 16a-16e suitable for incorporation of the LNA-type aryl C-glycosides 17a-17e are shown in Scheme 1 and Scheme 2 and described in details in the experimental section. In the design of an appropriate synthetic route, it was decided to utilize a reaction similar to one described recently in the literature. Thus, stereoselective attack of Grignard reagents of various heterocycles on a carbonyl group of an aldehyde corresponding to aldehyde 11 (Scheme 2) but with two O-benzyl groups instead of the two p-methoxybenzyl groups of aldehyde 11 (Scheme 2) has been reported to furnish locked-C-nucleosides [S. Obika, Y. Hari, K. Morio and T. Imanishi, Tetrahedron Lett., 2000, 41, 215; S. Obika, Y. Hari, K. Morio and T. Imanishi, Tetrahedron Lett., 2000, 41, 221]. The key intermediate in the synthetic route selected herein, namely the novel aldehyde 11 was synthesized from the known furanoside 1 [R. Yamaguchi, T. Imanishi, S. Kohgo, H. Horie and H. Ohrui, Biosci. Biotechnol. Biochem., 1999, 63, 736] following two different routes. In general, O-(p-Methoxy)benzyl protection was desirable instead of O-benzyl protection as removal of the benzyl protection at a later stage (i.e. 13→14) could also likely result in the cleavage of the benzylic O—C$_1$ bond present, e.g., in compounds 13 and 14 (Scheme 2). In one route to give aldehyde 11, regioselective p-methoxybenzylation of the furanoside 1, followed by mesylation and methanolysis yielded the anomeric mixture of the methyl furanosides 9. Base induced cyclization followed by acetyl hydrolysis afforded the aldehyde 11 in approximately 24% overall yield from 1 (Scheme 1 and Scheme 2). This yield was improved to following a different strategy. Thus, di-O-mesylation of 1 followed by methanolysis and base induced intramolecular nucleophilic attack from the 2-OH group afforded the cyclized anomeric mixture of methyl furanoside 4. Substitution of the remaining mesyloxy group of 4 with an acetate group, followed by deacetylation, p-methoxybenzylation and then acetyl hydrolysis afforded the required aldehyde 11 (Scheme 1).

Coupling of the aldehyde 11 with different aryl Grignard reagents yielded selectively one epimer of each of the compounds 12a-e in good yields (see experimental section for further details on this and other synthetic steps). Each of the diols 12a-e was cyclized under Mitsunobu conditions (TMAD, PBu$_3$) to afford the bicyclic β-C-nucleoside derivatives 13a-e. Oxidative removal of the p-methoxybenzyl protections was achieved in satisfactory yields using DDQ. Subsequent, selective 4,4'-dimethoxytritylation (to give compounds 15a-e) followed by phosphorylation afforded the phosphoramidite building blocks 16a-e in satisfactory yields. The configuration of compounds 13, and thus also compounds 11, 12 and 14-17 were assigned based on 1H NMR spectroscopy, including NOE experiments.

All oligomers were prepared in the 0.2 µmol scale using the phosphoramidite approach. The stepwise coupling efficiencies for phosphoramidites 16a-c (10 min coupling time) and phosphoramidites 16d and 16e (20 min coupling time) were >96% and for unmodified deoxynucleoside and ribonucleoside phosphoramidites (with standard coupling time) generally >99%, in all cases using 1H-tetrazole as activator. After standard deprotection and cleavage from the solid support using 32% aqueous ammonia (12 h, 55° C.), the oligomers were purified by precipitation from ethanol. The composition of the oligomers were verified by MALDI-MS analysis and the purity (>80%) by capillary gel electrophoresis.

EXAMPLE 46

Thermal Denaturation Studies to Evaluate Hybridization Properties

The hybridization of the oligonucleotides ON1-ON11 (Table 8 below) toward four 9-mer DNA targets with the central base being each of four natural bases were studied by thermal denaturation experiments ($T_m$ measurements; see the experimental section for details). Compared to the DNA reference ON1, introduction of one abasic LNA monomer Ab$^L$ (ON2) has earlier been reported to prevent the formation of a stable duplex above 0° C. (only evaluated with adenine as the opposite base) [L. Kværnø and J. Wengel, *Chem. Commun.*, 1999, 657]. With the phenyl monomer 17a (ON3), T$_m$ values in the range of 5-12° C. was observed. Thus, the phenyl moiety stabilizes the duplexes compared to Ab$^L$, but universal hybridization is not achieved as a preference for a central adenine base in the complementary target strand is indicated (Table 8). In addition, significant destabilization compared to the ON1:DNA reference duplex was observed. Results similar to those obtained for ON3 were obtained for oligomers isosequential with ON3 but containing 17b, 17c or 17e instead of 17a as the central monomer (Table 8, ON7, ON8 and ON9, respectively).

TABLE 8

Thermal denaturation experiments (T$_m$ values shown) for ON1-ON11 towards DNA complements with each of the four natural bases in the central position$^a$

| | | Y: | | | |
|---|---|---|---|---|---|
| DNA target: 3'-d(CACTYTACG) | | A | C | G | T |
| ON1 | 5'-d(GTGATATGC) | 28 | 11 | 12 | 19 |
| ON2 | 5'-d(GTGAAb$^L$ATGC) | <3 | n.d. | n.d. | n.d. |
| ON3 | 5'-d(GTGA17aATGC) | 12 | 5 | 6 | 7 |
| ON4 | 5'-d(GTGA17dATGC) | 18 | 17 | 18 | 19 |
| ON5 | 5'-d[2'-OMe(GTGATATGC)] | 35 | 14 | 19 | 21 |
| ON6 | 5'-d[2'-OMe(GT$^L$GA17dAT$^L$GC)] | 39 | 38 | 37 | 40 |
| ON7 | 5'-d(GTGA17bATGC) | 15 | 7 | 6 | 8 |
| ON8 | 5'-d(GTGA17cATGC) | 15 | 7 | 6 | 9 |
| ON9 | 5'-d(GTGA17eATGC) | 13 | 6 | 6 | 7 |
| ON10 | 5'-d[2'-OMe(GT$^L$GA17bAT$^L$GC)] | 31 | 25 | 26 | 27 |
| ON11 | 5'-d[2'-OMe(GT$^L$GA17cAT$^L$GC)] | 34 | 27 | 27 | 32 |

$^a$Melting temperatures (T$_m$ values/° C.) measured as the maximum of the first derivative of the melting curve (A$_{260}$ vs temperature) recorded in medium salt buffer (10 mM sodium phosphate, 100 mM sodium chloride, 0.1 mM EDTA, pH 7.0) using 1.5 μM concentrations of the two strands; A = adenine monomer, C = cytosine monomer, G = guanine monomer, T = thymine monomer; See FIG. 1 and/or Scheme 2 for structures of T$^L$, Ab$^L$ and 17a-17e; DNA sequences are shown as d(sequence) and 2'-OMe-RNA sequences as 2'-OMe(sequence); "n.d." denotes "not determined". The data reported for ON1 have been reported earlier [A. A. Koshkin, S. K. Singh, P. Nielsen, V. K. Rajwanshi, R. Kumar, M. Meldgaard, C. E. Olsen and J. Wengel, *Tetrahedron*, 1998, 54, 3607]. The data reported for ON2 has been reported earlier [L. Kværnø and J. Wengel, *Chem. Commun.*, 1999, 657].

The pyrene LNA nucleotide 17d (in ON4) displays more encouraging properties (Table 8). Firstly, the binding affinity towards all four complements is increased compared to ON3 (containing 17a). Secondly, universal hybridization is observed as shown by the four T$_m$ values all being within 17-19° C. With respect to universal hybridization, 17d thus parallels the pyrene DNA derivative Py [T. J. Matray and E. T. Kool, *J. Am. Chem. Soc.*, 1998, 120, 6191], but the decrease in thermal stability compared to the ON1:DNA reference is more pronounced for 17d (~10° C.) than reported for Py (~5° C. in a 12-mer polypyrimidine DNA sequence) [T. J. Matray and E. T. Kool, *J. Am. Chem. Soc.*, 1998, 120, 6191]. It therefore appears that stacking (or intercalation) by the0 pyrene moiety is not favored by the conformational restriction of the furanose ring of 17d, although comparison of the thermal stabilities of ON2, ON3 and ON4 strongly indicate interaction of the pyrene moiety within the helix.

When measured against an RNA target [3'-r(CAC-UAUACG)], the T$_m$ values (using identical experimental conditions as for the experiments descried above) of ON3 was 11.9° C. and of ON4 was 12.7° C. For oligomers ON7, ON8 and ON9 (Table 8), the corresponding T$_m$ values were 11.7, 8.8 and 10.2° C., respectively.

EXAMPLE 47

The Effect of Pyrene LNA Monomers in an RNA-Like Strand

ON5, ON6, ON10 and ON11 (see Table 8 above), were synthesized. The former being composed entirely of 2'-OMe-RNA monomers and the latter three of six 2'-OMe-RNA monomers (see FIG. 1), two LNA thymine monomers T$^L$ (see FIG. 1), and one central LNA pyrene monomer 17d (oligomer ON6), or one central monomer 17b (ON10) or 17c (ON11). A sequence corresponding to ON6 but with three T$^L$ monomers has earlier been shown to form a duplex with complementary DNA of very high thermal stability. ON6 is therefore suitable for evaluation of the effect of introducing high-affinity monomers around a universal base. As seen in Table 8, the 2'-OMe-RNA reference ON5 binds to the DNA complement with slightly increased thermal stability and conserved Watson-Crick discrimination (compared to the DNA reference ON1). Indeed, the LNA/2'-OMe-RNA chimera ON6 displays universal hybridization behavior as revealed from the four T$_m$ values (37, 38, 39 and 40° C.). All four T$_m$ values obtained for ON6 are higher than the T$_m$ values obtained for the two fully complementary reference duplexes ON1:DNA (T$_m$=28° C.) and ON5:DNA (T$_m$=35° C.).

These novel data demonstrate that the pyrene LNA monomer 17d display universal hybridization behavior both in a DNA context (ON4) and in an RNA-like context (ON6), and that the problem of decreased affinity of universal hybridization probes can be solved by the introduction of high-affinity monomers, e.g. 2'-OMe-RNA and/or LNA monomers. Increased affinities compared to ON7 and ON8 were obtained for ON10 and ON11, respectively, but universal hybridization behavior was not obtained as a preference for a central adenine base in the complementary target strand is indicated (Table 8 above).

EXAMPLE 48

Base-Pairing Selectivity in Hybridization Probes

A systematic thermal denaturation study with ON6 (Table 11) was performed to determine base-pairing selectivity. For each of the four DNA complements (DNA target strands; monomer Y=A, C, G or T) used in the study shown in Table 8 above, ON6, containing a central pyrene LNA monomer 17d, was hybridized with all four base combinations in the neighboring position towards the 3'-end of ON6 (DNA target strands; monomer Z=A, C, G or T, monomer X=T) and the same towards the 5'-end of ON6 (DNA target strands; monomer X=A, C, G or T, monomer Z=T). In all eight subsets of four data points, satisfactory to excellent Watson-Crick discrimination was observed between the match and the three mismatches (Table 11 below, ΔT$_m$ values in the range of 5-25° C.).

TABLE 11

Thermal denaturation experiments ($T_m$ values shown) to evaluate the base-pairing selectivity of the bases neighboring the universal pyrene LNA monomer 17d in the 2'-OMe-RNA/LNA chimera ON6. In the target strand [3'-d(CAC-XYZ-ACG)], the central three bases XYZ are varied among each of the four natural bases[a]
5'-[2'-OMe(GT$^L$G-A17dA-T$^L$GC)]
3'-d(CAC -X Y Z-ACG)

| XYZ | $T_m$/° C. | XYZ | $T_m$/° C. | XYZ | $T_m$/° C. | XYZ | $T_m$/° C. |
|-----|-----|-----|-----|-----|-----|-----|-----|
| TAA | 26 | TCA | 22 | TGA | 22 | TTA | 29 |
| TAC | 26 | TCC | 29 | TGC | 26 | TTG | 31 |
| TAG | 24 | TCG | 24 | TGG | 30 | TTC | 32 |
| TAT | 39 | TCT | 38 | TGT | 37 | TTT | 40 |
| AAT | 18 | ACT | 27 | AGT | 22 | ATT | 28 |
| CAT | 30 | CCT | 31 | CGT | 27 | CTT | 35 |
| GAT | 14 | GCT | 28 | GGT | 16 | GTT | 27 |
| TAT | 39 | TCT | 38 | TGT | 37 | TTT | 40 |

[a]See caption below Table 8 for abbreviations and conditions used; The data for matched neighboring bases (X = Z = T) are shown in bold.

The results reported herein have several important implications for the design of probes for universal hybridization: (1) Universal hybridization is possible with a conformationally restricted monomer as demonstrated for the pyrene LNA monomer; (2) Universal hybridization behavior is feasible in an RNA context; (3) The binding affinity of probes for universal hybridization can be increased by the introduction of high-affinity monomers without compromising the universal hybridization and the base-pairing selectivity of bases neighboring the universal base.

Based on the results reported herein, that chimeric oligonucleotides comprising pyrene and other known universal bases attached at various backbones (e.g. LNA-type monomers, ribofuranose monomers or deoxyribose monomers in 2'-OMe-RNA/LNA chimeric oligos) likewise will display attractive properties with respect to universal hybridization behavior. For example, an oligomer identical with the 2'-OMe-RNA/LNA oligo ON6 but with the 17d monomer substituted by a pyrenyl-2'-OMe-ribonucleotide monomer.

EXAMPLE 49

Chimeric Oligonucleotides

These chimeric oligonucleotides are comprised of pyrene and other known universal bases attached at various backbones (e.g. LNA-type monomers, ribofuranose monomers or deoxyribose monomers in 2'-OMe-RNA/LNA oligos). Experimentation with these chimeric oligonucleotides are for evaluating the possibility of obtaining similar results to the 2'-OMe-RNA/LNA oligo ON6 at a lower cost, for example, by substituting Py$^L$ with a pyrenyl-2'-OMe-ribonucleotide monomer.

EXAMPLE 50

The Use of LNA Oligonucleotide Microarrays Provides Superior Sensitivity and Specificity in Expression Profiling A. In vitro Synthesis of the Yeast Spike RNAs Amplification of the yeast genes was carried out by standard two-step PCR using yeast genomic DNA as template (21). In the second PCR, a poly-$T_{20}$ tail was inserted in the amplicon. The DNA fragments were ligated into the pTRIamp18 vector (Ambion, USA) using the Quick Ligation Kit (New England Biolabs, USA) according to the manufacturers instructions and transformed into E. coli DH-5α (21). Synthesis of in vitro RNA was done using the MEGAscript™ T7 Kit (Ambion, USA) according to the manufacturers instructions.

B. Design of the LNA Expression Arrays

Capture probes were designed using the OligoDesign™ software as described in the previous examples.

C. Printing and Hybridisation of the LNA Expression Microarrays

The LNA oligonucleotide microarrays were printed onto Immobilizer™ MicroArray Slides (Exiqon, Denmark) using the Packard Biochip I Arrayer (Packard, USA), with a spot volume of 2×300 pl of a 10 µM capture probe solution. Four replicas of each capture probe were printed on each slide. Mixed staged Caenorhabditis elegans worm cultures were cultivated according to standard protocols. RNA was extracted from worm samples using the FastRNA Kit, GREEN (Q-BIO, USA) according to the supplier's instructions. Fluorochrome-labelled first strand cDNA was synthesized from worm total RNA or in vitro synthesized RNA as described (22) followed by purification of the cDNA target, hybridisation of the microarrays overnight at 65° C., washing of the slides and drying of the arrays (22). The slides were scanned using a ScanArray 4000 XL scanner (Perkin-Elmer, USA), and the array data were processed using the GenePix™ Pro 4.0 software package (Axon, USA).

D. Assessment of Sensitivity and Specificity in LNA Expression Microarrays

To enable direct comparisons between LNA and DNA capture probes in measuring gene expression levels, specific oligonucleotide capture probes for the Saccharomyces cerevisiae genes SWI5 and THI4 were designed in the 3'-end of the two ORFs. The capture probes were synthesized as 50-mer DNA and corresponding LNA-modified oligonucleotides, respectively, with an LNA substitution at every 3rd nucleotide position. In addition, 40-mer DNA and LNA oligonucleotides were designed as truncated versions of the 50-mer capture probes, along with oligonucleotides with 1 to 5 consecutive mismatches positioned centrally in the 50-mer and 40-mer capture probes. All capture probes were synthesized with an anthraquinone group at the 5'-end and a hexaethyleneglycol dimer linker region (HEG2 spacer arm) enabling photocoupling onto polymer microarray slides as described in U.S. Pat. No. 6,531,591.

Figure 36:
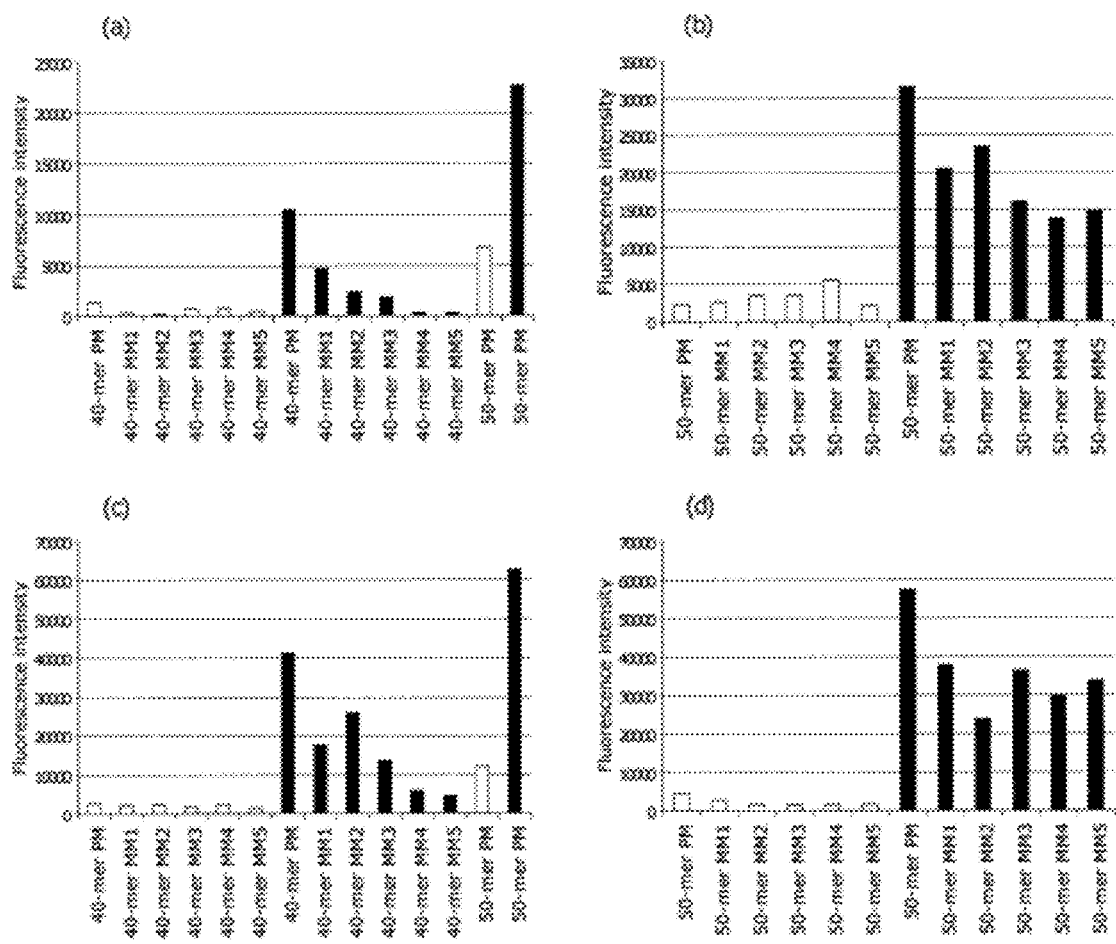
FIGS. 36a-36d show the sensitivity and specificity of LNA oligonucleotide capture probes (black solid bars) compared to DNA capture probes (white, open bars) on expression microarrays. Fluorescence intensity is shown in arbitrary units (relative measurements). The arrays comprising 50-mer and 40-mer perfect match and 1-5 mismatch capture probes were hybridized at 65° C. in 3×SSC with Cy3-labelled cDNA from 10 μg C. elegans total RNA spiked with yeast a) SWI5 RNA and c) THI4 RNA.

To assess the sensitivity and specificity of the oligonucleotide microarrays, in vitro synthesized yeast RNA for either SWI5 or THI4 was spiked into C. elegans total RNA for cDNA target synthesis followed by hybridization of the microarrays with fluorochrome-labelled cDNA target pools. The incorporation of LNA nucleotides into 50-mer DNA oligonucleotide capture probes results in a 3 to 4-fold increase in fluorescence intensity levels, when hybridized with the spiked, complex cDNA target pools under standard stringency conditions (FIGS. 36a and 36c). The sensitivity increase is even more pronounced, 5 to 12-fold, when 40-mer LNA capture probes are employed. None of the yeast capture probes showed cross-hybridization to *C. elegans* cDNA target control without yeast spike RNA under the same conditions.

The specificity of the oligonucleotide capture probes was examined using a panel of LNA mismatch oligonucleotides together with the DNA controls. As demonstrated in FIGS. 36a and 36c, the fluorescence intensities obtained with the LNA-modified 40-mer triple mismatch oligonucleotides show a 3-fold intensity decrease relative to the perfectly matched duplexes. In contrast, the corresponding 40-mer standard DNA capture probes are neither capable of forming stable duplexes nor discriminating between the perfect match and mismatched targets under standard hybridization stringency conditions, resulting in low intensity values from all 40-mer DNA capture probes (FIGS. 36a and 36c). Interestingly, mismatch discrimination with the 50-mer LNA probes could be significantly improved by increasing the hybridization temperature from 65° C. to 70° C. (FIGS. 36b and 36d), without compromising their capture sensitivity. By comparison, the signal intensities from all 50-mer DNA capture probes including the perfect match oligonucleotides were reduced under the same conditions (FIGS. 36b and 36d). Considered together, our results strongly support the contention that LNA oligonucleotide capture probes are significantly more sensitive and specific than DNA probes, being able to discriminate between highly homologous (90%) mRNAs with a 5 to 10-fold increase in sensitivity.

In a typical cell, mRNAs can be subdivided into three kinetic classes: (i) highly abundant (30-90% of the total mRNA mass, 0.1% of the sequence complexity); (ii) medium abundant (50% mass, 2-5% of complexity); and (iii) low-abundant mRNAs (<1% mass, >90% of complexity). In addition, alternative splicing has been shown to be prevalent in higher eukaryotes, where at least 50% of the genes appear to be alternatively spliced, thereby generating additional diversity within the transcriptome. It is thus of utmost importance that the dynamic range, sensitivity and specificity of the expression profiling technology used are optimal, especially when analyzing expression levels of messages and mRNA splice variants belonging to the low-abundant class of high mRNA sequence complexity. A common problem for all DNA oligonucleotide microarrays is the need for an adequate compromise with respect to the sensitivity and specificity of the platform. In the present example LNA oligonucleotide microarrays perform better in expression profiling than microarrays with corresponding DNA probes. Our results clearly demonstrate that both the specificity and sensitivity in target molecule capture can be improved using LNA oligonucleotide microarrays, enabling discrimination between highly homologous mRNAs and alternative splice variants with a simultaneous increase in sensitivity.

FIGS. 36a-36d shows the sensitivity and specificity of LNA oligonucleotide capture probes (black bars) compared to DNA capture probes (white bars) on expression microarrays. Fluorescence intensity is shown in arbitrary units (relative measurements). The arrays comprising 50-mer and 40-mer perfect match and 1-5 mismatch capture probes were hybridized at 65° C. in 3×SSC with Cy3-labelled cDNA from 10 μg *C. elegans* total RNA spiked with yeast a) SWI5 RNA and c) THI4 RNA. Demonstration of improved mismatch discrimination with the 50-mer LNA probes by increasing the hybridization temperature from 65° C. to 70° C. hybridized with Cy3-labelled cDNA from 10 μg *C. elegans* total RNA spiked with yeast b) SWI5 RNA and d) THI4 RNA.

EXAMPLE 51

Improved Sensitivity in the On-Chip Capture of Yeast HSP78 mRNA Using LNA-Substituted 25-mer Oligonucleotide Capture Probes A. Capture Probe Design Unique capture probes for the yeast HSP78 gene were designed using the OligoDesign software, described in FIGS. 19A-19F. The design options used were: (i) length of each oligonucleotide probe was 25 nucleotides; (ii) Blast word length 7; (iii) Blast expectation cut-off 1000; other options were as default; 24 DNA capture probes were selected. Furthermore, three different LNA-substituted probes were designed based on the sequences of the 24 DNA capture probes, selected by OligoDesign: optimal LNA_T, optimal LNA_TC and LNA_3. In the LNA_T design the DNA t nucleotides were substituted with LNA T. For the LNA_TC design, LNA_T and C nucleotides were used to substitute DNA t and c. In the LNA_3 design every third DNA nucleotide was substituted with the corresponding LNA nucleotide. For the LNA_T and LNA_TC design, no blocks of LNAs were allowed; in addition the LNAs were substituted in a pattern providing a more narrow duplex melting temperature range compared to the DNA Tm range. In addition, an equivalent set of capture probes with a single mismatch in the central nucleotide position was designed. Altogether, 192 capture probes were designed including a anthraquinone (AQ29) 5'-modifier and a hexaethyleneglycol dimer (HEG2) at the 5' end of each probe—as shown in Table 13.

B. Determination of the Duplex Melting Temperatures (Tm).

The duplex melting temperatures of the DNA, LNA T and LNA TC designed probes were measured using the Perkin Elmer Lambda 40 Spectrophotometer and according to Wahlestedt et al. *PNAS* 97/10 2000. All oligos were measured twice and if the replica values deviated more than 1° C., then a third or a fourth measurement was carried out. The average Tm for each oligonucleotide duplex is presented in Table 14.

C. In Vitro Synthesis of Fluorochrome-Labeled Yeast HSP78 RNA

C1. Genomic DNA was prepared from a wild type standard laboratory strain of *Saccharomyces cerevisiae* using the Nucleon MiY DNA extraction kit (Amersham Biosciences) according to supplier's instructions.

C2. PCR amplification of the partial yeast gene was done by standard PCR using yeast genomic DNA as template. In the first step of amplification, a forward primer containing a restriction enzyme site and a reverse primer containing a universal linker sequence were used. In this step 20 bp was added to the 3'-end of the amplicon, next to the stop codon. In the second step of amplification, the reverse primer was exchanged with a nested primer containing a poly-$T_{20}$ tail and a restriction enzyme site. The SWI5 amplicon contains 730 bp of the SWI5 ORF plus 20 bp universal linker sequence and a poly-$A_{20}$ tail.

The PCR primers used were:

```
YDR258C-For-SacI:
                                       (SEQ ID NO: 475)
acgtgagctcttttgacatgtcagaatttcaag YDR258C-Rev-Uni:
                                       (SEQ ID NO: 476)
gatccccgggaattgccatgttactttcagcttcctcttcaac Uni-polyT-BamHI:
                                       (SEQ ID NO: 99)
acgtggatcctttttttttttttttttttgatccccgggaattgccat
g,
```

C3. Plasmid DNA Constructs

The PCR amplicon was cut with the restriction enzymes, EcoRI+BamHI. The DNA fragment was ligated into the pTRIamp18 vector (Ambion) using the Quick Ligation Kit (New England Biolabs) according to the supplier's instructions and transformed into E. coli DH-5α by standard methods.

C4. DNA Sequencing

To verify the cloning of the PCR amplicon, plasmid DNA was sequenced using M13 forward and M13 reverse primers and analysed on an ABI 377.

C5. Biotin Labeling of cRNA

One µg of plasmid containing the HSP78 sequence was linearized with restriction enzyme BamHI (Amersham Pharmacia Biotech, USA) for 2 hours at 37° C. The RNA was labeled with biotin-CTP and biotin-UTP using the Message AMP aRNA kit from Ambion (USA) according to the manufacturer's instructions. Following hybridisation, the slides were stained with Streptavidin Phycoerythrin (Molecular Probes, S-866, USA) according to the GeneChip Expression Analysis Technical Manual (Affymetrix, USA)

C6. Fluorochrome Labeling of Spike RNA

In vitro synthesized spike RNA from the HSP78 plasmid construct was labeled with either Cy3-ULS or Cy5-ULS (Amersham Biosciences, USA) according to the manufacturer's instructions, followed by filtration through a ProbeQuant G50 Micro Column and Microcon30 (Millipore, USA). The labeling efficiency was monitored using the Nanodrop spectrophotometer (Nanodrop Technologies, USA)

D. Microarray Fabrication

The microarrays were printed on Immobilizer™ MicroArray Slides (Exiqon, Denmark) using the MicroGrid II from Biorobotics (UK) using a 20 µM capture probe solution for each oligonucleotide probe. Four replicas of each capture probe were printed on the slides.

E. Hybridization with Fluorochrome-Labelled cRNA

The arrays were hybridized for 16 hours using the following protocol. The labelled RNA samples were hybridized in a hybridization solution (20 µL final volume) containing 3×SSC (final concentration), 25 mM HEPES, pH 7.0 (final concentration), 1.25 µg/µL yeast tRNA, 0.3% SDS. The labeled RNA target sample was filtered in a Millipore 0.22 micron spin column according to the manufacturer's instructions (Millipore, USA), and the probe was denatured by incubating the reaction at 100° C. for 2 min. The sample was cooled at 20-25° C. for 5 min. by spinning at max speed in a microcentrifuge. A LifterSlip (Erie Scientific Company, USA) was carefully placed on top of the microarray spotted on Immobilizer™ MicroArray Slide and the hybridization mixture was applied to the array from the side. An aliquot of 30 µL of 3×SSC was added to both ends of the hybridization chamber, and the Immobilizer™ MicroArray Slide was placed in the hybridization chamber. The chamber was sealed watertight and incubated at 45° C., 55° C. or 65° C. for 16-18 hours submerged in a water bath. After hybridisation, the slide was removed carefully from the hybridization chamber and washed using the following protocol. The Lifterslip coverslip was washed off in 6×SSC, pH 7.0 containing 0.1% Tween20 at 50° C. for 15 min., followed by washing of the microarrays in 0.4×SSC, pH 7.0 at 50° C. for 30 min. Finally the slides were washed for 5 seconds in 0.05×SSC, pH 7.0. The slides were then dried by centrifugation in a swinging bucket rotor at approximately 200 G for 2 min.

F. Data Analysis.

Following washing and drying, the slides were scanned using a ScanArray 4000XL scanner (Perkin-Elmer Life Sciences, USA), and the array data were processed using the GenePix™ Pro 4.0 software package (Axon, USA).

G. Results

G1. Duplex Melting Temperatures

The Tm data clearly shows that LNA-substituted oligonucleotide capture probes have a significantly increased average duplex melting temperature compared to the corresponding DNA probes. Furthermore, the difference in melting temperature between the perfectly matched (PM) and single mismatched (MM) probes, designated as ΔTm, is significantly higher than the corresponding ΔTm for DNA probes (Table 12).

TABLE 12

The average difference in melting temperature between the perfectly matched (PM) and single mismatched (MM) probes in different capture probe designs.

|  | Average | Max | Min | Δ Tm | St. dev. | T-Test |
| --- | --- | --- | --- | --- | --- | --- |
| MM-DNA | 60.4 | 68.5 | 54.3 |  |  |  |
| MM- LNA T | 67.6 | 74 | 58.1 |  |  |  |
| MM-LNA TC | 72.0 | 79.3 | 61.6 |  |  |  |
| PM-DNA | 66.3 | 72.8 | 61 | 5.9 | 1.52 |  |
| PM-LNA T | 74.2 | 80.8 | 66.3 | 6.6 | 1.32 | 0.047 |
| PM-LNA TC | 80.0 | 86.8 | 71.4 | 8.0 | 2.65 | 0.001/ 0.017 |

The observed difference between the DNA and LNA substituted probes is statistically significant as revealed by a t-Test; Two-Sample Assuming Unequal Variances.

G2. Microarray Hybridization Results

Figure 37:
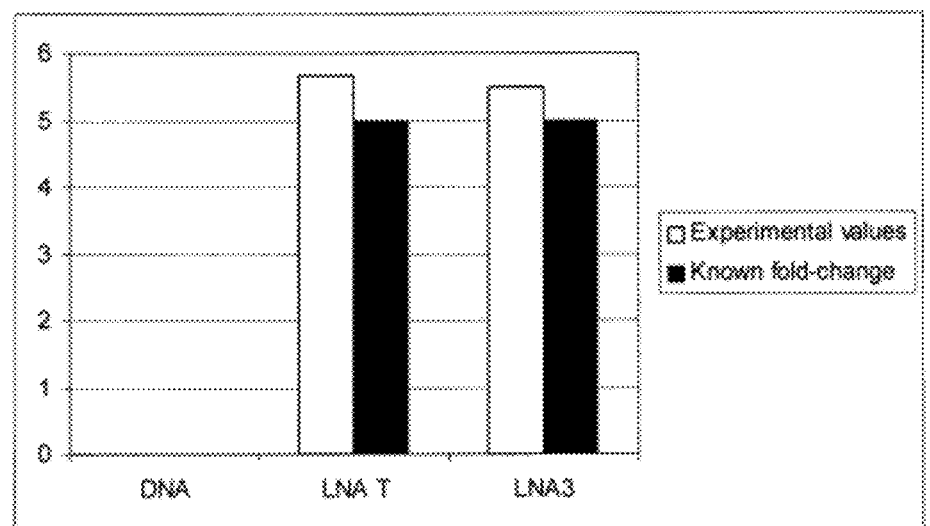
FIG. 37 shows the expected (black, solid bars) and observed (white, open bars) fold-of-change in the expression levels of the Cy3-ULS-labelled yeast HSP78 spike RNA as measured by on-chip capture using three different 25-mer oligonucleotide capture probes (DNA control, LNA-T substituted, LNA_3 substituted in which every third nucleotide was substituted with an LNA monomer). In the hybridization experiment, one ng of HSP78 in vitro spike RNA or 200 pg HSP78 in vitro spike RNA was used, respectively. Thus, the fold change of the HSP78 RNA in the two hybridizations in the comparison is 5-fold. Fourteen additional synthetic in vitro mRNA spike controls were included in the hybridisation solution as a semi-complex background RNA mixture. Seven of these spikes were used as normalization controls, the remaining seven were used as negative controls. Hybridization temperature was 65° C. for 16 hours, and post-hybridization washes as described. Both LNA_T and LNA_3 substituted 25-mer probes are capable of providing highly accurate measurements for fold-of-changes in gene expression levels, as depicted in FIG. 37. Under these conditions the DNA capture probes did not hybridize.
Figure 38:
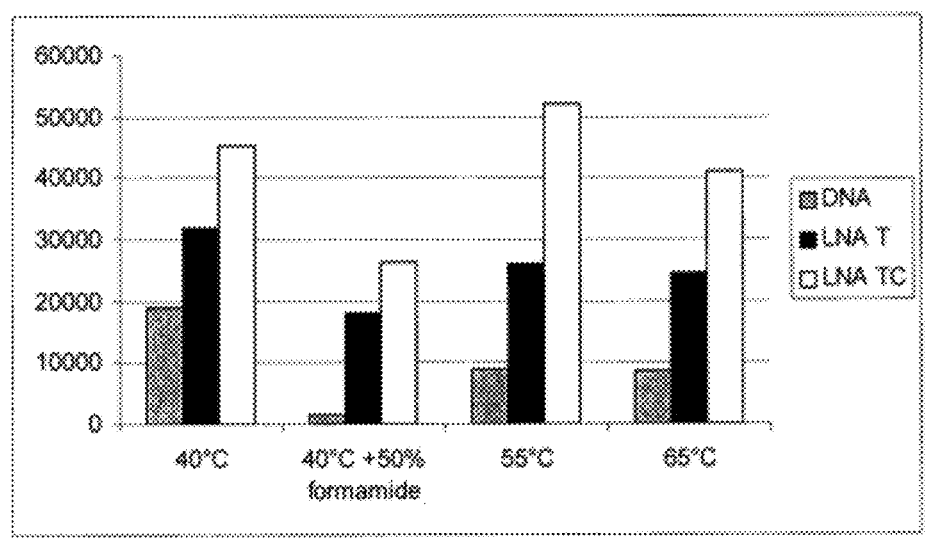
FIG. 38 shows the measured intensity levels by on-chip capture using three different 25-mer oligonucleotide capture probe designs (DNA control, LNA_T substituted and LNA C and T substituted probes). One (1) ng biotin-labeled HSP78 target was used in the hybridization experiments, followed by staining with Streptavidin Phycoerythrin. The LNA_T and LNA_TC substituted 25-mer capture probes show a significantly enhanced on-chip capture of the HSP78 RNA target, compared to the DNA 25-mer control probes under four different hybridization stringency conditions in dicated on the graph.

Both LNA_T and LNA_3 substituted 25-mer probes are capable of providing highly accurate measurements for fold-of-changes in gene expression levels, as depicted in FIG. 37. The DNA capture probes did not provide any hybridisation signals under the given microarray hybridisation conditions (FIG. 37). FIG. 37 shows the expected (black bars) and observed (white bars) fold-of-change in the expression levels of the Cy3-ULS labelled HSP78 spike RNA as measured by on-chip capture using different oligonucleotide capture probes. In the hybridization experiment, 1 ng HSP78 in vitro spike RNA or 200 pg HSP78 in vitro spike RNA was used, respectively. Thus, the fold change of the HSP78 RNA in the two hybridizations in the comparison is 5-fold. Fourteen additional synthetic in vitro mRNA spike controls were included in the hybridisation solution as a semi-complex background RNA mixture. Seven of these spikes were used as normalization controls, the other seven were used as negative controls. Hybridization temperature was 65° C. for 16 hours, and post-hybridization washes as described above. Under these conditions the DNA capture probes did not produce hybridization signals. FIG. 38 shows measured intensity levels by on-chip capture using three different 25-mer oligonucleotide capture probe designs. One (1) ng biotin-labeled HSP78 target was used in the hybridization experiments, followed by staining with Streptavidin Phycoerythrin. The LNA_T and LNA_TC substituted 25-mer capture probes show a significantly enhanced on-chip capture of the HSP78 RNA target, compared to the DNA 25-mer control probes under four different hybridization stringency conditions.

TABLE 13

Design of the yeast HSP78 capture probes.

| Oligo name | Sequence | Oligo name | Sequence |
|---|---|---|---|
| YDR258C_PM_043 | tttggtagcacgacaagcttagtat (SEQ ID NO: 477) | YDR258C_PM_043T | TTTggTagcacgacaagcTTagTat (SEQ ID NO: 478) |
| YDR258C_PM_078 | cactctaacagtttcgccgtttcta (SEQ ID NO: 479) | YDR258C_PM_078T | cacTcTaacagtTtcgccgTTTcTa (SEQ ID NO: 480) |
| YDR258C_PM_124 | gttgccatggagttcaaaatctgtc (SEQ ID NO: 481) | YDR258C_PM_124T | gTTgccaTggagTtcaaaaTcTgTc (SEQ ID NO: 482) |
| YDR258C_PM_164 | tcaatggccttgcaccatataattg (SEQ ID NO: 483) | YDR258C_PM_164T | TcaaTggccTTgcaccaTaTaaTTg (SEQ ID NO: 484) |
| YDR258C_PM_201 | tcagttagccaatccttcgcttcat (SEQ ID NO: 485) | YDR258C_PM_201T | TcagTTagccaaTccTTcgcTTcat (SEQ ID NO: 486) |
| YDR258C_PM_249 | tttttcggccaaacgatcttgaatt (SEQ ID NO: 487) | YDR258C_PM_249T | TtTTTcggccaaacgaTcTTgaaTt (SEQ ID NO: 488) |
| YDR258C_PM_295 | attgacctcaaaactttcttggata (SEQ ID NO: 489) | YDR258C_PM_295T | aTTgaccTcaaaacTTTcTTggaTa (SEQ ID NO: 490) |
| YDR258C_PM_356 | gatgaactcaggtggataggatctt (SEQ ID NO: 491) | YDR258C_PM_356T | gaTgaacTcaggTggaTaggaTcTt (SEQ ID NO: 492) |
| YDR258C_PM_424 | accatcatcacccaactttgtgtcg (SEQ ID NO: 493) | YDR258C_PM_424T | accaTcaTcacccaacTTTgTgTcg (SEQ ID NO: 494) |
| YDR258C_PM_433 | cccaactttgtgtcgtttaataaaa (SEQ ID NO: 495) | YDR258C_PM_433T | cccaacTTTgTgTcgTTTaaTaaaa (SEQ ID NO: 496) |
| YDR258C_PM_486 | caatgatcgtgttacggaaatcaac (SEQ ID NO: 497) | YDR258C_PM_486T | caaTgaTcgTgtTacggaaaTcaac (SEQ ID NO: 498) |
| YDR258C_PM_515 | tggcctagggaatcggtcagcttac (SEQ ID NO: 499) | YDR258C_PM_515T | TggccTagggaaTcggTcagcTTac (SEQ ID NO: 500) |
| YDR258C_PM_566 | ttggaaacatcggggtgcgcttttt (SEQ ID NO: 501) | YDR258C_PM_566T | TTggaaacaTcggggTgcgcTTTTt (SEQ ID NO: 502) |
| YDR258C_PM_569 | gaaacatcggggtgcgcttttttcaa (SEQ ID NO: 503) | YDR258C_PM_569T | gaaacaTcggggTgcgcTTTTTcaa (SEQ ID NO: 504) |
| YDR258C_PM_604 | aaaacgacagcataaggctttcttc (SEQ ID NO: 505) | YDR258C_PM_604T | aaaacgacagcaTaaggcTTTcTTc (SEQ ID NO: 506) |
| YDR258C_PM_631 | gacagcctcagttaattggccacca (SEQ ID NO: 507) | YDR258C_PM_631T | gacagccTcagtTaaTTggccacca (SEQ ID NO: 508) |
| YDR258C_PM_686 | ccgattaaacgagagacagtatgct (SEQ ID NO: 509) | YDR258C_PM_686T | ccgaTTaaacgagagacagTaTgct (SEQ ID NO: 510) |
| YDR258C_PM_757 | atcaaataggaattcagctaaagcc (SEQ ID NO: 511) | YDR258C_PM_757T | aTcaaaTaggaaTTcagcTaaagcc (SEQ ID NO: 512) |
| YDR258C_PM_813 | gacctaagaacataaagctggcaat (SEQ ID NO: 513) | YDR258C_PM_813T | gaccTaagaacaTaaagcTggcaat (SEQ ID NO: 514) |
| YDR258C_PM_823 | ataaagctggcaataggtctctttt (SEQ ID NO: 515) | YDR258C_PM_823T | aTaaagcTggcaaTaggTcTcTTTt (SEQ ID NO: 516) |
| YDR258C_PM_870 | agacgtacagcatcagaaatagcag (SEQ ID NO: 517) | YDR258C_PM_870T | agacgTacagcaTcagaaaTagcag (SEQ ID NO: 518) |
| YDR258C_PM_888 | aaatagcagcaatggcctcgtcttg (SEQ ID NO: 519) | YDR258C_PM_888T | aaaTagcagcaaTggccTcgTcTTg (SEQ ID NO: 520) |
| YDR258C_PM_890 | atagcagcaatggcctcgtcttggc (SEQ ID NO: 521) | YDR258C_PM_890T | aTagcagcaaTggccTcgTcTTggc (SEQ ID NO: 522) |
| YDR258C_PM_896 | gcaatggcctcgtcttggccaacga (SEQ ID NO: 523) | YDR258C_PM_896T | gcaaTggccTcgTcTTggccaacga (SEQ ID NO: 524) |

TABLE 13-continued

Design of the yeast HSP78 capture probes.

| Oligo name | Sequence | Oligo name | Sequence |
| --- | --- | --- | --- |
| YDR258C_PM_043 TC | TtTggTagmCamCgamCaagmCtTagTat (SEQ ID NO: 525) | YDR258C_PM_LNA3_043 | TttGgtAgcAcgAcaAgcTtaGtat (SEQ ID NO: 526) |
| YDR258C_PM_078 TC | mCamCtmCtaamCagtTtcgmCcgTtTmCTa (SEQ ID NO: 527) | YDR258C_PM_LNA3_078 | mCacTctAacAgtTtcGccGttTcta (SEQ ID NO: 528) |
| YDR258C_PM_124 TC | gTtgmCmCaTggagTtmCaaaaTmCtgTc (SEQ ID NO: 529) | YDR258C_PM_LNA3_124 | GttGccAtgGagTtcAaaAtcTgtc (SEQ ID NO: 530) |
| YDR258C_PM_164 TC | TmCaaTggmCcTTgmCacmCaTaTaaTTg (SEQ ID NO: 531) | YDR258C_PM_LNA3_164 | TcaAtgGccTtgmCacmCatAtaAttg (SEQ ID NO: 532) |
| YDR258C_PM_201 TC | TmCagTtagcmCaaTcmCtTmCgmCttmCat (SEQ ID NO: 533) | YDR258C_PM_LNA3_424 | AccAtcAtcAccmCaamCttTgtGtcg (SEQ ID NO: 534) |
| YDR258C_PM_249 TC | TtTtTmCggmCmCaaamCgatmCtTgaaTt (SEQ ID NO: 535) | YDR258C_PM_LNA3_486 | mCaaTgaTcgTgtTacGgaAatmCaac (SEQ ID NO: 536) |
| YDR258C_PM_295 TC | aTTgamCmCTmCaaaamCTTtmCTTggaTa (SEQ ID NO: 537) | YDR258C_PM_LNA3_515 | TggmCctAggGaaTcgGtcAgcTtac (SEQ ID NO: 538) |
| YDR258C_PM_356 TC | gaTgaamCTmCaggTggaTaggaTmCTt (SEQ ID NO: 539) | YDR258C_PM_LNA3_566 | TtgGaaAcaTcgGggTgcGctTttt (SEQ ID NO: 540) |
| YDR258C_PM_424 TC | amCcaTcaTcacmCmCaaccTtgTgtmCg (SEQ ID NO: 541) | YDR258C_PM_LNA3_569 | GaaAcaTcgGggTgcGctTttTcaa (SEQ ID NO: 542) |
| YDR258C_PM_433 TC | mCmCmCaacTTtgTgTcgTTTaaTaaaa (SEQ ID NO: 543) | YDR258C_PM_LNA3_604 | AaaAcgAcaGcaTaaGgcTttmCttc (SEQ ID NO: 544) |
| YDR258C_PM_486 TC | mCaaTgaTmCgTgtTamCggaaaTmCaac (SEQ ID NO: 545) | YDR258C_PM_LNA3_757 | AtcAaaTagGaaTtcAgcTaaAgcc (SEQ ID NO: 546) |
| YDR258C_PM_515 TC | TggmCcTagggaaTmCggTcagmCtTac (SEQ ID NO: 547) | YDR258C_PM_LNA3_813 | GacmCtaAgaAcaTaaAgcTggmCaat (SEQ ID NO: 548) |
| YDR258C_PM_566 TC | TTggaaamCatmCgggTgmCgctTtTt (SEQ ID NO: 549) | YDR258C_PM_LNA3_823 | AtaAagmCtgGcaAtaGgtmCtcTttt (SEQ ID NO: 550) |
| YDR258C_PM_569 TC | gaaamCaTmCggggTgmCgctttTtmCaa (SEQ ID NO: 551) | YDR258C_PM_LNA3_870 | AgamCgtAcaGcaTcaGaaAtaGcag (SEQ ID NO: 552) |
| YDR258C_PM_604 TC | aaaamCgamCagmCaTaaggmCTtTmCtTc (SEQ ID NO: 553) | YDR258C_PM_LNA3_888 | AaaTagmCagmCaaTggmCctmCgtmCttg (SEQ ID NO: 554) |
| YDR258C_PM_631 TC | gamCagmCcTcagtTaaTTggcmCacmCa (SEQ ID NO: 555) | YDR258C_PM_LNA3_890 | AtaGcaGcaAtgGccTcgTctTggc (SEQ ID NO: 556) |
| YDR258C_PM_686 TC | mCmCgaTTaaamCgagagamCagTaTgmCt (SEQ ID NO: 557) | YDR258C_PM_LNA3_896 | GcaAtgGccTcgTctTggmCcaAcga (SEQ ID NO: 558) |
| YDR258C_PM_757 TC | aTmCaaaTaggaaTtmCagmCTaaagmCc (SEQ ID NO: 559) | YDR258C_PM_LNA3_631 | GacAgcmCtcAgtTaaTtgGccAcca (SEQ ID NO: 560) |
| YDR258C_PM_813 TC | gamCmCTaagaamCaTaaagmCTggmCaat (SEQ ID NO: 561) | YDR258C_PM_LNA3_686 | mCcgAttAaamCgaGagAcaGtaTgct (SEQ ID NO: 562) |
| YDR258C_PM_823 TC | aTaaagmCTggmCaaTaggTmCTcTTTt (SEQ ID NO: 563) | YDR258C_PM_LNA3_356 | GatGaamCtcAggTggAtaGgaTctt (SEQ ID NO: 564) |
| YDR258C_PM_870 TC | agamCgTamCagmCaTmCagaaaTagmCag (SEQ ID NO: 565) | YDR258C_PM_LNA3_201 | TcaGttAgcmCaaTccTtcGctTcat (SEQ ID NO: 566) |
| YDR258C_PM_888 TC | aaaTagmCagmCaaTggmCcTmCgTctTg (SEQ ID NO: 567) | YDR258C_PM_LNA3_249 | TttTtcGgcmCaaAcgAtcTtgAatt (SEQ ID NO: 568) |
| YDR258C_PM_890 TC | aTagmCagcaaTggmCcTcgtmCtTggc (SEQ ID NO: 569) | YDR258C_PM_LNA3_295 | AttGacmCtcAaaActTtcTtgGata (SEQ ID NO: 570) |
| YDR258C_PM_896 TC | gcaatggcctmCgTmCttggccaacga (SEQ ID NO: 571) | YDR258C_PM_LNA3_433 | mCccAacTttGtgTcgTttAatAaaa (SEQ ID NO: 572) |
| YDR258C_MM_043 | tttggtagcacgtcaagcttagtat (SEQ ID NO: 573) | YDR258C_MM_043T | TTTggTagcacgtcaagcTTagTat (SEQ ID NO: 574) |

TABLE 13-continued

Design of the yeast HSP78 capture probes.

| Oligo name | Sequence | Oligo name | Sequence |
| --- | --- | --- | --- |
| YDR258C_MM_078 | cactctaacagtatcgccgtttcta (SEQ ID NO: 575) | YDR258C_MM_078T | cacTcTaacagtatcgccgTTTcTa (SEQ ID NO: 576) |
| YDR258C_MM_124 | gttgccatggagatcaaaatctgtc (SEQ ID NO: 577) | YDR258C_MM_124T | gTTgccaTggagatcaaaaTcTgTc (SEQ ID NO: 578) |
| YDR258C_MM_164 | tcaatggccttggaccatataattg (SEQ ID NO: 579) | YDR258C_MM_164T | TcaaTggccTTggaccaTaTaaTTg (SEQ ID NO: 580) |
| YDR258C_MM_201 | tcagttagccaaaccttcgcttcat (SEQ ID NO: 581) | YDR258C_MM_201T | TcagTTagccaaaccTTcgcTTcat (SEQ ID NO: 582) |
| YDR258C_MM_249 | tttttcggccaatcgatcttgaatt (SEQ ID NO: 583) | YDR258C_MM_249T | TtTTTcggccaatcgaTcTTgaaTt (SEQ ID NO: 584) |
| YDR258C_MM_295 | attgacctcaaatctttcttggata (SEQ ID NO: 585) | YDR258C_MM_295T | aTTgaccTcaaatcTTTcTTggaTa (SEQ ID NO: 586) |
| YDR258C_MM_356 | gatgaactcaggaggataggatctt (SEQ ID NO: 587) | YDR258C_MM_356T | gaTgaacTcaggaggaTaggaTcTt (SEQ ID NO: 588) |
| YDR258C_MM_424 | accatcatcaccgaactttgtgtcg (SEQ ID NO: 589) | YDR258C_MM_424T | accaTcaTcaccgaacTTTgTgTcg (SEQ ID NO: 590) |
| YDR258C_MM_433 | cccaactttgtgacgtttaataaaa (SEQ ID NO: 591) | YDR258C_MM_433T | cccaacTTTgTgacgTTTaaTaaaa (SEQ ID NO: 592) |
| YDR258C_MM_486 | caatgatcgtgtaacggaaatcaac (SEQ ID NO: 593) | YDR258C_MM_486T | caaTgaTcgTgtaacggaaaTcaac (SEQ ID NO: 594) |
| YDR258C_MM_515 | tggcctagggaaacggtcagcttac (SEQ ID NO: 595) | YDR258C_MM_515T | TggccTagggaaacggTcagcTTac (SEQ ID NO: 596) |
| YDR258C_MM_566 | ttggaaacatcgcggtgcgctttttt (SEQ ID NO: 597) | YDR258C_MM_566T | TTggaaacaTcgcggTgcgcTTTTt (SEQ ID NO: 598) |
| YDR258C_MM_569 | gaaacatcggggagcgcttttttcaa (SEQ ID NO: 599) | YDR258C_MM_569T | gaaacaTcggggagcgcTTTTTcaa (SEQ ID NO: 600) |
| YDR258C_MM_604 | aaaacgacagcaaaaggctttcttc (SEQ ID NO: 601) | YDR258C_MM_604T | aaaacgacagcaaaaggcTTTcTTc (SEQ ID NO: 602) |
| YDR258C_MM_631 | gacagcctcagtaaattggccacca (SEQ ID NO: 603) | YDR258C_MM_631T | gacagccTcagtaaaTTggccacca (SEQ ID NO: 604) |
| YDR258C_MM_686 | ccgattaaacgacagacagtatgct (SEQ ID NO: 605) | YDR258C_MM_686T | ccgaTTaaacgacagacagTaTgct (SEQ ID NO: 606) |
| YDR258C_MM_757 | atcaaataggaaatcagctaaagcc (SEQ ID NO: 607) | YDR258C_MM_757T | aTcaaaTaggaaatcagcTaaagcc (SEQ ID NO: 608) |
| YDR258C_MM_813 | gacctaagaacaaaaagctggcaat (SEQ ID NO: 609) | YDR258C_MM_813T | gaccTaagaacaaaaagcTggcaat (SEQ ID NO: 610) |
| YDR258C_MM_823 | ataaagctggcattaggtctctttt (SEQ ID NO: 611) | YDR258C_MM_823T | aTaaagcTggcaaaaggTcTcTTTt (SEQ ID NO: 612) |
| YDR258C_MM_870 | agacgtacagcaacagaaatagcag (SEQ ID NO: 613) | YDR258C_MM_870T | agacgTacagcaacagaaaTagcag (SEQ ID NO: 614) |
| YDR258C_MM_888 | aaatagcagcaaaggcctcgtcttg (SEQ ID NO: 615) | YDR258C_MM_888T | aaaTagcagcaaaggccTcgTcTTg (SEQ ID NO: 616) |
| YDR258C_MM_890 | atagcagcaatgccctcgtcttggc (SEQ ID NO: 617) | YDR258C_MM_890T | aTagcagcaaTgcccTcgTcTTggc (SEQ ID NO: 618) |
| YDR258C_MM_896 | gcaatggcctcgacttggccaacga (SEQ ID NO: 619) | YDR258C_MM_896T | gcaaTggccTcgacTTggccaacga (SEQ ID NO: 620) |
| YDR258C_MM_043 TC | TtTggTagmCamCgtcaagmCtTagTat (SEQ ID NO: 621) | YDR258C_MM_LNA3_043 | TttGgtAgcAcgTcaAgcTtaGtat (SEQ ID NO: 622) |
| YDR258C_MM_078 TC | mCamCtmCtaamCagtatcgmCcgTtTmCTa (SEQ ID NO: 623) | YDR258C_MM_LNA3_078 | mCacTctAacAgtAtcGccGttTcta (SEQ ID NO: 624) |

TABLE 13-continued

Design of the yeast HSP78 capture probes.

| Oligo name | Sequence | Oligo name | Sequence |
|---|---|---|---|
| YDR258C_MM_124 TC | gTtgmCmCaTggagatmCaaaaTmC tgTc (SEQ ID NO: 625) | YDR258C_MM_LNA3_124 | GttGccAtgGagAtcAaaAtcTgtc (SEQ ID NO: 626) |
| YDR258C_MM_164 TC | TmCaaTggmCcTTggacmCaTaTa aTTg (SEQ ID NO: 627) | YDR258C_MM_LNA3_164 | TcaAtgGccTtgGacmCatAtaAttg (SEQ ID NO: 628) |
| YDR258C_MM_201 TC | tmCagTtagcmCaaaccTtCgmCttm Cat (SEQ ID NO: 629) | YDR258C_MM_LNA3_201 | TcaGttAgcmCaaAccTtcGctTcat (SEQ ID NO: 630) |
| YDR258C_MM_249 TC | TtTtTmCggmCmCaatcgatmCtTg aaTt (SEQ ID NO: 631) | YDR258C_MM_LNA3_249 | TttTtcGgcmCaaTcgAtcTtgAatt (SEQ ID NO: 632) |
| YDR258C_MM_295 TC | aTTgamCmCTmCaaatcTTtmCTT ggaTa (SEQ ID NO: 633) | YDR258C_MM_LNA3_295 | AttGacmCtcAaaTctTtcTtgGata (SEQ ID NO: 634) |
| YDR258C_MM_356 TC | gaTgaamCTmCaggaggaTaggaTm CTt (SEQ ID NO: 635) | YDR258C_MM_LNA3_356 | GatGaamCtcAggAggAtaGgaTctt (SEQ ID NO: 636) |
| YDR258C_MM_424 TC | amCcaTcaTcacccaaccTtgTgtmCg (SEQ ID NO: 637) | YDR258C_MM_LNA3_424 | AccAtcAtcAccGaamCttTgtGtcg (SEQ ID NO: 638) |
| YDR258C_MM_433 TC | mCmCmCaacTTtgTgacgTTTaaT aaaa (SEQ ID NO: 639) | YDR258C_MM_LNA3_433 | mCccAacTttGtgAcgTttAatAaaa (SEQ ID NO: 640) |
| YDR258C_MM_486 TC | mCaaTgaTmCgTgttamCggaaaTm Caac (SEQ ID NO: 641) | YDR258C_MM_LNA3_486 | mCaaTgaTcgTgtAacGgaAatmCaac (SEQ ID NO: 642) |
| YDR258C_MM_515 TC | TggmCcTagggaaacggTcagmCtTa c (SEQ ID NO: 643) | YDR258C_MM_LNA3_515 | TggmCctAggGaaAcgTcAgcTtac (SEQ ID NO: 644) |
| YDR258C_MM_566 TC | TTggaaamCatmCgcggTgmCgctTt Tt (SEQ ID NO: 645) | YDR258C_MM_LNA3_566 | TtgGaaAcaTcgmCggTgcGctTttt (SEQ ID NO: 646) |
| YDR258C_MM_569 TC | gaaamCaTmCggggagmCgctttTtm Caa (SEQ ID NO: 647) | YDR258C_MM_LNA3_569 | GaaAcaTcgGggAgcGctTttTcaa (SEQ ID NO: 648) |
| YDR258C_MM_604 TC | aaaamCgamCagmCaaaaggmCTtT mCtTc (SEQ ID NO: 649) | YDR258C_MM_LNA3_604 | AaaAcgAcaGcaAaaGcTttmCttc (SEQ ID NO: 650) |
| YDR258C_MM_631 TC | gamCagmCcTcagtaaaTTggcmCa cmCa (SEQ ID NO: 651) | YDR258C_MM_LNA3_631 | GacAgcmCtcAgtAaaTtgGccAcca (SEQ ID NO: 652) |
| YDR258C_MM_686 TC | mCmCgaTTaaamCgacagamCagT aTgmCt (SEQ ID NO: 653) | YDR258C_MM_LNA3_686 | mCcgAttAaamCgamCagAcaGtaTgct (SEQ ID NO: 654) |
| YDR258C_MM_757 TC | aTmCaaaTaggaaatmCagmCTaaag mCc (SEQ ID NO: 655) | YDR258C_MM_LNA3_757 | AtcAaaTagGaaAtcAgcTaaAgcc (SEQ ID NO: 656) |
| YDR258C_MM_813 TC | gamCmCTaagaamCaaaaagmCTg gmCaat (SEQ ID NO: 657) | YDR258C_MM_LNA3_813 | GacmCtaAgaAcaAaaAgcTggmCaat (SEQ ID NO: 658) |
| YDR258C_MM_823 TC | aTaaagmCTggmCattaggTmCTcT TTt (SEQ ID NO: 659) | YDR258C_MM_LNA3_823 | AtaAagmCtgGcaTtaGgtmCtcTttt (SEQ ID NO: 660) |
| YDR258C_MM_870 TC | agamCgTamCagmCaacagaaaTag mCag (SEQ ID NO: 661) | YDR258C_MM_LNA3_870 | AgamCgtAcaGcaAcaGaaAtaGcag (SEQ ID NO: 662) |
| YDR258C_MM_888 TC | aaaTagmCagmCaaaggmCcTmCg TctTg (SEQ ID NO: 663) | YDR258C_MM_LNA3_888 | AaaTagmCagmCaaAggmCctmCgtmCt tg (SEQ ID NO: 664) |
| YDR258C_MM_890 TC | aTagmCagcaaTgcccTcgtmCtTggc (SEQ ID NO: 665) | YDR258C_MM_LNA3_890 | AtaGcaGcaAtgmCccTcgTctTggc (SEQ ID NO: 666) |
| YDR258C_MM_896 TC | gmCaaTggcctmCgactggccaamCg a (SEQ ID NO: 667) | YDR258C_MM_LNA3_896 | GcaAtgGccTcgActTggmCcaAcga (SEQ ID NO: 668) |

YDR258C denotes the ORF name of the *S. cerevisiae* HSP78 gene.
The numbers refer to the nucleotide position from the 3'-end of the HSP78 mRNA sequence.
PM = perfectly matched probe,
MM = single mismatch probe,
LNA substitutions are depicted by capital letters,
$^m$C denotes LNA methyl-C

TABLE 14

Duplex melting temperatures (Tm) for the 144 different 25-mer oligonucleotide capture probes.

| Probe number | Oligonucleotide target name | Complementary target sequence | Design | Average duplex melting temp. (° C.) |
|---|---|---|---|---|
| 12696 | YDR258C_Tm_predic_043 | tttggtagcacgtcaagcttagtat | MM-DNA | 59.2 |
| 12699 | YDR258C_Tm_predic_078 | cactctaacagtatcgccgtttcta | MM-DNA | 61.1 |
| 12694 | YDR258C_Tm_predic_124 | gttgccatggagatcaaaatctgtc | MM-DNA | 60 |
| 12700 | YDR258C_Tm_predic_164 | tcaatggccttggaccatataattg | MM-DNA | 59.5 |
| 12693 | YDR258C_Tm_predic_201 | tcagttagccaaaccttcgcttcat | MM-DNA | 61.4 |
| 12698 | YDR258C_Tm_predic_249 | tttttcggccaatcgatcttgaatt | MM-DNA | 58.8 |
| 12702 | YDR258C_Tm_predic_295 | attgacctcaaatctttcttggata | MM-DNA | 54.5 |
| 12692 | YDR258C_Tm_predic_356 | gatgaactcaggaggataggatctt | MM-DNA | 58.2 |
| 12680 | YDR258C_Tm_predic_424 | accatcatcaccgaactttgtgtcg | MM-DNA | 63.6 |
| 12703 | YDR258C_Tm_predic_433 | cccaactttgtgacgtttaataaaa | MM-DNA | 56.2 |
| 12681 | YDR258C_Tm_predic_486 | caatgatcgtgtaacggaaatcaac | MM-DNA | 59.3 |
| 12682 | YDR258C_Tm_predic_515 | tggcctagggaaacggtcagcttac | MM-DNA | 65.2 |
| 12683 | YDR258C_Tm_predic_566 | ttggaaacatcgcggtgcgcttttt | MM-DNA | 61.5 |
| 12684 | YDR258C_Tm_predic_569 | gaaacatcggggagcgcttttttcaa | MM-DNA | 63.8 |
| 12701 | YDR258C_Tm_predic_604 | aaaacgacagcaaaaggctttcttc | MM-DNA | 58.8 |
| 12685 | YDR258C_Tm_predic_631 | gacagcctcagtaaattggccacca | MM-DNA | 64.8 |
| 12686 | YDR258C_Tm_predic_686 | ccgattaaacgacagacagtatgct | MM-DNA | 57.1 |
| 12687 | YDR258C_Tm_predic_757 | atcaaataggaaatcagctaaagcc | MM-DNA | 54.3 |
| 12688 | YDR258C_Tm_predic_813 | gacctaagaacaaaaagctggcaat | MM-DNA | 58.2 |
| 12697 | YDR258C_Tm_predic_823 | ataaagctggcattaggtctcttttt | MM-DNA | 58.4 |
| 12695 | YDR258C_Tm_predic_870 | agacgtacagcaacagaaatagcag | MM-DNA | 61.2 |
| 12689 | YDR258C_Tm_predic_888 | aaatagcagcaaaggcctcgtcttg | MM-DNA | 64 |
| 12690 | YDR258C_Tm_predic_890 | atagcagcaatgccctcgtcttggc | MM-DNA | 62.9 |
| 12691 | YDR258C_Tm_predic_896 | gcaatggcctcgacttggccaacga | MM-DNA | 68.5 |
| 12720 | YDR258C_Tm_predic_043T | TTTggTagcacgtcaagcTTagTat | MM-T | 68.6 |
| 12723 | YDR258C_Tm_predic_078T | cacTcTaacagtatcgccgTTTcTa | MM-T | 69.7 |
| 12718 | YDR258C_Tm_predic_124T | gTTgccaTggagatcaaaaTcTgTc | MM-T | 69.2 |
| 12724 | YDR258C_Tm_predic_164T | TcaaTggccTTggaccaTaTaaTTg | MM-T | 69.7 |
| 12717 | YDR258C_Tm_predic_201T | TcagTTagccaaaccTTcgcTTcat | MM-T | 69.4 |
| 12722 | YDR258C_Tm_predic_249T | TtTTTcggccaatcgaTcTTgaaTt | MM-T | 65.9 |
| 12726 | YDR258C_Tm_predic_295T | aTTgaccTcaaatcTTTcTTggaTa | MM-T | 65.1 |
| 12716 | YDR258C_Tm_predic_356T | gaTgaacTcaggaggaTaggaTcTt | MM-T | 64.9 |
| 12704 | YDR258C_Tm_predic_424T | accaTcaTcaccgaacTTTgTgTcg | MM-T | 74 |
| 12727 | YDR258C_Tm_predic_433T | cccaacTTTgTgacgTTTaaTaaaa | MM-T | 66.5 |
| 12705 | YDR258C_Tm_predic_486T | caaTgaTcgTgTaacggaaaTcaac | MM-T | 65.2 |
| 12706 | YDR258C_Tm_predic_515T | TggccTagggaaacggTcagcTTac | MM-T | 71.6 |

TABLE 14-continued

Duplex melting temperatures (Tm) for the 144 different 25-mer oligonucleotide capture probes.

| Probe number | Oligonucleotide target name | Complementary target sequence | Design | Average duplex melting temp. (° C.) |
|---|---|---|---|---|
| 12707 | YDR258C_Tm_predic_566T | TTggaaacaTcgcggTgcgcTTTTt | MM-T | 68.6 |
| 12708 | YDR258C_Tm_predic_569T | gaaacaTcggggagcgcTTTTTcaa | MM-T | 69.9 |
| 12725 | YDR258C_Tm_predic_604T | aaaacgacagcaaaaggcTTTcTTc | MM-T | 65.9 |
| 12709 | YDR258C_Tm_predic_631T | gacagccTcagtaaaTTggccacca | MM-T | 68.8 |
| 12710 | YDR258C_Tm_predic_686T | ccgaTTaaacgacagacagTaTgct | MM-T | 63.5 |
| 12711 | YDR258C_Tm_predic_757T | aTcaaaTaggaaatcagcTaaagcc | MM-T | 58.1 |
| 12712 | YDR258C_Tm_predic_813T | gaccTaagaacaaaaagcTggcaat | MM-T | 61.1 |
| 12721 | YDR258C_Tm_predic_823T | aTaaagcTggcaaaaggTcTcTTTt | MM-T 13 + 14 | 67.2 |
| 12719 | YDR258C_Tm_predic_870T | agacgTacagcaacagaaaTagcag | MM-T | 65 |
| 12713 | YDR258C_Tm_predic_888T | aaaTagcagcaaaaggccTcgTcTTg | MM-T | 70.4 |
| 12714 | YDR258C_Tm_predic_890T | aTagcagcaaTgcccTcgTcTTggc | MM-T | 71.3 |
| 12715 | YDR258C_Tm_predic_896T | gcaaTggccTcgacTTggccaacga | MM-T | 73.7 |
| 12744 | YDR258C_Tm_predic_043TC | TtTggTagmCamCgtcaagmCtTagTat | MM-TC | 73.3 |
| 12747 | YDR258C_Tm_predic_078TC | mCamCtmCtaamCagtatcgmCcgTtTmCTa | MM-TC | 75.2 |
| 12742 | YDR258C_Tm_predic_124TC | gTtgmCmCaTggagatmCaaaaTmCtgTc | MM-TC | 61.6 |
| 12748 | YDR258C_Tm_predic_164TC | TmCaaTggmCcTTggacmCaTaTaaTTg | MM-TC | 74.8 |
| 12741 | YDR258C_Tm_predic_201TC | tmCagTtagcmCaaacctTcgmCttmCat | MM-TC | 70.6 |
| 12746 | YDR258C_Tm_predic_249TC | TtTtTmCggmCmCaatcgatmCtTgaaTt | MM-TC | 71 |
| 12750 | YDR258C_Tm_predic_295TC | aTTgamCmCTmCaaatcTTtmCTTggaTa | MM-TC | 72.2 |
| 12740 | YDR258C_Tm_predic_356TC | gaTgaamCTmCaggaggaTaggaTmCTt | MM-TC | 70.4 |
| 12728 | YDR258C_Tm_predic_424TC | amCcaTcaTcacccaaccTtgTgtmCg | MM-TC 13 + 16 | 70.2 |
| 12751 | YDR258C_Tm_predic_433TC | mCmCmCaacTTtgTgacgTTTaaTaaaa | MM-TC | 67.6 |
| 12730 | YDR258C_Tm_predic_515TC | TggmCcTagggaaacggTcagmCtTac | MM-TC | 75.5 |
| 12731 | YDR258C_Tm_predic_566TC | TTggaaamCatmCgcggTgmCgctTtTt | MM-TC | 72 |
| 12732 | YDR258C_Tm_predic_569TC | gaaamCaTmCggggagmCgctttTtmCaa | MM-TC | 74.8 |
| 12749 | YDR258C_Tm_predic_604TC | aaaamCgamCagmCaaaaggmCTtTmCtTc | MM-TC | 72 |
| 12733 | YDR258C_Tm_predic_631TC | gamCagmCcTcagtaaaTTggcmCacmCa | MM-TC | 77.4 |
| 12734 | YDR258C_Tm_predic_686TC | mCmCgaTTaaamCgacagamCagTaTgmCt | MM-TC | 70.2 |
| 12735 | YDR258C_Tm_predic_757TC | aTmCaaaTaggaaatmCagmCTaaagmCc | MM-TC | 64.6 |
| 12736 | YDR258C_Tm_predic_813TC | gamCmCTaagaamCaaaaagmCTggmCaat | MM-TC | 71.4 |
| 12745 | YDR258C_Tm_predic_823TC | aTaaagmCTggmCattaggTmCTcTTTt | MM-TC | 74 |
| 12743 | YDR258C_Tm_predic_870TC | agamCgTamCagmCaacagaaaTagmCag | MM-TC | 73.6 |
| 12737 | YDR258C_Tm_predic_888TC | aaaTagmCagmCaaaggmCcTmCgTctTg | MM-TC | 79.3 |
| 12738 | YDR258C_Tm_predic_890TC | aTagmCagcaaTgcccTcgtmCtTggc | MM-TC | 71.5 |
| 12739 | YDR258C_Tm_predic_896TC | gcaatggccTmCgamCttggccaacga | MM-TC | 73.1 |

TABLE 14-continued

Duplex melting temperatures (Tm) for the 144 different 25-mer oligonucleotide capture probes.

| Probe number | Oligonucleotide target name | Complementary target sequence | Design | Average duplex melting temp. (° C.) |
|---|---|---|---|---|
| 12768 | YDR258C_Tm predic_043_PM | tttggtagcacgacaagcttagtat | PM-DNA | 65.7 |
| 12771 | YDR258C_Tm predic_078_PM | cactctaacagtttcgccgtttcta | PM-DNA | 66.3 |
| 12766 | YDR258C_Tm predic_124_PM | gttgccatggagttcaaaatctgtc | PM-DNA | 65.8 |
| 12772 | YDR258C_Tm predic_164_PM | tcaatggccttgcaccatataattg | PM-DNA | 64 |
| 12765 | YDR258C_Tm predic_201_PM | tcagttagccaatccttcgcttcat | PM-DNA | 66.1 |
| 12770 | YDR258C_Tm predic_249_PM | tttttcggccaaacgatcttgaatt | PM-DNA | 65 |
| 12774 | YDR258C_Tm predic_295_PM | attgacctcaaaactttcttggata | PM-DNA | 61.8 |
| 12764 | YDR258C_Tm predic_356_PM | gatgaactcaggtggataggatctt | PM-DNA | 64 |
| 12752 | YDR258C_Tm predic_424_PM | accatcatcacccaactttgtgtcg | PM-DNA | 67.5 |
| 12775 | YDR258C_Tm predic_433_PM | cccaactttgtgtcgtttaataaaa | PM-DNA | 61 |
| 12753 | YDR258C_Tm predic_486_PM | caatgatcgtgttacggaaatcaac | PM-DNA | 64.2 |
| 12754 | YDR258C_Tm predic_515_PM | tggcctagggaatcggtcagcttac | PM-DNA | 70.1 |
| 12755 | YDR258C_Tm predic_566_PM | ttggaaacatcggggtgcgcttttt | PM-DNA | 70.8 |
| 12756 | YDR258C_Tm predic_569_PM | gaaacatcggggtgcgcttttcaa | PM-DNA | 68.7 |
| 12773 | YDR258C_Tm predic_604_PM | aaaacgacagcataaggctttcttc | PM-DNA | 64.5 |
| 12757 | YDR258C_Tm predic_631_PM | gacagcctcagttaattggccacca | PM-DNA | 70.2 |
| 12758 | YDR258C_Tm predic_686_PM | ccgattaaacgagagacagtatgct | PM-DNA | 65.4 |
| 12759 | YDR258C_Tm predic_757_PM | atcaaataggaattcagctaaagcc | PM-DNA | 61.5 |
| 12760 | YDR258C_Tm predic_813_PM | gacctaagaacataaagctggcaat | PM-DNA | 63.5 |
| 12769 | YDR258C_Tm predic_823_PM | ataaagctggcaataggtctctttt | PM-DNA | 63.6 |
| 12767 | YDR258C_Tm predic_870_PM | agacgtacagcatcagaaatagcag | PM-DNA | 66.6 |
| 12761 | YDR258C_Tm predic_888_PM | aaatagcagcaatggcctcgtcttg | PM-DNA | 69.2 |
| 12762 | YDR258C_Tm predic_890_PM | atagcagcaatggcctcgtcttggc | PM-DNA | 72.7 |
| 12763 | YDR258C_Tm predic_896_PM | gcaatggcctcgtcttggccaacga | PM-DNA | 72.8 |
| 12792 | YDR258C_Tm predic_043T_PM | TTTggTagcacgacaagcTTagTat | PM-T | 74.2 |
| 12795 | YDR258C_Tm predic_078T_PM | cacTcTaacagtTtcgccgTTTcTa | PM-T | 75.5 |
| 12790 | YDR258C_Tm predic_124T_PM | gTTgccaTggagTtcaaaaTcTgTc | PM-T | 74.7 |
| 12796 | YDR258C_Tm predic_164T_PM | TcaaTggccTTgcaccaTaTaaTTg | PM-T | 74 |
| 12789 | YDR258C_Tm predic_201T_PM | TcagTTagccaaTccTTcgcTTcat | PM-T | 75.7 |
| 12794 | YDR258C_Tm predic_249T_PM | TtTTTcggccaaacgaTcTTgaaTt | PM-T | 71 |
| 12798 | YDR258C_Tm predic_295T_PM | aTTgaccTcaaaacTTTcTTggaTa | PM-T | 70.2 |
| 12788 | YDR258C_Tm predic_356T_PM | gaTgaacTcaggTggaTaggaTcTt | PM-T | 71 |
| 12776 | YDR258C_Tm predic_424T_PM | accaTcaTcacccaacTTTgTgTcg | PM-T | 79.2 |
| 12799 | YDR258C_Tm predic_433T_PM | cccaacTTTgTgTcgTTTaaTaaaa | PM-T | 75.1 |
| 12777 | YDR258C_Tm predic_486T_PM | caaTgaTcgTgTTacggaaaTcaac | PM-T | 72.2 |
| 12778 | YDR258C_Tm predic_515T_PM | TggccTagggaaTcggTcagcTTac | PM-T | 76.9 |

TABLE 14-continued

Duplex melting temperatures (Tm) for the 144 different 25-mer oligonucleotide capture probes.

| Probe number | Oligonucleotide target name | Complementary target sequence | Design | Average duplex melting temp. (° C.) |
|---|---|---|---|---|
| 12779 | YDR258C_Tm predic_566T_PM | TTggaaacaTcggggTgcgcTTTTt | PM-T | 76.7 |
| 12780 | YDR258C_Tm predic_569T_PM | gaaacaTcggggTgcgcTTTTTcaa | PM-T | 78 |
| 12797 | YDR258C_Tm predic_604T_PM | aaaacgacagcaTaaggcTTTcTTc | PM-T | 71.7 |
| 12781 | YDR258C_Tm predic_631T_PM | gacagccTcagtTaaTTggccacca | PM-T | 75.4 |
| 12782 | YDR258C_Tm predic_686T_PM | ccgaTTaaacgagagacagTaTgct | PM-T | 72.2 |
| 12783 | YDR258C_Tm predic_757T_PM | aTcaaaTaggaaTTcagcTaaagcc | PM-T | 66.3 |
| 12784 | YDR258C_Tm predic_813T_PM | gaccTaagaacaTaaagcTggcaat | PM-T | 67.5 |
| 12793 | YDR258C_Tm predic_823T_PM | aTaaagcTggcaaTaggTcTcTTTt | PM-T | 74.3 |
| 12791 | YDR258C_Tm predic_870T_PM | agacgTacagcaTcagaaaTagcag | PM-T | 71.4 |
| 12785 | YDR258C_Tm predic_888T_PM | aaaTagcagcaaTggccTcgTcTTg | PM-T | 77.2 |
| 12786 | YDR258C_Tm predic_890T_PM | aTagcagcaaTggccTcgTcTTggc | PM-T | 80.1 |
| 12787 | YDR258C_Tm predic_896T_PM | gcaaTggccTcgTcTTggccaacga | PM-T | 80.8 |
| 12816 | YDR258C_Tm predic_043TC_PM | TtTggTagmCamCgamCaagmCtTagTat | PM-TC | 79 |
| 12819 | YDR258C_Tm predic_078TC_PM | mCamCtmCtaamCagtTtcgmCcgTtTmCTa | PM-TC | 81.9 |
| 12814 | YDR258C_Tm predic_124TC_PM | gTtgmCmCaTggagTtmCaaaaTmCtgTc | PM-TC | 78.3 |
| 12820 | YDR258C_Tm predic_164TC_PM | TmCaaTggmCcTTgmCacmCaTaTaaTTg | PM-TC | 83.5 |
| 12813 | YDR258C_Tm predic_201TC_PM | TmCagTtagcmCaaTcmCtTmCgmCttmCat | PM-TC | 81.8 |
| 12818 | YDR258C_Tm predic_249TC_PM | TtTtTmCggmCmCaaamCgatmCtTgaaTt | PM-TC | 77.8 |
| 12822 | YDR258C_Tm predic_295TC_PM | aTTgamCmCTmCaaaamCTTtmCTTggaTa | PM-TC | 75.6 |
| 12812 | YDR258C_Tm predic_356TC_PM | gaTgaamCTmCaggTggaTaggaTmCTt | PM-TC | 77.3 |
| 12800 | YDR258C_Tm predic_424TC_PM | amCcaTcaTcacmCmCaaccTtgTgtmCg | PM-TC | 74.2 |
| 12823 | YDR258C_Tm predic_433TC_PM | mCmCmCaacTTtgTgTcgTTTaaTaaaa | PM-TC | 74.8 |
| 12729 | YDR258C_Tm_predic_486TC_PM | mCaaTgaTmCgTgttamCggaaaTmCaac | PM-TC | 75.5 |
| 12802 | YDR258C_Tm predic_515TC_PM | TggmCcTagggaaTmCggTcagmCtTac | PM-TC | 83.6 |
| 12803 | YDR258C_Tm predic_566TC_PM | TTggaaamCatmCggggTgmCgcTtTt | PM-TC | 80.8 |
| 12804 | YDR258C_Tm predic_569TC_PM | gaaamCaTmCggggTgmCgctttTtmCaa | PM-TC | 83.2 |
| 12821 | YDR258C_Tm predic_604TC_PM | aaaamCgamCagmCaTaaggmCTtTmCtTc | PM-TC | 79 |
| 12805 | YDR258C_Tm predic_631TC_PM | gamCagmCcTcagtTaaTTggcmCacmCa | PM-TC | 82.5 |
| 12806 | YDR258C_Tm predic_686TC_PM | mCmCgaTTaaamCgagagamCagTaTgmCt | PM-TC | 79.4 |
| 12807 | YDR258C_Tm predic_757TC_PM | aTmCaaaTaggaaTtmCagmCTaaagmCc | PM-TC | 71.4 |
| 12808 | YDR258C_Tm predic_813TC_PM | gamCmCTaagaamCaTaaagmCTggmCaat | PM-TC | 78.9 |
| 12817 | YDR258C_Tm predic_823TC_PM | aTaaagmCTggcaaTaggTmCTcTTTt | PM-TC | 81.2 |
| 12815 | YDR258C_Tm predic_870TC_PM | agamCgTamCagmCaTmCagaaaTagmCag | PM-TC | 81.9 |
| 12809 | YDR258C_Tm predic_888TC_PM | aaaTagmCagmCaaTggmCcTmCgTctTg | PM-TC | 86.8 |

TABLE 14-continued

Duplex melting temperatures (Tm) for the 144 different 25-mer oligonucleotide capture probes.

| Probe number | Oligonucleotide target name | Complementary target sequence | Design | Average duplex melting temp. (° C.) |
|---|---|---|---|---|
| 12810 | YDR258C_Tm predic_890TC_PM | aTagmCagcaaTggmCcTcgtmCtTggc | PM-TC | 83 |
| 12811 | YDR258C_Tm predic_896TC_PM | gcaatggcctmCgTmCttggccaacga | PM-TC | 79.3 |

The design column denotes the sequence design of the probe.
PM = perfectly matched probe,
MM = single mismatch probe,
LNA substitutions are depicted by capital letters,
$^m$C denotes LNA methyl-C (SEQ ID NOs: 669-811, in sequential order)

EXAMPLE 52

Performance Analysis of LNA Substituted Oligonucleotide Capture Probes Designed to Detect Splice Variants in Complex RNA Pools A. Oligonucleotide Design for Microarrays. The Methods for Designing Exon-Specific Internal Oligonucleotide Capture Probes has been Described in Example 2.

A1. Design of the LNA-Modified Capture Probes

For the internal LNA-modified oligonucleotide capture probes, every third DNA nucleotide was substituted with an LNA nucleotide. The probes designed to capture the splice junction of the recombinant splice variants were designed with LNA substitutions at every third nucleotide position. All capture probes are shown in Table 15.

TABLE 15

Internal, exon-specific and merged, exon-exon splice junction specific oligonucleotide capture probes used in the example.

| EQ No | Oligo Name | Sequence | SEQ ID NO: |
|---|---|---|---|
| 10716 | >gene78.01a | cctgaaagtagatttgttatttccgaaacgccttctcccgttcttaagtc | 81 |
| 10717 | >gene78.01b | catataccacaaatagtccctcaaaaatcacaagaaaactcacaacactg | 82 |
| 10718 | >gene78.03a | gatttgcagcggtggtaaaaagtatgaaaacgtggtaattaaaaggtctc | 83 |
| 10719 | >gene78.03b | ccaatgaaaactaatcaaaggtaaacgtggatcccatggcaattcccggg | 84 |
| 10720 | >gene78.m0103 | cacaacactgcccagaggttcaatcgataaatatgtgaaggaaatgcctg | 812 |
| 10721 | >gene78.m01INS3 | caacactgcccagaggttcaatcgatccgatgatcctaatgaaggcgccc | 85 |
| 10722 | >gene78.mINS303 | gtccagtatcgtccatcatagtatcgataaatatgtgaaggaaatgcctg | 86 |
| 10723 | >gene78.INS3 | ctccttcttgcattcttcaacttccttcaacacttgagcggagtcggtgc | 813 |
| 10724 | >gene78.m01INS4 | caacactgcccagaggttcaatcgatgtgtgataggatcagtgttcaggg | 87 |
| 10725 | >gene78.mINS403 | gaaggcgaaggagactgctaatatcgataaatatgtgaaggaaatgcctg | 88 |
| 10726 | >gene78.INS4a | gaacgtatgagcatgcgagagacgctgtagttggaaaaacccacgaagcg | 814 |
| 10727 | >gene78.INS4b | gaaaccgctgattatactgcggagaaggtgggtgagtataaagactatac | 815 |
| 11345 | >gene78.01a_40 | aagtagatttgttatttccgaaacgccttctcccgttctt | 816 |
| 11346 | >gene78.01b_40 | accacaaatagtccctcaaaaatcacaagaaaactcacaa | 817 |
| 11347 | >gene78.03a_40 | gcagcggtggtaaaaagtatgaaaacgtggtaattaaaag | 818 |
| 11348 | >gene78.03b_40 | gaaaactaatcaaaggtaaacgtggatcccatggcaattc | 819 |
| 11349 | >gene78.m0103_40 | cactgcccagaggttcaatcgataaatatgtgaaggaaat | 820 |
| 11350 | >gene78.m01INS3_40 | ctgcccagaggttcaatcgatccgatgatcctaatgaagg | 821 |
| 11351 | >gene78.mINS303_40 | gtatcgtccatcatagtatcgataaatatgtgaaggaaat | 822 |
| 11352 | >gene78.INS3_40 | tcttgcattcttcaacttccttcaacacttgagcggagtc | 823 |
| 11353 | >gene78.m01INS4_40 | ctgcccagaggttcaatcgatgtgtgataggatcagtgtt | 824 |

TABLE 15-continued

Internal, exon-specific and merged, exon-exon splice junction specific oligonucleotide capture probes used in the example.

| EQ No | Oligo Name | Sequence | SEQ ID NO: |
|---|---|---|---|
| 11354 | >gene78.mINS403_40 | cgaaggagactgctaatatcgataaatatgtgaaggaaat | 825 |
| 11355 | >gene78.INS4a_40 | tatgagcatgcgagagacgctgtagttggaaaaacccacg | 826 |
| 11356 | >gene78.INS4b_40 | cgctgattatactgcggagaaggtgggtgagtataaagac | 827 |
| 11357 | >gene78.01a_50_LNA3 | mCctGaaAgtAgaTttGttAttTccGaaAcgmCctTctmCccGttmCttAagTc | 89 |
| 11358 | >gene78.01b_50_LNA3 | mCatAtamCcamCaaAtaGtcmCctmCaaAaaTcamCaaGaaAacTcamCaamCacTg | 90 |
| 11359 | >gene78.03a_50_LNA3 | GatTtgmCagmCggTggTaaAaaGtaTgaAaamCgtGgtAatTaaAagGtcTc | 91 |
| 11360 | >gene78.03b_50_LNA3 | mCcaAtgAaaActAatmCaaAggTaaAcgTggAtcmCcaTggmCaaTtcmCcgGg | 82 |
| 11361 | >gene78.m0103_50_LNA3 | mCacAacActGccmCagAggTtcAatmCgaTaaAtaTgtGaaGgaAatGccTg | 828 |
| 11362 | >gene78.m01INS3_50_LNA3 | mCaamCacTgcmCcaGagGttmCaaTcgAtcmCgaTgaTccTaaTgaAggmCgcmCc | 829 |
| 11363 | >gene78.mINS303_50_LNA3 | GtcmCagTatmCgtmCcaTcaTagTatmCgaTaaAtaTgtGaaGgaAatGccTg | 830 |
| 11364 | >gene78.INS3_50_LNA3 | mCtcmCttmCttGcaTtcTtcAacTtcmCttmCaamCacTtgAgcGgaGtcGgtGc | 831 |
| 11365 | >gene78.m01INS4_50_LNA3 | mCaamCacTgcmCcaGagGttmCaaTcgAtgTgtGatAggAtcAgtGttmCagGg | 832 |
| 11366 | >gene78.mINS403_50_LNA3 | GaaGgcGaaGgaGacTgcTaaTatmCgaTaaAtaTgtGaaGgaAatGccTg | 833 |
| 11367 | >gene78.INS4a_50_LNA3 | GaamCgtAtgAgcAtgmCgaGagAcgmCtgTagTtgGaaAaamCccAcgAagmCg | 834 |
| 11368 | >gene78.INS4b_50_LNA3 | GaaAccGctGatTatActGcgGagAagGtgGgtGagTatAaaGacTatAc | 835 |
| 11369 | >gene78.01a_40_LNA3 | aAgtAgaTttGttAttTccGaaAcgmCctTctmCccGttmCtt | 836 |
| 11370 | >gene78.01b_40_LNA3 | amCcamCaaAtaGtcmCctmCaaAaaTcamCaaGaaAacTcamCaa | 837 |
| 11371 | >gene78.03a_40_LNA3 | gmCagmCggTggTaaAaaGtaTgaAaamCgtGgtAatTaaAag | 838 |
| 11372 | >gene78.03b_40_LNA3 | gAaaActAatmCaaAggTaaAcgTggAtcmCcaTggmCaaTtc | 839 |
| 11373 | >gene78.m0103_40_LNA3 | cActGccmCagAggTtcAatmCgaTaaAtaTgtGaaGgaAat | 840 |
| 11374 | >gene78.m01INS3_40_LNA3 | cTgcmCcaGagGttmCaaTcgAtcmCgaTgaTccTaaTgaAgg | 841 |
| 11375 | >gene78.mINS303_40_LNA3 | gTatmCgtmCcaTcaTagTatmCgaTaaAtaTgtGaaGgaAat | 842 |
| 11376 | >gene78.INS3_40_LNA3 | tmCttGcaTtcTtcAacTtcmCttmCaamCacTtgAgcGgaGtc | 843 |
| 11377 | >gene78.m01INS4_40_LNA3 | cTgcmCcaGagGttmCaaTcgAtgTgtGatAggAtcAgtGtt | 844 |
| 11378 | >gene78.mINS403_40_LNA3 | cGaaGgaGacTgcTaaTatmCgaTaaAtaTgtGaaGgaAat | 845 |
| 11379 | >gene78.INS4a_40_LNA3 | tAtgAgcAtgmCgaGagAcgmCtgTagTtgGaaAaamCccAcg | 846 |
| 11380 | >gene78.INS4b_40_LNA3 | cGctGatTatActGcgGagAagGtgGgtGagTatAaaGac | 847 |

Capital letters denote LNA nucleotides and $^m$C LNA methyl-cytosine

B. Printing and Coupling of the Splice Isoform-Specific Microarrays

The splice variant capture probes were synthesized with a 5' anthraquinone (AQ)-modification, followed by a hexaethyleneglycol-2 (HEG2) linker. The capture probes were first diluted to a 20 µM final concentration in 100 mM Na-phosphate buffer pH 7.0, and spotted on the Immobilizer polymer microarray slides (Exiqon, Denmark) using the Biochip Arrayer One (Packard Biochip Technologies, USA) with a spot volume of 2×300 pl and 300 µm between the spots. The capture probes were immobilized onto the microarray slide by UV irradiation in a Stratalinker with 2300 µjoules (Stratagene, USA). Non-immobilized capture probe oligonucleotides were removed from the slides by washing the slides two times 15 min. in 1×SSC. After washing, the slides were dried by centrifugation at 1000×g for 2 min., and stored in a slide box until microarray hybridization.

C. Construction of the Splice Variant Clones

The recombinant splice variant constructs were cloned into the Triamp18 vector (Ambion, USA). The constructs were sequenced to confirm their construction. The plasmid clones were transformed into *E. coli* XL10-Gold (Stratagene, USA).

Genomic DNA was prepared from a wild type standard laboratory strain of *Saccharomyces cerevisiae* using the Nucleon MiY DNA extraction kit (Amersham Biosciences, USA) according to the supplier's instructions. Amplification of the partial yeast gene was done by standard PCR using yeast genomic DNA as template. In the first step of amplification, a forward primer containing a restriction enzyme site and a reverse primer containing a universal linker sequence were used. In this step 20 bp was added to the 3'-end of the amplicon, next to the stop codon. In the second step of amplification, the reverse primer was exchanged with a nested primer containing a poly-$T_{20}$ tail and a restriction enzyme site. The SWI5 amplicon contains 730 bp of the SWI5 ORF plus 20 bp universal linker sequence and a poly-$A_{20}$ tail.

The PCR primers used were;

```
YDR146C-For-EcoRI:
                                    (SEQ ID NO: 97)
acgtgaattcaaatacagacaatgaaggagatga YDR146C-Rev-Uni:
                                    (SEQ ID NO: 98)
gatccccgggaattgccatgttacctttgattagttttcattggc Uni-polyT-BamHI:
                                    (SEQ ID NO: 99)
acgtggatccttttttttttttttttttttgatccccgggaattgcc atg,
```

The PCR amplicon was cut with the restriction enzymes, EcoRI+BamHI. The DNA fragment was ligated into the pTRIamp18 vector (Ambion, USA) using the Quick Ligation Kit (New England Biolabs, USA) according to the supplier's instructions and transformed into *E. coli* DH-5α by standard methods.

C1. Construction of the recombinant splice variant #1 (Triamp18/swi5-Rubisco)

The *Arabidopsis thaliana* Rubisco small subunit ssu2b gene fragment (gi17064721) was amplified from genomic DNA by primers named DJ305 5'-ACTATGATGGACGA-TACTGGAC-3' (SEQ ID NO: 100) and DJ306 5'-ATTG-GATCGATCCGATGATCCTAATGAAGGC-3' (SEQ ID NO: 101), containing ClaI restriction site linkers. The purified PCR fragment was digested with ClaI and then cloned into the swi5 (gI:7839148) vector at the unique ClaI site (atcgat) giving each insert a flanking sequence from the original yeast SWI5 insert (named exon01 and exon 03, see FIG. 19). The product was inserted in the reverse orientation, so that the insert sequence is:

```
                                    (SEQ ID NO: 102)
atcgatCCGATGATCCTAATGAAGGCGCCCGGGTACTCCTTCTTGCATTC

TTCAACTTCCTTCAACACTTGAGCGGAGTCGGTGCATCCGAACAATGGAA

GCTTCCACATTGTCCAGTATCGTCCATCATAGTatcgat
```

Nucleotide sequence analysis revealed a difference between the sequence of *A. thaliana* Rubisco expected from the GenBank database and that obtained from all sequenced constructs and PCR products. Position 30 in the Rubisco insert is C rather than the expected A. This SNP was probably created by PCR. None of the oligonucleotide capture probes used in the example cover this region.

```
Rubisco seq. in genbank
                                    (SEQ ID NO: 103)
TCCTAATGAAGGCGCCA The sequence obtained from the plasmid contruct
                                    (SEQ ID NO: 104)
TCCTAATGAAGGCGCCC
```

C2. Construction of the Recombinant Splice Variant #2 (Triamp18/swi5-Lea)

The *Arabidopsis thaliana* Lea gene (gi1526423) was amplified from genomic DNA with primers named DJ307 5'-GGAATTATCGATGTGTGATAGGATCAGTGTTCAG-3' (SEQ ID NO: 105), and DJ308 5'-AATTGGATCGAT-ATTAGCAGTCTCCTTCGCC-3' (SEQ ID NO: 106), including the ClaI linker sites as above. The PCR fragment was digested with ClaI cloned into the yeast SWI5 IVT construct as above at the unique ClaI site.

The fragment was inserted in the forward orientation, resulting in the following insert sequence:

```
                                    (SEQ ID NO: 107)
atcgatGTGTGATAGGTTCAGTGTTCAGGGCTGTCCAAGGAACGTATGAG

CATGCGAGAGACGCTGTAGTTGGAAAAACCCACGAAGCGGCTGAGTCTAC

CAAAGAAGGAGCTCAGATAGCTTCAGAGAAAGCGGTTGGAGCAAAGGACG

CAACCGTCGAGAAAGCTAAGGAAACCGCTGATTATACTGCGGAGAAGGTG

GGTGAGTATAAAGACTATACGGTTGATAAAGCTAAAGAGGCTAAGGACAC

AACTGCAGAGAAGGCGAAGGAGACTGCTAATatcgat.
```

Figure 11:
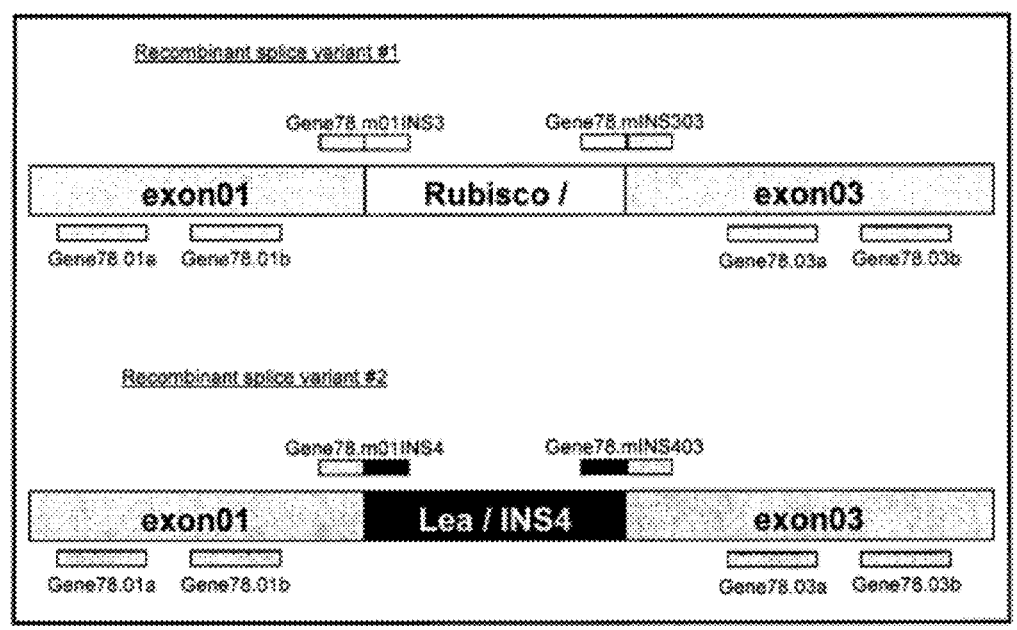
FIG. 11 shows the construction of the recombinant splice variants in the in vitro transcription vector. The small bars show the location of the hybridization for the oligonucleotide capture probes used in this example. The sequences of the capture probes are described herein.

FIG. 11 shows the construction of the recombinant splice variants in the in vitro transcription vector. The small bars show the location of the oligonucleotide capture probes used in this example. The sequences of the capture probes are shown in Table 15.

D. Preparation of Target

D1. In Vitro RNA Preparation from Splice Variant Vectors

In vitro RNA from the splice variants were made using the MEGAscript™ high yield transcription kit according to the manufacturer's instructions (Ambion, USA). The yield of IVT RNA was quantified at a Nanodrop spectrophotometer (Nanodrop Technologies, USA)

D2. Isolation of Total RNA from C. elegans

Strains and growth conditions: C. elegans wild-type strain (Bristol-N2) was maintained on nematode growth medium (NG) plates seeded with Escherichia coli strain OP50 at 20° C., and the mixed stages of the nematode were prepared as described in Hope, I. A. (ed.) "C. elegans—A Practical Approach", Oxford University Press 1999. The samples were immediately flash frozen in liquid $N_2$ and stored at −80° C. until RNA isolation.

A 100 µl aliquot of packed C. elegans worms from a mixed stage population was homogenized using the Fast-Prep Bio101 from Kem-En-Tec for 1 min, speed 6 followed by isolation of total RNA from the extracts using the FastPrep Bio101 kit (Kem-En-Tec) according to the manufacturer's instructions. The eluted total RNA was ethanol precipitated for 24 hours at −20° C. by addition of 2.5 volumes of 96% EtOH and 0.1 volume of 3M Na-acetate, pH 5.2 (Ambion, USA), followed by centrifugation of the total RNA sample for 30 min at 13200 rpm. The total RNA pellet was air-dried and redissolved in 10 µl of diethylpyrocarbonate (DEPC)-treated water (Ambion, USA) and stored at −80° C.

E. Fluorochrome-Labelling of the Target

The following fluorochrome-labelled cDNA targets were synthesized to test the performance of 'merged' splice junction probes that encompass exon borders. Synthetic RNAs corresponding to three artificial splice variants; #1 (exon01-INS3-exon03 (1-INS3-3), #2 (exon01-INS4-exon03) (01-INS3-3) and #3 without the middle exon (01-03) were spiked into 10 µg of C. elegans reference total RNA samples in various combinations and concentrations prior to fluorochrome-labelling with either Cy3 or Cy5 as indicated in Table 16. At the same time 10 µg of C. elegans reference total RNA was labeled with Cy3 for control experiments. Hybridizations were performed with Cy3- and Cy5 labeled C. elegans RNA+spike RNA mix. The details of RNA samples and synthetic RNA spikes are shown in Table 16. The RNA samples were combined in individual labeling reactions with 5 µg anchored oligo($dT_{20}$) primer and DEPC-treated water to a final volume of 8 µl. The mixture was heated at 70° C. for 10 min, quenched on ice for 5 min, followed by addition of 20 units of Superasin RNase inhibitor (Ambion, USA), 1 µl dNTP solution (10 mM each dATP, dGTP, dTTP and 0.4 mM dCTP, and 3 µl of Cy3-dCTP or Cy5-dCTP, Amersham Biosciensces, USA), 4 µl 5×RTase buffer (Invitrogen), 2 µl 0.1 mM DTT (Invitrogen), 400 units of Superscript II reverse transcriptase (Invitrogen, USA) and DEPC-treated water to 20 µl final volume. Background hybridization to merged capture probes was monitored with 10 µg of C. elegans reference RNA alone labeled with Cy3-dCTP; according to the labeling method described above for the splice variant spikes. All cDNA syntheses were carried out at 42° C. for 2 hours, and the reaction was stopped by incubation at 70° C. for 5 min., followed by incubation on ice for 5 min.

Unincorporated dNTPs were removed by gel filtration using MicroSpin S-400 HR columns as described in the following: Pre-spin the column 1 min at 1500×g in a 1.5 ml tube and place the column in a new 1.5 ml tube. Slowly apply the cDNA sample to the top centre of the resin, spin 1500-×g for 2 min and collect the eluate. The RNA was hydrolyzed by adding 3 µl of 0.5 M NaOH, mixing and incubating at 70° C. for 15 min. The samples were neutralized by adding 3 µl of 0.5 M HCl and mixing, followed by addition of 450 µl 1×TE, pH 7.5 to the neutralized sample and transfer onto a Microcon-30 concentrator (prior to use, spin 500 µl 1×TE through the column to remove residual glycerol). The samples were centrifuged at 14000-x g in a microcentrifuge for 12 min. Spinning was continued until volume was reduced to 5 µl. The labelled cDNA probes were eluted by inverting the Microcon-30 tube and spinning at 1000-×g for 3 min.

TABLE 16

Synthetic splice variant RNAs spiked into C. elegans samples*.

| Spike RNA concentration | Ratio | Splice variant RNAs | Observed ratio LNA 50 mer | STDEV LNA 50 mer | Observed ratio LNA 40 mer | STDEV LNA 40 mer | Expected ratio |
|---|---|---|---|---|---|---|---|
| 1000 ppm | 5 | Cy3: spike 01-INS3-03 | 0.76 | 0.05 | 0.61 | 0.19 | 0.83 |
|  | 1 | Cy3: spike 01-03 | 0.24 | 0.05 | 0.39 | 0.19 | 0.17 |
|  | 1 | Cy5: spike 01-INS3-03 | 0.16 | 0.04 | 0.06 | 0.03 | 0.17 |
|  | 5 | Cy5: spike 01-03 | 0.84 | 0.04 | 0.94 | 0.03 | 0.83 |
| 1000 ppm | 5 | Cy3: spike 01-INS3-03 | 0.77 | 0.11 | 0.68 | 0.22 | 0.83 |
|  | 1 | Cy3: spike 01-INS4-03 | 0.23 | 0.11 | 0.32 | 0.22 | 0.17 |
|  | 1 | Cy5: spike 01-INS3-03 | 0.12 | 0.04 | 0.11 | 0.15 | 0.17 |
|  | 5 | Cy5: spike 01-INS4-03 | 0.88 | 0.04 | 0.89 | 0.15 | 0.83 |
| 1000 ppm | 5 | Cy3: spike 01-INS3-03 | 0.88 | 0.08 | 0.87 | 0.10 | 0.83 |
|  | 1 | Cy3: spike 01-INS4-03 | 0.12 | 0.08 | 0.13 | 0.10 | 0.17 |
|  | 1 | Cy5: spike 01-INS3-03 | 0.22 | 0.12 | 0.15 | 0.12 | 0.17 |
|  | 5 | Cy5: spike 01-INS4-03 | 0.78 | 0.12 | 0.85 | 0.12 | 0.83 |
| 100 ppm | 5 | Cy3: spike 01-INS3-03 | 0.89 | 0.15 | 0.11 | 0.08 | 0.83 |
|  | 1 | Cy3: spike 01-INS4-03 | 0.11 | 0.15 | 0.89 | 0.08 | 0.17 |
|  | 1 | Cy5: spike 01-INS3-03 | 0.48 | 0.2 | 0.57 | 0.31 | 0.17 |
|  | 5 | Cy5: spike 01-INS4-03 | 0.52 | 0.2 | 0.43 | 0.31 | 0.83 |
| 10 ppm | 5 | Cy3: spike 01-INS3-03 | 0.61 | 0.2 | 0.09 | 0.14 | 0.83 |
|  | 1 | Cy3: spike 01-INS4-03 | 0.39 | 0.2 | 0.91 | 0.14 | 0.17 |
|  | 1 | Cy5: spike 01-INS3-03 | 0.34 | 0.18 | 0.19 | 0.22 | 0.17 |
|  | 5 | Cy5: spike 01-INS4-03 | 0.66 | 0.18 | 0.81 | 0.22 | 0.83 |

*Parts per million (ppm) calculations indicate spike transcripts per total transcripts in the hybridisation mix. Calculations are based on an average C. elegans RNA being 1000 nucleotides as in Hill et al. (2000). Science 290: 809-812.

F. Microarray Hybridization

The fluorochrome-labelled cDNA samples, respectively, were combined. The following was added: 3.75 µl 20×SSC (3×SSC final, pass through 0.22µ filter prior to use to remove particulates) yeast tRNA (1 µg/µl final) 0.625 µl 1 M HEPES, pH 7.0 (25 mM final, pass through 0.22 µfilter prior to use to remove particulates) 0.75 µl 10% SDS (0.3% final) and DEPC-water to 25 µl final volume. The labelled cDNA target samples were filtered in Millipore 0.22 µfilter spin column (Ultrafree-MC, Millipore, USA) according to the manufacturer's instructions, followed by incubation of the reaction mixture at 100° C. for 2-5 min. The cDNA probes were cooled at room temp for 2-5 min by spinning at max speed in a microcentrifuge. A LifterSlip (Erie Scientific Company, USA) was carefully placed on top of the microarray spotted on Immobilizer™ MicroArray Slide and the hybridization mixture was applied to the array from the side. An aliquot of 30 µL of 3×SSC was added to both ends of the hybridization chamber, and the Immobilizer™ MicroArray Slide was placed in the hybridization chamber (DieTech, USA). The chamber was sealed watertight and incubated at 65° C. for 16-18 hours submerged in a water bath. After hybridisation, the slide was removed carefully from the hybridization chamber and washed using the following protocol. The slides were washed sequentially by plunging gently in 2×SSC/0.1% SDS at room temperature until the cover slip falls of into the washing solution, then in 1×SSC pH 7.0 (150 mM NaCl, 15 mM Sodium Citrate) at room temperature for 1 min, then in 0.2×SSC, pH 7.0 (30 mM NaCl, 3 mM Sodium Citrate) at room temperature for 1 min, and finally in 0.05×SSC (7.5 mM NaCl, 0.75 mM Sodium Citrate) for 5 sec, followed by drying of the slides by spinning at 1000×g for 2 min. The slides were stored in a slide box in the dark until scanning.

G. Microarray Data Analysis.

The splice variant microarray was scanned in a ScanArray 4000XL confocal laser scanner (Packard Instruments, USA). The hybridisation data were analysed using the GenePix Pro 4.01 microarray analysis software (Axon, USA). The *C. elegans* reference RNA alone converted to first strand cDNA and labelled with Cy3-dCTP did not produce significant fluorescence intensity signals from the LNA substituted spike RNA specific capture probes.

G1. A Mathematical Formula for Analysis of the Microarray Data for Alternative Splicing One of the major limitations to comparative microarray hybridisation assays is that only identical probes can be compared between samples. Different alternative splice forms are detected using different probes, and this will tell directly if one splice form is more abundant in a given tissue compared to another. However, the estimation of the ratios between splice forms in a single tissue is not directly accessible. Given an example similar to that described below we employ the following calculations to calculate quantities of splice variants from array data. The theoretical justification is shown. To our knowledge this justification has not been used by any previous analysis.

The above scenario is tested in a comparative hybridisation, with two channels: I & II (signal from probe2 in channel I is called probe2(I), and so forth). Probe1 hybridises to both splice forms, Probe2 hybridises to A only, Probe3 hybridises to B only.

Since every transcript will hybridise to probe1, and every transcript will hybridise to either probe2 or probe3, there exists some relationship between the following:

probe1(I)~{probe2(I) and probe3(I)}.

probe1(II)~{probe2(II) and probe3(II)}.

For simplicity we assume that systematic differences between channels have already been eliminated through normalisation, although this is not essential.

We now imagine a factor (x) that will transform the signal of probe2 into a value directly comparable to probe1. Likewise we imagine factor (y) for probe3. As long as we are not facing saturation in the hybridisations, the assumption of a linear relationship between absolute probe signals is reasonable.

The introduction of variables x & y will give the following equations:

probe1(*I*)=(x)probe2(*I*)+(*y*)probe3(*I*).

probe1(*II*)=(*x*)probe2(*II*)+(*y*)probe3(*II*).

Since all signals are measurable, the above is two linear equations with two unknown variables, that can easily be solved. Further the ratio between (x)probe2(I) & (y)probe3(I) will provide the ratio between splice form A and B in channel I. Similarly, the ratio of (x)probe2(II) to (y)probe3(II) is used for channel II.

Data normalization is not required for this method.

In the above equations, probe1 denotes all probes that will hybridize to both spliceforms, probe2 denotes probes that specifically will hybridize to spliceform A but not B, and probe3 denotes probes that will specifically hybridize to spliceform B but not A.

In the case where two spliceforms consist of gene78 with two different inserts middle exons (INS3& INS4), probes can be grouped as in Table 20 (only LNA 40mers are considered here):

TABLE 20

| Probes that will hybridize to both constructs | Probes that will hybridize to INS3 constructs only | Probes that will hybridize to INS4 constructs only |
|---|---|---|
| Gene78.01a_40_LNA3 | Gene78.INS3_40_LNA3 | Gene78.INS4_40_LNA3 |
| Gene78.01b_40_LNA3 | Gene78.m01INS3_40_LNA3 | Gene78.m01INS4_40_LNA3 |
| Gene78.03a_40_LNA3 | Gene78.mINS303_40_LNA3 | Gene78.mINS403_40_LNA3 |
| Gene78.03b_40_LNA3 | | |

The equations can be solved with any combinations of one representative from each probe group. This gives a total of 48 (4×3×3) possible ways of solving the equations. The estimated quantities of the constructs are given as the average of all possible solutions (equations yielding non-positive solutions are ignored). This was done for all comparative hybridizations. Note that when comparing with gene78 with no insert, only 12 equations are possible (The, since the artificial splice variant construct with no insert has only one specific probe). The results from analysis of the microarray hybridization data from the RNA pools spiked with different splice isoforms at different ratios and concentrations are shown in FIGS. 39 and 40.

Results

Figure 39:
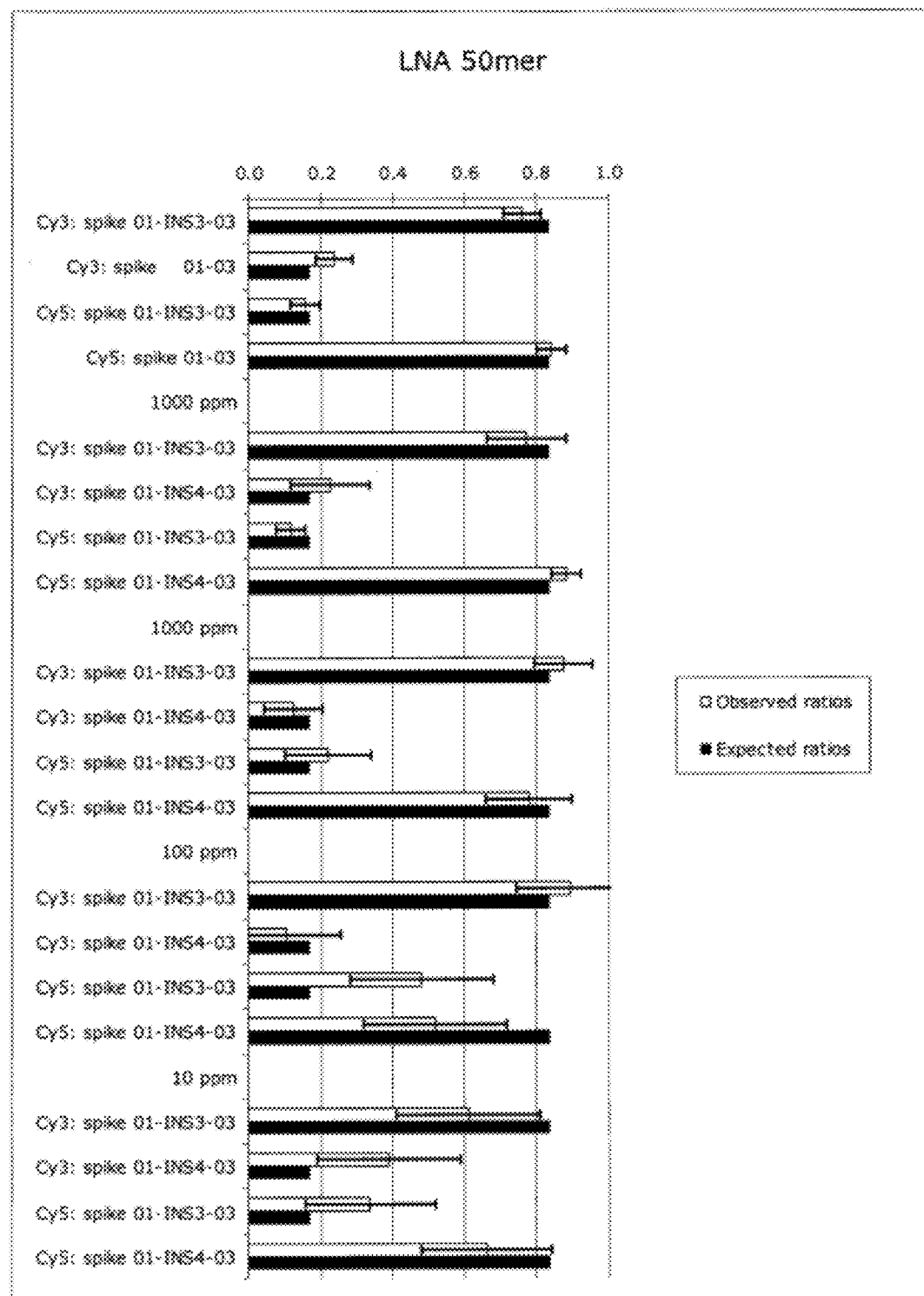
FIG. 39 shows the detection of alternatively spliced mRNAs using LNA-substituted 50-mer oligonucleotide capture probes. Parts per million (ppm) calculations indicate spike transcripts per total transcripts in the hybridisation mix. Calculations are based on an average C. elegans RNA being 1000 nucleotides as in Hill et al. (2000) Science 290:809-812. The 50-mer LNA-DNA mixmer capture probes, substituted with an LNA nucleotide at every third nucleotide position, are able to provide highly accurate measurements for fold-changes in the expression of three homologous, alternatively spliced mRNA variants in the concentration range of 1000 ppm to 10 ppm. The quantification of the splice isoforms was carried out using a set of both internal, exon-specific probes and merged, splice junction specific probes, printed onto microarrays and hybridized with complex cDNA target pools spiked with different cloned artificial splice isoforms in which the middle exon was either alternatively skipped or excluded completely resulting in the three different splice isoforms; 01-INS3-03, 01-INS4-03 and 01-03.
Figure 40:
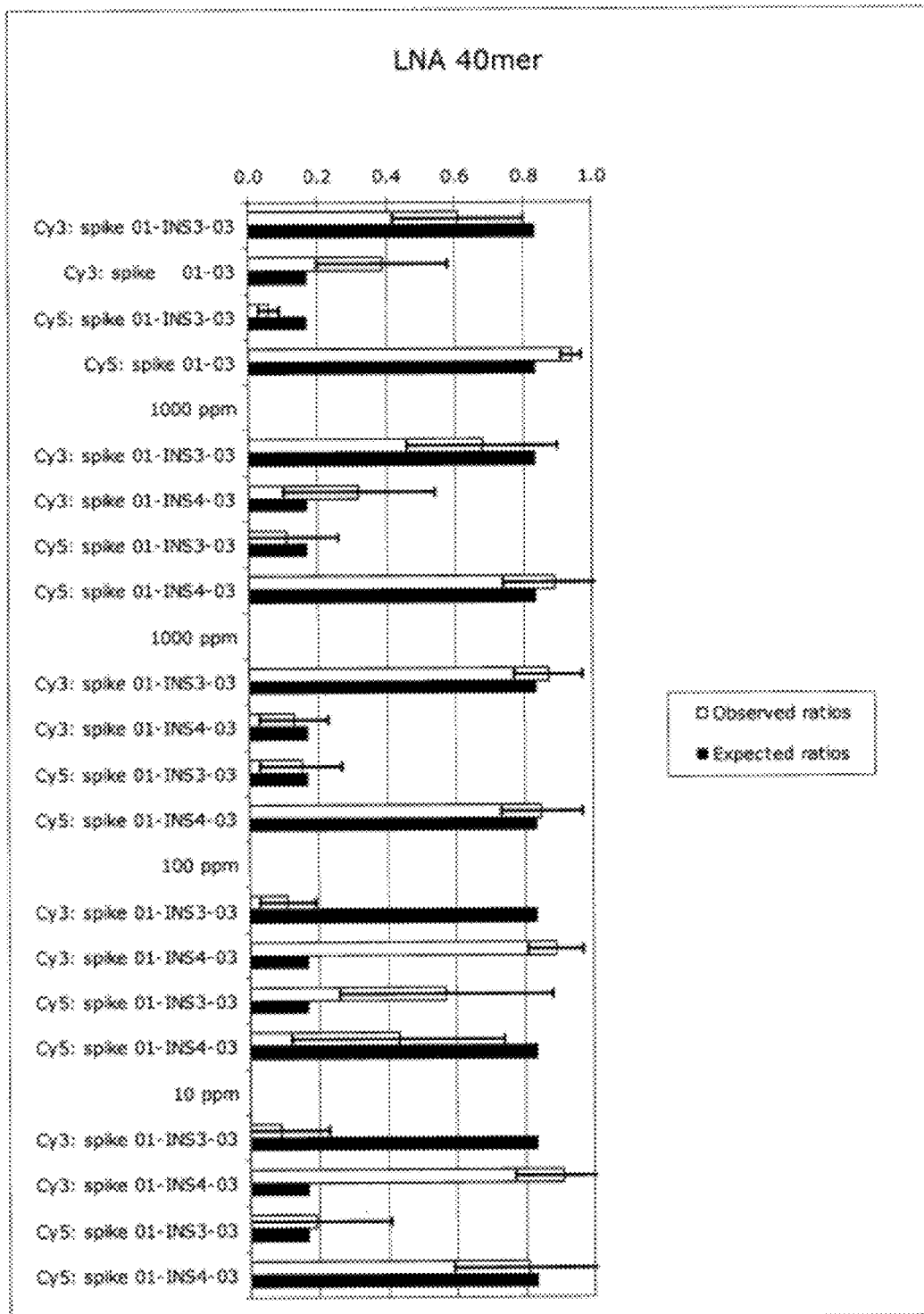
FIG. 40 shows the detection of alternatively spliced mRNAs using LNA-substituted 40-mer oligonucleotide capture probes. Parts per million (ppm) calculations indicate spike transcripts per total transcripts in the hybridisation mix. Calculations are based on an average C. elegans RNA being 1000 nucleotides as in Hill et al. (2000) Science 290:809-812. The 40-mer LNA-DNA mixmer capture probes, substituted with an LNA nucleotide at every third nucleotide position, are able to provide highly accurate measurements for fold-changes in the expression of three homologous, alternatively spliced mRNA variants in the concentration range of 1000 ppm to 10 ppm. The quantification of the splice isoforms was carried out using a set of both internal, exon-specific probes and merged, splice junction specific probes, printed onto microarrays and hybridized with complex cDNA target pools spiked with different cloned artificial splice isoforms in which the middle exon was either alternatively skipped or excluded completely resulting in the three different splice isoforms; 01-INS3-03, 01-INS4-03 and 01-03.

FIG. 39 shows detection of alternatively spliced mRNAs using LNA-substituted 50-mer oligonucleotide capture probes in a bar diagram format. FIG. 40 shows detection of alternatively spliced mRNAs using LNA-substituted 40-mer oligonucleotide capture probes. Both 50-mer and 40-mer LNA-DNA mixmer substituted oligonucleotide capture probes, substituted with an LNA nucleotide at every third nucleotide position, were able to provide highly accurate measurements for fold-changes in the expression of three homologous, alternatively spliced mRNA variants in the concentration range of 1000 ppm to 10 ppm. The quantification of the splice isoforms was carried out using a set of both internal, exon-specific probes and merged, splice junction specific probes, printed onto microarrays and hybridized with complex cDNA target pools spiked with different cloned artificial splice isoforms in which the middle exon was either alternatively skipped or excluded completely resulting in the three different splice isoforms; 01-INS3-03, 01-INS4-03 and 01-03.

EXAMPLE 53

Expression Profiling of Toxicological Responses in *Caenorhabditis Elegans* Using LNA Oligonucleotide Microarrays and Beta-Naphthoflavone and Primaquine as Model Compounds The present patent example demonstrates the use of the Exiqon *C. elegans* LNA tox oligoarray in gene expression profiling experiments in the nematode *Caenorhabditis elegans*. The *C. elegans* tox oligoarray will monitor the expression of a selection of 110 genes relevant for general stress response and for the metabolism of toxic compounds. Two different capture probes for each of these target genes have been designed, and included on the LNA tox array. In addition, the *C. elegans* LNA tox oligoarray contains capture probes providing control for cDNA synthesis efficiency and the developmental stage of the nematode. Capture probes for constitutively expressed genes for data set normalization is also included on the *C. elegans* LNA tox oligoarray.

A. Cultivation of *C. elegans* Worms

For all cultures the sample is divided into two, and one half of the sample is used as the control, the other as the treated sample. Worm samples are harvested and sucrose cleaned by standard methods. For heat shock treatment: the heat shock sample is added to S-media preheated to 33° C. in a 1 L flask suspended in a water bath at 33° C., the other sample is added to a 1 L flask with S-media at 25° C. Both samples are shaken at approximately 100 rpm. for an hour. For β-naphthoflavone and primaquine treatment: 0.5 mL of 5 mg/mL β-naphthoflavone in DMSO or 0.5 mL of 20 mg/mL primaquine in DMSO were added to each 500 mL volume of S-media culture after 28 hours of growth from L1. At the same time 0.5 mL of DMSO was added to the control. Incubation was for 24 hours. Samples are then harvested by centrifugation at 3000×g suspended in RNALater™ (Ambion) and immediately frozen in liquid nitrogen.

B. RNA Extraction

RNA was extracted from the worm samples using the FastRNA® Kit, GREEN (Q-BIO) essentially according to the suppliers' instructions.

C. Design and Synthesis of the LNA Capture Probes

Capture probes were designed using an in-house developed software. Regions with unique mRNA sequence of the selected target genes were identified. The optimal 50-mer oligonucleotide sequences with respect to Tm, self-complementarity and secondary structure were selected. LNA modifications were incorporated to increase affinity and specificity.

D. Printing of the LNA Microarrays

The microarrays were printed on Immobilizer™ MicroArray Slides (Exiqon, Denmark) using the MicroGrid II from Biorobotics (UK). The arrays were printed with a 10 µM capture probe solution. Two replicas of the capture probes were printed on each slide.

E. Synthesis of Fluorochrome Labelled First Strand cDNA from Total RNA

15 µg of *C. elegans* total RNA was combined with 5 µg oligo dT primer (T20VN) in an RNase free, pre-siliconized 1.5 mL tube, and the final volume was adjusted with DEPC-water to 14.5 µL. The reaction mixture was heated at +70° C. for 10 min., quenched on ice 5 min., spin 20 seconds, followed by addition of 1 µL SUPERase-In™ (20 U/µL, Ambion, USA), 6 µL 5×RTase buffer (Invitrogen, USA), 3 µL 0.1 M DTT (Invitrogen, USA), 1.5 µL dNTP (20 mM dATP, dGTP, dTTP; 4 mM dCTP in DEPC-water, Amersham Biosciences, USA), and 3 µL Cy3™-dCTP or Cy5™-dCTP (Amersham Biosciences, USA). First strand cDNA synthesis was carried out by adding 1 µL of Superscript™ II (Invitrogen, 200 U/mL), mixing and incubating the reaction mixture for 1 hour at 42° C. An additional 1 µL of Superscript™ II was added and the cDNA synthesis reaction mixture was incubated for an additional 1 hour at 42° C.; the reaction was stopped by heating at 70° C. for 5 min., and quenching on ice for 2 min. The RNA was hydrolyzed by adding 5 µL of 1 M NaOH, and incubating at 70° C. for 15 min. The samples were neutralized by adding 5 µL of 1 M HCl, and purified by adding 450 µL 1×TE buffer, pH 7.5 to the neutralized sample and transferring the samples onto a Microcon-30 concentrator. The samples were centrifuged at 14000×g in a microcentrifuge for ~8 min, the flow-through was discarded and the washing step was repeated twice by refilling the filter with 450 µl 1×TE buffer and by spinning for ~12 min. centrifugation was continued until the volume was reduced to about 5 µL, and finally the labelled cDNA probe was eluted by inverting the Microcon-30 tube and spinning at 1000×g for 3 min.

F. Synthesis of Fluorochrome Labelled Crna from Total RNA

First and second strand cDNA syntheses were made using the MessageAmp™ aRNA Kit (Ambion) according to suppliers' instructions. Five microgram of *C. elegans* total RNA was used as template for cDNA syntheses. Syntheses of fluorescent cRNA were made according to the MessageAmp™ aRNA Kit (Ambion) protocol with minor modifications. Cy3™-UTP or Cy5™-UTP (6 µl of a 5 mM solution Amersham Biosciences, USA) replaced biotin-CTP. The final concentration of ATP, CTP, and GTP was 7.5 mM whereas the concentration of UTP was reduced to 4.9 mM.

G. Hybridization with Fluorochrome-Labelled cDNA or cRNA

The arrays were hybridized overnight using the following protocol. The Cy3™ and Cy5™-labelled cDNA or cRNA samples were combined in one tube followed by addition of 3 µL 20×SSC (3×SSC final), 0.5 µL 1 M HEPES, pH 7.0 (25 mM final), 25 µg yeast tRNA (1.25 µg/µL final), 0.6 µL 10% SDS (0.3% final), and DEPC-treated water to 20 µL final volume. The labelled cDNA target sample was filtered in a Millipore 0.22 micron spin column according to the manufacturer's instructions (Millipore, USA), and the probe was denatured by incubating the reaction at 100° C. for 2 min. The sample was cooled at 20-25° C. for 5 min. by spinning at max speed in a microcentrifuge. A LifterSlip (Erie Scientific Company, USA) was carefully placed on top of the microarray spotted on Immobilizer™ MicroArray Slide and the hybridization mixture was applied to the array from the side. An aliquot of 30 µL of 3×SSC was added to both ends of the hybridization chamber, and the Immobilizer™ MicroArray Slide was placed in the hybridization chamber. The chamber was sealed watertight and incubated at 65° C.

for 16-18 hours submerged in a water bath. After hybridisation, the slide was removed carefully from the hybridization chamber and washed using the following protocol. The Lifterslip coverslip was washed off in 2×SSC, pH 7.0 containing 0.1% SDS at room temperature for 1 min., followed by washing of the microarrays subsequently in 1.0×SSC, pH 7.0 at room temperature for 1 min, and then in 0.2×SSC, pH 7.0 at room temperature for 1 min. Finally the slides were washed for 5 seconds in 0.05×SSC, pH 7.0. The slides were then dried by centrifugation in a swinging bucket rotor at approximately 200 G for 2 min. The slide is now ready for scanning.

H. Data Analysis.

Following washing and drying, the slides were scanned using a ScanArray 4000XL scanner (Perkin-Elmer Life Sciences, USA), and the array data were processed using the GenePix™ Pro 4.0 software package (Axon, USA). The data in each image was normalized so that the ratio of means of all of the features is equal to 1.

Results

Use of LNA-modified oligonucleotide capture probes in Exiqons C. elegans LNA tox oligoarray clearly allows the identification of distinct expression profiles for C. elegans genes relevant for general stress response and for the metabolism of toxic compounds.

TABLE 17

Expression profiling using LNA Oligonucleotide Microarrays.

| | Tox compound | |
|---|---|---|
| Gene name | Primaquine | beta-naphthoflavone |
| ABC_C34G6.4 | | 1.01 |
| ABC_F57C12.4 | −1.11 | |
| CYP_C03G6.15 | | 2.35 |
| CYP_C06B3.3 | | 2.47 |
| CYP_C49G7.8 | | 2.40 |
| CYP_F14F7.2 | −1.24 | −1.03 |
| CYP_K07C6.5 | | 2.68 |
| CYP_K09D9.2 | | 2.14 |
| DC_W05G11.3 | 1.16 | |
| ER_26S | −1.09 | −1.01 |
| HSP_C47E8.5 | | 1.17 |
| HSP_F26D10.3 | | 1.05 |
| HSP_F43D9.4 | | 1.27 |
| NAP_D2096.8 | | 1.14 |
| PPGB_F13D12.6 | 1.08 | 1.21 |
| RAD_Y116A8C.133 | | 1.13 |
| RPL_K11H12.2 | 1.15 | 1.42 |
| Ubi_F25B5.4 | | 1.37 |

Log2 transformed fold of changes for selected genes in the two expression profiling experiments hybridised with cRNA target.

TABLE 18

LNA-modified oligonucleotide capture probes.

| Oligo Name | Sequence |
|---|---|
| CEABC_C34G6.4_u293_LNA3 | TgcmCatTgcAcgGgcActTgtTcgAtcTccTtcTgtTttActTttGgaTg |
| CEABC_C34G6.4_u375_LNA3 | TcaTtcTagGatTgcmCagAtgGttAtgAtamCtcAtgTcgGagAgaAagGa |
| CEABC_F57C12.4_u15_LNA3 | mCcaAtgTtgTttAatTggTtgTaaTgtmCttGatGacmCtgmCatAatmCatAt |
| CEABC_F57C12.4_u480_LNA3 | mCacAagAtcmCtgTgtTgtTctmCcgGaamCaaTgaAaaTgaActTagAtcmCa |
| CEABC_F57C12.5_u111_LNA3 | TacTtgTtcTcgAcaAagGttGtgTagmCcgAgtTtgAcamCtcmCgaAgaAa |
| CEABC_F57C12.5_u444_LNA3 | TgaActTggAtcmCctTctTtgmCatTtaGcgAtgAtcAaaTttGggAagmCg |
| CEABC_K08E7.9_d8_LNA3 | TcaTtaAttTtgTgtAgcTttmCttTctmCgaTttTtgmCacGatmCttTccmCc |
| CEABC_K08E7.9_u51_LNA3 | AggGtgmCctActAcaAacTgamCccAaaAgcAgaTgamCcgAgaAgaAatAa |
| CEABC_Y39D8C.1_u37_LNA3 | AttGaaAgcGacGcgGaaAgtGccAtgTatTtcTaaTttTgtTttmCttTa |
| CEABC_Y39D8C.1_u422_LNA3 | TtgTcaGcaTatmCaaGagTagAtaTggAagTggAtamCacTctGctAatmCc |
| CEADH_H24K24.3a_d3_LNA3 | mCacmCttAttGcgTtcAatTttTgtTtcmCacmCtamCtamCtamCgaAtamCgtTg |
| CEADH_H24K24.3a_u50_LNA3 | TcamCaaGggAgaGagTctGcgGtcGgtGctGgcGttmCgaGaaAatAtaAc |
| CEAPEX_R09B3.1_u191_LNA3 | mCatGcaTccmCgamCgaGaaGaaGtamCtcAttTtgGagTtaTctGgcGaaTt |
| CEAPEX_R09B3.1_u37_LNA3 | GacmCatGctmCcgGtcGtcAtgmCaaAtcGacTtcTaaAttGctTctGatTa |
| CEAPO_C35D10.9_u15_LNA3 | TtgmCatGctGttAaaAccTatmCgtGtamCaaTatTgcmCtgTatAttmCccmCt |
| CEAPO_C35D10.9_u609_LNA3 | TggmCacAgcTtaAtaAcaAatTggAaaGtcGagGatTagTcgGtgTtgAa |
| CEAPO_C48D1.2_u176_LNA3 | GacAcamCgcAaaGgaTatGgaTgtTgtTgaGctGctGacTgaAgtmCaaTa |
| CEAPO_C48D1.2_u23_LNA3 | AgcAcgAaamCtcTgcmCgtmCtaAaaTtcActmCgtGatTcaTtgmCccAatTg |
| CEAPO_F20C5.1_u453_LNA3 | AtgGtcAtamCtcTaaAatGggmCagAacTtcAacmCaaAtcAttmCtcGtcAg |
| CEAPO_F20C5.1_u96_LNA3 | AacmCcgAgcTtgmCcgmCaaAgtGcaAgaAaaTtaTagAacGaaTgaAacAg |
| CEATPase_B0365.3_u31_LNA3 | GgaTggGtcGagmCgtGagAccTacTacTaaAgaAcaGctTgtGaaTctTt |
| CEATPase_B0365.3_u386_LNA3 | mCaamCgtTctmCgaTtcmCtamCggAcaAgaAtgGacmCtaTgcmCaamCagAaaGa |

TABLE 18-continued

LNA-modified oligonucleotide capture probes.

| Oligo Name | Sequence |
|---|---|
| CEATPase_C17H12.14_u356_LNA3 | TgcTcgTtaTccAgcTatTttGaaGggActTgtmCatGcaAggActTctTc |
| CEATPase_C17H12.14_u89_LNA3 | mCcgTttAgaGctTatTgcTaamCcaGatTgtmCccAcaAgtmCagAacAgcTc |
| CEATPase_F55F3.3_u215_LNA3 | TgamCggAcgmCtamCtamCccAtaTgtAttTgtTccAtcTtamCcaGcaAccAa |
| CEATPase_F55F3.3_u275_LNA3 | AgcTacTtcAttmCgamCaaGgaAcaTctmCggAaaAgtmCaaGtamCatmCccGg |
| CEATPase_Y49A3A.2_u103_LNA3 | AaaTtcAagGatmCcaGttGccGatGgtGaaGccAagAttmCgcAagGatTa |
| CEATPase_Y49A3A.2_u272_LNA3 | mCgaTcgTttmCtgmCccAttmCtamCaaGacTgtmCggTatGctmCaaGaaTatGa |
| CECALR_Y38A10A.5_u238_LNA3 | TcaGgaAcgAtcTttGacAacAttAtcAtcAccGacTctGttGagGagGc |
| CECALR_Y38A10A.5_u296_LNA3 | TgaActmCtamCtcTtaTgaAagmCtgGggAgcmCatmCggAttmCgaTttGtgGc |
| CECAT_Y54G11A.5b_u137_LNA3 | GaamCttTgcAggGccGctmCggGgaAtgTcaTgaTtttmCatTatTaaGggAa |
| CECAT_Y54G11A.5b_u189_LNA3 | GtcAatTctGggAgaAggTgtTggAtamCcgGggmCtcGggAgaGaaTgtGc |
| CECC_C03D6.3_u275_LNA3 | AtgTaaAgaAggAatGctTccmCgaAtgGatTggAtaTttAttTgtmCcaGa |
| CECC_C03D6.3_u430_LNA3 | GgamCcgAaaTttGtgmCagmCatGtcGgamCacGaaAttGatGgtmCtcAttTt |
| CECC_C07G2.3_d9_LNA3 | mCagAcamCgaAggTtamCgaTagAtaAccAtcTctmCaaAgtmCtaTcgAccTc |
| CECC_C07G2.3_u44_LNA3 | mCgamCgaTgtGcgTgtTccTgamCgaTgaAagAatGggAtaTtaAgaAaamCc |
| CECC_Y46G5A.2_u331_LNA3 | TtgTgcTccAtcGctGctmCcgmCttAcaGacTtgAcaAcgmCtcAccTttGc |
| CECC_Y46G5A.2_u385_LNA3 | AatGagmCggTtgTgcmCgtGtgAcgTcamCttmCgtmCacAgtGttGctmCtamCt |
| CECoA_C29F3.1_u316_LNA3 | AaaTtgAcamCcaAtcAaaTctGtcTcaTctmCctGagGacmCgtmCaamCttmCg |
| CECoA_C29F3.1_u392_LNA3 | AatmCttTgtGtamCggAgaTggGgcAaaAggmCagmCaaGaaAgtAaamCcaAg |
| CECoA_F08A8.4_u1094_LNA3 | AggAcaAggGgcActActGgcAcaGgcTttGatTatTgcAgtGagAtaTt |
| CECoA_F08A8.4_u1260_LNA3 | TtaAtgGagGtgAcaAtgGgtTccTtgGatTcgAtaAatTccGagTgcmCc |
| CECoA_F59F4.1_u109_LNA3 | GctmCttmCtcmCagTggGctmCaaAatAgtmCaamCtcAacAgaTcgGaaGttmCt |
| CECoA_F59F4.1_u424_LNA3 | AaaGctTcgAgaTggmCacGttmCgtmCtgTatmCtcGtgAagAacTtaTtgmCa |
| CECoA_Y25C1A.13_u115_LNA3 | GatTcgmCtgAacTttAtcAagAcgTggAatAtgAgcmCagmCtcmCtgTcgAc |
| CECoA_Y25C1A.13_u451_LNA3 | GatmCttAtcAccGcgTgcGatAttmCgaGtaGctTcamCagGatGcgAttTt |
| CECOL_C27H5.5_u493_LNA3 | GgaAagGaaGgaTccAttmCtcAgcTctGcamCttmCcamCcaTcaGagmCcaTg |
| CECOL_C27H5.5_u680_LNA3 | TggAtamCaaGgaGggAtcTggmCagTggTggAtcTggAagTggTggAtaTg |
| CECOQ_ZC395.2_u199_LNA3 | TtgAaaGaamCtcmCttGccGacGatmCctGaaAcamCacAaaGaaTtgmCtgAa |
| CECOQ_ZC395.2_u400_LNA3 | AtgTggGatGagGagAaaGaamCatTtaGatAcaAtgGaaAgaTtaGctGc |
| CECRYZ_F39B2.3_u171_LNA3 | AggmCtgAgcTctTggActTtgGcaTcaAcaTtgTctmCatTctTgaAggAa |
| CECRYZ_F39B2.3_u222_LNA3 | TtaTggTtamCagAagGagmCtgTttAcgGtgTagmCatTggGaaTgtmCttmCc |
| CECyclin_R02F2.1a_u24_LNA3 | mCacTtcAacmCaamCtcmCgtGttAatmCaaGcaAgcmCgcmCacmCatmCtaAtgAg |
| CECyclin_R02F2.1a_u312_LNA3 | TctmCatTgcTcgTcgAggmCtamCcaAcaAacActGgcAatAccmCaaTtaAt |
| CECyclin_ZC168.4_u203_LNA3 | TaaGaaAgtmCatTgaGgaTgcTgtmCgcTttGctmCgcmCgaAgtmCtcGtaTa |
| CECyclin_ZC168.4_u273_LNA3 | AagTtcAtcmCtgTtgAcgGaaTcgAggmCggAgaAtgmCtgTatmCggTcaTt |
| CECYP_B0213.15_u133_LNA3 | AcaGgaAatAtgAttTtgGatTtcGatTttGaaTcgGttGgtGctGccmCc |
| CECYP_B0213.15_u202_LNA3 | GctGagmCtgTatTtgGctAgtGaaAtgTgtGttTttGatActTtaAatGa |
| CECYP_B0304.3_u38_LNA3 | AcgAggTttGgaTcamCaaTcaGaaTtcTgtGaaAtaAgcGttTttTggGa |

TABLE 18-continued

LNA-modified oligonucleotide capture probes.

| Oligo Name | Sequence |
|---|---|
| CECYP_B0304.3_u89_LNA3 | AgtTctmCggTctAacAgtGtcTccmCgtTgaAtaTtcTtgTaaAatmCacAc |
| CECYP_C03G6.14_u706_LNA3 | AtgAccActmCaaAatActGctAaaAgaTttGcaGcgGcaGaaGccGttAa |
| CECYP_C03G6.14_u768_LNA3 | TtgAtaTggmCtgTacmCtgTatGgtTtttTgaGgamCgtTtttTaGgaGtcGa |
| CECYP_C03G6.15_d9_LNA3 | AttTatTcaTtcAtcmCatGtaAacTgtAtaTtttTgaAttTgtGttGtaAa |
| CECYP_C03G6.15_u148_LNA3 | GccAaaGcaGaaTtgTatTtgAtcTtcGgtAacmCttmCtcmCttmCgcTacAa |
| CECYP_C06B3.3_u102_LNA3 | AttTtgAatmCttmCtgGgaAaaTgcmCatmCcamCtcGagAaamCcgTtcmCgtTt |
| CECYP_C06B3.3_u474_LNA3 | mCtaAcgGagGatmCtcGccAatTatmCttTgaGagAcaAaamCtgAaamCtcmCt |
| CECYP_C12D5.7_u399_LNA3 | AtcTagTccmCaaTgaAtcTccmCacAtgmCtgTtamCtcGtgAtgTtcAacTc |
| CECYP_C12D5.7_u65_LNA3 | TttTgcTttmCatmCgcAaaAgcTcaAgaTtamCacAtgTcaGgtmCaaGccAa |
| CECYP_C45H4.17_u27_LNA3 | mCcgmCgamCttTaaAgaGaaGatmCatAaaTttGcaTtgTttTttGttTgtAt |
| CECYP_C45H4.17_u598_LNA3 | mCgaGggTgaTtcGgaGacTttmCagTaaTgtmCcaActTtcAaaTgtTtgmCa |
| CECYP_C45H4.2_u110_LNA3 | TagAtamCaaGatAcaTccmCtcAaaAgaAggmCctAccGtcAatGgcmCaaAg |
| CECYP_C45H4.2_u429_LNA3 | TcaAcgmCgtmCtaTaaAtgAatmCacAacGagGtaTcaAcaTtcTccmCccTg |
| CECYP_C49C8.4_u363_LNA3 | AtgmCtgAtgTtgAaaTtgmCtgGctAccGtaTtcmCaaAagAtamCtgTaaTc |
| CECYP_C49C8.4_u883_LNA3 | AtgAatmCcaTggmCttGgamCatmCtcmCcgTttTtcAagGgaTatAaaAatGt |
| CECYP_C49G7.8_d6_LNA3 | AtgmCaamCgaAttAgtGaaAaaTtcAtcmCtgGaaTaaAaaAtaAttmCtaAa |
| CECYP_C49G7.8_u795_LNA3 | AtcGctAcgAcaAtcTttmCcgAtgmCctTcgAagTttmCgaAagmCttTctmCt |
| CECYP_F01D5.9_u374_LNA3 | GagGtcGgtGgaGgaGgaAgtGgaAatTgamCggmCaaAatmCctGccmCaaGg |
| CECYP_F01D5.9_u46_LNA3 | mCccTctTtgGgaTtttmCcamCtcAagTttActGttmCggmCagmCagTgaTatAa |
| CECYP_F08F3.7_u25_LNA3 | GagTtgGttmCcamCagAatGctTagGacGttTaaAttmCgtmCacAaamCttTt |
| CECYP_F08F3.7_u401_LNA3 | mCaaTatGgtTccmCatTttAgcAacTcaTatGaamCacAgaAgaTgtmCctTg |
| CECYP_F14F7.2_u397_LNA3 | GaaAaaGgcGtcGacAttTtaTgtGacAcgTggAcamCttmCacTatGacAa |
| CECYP_F14F7.2_u68_LNA3 | TaaTtgAatTacGggTctTttGtamCatAttAatTttAgtAtamCttTgtGa |
| CECYP_F42A9.5_u435_LNA3 | AtaTcaAtgmCaamCtaTtaAtgAatmCacAacGtcTtgmCcaAtcTtcTccmCg |
| CECYP_F42A9.5_u55_LNA3 | GgaGtgActAtgAaaGcaAagAgtTacmCgaTtgAaamCtgAaaGacAgamCa |
| CECYP_K07C6.3_u3_LNA3 | AatmCttTaaTgaTaaTtttAtgGgaTctGtaTttmCtcTttmCtgTcaAtaAa |
| CECYP_K07C6.3_u354_LNA3 | AtgAgcmCcamCaaAtgTaaAagGatAcgAgaTtgAttmCggGaamCagTcaTg |
| CECYP_K07C6.4_u118_LNA3 | AtcmCtgmCgaTatGacAttAagmCcamCatGgtTctGaamCctTcaAcaGaaGa |
| CECYP_K07C6.4_u87_LNA3 | mCtgAacmCttmCaamCagAagAtaAacTtcmCgtAtaGcgmCtgGaaAaamCtcmCt |
| CECYP_K07C6.5_u7_LNA3 | AttTaaAggAatTcamCagmCtcAaaAaaTaaTaamCtamCcgGttmCagAgaTt |
| CECYP_K07C6.5_u99_LNA3 | AatTtgAgcmCacAtgGcaAgtTatmCaamCagAggAgamCaaTgcmCgtAcaGt |
| CECYP_K09A11.3_u362_LNA3 | TgamCatTctActTaaAggGaaGaaAatAccAacTggTacmCctTgtAttTg |
| CECYP_K09A11.3_u48_LNA3 | TcamCcamCaaAgcmCatAcaTatGcgAgcTagTtcmCtcAggmCtgmCttAaamCc |
| CECYP_K09A11.4_u238_LNA3 | TtcGacAaaActAttTtgGaaAgaAcaAtcmCcaTtcAgtGtcGgcAaamCg |
| CECYP_K09A11.4_u68_LNA3 | TctGacAacAaaGccAtamCacGtgmCcgActAatTccAcaAtcAgcTagAa |
| CECYP_K09D9.2_u151_LNA3 | TtgGcaAaaGcaGaaTtgTatTtaAtcTttGgaAacmCtcmCttmCttmCgcTa |
| CECYP_K09D9.2_u866_LNA3 | TgaAtcTttmCaaActTatmCacTccTtttTaaTacTacmCgtTccTgtTtgGa |

TABLE 18-continued

LNA-modified oligonucleotide capture probes.

| Oligo Name | Sequence |
|---|---|
| CECYP_T10B9.10_u410_LNA | AttGagAttGtaTccAttGgcGtcTctTgtTcamCaaTcgAaaAtgTctmCa |
| CECYP_T10B9.10_u56_LNA | AacTgcTacTatTgcGccAtcAagTgtGctGctmCaaActTaaAtcmCagGt |
| CECYP_T10B9.7_u102_LNA3 | TtgAgamCagGaaAtaAgamCtaGaaTtcmCttTgaAacTggTggGaaGtgmCt |
| CECYP_T10B9.7_u267_LNA3 | AagAtgTcaAagAatTcaAgcmCagAacGatGgtmCcamCcgAcgAgcmCatTa |
| CECYP_T19B10.1_u100_LNA3 | AttGaamCcaActmCtgAaaTatAatGacAcaAaamCcaTgtmCtgGaaGtgGt |
| CECYP_T19B10.1_u319_LNA3 | GgcAatGtgAcaAtaTctmCcaAtgGttmCttmCacAgcAatmCatmCacGtgTt |
| CECYP_Y49C4A.9_u121_LNA3 | mCtaTtcAatmCgaTatTttAtcAcamCcaTccAgtGctGgamCctmCcaTcaTt |
| CECYP_Y49C4A.9_u413_LNA3 | GtcTcaGagAtgTgtAaaTttActTccmCtgmCaaTttGttTcamCgcAacTa |
| CECYP_ZK177.5_u394_LNA3 | TtcmCgaAtgTttmCcaAttGggActGaaGttTcaAgaGtcAccmCagAaaAa |
| CECYP_ZK177.5_u445_LNA3 | GatmCcaGcaTctTccAagmCttAcaTtcmCtcmCgtGctTgtAtcAagGaaAc |
| CEDAO_C47A10.5_d9_LNA3 | TttGaaAacmCtgTttTatTatTaaAatAgaTaaTtgAttAgtTctGtamCg |
| CEDAO_C47A10.5_u269_LNA3 | AtamCgtTgcActGcaTccGgcTatGagGgaGccAaaAatmCttAggGgaGt |
| CEDC_C01A2.3_u373_LNA3 | GcamCttmCcaTtcAtcTctGcaGctActAtgGctTtgGtgAcaAaaGttGg |
| CEDC_C01A2.3_u96_LNA4 | mCcgTccAaaAgaAtgmCcaTctmCacAagTctTgaAatmCttAtaAagGtaGt |
| CEDC_C34F6.1_u301_LNA3 | GagGgaTcaAcaGtaAccTcgTgcGgtAttGacAagGgaTgtmCcgGaaGg |
| CEDC_C34F6.1_u450_LNA3 | GatGgtTctTcgAtcGcaAacAaaAcaGatGtgmCtcmCatTtamCatAcgGa |
| CEDC_F33D11.3_u126_LNA3 | AtgGagAaaAtgGatmCtgAtgGagTtgmCagGaaGtgAtgGagmCtcmCagGa |
| CEDC_F33D11.3_u14_LNA3 | TgaAtcTccAtaAatTatTcaAtgTttmCcaAatAttTaaTttAtcAatTg |
| CEDC_F46E10.2_u392_LNA3 | GctmCaamCacGgtAggAtcmCtaTggAacmCgtmCggAggAgcAggmCctmCggAg |
| CEDC_F46E10.2_u54_LNA3 | mCgtGacAacmCtcTtaTttAttTctGtaAaamCtgAttmCgcmCaaActTttGt |
| CEDC_F56G4.2_u382_LNA3 | GaaGctTtcAaamCcaAatGagTtcmCttmCccGgaAtcmCcaAagAatAccAa |
| CEDC_F56G4.2_u82_LNA3 | AcaAtgAaaAgaGagGatGgaAagGaaAtcGaaGtcTctGttmCttGacGa |
| CEDC_M162.2_u103_LNA3 | GatGagGtamCatAacTttGtgTgcAgtTatAggmCcaTctAcaGtamCctGc |
| CEDC_M162.2_u480_LNA3 | TtcmCatmCatmCacTaamCcgAttGtcmCtgAcaTtgAtgGccAaamCcaGggAa |
| CEDC_R10E4.11_u274_LNA3 | TcamCatTatmCgaAcaAgtActAgtAagmCatGctGtgAtgGagTgcmCgcTa |
| CEDC_R10E4.11_u397_LNA3 | mCacGgaGatmCacGacAtcAaaGcgGatTgcTtaGagTgtGgaAacmCgtmCt |
| CEDC_T04C9.1_u321_LNA3 | ActAtcTacGtgGcamCgtTggActmCatmCatmCgaTggGaamCgamCgtAtaAg |
| CEDC_T04C9.1_u64_LNA3 | TctmCtgGccAgtTcamCttTgtGatmCaaTctmCagAttmCgtmCcamCacAagAt |
| CEDC_W02A2.3_u32_LNA3 | mCtamCttmCcgmCaaGaaGgcmCcgTcgTttmCtaAtcGatmCgaAcaTctmCacAc |
| CEDC_W02A2.3_u374_LNA3 | AtgGatGatmCgamCccActTgcmCacTgamCccAcaAtcmCcgmCacTcamCtamCc |
| CEDC_W05G11.3_u153_LNA3 | AagAcgGagAggmCtgGagAgaAcgGtamCcgAtgGagAgcmCagGaamCtgAt |
| CEDC_W05G11.3_u51_LNA3 | mCcamCccAggAggAggGatAcaAgaGaaGaaAgtAcaGatTctmCcaActAa |
| CEDC_ZK863.5_u256_LNA3 | AgtTtcAcamCttmCttTttGccGttTtgGttmCccGttAtcAatmCcaTtgAt |
| CEDC_ZK863.5_u324_LNA3 | mCttTtaTatTctmCatmCaaTttGttTccTacTtgGtcAgcTgaGgaTcgTt |
| CEEPHX_Y55B1BR.4_u161_LNA3 | TtcGgcAcaAatGgaGcaAaaGtaTcgTggTtaTtgTgaTgcGatTatTc |
| CEEPHX_Y55B1BR.4_u93_LNA3 | mCtamCtaTgaAtgAgcTcamCtgGacTcaTttAtcAacTcgAgtmCaaAagmCc |
| CEER_18S_u388_LNA3 | GttGgcGaaTctTcgGgtTcgTatAacTtcTtaGagGgaTaaGcgGtgTt |

TABLE 18-continued

LNA-modified oligonucleotide capture probes.

| Oligo Name | Sequence |
|---|---|
| CEER_18S_u82_LNA3 | GaamCtgAttmCgaGaaGagTggGgamCtgTcgmCttmCgaGgtTtaAcgActTc |
| CEER_26S_u342_LNA3 | TgtTatTgcGaaAgtAatmCctGctTagTacGagAggAacAgcGggTtcAa |
| CEER_26S_u38_LNA3 | TgcAtamCgamCttGgtmCtcTtgGtcAagGtgTtgTatTcaGtaGagmCagTc |
| CEFOXO_R13H8.1b_u331_LNA3 | TgtGctmCagAatmCcamCttmCttmCgaAatmCcaAttGtgmCcaAgcActAacTt |
| CEFOXO_R13H8.1b_u393_LNA3 | TtaAgamCggAacmCaaTtgmCtcmCacmCacmCatmCatAccAcgAgtTgaAcaGt |
| CEGAPDH_K10B3.7_u21_LNA3 | AcaTtgmCtamCcaAggmCctAagmCcgmCttmCaaAttmCtcTaaGtcTgaAatGa |
| CEGAPDH_K10B3.7_u727_LNA3 | GttGagTccAccGgaGtcTtcAccAccAtcGagAagGccAatGctmCacTt |
| CEGBA_F11E6.1a_u232_LNA3 | AgtAaaTtcmCttmCcamCgtGgaTctActmCgtGtgTtcAcaAagAtcGagGg |
| CEGBA_F11E6.1a_u451_LNA3 | GgtmCcaAtaAtgGgaGacTggTtcmCgcGcaGaaAgtTatGcaGatGatAt |
| CEGLU_C02A12.1_u264_LNA3 | AgaAaamCttmCgtTggAccmCtgmCtaAggAgaAgtAttTcaAgcTtcTgaGc |
| CEGLU_C02A12.1_u55_LNA3 | GagmCacmCcgAagmCtcAagmCcaTatTtgGaaAcaAgamCcaTacTctTcaAa |
| CEGLU_C46F11.2_u271_LNA3 | GttAccmCtcTacAaaTctmCgcTtcAatmCcaAtgTtgTtcGcaGtcAccAa |
| CEGLU_C46F11.2_u45_LNA3 | mCcgAagAgcTcgTtamCtaTgcGagGagGtgTgaAgcmCggAatAatTttTt |
| CEGLU_F26E4.12_u109_LNA3 | AagTtcTtgGttGgamCgcGatGggAaaAttAtcAagAgaTttGgamCcaAc |
| CEGLU_F26E4.12_u480_LNA3 | AcgAttTcaAcgTcaAaaAtgmCtaAtgGtgAtgAcgTgtmCacTttmCggAt |
| CEGLU_R07B1.4_u166_LNA3 | AccTggGttGatGttTttGcgGctGaaAgtTtcTccAagmCtcAttGatTa |
| CEGLU_R07B1.4_u38_LNA3 | GaaGtamCgtmCtcmCcaAagAaaAgcTacmCccAgcTtaAggmCatTgcAcaAt |
| CEGLU_T09A12.2_u220_LNA3 | GcgmCcaGatAtgTatTcaAagAtcGagGtaAatGgtmCagAacActmCatmCc |
| CEGLU_T09A12.2_u335_LNA3 | AatmCtamCagGgaAaaAggAttTcgAgtTgcmCgcGttTccAtgmCaaTcaAt |
| CEGLU_T28A11.11_u299_LNA3 | AgaTggmCaaAgaAgcAtamCatAacTgaAacTctTccmCggGgaGctActAc |
| CEGLU_T28A11.11_u54_LNA3 | TgaAtaAacGggmCcgAacTaaAtcmCatTcgTcaGtgGaaAtgGgaAacAa |
| CEGPD_B0035.5_u256_LNA3 | GtcmCgtmCttmCctGatGctTatGaamCgcmCtaTtttmCtcGaaGtaTtcAtgGg |
| CEGPD_B0035.5_u478_LNA3 | TgtGgaAaaGctmCtcAacGagAagAaaGcaGaaGttmCgtAtamCaaTtcAa |
| CEHSP_C09B8.6_d8_LNA3 | AtaTcgmCcgmCctGctTccTcamCcaAccmCgaAtaAcgmCaamCaaAaamCttTa |
| CEHSP_C09B8.6_u286_LNA3 | AagAgcmCcamCtcAtcAagGatGaaAgtGatGgaAagActmCttmCgtmCtcAg |
| CEHSP_C12C8.1_u127_LNA3 | mCaaGatAttTtaAcaAaaAtgmCatmCaamCaaGaaGccmCaaTcaGgtTccGg |
| CEHSP_C12C8.1_u1531_LNA3 | mCttGggmCatTctGtamCggGatGctGtcAttActGtgmCctGcaTatTttAa |
| CEHSP_C47E8.5_u310_LNA3 | AagAagmCatmCtcGaaAtcAacmCcaGacmCacGctAtcAtgAagAcamCttmCg |
| CEHSP_C47E8.5_u361_LNA3 | AtgAaaGctmCaaGctmCttmCgtGatTccTctActAtgGgaTacAtgGccGc |
| CEHSP_F26D10.3_u276_LNA3 | TtaAgcAgamCcaTtgAggAcgAgaAgcTcaAggAtAgaTcaGccmCagAa |
| CEHSP_F26D10.3_u397_LNA3 | mCgtmCttTccAagGatGacAttGaamCgcAtgGtcAacGaaGctGagAaaTa |
| CEHSP_F43D9.4_u169_LNA3 | GtcGacTtgGctmCacAtcmCacAccGtcAtcAacAagGaaGgamCagAtgAc |
| CEHSP_F43D9.4_u275_LNA3 | mCaaTctTgaGggAcamCgtTctmCacmCatTgaGggAcamCcamCgaGgtmCaaGa |
| CEHSP_F44E5.4/5_u123_LNA3 | TcamCtaAaaTgcAccAatmCtgGacAatmCttmCgtmCttmCtgmCtgGatGcgmCt |
| CEHSP_F44E5.4/5_u380_LNA3 | TcaTgaAgcTaaAcaAttmCgaAaaGgaAgaTggTgaAcaAcgGgaAcgTg |
| CEHSP_F52E1.7_u175_LNA3 | AagTatAacmCttmCcaAcaGggGtcmCgtmCcaGaamCaaAtcAagTccGaaTt |

TABLE 18-continued

LNA-modified oligonucleotide capture probes.

| Oligo Name | Sequence |
|---|---|
| CEHSP_F52E1.7_u448_LNA3 | TttAacmCatGgcmCgcAgaTtcTtcGatGacGtcGacTttGatmCgcmCacAt |
| CEHSP_F54D5.8_u252_LNA3 | GcgTcgAaaAgaTctmCccTgaAgtmCtgmCatTgamCtgGccTtgAtaTtaTg |
| CEHSP_F54D5.8_u318_LNA3 | AcaTagTctTcgTcaTcaAggAtaAgcmCacAccmCgaAatTcaAgcGagAg |
| CEHUS_H26D21.1_u117_LNA3 | TcgmCcaAcamCtcGgamCacGtgmCcaAaaTgaAtaTcaTctmCaaAtcGaaTg |
| CEHUS_H26D21.1_u478_LNA3 | GtcGaaGttAgaAatmCcaGaaGccGatAttGttTctmCatmCaaAttmCcaAt |
| CEMRE_ZC302.1_u169_LNA3 | ActActmCgtGgaAgaTccAatAaaGttGttTcaAcgmCgamCaaAtcGatTc |
| CEMRE_ZC302.1_u292_LNA3 | GgcAgtGaaGatGaaGtgGcaAatTctGatGaaGaaAtgGgaAgcAgtAt |
| CEMTL_T08G5.10_d127_LNA3 | TtgTcaAcgAccAgaAgcAaaAatTatGggAatmCgcGatAaaAttmCaaGg |
| CEMTL_T08G5.10_u45_LNA3 | GatGcaAgtGtgmCcaActGcgAatGtgmCtcAggmCtgmCtcAttAatTtgAa |
| CENAP_D2096.8_u356_LNA3 | GacGatAtgTtcGatTtcmCcaGgaGagGacGgtGatGatGtgTcaGacTt |
| CENAP_D2096.8_u70_LNA3 | GacGatAtgTtcGatTtcmCcaGgaGagGacGgtGatGatGtgTcaGacTt |
| CEPAI_F56D12.5_u241_LNA3 | GagGtcGtcGtaAtcmCacAagGctmCcaAgaAagmCaaGtgmCtcGacAttTc |
| CEPAI_F56D12.5_u301_LNA3 | GatActTttGgcAagmCtcGttmCcaAtcAagAagGagGtcAtcmCcaGatmCg |
| CEPDI_C07A12.4_u28_LNA3 | GatGagGagGgamCacAccGagmCtcTaaAtcmCacAttmCcaAtamCagTtcAa |
| CEPDI_C07A12.4_u433_LNA3 | mCttAtgTccGaaGatAtcmCcaGagGatTggGacAagAacmCcaGtcAagAt |
| CEPDI_C14B1.1_u119_LNA3 | TacmCccAgtmCgamCtaTgaTggAgamCagAaamCctmCgaGaaGttmCgaAgaAt |
| CEPDI_C14B1.1_u358_LNA3 | mCtcGtcGccTccAacTtcAacGaaAttGccmCttGatGaaAccAagActGt |
| CEPGK_T03F1.3_d9_LNA3 | TtcTatTgtTtaTtcmCttGccmCaaTagTgtAttTgtAttTatTctTtcTc |
| CEPGK_T03F1.3_u424_LNA3 | mCaaAtcmCatmCtcmCcaGtgGatTtcGtcAttGctGacAagTtcGccGagGa |
| CEPON_E01A2.7_u223_LNA3 | GttTctGatTcgAcamCttTatGgamCcaTctmCaaGttmCtgmCgaGttTctTt |
| CEPON_E01A2.7_u79_LNA3 | GggAaamCaaAtgAttGttGgtAcaGtaGccmCgcmCctGctAttmCacTgtGa |
| CEPPGB_F13D12.6_u44_LNA3 | mCgaGcamCatmCatmCcaAtcGttmCctGttmCaamCaaGgcmCttmCtaAtcGttAg |
| CEPPGB_F13O12.6_u440_LNA3 | TgaTgaGagmCccAgtAacmCaaTtaTttGaamCcgTcaGgaTgtGcgTaaGg |
| CEPPS_T14G10.1_d2_LNA3 | mCgtmCtaAtcGaaGaaGggGatmCgtGggmCaaTcaTaamCtaAttAacmCttmCa |
| CEPPS_T14G10.1_u240_LNA3 | mCaaTggmCtcmCagGtcTttmCtgmCtcTtcAtaTacTtcmCatTccGagTtgmCt |
| CEPRDX_R07E5.2_u405_LNA3 | GttmCtcTtgGagmCtgAagTtgTcgCgtGctmCgtGtgAttmCtcActTctmCt |
| CEPRDX_R07E5.2_u42_LNA3 | TcgmCtamCcaGcaAggAatActTcaAcaAggTcaAcaAgtGatmCacAcaGa |
| CEPYC_D2023.2_u256_LNA3 | AagGaaAttGtaActmCgcmCcaAgaGctmCtcmCcaGgtGtcmCgtGgamCatAt |
| CEPYC_D2023.2_u427_LNA3 | TtgActGgaTtgGagAttGcgGaaGaaGttGatGttGaaAtcGagAgtGg |
| CERAD_F10G7.4_u169_LNA3 | GccAagTctmCaaGcaAtaAgtGttGatmCaaTcaGagmCcaTacGgaGagAt |
| CERAD_F10G7.4_u267_LNA3 | AtaTtgAgamCttmCggGacAagmCggActTctmCatmCtgTcamCagmCaamCtgmCc |
| CERAD_F32A11.2_u250_LNA3 | GatmCcgmCagAgaAtcGagTatTtcmCtcTcgAgamCccAtgGatAtcAacTg |
| CERAD_F32A11.2_u380_LNA3 | TccGttAagAagmCtcActGgaAaaAcamCacGgcTcgAacGaaAttGgaAt |
| CERAD_T04H1.4_u274_LNA3 | AatTtgGatGagAgcAaaGtgGaaGgaAtgGctAtcGttTtgGcaGatAt |
| CERAD_T04H1.4_u375_LNA3 | GtgmCtgGtcAaaAaaTgcTtgmCttmCgtTgcTtaTtcGcaTtgmCacTcgmCa |
| CERAD_W06D4.6_u325_LNA3 | mCttmCgaGaamCtcTtcAagTtgGaaTcaAcaGtgGcaTcgGatAcamCatGa |

TABLE 18-continued

LNA-modified oligonucleotide capture probes.

| Oligo Name | Sequence |
| --- | --- |
| CERAD_W06D4.6_u34_LNA3 | GtgmCctTctGaaGccGaaGaaAacGacGatTagTtaAatGttTccAagTt |
| CERAD_Y116A8C.13_u289_LNA3 | GatAaaAtcGatAgcGacGacGatGagGaaGccGatGatGagGagmCtcGa |
| CERAD_Y116A8C.13_u59_LNA3 | GcaGgtGgaTacGgaTgtGgaGctGacTttTgcGttTtaTcaAgaAtcTc |
| CERAD_Y39A1A.23_u221_LNA3 | TccmCgtAgaAgtAgaAatGctAgaAgaAccTgaAcaAgaAgaTcaAgaAa |
| CERAD_Y39A1A.23_u276_LNA3 | TgcAagAtgTcaGtaTtgAaamCaaTtcmCtgTagAgamCccmCcgAagAaaAt |
| CERAD_Y41C4A.14_u509_LNA3 | AgtmCtcGtaTccGggAatGttTcaGccTgtGaaAatGctTgtTgaAgamCg |
| CERAD_Y41C4A.14_u731_LNA3 | mCttmCaaAacmCgtmCgcTttTaaGgaTacAggAacGtgGcamCgcTtcmCgaGg |
| CERAD_Y43C5A.6_u131_LNA3 | mCagAttGtamCctTcgAaaAggAaaAggAgaGaaTcgmCgtmCgcAaaAatGg |
| CERAD_Y43C5A.6_u429_LNA3 | TgaTggmCttTgaTtaTtcGagmCagGagmCaaTgaTgtmCcgAgaGtcGttAt |
| CERFC_F31E3.3_u128_LNA3 | mCaaTgamCgaGaaTatTggAgtAatGggGaaActGgtTgcGacTtgmCgaAa |
| CERFC_F31E3.3_u55_LNA3 | TtgGaaAacAatmCtcmCtcGacTtttmCtgmCtcActmCttmCgtGaaActAtcmCa |
| CERPL_K11H12.2_d1_LNA3 | TctTgtTatTttAttTtgTttTggGctTgtTccGaaAatGaaAtgGttGt |
| CERPL_K11H12.2_u172_LNA3 | mCaaTggAtcAccAagmCcaGttmCacAagmCacmCgtGagmCaaAgaGgamCtcAc |
| CERT_F36A4.7_u1396_LNA3 | mCttTgtGatGtgAtgActGcgAagGgamCacTtgAtgGctAttAcgAgamCa |
| CERT_F36A4.7_u2302_LNA3 | GagmCcaGctActmCagAtgAcamCtcAacAcgTtcmCatTatGcaGgaGttTc |
| CERT_F36A4.7_u289_LNA3 | TacActmCcaTccTcgmCcgAcaTacAatmCcaAcaTctmCcamCgcGgaTtcTc |
| CERT_F36A4.7_u2919_LNA3 | AtgGagAagAtgGttTggAtgGaaTgtGggTtgAgaAtcAgaAtaTgcmCg |
| CERT_F36A4.7_u4269_LNA3 | AacmCggGatAccGtgTcgAacGtcAcaTgaAagAtgGcgAtaTaaTcgTc |
| CERT_F36A4.7_u5485_LNA3 | GagGagAttAaamCgcAtgTcaGtgGctmCatGtcGagTttmCcaGaaGtcTa |
| CESLC_F52F12.1a_u249_LNA3 | AgaTatTgcmCtcTacTtaTcaTggGccTgaTggmCttTgtmCtgmCcgGtaTt |
| CESLC_F52F12.1a_u76_LNA3 | GaaTctmCaamCcamCttmCtgGaamCccmCatAcamCcaAtgGatAgaAgamCggAg |
| CESLC_K11G9.5_u400_LNA3 | GttGttmCttTttTccGtgAtcTtttTcaTgtTtaTgtmCtgAacGtgGcaGg |
| CESLC_K11G9.5_u462_LNA3 | GacTcgTtgGtgTctTgcTagGatGtcTtgGgtTcaTtcmCtcAatmCgtTg |
| CESLC_Y32F6B.1_u179_LNA3 | GtamCtgGgcTcgAggGctGaaActAatmCgaAgaAgaAacTccAgaAgaTa |
| CESLC_Y32F6B.1_u280_LNA3 | GgaTcaTgcTctGttTacGacActGatGagTtaAgaGtcAgamCtgmCacGt |
| CESLC_Y37A1C.1a_u104_LNA3 | mCgaTggTtcTtcTcgTctAtcAtaTcgGggTagTtgmCcgAagTgtTgaAa |
| CESLC_Y37A1C.1a_u404_LNA3 | mCaaAtcGaamCtgGtaTaaAggAggAccGacGgaGacGaaTttGaamCgaGa |
| CESLC_Y70G10A.3_u383_LNA3 | AttmCgaTcaAagAacTctGgcTctmCggmCgtTaamCtgGacAttTgtTcgTc |
| CESLC_Y70G10A.3_u46_LNA3 | mCtcmCccGagmCagGcgAttAttmCacGctAgtTatGctmCaaAtgTgaTctGt |
| CESOD_C15F1.7_u435_LNA3 | mCcgGtamCtaTctGgaTcamCacAgaAgtmCcgAaaAtgAccAggmCagTtaTt |
| CESOD_C15F1.7_u9_LNA3 | mCccAgtGacTacmCtgAatmCgcGtcTctGaaTctmCcamCacAatTccTacTa |
| CESOD_F10D11.1_u326_LNA3 | GgaGttGctmCacmCgcAatTaaGagmCgamCttmCggAtcTctGgaTaaTctTc |
| CESOD_F10D11.1_u477_LNA3 | AaaTtgAggAaaAgcTtcAcgAggmCggTctmCcaAagGaaAcgTcaAagAa |
| CESULT_EEED8.2_u316_LNA3 | mCaaTcgTacmCatGaaAgaAgtTggAagmCcamCgtGcaAgaGaaGaaAtcmCa |
| CESULT_EEED8.2_u82_LNA3 | AagAagAttmCctGacmCagAgaGacTcamCgtGctTacmCcaAgaAgcAtcTa |
| CESULT_Y113G7A.11_u252_LNA3 | AgcAttGgtGgaAatAcgAaaTggmCatGggAagAgaAacmCccTctmCaaTt |
| CESULT_Y113G7A.11_u96_LNA3 | mCtgGttAcgGtaGtgTatGgtmCccTgtmCctmCtcAgaAtgmCaaAtaTgtmCg |

TABLE 18-continued

LNA-modified oligonucleotide capture probes.

| Oligo Name | Sequence |
|---|---|
| CESULT_Y67A10A.4_u108_LNA3 | TctAcgTcgAtgGaaAagmCcgAttTaamCaaTcaAagmCcaAcaAcgmCagTt |
| CESULT_Y67A10A.4_u327_LNA3 | GgaAagGtgmCcaAaaAgtTgamCagmCaaTtgGagGatmCttAttmCatTgcmCa |
| CETOPO_K12D12.1_u398_LNA3 | AgaTgaTgaTgaAgtTccTgcAaaGaaGccTgcTccAgcGaaGaaAgcTg |
| CETOPO_K12D12.1_u449_LNA3 | AaaAccTcgTacTggAaaAggAgcTgcGaaAgcGgaAgtTatmCgaTttGt |
| CETOPO_M01E5.5b_u256_LNA3 | GagAagGccmCagAagAagTacGacAgamCtgAagGagmCagTtgAaaAagTt |
| CETOPO_M01E5.5b_u429_LNA3 | TtcTgtmCatAcaAtcGtgmCtaAtcGgcAggTtgmCgaTccTttGtaAccAt |
| CEUbi_F25B5.4_u186_LNA3 | AagmCttmCggAcamCcaTtgAgaAtgTcaAagmCcaAaaTccAggAtaAggAg |
| CEUbi_F25B5.4_u2_LNA3 | AatmCgaAccmCatmCaaTtcActmCgtTatTccTccTcgAtcTccGttmCaaGt |
| CEUbi_F29B9.6_u145_LNA3 | mCtgAacmCatmCcaAatAttGaaGatmCcaGctmCagGctGaaGccTatmCagAt |
| CEUbi_F29B9.6_u230_LNA3 | mCgtGtgmCttAtcTctTctGgaTgaAaamCaaGgaTtgGaaGccGtcAatmCt |
| CEUbi_M7.1_u239_LNA3 | mCggAagmCatmCtgmCctTgamCatTctmCcgTtcGcaGtgGtcGccGgcTctG |
| CEUbi_M7.1_u53_LNA3 | AaaGtamCgcTatGtgAggAggmCtaAcamCcaTtcAtaTaaGaamCgcAgcmCa |
| CEUGT_F39G3.1_u40_LNA3 | TgtTgcmCgtAgaAgaGagActAaaActAagAacGatTgaTtgAagGtcTg |
| CEUGT_F39G3.1_u466_LNA3 | TacAatTctTtgmCagGaaGcaAtaTccGccGgaGtcmCcmCttAtcActAt |
| CEUGT_M88.1_u480_LNA3 | mCtcAcgGagGttAtaAttmCtaTgcAggAggmCaaTttmCtgmCtgGagTtcmCa |
| CEUGT_M88.1_u72_LNA3 | AccGttTcaTgaGagmCtgTaaTcaGgtGttGttTctGtaAaaAgtGtgAa |
| YAL009W_u145_LNA3 | GtgGatGtgAaaTtaGtcmCtcAacmCccAgaGcaTttAgtGcaGagAttAg |
| YAL009W_u341_LNA3 | GcaGttTaaTgtGaaGctAgtTaaAgtAcaGtcTacGtgGgamCgaGaaAt |
| YAL059W_u262_LNA3 | AttGccAagTccAttTctmCgtGccAagTacAttmCaaAatAcaAgaAagGc |
| YAL059W_u51_LNA3 | AgamCtcmCtamCaaAtaGatTcgGtgTccTgcmCagAcgAtgTtgAagAatAg |
| YER109C_u109_LNA3 | TtgAagTttGggAatAttGgtAtgGttGaaGacmCaaGgamCcgGatTacGa |
| YER109C_u436_LNA3 | GagGcgmCaaGtaGgcAatGatTcaAgaAgtAgtAaaGgcAatmCgtAacAc |
| YHR152W_u128_LNA3 | TgaGcamCaaAgtTaaGatGttmCggAaaGaaAaaGaaAgtmCaaTccTatGa |
| YHR152W_u510_LNA3 | mCaaGtgAccAatmCagmCacGcamCggmCttmCcaTccTcaAgamCtgAtaTtamCc |
| YKL130C_u211_LNA3 | AttAaaTgcGcaGatGagGacGgaAcgAatAtcGgaGaaActGatAatAt |
| YKL130C_u85_LNA3 | GatGgtAagmCtgAgcGccTtgGacGaaGaaTttGatGttGtcGctActAa |
| YKL178C_u199_LNA3 | TacGtcAcgmCaaGgamCagAgcTttGacGacGaaAtaTcamCttGgaGgaTt |
| YKL178C_u367_LNA3 | TctmCccTgtGtaGgtAcamCcaAtaTcamCaaGcgmCatTtcTatGtcGacTa |
| YLR443W_u179_LNA3 | TgcTaamCacmCagTttAgamCcaTggAaaTccmCacmCgcAaaTatAagmCaaTg |
| YLR443W_u86_LNA3 | GcaGgamCatAagAttmCcgGtcAagmCaamCgamCagTgaAgaAagTatGcaAa |
| YOR092W_u251_LNA3 | mCcgTctAgtGaaAgcGggAtgGctAaaTtgGgaAaamCgamCaaGatGttAt |
| YOR092W_u82_LNA3 | GatGctTcaAtaTccTttGatGgtmCgtTagTttAccAttTttGgtGtcTt |
| YPL263C_u132_LNA3 | AgtmCatTtgAgtTatGtgAagAccGttGgtGggAaaGaaGagAtcAggTg |
| YPL263C_u257_LNA3 | GtcTtgGctAccAcamCccAaaAccGttmCgaAacTttAagAgcAttmCtamCt |

LNA modifications are depicted by uppercase letters in the sequence,
mC denotes LNA methyl cytosine.
(SEQ ID NOs: 162-437, in sequential order)

EXAMPLE 54

Evaluation of Different LNA Substituted Oligonucleotides as Probes for Fluorescence In Situ Hybridization (FISH) on Metaphase Chromosomes and Interphase Nuclei Locked Nucleic Acids (LNA) constitute a novel class of DNA analogues that have an exceptionally high affinity towards complementary DNA and RNA. Using human classical satellite-2 repeat sequence clusters as targets, we demonstrate that LNA/DNA mixmer oligonucleotides are excellent probes for FISH combining high binding affinity with short hybridization time and even with the ability to hybridize without prior termal denaturation of the template. The development of molecular probes and image analysis has made fluorescence in situ hybridization (FISH) a powerful investigative tool. Although FISH has proved to be a useful technique in many areas, it is a fairly time-consuming procedure with limitations in sensitivity. Probes with higher DNA affinity may potentially reduce the time needed for hybridization and the sensitivity of the technique. Thus, improvement in hybridization characteristics has been reported for the DNA mimic peptide nucleic acid (PNA). This example describes the development of LNA substituted oligonucleotides as probes for fluorescence in situ hybridization on metaphase chromosomes and interphase nuclei. In each experiment a different LNA substituted oligonucleotide of the same 23-bp human satellite-2 repeat sequence (attccattcgattccattcgatc) have been used, cf. Jeanpierre, M. (1994). Human satellites 2 and 3. *Annals of Genetics* 37, 163-171. Oligomers with various LNA content, different labels, and hybridization conditions have been used and compared with each other and the optimal conditions have been determined for an efficient LNA-FISH protocol.

A. Materials and Methods

A1. Chromosome Preparations

Chromosome preparations were made by standard methods from peripheral lymphocyte cultures of normal males. Slides were prepared 1-4 days prior to an experiment and treated with RNAse (10 µg/µl) at 37° C. for one hour before hybridization.

A2. Probe Preparation

The 23 bp human satellite-2 repeat sequence, attccattcgattccattcgatc, was used to prepare the LNA/DNA mixmers with different content and sequence order of LNA modifications (Table 19). All mixmers were labeled in the 5' end with either Cy3 or biotin. Biotin amidite was purchased from Applied Biosystems and Cy3 amidite was purchased from Amersham Bioscience. A DNA oligonucleotide of the same sequence without any LNA modifications was used as a control in each experiment.

A3. Fluorescence In Situ Hybridization

FISH was carried out as described by Silahtaroglu A N, Hacihanefioglu S, Guven G S, Cenani A, Wirth J, Tommerup N, Turner Z. (1998) Not para-, not peri-, but centric inversion of chromosome 12. *J Med Genet*. 35(8):682-4. (1); with the following modifications including: The amounts of probe were 6.4, 10, 13.4 and 20 pmoles. Denaturation of the target DNA and the probe were performed at 75° C. for 5 minutes either separately using 70% formamide or simultaneously under the coverslip in the presence of the hybridization mixture containing 50% formamide. In addition the effect of denaturation was also tested. Two alternative hybridization mixtures were used: 50% formamide/2×SSC (pH 7.0)/10% dextran sulphate or 2×SSC (pH 7.0)/10% dextran sulphate. Hybridization times included 30 min, 1 hr, 2 hrs, 3 hrs and overnight. Hybridization temperatures included: 37° C., 55° C., 60° C. and 72° C. Post washing was either as for standard FISH (1), or with 50% formamide/2× SSC at 60° C., or without formamide. Hybridization signals with biotin labeled LNA substituted oligonucleotide probes were visualized indirectly using two layers of fluorescein-labeled avidin (Vector Labs) linked by a biotinylated anti-avidin molecule, which amplified the signal 8-64 times. The hybridization of Cy3 labeled molecules however, was visualized directly after a short washing procedure. Slides were mounted in Vectashield (Vector Laboratories) containing 4'-6'-diamidino-2-phenylindole (DAPI). The whole procedure was carried out in the dark. The signals were visualized using a Leica DMRB epifluorescence microscope equipped with a SenSys charge-coupled device camera (Photometrics, Tucson, Ariz.), and IPLAB Spectrum Quips FISH software (Applied Imaging international Ltd, Newcastle, UK) within two days after hybridization.

B. Results and Discussion

Figure 41:
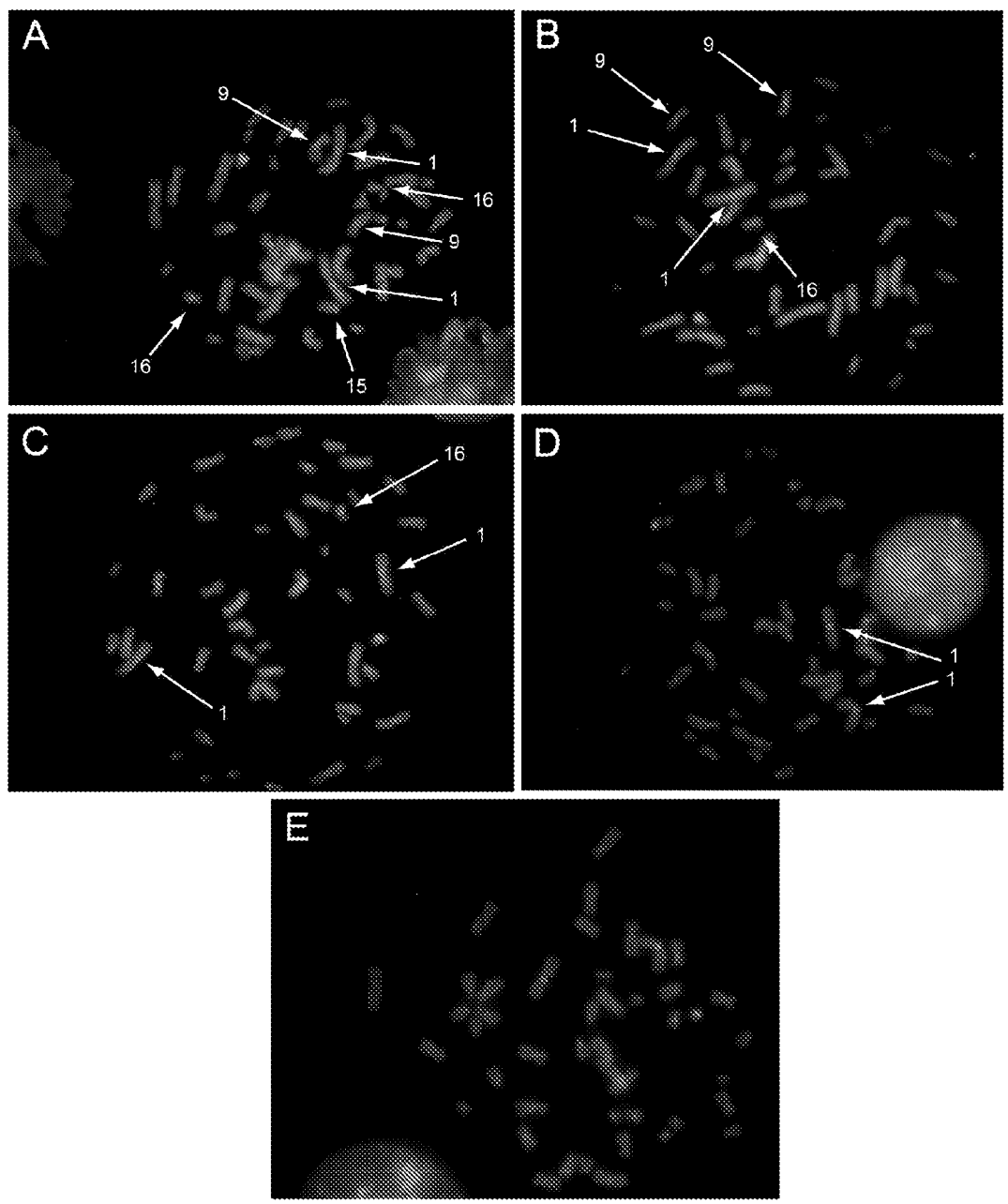
FIGS. 41A-41E show the comparison of different LNA/DNA mixmer oligonucleotide probes in the detection of human satellite-2 repeats by fluorescence in situ hybridization. Experiment conditions: 6.4 pmoles of Cy3 labeled probe was hybridized for 30 minutes at 37° C., after simultaneous denaturation of the target and the probe at 75° C. for 5 minutes. A. LNA-2 giving signals on chromosomes 1, 16, 9 and 15, B. LNA-3 giving bright signals on chromosomes 1, 16 and 9, C. Dispersed LNA giving signals on chromosomes 1 and 16 only, D. LNA Block giving smaller signals on chromosome 1, E. DNA control oligonucleotide FISH probe giving no signals on any of the chromosomes.

Satellite-II DNA, composed of multiple repeats of a 23 bp and a 26 bp sequence, is especially concentrated in the large heterochromatic regions of human chromosomes 1 and 16, but is also found in the heterochromatic regions of chromosomes 9, Y, 15 and in other minor sites like the short arms/satellites of the acrocentric chromosomes and some centromeric regions. Classical satellite DNA can be visualised by FISH with traditional genomic and DNA oligonucleotide probes (see Kokalj-Vokac N, Alemeida A, Gerbault-Seureau M, Malfoy B, Dutrillaux B. (1993) Two-color FISH characterization of i(1q) and der(1;16) in human breast cancer cells. *Genes Chromosomes Cancer*. 7, 8-14; and Tagarro I, Fernandez-Peralta A M, Gonzales-Aguilera J J. (1994) Chromosomal localization of human satellites 2 and 3 by a FISH method using oligonucleotides as probes. *Hum Genet*. 93(4):383-8). Due to this and the presence of distinct major and minor sites of satellite-2 DNA in the genome, we used the 23-bp satellite-2 repeat sequence, attccattcgattccattcgatc, as a convenient model to test the efficiency of various DNA/LNA mixmers for FISH analysis and the effect of different experimental conditions by recording the number, location and strength of signals on each metaphase. To compare the efficiency of mixmers with different LNA content (Table 19) and to optimize the LNA-FISH protocol, different conditions were tried at each step of a standard FISH protocol as described in Materials and Methods. All LNA substituted oligonucleotides (LNA/DNA mixmer oligonucleotides) for human satellite-2 sequence gave very prominent signals when used as FISH probes. In general, the signal on chromosome 1 was always stronger and appeared earlier, followed by signals on chromosomes 16, 9, Y, 15, other acrocentric chromosomes and the centromeric regions of other chromosomes, respectively (FIG. 41). In general, biotin labeled mixmers gave stronger signals with a higher background, whereas Cy3-labeled molecules gave a significantly lower background.

B1. Effect of LNA Content of the LNA Substituted Oligonucleotides (LNA/DNA Mixmers)

The LNA-2 molecule which had every other nucleotide modified as LNA. (aTtCcAtTcGaTtCcAtTcGaTc (SEQ ID NO: 848)) gave the best results in all the experiment performed. The LNA-3 molecule, with every third oligonucleotide modified as LNA, (aTtcCatTcgAtTccAttCgaTc (SEQ ID NO: 848)) also gave hybridization signals, but with less efficiency than the LNA-2 probes. Preferably, an LNA-2 oligonucleotide molecule has an LNA unit at every other nucleotide position in the sequence and an LNA-3 oligonucleotide molecule has an LNA unit at every third position of the sequence. However, minor deviations, e.g. in one position or less than 5-10 percent of the nucleotide positions in the sequence may still provide the general features of an LNA-2 or an LNA-3 molecule.

The Dispersed LNA (aTtccatTcgaTtccAttcgaTc (SEQ ID NO: 848)), which had 5 dispersed LNA modifications, was less efficient in short term hybridization, but gave signals on both chromosomes 1 and 16 after overnight hybridizations. LNA/DNA mixmers with 3 LNA Blocks (aTTCcattcgAT-TccattcGATc (SEQ ID NO: 848)) was comparably inferior as a FISH-probe.

B2. Effect of Amount of the LNA/DNA Mixmers

The initial experiments performed with 20 pmol of LNA/DNA mixmer resulted in bright and large signals, but with an extremely high background. Thus, lower concentrations were tested (13.4 pmol, 10 pmol and 6.4 pmol). The concentration giving the optimal signal to noise ratio was found to be 6.4 pmol.

B3. Effect of Denaturation

The signals on the major sites of hybridization (1q, 16q) were equally bright after both types of denaturation. However, smaller and weaker signals were observed on the minor sites with the simultaneous denaturation protocol. To check the potential "strand invasion" property of LNA, some of the experiments were performed without a denaturation step. As expected, no signals were obtained by the control DNA oligonucleotide probe. In contrast, hybridization signals on chromosomes 1 and 16 were observed after overnight hybridization with LNA probes, with LNA-2 mixmer giving the best signals. Compared to the signals obtained in experiments involving a denaturation step, the signals were smaller, but prominent and without any background.

B4. Effect of Hybridization Time, Temperature and Post-Hybridization Washes

Although signals could be observed after only 30 min of hybridization, the optimal hybridization time and temperature for LNA-2, which gave the best signals, was 1 hr at 37° C. A 3×5 min wash with 0.1×SSC/60° C. and 4×SSC/0.05% Tween/37° C., respectively, followed by a 5 min PBS wash was found to be sufficient for washing the slides after hybridization with DNA-LNA mixmers. There was no specific difference between a wash with 50% formamide at 42° C. or 60° C.

The signals faded away in most of the slides within two days. When hybridized with directly labeled LNA, the whole slide was stained with Cy3 after three days. Thus, slides had to be analyzed within 48 hours after hybridization.

C. Conclusion

The experiments have demonstrated, that LNA substituted oligonucleotides are very efficient FISH probes. LNA substituted oligonucleotide probes gave strong signals after only 1 hr of hybridization, and it was possible to omit the use of formamide both from the denaturation and from the post hybridization washing steps and still obtain a very good signal to noise ratio. The ability of LNA to hybridize without prior denaturation could be due to a strand invasion property of LNA and this warrants further investigation with other LNA probes and at different conditions. Based on the combined results of these experiments, the optimal LNA-FISH procedure was defined as follows: 6.4 pmoles of Cy-3 labeled LNA-2 probe was denatured together with the target at 75° C. for 5 minutes, and hybridized for one hour then followed by a short post wash without any formamide (3×5 minutes 0.1×SSC at 60° C.; 2×5 minutes 4×SSC/0.05% Tween at 37° C.; 5 minute PBS). The FISH experiments indicate that LNA containing probes would be valuable for the detection of a variety of other repetitive elements, such as centromeric α-repeats and telomeric repeats. In addition, the superior hybridization characteristics of LNA containing oligonucleotides could lead to detection of single base pair differences between repetitive sequences as well as single copy sequences.

C1. FIG. 41 shows a comparison of different LNA/DNA mixmer oligonucleotides. Experiment conditions: 6.4 pmoles of Cy3 labeled probe was hybridized for 30 minutes at 37° C., after simultaneous denaturation of the target and the probe at 75° C. for 5 minutes. A. LNA-2 giving signals on chromosomes 1, 16, 9 and 15, B. LNA-3 giving bright signals on chromosomes 1, 16 and 9, C. Dispersed LNA giving signals on chromosomes 1 and 16 only, D. LNA Block giving smaller signals on chromosome 1, E. DNA oligo giving no signals on any of the chromosomes.

TABLE 19

DNA/LNA mixmers for human satellite 2 repeat sequence used in this study. (SEQ ID NO: 848)

| Name | FISH probe sequences | LNA monomers | Tm* |
|---|---|---|---|
| DNA oligo | attccattcgattccattcgatc | 0 | 60 |
| Dispersed LNA | aTtccatTcgaTtccAttcgaTc | 5 | 71 |
| LNA-3 | aTtcCatTcgAtTccAttCgaTc | 8 | 77 |
| LNA Blocks | aTTCcattcgATTccattcGATc | 9 | 73 |
| LNA-2 | ATtCcAtTcGaTtCcAtTcGaTc | 11 | 84 |

LNA modifications are depicted in capital letters and
*Tm values for each molecule have been calculated using Exiqon's Tm Prediction program accessible at http://lna-tm.com/ and as appears in FIGS. 19A-19F herein.

EXAMPLE 55

Highly Efficient Fluorescence In Situ Hybridization (FISH) Using an LNA Probe Specific for Human Telomere Repeat 1. Chromosome Preparations Chromosome preparations were made by standard methods from peripheral lymphocyte cultures of two normal males. Slides were prepared 1-6 days prior to an experiment and treated with RNAse (10 μg/μl) at 37° C. for one hour before hybridization.

2. FISH Probe Preparation

A Cy3-labelled, LNA-2 design of the 24-bp telomere sequence (ttagggttagggttagggttaggg SEQ ID NO: 849) representing 4 blocks of 6-bp telomere repeat (ttaggg) was used as a probe. A DNA oligomer of the same sequence without any LNA modifications was used as a control in each experiment.

3. Fluorescence In Situ Hybridization

FISH was carried out as described previously (Silahtaroglu et al, 1998) with the following modifications. The amount of probe was 5 pmoles. Denaturation of the target DNA and the probe were performed at 75° C. for 5 minutes simultaneously under the coverslip in the presence of hybridization mix containing 50% formamide. Slides were washed after 30 min. hybridization at 37° C. Post washing steps included a 2×5 min 0.1×SSC at 60° C.; 5 min 2×SSC at 37° C.; 3 min 4×SSC/0.05% Tween20 at 37° C. and 5 min PBS. Slides were mounted in Vectashield (Vector Laboratories) containing 4'-6'-diamidino-2-phenylindole (DAPI). The whole procedure was carried out in the dark. The signals were visualized using a Leica DMRB epifluorescence microscope equipped with a SenSys charge-coupled device camera (Photometrics, Tucson, Ariz.), and IPLAB Spectrum Quips FISH software (Applied Imaging international Ltd., Newcastle, UK).

4. Results

Figure 42:
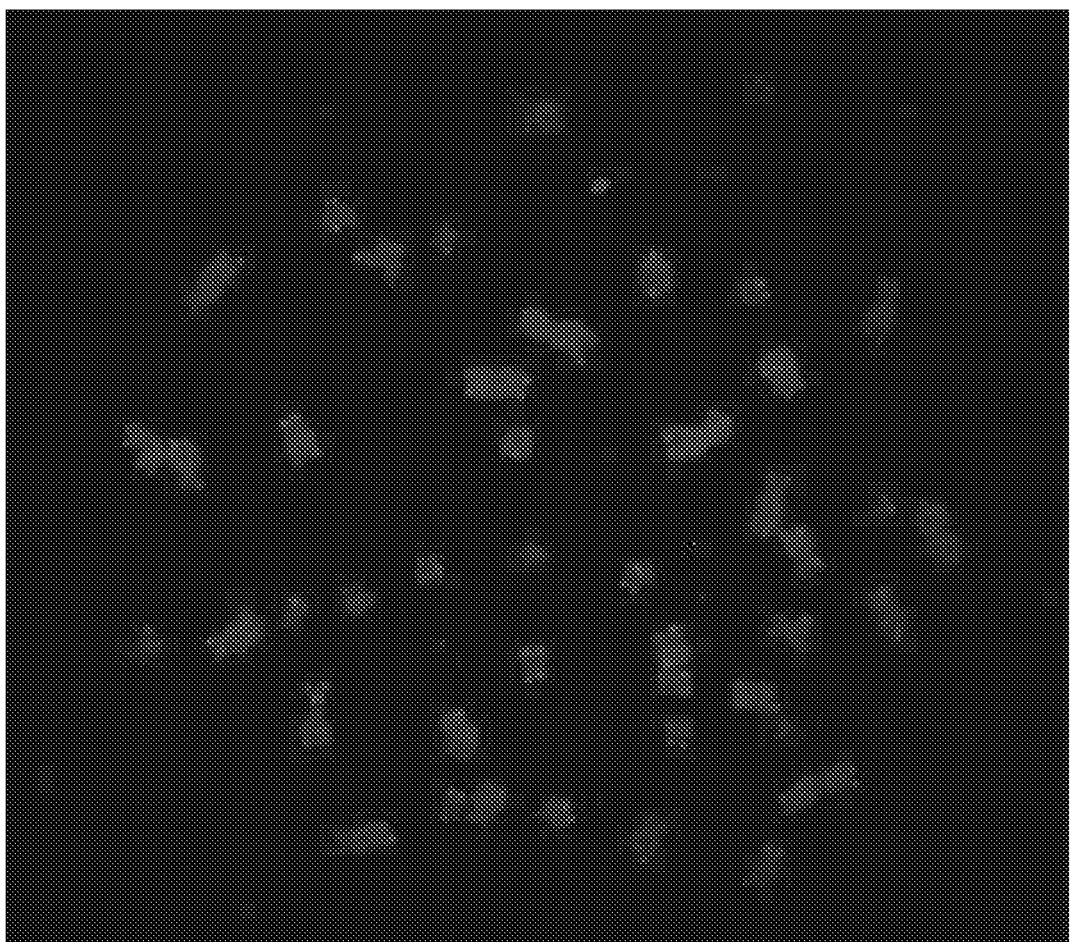
FIG. 42. Illustrates the hybridisation of the Cy3-labelled human telomere repeat specific, LNA-2 substituted oligonucleotide probe on human metaphase chromosomes resulted in prominent signals on the telomeres.

The human telomere repeat specific LNA oligonucleotide probe gave prominent signals on the telomeres, when used as a FISH probe (FIG. 42), whereas no signals could be detected with the corresponding DNA control probe when using the hybridization conditions specified above. Thus, the experiments described here for human telomere repeat, demonstrates that LNA substituted oligonucleotides are highly efficient as FISH probes.

5. References

Silahtaroglu, A. N., Hacihanefioglu, S., Guven, G. S., Cenani, A., Wirth, J., Tommerup, N., Tumer, Z. (1998) Not para-, not peri-, but centric inversion of chromosome 12. *Journal of Medical Genetics* 35(8), 682-684.

EXAMPLE 56

Fluorescence In Situ Hybridization Using Chromosome-21 Specific Centromere LNA Probes 1. Chromosome Preparations Chromosome preparations were made by standard methods from peripheral lymphocyte cultures of a normal female. Slides were prepared 5 days prior to use. Before use slides were treated with RNAse A (10 µg/µl) at 37° C. for one hour and proteinase K for 10 minutes washed, with 2×SSC 3 times 3 min, before dehydration through a cold ethanol series.

2. Probe Preparation

A 5' biotin-labelled, LNA substituted 15-mer FISH probe (aCcCaGcCaAaGgAg (SEQ ID NO: 850)), LNA uppercase, DNA lowercase) and a 5' biotin-labelled LNA substituted 24-mer FISH probe (TgTgTaCcCaGcCaAaGgAgTtGa (SEQ ID NO: 851)), LNA uppercase, DNA lowercase) specific for the centromeric human chromosome 21 alphaRI (680) locus alpha-satellite repeat were used as probes. Biotin-labelled DNA probes of the same sequence without any LNA modifications were used as controls in each experiment.

3. Fluorescence In Situ Hybridization

FISH was carried out as described previously (Silahtaroglu et al, 1998) with the following modifications. The amount of probe was 1 µM for 1the 15-mer chromocsome 21 FISH probe and 1.4 µM for the 24.mer FISH probe. Denaturation of the target DNA and the probe were performed simultaneously at 79° C. for 4 minutes under the coverslip in the presence of hybridization mix containing 50% formamide. Slides were washed after 40 min. hybridization at RT. Post washing steps included a 2×5 min 0.1×SSC at 65° C.; 5 min 3 min 4×SSC/0.05% Tween20 at 37° C. Slides are then incubated 10 min with 1% blocking reagent and a layer of Flourescein conjugated Avidin (Vector Labs) has been applied for 20 minutes at 37° C. After a 3 times 3 minute wash with 4×SSC/0.05% Tween20, slides are dehydrated and mounted in Vectashield (Vector Laboratories) containing 4'-6'-diamidino-2-phenylindole (DAPI). The whole procedure was carried out in the dark. The signals were visualized using a Leica DMRB epifluorescence microscope equipped with a SenSys charge-coupled device camera (Photometrics, Tucson, Ariz.), and IPLAB Spectrum Quips FISH software (Applied Imaging international Ltd., Newcastle, UK).

4. Results

The LNA substituted 15-mer oligonucleotide probe specific for the centromeric human chromosome 21 alphaRI (680) locus alpha-satellite repeat gave prominent signals on chromosome 21, when used as a FISH probe, whereas no signals could be detected with the corresponding DNA control probe when using the hybridization conditions specified above. The LNA substituted 24-mer oligonucleotide probe specific for the centromeric alphaRI(680) locus alpha-satellite repeat gave prominent signals both on chromosomes 13 and 21, when used as a FISH probe, while no signals were observed with the DNA control probe. This is expected, since the aforementioned chromosomes differ only at one nucleotide position in the given probe sequence. On the other hand, the results obtained by the 15-mer LNA FISH probe clearly demonstrates that the LNA substituted probe is capable of discriminating a single mismatch between chromosomes 13 and 21 in the centromeric alpha-satellite repeat. Thus, the experiments described here for the centromeric repeat-specific LNA probes in the human chromosome 21, demonstrates that LNA substituted oligonucleotides are highly efficient as FISH probes and can be used in diagnosis of chromosome 21 trisomy.

OTHER EMBODIMENTS

From the foregoing description, it will be apparent that variations and modifications may be made to the invention described herein to adopt it to various usages and conditions. The foregoing description of the invention is merely illustrative thereof, and it understood that variations and modifications can be effected without departing from the scope or spirit of the invention.

All publications, patent applications, and patents mentioned in this specification are herein incorporated by reference to the same extent as if each independent publication, patent, or patent application was specifically and individually indicated to be incorporated by reference.

Other embodiments are in the claims.

What is claimed is:

1. A method of detecting a cDNA, said method comprising conducting PCR on said cDNA using an oligomer to hybridize to said cDNA, wherein said oligomer has a total of 8 or 9 nucleotides and at least 50% of said nucleotides are LNA nucleotide analogues, wherein said oligomer comprises at least one non-modified deoxyribonucleotide, and wherein said oligomer comprises a fluorophor and a quencher; and said method further comprising:
   (i) when said oligomer is hybridized to said cDNA, detaching said fluorophor or said quencher from said oligomer using a polymerase having exonuclease activity during said PCR; and
   (ii) detecting fluorescence from said fluorophor after its physical separation from said quencher, wherein said fluorescence is indicative of the presence of the cDNA.

2. The method of claim 1, wherein at least 70% of said nucleotides are LNA nucleotide analogues.

* * * * *

SEQUENCE LISTING

```
<160> NUMBER OF SEQ ID NOS: 852

<210> SEQ ID NO 1
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 1
```
acggggatta tggtttcgcc aatgaaaact aatcaaaggt        40

<210> SEQ ID NO 2
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 2
acggggatta tggtttcgcc tatgaaaact aatcaaaggt        40

<210> SEQ ID NO 3
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 3
acggggatta tggtttcgcg tatgaaaact aatcaaaggt        40

<210> SEQ ID NO 4
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 4
acggggatta tggtttcggg tatgaaaact aatcaaaggt        40

<210> SEQ ID NO 5
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 5
acggggatta tggtttcggg tttgaaaact aatcaaaggt        40

<210> SEQ ID NO 6
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 6
acggggatta tggtttcggg ttagaaaact aatcaaaggt        40

<210> SEQ ID NO 7
<211> LENGTH: 40
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 19
<223> OTHER INFORMATION: n = LNA methyl cytosine

<400> SEQUENCE: 7
acggggatta tggtttcgnc aatgaaaact aatcaaaggt        40

<210> SEQ ID NO 8

```
<211> LENGTH: 40
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 19
<223> OTHER INFORMATION: n = LNA methyl cytosine

<400> SEQUENCE: 8
acggggatta tggtttcgnc tatgaaaact aatcaaaggt                              40

<210> SEQ ID NO 9
<211> LENGTH: 40
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 19
<223> OTHER INFORMATION: n = LNA methyl cytosine

<400> SEQUENCE: 9
acggggatta tggtttcgng tatgaaaact aatcaaaggt                              40

<210> SEQ ID NO 10
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 10
acggggatta tggtttcggg tatgaaaact aatcaaaggt                              40

<210> SEQ ID NO 11
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 11
acggggatta tggtttcggg tttgaaaact aatcaaaggt                              40

<210> SEQ ID NO 12
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 12
acggggatta tggtttcggg ttagaaaact aatcaaaggt                              40

<210> SEQ ID NO 13
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 13
tgggaatgga acggggatta tggtttcgcc aatgaaaact aatcaaaggt                   50

<210> SEQ ID NO 14
<211> LENGTH: 50
```

<212> TYPE: DNA
<213> ORGANISM: Artificial Sequence
<220> FEATURE:
<223> OTHER INFORMATION: Synthetic Oligonucleotide Sequence

<400> SEQUENCE: 14
tgggaatgga acggggatta tggtatcgcc aatgaaaact aatcaaaggt    50

<210> SEQ ID NO 15
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 15
tgggaatgga acggggatta tggtaacgcc aatgaaaact aatcaaaggt    50

<210> SEQ ID NO 16
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 16
tgggaatgga acggggatta tggtaaggcc aatgaaaact aatcaaaggt    50

<210> SEQ ID NO 17
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 17
tgggaatgga acggggatta tggaaaggcc aatgaaaact aatcaaaggt    50

<210> SEQ ID NO 18
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 18
tgggaatgga acggggatta tggaaagccc aatgaaaact aatcaaaggt    50

<210> SEQ ID NO 19
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 27, 29, 39
<223> OTHER INFORMATION: n = LNA methyl cytosine

<400> SEQUENCE: 19
tgggaatgga acggggatta tggtttngnc aatgaaaant aatcaaaggt    50

<210> SEQ ID NO 20
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 20
tgggaatgga acggggatta tggtttcgcc aatgaaaact aatcaaaggt          50

<210> SEQ ID NO 21
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 29
<223> OTHER INFORMATION: n = LNA methyl cytosine

<400> SEQUENCE: 21
tgggaatgga acggggatta tggtttcgnc aatgaaaact aatcaaaggt          50

<210> SEQ ID NO 22
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 22
tgggaatgga acggggatta tggtttcgcc aatgaaaact aatcaaaggt          50

<210> SEQ ID NO 23
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 23
tgggaatgga acggggatta tggtttcgcc aatgaaaact aatcaaaggt          50

<210> SEQ ID NO 24
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 24
tgggaatgga acggggatta tggtatcgcc aatgaaaact aatcaaaggt          50

<210> SEQ ID NO 25
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 25
tgggaatgga acggggatta tggtaacgcc aatgaaaact aatcaaaggt          50

<210> SEQ ID NO 26
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 26
tgggaatgga acggggatta tggtaaggcc aatgaaaact aatcaaaggt          50

<210> SEQ ID NO 27
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 27
tgggaatgga acggggatta tggaaaggcc aatgaaaact aatcaaaggt           50

<210> SEQ ID NO 28
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 28
<223> OTHER INFORMATION: n = LNA methyl cytosine

<400> SEQUENCE: 28
tgggaatgga acggggatta tggaaagncc aatgaaaact aatcaaaggt           50

<210> SEQ ID NO 29
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 29
ttgctgaact ggatggatta aaccgtatgg gtccaacttt                     40

<210> SEQ ID NO 30
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 30
ttgctgaact ggatggattt aaccgtatgg gtccaacttt                     40

<210> SEQ ID NO 31
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 31
ttgctgaact ggatggatat aaccgtatgg gtccaacttt                     40

<210> SEQ ID NO 32
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 32
ttgctgaact ggatggatat taccgtatgg gtccaacttt                     40

<210> SEQ ID NO 33
<211> LENGTH: 40

```
<212> TYPE: DNA
<213> ORGANISM: Artificial Sequence
<220> FEATURE:
<223> OTHER INFORMATION: Synthetic Oligonucleotide Sequence

<400> SEQUENCE: 33
ttgctgaact ggatggatat ttccgtatgg gtccaacttt                              40

<210> SEQ ID NO 34
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 34
ttgctgaact ggatggatat ttgcgtatgg gtccaacttt                              40

<210> SEQ ID NO 35
<211> LENGTH: 40
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 23
<223> OTHER INFORMATION: n = LNA methyl cytosine

<400> SEQUENCE: 35
ttgctgaact ggatggatta aancgtatgg gtccaacttt                              40

<210> SEQ ID NO 36
<211> LENGTH: 40
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 23
<223> OTHER INFORMATION: n = LNA methyl cytosine

<400> SEQUENCE: 36
ttgctgaact ggatggattt aancgtatgg gtccaacttt                              40

<210> SEQ ID NO 37
<211> LENGTH: 40
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 23
<223> OTHER INFORMATION: n = LNA methyl cytosine

<400> SEQUENCE: 37
ttgctgaact ggatggatat aancgtatgg gtccaacttt                              40

<210> SEQ ID NO 38
<211> LENGTH: 40
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 23
<223> OTHER INFORMATION: n = LNA methyl cytosine

<400> SEQUENCE: 38
```
ttgctgaact ggatggatat tancgtatgg gtccaacttt       40

<210> SEQ ID NO 39
<211> LENGTH: 40
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 23
<223> OTHER INFORMATION: n = LNA methyl cytosine

<400> SEQUENCE: 39
ttgctgaact ggatggatat ttncgtatgg gtccaacttt       40

<210> SEQ ID NO 40
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 40
ttgctgaact ggatggatat ttgcgtatgg gtccaacttt       40

<210> SEQ ID NO 41
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 41
ggtatggaag ttgctgaact ggatggatta aaccgtatgg gtccaacttt       50

<210> SEQ ID NO 42
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 42
ggtatggaag ttgctgaact ggatcgatta aaccgtatgg gtccaacttt       50

<210> SEQ ID NO 43
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 43
ggtatggaag ttgctgaact ggatccatta aaccgtatgg gtccaacttt       50

<210> SEQ ID NO 44
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 44
ggtatggaag ttgctgaact ggaaccatta aaccgtatgg gtccaacttt       50

<210> SEQ ID NO 45

```
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 45
ggtatggaag ttgctgaact ggaaccttta aaccgtatgg gtccaacttt        50

<210> SEQ ID NO 46
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 46
ggtatggaag ttgctgaact ggaacctata aaccgtatgg gtccaacttt         50

<210> SEQ ID NO 47
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 19, 34, 43
<223> OTHER INFORMATION: n = LNA methyl cytosine

<400> SEQUENCE: 47
ggtatggaag ttgctgaant ggatggatta aacngtatgg gtncaacttt         50

<210> SEQ ID NO 48
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 19, 25, 34, 43
<223> OTHER INFORMATION: n = LNA methyl cytosine

<400> SEQUENCE: 48
ggtatggaag ttgctgaant ggatngatta aacngtatgg gtncaacttt         50

<210> SEQ ID NO 49
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 19, 25, 34, 43
<223> OTHER INFORMATION: n = LNA methyl cytosine

<400> SEQUENCE: 49
ggtatggaag ttgctgaant ggatncatta aacngtatgg gtncaacttt         50

<210> SEQ ID NO 50
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 19, 25, 34, 43
<223> OTHER INFORMATION: n = LNA methyl cytosine

<400> SEQUENCE: 50
```
ggtatggaag ttgctgaant ggaancatta aacngtatgg gtncaactttt    50

<210> SEQ ID NO 51
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 19, 25, 34, 43
<223> OTHER INFORMATION: n = LNA methyl cytosine

<400> SEQUENCE: 51
ggtatggaag ttgctgaant ggaanctta aacngtatgg gtncaactttt    50

<210> SEQ ID NO 52
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 19, 25, 34, 43
<223> OTHER INFORMATION: n = LNA methyl cytosine

<400> SEQUENCE: 52
ggtatggaag ttgctgaant ggaanctata aacngtatgg gtncaactttt    50

<210> SEQ ID NO 53
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 9, 21, 41
<223> OTHER INFORMATION: n = LNA methyl cytosine

<400> SEQUENCE: 53
ggctggatnc ccaggaaacc naggaatcgg aagcattgga ncaaaaggag    50

<210> SEQ ID NO 54
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 9, 13, 29, 37
<223> OTHER INFORMATION: n = LNA methyl cytosine

<400> SEQUENCE: 54
naccggatnc ggntcaattg tcggacctng cggaaancct ggagaaaagg    50

<210> SEQ ID NO 55
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 5, 21, 25
<223> OTHER INFORMATION: n = LNA methyl cytosine

<400> SEQUENCE: 55
tccgncaggc ccaatcgcct ncacnatgtc caagggaacc attatcggtc    50

```
<210> SEQ ID NO 56
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 5
<223> OTHER INFORMATION: n = LNA methyl cytosine

<400> SEQUENCE: 56
gagcnaggag agggaggtca acgcggttac ccaggaaatg gaggactctc            50

<210> SEQ ID NO 57
<211> LENGTH: 31
<212> TYPE: DNA
<213> ORGANISM: Artificial Sequence
<220> FEATURE:
<223> OTHER INFORMATION: Synthetic Oligonucleotide Sequence

<400> SEQUENCE: 57
gatcgaattc ctccaggaga gaagggagat g                               31

<210> SEQ ID NO 58
<211> LENGTH: 33
<212> TYPE: DNA
<213> ORGANISM: Artificial Sequence
<220> FEATURE:
<223> OTHER INFORMATION: Synthetic Oligonucleotide Sequence

<400> SEQUENCE: 58
gatcaagctt atctcttcct gggtatccag ctt                             33

<210> SEQ ID NO 59
<211> LENGTH: 69
<212> TYPE: DNA
<213> ORGANISM: Artificial Sequence
<220> FEATURE:
<223> OTHER INFORMATION: Synthetic Oligonucleotide Sequence

<400> SEQUENCE: 59
gctggaacag aagtttgttg gtgcgtgaca aggtatggaa gaagattatc cggaaaagaa    60
agcaaagac                                                        69

<210> SEQ ID NO 60
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 60
ggctggaaca gaagtttgtt ggtgcgtgac aaggtatgga agaagattat            50

<210> SEQ ID NO 61
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 61
ggctggaaca gaagtttgtt ggtgcgtgac aaggtatgga                      40

<210> SEQ ID NO 62
<211> LENGTH: 30
```

```
<212> TYPE: DNA
<213> ORGANISM: Artificial Sequence
<220> FEATURE:
<223> OTHER INFORMATION: Synthetic Oligonucleotide Sequence

<400> SEQUENCE: 62
gaacagaagt tgttggtgc gtgacaaggt                                    30

<210> SEQ ID NO 63
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 9, 25
<223> OTHER INFORMATION: n = LNA methyl cytosine

<400> SEQUENCE: 63
ggctggaana gaagtttgtt ggtgngtgac aaggtatgga agaagattat             50

<210> SEQ ID NO 64
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 9, 25
<223> OTHER INFORMATION: n = LNA methyl cytosine

<400> SEQUENCE: 64
ggctggaana gaagtttgtt ggtgngtgac aaggtatgga agaagattat             50

<210> SEQ ID NO 65
<211> LENGTH: 40
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 9, 25
<223> OTHER INFORMATION: n = LNA methyl cytosine

<400> SEQUENCE: 65
ggctggaana gaagtttgtt ggtgngtgac aaggtatgga                        40

<210> SEQ ID NO 66
<211> LENGTH: 40
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 9, 25
<223> OTHER INFORMATION: n = LNA methyl cytosine

<400> SEQUENCE: 66
ggctggaana gaagtttgtt ggtgngtgac aaggtatgga                        40

<210> SEQ ID NO 67
<211> LENGTH: 30
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 25
<223> OTHER INFORMATION: n = LNA methyl cytosine
```

<400> SEQUENCE: 67
gaacagaagt tgttggtgc gtganaaggt                30

<210> SEQ ID NO 68
<211> LENGTH: 30
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 25
<223> OTHER INFORMATION: n = LNA methyl cytosine

<400> SEQUENCE: 68
gaacagaagt tgttggtgc gtganaaggt                30

<210> SEQ ID NO 69
<211> LENGTH: 70
<212> TYPE: DNA
<213> ORGANISM: Artificial Sequence
<220> FEATURE:
<223> OTHER INFORMATION: Synthetic Oligonucleotide Sequence

<400> SEQUENCE: 69
tatgtggcgc gaatgagcaa tattcagcat gtttctcctc ttgtcaacca tcatgtcaag    60
atccttcaac                                                          70

<210> SEQ ID NO 70
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 70
tatgtggcgc gaatgagcaa tattcagcat gtttctcctc ttgtcaacca               50

<210> SEQ ID NO 71
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 71
tatgtggcgc gaatgagcaa tattcagcat gtttctcctc                          40

<210> SEQ ID NO 72
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 72
tatgtggcgc gaatgagcaa tattcagcat                                     30

<210> SEQ ID NO 73
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 25, 37, 45, 49

<223> OTHER INFORMATION: n = LNA methyl cytosine

<400> SEQUENCE: 73
tatgtggcgc gaatgagcaa tattnagcat gtttctnctc ttgtnaacna        50

<210> SEQ ID NO 74
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 25, 37, 45, 49
<223> OTHER INFORMATION: n = LNA methyl cytosine

<400> SEQUENCE: 74
tatgtggcgc gaatgagcaa tattnagcat gtttctnctc ttgtnaacna        50

<210> SEQ ID NO 75
<211> LENGTH: 40
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 25, 37
<223> OTHER INFORMATION: n = LNA methyl cytosine

<400> SEQUENCE: 75
tatgtggcgc gaatgagcaa tattnagcat gtttctnctc        40

<210> SEQ ID NO 76
<211> LENGTH: 40
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 25, 37
<223> OTHER INFORMATION: n = LNA methyl cytosine

<400> SEQUENCE: 76
tatgtggcgc gaatgagcaa tattnagcat gtttctnctc        40

<210> SEQ ID NO 77
<211> LENGTH: 30
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 25
<223> OTHER INFORMATION: n = LNA methyl cytosine

<400> SEQUENCE: 77
tatgtggcgc gaatgagcaa tattnagcat        30

<210> SEQ ID NO 78
<211> LENGTH: 30
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 25
<223> OTHER INFORMATION: n = LNA methyl cytosine

<400> SEQUENCE: 78
tatgtggcgc gaatgagcaa tattnagcat                           30

<210> SEQ ID NO 79
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 79
accttgtcac gcaccaacaa acttctgttc                           30

<210> SEQ ID NO 80
<211> LENGTH: 30
<212> TYPE: DNA
<213> ORGANISM: Artificial Sequence
<220> FEATURE:
<223> OTHER INFORMATION: Synthetic Oligonucleotide Sequence

<400> SEQUENCE: 80
atgctgaata ttgctcattc gcgccacata                           30

<210> SEQ ID NO 81
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 81
cctgaaagta gatttgttat ttccgaaacg ccttctcccg ttcttaagtc     50

<210> SEQ ID NO 82
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 82
catataccac aaatagtccc tcaaaaatca caagaaaact cacaacactg     50

<210> SEQ ID NO 83
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 83
gatttgcagc ggtggtaaaa agtatgaaaa cgtggtaatt aaaaggtctc     50

<210> SEQ ID NO 84
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 84
ccaatgaaaa ctaatcaaag gtaaacgtgg atcccatggc aattcccggg     50

<210> SEQ ID NO 85
<211> LENGTH: 50
<212> TYPE: DNA
<213> ORGANISM: Artificial Sequence

```
<220> FEATURE:
<223> OTHER INFORMATION: Synthetic Oligonucleotide Sequence

<400> SEQUENCE: 85
caacactgcc cagaggttca atcgatccga tgatcctaat gaaggcgccc           50

<210> SEQ ID NO 86
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 86
gtccagtatc gtccatcata gtatcgataa atatgtgaag gaaatgcctg           50

<210> SEQ ID NO 87
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 87
caacactgcc cagaggttca atcgatgtgt gataggatca gtgttcaggg           50

<210> SEQ ID NO 88
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 88
gaaggcgaag gagactgcta atatcgataa atatgtgaag gaaatgcctg           50

<210> SEQ ID NO 89
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 31, 37, 43
<223> OTHER INFORMATION: n = LNA methyl cytosine

<400> SEQUENCE: 89
nctgaaagta gatttgttat ttccgaaacg ncttctnccg ttnttaagtc           50

<210> SEQ ID NO 90
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 7, 10, 19, 22, 31, 43, 46
<223> OTHER INFORMATION: n = LNA methyl cytosine

<400> SEQUENCE: 90
natatancan aaatagtcnc tnaaaaatca naagaaaact canaanactg           50

<210> SEQ ID NO 91
<211> LENGTH: 50
<212> TYPE: DNA
<213> ORGANISM: Artificial Sequence
<220> FEATURE:
```

```
<223> OTHER INFORMATION: Synthetic Oligonucleotide Sequence
<221> NAME/KEY: misc_feature
<222> LOCATION: 7, 10, 31
<223> OTHER INFORMATION: n = LNA methyl cytosine

<400> SEQUENCE: 91
gatttgnagn ggtggtaaaa agtatgaaaa ngtggtaatt aaaaggtctc        50

<210> SEQ ID NO 92
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 16, 34, 40, 46
<223> OTHER INFORMATION: n = LNA methyl cytosine

<400> SEQUENCE: 92
ncaatgaaaa ctaatnaaag gtaaacgtgg atcncatggn aattcncggg        50

<210> SEQ ID NO 93
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 27, 28
<223> OTHER INFORMATION: n = LNA methyl cytosine

<400> SEQUENCE: 93
caacactgcc cagaggttca atcgatnnga tgatcctaat gaaggcgccc        50

<210> SEQ ID NO 94
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 94
gtccagtatc gtccatcata gtatcgataa atatgtgaag gaaatgcctg        50

<210> SEQ ID NO 95
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 95
caacactgcc cagaggttca atcgatgtgt gataggatca gtgttcaggg        50

<210> SEQ ID NO 96
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 96
gaaggcgaag gagactgcta atatcgataa atatgtgaag gaaatgcctg        50

<210> SEQ ID NO 97
<211> LENGTH: 34
<212> TYPE: DNA
```

<213> ORGANISM: Artificial Sequence
<220> FEATURE:
<223> OTHER INFORMATION: Synthetic Oligonucleotide Sequence

<400> SEQUENCE: 97
acgtgaattc aaatacagac aatgaaggag atga         34

<210> SEQ ID NO 98
<211> LENGTH: 45
<212> TYPE: DNA
<213> ORGANISM: Artificial Sequence
<220> FEATURE:
<223> OTHER INFORMATION: Synthetic Oligonucleotide Sequence

<400> SEQUENCE: 98
gatccccggg aattgccatg ttacctttga ttagttttca ttggc         45

<210> SEQ ID NO 99
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 99
acgtggatcc tttttttttt tttttttttt gatccccggg aattgccatg         50

<210> SEQ ID NO 100
<211> LENGTH: 22
<212> TYPE: DNA
<213> ORGANISM: Artificial Sequence
<220> FEATURE:
<223> OTHER INFORMATION: Synthetic Oligonucleotide Sequence

<400> SEQUENCE: 100
actatgatgg acgatactgg ac         22

<210> SEQ ID NO 101
<211> LENGTH: 31
<212> TYPE: DNA
<213> ORGANISM: Artificial Sequence
<220> FEATURE:
<223> OTHER INFORMATION: Synthetic Oligonucleotide Sequence

<400> SEQUENCE: 101
attggatcga tccgatgatc ctaatgaagg c         31

<210> SEQ ID NO 102
<211> LENGTH: 139
<212> TYPE: DNA
<213> ORGANISM: Artificial Sequence
<220> FEATURE:
<223> OTHER INFORMATION: Synthetic Oligonucleotide Sequence

<400> SEQUENCE: 102
atcgatccga tgatcctaat gaaggcgccc gggtactcct tcttgcattc ttcaacttcc         60
ttcaacactt gagcggagtc ggtgcatccg aacaatggaa gcttccacat tgtccagtat         120
cgtccatcat agtatcgat         139

<210> SEQ ID NO 103
<211> LENGTH: 17
<212> TYPE: DNA
<213> ORGANISM: Artificial Sequence
<220> FEATURE:
<223> OTHER INFORMATION: Synthetic Oligonucleotide Sequence

```
<400> SEQUENCE: 103
tcctaatgaa ggcgcca                                                      17

<210> SEQ ID NO 104
<211> LENGTH: 17
<212> TYPE: DNA
<213> ORGANISM: Artificial Sequence
<220> FEATURE:
<223> OTHER INFORMATION: Synthetic Oligonucleotide Sequence

<400> SEQUENCE: 104
tcctaatgaa ggcgccc                                                      17

<210> SEQ ID NO 105
<211> LENGTH: 34
<212> TYPE: DNA
<213> ORGANISM: Artificial Sequence
<220> FEATURE:
<223> OTHER INFORMATION: Synthetic Oligonucleotide Sequence

<400> SEQUENCE: 105
ggaattatcg atgtgtgata ggatcagtgt tcag                                   34

<210> SEQ ID NO 106
<211> LENGTH: 31
<212> TYPE: DNA
<213> ORGANISM: Artificial Sequence
<220> FEATURE:
<223> OTHER INFORMATION: Synthetic Oligonucleotide Sequence

<400> SEQUENCE: 106
aattggatcg atattagcag tctccttcgc c                                      31

<210> SEQ ID NO 107
<211> LENGTH: 287
<212> TYPE: DNA
<213> ORGANISM: Artificial Sequence
<220> FEATURE:
<223> OTHER INFORMATION: Synthetic Oligonucleotide Sequence

<400> SEQUENCE: 107
atcgatgtgt gataggttca gtgttcaggg ctgtccaagg aacgtatgag catgcgagag       60
acgctgtagt tggaaaaacc cacgaagcgg ctgagtctac caaagaagga gctcagatag      120
cttcagagaa agcggttgga gcaaaggacg caaccgtcga gaaagctaag gaaaccgctg      180
attatactgc ggagaaggtg ggtgagtata aagactatac ggttgataaa gctaagagg       240 ctaaggacac aactgcagag aaggcgaagg agactgctaa tatcgat                    287

<210> SEQ ID NO 108
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 108
tctgttgagg gtatgacttg caattcctgt gtttggacca ttgagcagca                  50

<210> SEQ ID NO 109
<211> LENGTH: 50
<212> TYPE: DNA
<213> ORGANISM: Artificial Sequence
<220> FEATURE:
```

<223> OTHER INFORMATION: Synthetic Oligonucleotide Sequence
<221> NAME/KEY: misc_feature
<222> LOCATION: 17, 21, 49
<223> OTHER INFORMATION: n = LNA methyl cytosine

<400> SEQUENCE: 109
tctgttgagg gtatganttg naattcctgt gtttggacca ttgagcagna        50

<210> SEQ ID NO 110
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 46, 49
<223> OTHER INFORMATION: n = LNA methyl cytosine

<400> SEQUENCE: 110
tctgttgagg gtatgacttg caattcctgt gtttggacca ttgagnagna        50

<210> SEQ ID NO 111
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 17, 21, 27, 39, 49
<223> OTHER INFORMATION: n = LNA methyl cytosine

<400> SEQUENCE: 111
tctgttgagg gtatganttg naattcntgt gtttggacna ttgagcagna        50

<210> SEQ ID NO 112
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 112
agaaaagcaa tagaggctgt atcaccgggg ctatatagag ttagtatcac        50

<210> SEQ ID NO 113
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 17, 25
<223> OTHER INFORMATION: n = LNA methyl cytosine

<400> SEQUENCE: 113
agaaaagcaa tagaggntgt atcancgggg ctatatagag ttagtatcac        50

<210> SEQ ID NO 114
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 25, 31
<223> OTHER INFORMATION: n = LNA methyl cytosine

<400> SEQUENCE: 114
agaaaagcaa tagaggctgt atcancgggg ntatatagag ttagtatcac    50

<210> SEQ ID NO 115
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 17, 23, 25, 31
<223> OTHER INFORMATION: n = LNA methyl cytosine

<400> SEQUENCE: 115
agaaaagcaa tagaggntgt atnancgggg ntatatagag ttagtatcac    50

<210> SEQ ID NO 116
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 116
gctgttatac aaccccaat gatagcagag ttcatccgag aacttggatt    50

<210> SEQ ID NO 117
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 13, 17, 33, 37
<223> OTHER INFORMATION: n = LNA methyl cytosine

<400> SEQUENCE: 117
gctgttatac aancccnaat gatagcagag ttnatcngag aacttggatt    50

<210> SEQ ID NO 118
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 13, 16, 37, 43
<223> OTHER INFORMATION: n = LNA methyl cytosine

<400> SEQUENCE: 118
gctgttatan aanccncaat gatagcagag ttcatcngag aanttggatt    50

<210> SEQ ID NO 119
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 13, 15, 17, 33, 37, 43
<223> OTHER INFORMATION: n = LNA methyl cytosine

<400> SEQUENCE: 119
gctgttatac aancncnaat gatagcagag ttnatcngag aanttggatt    50

<210> SEQ ID NO 120
<211> LENGTH: 50
<212> TYPE: DNA
<213> ORGANISM: Artificial Sequence

```
<220> FEATURE:
<223> OTHER INFORMATION: Synthetic Oligonucleotide Sequence

<400> SEQUENCE: 120
tctttggtca agaaggatcg gtcagcaagt cacttagatc ataaacgaga          50

<210> SEQ ID NO 121
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 9, 33
<223> OTHER INFORMATION: n = LNA methyl cytosine

<400> SEQUENCE: 121
tctttggtna agaaggatcg gtcagcaagt canttagatc ataaacgaga          50

<210> SEQ ID NO 122
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 19, 31, 40, 46
<223> OTHER INFORMATION: n = LNA methyl cytosine

<400> SEQUENCE: 122
tctttggtca agaaggatng gtcagcaagt nacttagatn ataaangaga          50

<210> SEQ ID NO 123
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 9, 19, 23, 31, 33
<223> OTHER INFORMATION: n = LNA methyl cytosine

<400> SEQUENCE: 123
tctttggtna agaaggatng gtnagcaagt nanttagatc ataaacgaga          50

<210> SEQ ID NO 124
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 124
ttataaagca ctgaagcata agacagcaaa tatggacgta ctgattgtgc          50

<210> SEQ ID NO 125
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 9, 17, 37, 41
<223> OTHER INFORMATION: n = LNA methyl cytosine

<400> SEQUENCE: 125
ttataaagna ctgaagnata agacagcaaa tatggangta ntgattgtgc          50
```

```
<210> SEQ ID NO 126
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 37
<223> OTHER INFORMATION: n = LNA methyl cytosine

<400> SEQUENCE: 126
ttataaagca ctgaagcata agacagcaaa tatggangta ctgattgtgc            50

<210> SEQ ID NO 127
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 9, 11, 17, 27, 37, 41
<223> OTHER INFORMATION: n = LNA methyl cytosine

<400> SEQUENCE: 127
ttataaagna ntgaagnata agacagnaaa tatggangta ntgattgtgc            50

<210> SEQ ID NO 128
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 128
aacaagtgga tgtggaactt gtacaacgtg gagatatcat taaagtagtt            50

<210> SEQ ID NO 129
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 129
aacaagtgga tgtggaactt gtacaacgtg gagatatcat taaagtagtt            50

<210> SEQ ID NO 130
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 130
aacaagtgga tgtggaactt gtacaacgtg gagatatcat taaagtagtt            50

<210> SEQ ID NO 131
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 3, 27
<223> OTHER INFORMATION: n = LNA methyl cytosine

<400> SEQUENCE: 131
```
aanaagtgga tgtggaactt gtacaangtg gagatatcat taaagtagtt    50

<210> SEQ ID NO 132
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 132
ccattgccac cctcttggta tggattgtaa ttggatttct gaattttgaa    50

<210> SEQ ID NO 133
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1
<223> OTHER INFORMATION: n = LNA methyl cytosine

<400> SEQUENCE: 133
ncattgccac cctcttggta tggattgtaa ttggatttct gaattttgaa    50

<210> SEQ ID NO 134
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 7, 10
<223> OTHER INFORMATION: n = LNA methyl cytosine

<400> SEQUENCE: 134
ncattgncan cctcttggta tggattgtaa ttggatttct gaattttgaa    50

<210> SEQ ID NO 135
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 7, 11, 39
<223> OTHER INFORMATION: n = LNA methyl cytosine

<400> SEQUENCE: 135
ncattgncac nctcttggta tggattgtaa ttggatttnt gaattttgaa    50

<210> SEQ ID NO 136
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 136
ggtatttgat aagactggaa ccattactca cggaacccca gtggtgaatc    50

<210> SEQ ID NO 137
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 21, 29, 37
<223> OTHER INFORMATION: n = LNA methyl cytosine

<400> SEQUENCE: 137
ggtatttgat aagactggaa ncattactna cggaacncca gtggtgaatc        50

<210> SEQ ID NO 138
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 22, 31, 37
<223> OTHER INFORMATION: n = LNA methyl cytosine

<400> SEQUENCE: 138
ggtatttgat aagactggaa cnattactca nggaacncca gtggtgaatc        50

<210> SEQ ID NO 139
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 15, 21, 27, 29, 31, 37, 39
<223> OTHER INFORMATION: n = LNA methyl cytosine

<400> SEQUENCE: 139
ggtatttgat aagantggaa ncattantna nggaacncna gtggtgaatc        50

<210> SEQ ID NO 140
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 140
attggtaacc gggagtggat gattagaaat ggtcttgtca ttaataacga        50

<210> SEQ ID NO 141
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 9
<223> OTHER INFORMATION: n = LNA methyl cytosine

<400> SEQUENCE: 141
attggtaanc gggagtggat gattagaaat ggtcttgtca ttaataacga        50

<210> SEQ ID NO 142
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 34
<223> OTHER INFORMATION: n = LNA methyl cytosine

<400> SEQUENCE: 142
attggtaacn gggagtggat gattagaaat ggtnttgtca ttaataacga        50

<210> SEQ ID NO 143
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 9, 39
<223> OTHER INFORMATION: n = LNA methyl cytosine

<400> SEQUENCE: 143
attggtaanc gggagtggat gattagaaat ggtcttgtna ttaataacga            50

<210> SEQ ID NO 144
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 144
tggcacaggc acagatgtag ccattgaagc agctgatgtg gttttgataa            50

<210> SEQ ID NO 145
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 21, 33
<223> OTHER INFORMATION: n = LNA methyl cytosine

<400> SEQUENCE: 145
tggcacaggc acagatgtag ncattgaagc agntgatgtg gttttgataa            50

<210> SEQ ID NO 146
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 10, 22
<223> OTHER INFORMATION: n = LNA methyl cytosine

<400> SEQUENCE: 146
tggnacaggn acagatgtag cnattgaagc agctgatgtg gttttgataa            50

<210> SEQ ID NO 147
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 21, 33
<223> OTHER INFORMATION: n = LNA methyl cytosine

<400> SEQUENCE: 147
tggcacaggc acagatgtag ncattgaagc agntgatgtg gttttgataa            50

<210> SEQ ID NO 148
<211> LENGTH: 50
<212> TYPE: DNA
<213> ORGANISM: Artificial Sequence
<220> FEATURE:
<223> OTHER INFORMATION: Synthetic Oligonucleotide Sequence

```
<221> NAME/KEY: misc_feature
<222> LOCATION: 5, 11, 23, 35
<223> OTHER INFORMATION: n = LNA methyl cytosine

<400> SEQUENCE: 148
gtganttctc ngattgtgtg agntttgttg gagcntgcgt acgtggattt            50

<210> SEQ ID NO 149
<211> LENGTH: 49
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 6, 10, 12, 20, 24, 30, 36, 38, 42, 48
<223> OTHER INFORMATION: n = LNA methyl cytosine

<400> SEQUENCE: 149
tttaantgan ancttgtttn tgantgttan ggcgtnantg antttgcna             49

<210> SEQ ID NO 150
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 5, 21, 25, 27, 31, 39, 43
<223> OTHER INFORMATION: n = LNA methyl cytosine

<400> SEQUENCE: 150
natanaggtc actggcatga nttgngnttc ntgtgtagna aanattgaac            50

<210> SEQ ID NO 151
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 13, 19, 23, 43
<223> OTHER INFORMATION: n = LNA methyl cytosine

<400> SEQUENCE: 151 tgagggaat gangtgtgnc tcntgcgtac ataaaataga gtntagtctc             50

<210> SEQ ID NO 152
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 19, 45, 49
<223> OTHER INFORMATION: n = LNA methyl cytosine

<400> SEQUENCE: 152
tgtattnctg taatggggnt gatgacatat atgatggtta tggancacna            50

<210> SEQ ID NO 153
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 5, 11, 13, 17, 29, 31, 41, 47
<223> OTHER INFORMATION: n = LNA methyl cytosine
```

<400> SEQUENCE: 153
acatnagagg ntnttgnaaa gttaatttna ntacaagcta nagaagnaac                50

<210> SEQ ID NO 154
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 3, 11, 21, 23, 31, 39, 41
<223> OTHER INFORMATION: n = LNA methyl cytosine

<400> SEQUENCE: 154
ttncattaac nagaacgggt nantgcttat ntgcgcaana natgttggag                50

<210> SEQ ID NO 155
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 7, 11, 39
<223> OTHER INFORMATION: n = LNA methyl cytosine

<400> SEQUENCE: 155
ncattgncac nctcttggta tggattgtaa ttggatttnt gaattttgaa                50

<210> SEQ ID NO 156
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 5, 13, 25, 29, 43, 49
<223> OTHER INFORMATION: n = LNA methyl cytosine

<400> SEQUENCE: 156
gaaangataa tangatttgc tttcnaagnc tctatcacag ttntgttgna                50

<210> SEQ ID NO 157
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 13, 19, 25, 41, 47, 49
<223> OTHER INFORMATION: n = LNA methyl cytosine

<400> SEQUENCE: 157
atgaacagtc atnaacttng tcttncatga ttattgatgc ncagatntna                50

<210> SEQ ID NO 158
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 11, 21, 29, 47, 49
<223> OTHER INFORMATION: n = LNA methyl cytosine

<400> SEQUENCE: 158
gttctgatga ntggagacaa nagtaaaana gctagatcta ttgcttntna                50

<210> SEQ ID NO 159
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 19
<223> OTHER INFORMATION: n = LNA methyl cytosine

<400> SEQUENCE: 159
tggcaagtat tgacttatna agaaagacag tcaagaggat tcggataaat        50

<210> SEQ ID NO 160
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 3, 5, 19, 23, 31, 33, 35, 37
<223> OTHER INFORMATION: n = LNA methyl cytosine

<400> SEQUENCE: 160
gcntntataa actcactant gtntgataaa ngntncntaa acagtgttgt        50

<210> SEQ ID NO 161
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 15, 27, 33, 39, 47
<223> OTHER INFORMATION: n = LNA methyl cytosine

<400> SEQUENCE: 161
ntggatggga tctgnagcaa tggctgnttc atntgtttnt gtagtanttt        50

<210> SEQ ID NO 162
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4
<223> OTHER INFORMATION: n = LNA methyl cytosine

<400> SEQUENCE: 162
tgcnattgca cgggcacttg ttcgatctcc ttctgtttta cttttggatg        50

<210> SEQ ID NO 163
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 16, 31
<223> OTHER INFORMATION: n = LNA methyl cytosine

<400> SEQUENCE: 163
tcattctagg attgcnagat ggttatgata ntcatgtcgg agagaaagga        50

<210> SEQ ID NO 164
<211> LENGTH: 50
<212> TYPE: DNA

<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 28, 37, 40, 46
<223> OTHER INFORMATION: n = LNA methyl cytosine

<400> SEQUENCE: 164
ncaatgttgt ttaattggtt gtaatgtntt gatgacntgn ataatnatat    50

<210> SEQ ID NO 165
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 10, 22, 28, 49
<223> OTHER INFORMATION: n = LNA methyl cytosine

<400> SEQUENCE: 165
nacaagatcn tgtgttgttc tncggaanaa tgaaaatgaa cttagatcna    50

<210> SEQ ID NO 166
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 28, 40, 43
<223> OTHER INFORMATION: n = LNA methyl cytosine

<400> SEQUENCE: 166
tacttgttct cgacaaaggt tgtgtagncg agtttgacan tcngaagaaa    50

<210> SEQ ID NO 167
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 13, 22, 49
<223> OTHER INFORMATION: n = LNA methyl cytosine

<400> SEQUENCE: 167
tgaacttgga tcncttcttt gnatttagcg atgatcaaat ttgggaagng    50

<210> SEQ ID NO 168
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 22, 28, 37, 43, 49
<223> OTHER INFORMATION: n = LNA methyl cytosine

<400> SEQUENCE: 168
tcattaattt tgtgtagctt tntttctnga tttttgnacg atntttccnc    50

<210> SEQ ID NO 169
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature

```
<222> LOCATION: 7, 22, 37
<223> OTHER INFORMATION: n = LNA methyl cytosine

<400> SEQUENCE: 169
agggtgncta ctacaaactg anccaaaagc agatgancga gaagaaataa        50

<210> SEQ ID NO 170
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 46
<223> OTHER INFORMATION: n = LNA methyl cytosine

<400> SEQUENCE: 170
attgaaagcg acgcggaaag tgccatgtat ttctaattt gttttnttta         50

<210> SEQ ID NO 171
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 13, 37, 49
<223> OTHER INFORMATION: n = LNA methyl cytosine

<400> SEQUENCE: 171
ttgtcagcat atnaagagta gatatggaag tggatanact ctgctaatnc         50

<210> SEQ ID NO 172
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 4, 28, 31, 34, 37, 40, 46
<223> OTHER INFORMATION: n = LNA methyl cytosine

<400> SEQUENCE: 172
nacnttattg cgttcaattt ttgtttcnac ntantantan gaatangttg         50

<210> SEQ ID NO 173
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 37
<223> OTHER INFORMATION: n = LNA methyl cytosine

<400> SEQUENCE: 173
tcanaaggga gagagtctgc ggtcggtgct ggcgttngag aaaatataac         50

<210> SEQ ID NO 174
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 10, 13, 25
<223> OTHER INFORMATION: n = LNA methyl cytosine

<400> SEQUENCE: 174
```
natgcatccn gangagaaga agtantcatt ttggagttat ctggcgaatt    50

<210> SEQ ID NO 175
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 10, 22
<223> OTHER INFORMATION: n = LNA methyl cytosine

<400> SEQUENCE: 175
gacnatgctn cggtcgtcat gnaaatcgac ttctaaattg cttctgatta    50

<210> SEQ ID NO 176
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 22, 28, 37, 46, 49
<223> OTHER INFORMATION: n = LNA methyl cytosine

<400> SEQUENCE: 176
ttgnatgctg ttaaaaccta tngtgtanaa tattgcntgt atattnccnt    50

<210> SEQ ID NO 177
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4
<223> OTHER INFORMATION: n = LNA methyl cytosine

<400> SEQUENCE: 177
tggnacagct taataacaaa ttggaaagtc gaggattagt cggtgttgaa    50

<210> SEQ ID NO 178
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 46
<223> OTHER INFORMATION: n = LNA methyl cytosine

<400> SEQUENCE: 178
gacacangca aaggatatgg atgttgttga gctgctgact gaagtnaata    50

<210> SEQ ID NO 179
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 16, 19, 31, 43
<223> OTHER INFORMATION: n = LNA methyl cytosine

<400> SEQUENCE: 179
agcacgaaan tctgcngtnt aaaattcact ngtgattcat tgnccaattg    50

```
<210> SEQ ID NO 180
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 22, 34, 43
<223> OTHER INFORMATION: n = LNA methyl cytosine

<400> SEQUENCE: 180
atggtcatan tctaaaatgg gnagaacttc aacnaaatca ttntcgtcag              50

<210> SEQ ID NO 181
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 13, 16
<223> OTHER INFORMATION: n = LNA methyl cytosine

<400> SEQUENCE: 181
aacncgagct tgncgnaaag tgcaagaaaa ttatagaacg aatgaaacag              50

<210> SEQ ID NO 182
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 13
<223> OTHER INFORMATION: n = LNA methyl cytosine

<400> SEQUENCE: 182
ggatgggtcg agngtgagac ctactactaa agaacagctt gtgaatcttt              50

<210> SEQ ID NO 183
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 4, 10, 16, 19, 34, 40, 43
<223> OTHER INFORMATION: n = LNA methyl cytosine

<400> SEQUENCE: 183
naangttctn gattcntang gacaagaatg gacntatgcn aanagaaaga              50

<210> SEQ ID NO 184
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 34
<223> OTHER INFORMATION: n = LNA methyl cytosine

<400> SEQUENCE: 184
tgctcgttat ccagctattt tgaagggact tgtnatgcaa ggacttcttc              50

<210> SEQ ID NO 185
<211> LENGTH: 50
<212> TYPE: DNA
<213> ORGANISM: Artificial Sequence
```

```
<220> FEATURE:
<223> OTHER INFORMATION: Synthetic Oligonucleotide Sequence
<221> NAME/KEY: misc_feature
<222> LOCATION: 1, 22, 31, 40
<223> OTHER INFORMATION: n = LNA methyl cytosine

<400> SEQUENCE: 185
ncgtttagag cttattgcta ancagattgt nccacaagtn agaacagctc            50

<210> SEQ ID NO 186
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 10, 13, 16, 40
<223> OTHER INFORMATION: n = LNA methyl cytosine

<400> SEQUENCE: 186
tganggacgn tantanccat atgtatttgt tccatcttan cagcaaccaa            50

<210> SEQ ID NO 187
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 13, 16, 28, 37, 43, 46
<223> OTHER INFORMATION: n = LNA methyl cytosine

<400> SEQUENCE: 187
agctacttca ttnganaagg aacatctngg aaaagtnaag tanatnccgg            50

<210> SEQ ID NO 188
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 13, 40
<223> OTHER INFORMATION: n = LNA methyl cytosine

<400> SEQUENCE: 188
aaattcaagg atncagttgc cgatggtgaa gccaagattn gcaaggatta            50

<210> SEQ ID NO 189
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 10, 13, 19, 22, 31, 40
<223> OTHER INFORMATION: n = LNA methyl cytosine

<400> SEQUENCE: 189
ngatcgtttn tgnccattnt anaagactgt nggtatgctn aagaatatga            50

<210> SEQ ID NO 190
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 190
```
tcaggaacga tctttgacaa cattatcatc accgactctg ttgaggaggc            50

<210> SEQ ID NO 191
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 10, 22, 31, 34, 40
<223> OTHER INFORMATION: n = LNA methyl cytosine

<400> SEQUENCE: 191
tgaactntan tcttatgaaa gntggggagc natnggattn gatttgtggc            50

<210> SEQ ID NO 192
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 19, 37
<223> OTHER INFORMATION: n = LNA methyl cytosine

<400> SEQUENCE: 192
gaantttgca gggccgctng gggaatgtca tgatttnatt attaagggaa            50

<210> SEQ ID NO 193
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 28, 34
<223> OTHER INFORMATION: n = LNA methyl cytosine

<400> SEQUENCE: 193
gtcaattctg ggagaaggtg ttggatancg gggntcggga gagaatgtgc            50

<210> SEQ ID NO 194
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 22, 46
<223> OTHER INFORMATION: n = LNA methyl cytosine

<400> SEQUENCE: 194
atgtaaagaa ggaatgcttc cngaatggat tggatattta tttgtncaga            50

<210> SEQ ID NO 195
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 16, 19, 28, 43
<223> OTHER INFORMATION: n = LNA methyl cytosine

<400> SEQUENCE: 195
ggancgaaat ttgtgnagna tgtcgganac gaaattgatg gtntcatttt            50

```
<210> SEQ ID NO 196
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 7, 16, 34, 40
<223> OTHER INFORMATION: n = LNA methyl cytosine

<400> SEQUENCE: 196
nagacangaa ggttangata gataaccatc tctnaaagtn tatcgacctc                50

<210> SEQ ID NO 197
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 4, 22, 49
<223> OTHER INFORMATION: n = LNA methyl cytosine

<400> SEQUENCE: 197
ngangatgtg cgtgttcctg angatgaaag aatgggatat taagaaaanc                50

<210> SEQ ID NO 198
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 19, 22, 40
<223> OTHER INFORMATION: n = LNA methyl cytosine

<400> SEQUENCE: 198
ttgtgctcca tcgctgctnc gnttacagac ttgacaacgn tcacctttgc                50

<210> SEQ ID NO 199
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 16, 28, 31, 34, 46, 49
<223> OTHER INFORMATION: n = LNA methyl cytosine

<400> SEQUENCE: 199
aatgagnggt tgtgcngtgt gacgtcantt ngtnacagtg ttgctntant                50

<210> SEQ ID NO 200
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 31, 40, 43, 46, 49
<223> OTHER INFORMATION: n = LNA methyl cytosine

<400> SEQUENCE: 200
aaattgacan caatcaaatc tgtctcatct nctgaggacn gtnaanttng                50

<210> SEQ ID NO 201
<211> LENGTH: 50
<212> TYPE: DNA
<213> ORGANISM: Artificial Sequence
```

```
<220> FEATURE:
<223> OTHER INFORMATION: Synthetic Oligonucleotide Sequence
<221> NAME/KEY: misc_feature
<222> LOCATION: 4, 13, 31, 34, 46
<223> OTHER INFORMATION: n = LNA methyl cytosine

<400> SEQUENCE: 201
aatntttgtg tanggagatg gggcaaaagg nagnaagaaa gtaaancaag                50

<210> SEQ ID NO 202
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 202
aggacaaggg gcactactgg cacaggcttt gattattgca gtgagatatt                50

<210> SEQ ID NO 203
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 49
<223> OTHER INFORMATION: n = LNA methyl cytosine

<400> SEQUENCE: 203
ttaatggagg tgacaatggg ttccttggat tcgataaatt ccgagtgcnc                50

<210> SEQ ID NO 204
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 7, 10, 19, 28, 31, 49
<223> OTHER INFORMATION: n = LNA methyl cytosine

<400> SEQUENCE: 204
gctnttntcn agtgggctna aaatagtnaa ntcaacagat cggaagttnt                50

<210> SEQ ID NO 205
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 16, 22, 25, 31, 49
<223> OTHER INFORMATION: n = LNA methyl cytosine

<400> SEQUENCE: 205
aaagcttcga gatggnacgt tngtntgtat ntcgtgaaga acttattgna                50

<210> SEQ ID NO 206
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 37, 40, 43
<223> OTHER INFORMATION: n = LNA methyl cytosine

<400> SEQUENCE: 206
```
gattcgntga actttatcaa gacgtggaat atgagcnagn tcntgtcgac        50

<210> SEQ ID NO 207
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 25, 37
<223> OTHER INFORMATION: n = LNA methyl cytosine

<400> SEQUENCE: 207
gatnttatca ccgcgtgcga tattngagta gcttcanagg atgcgatttt        50

<210> SEQ ID NO 208
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 19, 31, 34, 37, 46
<223> OTHER INFORMATION: n = LNA methyl cytosine

<400> SEQUENCE: 208
ggaaaggaag gatccattnt cagctctgca nttncancat cagagncatg        50

<210> SEQ ID NO 209
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 22
<223> OTHER INFORMATION: n = LNA methyl cytosine

<400> SEQUENCE: 209
tggatanaag gagggatctg gnagtggtgg atctggaagt ggtggatatg        50

<210> SEQ ID NO 210
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 13, 25, 34, 46
<223> OTHER INFORMATION: n = LNA methyl cytosine

<400> SEQUENCE: 210
ttgaaagaan tcnttgccga cgatnctgaa acanacaaag aattgntgaa        50

<210> SEQ ID NO 211
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 22
<223> OTHER INFORMATION: n = LNA methyl cytosine

<400> SEQUENCE: 211
atgtgggatg aggagaaaga anatttagat acaatggaaa gattagctgc        50

```
<210> SEQ ID NO 212
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 37
<223> OTHER INFORMATION: n = LNA methyl cytosine

<400> SEQUENCE: 212
aggntgagct cttggacttt ggcatcaaca ttgtctnatt cttgaaggaa          50

<210> SEQ ID NO 213
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 19, 34, 46, 49
<223> OTHER INFORMATION: n = LNA methyl cytosine

<400> SEQUENCE: 213
ttatggttan agaaggagnt gtttacggtg tagnattggg aatgtnttnc          50

<210> SEQ ID NO 214
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 10, 13, 16, 25, 34, 37, 40, 43
<223> OTHER INFORMATION: n = LNA methyl cytosine

<400> SEQUENCE: 214
nacttcaacn aantcngtgt taatnaagca agcngcnacn atntaatgag          50

<210> SEQ ID NO 215
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 19, 22, 43
<223> OTHER INFORMATION: n = LNA methyl cytosine

<400> SEQUENCE: 215
tctnattgct cgtcgaggnt ancaacaaac actggcaata ccnaattaat          50

<210> SEQ ID NO 216
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 25, 34, 37, 43
<223> OTHER INFORMATION: n = LNA methyl cytosine

<400> SEQUENCE: 216
taagaaagtn attgaggatg ctgtngcttt gctngcngaa gtntcgtata          50

<210> SEQ ID NO 217
<211> LENGTH: 50
<212> TYPE: DNA
<213> ORGANISM: Artificial Sequence
```

```
<220> FEATURE:
<223> OTHER INFORMATION: Synthetic Oligonucleotide Sequence
<221> NAME/KEY: misc_feature
<222> LOCATION: 10, 28, 37, 43
<223> OTHER INFORMATION: n = LNA methyl cytosine

<400> SEQUENCE: 217
aagttcatcn tgttgacgga atcgaggngg agaatgntgt atnggtcatt            50

<210> SEQ ID NO 218
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 49
<223> OTHER INFORMATION: n = LNA methyl cytosine

<400> SEQUENCE: 218
acaggaaata tgattttgga tttcgatttt gaatcggttg gtgctgccnc            50

<210> SEQ ID NO 219
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7
<223> OTHER INFORMATION: n = LNA methyl cytosine

<400> SEQUENCE: 219
gctgagntgt atttggctag tgaaatgtgt gttttgata ctttaaatga             50

<210> SEQ ID NO 220
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 16
<223> OTHER INFORMATION: n = LNA methyl cytosine

<400> SEQUENCE: 220
acgaggtttg gatcanaatc agaattctgt gaaataagcg ttttttggga            50

<210> SEQ ID NO 221
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 25, 46
<223> OTHER INFORMATION: n = LNA methyl cytosine

<400> SEQUENCE: 221
agttctnggt ctaacagtgt ctccngttga atattcttgt aaaatnacac            50

<210> SEQ ID NO 222
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10
```

<223> OTHER INFORMATION: n = LNA methyl cytosine

<400> SEQUENCE: 222
atgaccactn aaaatactgc taaaagattt gcagcggcag aagccgttaa       50

<210> SEQ ID NO 223
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 16, 34
<223> OTHER INFORMATION: n = LNA methyl cytosine

<400> SEQUENCE: 223
ttgatatggn tgtacntgta tggtttttga ggangttttt taggagtcga       50

<210> SEQ ID NO 224
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 16
<223> OTHER INFORMATION: n = LNA methyl cytosine

<400> SEQUENCE: 224
atttattcat tcatcnatgt aaactgtata ttttgaattt gtgttgtaaa       50

<210> SEQ ID NO 225
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 34, 37, 40, 43
<223> OTHER INFORMATION: n = LNA methyl cytosine

<400> SEQUENCE: 225
gccaaagcag aattgtattt gatcttcggt aacnttntcn ttngctacaa       50

<210> SEQ ID NO 226
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 13, 25, 28, 31, 40, 46
<223> OTHER INFORMATION: n = LNA methyl cytosine

<400> SEQUENCE: 226
attttgaatn ttntgggaaa atgcnatnca ntcgagaaan cgttcngttt       50

<210> SEQ ID NO 227
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 13, 25, 40, 46, 49
<223> OTHER INFORMATION: n = LNA methyl cytosine

<400> SEQUENCE: 227
ntaacggagg atntcgccaa ttatntttga gagacaaaan tgaaantcnt            50

<210> SEQ ID NO 228
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 22, 28, 34
<223> OTHER INFORMATION: n = LNA methyl cytosine

<400> SEQUENCE: 228
atctagtccn aatgaatctc cnacatgntg ttantcgtga tgttcaactc            50

<210> SEQ ID NO 229
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 13, 31, 43
<223> OTHER INFORMATION: n = LNA methyl cytosine

<400> SEQUENCE: 229
ttttgctttn atngcaaaag ctcaagatta nacatgtcag gtnaagccaa            50

<210> SEQ ID NO 230
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 4, 7, 22
<223> OTHER INFORMATION: n = LNA methyl cytosine

<400> SEQUENCE: 230
ncgnganttt aaagagaaga tnataaattt gcattgtttt ttgtttgtat            50

<210> SEQ ID NO 231
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 22, 31, 49
<223> OTHER INFORMATION: n = LNA methyl cytosine

<400> SEQUENCE: 231
ngagggtgat tcggagactt tnagtaatgt ncaactttca aatgtttgna            50

<210> SEQ ID NO 232
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 19, 31, 46
<223> OTHER INFORMATION: n = LNA methyl cytosine

<400> SEQUENCE: 232
tagatanaag atacatccnt caaaagaagg nctaccgtca atggcnaaag            50

<210> SEQ ID NO 233

```
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 10, 22, 46
<223> OTHER INFORMATION: n = LNA methyl cytosine

<400> SEQUENCE: 233
tcaacgngtn tataaatgaa tnacaacgag gtatcaacat tctccncctg            50

<210> SEQ ID NO 234
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 19, 34, 43
<223> OTHER INFORMATION: n = LNA methyl cytosine

<400> SEQUENCE: 234
atgntgatgt tgaaattgnt ggctaccgta ttcnaaaaga tantgtaatc            50

<210> SEQ ID NO 235
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 13, 19, 22, 25
<223> OTHER INFORMATION: n = LNA methyl cytosine

<400> SEQUENCE: 235
atgaatncat ggnttggana tntcncgttt ttcaagggat ataaaaatgt            50

<210> SEQ ID NO 236
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 7, 28, 46
<223> OTHER INFORMATION: n = LNA methyl cytosine

<400> SEQUENCE: 236
atgnaangaa ttagtgaaaa attcatcntg gaataaaaaa taattntaaa            50

<210> SEQ ID NO 237
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 19, 25, 37, 43, 49
<223> OTHER INFORMATION: n = LNA methyl cytosine

<400> SEQUENCE: 237
atcgctacga caatctttnc gatgncttcg aagtttngaa agntttctnt            50

<210> SEQ ID NO 238
<211> LENGTH: 50
<212> TYPE: DNA
<213> ORGANISM: Artificial Sequence
<220> FEATURE:
```

```
<223> OTHER INFORMATION: Synthetic Oligonucleotide Sequence
<221> NAME/KEY: misc_feature
<222> LOCATION: 31, 34, 40, 46
<223> OTHER INFORMATION: n = LNA methyl cytosine

<400> SEQUENCE: 238
gaggtcggtg gaggaggaag tggaaattga nggnaaaatn ctgccnaagg            50

<210> SEQ ID NO 239
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 16, 19, 34, 37, 40
<223> OTHER INFORMATION: n = LNA methyl cytosine

<400> SEQUENCE: 239
ncctctttgg gatttncant caagtttact gttnggnagn agtgatataa            50

<210> SEQ ID NO 240
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 13, 37, 40, 46
<223> OTHER INFORMATION: n = LNA methyl cytosine

<400> SEQUENCE: 240
gagttggttn canagaatgc ttaggacgtt taaattngtn acaaantttt            50

<210> SEQ ID NO 241
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 13, 34, 46
<223> OTHER INFORMATION: n = LNA methyl cytosine

<400> SEQUENCE: 241
naatatggtt ccnattttag caactcatat gaanacagaa gatgtncttg            50

<210> SEQ ID NO 242
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 37, 40
<223> OTHER INFORMATION: n = LNA methyl cytosine

<400> SEQUENCE: 242
gaaaaaggcg tcgacatttt atgtgacacg tggacanttn actatgacaa            50

<210> SEQ ID NO 243
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 25, 43
<223> OTHER INFORMATION: n = LNA methyl cytosine
```

<400> SEQUENCE: 243
taattgaatt acgggtcttt tgtanatatt aattttagta tantttgtga         50

<210> SEQ ID NO 244
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 13, 25, 37, 49
<223> OTHER INFORMATION: n = LNA methyl cytosine

<400> SEQUENCE: 244
atatcaatgn aantattaat gaatnacaac gtcttgncaa tcttctccng         50

<210> SEQ ID NO 245
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 28, 37, 49
<223> OTHER INFORMATION: n = LNA methyl cytosine

<400> SEQUENCE: 245
ggagtgacta tgaaagcaaa gagttacnga ttgaaantga aagacagana         50

<210> SEQ ID NO 246
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 34, 40
<223> OTHER INFORMATION: n = LNA methyl cytosine

<400> SEQUENCE: 246
aatntttaat gataatttat gggatctgta tttntctttn tgtcaataaa         50

<210> SEQ ID NO 247
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 10, 37, 43
<223> OTHER INFORMATION: n = LNA methyl cytosine

<400> SEQUENCE: 247
atgagcncan aaatgtaaaa ggatacgaga ttgattnggg aanagtcatg         50

<210> SEQ ID NO 248
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 7, 22, 25, 37
<223> OTHER INFORMATION: n = LNA methyl cytosine

<400> SEQUENCE: 248
atcntgngat atgacattaa gncanatggt tctgaanctt caacagaaga         50

<210> SEQ ID NO 249
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 7, 10, 13, 28, 37, 46, 49
<223> OTHER INFORMATION: n = LNA methyl cytosine

<400> SEQUENCE: 249
ntgaacnttn aanagaagat aaacttcngt atagcgntgg aaaaantcnt          50

<210> SEQ ID NO 250
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 16, 19, 34, 37, 43
<223> OTHER INFORMATION: n = LNA methyl cytosine

<400> SEQUENCE: 250
atttaaagga attcanagnt caaaaaataa taantancgg ttnagagatt          50

<210> SEQ ID NO 251
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 25, 28, 37, 43
<223> OTHER INFORMATION: n = LNA methyl cytosine

<400> SEQUENCE: 251
aatttgagcn acatggcaag ttatnaanag aggaganaat gcngtacagt          50

<210> SEQ ID NO 252
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 40
<223> OTHER INFORMATION: n = LNA methyl cytosine

<400> SEQUENCE: 252
tganattcta cttaaaggga agaaaatacc aactggtacn cttgtatttg          50

<210> SEQ ID NO 253
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 7, 13, 34, 40, 43, 49
<223> OTHER INFORMATION: n = LNA methyl cytosine

<400> SEQUENCE: 253
tcancanaaa gcnatacata tgcgagctag ttcntcaggn tgnttaaanc          50

<210> SEQ ID NO 254
<211> LENGTH: 50

```
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 31, 49
<223> OTHER INFORMATION: n = LNA methyl cytosine

<400> SEQUENCE: 254
ttcgacaaaa ctattttgga aagaacaatc ncattcagtg tcggcaaang                50

<210> SEQ ID NO 255
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 19, 25
<223> OTHER INFORMATION: n = LNA methyl cytosine

<400> SEQUENCE: 255
tctgacaaca aagccatana cgtgncgact aattccacaa tcagctagaa                50

<210> SEQ ID NO 256
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 37, 40, 43, 46
<223> OTHER INFORMATION: n = LNA methyl cytosine

<400> SEQUENCE: 256
ttggcaaaag cagaattgta tttaatcttt ggaaacntcn ttnttngcta                50

<210> SEQ ID NO 257
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 19, 37
<223> OTHER INFORMATION: n = LNA methyl cytosine

<400> SEQUENCE: 257
tgaatctttn aaacttatna ctccttttaa tactacngtt cctgtttgga                50

<210> SEQ ID NO 258
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 34, 49
<223> OTHER INFORMATION: n = LNA methyl cytosine

<400> SEQUENCE: 258
attgagattg tatccattgg cgtctcttgt tcanaatcga aaatgtctna                50

<210> SEQ ID NO 259
<211> LENGTH: 50
<212> TYPE: DNA
<213> ORGANISM: Artificial Sequence
<220> FEATURE:
<223> OTHER INFORMATION: Synthetic Oligonucleotide Sequence
```

```
<221> NAME/KEY: misc_feature
<222> LOCATION: 34, 46
<223> OTHER INFORMATION: n = LNA methyl cytosine

<400> SEQUENCE: 259
aactgctact attgcgccat caagtgtgct gctnaaactt aaatcnaggt            50

<210> SEQ ID NO 260
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 19, 28, 49
<223> OTHER INFORMATION: n = LNA methyl cytosine

<400> SEQUENCE: 260
ttgaganagg aaataagant agaattcntt tgaaactggt gggaagtgnt            50

<210> SEQ ID NO 261
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 22, 34, 37, 46
<223> OTHER INFORMATION: n = LNA methyl cytosine

<400> SEQUENCE: 261
aagatgtcaa agaattcaag cnagaacgat ggtncancga cgagcnatta            50

<210> SEQ ID NO 262
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 13, 34, 40
<223> OTHER INFORMATION: n = LNA methyl cytosine

<400> SEQUENCE: 262
attgaancaa ctntgaaata taatgacaca aaancatgtn tggaagtggt            50

<210> SEQ ID NO 263
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 19, 28, 31, 40, 43
<223> OTHER INFORMATION: n = LNA methyl cytosine

<400> SEQUENCE: 263
ggcaatgtga caatatctnc aatggttntt nacagcaatn atnacgtgtt            50

<210> SEQ ID NO 264
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 10, 25, 40, 43
<223> OTHER INFORMATION: n = LNA methyl cytosine
```

<400> SEQUENCE: 264
ntattcaatn gatattttat cacancatcc agtgctggan ctncatcatt    50

<210> SEQ ID NO 265
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 28, 31, 43
<223> OTHER INFORMATION: n = LNA methyl cytosine

<400> SEQUENCE: 265
gtctcagaga tgtgtaaatt tacttccntg naatttgttt cangcaacta    50

<210> SEQ ID NO 266
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 13, 43
<223> OTHER INFORMATION: n = LNA methyl cytosine

<400> SEQUENCE: 266
ttcngaatgt ttncaattgg gactgaagtt tcaagagtca ccnagaaaaa    50

<210> SEQ ID NO 267
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 19, 28, 31
<223> OTHER INFORMATION: n = LNA methyl cytosine

<400> SEQUENCE: 267
gatncagcat cttccaagnt tacattcntc ngtgcttgta tcaaggaaac    50

<210> SEQ ID NO 268
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 49
<223> OTHER INFORMATION: n = LNA methyl cytosine

<400> SEQUENCE: 268
tttgaaaacn tgttttatta ttaaaataga taattgatta gttctgtang    50

<210> SEQ ID NO 269
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 40
<223> OTHER INFORMATION: n = LNA methyl cytosine

<400> SEQUENCE: 269
atangttgca ctgcatccgg ctatgaggga gccaaaaatn ttaggggagt    50

<210> SEQ ID NO 270
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 7
<223> OTHER INFORMATION: n = LNA methyl cytosine

<400> SEQUENCE: 270
gcanttncat tcatctctgc agctactatg gctttggtga caaaagttgg                50

<210> SEQ ID NO 271
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 16, 22, 37
<223> OTHER INFORMATION: n = A,T,C or G

<400> SEQUENCE: 271
ncgtccaaaa gaatgncatc tnacaagtct tgaaatntta taaaggtagt                50

<210> SEQ ID NO 272
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 43
<223> OTHER INFORMATION: n = LNA methyl cytosine

<400> SEQUENCE: 272
gagggatcaa cagtaacctc gtgcggtatt gacaagggat gtncggaagg                50

<210> SEQ ID NO 273
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 34, 37, 43
<223> OTHER INFORMATION: n = LNA methyl cytosine

<400> SEQUENCE: 273
gatggttctt cgatcgcaaa caaaacagat gtgntcnatt tanatacgga                50

<210> SEQ ID NO 274
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 16, 28, 43, 46
<223> OTHER INFORMATION: n = LNA methyl cytosine

<400> SEQUENCE: 274
atggagaaaa tggatntgat ggagttgnag gaagtgatgg agntcnagga                50

<210> SEQ ID NO 275
<211> LENGTH: 50
<212> TYPE: DNA

<213> ORGANISM: Artificial Sequence
<220> FEATURE:
<223> OTHER INFORMATION: Synthetic Oligonucleotide Sequence
<221> NAME/KEY: misc_feature
<222> LOCATION: 28
<223> OTHER INFORMATION: n = LNA methyl cytosine

<400> SEQUENCE: 275
tgaatctcca taaattattc aatgtttnca aatatttaat ttatcaattg            50

<210> SEQ ID NO 276
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 7, 19, 28, 31, 43, 46
<223> OTHER INFORMATION: n = LNA methyl cytosine

<400> SEQUENCE: 276
gctnaanacg gtaggatcnt atggaacngt nggaggagca ggnctnggag            50

<210> SEQ ID NO 277
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 10, 31, 37, 40
<223> OTHER INFORMATION: n = LNA methyl cytosine

<400> SEQUENCE: 277
ngtgacaacn tcttatttat ttctgtaaaa ntgattngcn aaactttgt            50

<210> SEQ ID NO 278
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 13, 25, 28, 37
<223> OTHER INFORMATION: n = LNA methyl cytosine

<400> SEQUENCE: 278
gaagctttca aancaaatga gttcnttncc ggaatcncaa agaataccaa            50

<210> SEQ ID NO 279
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 43
<223> OTHER INFORMATION: n = LNA methyl cytosine

<400> SEQUENCE: 279
acaatgaaaa gagaggatgg aaaggaaatc gaagtctctg ttnttgacga            50

<210> SEQ ID NO 280
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature

```
<222> LOCATION: 10, 34, 46
<223> OTHER INFORMATION: n = LNA methyl cytosine

<400> SEQUENCE: 280
gatgaggtan ataactttgt gtgcagttat aggncatcta cagtanctgc          50

<210> SEQ ID NO 281
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 7, 10, 16, 25, 43
<223> OTHER INFORMATION: n = LNA methyl cytosine

<400> SEQUENCE: 281
ttcnatnatn actaancgat tgtcntgaca ttgatggcca aancagggaa          50

<210> SEQ ID NO 282
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 10, 28, 46
<223> OTHER INFORMATION: n = LNA methyl cytosine

<400> SEQUENCE: 282
tcanattatn gaacaagtac tagtaagnat gctgtgatgg agtgcngcta          50

<210> SEQ ID NO 283
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 10, 46, 49
<223> OTHER INFORMATION: n = LNA methyl cytosine

<400> SEQUENCE: 283
nacggagatn acgacatcaa agcggattgc ttagagtgtg aaacngtnt           50

<210> SEQ ID NO 284
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 16, 25, 28, 31, 40, 43
<223> OTHER INFORMATION: n = LNA methyl cytosine

<400> SEQUENCE: 284
actatctacg tggcangttg gactnatnat ngatgggaan gangtataag          50

<210> SEQ ID NO 285
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 16, 25, 31, 37, 40, 43
<223> OTHER INFORMATION: n = LNA methyl cytosine

<400> SEQUENCE: 285
```
tctntggcca gttcantttg tgatnaatct nagattngtn canacaagat    50

<210> SEQ ID NO 286
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 4, 7, 10, 19, 28, 37, 46
<223> OTHER INFORMATION: n = LNA methyl cytosine

<400> SEQUENCE: 286
ntanttncgn aagaaggcnc gtcgtttnta atcgatngaa catctnacac    50

<210> SEQ ID NO 287
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 13, 22, 28, 37, 40, 46, 49
<223> OTHER INFORMATION: n = LNA methyl cytosine

<400> SEQUENCE: 287
atggatgatn ganccacttg cnactgancc acaatcncgn actcantanc    50

<210> SEQ ID NO 288
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 13, 28, 40, 46
<223> OTHER INFORMATION: n = LNA methyl cytosine

<400> SEQUENCE: 288
aagacggaga ggntggagag aacggtancg atggagagcn aggaantgat    50

<210> SEQ ID NO 289
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 4, 43
<223> OTHER INFORMATION: n = LNA methyl cytosine

<400> SEQUENCE: 289
ncanccagga ggagggatac aagagaagaa agtacagatt ctncaactaa    50

<210> SEQ ID NO 290
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 13, 31, 43
<223> OTHER INFORMATION: n = LNA methyl cytosine

<400> SEQUENCE: 290
agtttcacan ttntttttgc cgttttggtt nccgttatca atncattgat    50

```
<210> SEQ ID NO 291
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 13, 16
<223> OTHER INFORMATION: n = LNA methyl cytosine

<400> SEQUENCE: 291
nttttatatt ctnatnaatt tgtttcctac ttggtcagct gaggatcgtt            50

<210> SEQ ID NO 292
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 292
ttcggcacaa atggagcaaa agtatcgtgg ttattgtgat gcgattattc            50

<210> SEQ ID NO 293
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 4, 19, 43, 49
<223> OTHER INFORMATION: n = LNA methyl cytosine

<400> SEQUENCE: 293
ntantatgaa tgagctcant ggactcattt atcaactcga gtnaaaagnc            50

<210> SEQ ID NO 294
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 294
gttggcgaat cttcgggttc gtataacttc ttagagggat aagcggtgtt            50

<210> SEQ ID NO 295
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 10, 25, 31, 34
<223> OTHER INFORMATION: n = LNA methyl cytosine

<400> SEQUENCE: 295
gaantgattn gagaagagtg gggantgtcg nttngaggtt taacgacttc            50

<210> SEQ ID NO 296
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 19
<223> OTHER INFORMATION: n = LNA methyl cytosine
```

<400> SEQUENCE: 296
tgttattgcg aaagtaatnc tgcttagtac gagaggaaca gcgggttcaa            50

<210> SEQ ID NO 297
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 10, 16, 46
<223> OTHER INFORMATION: n = LNA methyl cytosine

<400> SEQUENCE: 297
tgcatangan ttggtntctt ggtcaaggtg ttgtattcag tagagnagtc            50

<210> SEQ ID NO 298
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 13, 16, 19, 22, 28, 37
<223> OTHER INFORMATION: n = LNA methyl cytosine

<400> SEQUENCE: 298
tgtgctnaga atncanttnt tngaaatnca attgtgncaa gcactaactt            50

<210> SEQ ID NO 299
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 13, 19, 22, 25, 28, 31
<223> OTHER INFORMATION: n = LNA methyl cytosine

<400> SEQUENCE: 299
ttaagangga acnaattgnt cnacnacnat nataccacga gttgaacagt            50

<210> SEQ ID NO 300
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 10, 16, 22, 25, 28, 34
<223> OTHER INFORMATION: n = LNA methyl cytosine

<400> SEQUENCE: 300
acattgntan caaggnctaa gncgnttnaa attntctaag tctgaaatga            50

<210> SEQ ID NO 301
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 46
<223> OTHER INFORMATION: n = LNA methyl cytosine

<400> SEQUENCE: 301
gttgagtcca ccggagtctt caccaccatc gagaaggcca atgctnactt            50

<210> SEQ ID NO 302
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 13, 16, 28
<223> OTHER INFORMATION: n = LNA methyl cytosine

<400> SEQUENCE: 302
agtaaattcn ttncangtgg atctactngt gtgttcacaa agatcgaggg          50

<210> SEQ ID NO 303
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 25
<223> OTHER INFORMATION: n = LNA methyl cytosine

<400> SEQUENCE: 303
ggtncaataa tgggagactg gttcngcgca gaaagttatg cagatgatat          50

<210> SEQ ID NO 304
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 10, 19, 22
<223> OTHER INFORMATION: n = LNA methyl cytosine

<400> SEQUENCE: 304
agaaaanttn gttggaccnt gntaaggaga agtatttcaa gcttctgagc          50

<210> SEQ ID NO 305
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 7, 13, 19, 37
<223> OTHER INFORMATION: n = LNA methyl cytosine

<400> SEQUENCE: 305
gagnacncga agntcaagnc atatttggaa acaagancat actcttcaaa          50

<210> SEQ ID NO 306
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 19, 28
<223> OTHER INFORMATION: n = LNA methyl cytosine

<400> SEQUENCE: 306
gttaccntct acaaatctng cttcaatnca atgttgttcg cagtcaccaa          50

<210> SEQ ID NO 307
<211> LENGTH: 50
<212> TYPE: DNA

```
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 16, 37
<223> OTHER INFORMATION: n = LNA methyl cytosine

<400> SEQUENCE: 307
ncgaagagct cgttantatg cgaggaggtg tgaagcngga ataatttttt         50

<210> SEQ ID NO 308
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 16, 46
<223> OTHER INFORMATION: n = LNA methyl cytosine

<400> SEQUENCE: 308
aagttcttgg ttggangcga tgggaaaatt atcaagagat tggancaac          50

<210> SEQ ID NO 309
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 22, 40, 46
<223> OTHER INFORMATION: n = LNA methyl cytosine

<400> SEQUENCE: 309
acgatttcaa cgtcaaaaat gntaatggtg atgacgtgtn actttnggat         50

<210> SEQ ID NO 310
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 40
<223> OTHER INFORMATION: n = LNA methyl cytosine

<400> SEQUENCE: 310
acctgggttg atgtttttgc ggctgaaagt ttctccaagn tcattgatta         50

<210> SEQ ID NO 311
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 10, 13, 28, 40
<223> OTHER INFORMATION: n = LNA methyl cytosine

<400> SEQUENCE: 311
gaagtangtn tcncaaagaa aagctacncc agcttaaggn attgcacaat         50

<210> SEQ ID NO 312
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
```

<222> LOCATION: 4, 37, 46, 49
<223> OTHER INFORMATION: n = LNA methyl cytosine

<400> SEQUENCE: 312
gcgncagata tgtattcaaa gatcgaggta aatggtnaga acactnatnc          50

<210> SEQ ID NO 313
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 7, 31, 43
<223> OTHER INFORMATION: n = LNA methyl cytosine

<400> SEQUENCE: 313
aatntanagg gaaaaaggat ttcgagttgc ngcgtttcca tgnaatcaat          50

<210> SEQ ID NO 314
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 19, 37
<223> OTHER INFORMATION: n = LNA methyl cytosine

<400> SEQUENCE: 314
agatggnaaa gaagcatana taactgaaac tcttccnggg gagctactac          50

<210> SEQ ID NO 315
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 13, 25
<223> OTHER INFORMATION: n = LNA methyl cytosine

<400> SEQUENCE: 315
tgaataaacg ggncgaacta aatcnattcg tcagtggaaa tgggaaacaa          50

<210> SEQ ID NO 316
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 7, 10, 25, 28, 34
<223> OTHER INFORMATION: n = LNA methyl cytosine

<400> SEQUENCE: 316
gtcngtnttn ctgatgctta tgaangcnta tttntcgaag tattcatggg          50

<210> SEQ ID NO 317
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 13, 37, 43
<223> OTHER INFORMATION: n = LNA methyl cytosine

<400> SEQUENCE: 317
tgtggaaaag ctntcaacga aagaaagca gaagttngta tanaattcaa            50

<210> SEQ ID NO 318
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 10, 22, 28, 37, 40, 46
<223> OTHER INFORMATION: n = LNA methyl cytosine

<400> SEQUENCE: 318
atatcgncgn ctgcttcctc ancaaccnga ataacgnaan aaaaanttta            50

<210> SEQ ID NO 319
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 10, 40, 43, 46
<223> OTHER INFORMATION: n = LNA methyl cytosine

<400> SEQUENCE: 319
aagagcncan tcatcaagga tgaaagtgat ggaaagactn ttngtntcag            50

<210> SEQ ID NO 320
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 22, 25, 28, 37
<223> OTHER INFORMATION: n = LNA methyl cytosine

<400> SEQUENCE: 320
naagatattt taacaaaaat gnatnaanaa gaagccnaat caggttccgg            50

<210> SEQ ID NO 321
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 7, 16, 37
<223> OTHER INFORMATION: n = LNA methyl cytosine

<400> SEQUENCE: 321
nttgggnatt ctgtanggga tgctgtcatt actgtgnctg catattttaa            50

<210> SEQ ID NO 322
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 10, 22, 28, 46, 49
<223> OTHER INFORMATION: n = LNA methyl cytosine

<400> SEQUENCE: 322
aagaagnatn tcgaaatcaa cncagacnac gctatcatga agacanttng            50

```
<210> SEQ ID NO 323
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 16, 19
<223> OTHER INFORMATION: n = LNA methyl cytosine

<400> SEQUENCE: 323
atgaaagctn aagctnttng tgattcctct actatgggat acatggccgc              50

<210> SEQ ID NO 324
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 46
<223> OTHER INFORMATION: n = LNA methyl cytosine

<400> SEQUENCE: 324
ttaagcagan cattgaggac gagaagctca aggataagat cagccnagaa              50

<210> SEQ ID NO 325
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 4, 25
<223> OTHER INFORMATION: n = LNA methyl cytosine

<400> SEQUENCE: 325
ngtntttcca aggatgacat tgaangcatg gtcaacgaag ctgagaaata              50

<210> SEQ ID NO 326
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 13, 19, 43
<223> OTHER INFORMATION: n = LNA methyl cytosine

<400> SEQUENCE: 326
gtcgacttgg ctnacatcna caccgtcatc aacaaggaag ganagatgac              50

<210> SEQ ID NO 327
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 16, 22, 25, 37, 40, 46
<223> OTHER INFORMATION: n = LNA methyl cytosine

<400> SEQUENCE: 327
naatcttgag ggacangttc tnacnattga gggacancan gaggtnaaga              50

<210> SEQ ID NO 328
<211> LENGTH: 50
<212> TYPE: DNA
<213> ORGANISM: Artificial Sequence
```

```
<220> FEATURE:
<223> OTHER INFORMATION: Synthetic Oligonucleotide Sequence
<221> NAME/KEY: misc_feature
<222> LOCATION: 4, 19, 28, 31, 34, 37, 40, 49
<223> OTHER INFORMATION: n = LNA methyl cytosine

<400> SEQUENCE: 328
tcantaaaat gcaccaatnt ggacaatntt ntgnttntgn tggatgcgnt                 50

<210> SEQ ID NO 329
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 19
<223> OTHER INFORMATION: n = LNA methyl cytosine

<400> SEQUENCE: 329
tcatgaagct aaacaattng aaaaggaaga tggtgaacaa cgggaacgtg                 50

<210> SEQ ID NO 330
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 13, 25, 28, 34
<223> OTHER INFORMATION: n = LNA methyl cytosine

<400> SEQUENCE: 330
aagtataacn ttncaacagg ggtcngtnca gaanaaatca agtccgaatt                 50

<210> SEQ ID NO 331
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 13, 43, 46
<223> OTHER INFORMATION: n = LNA methyl cytosine

<400> SEQUENCE: 331
tttaacnatg gcngcagatt cttcgatgac gtcgactttg atngcnacat                 50

<210> SEQ ID NO 332
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 16, 25, 28, 34
<223> OTHER INFORMATION: n = LNA methyl cytosine

<400> SEQUENCE: 332
gcgtcgaaaa gatctncctg aagtntgnat tgantggcct tgatattatg                 50

<210> SEQ ID NO 333
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 28, 34
```

```
<223> OTHER INFORMATION: n = LNA methyl cytosine

<400> SEQUENCE: 333
acatagtctt cgtcatcaag gataagcnac accngaaatt caagcgagag                50

<210> SEQ ID NO 334
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 10, 16, 22, 40
<223> OTHER INFORMATION: n = LNA methyl cytosine

<400> SEQUENCE: 334
tcgncaacan tcgganacgt gncaaaatga atatcatctn aaatcgaatg                50

<210> SEQ ID NO 335
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 16, 37, 40, 46
<223> OTHER INFORMATION: n = LNA methyl cytosine

<400> SEQUENCE: 335
gtcgaagtta gaaatncaga agccgatatt gtttctnatn aaattncaat                50

<210> SEQ ID NO 336
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 37, 40
<223> OTHER INFORMATION: n = LNA methyl cytosine

<400> SEQUENCE: 336
actactngtg gaagatccaa taaagttgtt tcaacgngan aaatcgattc                50

<210> SEQ ID NO 337
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 337
ggcagtgaag atgaagtggc aaattctgat gaagaaatgg gaagcagtat                50

<210> SEQ ID NO 338
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 34, 46
<223> OTHER INFORMATION: n = LNA methyl cytosine

<400> SEQUENCE: 338
ttgtcaacga ccagaagcaa aaattatggg aatngcgata aaattnaagg                50
```

```
<210> SEQ ID NO 339
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 13, 28, 34, 37
<223> OTHER INFORMATION: n = LNA methyl cytosine

<400> SEQUENCE: 339
gatgcaagtg tgncaactgc gaatgtgntc aggntgntca ttaatttgaa          50

<210> SEQ ID NO 340
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 19
<223> OTHER INFORMATION: n = LNA methyl cytosine

<400> SEQUENCE: 340
gacgatatgt tcgatttcnc aggagaggac ggtgatgatg tgtcagactt          50

<210> SEQ ID NO 341
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 19
<223> OTHER INFORMATION: n = A,T,C or G

<400> SEQUENCE: 341
gacgatatgt tcgatttcnc aggagaggac ggtgatgatg tgtcagactt          50

<210> SEQ ID NO 342
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 16, 25, 34, 40
<223> OTHER INFORMATION: n = LNA methyl cytosine

<400> SEQUENCE: 342
gaggtcgtcg taatcnacaa ggctncaaga aagnaagtgn tcgacatttc          50

<210> SEQ ID NO 343
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 16, 22, 43, 49
<223> OTHER INFORMATION: n = LNA methyl cytosine

<400> SEQUENCE: 343 gatactttg gcaagntcgt tncaatcaag aaggaggtca tcncagatng           50

<210> SEQ ID NO 344
<211> LENGTH: 50
<212> TYPE: DNA
<213> ORGANISM: Artificial Sequence
```

<220> FEATURE:
<223> OTHER INFORMATION: Synthetic Oligonucleotide Sequence
<221> NAME/KEY: misc_feature
<222> LOCATION: 13, 22, 31, 37, 43
<223> OTHER INFORMATION: n = LNA methyl cytosine

<400> SEQUENCE: 344
gatgaggagg ganacaccga gntctaaatc nacattncaa tanagttcaa            50

<210> SEQ ID NO 345
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 19, 40
<223> OTHER INFORMATION: n = LNA methyl cytosine

<400> SEQUENCE: 345
nttatgtccg aagatatcnc agaggattgg gacaagaacn cagtcaagat            50

<210> SEQ ID NO 346
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 10, 13, 25, 31, 34, 43
<223> OTHER INFORMATION: n = LNA methyl cytosine

<400> SEQUENCE: 346
tacnccagtn gantatgatg gaganagaaa nctngagaag ttngaagaat            50

<210> SEQ ID NO 347
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 31
<223> OTHER INFORMATION: n = LNA methyl cytosine

<400> SEQUENCE: 347
ntcgtcgcct ccaacttcaa cgaaattgcc nttgatgaaa ccaagactgt            50

<210> SEQ ID NO 348
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 16, 22
<223> OTHER INFORMATION: n = LNA methyl cytosine

<400> SEQUENCE: 348
ttctattgtt tattcnttgc cnaatagtgt atttgtattt attctttctc            50

<210> SEQ ID NO 349
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 7, 10, 13

<223> OTHER INFORMATION: n = LNA methyl cytosine

<400> SEQUENCE: 349
naaatcnatn tcncagtgga tttcgtcatt gctgacaagt tcgccgagga          50

<210> SEQ ID NO 350
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 16, 25, 31, 37, 40
<223> OTHER INFORMATION: n = LNA methyl cytosine

<400> SEQUENCE: 350
gtttctgatt cgacanttta tggancatct naagttntgn gagtttcttt          50

<210> SEQ ID NO 351
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 31, 34, 43
<223> OTHER INFORMATION: n = LNA methyl cytosine

<400> SEQUENCE: 351
gggaaanaaa tgattgttgg tacagtagcc ngcnctgcta ttnactgtga          50

<210> SEQ ID NO 352
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 7, 10, 13, 22, 28, 31, 37, 40
<223> OTHER INFORMATION: n = LNA methyl cytosine

<400> SEQUENCE: 352
ngagcanatn atncaatcgt tnctgttnaa naaggcnttn taatcgttag          50

<210> SEQ ID NO 353
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 19, 31
<223> OTHER INFORMATION: n = LNA methyl cytosine

<400> SEQUENCE: 353
tgatgagagn ccagtaacna attatttgaa ncgtcaggat gtgcgtaagg          50

<210> SEQ ID NO 354
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 4, 22, 28, 37, 46, 49
<223> OTHER INFORMATION: n = LNA methyl cytosine

<400> SEQUENCE: 354
ngtntaatcg aagaagggga tngtgggnaa tcataantaa ttaacnttna        50

<210> SEQ ID NO 355
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 7, 10, 19, 22, 37, 49
<223> OTHER INFORMATION: n = LNA methyl cytosine

<400> SEQUENCE: 355
naatggntcn aggtctttnt gntcttcata tacttcnatt ccgagttgnt        50

<210> SEQ ID NO 356
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 13, 25, 31, 40, 49
<223> OTHER INFORMATION: n = LNA methyl cytosine

<400> SEQUENCE: 356
gttntcttgg agntgaagtt gtcgngtgct ngtgtgattn tcacttctnt        50

<210> SEQ ID NO 357
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 7, 43
<223> OTHER INFORMATION: n = LNA methyl cytosine

<400> SEQUENCE: 357
tcgntancag caaggaatac ttcaacaagg tcaacaagtg atnacacaga        50

<210> SEQ ID NO 358
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 16, 19, 28, 31, 40, 46
<223> OTHER INFORMATION: n = LNA methyl cytosine

<400> SEQUENCE: 358
aaggaaattg taactngcnc aagagctntc ncaggtgtcn gtgganatat        50

<210> SEQ ID NO 359
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 359
ttgactggat tggagattgc ggaagaagtt gatgttgaaa tcgagagtgg        50

<210> SEQ ID NO 360
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 28, 37
<223> OTHER INFORMATION: n = LNA methyl cytosine

<400> SEQUENCE: 360
gccaagtctn aagcaataag tgttgatnaa tcagagncat acggagagat            50

<210> SEQ ID NO 361
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 13, 22, 31, 34, 40, 43, 46, 49
<223> OTHER INFORMATION: n = LNA methyl cytosine

<400> SEQUENCE: 361
atattgagan ttngggacaa gnggacttct natntgtcan agnaantgnc            50

<210> SEQ ID NO 362
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 7, 25, 34
<223> OTHER INFORMATION: n = LNA methyl cytosine

<400> SEQUENCE: 362
gatncgnaga gaatcgagta tttcntctcg aganccatgg atatcaactg            50

<210> SEQ ID NO 363
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 13, 28
<223> OTHER INFORMATION: n = LNA methyl cytosine

<400> SEQUENCE: 363
tccgttaaga agntcactgg aaaaacanac ggctcgaacg aaattggaat            50

<210> SEQ ID NO 364
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 364
aatttggatg agagcaaagt ggaaggaatg gctatcgttt tggcagatat            50

<210> SEQ ID NO 365
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 22, 25, 43, 49
<223> OTHER INFORMATION: n = LNA methyl cytosine

<400> SEQUENCE: 365

```
gtgntggtca aaaaatgctt gnttngttgc ttattcgcat tgnactcgna         50
```

<210> SEQ ID NO 366
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 4, 10, 46
<223> OTHER INFORMATION: n = LNA methyl cytosine

<400> SEQUENCE: 366

```
nttngagaan tcttcaagtt ggaatcaaca gtggcatcgg atacanatga         50
```

<210> SEQ ID NO 367
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4
<223> OTHER INFORMATION: n = LNA methyl cytosine

<400> SEQUENCE: 367

```
gtgncttctg aagccgaaga aaacgacgat tagttaaatg tttccaagtt         50
```

<210> SEQ ID NO 368
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 46
<223> OTHER INFORMATION: n = LNA methyl cytosine

<400> SEQUENCE: 368

```
gataaaatcg atagcgacga cgatgaggaa gccgatgatg aggagntcga         50
```

<210> SEQ ID NO 369
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 369

```
gcaggtggat acggatgtgg agctgacttt tgcgttttat caagaatctc         50
```

<210> SEQ ID NO 370
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4
<223> OTHER INFORMATION: n = LNA methyl cytosine

<400> SEQUENCE: 370

```
tccngtagaa gtagaaatgc tagaagaacc tgaacaagaa gatcaagaaa         50
```

<210> SEQ ID NO 371
<211> LENGTH: 50
<212> TYPE: DNA

```
<213> ORGANISM: Artificial Sequence
<220> FEATURE:
<223> OTHER INFORMATION: Synthetic Oligonucleotide Sequence
<221> NAME/KEY: misc_feature
<222> LOCATION: 22, 28, 37, 40
<223> OTHER INFORMATION: n = LNA methyl cytosine

<400> SEQUENCE: 371
tgcaagatgt cagtattgaa anaattcntg tagaganccn cgaagaaaat            50

<210> SEQ ID NO 372
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 49
<223> OTHER INFORMATION: n = LNA methyl cytosine

<400> SEQUENCE: 372
agtntcgtat ccgggaatgt ttcagcctgt gaaaatgctt gttgaagang            50

<210> SEQ ID NO 373
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 4, 10, 13, 40, 46
<223> OTHER INFORMATION: n = LNA methyl cytosine

<400> SEQUENCE: 373
nttnaaaacn gtngctttta aggatacagg aacgtggcan gcttcngagg            50

<210> SEQ ID NO 374
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 10, 37, 40
<223> OTHER INFORMATION: n = LNA methyl cytosine

<400> SEQUENCE: 374
nagattgtan cttcgaaaag gaaaaggaga gaatcgngtn gcaaaaatgg            50

<210> SEQ ID NO 375
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 22, 28, 37
<223> OTHER INFORMATION: n = LNA methyl cytosine

<400> SEQUENCE: 375
tgatggnttt gattattcga gnaggagnaa tgatgtncga gagtcgttat            50

<210> SEQ ID NO 376
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
```

<222> LOCATION: 1, 7, 46
<223> OTHER INFORMATION: n = LNA methyl cytosine

<400> SEQUENCE: 376
naatgangag aatattggag taatggggaa actggttgcg acttgngaaa      50

<210> SEQ ID NO 377
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 13, 16, 25, 28, 34, 37, 49
<223> OTHER INFORMATION: n = LNA methyl cytosine

<400> SEQUENCE: 377
ttggaaaaca atntcntcga ctttntgntc actnttngtg aaactatcna      50

<210> SEQ ID NO 378
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 378
tcttgttatt ttattttgtt ttgggcttgt tccgaaaatg aaatggttgt      50

<210> SEQ ID NO 379
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 16, 22, 28, 31, 37, 46
<223> OTHER INFORMATION: n = LNA methyl cytosine

<400> SEQUENCE: 379
naatggatca ccaagncagt tnacaagnac ngtgagnaaa gaggantcac      50

<210> SEQ ID NO 380
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 28, 49
<223> OTHER INFORMATION: n = LNA methyl cytosine

<400> SEQUENCE: 380
ntttgtgatg tgatgactgc gaaggganac ttgatggcta ttacgagana      50

<210> SEQ ID NO 381
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 13, 22, 34
<223> OTHER INFORMATION: n = LNA methyl cytosine

<400> SEQUENCE: 381
gagncagcta ctnagatgac antcaacacg ttcnattatg caggagtttc      50

<210> SEQ ID NO 382
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 16, 28, 37, 40
<223> OTHER INFORMATION: n = LNA methyl cytosine

<400> SEQUENCE: 382
tacactncat cctcgncgac atacaatnca acatctncan gcggattctc         50

<210> SEQ ID NO 383
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 49
<223> OTHER INFORMATION: n = LNA methyl cytosine

<400> SEQUENCE: 383
atggagaaga tggtttggat ggaatgtggg ttgagaatca gaatatgcng         50

<210> SEQ ID NO 384
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4
<223> OTHER INFORMATION: n = LNA methyl cytosine

<400> SEQUENCE: 384
aacngggata ccgtgtcgaa cgtcacatga aagatggcga tataatcgtc         50

<210> SEQ ID NO 385
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 13, 28, 40
<223> OTHER INFORMATION: n = LNA methyl cytosine

<400> SEQUENCE: 385
gaggagatta aangcatgtc agtggctnat gtcgagtttn cagaagtcta         50

<210> SEQ ID NO 386
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 34, 40, 43
<223> OTHER INFORMATION: n = LNA methyl cytosine

<400> SEQUENCE: 386
agatattgcn tctacttatc atgggcctga tggntttgtn tgncggtatt         50

<210> SEQ ID NO 387
<211> LENGTH: 50
<212> TYPE: DNA

<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 10, 13, 16, 22, 25, 31, 46
<223> OTHER INFORMATION: n = LNA methyl cytosine

<400> SEQUENCE: 387
gaatctnaan canttntgga anccnataca ncaatggata gaaganggag            50

<210> SEQ ID NO 388
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 37
<223> OTHER INFORMATION: n = LNA methyl cytosine

<400> SEQUENCE: 388
gttgttnttt tttccgtgat cttttcatgt ttatgtntga acgtggcagg            50

<210> SEQ ID NO 389
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 40, 46
<223> OTHER INFORMATION: n = LNA methyl cytosine

<400> SEQUENCE: 389
gactcgttgg tgtcttgcta ggatgtcttg ggttcattcn tcaatngttg            50

<210> SEQ ID NO 390
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 28
<223> OTHER INFORMATION: n = LNA methyl cytosine

<400> SEQUENCE: 390
gtantgggct cgagggctga aactaatnga agaagaaact ccagaagata            50

<210> SEQ ID NO 391
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 43, 46
<223> OTHER INFORMATION: n = LNA methyl cytosine

<400> SEQUENCE: 391
ggatcatgct ctgtttacga cactgatgag ttaagagtca gantgnacgt            50

<210> SEQ ID NO 392
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 37
<223> OTHER INFORMATION: n = LNA methyl cytosine

<400> SEQUENCE: 392
ngatggttct tctcgtctat catatcgggg tagttgncga agtgttgaaa                50

<210> SEQ ID NO 393
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 10, 46
<223> OTHER INFORMATION: n = LNA methyl cytosine

<400> SEQUENCE: 393
naaatcgaan tggtataaag gaggaccgac ggagacgaat ttgaangaga                50

<210> SEQ ID NO 394
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 25, 28, 34
<223> OTHER INFORMATION: n = LNA methyl cytosine

<400> SEQUENCE: 394
attngatcaa agaactctgg ctctnggngt taantggaca tttgttcgtc                50

<210> SEQ ID NO 395
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 4, 10, 22, 37
<223> OTHER INFORMATION: n = LNA methyl cytosine

<400> SEQUENCE: 395
ntcnccgagn aggcgattat tnacgctagt tatgctnaaa tgtgatctgt                50

<210> SEQ ID NO 396
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 7, 19, 28, 43
<223> OTHER INFORMATION: n = LNA methyl cytosine

<400> SEQUENCE: 396
ncggtantat ctggatcana cagaagtncg aaaatgacca ggnagttatt                50

<210> SEQ ID NO 397
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 13, 19, 34, 37
<223> OTHER INFORMATION: n = LNA methyl cytosine

<400> SEQUENCE: 397
nccagtgact acntgaatng cgtctctgaa tctncanaca attcctacta 50

<210> SEQ ID NO 398
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 13, 25, 28, 31
<223> OTHER INFORMATION: n = LNA methyl cytosine

<400> SEQUENCE: 398
ggagttgctn acngcaatta agagngantt nggatctctg gataatcttc 50

<210> SEQ ID NO 399
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 25, 31
<223> OTHER INFORMATION: n = LNA methyl cytosine

<400> SEQUENCE: 399
aaattgagga aaagcttcac gaggnggtct ncaaggaaa cgtcaaagaa 50

<210> SEQ ID NO 400
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 10, 28, 31, 49
<223> OTHER INFORMATION: n = LNA methyl cytosine

<400> SEQUENCE: 400
naatcgtacn atgaaagaag ttggaagnca ngtgcaagag aagaaatcna 50

<210> SEQ ID NO 401
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 16, 28, 37
<223> OTHER INFORMATION: n = LNA methyl cytosine

<400> SEQUENCE: 401
aagaagattn ctgacnagag agactcangt gcttacncaa gaagcatcta 50

<210> SEQ ID NO 402
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 25, 40, 46
<223> OTHER INFORMATION: n = LNA methyl cytosine

<400> SEQUENCE: 402
agcattggtg gaaatacgaa atggnatggg aagagaaacn cctctnaatt 50

```
<210> SEQ ID NO 403
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 22, 28, 31, 40, 49
<223> OTHER INFORMATION: n = LNA methyl cytosine

<400> SEQUENCE: 403
ntggttacgg tagtgtatgg tncctgtnct ntcagaatgn aaatatgtng        50

<210> SEQ ID NO 404
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 19, 28, 37, 46
<223> OTHER INFORMATION: n = LNA methyl cytosine

<400> SEQUENCE: 404
tctacgtcga tggaaaagnc gatttaanaa tcaaagncaa caacgnagtt        50

<210> SEQ ID NO 405
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 22, 25, 37, 43, 49
<223> OTHER INFORMATION: n = LNA methyl cytosine

<400> SEQUENCE: 405
ggaaaggtgn caaaaagttg anagnaattg gaggatntta ttnattgcna        50

<210> SEQ ID NO 406
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 406
agatgatgat gaagttcctg caaagaagcc tgctccagcg aagaaagctg        50

<210> SEQ ID NO 407
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 43
<223> OTHER INFORMATION: n = LNA methyl cytosine

<400> SEQUENCE: 407
aaaacctcgt actggaaaag gagctgcgaa agcggaagtt atngatttgt        50

<210> SEQ ID NO 408
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
```

```
<222> LOCATION: 10, 28, 37
<223> OTHER INFORMATION: n = LNA methyl cytosine

<400> SEQUENCE: 408
gagaaggccn agaagaagta cgacagantg aaggagnagt tgaaaaagtt                50

<210> SEQ ID NO 409
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 19, 34
<223> OTHER INFORMATION: n = LNA methyl cytosine

<400> SEQUENCE: 409
ttctgtnata caatcgtgnt aatcggcagg ttgngatcct ttgtaaccat                50

<210> SEQ ID NO 410
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 7, 13, 31
<223> OTHER INFORMATION: n = LNA methyl cytosine

<400> SEQUENCE: 410
aagnttngga cancattgag aatgtcaaag ncaaaatcca ggataaggag                50

<210> SEQ ID NO 411
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 10, 13, 22, 46
<223> OTHER INFORMATION: n = LNA methyl cytosine

<400> SEQUENCE: 411
aatngaaccn atnaattcac tngttattcc tcctcgatct ccgttnaagt                50

<210> SEQ ID NO 412
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 7, 10, 25, 31, 46
<223> OTHER INFORMATION: n = LNA methyl cytosine

<400> SEQUENCE: 412
ntgaacnatn caaatattga agatncagct naggctgaag cctatnagat                50

<210> SEQ ID NO 413
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 7, 28, 49
<223> OTHER INFORMATION: n = LNA methyl cytosine

<400> SEQUENCE: 413
```
ngtgtgntta tctcttctgg atgaaaanaa ggattggaag ccgtcaatnt        50

<210> SEQ ID NO 414
<211> LENGTH: 49
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 7, 10, 13, 19, 25
<223> OTHER INFORMATION: n = LNA methyl cytosine

<400> SEQUENCE: 414
nggaagnatn tgncttgana ttctncgttc gcagtggtcg ccggctctg         49

<210> SEQ ID NO 415
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 22, 28, 43, 49
<223> OTHER INFORMATION: n = LNA methyl cytosine

<400> SEQUENCE: 415
aaagtangct atgtgaggag gntaacanca ttcatataag aangcagcna        50

<210> SEQ ID NO 416
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7
<223> OTHER INFORMATION: n = LNA methyl cytosine

<400> SEQUENCE: 416
tgttgcngta gaagagagac taaaactaag aacgattgat tgaaggtctg        50

<210> SEQ ID NO 417
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 13, 37, 40
<223> OTHER INFORMATION: n = LNA methyl cytosine

<400> SEQUENCE: 417
tacaattctt tgnaggaagc aatatccgcc ggagtcnccn ttatcactat        50

<210> SEQ ID NO 418
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 19, 31, 37, 40, 49
<223> OTHER INFORMATION: n = LNA methyl cytosine

<400> SEQUENCE: 418
ntcacggagg ttataattnt atgcaggagg naatttntgn tggagttcna        50

<210> SEQ ID NO 419
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 16
<223> OTHER INFORMATION: n = LNA methyl cytosine

<400> SEQUENCE: 419
accgtttcat gagagntgta atcaggtgtt gtttctgtaa aaagtgtgaa          50

<210> SEQ ID NO 420
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 19, 25
<223> OTHER INFORMATION: n = LNA methyl cytosine

<400> SEQUENCE: 420
gtggatgtga aattagtcnt caacnccaga gcatttagtg cagagattag          50

<210> SEQ ID NO 421
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 43
<223> OTHER INFORMATION: n = LNA methyl cytosine

<400> SEQUENCE: 421
gcagtttaat gtgaagctag ttaaagtaca gtctacgtgg gangagaaat          50

<210> SEQ ID NO 422
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 19, 34
<223> OTHER INFORMATION: n = LNA methyl cytosine

<400> SEQUENCE: 422
attgccaagt ccatttctng tgccaagtac attnaaaata caagaaaggc          50

<210> SEQ ID NO 423
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 7, 10, 31
<223> OTHER INFORMATION: n = LNA methyl cytosine

<400> SEQUENCE: 423
agantcntan aaatagattc ggtgtcctgc nagacgatgt tgaagaatag          50

<210> SEQ ID NO 424
<211> LENGTH: 50
<212> TYPE: DNA
<213> ORGANISM: Artificial Sequence

```
<220> FEATURE:
<223> OTHER INFORMATION: Synthetic Oligonucleotide Sequence
<221> NAME/KEY: misc_feature
<222> LOCATION: 34, 40
<223> OTHER INFORMATION: n = LNA methyl cytosine

<400> SEQUENCE: 424
ttgaagtttg ggaatattgg tatggttgaa gacnaaggan cggattacga            50

<210> SEQ ID NO 425
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 43
<223> OTHER INFORMATION: n = LNA methyl cytosine

<400> SEQUENCE: 425
gaggcgnaag taggcaatga ttcaagaagt agtaaaggca atngtaacac            50

<210> SEQ ID NO 426
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 22, 40
<223> OTHER INFORMATION: n = LNA methyl cytosine

<400> SEQUENCE: 426
tgagcanaaa gttaagatgt tnggaaagaa aaagaaagtn aatcctatga            50

<210> SEQ ID NO 427
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 13, 16, 22, 25, 28, 40, 49
<223> OTHER INFORMATION: n = LNA methyl cytosine

<400> SEQUENCE: 427
naagtgacca atnagnacgc anggnttnca tcctcaagan tgatattanc            50

<210> SEQ ID NO 428
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 428
attaaatgcg cagatgagga cggaacgaat atcggagaaa ctgataatat            50

<210> SEQ ID NO 429
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10
<223> OTHER INFORMATION: n = LNA methyl cytosine

<400> SEQUENCE: 429
```
gatggtaagn tgagcgcctt ggacgaagaa tttgatgttg tcgctactaa         50

<210> SEQ ID NO 430
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 16, 40
<223> OTHER INFORMATION: n = LNA methyl cytosine

<400> SEQUENCE: 430
tacgtcacgn aagganagag ctttgacgac gaaatatcan ttggaggatt         50

<210> SEQ ID NO 431
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 19, 28, 34
<223> OTHER INFORMATION: n = LNA methyl cytosine

<400> SEQUENCE: 431
tctncctgtg taggtacanc aatatcanaa gcgnatttct atgtcgacta         50

<210> SEQ ID NO 432
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 10, 19, 31, 34, 46
<223> OTHER INFORMATION: n = LNA methyl cytosine

<400> SEQUENCE: 432
tgctaanacn agtttaganc atggaaatcc nacngcaaat ataagnaatg         50

<210> SEQ ID NO 433
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 16, 25, 28, 31
<223> OTHER INFORMATION: n = LNA methyl cytosine

<400> SEQUENCE: 433
gcagganata agattncggt caagnaanga nagtgaagaa agtatgcaaa         50

<210> SEQ ID NO 434
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 37, 40
<223> OTHER INFORMATION: n = LNA methyl cytosine

<400> SEQUENCE: 434
ncgtctagtg aaagcgggat ggctaaattg ggaaaangan aagatgttat         50

```
<210> SEQ ID NO 435
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 25
<223> OTHER INFORMATION: n = LNA methyl cytosine

<400> SEQUENCE: 435
gatgcttcaa tatcctttga tggtngttag tttaccattt ttggtgtctt           50

<210> SEQ ID NO 436
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4
<223> OTHER INFORMATION: n = LNA methyl cytosine

<400> SEQUENCE: 436
agtnatttga gttatgtgaa gaccgttggt gggaaagaag agatcaggtg           50

<210> SEQ ID NO 437
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 16, 28, 46, 49
<223> OTHER INFORMATION: n = LNA methyl cytosine

<400> SEQUENCE: 437
gtcttggcta ccacanccaa aaccgttnga aactttaaga gcattntant           50

<210> SEQ ID NO 438
<211> LENGTH: 603
<212> TYPE: DNA
<213> ORGANISM: Artificial Sequence
<220> FEATURE:
<223> OTHER INFORMATION: Synthetic Oligonucleotide Sequence

<400> SEQUENCE: 438
ggtgaaagga caaggacaaa agacaacaat ctactgggta aatttgagtt gagcggtatt    60
ccacccgctc caagaggcgt accacaaatt gaagttacat ttgatatcga tgcaaatggt   120
attctgaacg tatctgccgt tgaaaaaggt actggtaaat ctaacaagat tacaattact   180
aacgataagg gaagattatc gaaggaagat atcgataaaa tggttgctga ggcagaaaag   240
ttcaaggccg aagatgaaca agaagctcaa cgtgttcaag ctaagaatca gctagaatcg   300
tacgcgttta ctttgaaaaa ttctgtgagc gaaaataact tcaaggagaa ggtgggtgaa   360
gaggatgcca ggaaattgga agccgccgcc caagatgcta taaattggtt agatgcttcg   420
caagcggcct ccaccgagga atacaaggaa aggcaaaagg aactagaagg tgttgcaaac   480
cccattatga gtaaatttta cggagctgca ggtggtgccc caggagcagg cccagttccg   540
ggtgctggag caggccccac tggagcacca gacaacggcc caacggttga agaggttgat   600
tag                                                                603

<210> SEQ ID NO 439
<211> LENGTH: 50
```

```
<212> TYPE: DNA
<213> ORGANISM: Artificial Sequence
<220> FEATURE:
<223> OTHER INFORMATION: Synthetic Oligonucleotide Sequence

<400> SEQUENCE: 439
gccccactgg agcaccagac aacggcccaa cggttgaaga ggttgattag          50

<210> SEQ ID NO 440
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 440
gccccaggag caggcccagt tccgggtgct ggagcaggcc ccactggagc          50

<210> SEQ ID NO 441
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 441
ccattatgag taaattttac ggagctgcag gtggtgcccc aggagcaggc          50

<210> SEQ ID NO 442
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 442
ctagaaggtg ttgcaaaccc cattatgagt aaattttacg gagctgcagg          50

<210> SEQ ID NO 443
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 443
cctccaccga ggaatacaag gaaaggcaaa aggaactaga aggtgttgca          50

<210> SEQ ID NO 444
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 444
ggtgaagagg atgccaggaa attggaagcc gccgcccaag atgctataaa          50

<210> SEQ ID NO 445
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 445
```
actttgaaaa attctgtgag cgaaaataac ttcaaggaga aggtgggtga           50

<210> SEQ ID NO 446
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 446
aagaatcagc tagaatcgta cgcgtttact ttgaaaaatt ctgtgagcga           50

<210> SEQ ID NO 447
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 447
aatggttgct gaggcagaaa agttcaaggc cgaagatgaa caagaagctc           50

<210> SEQ ID NO 448
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 448
taacaagatt acaattacta acgataaggg aagattatcg aaggaagata           50

<210> SEQ ID NO 449
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 449
cgatgcaaat ggtattctga acgtatctgc cgttgaaaaa ggtactggta           50

<210> SEQ ID NO 450
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 450
acccgctcca agaggcgtac cacaaattga agttacattt gatatcgatg           50

<210> SEQ ID NO 451
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 451
ggtgaaagga caaggacaaa agacaacaat ctactgggta aatttgagtt           50

<210> SEQ ID NO 452
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 7, 13, 16, 28, 31
<223> OTHER INFORMATION: n = LNA methyl cytosine

<400> SEQUENCE: 452
gccncantgg agnacnagac aacggccnaa nggttgaaga ggttgattag           50

<210> SEQ ID NO 453
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 16, 22, 40
<223> OTHER INFORMATION: n = LNA methyl cytosine

<400> SEQUENCE: 453
gccncaggag caggcncagt tncgggtgct ggagcaggcn ccactggagc           50

<210> SEQ ID NO 454
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 25, 28, 37, 40, 46
<223> OTHER INFORMATION: n = LNA methyl cytosine

<400> SEQUENCE: 454
ncattatgag taaattttac ggagntgnag gtggtgnccn aggagnaggc           50

<210> SEQ ID NO 455
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 19
<223> OTHER INFORMATION: n = LNA methyl cytosine

<400> SEQUENCE: 455
ntagaaggtg ttgcaaacnc cattatgagt aaattttacg gagctgcagg           50

<210> SEQ ID NO 456
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 4, 7, 49
<223> OTHER INFORMATION: n = LNA methyl cytosine

<400> SEQUENCE: 456
nctncancga ggaatacaag gaaaggcaaa aggaactaga aggtgttgna           50

<210> SEQ ID NO 457
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 37

<223> OTHER INFORMATION: n = LNA methyl cytosine

<400> SEQUENCE: 457
ggtgaagagg atgccaggaa attggaagcc gccgccnaag atgctataaa    50

<210> SEQ ID NO 458
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 458
actttgaaaa attctgtgag cgaaaataac ttcaaggaga aggtgggtga    50

<210> SEQ ID NO 459
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 10
<223> OTHER INFORMATION: n = LNA methyl cytosine

<400> SEQUENCE: 459
aagaatnagn tagaatcgta cgcgtttact ttgaaaaatt ctgtgagcga    50

<210> SEQ ID NO 460
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 25, 31
<223> OTHER INFORMATION: n = LNA methyl cytosine

<400> SEQUENCE: 460
aatggttgct gaggcagaaa agttnaaggc ngaagatgaa caagaagctc    50

<210> SEQ ID NO 461
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 22
<223> OTHER INFORMATION: n = LNA methyl cytosine

<400> SEQUENCE: 461
taanaagatt acaattacta angataaggg aagattatcg aaggaagata    50

<210> SEQ ID NO 462
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 22, 31
<223> OTHER INFORMATION: n = LNA methyl cytosine

<400> SEQUENCE: 462
ngatgcaaat ggtattctga angtatctgc ngttgaaaaa ggtactggta    50

```
<210> SEQ ID NO 463
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 16, 46
<223> OTHER INFORMATION: n = LNA methyl cytosine

<400> SEQUENCE: 463
accngctcca agaggngtac cacaaattga agttacattt gatatngatg                50

<210> SEQ ID NO 464
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 31, 34
<223> OTHER INFORMATION: n = LNA methyl cytosine

<400> SEQUENCE: 464
ggtgaaagga caaggacaaa agacaacaat ntantgggta aatttgagtt                50

<210> SEQ ID NO 465
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 465
acaagaatac gacgaaagtg gtccatctat cgttcaccac aagtgtttct                50

<210> SEQ ID NO 466
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10, 13, 31, 37, 40, 49
<223> OTHER INFORMATION: n = LNA methyl cytosine

<400> SEQUENCE: 466
acaagaatan gangaaagtg gtccatctat ngttcancan aagtgtttnt                50

<210> SEQ ID NO 467
<211> LENGTH: 12
<212> TYPE: DNA
<213> ORGANISM: Artificial Sequence
<220> FEATURE:
<223> OTHER INFORMATION: Synthetic Oligonucleotide Sequence

<400> SEQUENCE: 467
caacatccca ca                                                         12

<210> SEQ ID NO 468
<211> LENGTH: 12
<212> TYPE: DNA
<213> ORGANISM: Artificial Sequence
<220> FEATURE:
<223> OTHER INFORMATION: Synthetic Oligonucleotide Sequence

<400> SEQUENCE: 468
caacaaccca ca                                                         12
```

<210> SEQ ID NO 469
<211> LENGTH: 12
<212> TYPE: DNA
<213> ORGANISM: Artificial Sequence
<220> FEATURE:
<223> OTHER INFORMATION: Synthetic Oligonucleotide Sequence

<400> SEQUENCE: 469
tgtgggatgt tg                                                         12

<210> SEQ ID NO 470
<211> LENGTH: 12
<212> TYPE: DNA
<213> ORGANISM: Artificial Sequence
<220> FEATURE:
<223> OTHER INFORMATION: Synthetic Oligonucleotide Sequence

<400> SEQUENCE: 470
tgtgggdtgt tg                                                         12

<210> SEQ ID NO 471
<211> LENGTH: 12
<212> TYPE: DNA
<213> ORGANISM: Artificial Sequence
<220> FEATURE:
<223> OTHER INFORMATION: Synthetic Oligonucleotide Sequence

<400> SEQUENCE: 471
aagagtccag tg                                                         12

<210> SEQ ID NO 472
<211> LENGTH: 12
<212> TYPE: DNA
<213> ORGANISM: Artificial Sequence
<220> FEATURE:
<223> OTHER INFORMATION: Synthetic Oligonucleotide Sequence

<400> SEQUENCE: 472
aagaggccag tg                                                         12

<210> SEQ ID NO 473
<211> LENGTH: 12
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 3, 8
<223> OTHER INFORMATION: n = LNA methyl cytosine

<400> SEQUENCE: 473
cantggantc tt                                                         12

<210> SEQ ID NO 474
<211> LENGTH: 12
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 3, 8
<223> OTHER INFORMATION: n = LNA methyl cytosine

<400> SEQUENCE: 474
cantggdntc tt                                                         12

<210> SEQ ID NO 475
<211> LENGTH: 33
<212> TYPE: DNA
<213> ORGANISM: Artificial Sequence
<220> FEATURE:
<223> OTHER INFORMATION: Synthetic Oligonucleotide Sequence

<400> SEQUENCE: 475
acgtgagctc ttttgacatg tcagaatttc aag                           33

<210> SEQ ID NO 476
<211> LENGTH: 44
<212> TYPE: DNA
<213> ORGANISM: Artificial Sequence
<220> FEATURE:
<223> OTHER INFORMATION: Synthetic Oligonucleotide Sequence

<400> SEQUENCE: 476
gatccccggg aattgccatg ttacttttca gcttcctctt caac               44

<210> SEQ ID NO 477
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 477
tttggtagca cgacaagctt agtat                                    25

<210> SEQ ID NO 478
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 478
tttggtagca cgacaagctt agtat                                    25

<210> SEQ ID NO 479
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 479
cactctaaca gtttcgccgt ttcta                                    25

<210> SEQ ID NO 480
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 480
cactctaaca gtttcgccgt ttcta                                    25

<210> SEQ ID NO 481
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 481
gttgccatgg agttcaaaat ctgtc                                              25

<210> SEQ ID NO 482
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 482
gttgccatgg agttcaaaat ctgtc                                              25

<210> SEQ ID NO 483
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 483
tcaatggcct tgcaccatat aattg                                              25

<210> SEQ ID NO 484
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 484
tcaatggcct tgcaccatat aattg                                              25

<210> SEQ ID NO 485
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 485
tcagttagcc aatccttcgc ttcat                                              25

<210> SEQ ID NO 486
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 486
tcagttagcc aatccttcgc ttcat                                              25

<210> SEQ ID NO 487
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 487 ttttcggcc aaacgatctt gaatt                                               25

<210> SEQ ID NO 488

```
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 488
tttttcggcc aaacgatctt gaatt                                    25

<210> SEQ ID NO 489
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 489
attgacctca aactttctt ggata                                     25

<210> SEQ ID NO 490
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 490
attgacctca aactttctt ggata                                     25

<210> SEQ ID NO 491
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 491
gatgaactca ggtggatagg atctt                                    25

<210> SEQ ID NO 492
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 492
gatgaactca ggtggatagg atctt                                    25

<210> SEQ ID NO 493
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 493
accatcatca cccaactttg tgtcg                                    25

<210> SEQ ID NO 494
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 494
```
accatcatca cccaactttg tgtcg                                          25

<210> SEQ ID NO 495
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 495
cccaactttg tgtcgtttaa taaaa                                          25

<210> SEQ ID NO 496
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 496
cccaactttg tgtcgtttaa taaaa                                          25

<210> SEQ ID NO 497
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 497
caatgatcgt gttacggaaa tcaac                                          25

<210> SEQ ID NO 498
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 498
caatgatcgt gttacggaaa tcaac                                          25

<210> SEQ ID NO 499
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 499
tggcctaggg aatcggtcag cttac                                          25

<210> SEQ ID NO 500
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 500
tggcctaggg aatcggtcag cttac                                          25

<210> SEQ ID NO 501
<211> LENGTH: 25
<212> TYPE: DNA

```
<213> ORGANISM: Artificial Sequence
<220> FEATURE:
<223> OTHER INFORMATION: Synthetic Oligonucleotide Sequence

<400> SEQUENCE: 501
ttggaaacat cggggtgcgc ttttt                                         25

<210> SEQ ID NO 502
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 502
ttggaaacat cggggtgcgc ttttt                                         25

<210> SEQ ID NO 503
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 503
gaaacatcgg ggtgcgcttt ttcaa                                         25

<210> SEQ ID NO 504
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 504
gaaacatcgg ggtgcgcttt ttcaa                                         25

<210> SEQ ID NO 505
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 505
aaaacgacag cataaggctt tcttc                                         25

<210> SEQ ID NO 506
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 506
aaaacgacag cataaggctt tcttc                                         25

<210> SEQ ID NO 507
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 507
gacagcctca gttaattggc cacca                                         25
```

<210> SEQ ID NO 508
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 508
gacagcctca gttaattggc cacca                                      25

<210> SEQ ID NO 509
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 509
ccgattaaac gagagacagt atgct                                      25

<210> SEQ ID NO 510
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 510
ccgattaaac gagagacagt atgct                                      25

<210> SEQ ID NO 511
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 511
atcaaatagg aattcagcta aagcc                                      25

<210> SEQ ID NO 512
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 512
atcaaatagg aattcagcta aagcc                                      25

<210> SEQ ID NO 513
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 513
gacctaagaa cataaagctg gcaat                                      25

<210> SEQ ID NO 514
<211> LENGTH: 25
<212> TYPE: DNA
<213> ORGANISM: Artificial Sequence
<220> FEATURE:

<223> OTHER INFORMATION: Synthetic Oligonucleotide Sequence

<400> SEQUENCE: 514
gacctaagaa cataaagctg gcaat                                    25

<210> SEQ ID NO 515
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 515
ataaagctgg caataggtct ctttt                                    25

<210> SEQ ID NO 516
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 516
ataaagctgg caataggtct ctttt                                    25

<210> SEQ ID NO 517
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 517
agacgtacag catcagaaat agcag                                    25

<210> SEQ ID NO 518
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 518
agacgtacag catcagaaat agcag                                    25

<210> SEQ ID NO 519
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 519
aaatagcagc aatggcctcg tcttg                                    25

<210> SEQ ID NO 520
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 520
aaatagcagc aatggcctcg tcttg                                    25

```
<210> SEQ ID NO 521
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 521
atagcagcaa tggcctcgtc ttggc                                    25

<210> SEQ ID NO 522
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 522
atagcagcaa tggcctcgtc ttggc                                    25

<210> SEQ ID NO 523
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 523
gcaatggcct cgtcttggcc aacga                                    25

<210> SEQ ID NO 524
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 524
gcaatggcct cgtcttggcc aacga                                    25

<210> SEQ ID NO 525
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 9, 11, 14, 18
<223> OTHER INFORMATION: n = LNA methyl cytosine

<400> SEQUENCE: 525
tttggtagna nganaagntt agtat                                    25

<210> SEQ ID NO 526
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 526
tttggtagca cgacaagctt agtat                                    25

<210> SEQ ID NO 527
<211> LENGTH: 25
<212> TYPE: DNA
<213> ORGANISM: Artificial Sequence
```

```
<220> FEATURE:
<223> OTHER INFORMATION: Synthetic Oligonucleotide Sequence
<221> NAME/KEY: misc_feature
<222> LOCATION: 1, 3, 5, 9, 17, 23
<223> OTHER INFORMATION: n = LNA methyl cytosine

<400> SEQUENCE: 527
nantntaana gtttcgncgt ttnta                                   25

<210> SEQ ID NO 528
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1
<223> OTHER INFORMATION: n = LNA methyl cytosine

<400> SEQUENCE: 528
nactctaaca gtttcgccgt ttcta                                   25

<210> SEQ ID NO 529
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 5, 6, 15, 21
<223> OTHER INFORMATION: n = LNA methyl cytosine

<400> SEQUENCE: 529
gttgnnatgg agttnaaaat ntgtc                                   25

<210> SEQ ID NO 530
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 530
gttgccatgg agttcaaaat ctgtc                                   25

<210> SEQ ID NO 531
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 2, 8, 13, 16
<223> OTHER INFORMATION: n = LNA methyl cytosine

<400> SEQUENCE: 531
tnaatggnct tgnacnatat aattg                                   25

<210> SEQ ID NO 532
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 13, 16
<223> OTHER INFORMATION: n = LNA methyl cytosine

<400> SEQUENCE: 532
```
tcaatggcct tgnacnatat aattg 25

<210> SEQ ID NO 533
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 2, 10, 15, 18, 20, 23
<223> OTHER INFORMATION: n = LNA methyl cytosine

<400> SEQUENCE: 533
tnagttagcn aatcnttngn ttnat 25

<210> SEQ ID NO 534
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 13, 16
<223> OTHER INFORMATION: n = LNA methyl cytosine

<400> SEQUENCE: 534
accatcatca ccnaantttg tgtcg 25

<210> SEQ ID NO 535
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 6, 9, 10, 14, 18
<223> OTHER INFORMATION: n = LNA methyl cytosine

<400> SEQUENCE: 535
tttttnggnn aaangatntt gaatt 25

<210> SEQ ID NO 536
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 22
<223> OTHER INFORMATION: n = LNA methyl cytosine

<400> SEQUENCE: 536
naatgatcgt gttacggaaa tnaac 25

<210> SEQ ID NO 537
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 6, 7, 9, 14, 18
<223> OTHER INFORMATION: n = LNA methyl cytosine

<400> SEQUENCE: 537
attganntna aaanttntt ggata 25

```
<210> SEQ ID NO 538
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4
<223> OTHER INFORMATION: n = LNA methyl cytosine

<400> SEQUENCE: 538
tggnctaggg aatcggtcag cttac                                          25

<210> SEQ ID NO 539
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 9, 23
<223> OTHER INFORMATION: n = LNA methyl cytosine

<400> SEQUENCE: 539
gatgaantna ggtggatagg atntt                                          25

<210> SEQ ID NO 540
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 540
ttggaaacat cggggtgcgc ttttt                                          25

<210> SEQ ID NO 541
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 2, 12, 13, 24
<223> OTHER INFORMATION: n = LNA methyl cytosine

<400> SEQUENCE: 541
ancatcatca cnnaaccttg tgtng                                          25

<210> SEQ ID NO 542
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 542
gaaacatcgg ggtgcgcttt ttcaa                                          25

<210> SEQ ID NO 543
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 2, 3
<223> OTHER INFORMATION: n = LNA methyl cytosine
```

<400> SEQUENCE: 543
nnnaactttg tgtcgtttaa taaaa    25

<210> SEQ ID NO 544
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 22
<223> OTHER INFORMATION: n = LNA methyl cytosine

<400> SEQUENCE: 544
aaaacgacag cataaggctt tnttc    25

<210> SEQ ID NO 545
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 8, 15, 22
<223> OTHER INFORMATION: n = LNA methyl cytosine

<400> SEQUENCE: 545
naatgatngt gttanggaaa tnaac    25

<210> SEQ ID NO 546
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 546
atcaaatagg aattcagcta aagcc    25

<210> SEQ ID NO 547
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 14, 21
<223> OTHER INFORMATION: n = LNA methyl cytosine

<400> SEQUENCE: 547
tggnctaggg aatnggtcag nttac    25

<210> SEQ ID NO 548
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 22
<223> OTHER INFORMATION: n = LNA methyl cytosine

<400> SEQUENCE: 548
gacntaagaa cataaagctg gnaat    25

<210> SEQ ID NO 549
<211> LENGTH: 25

<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 8, 11, 18
<223> OTHER INFORMATION: n = LNA methyl cytosine

<400> SEQUENCE: 549
ttggaaanat ngggtgngc ttttt                                        25

<210> SEQ ID NO 550
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 19
<223> OTHER INFORMATION: n = LNA methyl cytosine

<400> SEQUENCE: 550
ataaagntgg caataggtnt ctttt                                       25

<210> SEQ ID NO 551
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 5, 8, 15, 23
<223> OTHER INFORMATION: n = LNA methyl cytosine

<400> SEQUENCE: 551
gaaanatngg ggtgngcttt ttnaa                                       25

<210> SEQ ID NO 552
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4
<223> OTHER INFORMATION: n = LNA methyl cytosine

<400> SEQUENCE: 552
agangtacag catcagaaat agcag                                       25

<210> SEQ ID NO 553
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 5, 8, 11, 18, 22
<223> OTHER INFORMATION: n = LNA methyl cytosine

<400> SEQUENCE: 553
aaaanganag nataaggntt tnttc                                       25

<210> SEQ ID NO 554
<211> LENGTH: 25
<212> TYPE: DNA
<213> ORGANISM: Artificial Sequence
<220> FEATURE:
<223> OTHER INFORMATION: Synthetic Oligonucleotide Sequence

```
<221> NAME/KEY: misc_feature
<222> LOCATION: 7, 10, 16, 19, 22
<223> OTHER INFORMATION: n = LNA methyl cytosine

<400> SEQUENCE: 554
aaatagnagn aatggnctng tnttg                                        25

<210> SEQ ID NO 555
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 3, 6, 21, 24
<223> OTHER INFORMATION: n = LNA methyl cytosine

<400> SEQUENCE: 555
ganagnctca gttaattggc nacna                                        25

<210> SEQ ID NO 556
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 556
atagcagcaa tggcctcgtc ttggc                                        25

<210> SEQ ID NO 557
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 2, 10, 17, 24
<223> OTHER INFORMATION: n = LNA methyl cytosine

<400> SEQUENCE: 557
nngattaaan gagaganagt atgnt                                        25

<210> SEQ ID NO 558
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 19
<223> OTHER INFORMATION: n = LNA methyl cytosine

<400> SEQUENCE: 558
gcaatggcct cgtcttggnc aacga                                        25

<210> SEQ ID NO 559
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 3, 15, 18, 24
<223> OTHER INFORMATION: n = LNA methyl cytosine

<400> SEQUENCE: 559
atnaaatagg aattnagnta aagnc                                        25
```

```
<210> SEQ ID NO 560
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7
<223> OTHER INFORMATION: n = LNA methyl cytosine

<400> SEQUENCE: 560
gacagcntca gttaattggc cacca                                              25

<210> SEQ ID NO 561
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 3, 4, 11, 18, 22
<223> OTHER INFORMATION: n = LNA methyl cytosine

<400> SEQUENCE: 561
ganntaagaa nataaagntg gnaat                                              25

<210> SEQ ID NO 562
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 10
<223> OTHER INFORMATION: n = LNA methyl cytosine

<400> SEQUENCE: 562
ncgattaaan gagagacagt atgct                                              25

<210> SEQ ID NO 563
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 11, 19
<223> OTHER INFORMATION: n = LNA methyl cytosine

<400> SEQUENCE: 563
ataaagntgg naataggtnt ctttt                                              25

<210> SEQ ID NO 564
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7
<223> OTHER INFORMATION: n = LNA methyl cytosine

<400> SEQUENCE: 564
gatgaantca ggtggatagg atctt                                              25

<210> SEQ ID NO 565
<211> LENGTH: 25
```

```
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 8, 11, 14, 23
<223> OTHER INFORMATION: n = LNA methyl cytosine

<400> SEQUENCE: 565
agangtanag natnagaaat agnag                                          25

<210> SEQ ID NO 566
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10
<223> OTHER INFORMATION: n = LNA methyl cytosine

<400> SEQUENCE: 566
tcagttagcn aatccttcgc ttcat                                          25

<210> SEQ ID NO 567
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 10, 16, 19
<223> OTHER INFORMATION: n = LNA methyl cytosine

<400> SEQUENCE: 567
aaatagnagn aatggnctng tcttg                                          25

<210> SEQ ID NO 568
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10
<223> OTHER INFORMATION: n = LNA methyl cytosine

<400> SEQUENCE: 568
tttttcggcn aaacgatctt gaatt                                          25

<210> SEQ ID NO 569
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 5, 14, 20
<223> OTHER INFORMATION: n = LNA methyl cytosine

<400> SEQUENCE: 569
atagnagcaa tggnctcgtn ttggc                                          25

<210> SEQ ID NO 570
<211> LENGTH: 25
<212> TYPE: DNA
<213> ORGANISM: Artificial Sequence
<220> FEATURE:
<223> OTHER INFORMATION: Synthetic Oligonucleotide Sequence
```

```
<221> NAME/KEY: misc_feature
<222> LOCATION: 7
<223> OTHER INFORMATION: n = LNA methyl cytosine

<400> SEQUENCE: 570
attgacntca aaactttctt ggata                                    25

<210> SEQ ID NO 571
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 11, 14
<223> OTHER INFORMATION: n = LNA methyl cytosine

<400> SEQUENCE: 571
gcaatggcct ngtnttggcc aacga                                    25

<210> SEQ ID NO 572
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1
<223> OTHER INFORMATION: n = LNA methyl cytosine

<400> SEQUENCE: 572
nccaactttg tgtcgtttaa taaaa                                    25

<210> SEQ ID NO 573
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 573
tttggtagca cgtcaagctt agtat                                    25

<210> SEQ ID NO 574
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 574
tttggtagca cgtcaagctt agtat                                    25

<210> SEQ ID NO 575
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 575
cactctaaca gtatcgccgt ttcta                                    25

<210> SEQ ID NO 576
<211> LENGTH: 25
<212> TYPE: DNA
<213> ORGANISM: Artificial Sequence
```

```
<220> FEATURE:
<223> OTHER INFORMATION: Synthetic Oligonucleotide Sequence

<400> SEQUENCE: 576
cactctaaca gtatcgccgt ttcta                                   25

<210> SEQ ID NO 577
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 577
gttgccatgg agatcaaaat ctgtc                                   25

<210> SEQ ID NO 578
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 578
gttgccatgg agatcaaaat ctgtc                                   25

<210> SEQ ID NO 579
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 579
tcaatggcct tggaccatat aattg                                   25

<210> SEQ ID NO 580
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 580
tcaatggcct tggaccatat aattg                                   25

<210> SEQ ID NO 581
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 581
tcagttagcc aaaccttcgc ttcat                                   25

<210> SEQ ID NO 582
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 582
tcagttagcc aaaccttcgc ttcat                                   25
```

<210> SEQ ID NO 583
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 583
tttttcggcc aatcgatctt gaatt                                                25

<210> SEQ ID NO 584
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 584
tttttcggcc aatcgatctt gaatt                                                25

<210> SEQ ID NO 585
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 585
attgacctca aatctttctt ggata                                                25

<210> SEQ ID NO 586
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 586
attgacctca aatctttctt ggata                                                25

<210> SEQ ID NO 587
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 587
gatgaactca ggaggatagg atctt                                                25

<210> SEQ ID NO 588
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 588
gatgaactca ggaggatagg atctt                                                25

<210> SEQ ID NO 589
<211> LENGTH: 25
<212> TYPE: DNA
<213> ORGANISM: Artificial Sequence
<220> FEATURE:
<223> OTHER INFORMATION: Synthetic Oligonucleotide Sequence

```
<400> SEQUENCE: 589
accatcatca ccgaactttg tgtcg                                               25

<210> SEQ ID NO 590
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 590
accatcatca ccgaactttg tgtcg                                               25

<210> SEQ ID NO 591
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 591
cccaactttg tgacgtttaa taaaa                                               25

<210> SEQ ID NO 592
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 592
cccaactttg tgacgtttaa taaaa                                               25

<210> SEQ ID NO 593
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 593
caatgatcgt gtaacggaaa tcaac                                               25

<210> SEQ ID NO 594
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 594
caatgatcgt gtaacggaaa tcaac                                               25

<210> SEQ ID NO 595
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 595
tggcctaggg aaacggtcag cttac                                               25

<210> SEQ ID NO 596
```

```
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 596
tggcctaggg aaacggtcag cttac                                        25

<210> SEQ ID NO 597
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 597
ttggaaacat cgcggtgcgc ttttt                                        25

<210> SEQ ID NO 598
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 598
ttggaaacat cgcggtgcgc ttttt                                        25

<210> SEQ ID NO 599
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 599
gaaacatcgg ggagcgcttt ttcaa                                        25

<210> SEQ ID NO 600
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 600
gaaacatcgg ggagcgcttt ttcaa                                        25

<210> SEQ ID NO 601
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 601
aaaacgacag caaaaggctt tcttc                                        25

<210> SEQ ID NO 602
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 602
```
aaaacgacag caaaaggctt tcttc                                   25

<210> SEQ ID NO 603
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 603
gacagcctca gtaaattggc cacca                                   25

<210> SEQ ID NO 604
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 604
gacagcctca gtaaattggc cacca                                   25

<210> SEQ ID NO 605
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 605
ccgattaaac gacagacagt atgct                                   25

<210> SEQ ID NO 606
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 606
ccgattaaac gacagacagt atgct                                   25

<210> SEQ ID NO 607
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 607
atcaaatagg aaatcagcta aagcc                                   25

<210> SEQ ID NO 608
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 608
atcaaatagg aaatcagcta aagcc                                   25

<210> SEQ ID NO 609
<211> LENGTH: 25
<212> TYPE: DNA

<213> ORGANISM: Artificial Sequence
<220> FEATURE:
<223> OTHER INFORMATION: Synthetic Oligonucleotide Sequence

<400> SEQUENCE: 609
gacctaagaa caaaaagctg gcaat                                              25

<210> SEQ ID NO 610
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 610
gacctaagaa caaaaagctg gcaat                                              25

<210> SEQ ID NO 611
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 611
ataaagctgg cattaggtct ctttt                                              25

<210> SEQ ID NO 612
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 612
ataaagctgg caaaaggtct ctttt                                              25

<210> SEQ ID NO 613
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 613
agacgtacag caacagaaat agcag                                              25

<210> SEQ ID NO 614
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 614
agacgtacag caacagaaat agcag                                              25

<210> SEQ ID NO 615
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 615
aaatagcagc aaaggcctcg tcttg                                              25

<210> SEQ ID NO 616
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 616
aaatagcagc aaaggcctcg tcttg                                    25

<210> SEQ ID NO 617
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 617
atagcagcaa tgccctcgtc ttggc                                    25

<210> SEQ ID NO 618
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 618
atagcagcaa tgccctcgtc ttggc                                    25

<210> SEQ ID NO 619
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 619
gcaatggcct cgacttggcc aacga                                    25

<210> SEQ ID NO 620
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 620
gcaatggcct cgacttggcc aacga                                    25

<210> SEQ ID NO 621
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 9, 11, 18
<223> OTHER INFORMATION: n = LNA methyl cytosine

<400> SEQUENCE: 621
tttggtagna ngtcaagntt agtat                                    25

<210> SEQ ID NO 622
<211> LENGTH: 25

<212> TYPE: DNA
<213> ORGANISM: Artificial Sequence
<220> FEATURE:
<223> OTHER INFORMATION: Synthetic Oligonucleotide Sequence

<400> SEQUENCE: 622
tttggtagca cgtcaagctt agtat                                         25

<210> SEQ ID NO 623
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 3, 5, 9, 17, 23
<223> OTHER INFORMATION: n = LNA methyl cytosine

<400> SEQUENCE: 623
nantntaana gtatcgncgt ttnta                                         25

<210> SEQ ID NO 624
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1
<223> OTHER INFORMATION: n = LNA methyl cytosine

<400> SEQUENCE: 624
nactctaaca gtatcgccgt ttcta                                         25

<210> SEQ ID NO 625
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 5, 6, 15, 21
<223> OTHER INFORMATION: n = LNA methyl cytosine

<400> SEQUENCE: 625
gttgnnatgg agatnaaaat ntgtc                                         25

<210> SEQ ID NO 626
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 626
gttgccatgg agatcaaaat ctgtc                                         25

<210> SEQ ID NO 627
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 2, 8, 16
<223> OTHER INFORMATION: n = LNA methyl cytosine

<400> SEQUENCE: 627
tnaatggnct tggacnatat aattg 25

<210> SEQ ID NO 628
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 16
<223> OTHER INFORMATION: n = LNA methyl cytosine

<400> SEQUENCE: 628
tcaatggcct tggacnatat aattg 25

<210> SEQ ID NO 629
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 2, 10, 20, 23
<223> OTHER INFORMATION: n = LNA methyl cytosine

<400> SEQUENCE: 629
tnagttagcn aaaccttcgn ttnat 25

<210> SEQ ID NO 630
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10
<223> OTHER INFORMATION: n = LNA methyl cytosine

<400> SEQUENCE: 630
tcagttagcn aaaccttcgc ttcat 25

<210> SEQ ID NO 631
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 6, 9, 10, 18
<223> OTHER INFORMATION: n = LNA methyl cytosine

<400> SEQUENCE: 631
tttttnggnn aatcgatntt gaatt 25

<210> SEQ ID NO 632
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 10
<223> OTHER INFORMATION: n = LNA methyl cytosine

<400> SEQUENCE: 632
tttttcggcn aatcgatctt gaatt 25

<210> SEQ ID NO 633

```
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 6, 7, 9, 18
<223> OTHER INFORMATION: n = LNA methyl cytosine

<400> SEQUENCE: 633
attganntna aatctttntt ggata                                           25

<210> SEQ ID NO 634
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7
<223> OTHER INFORMATION: n = LNA methyl cytosine

<400> SEQUENCE: 634
attgacntca aatctttctt ggata                                           25

<210> SEQ ID NO 635
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 9, 23
<223> OTHER INFORMATION: n = LNA methyl cytosine

<400> SEQUENCE: 635
gatgaantna ggaggatagg atntt                                           25

<210> SEQ ID NO 636
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7
<223> OTHER INFORMATION: n = LNA methyl cytosine

<400> SEQUENCE: 636
gatgaantca ggaggatagg atctt                                           25

<210> SEQ ID NO 637
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 2, 24
<223> OTHER INFORMATION: n = LNA methyl cytosine

<400> SEQUENCE: 637
ancatcatca cccaaccttg tgtng                                           25

<210> SEQ ID NO 638
<211> LENGTH: 25
<212> TYPE: DNA
<213> ORGANISM: Artificial Sequence
<220> FEATURE:
```

```
<223> OTHER INFORMATION: Synthetic Oligonucleotide Sequence
<221> NAME/KEY: misc_feature
<222> LOCATION: 16
<223> OTHER INFORMATION: n = LNA methyl cytosine

<400> SEQUENCE: 638
accatcatca ccgaantttg tgtcg                                              25

<210> SEQ ID NO 639
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 2, 3
<223> OTHER INFORMATION: n = LNA methyl cytosine

<400> SEQUENCE: 639
nnnaactttg tgacgtttaa taaaa                                              25

<210> SEQ ID NO 640
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1
<223> OTHER INFORMATION: n = LNA methyl cytosine

<400> SEQUENCE: 640
nccaactttg tgacgtttaa taaaa                                              25

<210> SEQ ID NO 641
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 8, 15, 22
<223> OTHER INFORMATION: n = LNA methyl cytosine

<400> SEQUENCE: 641
naatgatngt gttanggaaa tnaac                                              25

<210> SEQ ID NO 642
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 22
<223> OTHER INFORMATION: n = LNA methyl cytosine

<400> SEQUENCE: 642
naatgatcgt gtaacggaaa tnaac                                              25

<210> SEQ ID NO 643
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 21
<223> OTHER INFORMATION: n = LNA methyl cytosine
```

<400> SEQUENCE: 643
tggnctaggg aaacggtcag nttac                                      25

<210> SEQ ID NO 644
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4
<223> OTHER INFORMATION: n = LNA methyl cytosine

<400> SEQUENCE: 644
tggnctaggg aaacggtcag cttac                                      25

<210> SEQ ID NO 645
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 8, 11, 18
<223> OTHER INFORMATION: n = LNA methyl cytosine

<400> SEQUENCE: 645
ttggaaanat ngcggtgngc ttttt                                      25

<210> SEQ ID NO 646
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 13
<223> OTHER INFORMATION: n = LNA methyl cytosine

<400> SEQUENCE: 646
ttggaaacat cgnggtgcgc ttttt                                      25

<210> SEQ ID NO 647
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 5, 8, 15, 23
<223> OTHER INFORMATION: n = LNA methyl cytosine

<400> SEQUENCE: 647
gaaanatngg ggagngcttt ttnaa                                      25

<210> SEQ ID NO 648
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 648
gaaacatcgg ggagcgcttt ttcaa                                      25

<210> SEQ ID NO 649

```
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 5, 8, 11, 18, 22
<223> OTHER INFORMATION: n = LNA methyl cytosine

<400> SEQUENCE: 649
aaaanganag naaaaggntt tnttc                                              25

<210> SEQ ID NO 650
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 22
<223> OTHER INFORMATION: n = LNA methyl cytosine

<400> SEQUENCE: 650
aaaacgacag caaaaggctt tnttc                                              25

<210> SEQ ID NO 651
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 3, 6, 21, 24
<223> OTHER INFORMATION: n = LNA methyl cytosine

<400> SEQUENCE: 651
ganagnctca gtaaattggc nacna                                              25

<210> SEQ ID NO 652
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7
<223> OTHER INFORMATION: n = LNA methyl cytosine

<400> SEQUENCE: 652
gacagcntca gtaaattggc cacca                                              25

<210> SEQ ID NO 653
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 2, 10, 17, 24
<223> OTHER INFORMATION: n = LNA methyl cytosine

<400> SEQUENCE: 653
nngattaaan gacaganagt atgnt                                              25

<210> SEQ ID NO 654
<211> LENGTH: 25
<212> TYPE: DNA
<213> ORGANISM: Artificial Sequence
<220> FEATURE:
```

```
<223> OTHER INFORMATION: Synthetic Oligonucleotide Sequence
<221> NAME/KEY: misc_feature
<222> LOCATION: 1, 10, 13
<223> OTHER INFORMATION: n = LNA methyl cytosine

<400> SEQUENCE: 654
ncgattaaan ganagacagt atgct                                              25

<210> SEQ ID NO 655
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 3, 15, 18, 24
<223> OTHER INFORMATION: n = LNA methyl cytosine

<400> SEQUENCE: 655
atnaaatagg aaatnagnta aagnc                                              25

<210> SEQ ID NO 656
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 656
atcaaatagg aaatcagcta aagcc                                              25

<210> SEQ ID NO 657
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 3, 4, 11, 18, 22
<223> OTHER INFORMATION: n = LNA methyl cytosine

<400> SEQUENCE: 657
ganntaagaa naaaaagntg gnaat                                              25

<210> SEQ ID NO 658
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 22
<223> OTHER INFORMATION: n = LNA methyl cytosine

<400> SEQUENCE: 658
gacntaagaa caaaaagctg gnaat                                              25

<210> SEQ ID NO 659
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 11, 19
<223> OTHER INFORMATION: n = LNA methyl cytosine

<400> SEQUENCE: 659
```
ataaagntgg nattaggtnt ctttt                                    25

<210> SEQ ID NO 660
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 19
<223> OTHER INFORMATION: n = LNA methyl cytosine

<400> SEQUENCE: 660
ataaagntgg cattaggtnt ctttt                                    25

<210> SEQ ID NO 661
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 8, 11, 23
<223> OTHER INFORMATION: n = LNA methyl cytosine

<400> SEQUENCE: 661
agangtanag naacagaaat agnag                                    25

<210> SEQ ID NO 662
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4
<223> OTHER INFORMATION: n = LNA methyl cytosine

<400> SEQUENCE: 662
agangtacag caacagaaat agcag                                    25

<210> SEQ ID NO 663
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 10, 16, 19
<223> OTHER INFORMATION: n = LNA methyl cytosine

<400> SEQUENCE: 663
aaatagnagn aaaggnctng tcttg                                    25

<210> SEQ ID NO 664
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 10, 16, 19, 22
<223> OTHER INFORMATION: n = LNA methyl cytosine

<400> SEQUENCE: 664
aaatagnagn aaaggnctng tnttg                                    25

<210> SEQ ID NO 665

<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 5, 20
<223> OTHER INFORMATION: n = LNA methyl cytosine

<400> SEQUENCE: 665
atagnagcaa tgccctcgtn ttggc                                    25

<210> SEQ ID NO 666
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 13
<223> OTHER INFORMATION: n = LNA methyl cytosine

<400> SEQUENCE: 666
atagcagcaa tgncctcgtc ttggc                                    25

<210> SEQ ID NO 667
<211> LENGTH: 24
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 2, 11, 22
<223> OTHER INFORMATION: n = LNA methyl cytosine

<400> SEQUENCE: 667
gnaatggcct ngactggcca anga                                     24

<210> SEQ ID NO 668
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 19
<223> OTHER INFORMATION: n = LNA methyl cytosine

<400> SEQUENCE: 668
gcaatggcct cgacttggnc aacga                                    25

<210> SEQ ID NO 669
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 669
tttggtagca cgtcaagctt agtat                                    25

<210> SEQ ID NO 670
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 670
cactctaaca gtatcgccgt ttcta                                          25

<210> SEQ ID NO 671
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 671
gttgccatgg agatcaaaat ctgtc                                          25

<210> SEQ ID NO 672
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 672
tcaatggcct tggaccatat aattg                                          25

<210> SEQ ID NO 673
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 673
tcagttagcc aaaccttcgc ttcat                                          25

<210> SEQ ID NO 674
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 674
tttttcggcc aatcgatctt gaatt                                          25

<210> SEQ ID NO 675
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 675
attgacctca aatctttctt ggata                                          25

<210> SEQ ID NO 676
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 676
gatgaactca ggaggatagg atctt                                          25

<210> SEQ ID NO 677
<211> LENGTH: 25
<212> TYPE: DNA

```
<213> ORGANISM: Artificial Sequence
<220> FEATURE:
<223> OTHER INFORMATION: Synthetic Oligonucleotide Sequence

<400> SEQUENCE: 677
accatcatca ccgaactttg tgtcg                                               25

<210> SEQ ID NO 678
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 678
cccaactttg tgacgtttaa taaaa                                               25

<210> SEQ ID NO 679
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 679
caatgatcgt gtaacggaaa tcaac                                               25

<210> SEQ ID NO 680
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 680
tggcctaggg aaacggtcag cttac                                               25

<210> SEQ ID NO 681
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 681
ttggaaacat cgcggtgcgc ttttt                                               25

<210> SEQ ID NO 682
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 682
gaaacatcgg ggagcgcttt ttcaa                                               25

<210> SEQ ID NO 683
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 683
aaaacgacag caaaaggctt tcttc                                               25
```

<210> SEQ ID NO 684
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 684
gacagcctca gtaaattggc cacca          25

<210> SEQ ID NO 685
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 685
ccgattaaac gacagacagt atgct          25

<210> SEQ ID NO 686
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 686
atcaaatagg aaatcagcta aagcc          25

<210> SEQ ID NO 687
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 687
gacctaagaa caaaaagctg gcaat          25

<210> SEQ ID NO 688
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 688
ataaagctgg cattaggtct ctttt          25

<210> SEQ ID NO 689
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 689
agacgtacag caacagaaat agcag          25

<210> SEQ ID NO 690
<211> LENGTH: 25
<212> TYPE: DNA
<213> ORGANISM: Artificial Sequence
<220> FEATURE:

```
<223> OTHER INFORMATION: Synthetic Oligonucleotide Sequence

<400> SEQUENCE: 690
aaatagcagc aaaggcctcg tcttg                                           25

<210> SEQ ID NO 691
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 691
atagcagcaa tgccctcgtc ttggc                                           25

<210> SEQ ID NO 692
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 692
gcaatggcct cgacttggcc aacga                                           25

<210> SEQ ID NO 693
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 693
tttggtagca cgtcaagctt agtat                                           25

<210> SEQ ID NO 694
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 694
cactctaaca gtatcgccgt ttcta                                           25

<210> SEQ ID NO 695
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 695
gttgccatgg agatcaaaat ctgtc                                           25

<210> SEQ ID NO 696
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 696
tcaatggcct tggaccatat aattg                                           25
```

```
<210> SEQ ID NO 697
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 697
tcagttagcc aaaccttcgc ttcat                                            25

<210> SEQ ID NO 698
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 698
tttttcggcc aatcgatctt gaatt                                            25

<210> SEQ ID NO 699
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 699
attgacctca aatctttctt ggata                                            25

<210> SEQ ID NO 700
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 700
gatgaactca ggaggatagg atctt                                            25

<210> SEQ ID NO 701
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 701
accatcatca ccgaactttg tgtcg                                            25

<210> SEQ ID NO 702
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 702
cccaactttg tgacgtttaa taaaa                                            25

<210> SEQ ID NO 703
<211> LENGTH: 25
<212> TYPE: DNA
<213> ORGANISM: Artificial Sequence
<220> FEATURE:
<223> OTHER INFORMATION: Synthetic Oligonucleotide Sequence
```

```
<400> SEQUENCE: 703
caatgatcgt gtaacggaaa tcaac                                        25

<210> SEQ ID NO 704
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 704
tggcctaggg aaacggtcag cttac                                        25

<210> SEQ ID NO 705
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 705
ttggaaacat cgcggtgcgc ttttt                                        25

<210> SEQ ID NO 706
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 706
gaaacatcgg ggagcgcttt ttcaa                                        25

<210> SEQ ID NO 707
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 707
aaaacgacag caaaaggctt tcttc                                        25

<210> SEQ ID NO 708
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 708
gacagcctca gtaaattggc cacca                                        25

<210> SEQ ID NO 709
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 709
ccgattaaac gacagacagt atgct                                        25

<210> SEQ ID NO 710
<211> LENGTH: 25
```

```
<212> TYPE: DNA
<213> ORGANISM: Artificial Sequence
<220> FEATURE:
<223> OTHER INFORMATION: Synthetic Oligonucleotide Sequence

<400> SEQUENCE: 710
atcaaatagg aaatcagcta aagcc                                      25

<210> SEQ ID NO 711
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 711
gacctaagaa caaaaagctg gcaat                                      25

<210> SEQ ID NO 712
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 712
ataaagctgg caaaaggtct ctttt                                      25

<210> SEQ ID NO 713
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 713
agacgtacag caacagaaat agcag                                      25

<210> SEQ ID NO 714
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 714
aaatagcagc aaaggcctcg tcttg                                      25

<210> SEQ ID NO 715
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 715
atagcagcaa tgccctcgtc ttggc                                      25

<210> SEQ ID NO 716
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 716
```
gcaatggcct cgacttggcc aacga                                          25

<210> SEQ ID NO 717
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 9, 11, 18
<223> OTHER INFORMATION: n = LNA methyl cytosine

<400> SEQUENCE: 717
tttggtagna ngtcaagntt agtat                                          25

<210> SEQ ID NO 718
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 3, 5, 9, 17, 23
<223> OTHER INFORMATION: n = LNA methyl cytosine

<400> SEQUENCE: 718
nantntaana gtatcgncgt ttnta                                          25

<210> SEQ ID NO 719
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 5, 6, 15, 21
<223> OTHER INFORMATION: n = LNA methyl cytosine

<400> SEQUENCE: 719
gttgnnatgg agatnaaaat ntgtc                                          25

<210> SEQ ID NO 720
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 2, 8, 16
<223> OTHER INFORMATION: n = LNA methyl cytosine

<400> SEQUENCE: 720
tnaatggnct tggacnatat aattg                                          25

<210> SEQ ID NO 721
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 2, 10, 20, 23
<223> OTHER INFORMATION: n = LNA methyl cytosine

<400> SEQUENCE: 721
tnagttagcn aaaccttcgn ttnat                                          25

<210> SEQ ID NO 722

```
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 6, 9, 10, 18
<223> OTHER INFORMATION: n = LNA methyl cytosine

<400> SEQUENCE: 722
tttttnggnn aatcgatntt gaatt                                              25

<210> SEQ ID NO 723
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 6, 7, 9, 18
<223> OTHER INFORMATION: n = LNA methyl cytosine

<400> SEQUENCE: 723
attganntna aatctttntt ggata                                              25

<210> SEQ ID NO 724
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 9, 23
<223> OTHER INFORMATION: n = LNA methyl cytosine

<400> SEQUENCE: 724
gatgaantna ggaggatagg atntt                                              25

<210> SEQ ID NO 725
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 2, 24
<223> OTHER INFORMATION: n = LNA methyl cytosine

<400> SEQUENCE: 725
ancatcatca cccaaccttg tgtng                                              25

<210> SEQ ID NO 726
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 2, 3
<223> OTHER INFORMATION: n = LNA methyl cytosine

<400> SEQUENCE: 726
nnnaactttg tgacgtttaa taaaa                                              25

<210> SEQ ID NO 727
<211> LENGTH: 25
<212> TYPE: DNA
<213> ORGANISM: Artificial Sequence
<220> FEATURE:
```

```
<223> OTHER INFORMATION: Synthetic Oligonucleotide Sequence
<221> NAME/KEY: misc_feature
<222> LOCATION: 4, 21
<223> OTHER INFORMATION: n = LNA methyl cytosine

<400> SEQUENCE: 727
tggnctaggg aaacggtcag nttac                                               25

<210> SEQ ID NO 728
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 8, 11, 18
<223> OTHER INFORMATION: n = LNA methyl cytosine

<400> SEQUENCE: 728
ttggaaanat ngcggtgngc ttttt                                               25

<210> SEQ ID NO 729
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 5, 8, 15, 23
<223> OTHER INFORMATION: n = LNA methyl cytosine

<400> SEQUENCE: 729
gaaanatngg ggagngcttt ttnaa                                               25

<210> SEQ ID NO 730
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 5, 8, 11, 18, 22
<223> OTHER INFORMATION: n = LNA methyl cytosine

<400> SEQUENCE: 730
aaaanganag naaaaggntt tnttc                                               25

<210> SEQ ID NO 731
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 3, 6, 21, 24
<223> OTHER INFORMATION: n = LNA methyl cytosine

<400> SEQUENCE: 731
ganagnctca gtaaattggc nacna                                               25

<210> SEQ ID NO 732
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 2, 10, 17, 24
<223> OTHER INFORMATION: n = LNA methyl cytosine
```

```
<400> SEQUENCE: 732
nngattaaan gacaganagt atgnt                                          25

<210> SEQ ID NO 733
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 3, 15, 18, 24
<223> OTHER INFORMATION: n = LNA methyl cytosine

<400> SEQUENCE: 733
atnaaatagg aaatnagnta aagnc                                          25

<210> SEQ ID NO 734
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 3, 4, 11, 18, 22
<223> OTHER INFORMATION: n = LNA methyl cytosine

<400> SEQUENCE: 734
ganntaagaa naaaaagntg gnaat                                          25

<210> SEQ ID NO 735
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 11, 19
<223> OTHER INFORMATION: n = LNA methyl cytosine

<400> SEQUENCE: 735
ataaagntgg nattaggtnt ctttt                                          25

<210> SEQ ID NO 736
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 8, 11, 23
<223> OTHER INFORMATION: n = LNA methyl cytosine

<400> SEQUENCE: 736
agangtanag naacagaaat agnag                                          25

<210> SEQ ID NO 737
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 10, 16, 19
<223> OTHER INFORMATION: n = LNA methyl cytosine

<400> SEQUENCE: 737
aaatagnagn aaaggnctng tcttg                                          25
```

<210> SEQ ID NO 738
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 5, 20
<223> OTHER INFORMATION: n = LNA methyl cytosine

<400> SEQUENCE: 738
atagnagcaa tgccctcgtn ttggc     25

<210> SEQ ID NO 739
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 11, 14
<223> OTHER INFORMATION: n = LNA methyl cytosine

<400> SEQUENCE: 739
gcaatggcct nganttggcc aacga     25

<210> SEQ ID NO 740
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 740
tttggtagca cgacaagctt agtat     25

<210> SEQ ID NO 741
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 741
cactctaaca gtttcgccgt ttcta     25

<210> SEQ ID NO 742
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 742
gttgccatgg agttcaaaat ctgtc     25

<210> SEQ ID NO 743
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 743
tcaatggcct tgcaccatat aattg     25

<210> SEQ ID NO 744
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 744
tcagttagcc aatccttcgc ttcat                                              25

<210> SEQ ID NO 745
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 745
tttttcggcc aaacgatctt gaatt                                              25

<210> SEQ ID NO 746
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 746
attgacctca aaactttctt ggata                                              25

<210> SEQ ID NO 747
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 747
gatgaactca ggtggatagg atctt                                              25

<210> SEQ ID NO 748
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 748
accatcatca cccaactttg tgtcg                                              25

<210> SEQ ID NO 749
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 749
cccaactttg tgtcgtttaa taaaa                                              25

<210> SEQ ID NO 750
<211> LENGTH: 25
<212> TYPE: DNA
<213> ORGANISM: Artificial Sequence
<220> FEATURE:
<223> OTHER INFORMATION: Synthetic Oligonucleotide Sequence

```
<400> SEQUENCE: 750
caatgatcgt gttacggaaa tcaac                                      25

<210> SEQ ID NO 751
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 751
tggcctaggg aatcggtcag cttac                                      25

<210> SEQ ID NO 752
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 752
ttggaaacat cggggtgcgc ttttt                                      25

<210> SEQ ID NO 753
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 753
gaaacatcgg ggtgcgcttt ttcaa                                      25

<210> SEQ ID NO 754
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 754
aaaacgacag cataaggctt tcttc                                      25

<210> SEQ ID NO 755
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 755
gacagcctca gttaattggc cacca                                      25

<210> SEQ ID NO 756
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 756
ccgattaaac gagagacagt atgct                                      25

<210> SEQ ID NO 757
```

```
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 757
atcaaatagg aattcagcta aagcc                                              25

<210> SEQ ID NO 758
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 758
gacctaagaa cataaagctg gcaat                                              25

<210> SEQ ID NO 759
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 759
ataaagctgg caataggtct ctttt                                              25

<210> SEQ ID NO 760
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 760
agacgtacag catcagaaat agcag                                              25

<210> SEQ ID NO 761
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 761
aaatagcagc aatggcctcg tcttg                                              25

<210> SEQ ID NO 762
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 762
atagcagcaa tggcctcgtc ttggc                                              25

<210> SEQ ID NO 763
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 763
```
gcaatggcct cgtcttggcc aacga 25

<210> SEQ ID NO 764
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 764
tttggtagca cgacaagctt agtat 25

<210> SEQ ID NO 765
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 765
cactctaaca gtttcgccgt ttcta 25

<210> SEQ ID NO 766
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 766
gttgccatgg agttcaaaat ctgtc 25

<210> SEQ ID NO 767
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 767
tcaatggcct tgcaccatat aattg 25

<210> SEQ ID NO 768
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 768
tcagttagcc aatccttcgc ttcat 25

<210> SEQ ID NO 769
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 769
tttttcggcc aaacgatctt gaatt 25

<210> SEQ ID NO 770
<211> LENGTH: 25
<212> TYPE: DNA

```
<213> ORGANISM: Artificial Sequence
<220> FEATURE:
<223> OTHER INFORMATION: Synthetic Oligonucleotide Sequence

<400> SEQUENCE: 770
attgacctca aaactttctt ggata                                    25

<210> SEQ ID NO 771
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 771
gatgaactca ggtggatagg atctt                                    25

<210> SEQ ID NO 772
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 772
accatcatca cccaactttg tgtcg                                    25

<210> SEQ ID NO 773
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 773
cccaactttg tgtcgtttaa taaaa                                    25

<210> SEQ ID NO 774
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 774
caatgatcgt gttacggaaa tcaac                                    25

<210> SEQ ID NO 775
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 775
tggcctaggg aatcggtcag cttac                                    25

<210> SEQ ID NO 776
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 776
ttggaaacat cggggtgcgc ttttt                                    25
```

<210> SEQ ID NO 777
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 777
gaaacatcgg ggtgcgcttt ttcaa                                        25

<210> SEQ ID NO 778
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 778
aaaacgacag cataaggctt tcttc                                        25

<210> SEQ ID NO 779
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 779
gacagcctca gttaattggc cacca                                        25

<210> SEQ ID NO 780
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 780
ccgattaaac gagagacagt atgct                                        25

<210> SEQ ID NO 781
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 781
atcaaatagg aattcagcta aagcc                                        25

<210> SEQ ID NO 782
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 782
gacctaagaa cataaagctg gcaat                                        25

<210> SEQ ID NO 783
<211> LENGTH: 25
<212> TYPE: DNA
<213> ORGANISM: Artificial Sequence
<220> FEATURE:

<223> OTHER INFORMATION: Synthetic Oligonucleotide Sequence

<400> SEQUENCE: 783
ataaagctgg caataggtct cttttt                                      25

<210> SEQ ID NO 784
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 784
agacgtacag catcagaaat agcag                                       25

<210> SEQ ID NO 785
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 785
aaatagcagc aatggcctcg tcttg                                       25

<210> SEQ ID NO 786
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 786
atagcagcaa tggcctcgtc ttggc                                       25

<210> SEQ ID NO 787
<211> LENGTH: 25
<212> TYPE: DNA
<213> ORGANISM: Artificial Sequence
<220> FEATURE:
<223> OTHER INFORMATION: Synthetic Oligonucleotide Sequence

<400> SEQUENCE: 787
gcaatggcct cgtcttggcc aacga                                       25

<210> SEQ ID NO 788
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 9, 11, 14, 18
<223> OTHER INFORMATION: n = LNA methyl cytosine

<400> SEQUENCE: 788
tttggtagna nganaagntt agtat                                       25

<210> SEQ ID NO 789
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 3, 5, 9, 17, 23
<223> OTHER INFORMATION: n = LNA methyl cytosine

<400> SEQUENCE: 789
nantntaana gtttcgncgt ttnta    25

<210> SEQ ID NO 790
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 5, 6, 15, 21
<223> OTHER INFORMATION: n = LNA methyl cytosine

<400> SEQUENCE: 790
gttgnnatgg agttnaaaat ntgtc    25

<210> SEQ ID NO 791
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 2, 8, 13, 16
<223> OTHER INFORMATION: n = LNA methyl cytosine

<400> SEQUENCE: 791
tnaatggnct tgnacnatat aattg    25

<210> SEQ ID NO 792
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 2, 10, 15, 18, 20, 23
<223> OTHER INFORMATION: n = LNA methyl cytosine

<400> SEQUENCE: 792
tnagttagcn aatcnttngn ttnat    25

<210> SEQ ID NO 793
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 6, 9, 10, 14, 18
<223> OTHER INFORMATION: n = LNA methyl cytosine

<400> SEQUENCE: 793
tttttnggnn aaangatntt gaatt    25

<210> SEQ ID NO 794
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 6, 7, 9, 14, 18
<223> OTHER INFORMATION: n = LNA methyl cytosine

<400> SEQUENCE: 794
attganntna aaantttntt ggata    25

```
<210> SEQ ID NO 795
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 9, 23
<223> OTHER INFORMATION: n = LNA methyl cytosine

<400> SEQUENCE: 795
gatgaantna ggtggatagg atntt                                              25

<210> SEQ ID NO 796
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 2, 12, 13, 24
<223> OTHER INFORMATION: n = LNA methyl cytosine

<400> SEQUENCE: 796
ancatcatca cnnaaccttg tgtng                                              25

<210> SEQ ID NO 797
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 2, 3
<223> OTHER INFORMATION: n = LNA methyl cytosine

<400> SEQUENCE: 797
nnnaactttg tgtcgtttaa taaaa                                              25

<210> SEQ ID NO 798
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 8, 15, 22
<223> OTHER INFORMATION: n = LNA methyl cytosine

<400> SEQUENCE: 798
naatgatngt gttanggaaa tnaac                                              25

<210> SEQ ID NO 799
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 14, 21
<223> OTHER INFORMATION: n = LNA methyl cytosine

<400> SEQUENCE: 799
tggnctaggg aatnggtcag nttac                                              25

<210> SEQ ID NO 800
<211> LENGTH: 25
```

```
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 8, 11, 18
<223> OTHER INFORMATION: n = LNA methyl cytosine

<400> SEQUENCE: 800
ttggaaanat ngggtgngc ttttt                                          25

<210> SEQ ID NO 801
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 5, 8, 15, 23
<223> OTHER INFORMATION: n = LNA methyl cytosine

<400> SEQUENCE: 801
gaaanatngg ggtgngcttt ttnaa                                         25

<210> SEQ ID NO 802
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 5, 8, 11, 18, 22
<223> OTHER INFORMATION: n = LNA methyl cytosine

<400> SEQUENCE: 802
aaaanganag nataaggntt tnttc                                         25

<210> SEQ ID NO 803
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 3, 6, 21, 24
<223> OTHER INFORMATION: n = LNA methyl cytosine

<400> SEQUENCE: 803
ganagnctca gttaattggc nacna                                         25

<210> SEQ ID NO 804
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 2, 10, 17, 24
<223> OTHER INFORMATION: n = LNA methyl cytosine

<400> SEQUENCE: 804
nngattaaan gagaganagt atgnt                                         25

<210> SEQ ID NO 805
<211> LENGTH: 25
<212> TYPE: DNA
<213> ORGANISM: Artificial Sequence
<220> FEATURE:
<223> OTHER INFORMATION: Synthetic Oligonucleotide Sequence
```

```
<221> NAME/KEY: misc_feature
<222> LOCATION: 3, 15, 18, 24
<223> OTHER INFORMATION: n = LNA methyl cytosine

<400> SEQUENCE: 805
atnaaatagg aattnagnta aagnc                                           25

<210> SEQ ID NO 806
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 3, 4, 11, 18, 22
<223> OTHER INFORMATION: n = LNA methyl cytosine

<400> SEQUENCE: 806
ganntaagaa nataaagntg gnaat                                           25

<210> SEQ ID NO 807
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 11, 19
<223> OTHER INFORMATION: n = LNA methyl cytosine

<400> SEQUENCE: 807
ataaagntgg naataggtnt ctttt                                           25

<210> SEQ ID NO 808
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 8, 11, 14, 23
<223> OTHER INFORMATION: n = LNA methyl cytosine

<400> SEQUENCE: 808
agangtanag natnagaaat agnag                                           25

<210> SEQ ID NO 809
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 7, 10, 16, 19
<223> OTHER INFORMATION: n = LNA methyl cytosine

<400> SEQUENCE: 809
aaatagnagn aatggnctng tcttg                                           25

<210> SEQ ID NO 810
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 5, 14, 20
<223> OTHER INFORMATION: n = LNA methyl cytosine
```

<400> SEQUENCE: 810
atagnagcaa tggnctcgtn ttggc                                           25

<210> SEQ ID NO 811
<211> LENGTH: 25
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 11, 14
<223> OTHER INFORMATION: n = LNA methyl cytosine

<400> SEQUENCE: 811
gcaatggcct ngtnttggcc aacga                                           25

<210> SEQ ID NO 812
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 812
cacaacactg cccagaggtt caatcgataa atatgtgaag gaaatgcctg                50

<210> SEQ ID NO 813
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 813
ctccttcttg cattcttcaa cttccttcaa cacttgagcg gagtcggtgc                50

<210> SEQ ID NO 814
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 814
gaacgtatga gcatgcgaga gacgctgtag ttggaaaaac ccacgaagcg                50

<210> SEQ ID NO 815
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 815
gaaaccgctg attatactgc ggagaaggtg ggtgagtata aagactatac                50

<210> SEQ ID NO 816
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 816
aagtagattt gttatttccg aaacgccttc tcccgttctt                           40

```
<210> SEQ ID NO 817
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 817
accacaaata gtccctcaaa aatcacaaga aaactcacaa                              40

<210> SEQ ID NO 818
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 818
gcagcggtgg taaaaagtat gaaaacgtgg taattaaaag                              40

<210> SEQ ID NO 819
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 819
gaaaactaat caaaggtaaa cgtggatccc atggcaattc                              40

<210> SEQ ID NO 820
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 820
cactgcccag aggttcaatc gataaatatg tgaaggaaat                              40

<210> SEQ ID NO 821
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 821
ctgcccagag gttcaatcga tccgatgatc ctaatgaagg                              40

<210> SEQ ID NO 822
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 822
gtatcgtcca tcatagtatc gataaatatg tgaaggaaat                              40

<210> SEQ ID NO 823
<211> LENGTH: 40
<212> TYPE: DNA
<213> ORGANISM: Artificial Sequence
<220> FEATURE:
<223> OTHER INFORMATION: Synthetic Oligonucleotide Sequence
```

<400> SEQUENCE: 823
tcttgcattc ttcaacttcc ttcaacactt gagcggagtc                               40

<210> SEQ ID NO 824
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 824
ctgcccagag gttcaatcga tgtgtgatag gatcagtgtt                               40

<210> SEQ ID NO 825
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 825
cgaaggagac tgctaatatc gataaatatg tgaaggaaat                               40

<210> SEQ ID NO 826
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 826
tatgagcatg cgagagacgc tgtagttgga aaaacccacg                               40

<210> SEQ ID NO 827
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 827
cgctgattat actgcggaga aggtgggtga gtataaagac                               40

<210> SEQ ID NO 828
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 13, 25
<223> OTHER INFORMATION: n = LNA methyl cytosine

<400> SEQUENCE: 828
nacaacactg ccnagaggtt caatngataa atatgtgaag gaaatgcctg                    50

<210> SEQ ID NO 829
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 4, 10, 19, 28, 46, 49
<223> OTHER INFORMATION: n = LNA methyl cytosine

<400> SEQUENCE: 829
naanactgcn cagaggttna atcgatcnga tgatcctaat gaaggngcnc            50

<210> SEQ ID NO 830
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 10, 13, 25
<223> OTHER INFORMATION: n = LNA methyl cytosine

<400> SEQUENCE: 830
gtcnagtatn gtncatcata gtatngataa atatgtgaag gaaatgcctg            50

<210> SEQ ID NO 831
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 4, 7, 25, 28, 31
<223> OTHER INFORMATION: n = LNA methyl cytosine

<400> SEQUENCE: 831
ntcnttnttg cattcttcaa cttcnttnaa nacttgagcg gagtcggtgc            50

<210> SEQ ID NO 832
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 1, 4, 10, 19, 46
<223> OTHER INFORMATION: n = LNA methyl cytosine

<400> SEQUENCE: 832
naanactgcn cagaggttna atcgatgtgt gataggatca gtgttnaggg            50

<210> SEQ ID NO 833
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 25
<223> OTHER INFORMATION: n = LNA methyl cytosine

<400> SEQUENCE: 833
gaaggcgaag gagactgcta atatngataa atatgtgaag gaaatgcctg            50

<210> SEQ ID NO 834
<211> LENGTH: 50
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 4, 16, 25, 40, 49
<223> OTHER INFORMATION: n = LNA methyl cytosine

<400> SEQUENCE: 834
gaangtatga gcatgngaga gacgntgtag ttggaaaaan ccacgaagng            50

<210> SEQ ID NO 835
<211> LENGTH: 50
<212> TYPE: DNA
<213> ORGANISM: Artificial Sequence
<220> FEATURE:
<223> OTHER INFORMATION: Synthetic Oligonucleotide Sequence

<400> SEQUENCE: 835
gaaaccgctg attatactgc ggagaaggtg ggtgagtata aagactatac         50

<210> SEQ ID NO 836
<211> LENGTH: 40
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 26, 32, 38
<223> OTHER INFORMATION: n = LNA methyl cytosine

<400> SEQUENCE: 836
aagtagattt gttatttccg aaacgncttc tnccgttntt                   40

<210> SEQ ID NO 837
<211> LENGTH: 40
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 2, 5, 14, 17, 26, 38
<223> OTHER INFORMATION: n = LNA methyl cytosine

<400> SEQUENCE: 837
ancanaaata gtcnctnaaa aatcanaaga aaactcanaa                   40

<210> SEQ ID NO 838
<211> LENGTH: 40
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 2, 5, 26
<223> OTHER INFORMATION: n = LNA methyl cytosine

<400> SEQUENCE: 838
gnagnggtgg taaaaagtat gaaaangtgg taattaaaag                   40

<210> SEQ ID NO 839
<211> LENGTH: 40
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 11, 29, 35
<223> OTHER INFORMATION: n = LNA methyl cytosine

<400> SEQUENCE: 839
gaaaactaat naaaggtaaa cgtggatcnc atggnaattc                   40

<210> SEQ ID NO 840
<211> LENGTH: 40
<212> TYPE: DNA
<213> ORGANISM: Artificial Sequence
<220> FEATURE:
<223> OTHER INFORMATION: Synthetic Oligonucleotide Sequence

```
<221> NAME/KEY: misc_feature
<222> LOCATION: 8, 20
<223> OTHER INFORMATION: n = LNA methyl cytosine

<400> SEQUENCE: 840
cactgccnag aggttcaatn gataaatatg tgaaggaaat                              40

<210> SEQ ID NO 841
<211> LENGTH: 40
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 5, 14, 23
<223> OTHER INFORMATION: n = LNA methyl cytosine

<400> SEQUENCE: 841
ctgcncagag gttnaatcga tcngatgatc ctaatgaagg                              40

<210> SEQ ID NO 842
<211> LENGTH: 40
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 5, 8, 20
<223> OTHER INFORMATION: n = LNA methyl cytosine

<400> SEQUENCE: 842
gtatngtnca tcatagtatn gataaatatg tgaaggaaat                              40

<210> SEQ ID NO 843
<211> LENGTH: 40
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 2, 20, 23, 26
<223> OTHER INFORMATION: n = LNA methyl cytosine

<400> SEQUENCE: 843
tnttgcattc ttcaacttcn ttnaanactt gagcggagtc                              40

<210> SEQ ID NO 844
<211> LENGTH: 40
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 5, 14
<223> OTHER INFORMATION: n = LNA methyl cytosine

<400> SEQUENCE: 844
ctgcncagag gttnaatcga tgtgtgatag gatcagtgtt                              40

<210> SEQ ID NO 845
<211> LENGTH: 40
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 20
<223> OTHER INFORMATION: n = LNA methyl cytosine
```

```
<400> SEQUENCE: 845
cgaaggagac tgctaatatn gataaatatg tgaaggaaat                          40

<210> SEQ ID NO 846
<211> LENGTH: 40
<212> TYPE: DNA
<213> ORGANISM: Artificial Sequence
<220> FEATURE:
<223> OTHER INFORMATION: Synthetic Oligonucleotide Sequence
<221> NAME/KEY: misc_feature
<222> LOCATION: 11, 20, 35
<223> OTHER INFORMATION: n = LNA methyl cytosine

<400> SEQUENCE: 846
tatgagcatg ngagagacgn tgtagttgga aaaanccacg                          40

<210> SEQ ID NO 847
<211> LENGTH: 40
<212> TYPE: DNA
<213> ORGANISM: Artificial Sequence
<220> FEATURE:
<223> OTHER INFORMATION: Synthetic Oligonucleotide Sequence

<400> SEQUENCE: 847
cgctgattat actgcggaga aggtgggtga gtataaagac                          40

<210> SEQ ID NO 848
<211> LENGTH: 23
<212> TYPE: DNA
<213> ORGANISM: Artificial Sequence
<220> FEATURE:
<223> OTHER INFORMATION: Synthetic Oligonucleotide Sequence

<400> SEQUENCE: 848
attccattcg attccattcg atc                                            23

<210> SEQ ID NO 849
<211> LENGTH: 24
<212> TYPE: DNA
<213> ORGANISM: Artificial Sequence
<220> FEATURE:
<223> OTHER INFORMATION: Synthetic Oligonucleotide Sequence

<400> SEQUENCE: 849
ttagggttag ggttagggtt aggg                                           24

<210> SEQ ID NO 850
<211> LENGTH: 15
<212> TYPE: DNA
<213> ORGANISM: Artificial Sequence
<220> FEATURE:
<223> OTHER INFORMATION: Synthetic Oligonucleotide Sequence

<400> SEQUENCE: 850
acccagccaa aggag                                                     15

<210> SEQ ID NO 851
<211> LENGTH: 24
<212> TYPE: DNA
<213> ORGANISM: Artificial Sequence
<220> FEATURE:
<223> OTHER INFORMATION: Synthetic Oligonucleotide Sequence

<400> SEQUENCE: 851
tgtgtaccca gccaaaggag ttga                                           24
```

```
<210> SEQ ID NO 852
<211> LENGTH: 32
<212> TYPE: DNA
<213> ORGANISM: Artificial Sequence
<220> FEATURE:
<223> OTHER INFORMATION: Synthetic Oligonucleotide Sequence

<400> SEQUENCE: 852
ccagctctaa gagcggcgcg cttactgcgt gt                                    32
```